United States Patent
Kusakabe et al.

(10) Patent No.: US 9,540,359 B2
(45) Date of Patent: Jan. 10, 2017

(54) DIHYDROOXAZINE OR OXAZEPINE DERIVATIVES HAVING BACE1 INHIBITORY ACTIVITY

(71) Applicant: Shionogi & Co., Ltd., Osaka (JP)

(72) Inventors: Ken-ichi Kusakabe, Osaka (JP); Syuhei Yoshida, Osaka (JP); Kenji Nakahara, Osaka (JP); Tsuyoshi Hasegawa, Osaka (JP); Genta Tadano, Osaka (JP); Kouki Fuchino, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 14/434,013

(22) PCT Filed: Oct. 23, 2013

(86) PCT No.: PCT/JP2013/079472
§ 371 (c)(1),
(2) Date: Apr. 7, 2015

(87) PCT Pub. No.: WO2014/065434
PCT Pub. Date: May 1, 2014

(65) Prior Publication Data
US 2015/0266865 A1 Sep. 24, 2015

(30) Foreign Application Priority Data

Oct. 24, 2012 (JP) ................................. 2012-234461
Jul. 25, 2013 (JP) ................................. 2013-154451

(51) Int. Cl.
*C07D 413/12* (2006.01)
*C07D 498/04* (2006.01)
*C07D 413/14* (2006.01)
*C07D 498/10* (2006.01)

(52) U.S. Cl.
CPC ............ *C07D 413/12* (2013.01); *C07D 413/14* (2013.01); *C07D 498/04* (2013.01); *C07D 498/10* (2013.01)

(58) Field of Classification Search
CPC ..... C07D 413/12; C07D 498/04; C07D 413/14
USPC ....................................... 544/96; 514/211.15
See application file for complete search history.

(56) References Cited

U.S. PATENT DOCUMENTS

| | | | |
|---|---|---|---|
| 2,899,426 A | 8/1959 | Bloom | |
| 3,115,494 A | 12/1963 | Joseph et al. | |
| 3,227,713 A | 1/1966 | Behner | |
| 3,235,551 A | 2/1966 | Werner | |
| 3,577,428 A | 5/1971 | Suh et al. | |
| 3,636,116 A | 1/1972 | Trepanier | |
| 3,719,674 A | 3/1973 | Trepanier | |
| 3,775,409 A | 11/1973 | Harsanyi et al. | |
| 4,049,807 A | 9/1977 | Paulus et al. | |
| 4,311,840 A | 1/1982 | Condon | |
| 4,895,841 A | 1/1990 | Sugimoto et al. | |
| 4,906,626 A | 3/1990 | Amrein et al. | |

(Continued)

FOREIGN PATENT DOCUMENTS

| | | |
|---|---|---|
| CA | 2163724 | 5/1996 |
| CA | 2165386 | 6/1996 |

(Continued)

OTHER PUBLICATIONS

Edwards, et al., "Application of Fragment-Based Lead Generation to the Discovery of Novel, Cyclic Amidine β-Secretase Inhibitors with Nanomolar Potency, Cellular Activity, and High Ligand Efficiency", Journal of Medicinal Chemistry, vol. 50, No. 24, 2007, pp. 5912-5925.

Kuo, et al., "A Synthesis of Estrone via Novel Intermediates. Mechanism of the Coupling Reaction of a Vinyl Carbinol with a β Diketone", The Journal of Organic Chemistry, vol. 33, No. 8, Aug. 1968, pp. 3126-3132.

Cohen, et al., "Synthesis of 2-Amino-5,6-dihydro-4,H-1,3-thiazines and Related Compounds by Acid Catalyzed Cyclizationof Allylic Isothiuronium Salts", Journal of Heterocyclic Chemistry, vol. 14, 1977, pp. 717-723.

Hünig, et al., "Azofarbstoffe Durch Oxydative Kupplung, XVIII. Synthese von-3-substituierten Thiazolon-(2)-hydrazonen und Thiazolon-(2)-benzolsulfonylhydrazonen", European Journal of Organic Chemistry, vol. 647, No. 1, May 1961, pp. 66-76.

(Continued)

*Primary Examiner* — Kahsay Habte
(74) *Attorney, Agent, or Firm* — Hamre, Schumann, Mueller & Larson, P.C.

(57) ABSTRACT

The present invention provides a compound which has an effect of inhibiting amyloid β production, especially an effect of inhibiting BACE1, and which is useful as a therapeutic or prophylactic agent for diseases induced by production, secretion and/or deposition of amyloid β proteins.

A compound of the formula (I):

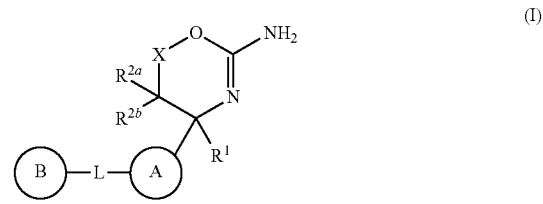

(I)

wherein X is —C($R^{3a}$)($R^{3b}$)—, —C($R^{3a}$)($R^{3b}$)—C($R^{3c}$)($R^{3d}$)— or —C($R^{3a}$)=C($R^{3c}$)—, $R^1$ is substituted or unsubstituted alkyl or the like,
$R^{2a}$, $R^{2b}$, $R^{3a}$, $R^{3b}$, $R^{3c}$ and $R^{3d}$ are each independently hydrogen, halogen or the like,
$R^4$ is hydrogen or halogen,
Ring B is substituted or unsubstituted carbocycle or a substituted or unsubstituted heterocycle,
or a pharmaceutically acceptable salt thereof.

19 Claims, No Drawings

(56) References Cited

U.S. PATENT DOCUMENTS

| | | | |
|---|---|---|---|
| 5,100,901 A | 3/1992 | Sugimoto et al. |
| 5,236,942 A | 8/1993 | Miller |
| 5,328,915 A | 7/1994 | Long et al. |
| 5,880,147 A | 3/1999 | Yoshida et al. |
| 5,952,374 A | 9/1999 | Clarkson, Jr. et al. |
| 6,096,753 A | 8/2000 | Spohr et al. |
| 6,590,123 B2 | 7/2003 | Bekesi et al. |
| 6,713,276 B2 | 3/2004 | Cordell et al. |
| 7,183,070 B2 | 2/2007 | Cordell et al. |
| 7,309,706 B2 | 12/2007 | Rupp et al. |
| 7,326,792 B2 | 2/2008 | Shum et al. |
| 7,414,050 B2 | 8/2008 | Illig et al. |
| 7,763,609 B2 | 7/2010 | Zhu et al. |
| 7,902,238 B2 | 3/2011 | Galley et al. |
| 7,964,594 B1 | 6/2011 | Banner et al. |
| 8,173,642 B2 | 5/2012 | Kobayashi et al. |
| 8,338,413 B1 | 12/2012 | Rueeger |
| 8,389,513 B2 | 3/2013 | Banner et al. |
| 8,637,504 B2 | 1/2014 | Hori et al. |
| 2002/0019427 A1 | 2/2002 | Carry et al. |
| 2005/0165080 A1 | 7/2005 | Rupp et al. |
| 2006/0173006 A1 | 8/2006 | Sun et al. |
| 2006/183790 A1 | 8/2006 | Cole et al. |
| 2006/0183792 A1 | 8/2006 | Fobare et al. |
| 2006/0183943 A1 | 8/2006 | Hu et al. |
| 2006/0287294 A1 | 12/2006 | Zhu et al. |
| 2007/0004730 A1 | 1/2007 | Zhou et al. |
| 2007/0004786 A1 | 1/2007 | Malamas et al. |
| 2007/0027199 A1 | 2/2007 | Malamas et al. |
| 2007/0224656 A1 | 9/2007 | Cordell et al. |
| 2008/0200445 A1 | 8/2008 | Zhu et al. |
| 2009/0023729 A1 | 1/2009 | Nakamuta et al. |
| 2009/0082560 A1 | 3/2009 | Kobayashi et al. |
| 2010/0075957 A1 | 3/2010 | Tamura et al. |
| 2010/0093999 A1 | 4/2010 | Motoki et al. |
| 2010/0125087 A1 | 5/2010 | Holenz et al. |
| 2010/0160290 A1 | 6/2010 | Kobayashi et al. |
| 2010/0234365 A1 | 9/2010 | Liu et al. |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2011/0237576 A1 | 9/2011 | Yonezawa et al. |
| 2012/0015961 A1 | 1/2012 | Tamura et al. |
| 2012/0016116 A1 | 1/2012 | Kobayashi et al. |
| 2012/0022249 A1 | 1/2012 | Kobayashi et al. |
| 2012/0172355 A1 | 7/2012 | Tamura et al. |
| 2012/0202828 A1 | 8/2012 | Castro Pineiro et al. |
| 2012/0238548 A1 | 9/2012 | Gabellieri et al. |
| 2012/0238557 A1 | 9/2012 | Masui et al. |
| 2012/0245154 A1 | 9/2012 | Anan et al. |
| 2012/0245155 A1 | 9/2012 | Yoshida et al. |
| 2012/0245157 A1 | 9/2012 | Masui et al. |
| 2012/0253035 A1 | 10/2012 | Narquizian et al. |
| 2012/0258961 A1 | 10/2012 | Suzuki et al. |
| 2012/0258962 A1 | 10/2012 | Hilpert et al. |
| 2012/0295900 A1 | 11/2012 | Hilpert et al. |
| 2013/0210839 A1 | 8/2013 | Masui et al. |
| 2013/0217705 A1 | 8/2013 | Mitsuoka et al. |
| 2013/0303755 A1 | 11/2013 | Kobayashi et al. |
| 2014/0051691 A1 | 2/2014 | Masui et al. |
| 2014/0058097 A1 | 2/2014 | Kobayashi et al. |
| 2014/0073815 A1 | 3/2014 | Tamura et al. |
| 2014/0235626 A1 | 8/2014 | Tada et al. |
| 2015/0105379 A1 | 4/2015 | Matsumoto et al. |

FOREIGN PATENT DOCUMENTS

| | | |
|---|---|---|
| DE | 140144 | 2/1980 |
| EP | 0 798 292 | 10/1995 |
| EP | 0 713 704 | 5/1996 |
| EP | 0 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1942105 | 7/2008 |
| EP | 2147914 | 1/2010 |
| EP | 2151435 | 2/2010 |
| EP | 2233474 | 9/2010 |
| EP | 2305672 | 4/2011 |
| EP | 2332943 | 6/2011 |
| EP | 2 360 155 | 8/2011 |
| EP | 2360155 | 8/2011 |
| EP | 2415756 | 2/2012 |
| EP | 2500344 | 9/2012 |
| EP | 2511268 | 10/2012 |
| EP | 2511269 | 10/2012 |
| EP | 2514747 | 10/2012 |
| EP | 2518059 | 10/2012 |
| EP | 2597087 | 5/2013 |
| EP | 2612854 | 7/2013 |
| EP | 2634186 | 9/2013 |
| EP | 2634188 | 9/2013 |
| EP | 2689780 | 1/2014 |
| EP | 2703399 | 3/2014 |
| EP | 2703401 | 3/2014 |
| GB | 1001093 | 8/1965 |
| JP | 62-120374 | 6/1987 |
| JP | 8-231521 | 9/1996 |
| JP | 9-067355 | 3/1997 |
| JP | 10-505862 | 6/1998 |
| JP | 11-349572 | 12/1999 |
| JP | 2005-509651 | 4/2004 |
| JP | 2004-149429 | 5/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-051828 | 3/2009 |
| JP | 2009-520685 | 5/2009 |
| JP | 2012250933 | 12/2012 |
| JP | 2014101353 | 6/2014 |
| JP | 2014101354 | 6/2014 |
| WO | WO 94/012165 | 6/1994 |
| WO | WO 95/009619 | 4/1995 |
| WO | WO 96/09286 | 3/1996 |
| WO | WO 96/14842 | 5/1996 |
| WO | WO 96/18608 | 6/1996 |
| WO | WO 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | WO 01/19788 | 3/2001 |
| WO | WO 01/78709 | 10/2001 |
| WO | WO 01/87293 | 11/2001 |
| WO | 02/062766 | 8/2002 |
| WO | 02/088101 | 11/2002 |
| WO | WO 02/096897 | 12/2002 |
| WO | 03/040096 | 5/2003 |
| WO | WO 03/039446 | 5/2003 |
| WO | WO 03/040115 | 5/2003 |
| WO | WO 03/040142 | 5/2003 |
| WO | WO 03/082191 | 10/2003 |
| WO | 2004/009549 | 1/2004 |
| WO | WO 2004/014843 | 2/2004 |
| WO | 2004/031154 | 4/2004 |
| WO | 2004/039404 | 5/2004 |
| WO | WO 2004/043916 | 5/2004 |
| WO | WO 2004/096795 | 11/2004 |
| WO | WO 2005/014555 | 2/2005 |
| WO | WO 2005/032493 | 4/2005 |
| WO | 2005/058311 | 6/2005 |
| WO | WO 2005/097767 | 10/2005 |
| WO | WO 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | WO 2006/041404 | 4/2006 |
| WO | WO 2006/041405 | 4/2006 |
| WO | 2005/065277 | 6/2006 |

(56) References Cited

FOREIGN PATENT DOCUMENTS

| | | |
|---|---|---|
| WO | WO 2006/065204 | 6/2006 |
| WO | 2006/076284 | 7/2006 |
| WO | 2006/099379 | 9/2006 |
| WO | WO 2006/138192 | 12/2006 |
| WO | WO 2006/138217 | 12/2006 |
| WO | WO 2006/138265 | 12/2006 |
| WO | WO 2006/138304 | 12/2006 |
| WO | 2007/002220 | 1/2007 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | 2007049532 | 5/2007 |
| WO | 2007058583 | 5/2007 |
| WO | WO 2007/058580 | 5/2007 |
| WO | WO 2007/058582 | 5/2007 |
| WO | WO 2007/058601 | 5/2007 |
| WO | WO 2007/058602 | 5/2007 |
| WO | WO 2007/073284 | 6/2007 |
| WO | WO 2007/078813 | 7/2007 |
| WO | 2007/092846 | 8/2007 |
| WO | 2007/092854 | 8/2007 |
| WO | WO 2007/114771 | 10/2007 |
| WO | WO 2007/120096 | 10/2007 |
| WO | WO 2007/146225 | 12/2007 |
| WO | WO 2008/011560 | 1/2008 |
| WO | 2008/022024 | 2/2008 |
| WO | 2008/073365 | 6/2008 |
| WO | WO 2008/073370 | 6/2008 |
| WO | 2008/103351 | 8/2008 |
| WO | 2008133273 | 11/2008 |
| WO | 2008133274 | 11/2008 |
| WO | WO 2009/010454 | 1/2009 |
| WO | 2009/064418 | 5/2009 |
| WO | 2009/091016 | 7/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009103626 | 8/2009 |
| WO | 2009/131974 | 10/2009 |
| WO | 2009/131975 | 10/2009 |
| WO | 2009/134617 | 11/2009 |
| WO | 2009134617 | 11/2009 |
| WO | 2009151098 | 12/2009 |
| WO | 2010/019392 | 2/2010 |
| WO | 2010/019393 | 2/2010 |
| WO | WO 2010/013302 | 2/2010 |
| WO | WO 2010/013794 | 2/2010 |
| WO | 2010/038686 | 4/2010 |
| WO | 2010047372 | 4/2010 |
| WO | 2010/056194 | 5/2010 |
| WO | 2010/056195 | 5/2010 |
| WO | 2010/056196 | 5/2010 |
| WO | 2010113848 | 10/2010 |
| WO | 2010/129864 | 11/2010 |
| WO | WO 2010/128058 | 11/2010 |
| WO | 2011/009897 | 1/2011 |
| WO | 2011009898 | 1/2011 |
| WO | 2011009943 | 1/2011 |
| WO | WO 2011/005738 | 1/2011 |
| WO | 2011020806 | 2/2011 |
| WO | 2011/029803 | 3/2011 |
| WO | WO 2011/044181 | 4/2011 |
| WO | WO 2011/044184 | 4/2011 |
| WO | WO 2011/044185 | 4/2011 |
| WO | WO 2011/044187 | 4/2011 |
| WO | 2011/058763 | 5/2011 |
| WO | 2011/060207 | 5/2011 |
| WO | 2011057973 | 5/2011 |
| WO | 2011069934 | 6/2011 |
| WO | 2011/070029 | 6/2011 |
| WO | 2011070781 | 6/2011 |
| WO | 2011071057 | 6/2011 |
| WO | 2011071109 | 6/2011 |
| WO | 2011071135 | 6/2011 |
| WO | 2011077726 | 6/2011 |
| WO | WO 2011/080176 | 7/2011 |
| WO | 2011138293 | 11/2011 |
| WO | 2011154431 | 12/2011 |
| WO | WO 2011/154374 | 12/2011 |
| WO | 2012006953 | 1/2012 |
| WO | WO 2012/000933 | 1/2012 |
| WO | 2012/019966 | 2/2012 |
| WO | 2012/038438 | 3/2012 |
| WO | 2012057247 | 5/2012 |
| WO | 2012057248 | 5/2012 |
| WO | 2012/085038 | 6/2012 |
| WO | 2012/093148 | 7/2012 |
| WO | 2012/095469 | 7/2012 |
| WO | 2012/098064 | 7/2012 |
| WO | 2012/098213 | 7/2012 |
| WO | 2012/098461 | 7/2012 |
| WO | 2012095451 | 7/2012 |
| WO | 2012095463 | 7/2012 |
| WO | 2012095469 | 7/2012 |
| WO | 2012095521 | 7/2012 |
| WO | 2012/104263 | 8/2012 |
| WO | 2012/110440 | 8/2012 |
| WO | 2012/110441 | 8/2012 |
| WO | 2012107371 | 8/2012 |
| WO | 2012110459 | 8/2012 |
| WO | 2012/117027 | 9/2012 |
| WO | 2012/119883 | 9/2012 |
| WO | 2012/120023 | 9/2012 |
| WO | 2012/126791 | 9/2012 |
| WO | 2012126791 | 9/2012 |
| WO | 2012/136603 | 10/2012 |
| WO | 2012/139993 | 10/2012 |
| WO | 2012139993 | 10/2012 |
| WO | 2012/156284 | 11/2012 |
| WO | 2012/162330 | 11/2012 |
| WO | 2012/162334 | 11/2012 |
| WO | 2012147762 | 11/2012 |
| WO | 2012147763 | 11/2012 |
| WO | 2012156284 | 11/2012 |
| WO | 2012/163790 | 12/2012 |
| WO | 2012/168164 | 12/2012 |
| WO | 2012168164 | 12/2012 |
| WO | 2012168175 | 12/2012 |
| WO | 2013027188 | 2/2013 |
| WO | 2013041499 | 3/2013 |
| WO | 2013083556 | 6/2013 |
| WO | 2013083557 | 6/2013 |
| WO | 2013110622 | 8/2013 |
| WO | 2013142613 | 9/2013 |
| WO | 2014001228 | 1/2014 |
| WO | 2014010748 | 1/2014 |
| WO | 2014065434 | 5/2014 |
| WO | 2014098831 | 6/2014 |
| WO | 2014114532 | 7/2014 |
| WO | 2014134341 | 9/2014 |
| WO | 2014138484 | 9/2014 |
| WO | 2014166906 | 10/2014 |

OTHER PUBLICATIONS

Schaumann, et al., "Cycloadditionsreaktionen von Heterokumulenen, XXIII. Stickstoffhaltige Fünfring-Heterocyclen aus Carbodiimiden oder Keteniminen mit 3-Dimethylamino-2H-azirinen", Liebigs Ann. Chem., 1981, pp. 290-305.

Cambie, et al., "vic-Iodothiocyanates and Iodoisothiocyanates. Part 2. New Syntheses of Thiazolidin-2-ones and 2-Amino-2-thiazolines", Journal of the Chemical Society, Perkin Transactions I, No. 3, 1979, pp. 765-770.

Fernández, et al., "Syntheses of β-iodourea derivatives of carbohydrates and glycosylamino-oxazolines", Carbohydrate Research, vol. 216, 1991, pp. 21-32.

Fernández, et al., "Syntheses and Spectral Properties of β-Iodoureas and 2-Amino-4,4-diphenyl-2-oxazolines", Journal of Heterocyclic Chemistry, vol. 28, 1991, pp. 777-780.

(56) References Cited

OTHER PUBLICATIONS

Liebscher, et al., "2-Arylimino-3-Thiazolines—Formation of Unusual Tautomers of 2-Arylamino-Thiazolines—a Revision", Tetrahedron Letters, vol. 26, No. 35, 1985, pp. 4179-4180.
Koriyama et al., "Reversal of diastereofacial selectivity in the nucleophilic addition reaction to chiral N-sulfinimine and application to the synthesis of indrizidine 223AB," Tetrahedron, vol. 58, 2002, pp. 9621-9628.
Fujisawa et al., "Switchover of diastereofacial selectivity in the condensation reaction of optically active N-sulfinimine with ester enolate," Tetrahedron Letters, vol. 37, No. 22, 1996, pp. 3881-3884.
Vilaivan et al., "Recent Advances in Catalytic Asymmetric Addition to Imines and Related C=N Systems," Current Organic Chemistry, vol. 9, 2005, pp. 1315-1392.
Hua et al., "N-Alkylidenesulfinamides," Sulfur Reports, vol. 21, 1999, pp. 211-239.
Savoca et al., "1,5-Diazabicyclo[4.3.0]non-5-ene," Encyclopedia of Reagents for Organic Synthesis, 2006, 10 pages total.
Creeke et al., "Synthesis and elaboration of heterocycles via iodocyclisation of unsaturated thioureas," Tetrahedron Letters, 1989, vol. 30, No. 33, pp. 4435-4438.
Mellor et al., A general route to spirocycles by radical additions to exocyclic unsaturated sulphides and related compounds, Tetrahedron Letters, 1991, vol. 32, No. 48, pp. 7111-7114.
Murai et al., "Iodo-cyclization of N-homoallyl thioamides leading to 2,4-diaryl-5,6-dihydro-4H-1,3-thiazines," Chemistry Letters, 2004, vol. 33, No. 5, pp. 508-509.
Singh et al., "Synthesis of heterocyclic compounds via enamines. Part 8. Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.
Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).
Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-yl)-1,3-dihydro-", XP002646872, Database accession No. 93599884-8.
Schubert et al., "Neue synthesen von 2-Amino-5,6-dihydro-4H-1,3-thiazinen," Archiv der Pharmazie, 1968, vol. 301, No. 10, pp. 750-762.
Huang et al., "Pharmacophore model construction of β-secretase inhibitors," 2008, Acta Chimica Sinica, vol. 66, No. 16, pp. 1889-1897 (English language abstract provided).
Clark, et al., "Antitumor Imidazotetrazines. 32. Synthesis of Novel Imidazotetrazinones and Related Bicyclic Heterocycles to Probe the Mode of Acion of the Antitumor Drug Temozolomide", J. Med. Chem., vol. 38, 1995, pp. 1493-1504.
Congreve, et al., "Application of Fragment Screening by X-ray Crystallography to the Discovery of Aminopyridines as Inhibitors of β-Secretase", J. Med. Chem., vol. 50, 2007, pp. 1124-1132.
Huang, et al., "Progress in the Development of Nonpeptidomimetic BACE 1 Inhibitors for Alzheimer's Disease", Current Medicinal Chemistry, vol. 16, 2009, pp. 1806-1820.
Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.
Siddiqui et al., "Some extensions of Von Bruan (BrCN) reaction on organic bases," Proc. Pakistan Acad. Sci., 1988, vol. 25, No. 3, pp. 231-240.
Ozawa et al., Pharmacological actions of 2-Aminoethylisothiuronium (AET) derivatives. I, Yakugaku Zasshi, 1968, vol. 88, No. 2, pp. 156-162 (English language abstract provided).
Curtis et al., The byozynsethis of Phenols. Part VIII. The synthesis of (2-carboxy-3,5-dihydroxyphynyl)propan-2-one (C-acetyl-o-orsellinic acid). Journal of the Chemical Society, 1964, pp. 5382-5385.

Burton et al., "Addition reactions of quinones. Part I. The reaction of cysteine and thiourea and its derivatives with some quinones," Journal of the Chemical Society, 1952, pp. 2193-2196.
Matsui, "Yomo bochuzai no kenkyu (the $6^{th}$ report) Kagaku kozo to yomo shokugai boshi koka tono kankei (III)," Journal of Synthetic Organic Chemistry, Japan, 1950, vol. 8, No. 10, pp. Ho61-Ho65 (and International Search Report issued in PCT/JP2010/055528, which corresponds to co-pending U.S. Appl. No. 13/260,103).
Desai et al., "The condensation of thiocarbamides with monochloroacetic acid and the conversion of arylformamidinethiolacetic acids into pseudothiohydantoin derivatives," Recuil des Travaux Chimiques des Pays-Bas et de la Belgique, 1935, pp. 118-121.
Cole et al., "Acylguanidines as small-molecule beta-secretase inhibitors," J. Med. Chem., 2006, pp. 6158-6161.
Bol'but et al., Heterocyclizations of Functionalized Heterocumulenes with C,N- and C,O-Dinucleophiles: III.* Cyclization of N-(1-Aryl-1-chloro-2,2,2-trifluoroethyl)-N'-arylcarbodiimides with 3-Substituted 1-Phenylpyrazol-5-ones, Russian Journal of Organic Chemistry, 2003, vol. 39, No. 12, pp. 1789-1791.
Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.
Sayed et al., "α-Enones in heterocyclic synthesis of indazole, thiazine, chromene and quinolone derivatives with their antimicrobial activities," Journal of Chemical Research, 2009, vol. 12, pp. 726-728.
Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 *abstract* Accessed Jul. 13, 2012.
Bol'but et al., "Synthesis of 4-imino-2-trifluoromethyl-3,4-dihydro-2h-Benzo-[1,3]Thiazines" Chemistry of Heterocyclic Compounds, 2001, vol. 37, No. 4, pp. 522-523.
Vovk et al., "Intramolecular thermal cyclization of N-(1-Aryl-1-aryloxy-2,2,2-trifluoroethyl)-N'-arylcarbodiimides" Russian Journal of Organic Chemistry, 2000, vol. 36, No. 12, pp. 1739-1742.
Vovk et al., "Regioselective cyclization of 1-chloroalkylcarbodiimides with 1,1- and 1,2-bifunctional nucleophilic reagents" Russian Journal of Organic Chemistry, 1997, vol. 33, No. 1, pp. 96-102.
Potts et al., "N-Acyl-β-enamino Ketones: Versatile Heterocyclic Synthons" J. Org. Chem., 1983, 48, pp. 623-625.
Rivkin et al., "Piperazinyl pyrimidine derivatives as potent γ-secretase modulators" Bioorganic & Medicinal Chemistry Letters, 2010, 20, pp. 1269-1271.
Rivkin et al., "Purine derivatives as potent γ-secretase modulators" Bioorganic & Medicinal Chemistry Letters, 2010, 20, pp. 2279-2282.
Vippagunta et al. "Crystalline Solids". Advanced Drug Delivery Reviews, vol. 48, 2001, pp. 3-26.
Gavezzotti. "Are Crystal Structures Predictable". Accounts of Chemical Research, vol. 27, 1994, pp. 309-314.
STN a the Web, RN 79005-45-1, 1964.
Zhu et al., Two novel Diastereoselective Three-Component Reactions of Alkenes or 3,4-Dihydro-(2H)-pyran with Urea/Thiourea-Aldehyde Mixtures: [4 + 2] Cycloaddition vs Biginelli-Type Reaction, Organic Letters, 2006, vol. 8, No. 12, pp. 2599-2602.
Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).
Kavya et al. "Nitric oxide synthase regulation and diversity: Implications in Parkinson's Disease". Nitric Oxide: Biology and Chemistry, vol. 15, No. 4, pp. 280-294 (2006).
Chiou et al. "Review: Effects of Nitric Oxide on Eye Diseases and Their Treatment", Journal of Ocular Pharmacology and Therapeutics, vol. 17, No. 2, pp. 189-198 (2001).
Ishii et al. "Subacute NO generation induced by Alzheimer's β-amyloid in the living brain: reversal by inhibition of the inducible

(56) References Cited

OTHER PUBLICATIONS

NO synthase". The Federation of American Societies for Experimental Biology Journal, vol. 14, pp. 1485-1489 (2000).
Pak et al, "Morphine via nitric oxide modulates β-amyloid metabolism: a novel protective mechanism for Alzheimer's disease". Medical Science Monitor, vol. 11, No. 10, pp. BR357-BR366 (2005).
Kiselyov et al., "Design and chemical synthesis of [1,2,4]triazol[1,5-c]pyrimidin-5-yl amines, a novel class of VEGFR-2 kinase inhibitors," 2009, Tetrahedron Letters, vol. 50, pp. 3809-3812.
Mulcahy et al., "A stereoselective synthesis of (+)-Gonyautoxin 3," Journal of the American Chemical Society, 2008, vol. 130, pp. 12630-12631.
"Diphenyl Cyanocarbonimidate," e-EROS Encyclopedia of Reagents for Organic Synthesis, 2001, 2 pages total.
Shafik et al., "Synthesis of novel 2-[2-(substituted amino)phenethyl]-1H-benzimidazoles; 3,4-dihydro and 1,2,3,4-tetrahydropyrimido[1,6-a]-benzimidazoles as potential antiulcer agents," 2004, Pharmazie, vol. 59, No. 12, pp. 899-905.
Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.
Buschauer et al., "Isohistamine und Homologe als Bausteine von $H_2$-Antagonisten,"Arzneimittel-Forschung, 1985, vol. 35, pp. 1025-1029 (English language abstract provided).
Buschauer et al., "7,8-Dihydroimidazo[1,2-c]pyrimidin-5(6H)-one, -5(6H)-thione and -5(6H)-ylidencyanamide," Chemische Berichte, 1984, vol. 117, pp. 2597-2614.
Borchers et al., "$H_2$-Antihystaminika, 19. Mitt. Syntheses und $H_2$-antihistaminische Wirkung $N^α$-substituierter Histamine," Archie der Pharmazie (Weinheim, Germany), 1984, vol. 317, pp. 455-459.
Cheong et al., "Pharmacophore elucidation for a new series of 2-aryl-pyrazolo-triazolo-pyrimidines as potent human $A_3$ adenosine receptor antagonists," Bioorganic & Medicinal Chemistry Letters, 2011, vol. 21, pp. 2898-2905.
Xu et al., "Copper-catalyzed cascade synthesis of benzimidazoquinazoline derivatives under mild condition," Chemical Communications, 2011, vol. 47, pp. 5596-5598.
Kishore et al., "QSAR of adenosine receptor antagonists: exploring physicochemical requirements for binding of pyrazolo[4,3-e]-1,2,4-triazolo[1,5-c]pyrimidine derivatives with human adenosine $A_3$ receptor subtype," Bioorganic & Medicinal Chemistry Letters, 2011, vol. 21, No. 2, pp. 818-823.
Dolzhenko et al., "8-methyl-2-[4-(trifluoromethyl)phenyl]-8H-pyrazolo[4,3-e][1,2,4]triazolo[1,5-c]-pyrimidin-5-amine methanol disolvate," Acta Crystallographica, Section E: Structure Reports Online, 2010, E66(7), 12 pages total.
Weinhardt et al. "Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No. 6, 1985, pp. 694-698.
Meschino et al., "2-Amino-5,6-dihydro-1,3-oxazines. The reduction of carboxylic esters with sodium borohydride," J. Org. Chem., vol. 28, 1963, pp. 3129-3134.
Poos et al., "2-amino-5-aryl-2-oxazolines. Potent new anorectic agent," J. Med. Chem., vol. 6, 1963, pp. 266-272.
Sandin et al., "A fast and parallel route to cyclic isothioureas and guanidines with use of microwave-assisted chemistry," J. Org. Chem., vol. 69, 2004, pp. 1571-1580.

Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.
Woodgate et al., "A new synthesis of 2-amino-2-thiazolines," Heterocycles, vol. 7, No. 1, 1977, pp. 109-112.
Dörwald, "Side reactions in organic synthesis: a guide to successful synthesis design" 2005 Wiley-VCH Verlag GmbH & Co., KGaA, Wienheim, chapter 1, 32 pages total.
Wermuth; Practice of Medicinal Chemistry, Third Ed., 2008, Elsevier, chapter 15.
Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.
Beaton et al., "The synthesis of 1-aminodihydroisoquinolines by an imine addition cyclisation reaction," 1998, Tetrahedron Letters, vol. 39, pp. 1227-1230.
Tian et al., "Radiosynthesis of 8-Fluoro-3-(4-[18F]Fluorophenyl)-3,4-Dihydro-1-Isoquinolinamine ([18F]FFD1), a potential PET radiotracer for the inducible nitric oxide synthase," 2008, Current Radiopharmaceuticals, vol. 1, pp. 49-53.
Emilio Testa et al.: "Auf das Zentralnervensystem wirkende Substanzen, XXXVI. Weitere Untersuchungen über die 2-substituierten Azetidine"; Justus Liebigs Annalen Der Chemie, vol. 673, No. 1., May 4, 1964, pp. 60-70 XP055091964.
Portnyagin et al.: Russian Journal of Organic Chemistry, Consultants Bureau, US, vol. 10, Jan. 1, 1974, pp. 95-98, XP009174887.
Database Caplus [Online]; Chemical Abstracts Service, Columbus, Oh, US; 2006, Bathich, Yaser: "Synthesis of Branched Amino Polyoly and Aminohydroxy Acids: Stereoselective Additiom of C-Nucleophiles ti Isoxazolines and Isoxazolinium Salts and Assignment of Configurations", XP002717806.
Database Registry [Online]; Chemical Abstracts Service, Columbus, Oh, US; 3-Pyridinepropanol, .beta., .gamma.-diamino-6-fluoro-.gamma.-(4-fluorophenyl)-, (.beta-R,.gamma.S)-, Apr. 29, 2004, XP002717807.
Bathich, "Synthesis of branched amino polyols and amino hydroxy acids: stereoselective addition of C-Nucleophiles to isoxazoline and isoxazolinium salts and assignment of configurations," 2006, pp. 148.
International Search Report for PCT/JP2013/079472, dated Feb. 18, 2014, 5 pages total.
Hilpert et al., "Beta-secretase (BACE1) inhibitors with high in vivo efficacy suitable for clinical evaluation in Alzheimer's disease," Journal of Medicinal Chemistry, 2013, 56, pp. 3980-3995.
Delgado et al., "A practical entry to beta-aryl-beta-alkyl amino alcohols: application to the synthesis of a potent BACE1 inhibitor," Organic & Biomolecular Chemistry 2012, 10, pp. 6758-6766.
Woltering et al., "BACE1 inhibitors: a head group scan on a series of amides," Bioorganic & Medicinal Chemistry Letters, 2013, vol. 23, issue14, pp. 4239-4243.
International Preliminary Report on Patentability and Written Opinion of the International Searching Authority for PCT/JP2013/079472, dated May 7, 2015, 8 pages total.
Medicinal Chemistry, Nozaki et al., Kagaku-Dojin, Jul. 1, 1995, p. 98-99 and English translation thereof, 4 pages total.
Hilpert et al.: "β-Secretase (BACE1) Inhibitors with High in Vivo Efficacy Suitable for Clinical Evaluation in Alzheimer's Disease"; Journal of Medicinal Chemistry, 2013, vol. 56, issue 10, pp. 3980-3995.
Schaumann et al., "Cycloadditionsreaktionen von Heterokumulenen, XVII)—Umsetzung von 3-dimethylamino-2-pheny1-2H-azirinen mit isocyanaten and isothiocyanaten," Liebigs Ann. Chem., 1978, pp. 1568-1585 (with English language abstract).

DIHYDROOXAZINE OR OXAZEPINE DERIVATIVES HAVING BACE1 INHIBITORY ACTIVITY

TECHNICAL FIELD

The present invention relates to a compound which has amyloid β production inhibitory activity, and is useful as an agent for treating or preventing disease induced by production, secretion and/or deposition of amyloid β proteins.

BACKGROUND ART

In the brain of Alzheimer's patient, the peptide composed of about 40 amino acids residue as is called amyloid β protein, that accumulates to form insoluble specks (senile specks) outside nerve cells is widely observed. It is concerned that these senile specks kill nerve cells to cause Alzheimer's disease, so the therapeutic agents for Alzheimer's disease, such as decomposition agents of amyloid β protein and amyloid vaccine, are under investigation.

Secretase is an enzyme which cleaves a protein called amyloid β precursor protein (APP) in cell and produces amyloid β protein. The enzyme which controls the production of N terminus of amyloid β protein is called as β-secretase (beta-site APP-cleaving enzyme 1, BACE1). It is thought that inhibition of this enzyme leads to reduction of producing amyloid β protein and that the therapeutic or prophylactic agent for Alzheimer's disease will be created due to the inhibition.

Patent Documents 1 to 44 and Non-Patent Documents 1 to 3 disclose compounds having a structure similar to those of the compounds of the present invention. Each of these documents discloses each compound is useful as therapeutic agent for Alzheimer's disease, Alzheimer's relating symptoms, or diabetes, but each of substantially disclosed compounds has a structure different from the compounds of the present invention.

PRIOR ART

Patent Document

[Patent Document 1] WO2007/049532
[Patent Document 2] WO2008/133273
[Patent Document 3] WO2008/133274
[Patent Document 4] WO2009/151098
[Patent Document 5] WO2010/047372
[Patent Document 6] WO2010/113848
[Patent Document 7] WO2011/071057
[Patent Document 8] WO2011/058763
[Patent Document 9] WO2011/070781
[Patent Document 10] WO2011/077726
[Patent Document 11] WO2011/071135
[Patent Document 12] WO2011/071109
[Patent Document 13] WO2012/057247
[Patent Document 14] WO2012/057248
[Patent Document 15] WO2012/147762
[Patent Document 16] WO2012/147763
[Patent Document 17] JP2012/250933A
[Patent Document 18] WO2011/009943
[Patent Document 18] WO2011/020806
[Patent Document 20] WO2011/070029
[Patent Document 21] WO2011/069934
[Patent Document 22] WO2011/138293
[Patent Document 23] WO2007/058583
[Patent Document 24] WO2011/154431
[Patent Document 25] WO2012/110459
[Patent Document 26] WO2012/107371
[Patent Document 27] WO2012/095521
[Patent Document 28] WO2012/006953
[Patent Document 29] WO2011/009898
[Patent Document 30] US2012/0258962
[Patent Document 31] WO2012/168164
[Patent Document 32] WO2012/168175
[Patent Document 33] WO2013/041499
[Patent Document 34] WO2013/027188
[Patent Document 35] WO2012/095463
[Patent Document 36] WO2012/095469
[Patent Document 37] WO2012/095451
[Patent Document 38] WO2011/057973
[Patent Document 39] WO2011/020806
[Patent Document 40] WO2009/103626
[Patent Document 41] WO2011/154431
[Patent Literature 42] WO2013/083557
[Patent Literature 43] WO2013/110622
[Patent Literature 44] WO2013/142613

Non-Patent Document

[Non-Patent Document 1] Journal of Medicinal Chemistry, 2013, 56(10), pp 3980-3995
[Non-Patent Document 2] Organic & Biomolecular Chemistry 2012, 10, 6758-6766
[Non-Patent Document 3] Bioorganic & Medicinal Chemistry Letters, 2013, 23(14), 4239-4243

SUMMARY OF THE INVENTION

Problems to be Solved by the Invention

The present invention provides compounds which have reducing effects to produce amyloid β protein, especially BACE1 inhibitory activity, and are useful as an agent for treating disease induced by production, secretion and/or deposition of amyloid β protein.

Means for Solving the Problem

The present invention, for example, provides the inventions described in the following items.
(1) A compound of formula (I):

[Chemical Formula 1]

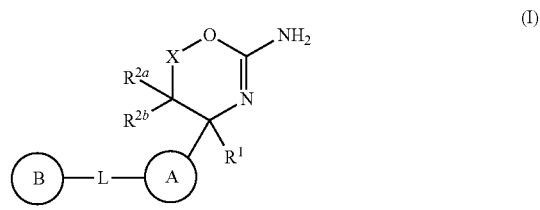

wherein
X is —C($R^{3a}$)($R^{3b}$)—, —C($R^{3a}$)($R^{3b}$)—C($R^{3c}$)($R^{3d}$)— or —C($R^{3a}$)=C($R^{3c}$)—, (i) when X is —C($R^{3a}$)($R^{3b}$)—, then L is —C(=O)NH—,
(ii) when X is —C($R^{3a}$)($R^{3b}$)—C($R^{3c}$)($R^{3d}$)— or —C($R^{3a}$)=C($R^{3c}$)—, then L is —C(=O)NH—, -$L^1$-NH-$L^2$- or a bond, $L^1$ and $L^2$ are each independently a bond, substituted or unsubstituted alkylene, substituted or unsubstituted alkenylene or substituted or unsubstituted alkynylene, ring A is a substituted or unsubstituted aromatic carbocycle, a substituted or unsubstituted non-aromatic carbocycle, a substituted or unsubstituted aromatic heterocycle or a substituted or unsubstituted non-aromatic heterocycle, ring B is a substituted or unsubstituted aromatic carbocycle, a substituted or unsubstituted non-aromatic carbocycle, a substituted or unsubstituted aromatic heterocycle or a substituted or unsubstituted non-aromatic heterocycle, $R^1$ is substituted or unsubstituted alkyl, substituted or unsubstituted alkenyl, substituted or unsubstituted alkynyl or substituted or unsubstituted cycloalkyl, $R^{2a}$ and $R^{2b}$ are each independently hydrogen, halogen, hydroxy, substituted or unsubstituted alkyl, substituted or unsubstituted alkenyl, substituted or unsubstituted alkyloxy, cyano or substituted or unsubstituted cycloalkyl, preferably hydrogen, halogen, substituted or unsubstituted alkyl, or substituted or unsubstituted alkyloxy, $R^{3a}$, $R^{3b}$, $R^{3c}$ and $R^{3d}$ are each independently hydrogen, halogen, hydroxy, substituted or unsubstituted alkyl, substituted or unsubstituted alkenyl, cyano or substituted or unsubstituted cycloalkyl, preferably hydrogen, halogen, or substituted or unsubstituted alkyl, $R^{2a}$ and $R^{3a}$ attached to adjacent carbon atoms, together with the carbon atoms to which they are attached, may form

[Chemical Formula 2]

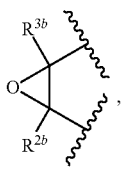
(i)

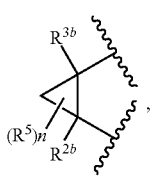
(ii)

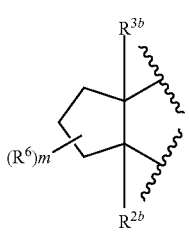
(iii)

or

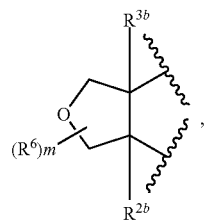
(iv)

$R^{3a}$ and $R^{3b}$ together with the carbon atom to which they are attached may form

[Chemical Formula 3]

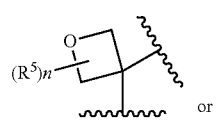
(v)

or

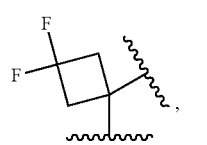
(vi)

$R^1$ and $R^{2a}$ together with the carbon atoms to which they are attached may form

[Chemical Formula 4]

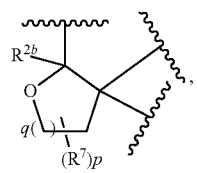
(vii)

and when $R^1$ and $R^{2a}$ together with the carbon atoms to which they are attached form the above (vii), then $R^{3a}$ and $R^{3b}$ together with the carbon atom to which they are attached may form

[Chemical Formula 5]

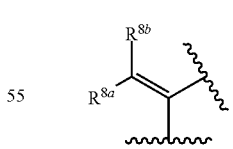
(viii)

$R^5$ is halogen or substituted or unsubstituted alkyl,
$R^6$ is substituted or unsubstituted alkyl,
$R^7$ is halogen or substituted or unsubstituted alkyl,
$R^{8a}$ and $R^{8b}$ are each independently hydrogen or substituted or unsubstituted alkyl,
n is an integer of 0 to 2,
m is an integer of 1 or 2,
p is an integer of 0 to 2, and
q is an integer of 1 or 2, provided that the following compounds are excluded:

[1] a compound wherein X is —CH$_2$—, and at least one of R$^{2a}$ and R$^{2b}$ is halogen, alkyl, or substituted or unsubstituted alkyloxy,

[2] a compound wherein X is —C(R$^{3a}$)(R$^{3b}$)—, R$^1$ is alkyl, and both of R$^{2a}$ and R$^{2b}$ are fluorine,

[3] a compound wherein X is —CH$_2$—, R$^1$ is alkyl, and both of R$^{2a}$ and R$^{2b}$ are hydrogen,

[4] a compound wherein X is —C(R$^{3a}$)(R$^{3b}$)—, R$^1$ is substituted or unsubstituted alkyl, and R$^{2a}$ and R$^{3a}$ attached to adjacent carbon atoms, together with the carbon atoms to which they are attached, may form the above group (iv), and

[5] the following compounds:

[Chemical Formula 6]

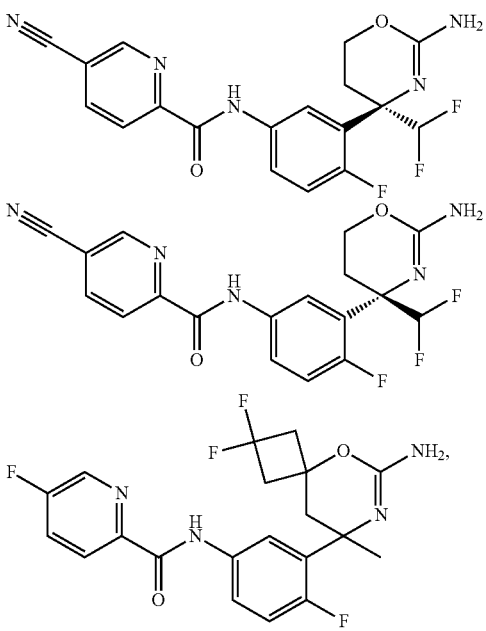

or a pharmaceutically acceptable salt thereof.

(1-1) A compound of formula (I):

[Chemical Formula 7]

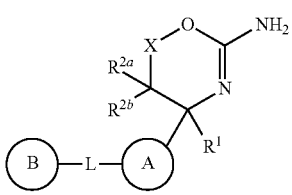 (I)

wherein X is —C(R$^{3a}$)(R$^{3b}$)—, —C(R$^{3a}$)(R$^{3b}$)—C(R$^{3c}$)(R$^{3d}$)— or —C(R$^{3a}$)=C(R$^{3c}$)—, (i) when X is —C(R$^{3a}$)(R$^{3b}$)—, then L is —C(=O)NH—, and ring A is a substituted or unsubstituted aromatic carbocycle, (ii) when X is —C(R$^{3a}$)(R$^{3b}$)—C(R$^{3c}$)(R$^{3d}$)— or —C(R$^{3a}$)=C(R$^{3c}$)—, then L is —C(=O)NH—, -L$^1$-NH-L$^2$- or a bond, L$^1$ and L$^2$ are each independently a bond, substituted or unsubstituted alkylene, substituted or unsubstituted alkenylene or substituted or unsubstituted alkynylene, ring A is a substituted or unsubstituted aromatic carbocycle, a substituted or unsubstituted non-aromatic carbocycle, a substituted or unsubstituted aromatic heterocycle or a substituted or unsubstituted non-aromatic heterocycle, ring B is a substituted or unsubstituted aromatic carbocycle, a substituted or unsubstituted non-aromatic carbocycle, a substituted or unsubstituted aromatic heterocycle or a substituted or unsubstituted non-aromatic heterocycle, R$^1$ is substituted or unsubstituted alkyl, substituted or unsubstituted alkenyl, substituted or unsubstituted alkynyl or substituted or unsubstituted cycloalkyl, R$^{2a}$, R$^{2b}$, R$^{3a}$, R$^{3b}$, R$^{3c}$ and R$^{3d}$ are each independently hydrogen, halogen, hydroxy, substituted or unsubstituted alkyl, substituted or unsubstituted alkenyl, cyano or substituted or unsubstituted cycloalkyl, R$^{2a}$ and R$^{3a}$ attached to adjacent carbon atoms, together with the carbon atoms to which they are attached, may form

[Chemical Formula 8]

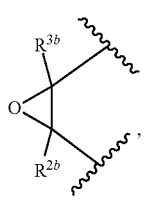 (i)

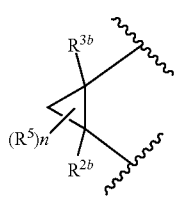 (ii)

or

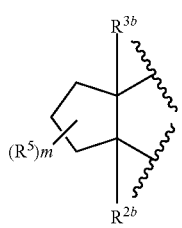 (iii)

wherein R$^5$ is halogen or substituted or unsubstituted alkyl, n is an integer of 0 to 2, m is an integer of 1 or 2, provided that the following compounds are excluded:
(a) a compound wherein R$^1$ is alkyl, X is —C(R$^{3a}$)(R$^{3b}$)—, and both of R$^{2a}$ and R$^{2b}$ are fluorine,
(b) a compound wherein R$^1$ is alkyl, X is —C(R$^{3a}$)(R$^{3b}$)—, and all of R$^{2a}$, R$^{2b}$, R$^{3a}$ and R$^{3b}$ are hydrogen, and
(c) the following compounds:

[Chemical Formula 9]

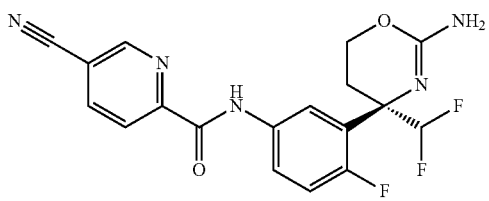

-continued

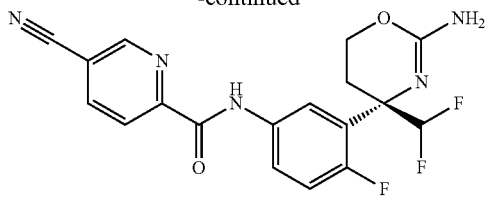

or a pharmaceutically acceptable salt.
(1-2) A compound of formula (I):

[Chemical Formula 10]

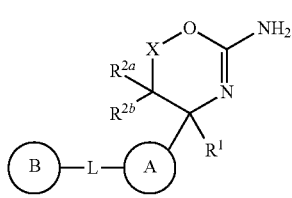

(I)

wherein X is —C($R^{3a}$)($R^{3b}$)—, —C($R^{3a}$)($R^{3b}$)—C($R^{3c}$)($R^{3d}$)— or —C($R^{3a}$)=C($R^{3c}$)—,
(i) when X is —C($R^{3a}$)($R^{3b}$)—, then L is —C(=O)NH—, and ring A is a substituted or unsubstituted aromatic carbocycle,
(ii) when X is —C($R^{3a}$)($R^{3b}$)—C($R^{3c}$)($R^{3d}$)— or —C($R^{3a}$)=C($R^{3c}$)—, then L is —C(=O)NH—, -$L^1$-NH-$L^2$- or a bond,
$L^1$ and $L^2$ are each independently a bond, substituted or unsubstituted alkylene, substituted or unsubstituted alkenylene or substituted or unsubstituted alkynylene,
ring A is a substituted or unsubstituted aromatic carbocycle, a substituted or unsubstituted non-aromatic carbocycle, a substituted or unsubstituted aromatic heterocycle or a substituted or unsubstituted non-aromatic heterocycle,
ring B is a substituted or unsubstituted aromatic carbocycle, a substituted or unsubstituted non-aromatic carbocycle, a substituted or unsubstituted aromatic heterocycle or a substituted or unsubstituted non-aromatic heterocycle,
$R^1$ is substituted or unsubstituted alkyl, substituted or unsubstituted alkenyl, substituted or unsubstituted alkynyl or substituted or unsubstituted cycloalkyl,
$R^{2a}$ and $R^{2b}$ are each independently hydrogen, halogen, hydroxy, substituted or unsubstituted alkyl, substituted or unsubstituted alkenyl, substituted or unsubstituted alkyloxy, cyano or substituted or unsubstituted cycloalkyl,
$R^{3a}$, $R^{3b}$, $R^{3c}$ and $R^{3d}$ are each independently hydrogen, halogen, hydroxy, substituted or unsubstituted alkyl, substituted or unsubstituted alkenyl, cyano or substituted or unsubstituted cycloalkyl,
$R^{2a}$ and $R^{3a}$ attached to adjacent carbon atoms, together with the carbon atoms to which they are attached, may form

[Chemical Formula 11]

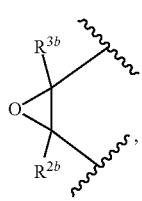

(i)

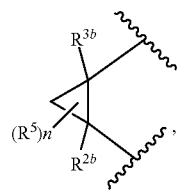

(ii)

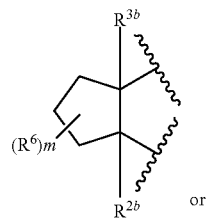

(iii)

or

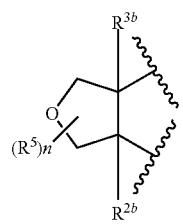

(iv)

and $R^{3a}$ and $R^{3b}$ together with the carbon atom to which they are attached may form

[Chemical Formula 12]

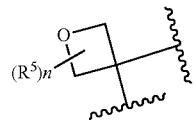

wherein $R^5$ is halogen or substituted or unsubstituted alkyl,
$R^6$ is substituted or unsubstituted alkyl,
$R^{8a}$ and $R^{8b}$ are each independently hydrogen or substituted or unsubstituted alkyl,
n is an integer of 0 to 2, and
m is an integer of 1 or 2,
provided that the following compounds are excluded:
[1] a compound wherein X is —$CH_2$—, and at least one of $R^{2a}$ and $R^{2b}$ is halogen, alkyl, or substituted or unsubstituted alkyloxy,
[2] a compound wherein X is —C($R^{3a}$)($R^{3b}$)—, $R^1$ is alkyl, and both of $R^{2a}$ and $R^{2b}$ are fluorine,
[3] a compound wherein X is —$CH_2$—, $R^1$ is alkyl, and both of $R^{2a}$ and $R^{2b}$ are hydrogen,
[4] a compound wherein X is —C($R^{3a}$)($R^{3b}$)—, $R^1$ is substituted or unsubstituted alkyl, and $R^{2a}$ and $R^{3a}$ attached to adjacent carbon atoms, together with the carbon atoms to which they are attached, may form the above group (iv), and

[5] the following compounds:

[Chemical Formula 13]

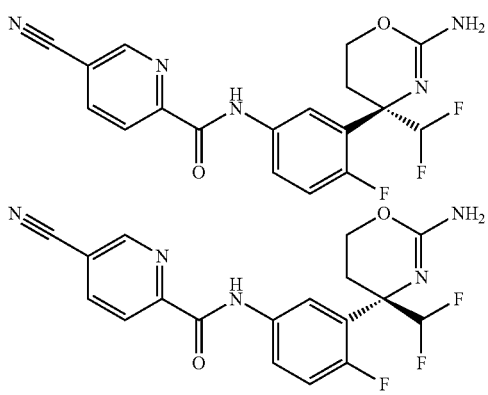

or a pharmaceutically acceptable salt thereof.

(1-3) The compound according to item (1) wherein each symbol is the same as defined in item (1),
provided that the following compounds are excluded:
[1] a compound wherein X is —$CH_2$—, and at least one of $R^{2a}$ and $R^{2b}$ is halogen, alkyl, or substituted or unsubstituted alkyloxy,
[2] a compound wherein X is —$C(R^{3a})(R^{3b})$—, $R^1$ is alkyl, and both of $R^{2a}$ and $R^{2b}$ are fluorine,
[3] a compound wherein X is —$CH_2$—, $R^1$ is alkyl, and both of $R^{2a}$ and $R^{2b}$ are hydrogen,
[4] a compound wherein X is —$C(R^{3a})(R^{3b})$—, $R^1$ is substituted or unsubstituted alkyl, and $R^{2a}$ and $R^{3a}$ attached to adjacent carbon atoms, together with the carbon atoms to which they are attached, may form the above group (iv), and
[5] the following compounds:

[Chemical Formula 14]

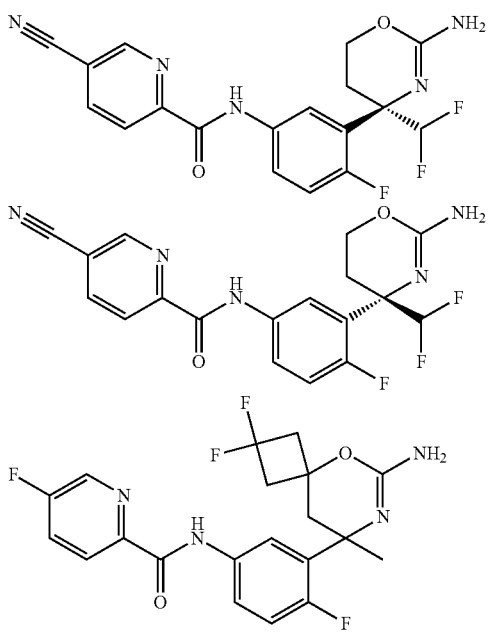

[6] a compound wherein X is —$C(CF_3)(H)$— and both of $R^{2a}$ and $R^{2b}$ are hydrogen, or a pharmaceutically acceptable salt thereof.

(1-4) The compound according to item (1-2) wherein each symbol is the same as defined in item (1-2),
provided that the following compounds are excluded:
[1] a compound wherein X is —$CH_2$—, and at least one of $R^{2a}$ and $R^{2b}$ is halogen, alkyl, or substituted or unsubstituted alkyloxy,
[2] a compound wherein X is —$C(R^{3a})(R^{3b})$—, $R^1$ is alkyl, and both of $R^{2a}$ and $R^{2b}$ are fluorine,
[3] a compound wherein X is —$CH_2$—, $R^1$ is alkyl, and both of $R^{2a}$ and $R^{2b}$ are hydrogen,
[4] a compound wherein X is —$C(R^{3a})(R^{3b})$—, $R^1$ is substituted or unsubstituted alkyl, and $R^{2a}$ and $R^{3a}$ attached to adjacent carbon atoms, together with the carbon atoms to which they are attached, may form the above group (iv), and
[5] the following compounds:

[Chemical Formula 15]

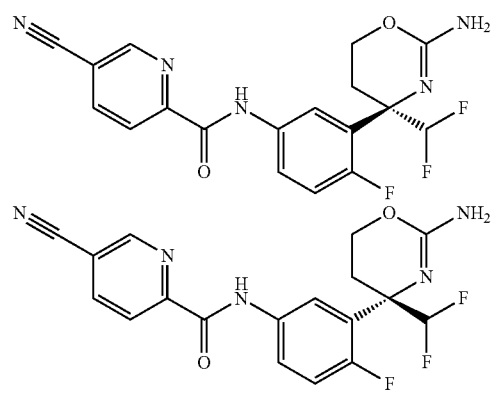

[6] a compound wherein X is —$C(CF_3)(H)$— and both of $R^{2a}$ and $R^{2b}$ are hydrogen, or a pharmaceutically acceptable salt thereof.

(1-5) The compound according to item (1) wherein each symbol is the same as defined in item (1),
provided that the following compounds are excluded:
[1] a compound wherein X is —$CH_2$—, and at least one of $R^{2a}$ and $R^{2b}$ is halogen, alkyl, or substituted or unsubstituted alkyloxy,
[2] a compound wherein X is —$C(R^{3a})(R^{3b})$—, $R^1$ is alkyl, and both of $R^{2a}$ and $R^{2b}$ are fluorine,
[3] a compound wherein X is —$CH_2$—, $R^1$ is alkyl, and both of $R^{2a}$ and $R^{2b}$ are hydrogen,
[4] a compound wherein X is —$C(R^{3a})(R^{3b})$—, $R^1$ is substituted or unsubstituted alkyl, and $R^{2a}$ and $R^{3a}$ attached to adjacent carbon atoms, together with the carbon atoms to which they are attached, may form the above group (iv), and
[5] the following compounds:

[Chemical Formula 16]

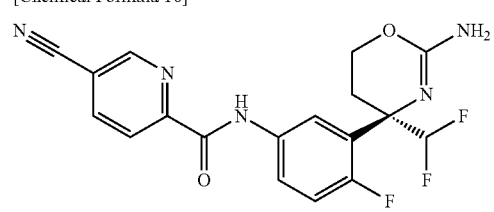

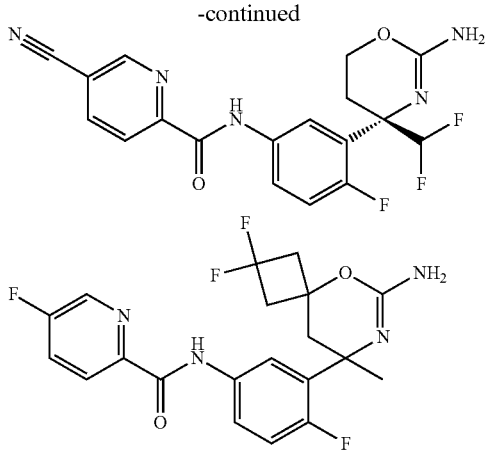

and

[6'] a compound wherein X is —C(CF$_3$)(H)—,
or a pharmaceutically acceptable salt thereof.
(1-6) The compound according to item (1-2) wherein each symbol is the same as defined in item (1-2),
provided that the following compounds are excluded:
[1] a compound wherein X is —CH$_2$—, and at least one of R$^{2a}$ and R$^{2b}$ is halogen, alkyl, or substituted or unsubstituted alkyloxy,
[2] a compound wherein X is —C(R$^{3a}$)(R$^{3b}$)—, R$^1$ is alkyl, and both of R$^{2a}$ and R$^{2b}$ are fluorine,
[3] a compound wherein X is —CH$_2$—, R$^1$ is alkyl, and both of R$^{2a}$ and R$^{2b}$ are hydrogen,
[4] a compound wherein X is —C(R$^{3a}$)(R$^{3b}$)—, R$^1$ is substituted or unsubstituted alkyl, and R$^{2a}$ and R$^{3a}$ attached to adjacent carbon atoms, together with the carbon atoms to which they are attached, may form the above group (iv), and
[5] the following compounds:

[Chemical Formula 17]

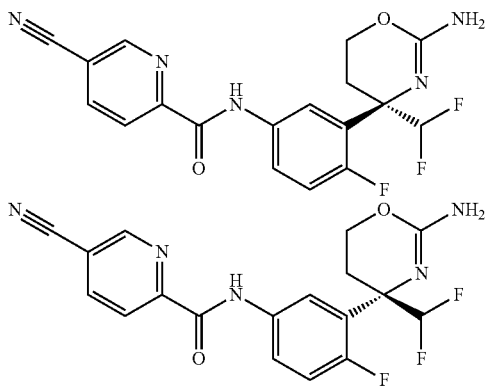

and
[6'] a compound wherein X is —C(CF$_3$)(H)—,
or a pharmaceutically acceptable salt thereof.
(2) The compound according to any one of items (1), (1-1) to (1-6) wherein R$^1$ is alkyl, haloalkyl, alkenyl, haloalkenyl, alkynyl, haloalkynyl or cycloalkyl, or a pharmaceutically acceptable salt thereof.
(3) The compound according to any one of items (1), (1-1) to (1-6) wherein R$^1$ is alkynyl or a pharmaceutically acceptable salt thereof.

(4) The compound according to any one of items (1), (1-1) to (1-6), (2) and (3) wherein X is —C(R$^{3a}$)(R$^{3b}$)—C(R$^{3c}$)(R$^{3d}$)— or a pharmaceutically acceptable salt thereof.

(5) The compound according to any one of items (1), (1-1) to (1-6), (2) and (3) wherein X is —C(R$^{3a}$)(R$^{3b}$)— and both of R$^{3a}$ and R$^{3b}$ are alkyl, or a pharmaceutically acceptable salt thereof.

(6) The compound according to any one of items (1), (1-1) to (1-6), (2) and (3) wherein X is —C(R$^{3a}$)(R$^{3b}$)—, and R$^{2a}$ and R$^{3a}$ which bind to adjacent carbon atoms together with the carbon atoms to which they are attached form

[Chemical Formula 18]

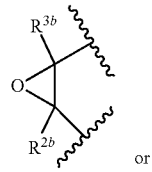

(i)

or

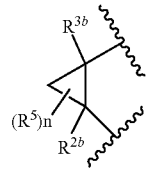

(ii)

or a pharmaceutically acceptable salt thereof.

(7) The compound according to any one of items (1), (1-1) to (1-6) wherein R$^1$ is haloalkyl, and at least one of R$^{2a}$, R$^{2b}$, R$^{3a}$, R$^{3b}$, R$^{3c}$ and R$^{3d}$ is halogen, hydroxy, substituted or unsubstituted alkyl, substituted or unsubstituted alkenyl, cyano or substituted or unsubstituted cycloalkyl, preferably at least one of R$^{2a}$, R$^{2b}$, R$^{3a}$, R$^{3b}$, R$^{3c}$ and R$^{3d}$ is halogen or substituted or unsubstituted alkyl, or a pharmaceutically acceptable salt thereof.

(8) The compound according to item (1), (1-1) to (1-6) or (2) wherein R$^1$ is haloalkyl, X is —CH(R$^{3b}$)—, and R$^{3b}$ is halogen, hydroxy, substituted or unsubstituted alkyl, substituted or unsubstituted alkenyl, cyano or substituted or unsubstituted cycloalkyl, preferably R$^{3b}$ is halogen or substituted or unsubstituted alkyl or a pharmaceutically acceptable salt thereof.

(9) The compound according to item (1), (1-1) to (1-6) or (2) wherein X is —CH(R$^{3b}$)—, and R$^{3b}$ is halogen, hydroxy, substituted or unsubstituted alkyl, substituted or unsubstituted alkenyl, cyano or substituted or unsubstituted cycloalkyl, preferably
R$^{3b}$ is halogen or substituted or unsubstituted alkyl, R$^{2a}$ and R$^{2b}$ are hydrogen, or a pharmaceutically acceptable salt thereof.

(10) The compound according to item (1), (1-1) to (1-6) or (2) wherein X is —CH(CH$_2$F)— or, CH(CHF$_2$)—, or a pharmaceutically acceptable salt thereof.

(11) The compound according to item (10) wherein one of R$^{2a}$ and R$^{2b}$ is halogen or alkyloxy and the other is hydrogen, or a pharmaceutically acceptable a pharmaceutically acceptable salt thereof.

(12) The compound according to item (1), (1-1) to (1-6) or (2) wherein R$^1$ is haloalkyl, X is —CH$_2$—, both of R$^{2a}$ and R$^{2b}$ are hydrogen and ring B is

[Chemical Formula 19]

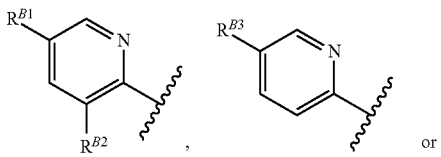

,

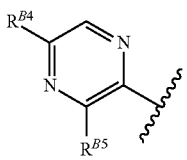

wherein $R^{B1}$ is halogen or cyano,
$R^{B2}$ is substituted or unsubstituted alkyl, halogen, hydroxy, substituted or unsubstituted amino or substituted or unsubstituted cycloalkyl,
$R^{B3}$ is halogen,
$R^{B4}$ is substituted or unsubstituted alkyl, or substituted or unsubstituted alkyloxy, and
$R^{B5}$ is hydrogen or substituted or unsubstituted amino, or a pharmaceutically acceptable salt thereof.
(13) The compound according to item (12) wherein $R^{B2}$ is substituted or unsubstituted alkyl, and $R^{B4}$ is substituted or unsubstituted alkyloxy, or a pharmaceutically acceptable salt thereof.
(14) The compound according to any one of items (1), (1-1) to (1-6) and (2) to (11) wherein ring B is

[Chemical Formula 20]

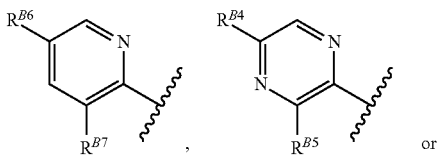

,

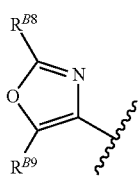

wherein $R^{B6}$ is halogen or cyano,
$R^{B7}$ is hydrogen, substituted or unsubstituted alkyl, halogen, hydroxy, substituted or unsubstituted amino or substituted or unsubstituted cycloalkyl,
$R^{B4}$ is substituted or unsubstituted alkyl or substituted or unsubstituted alkyloxy, and
$R^{B5}$ is hydrogen or substituted or unsubstituted amino, and
$R^{B8}$ and $R^{B9}$ are each independently hydrogen or substituted or unsubstituted alkyl,
or a pharmaceutically acceptable salt thereof.
(15) The compound according to any one of items (1), (1-1) to (1-6) and (2) to (11) wherein ring B is

[Chemical Formula 21]

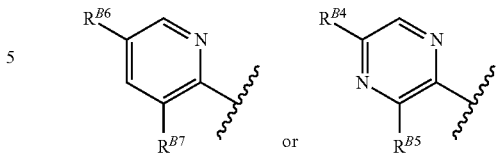

wherein $R^{B6}$ is halogen or cyano,
$R^{B7}$ is alkyl, haloalkyl, halogen, hydroxy, amino or cycloalkyl,
$R^{B4}$ is alkyl, haloalkyl, alkyloxy, or haloalkyloxy, and
$R^{B5}$ is hydrogen or amino,
or a pharmaceutically acceptable salt thereof.
(16) The compound according to item (1), (1-1) to (1-6), (2), (3), (7), (14) or (15) wherein X is —C($R^{3a}$)($R^{3b}$)—C($R^{3c}$)($R^{3d}$)— or —C($R^{3a}$)=C($R^{3c}$)—, L is —C(=O)NH—, —NH— or a bond, and ring A is a substituted or unsubstituted aromatic carbocycle or a substituted or unsubstituted aromatic heterocycle, or a pharmaceutically acceptable salt thereof.
(17) The compound according to item (1), (1-1) to (1-6), (2), (3), (14), (15) or (16) wherein X is —C($R^{3a}$)($R^{3b}$)—C($R^{3c}$)($R^{3d}$)— or —C($R^{3a}$)=C($R^{3c}$)—, L is —C(=O)NH—, and ring A is substituted or unsubstituted benzene or substituted or unsubstituted pyridine, or a pharmaceutically acceptable salt thereof.
(18) The compound according to any one of items (1), (1-1) to (1-6) and (2) to (17) wherein ring A is

[Chemical Formula 22]

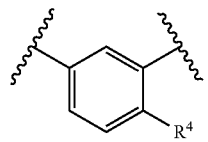

wherein $R^4$ is hydrogen or halogen,
or a pharmaceutically acceptable salt thereof.
(19) A pharmaceutical composition comprising the compound according to any one of items (1), (1-1) to (1-6) and (2) to (18), a pharmaceutically acceptable salt thereof.
(20) A pharmaceutical composition having BACE1 inhibitory activity comprising the compound according to any one of items (1), (1-1) to (1-6) and (2) to (18), or a pharmaceutically acceptable salt thereof.
(21) A method for inhibiting BACE1 activity comprising administering the compound according to any one of items (1), (1-1) to (1-6) and (2) to (18), or a pharmaceutically acceptable salt thereof.
(22) The compound according to any one of items (1), (1-1) to (1-6) and (2) to (18), or a pharmaceutically acceptable salt thereof for use in a method for inhibiting BACE1 activity.
(23) Use of a compound according to any one of items (1), (1-1) to (1-6) and (2) to (18), or a pharmaceutically acceptable salt thereof for manufacturing a medicament for inhibiting BACE1 activity.
(24) A method for treating or preventing diseases induced by production, secretion or deposition of amyloid β proteins comprising administering the compound according to any one of items (1), (1-1) to (1-6) and (2) to (18) or a pharmaceutically acceptable salt thereof.
(25) Use of a compound according to any one of items (1), (1-1) to (1-6) and (2) to (18), or a pharmaceutically acceptable salt thereof for manufacturing a medicament for treating or preventing diseases induced by production, secretion or deposition of amyloid β proteins.
(26) A compound according to any one of items (1), (1-1) to (1-6) and (2) to (18), or a pharmaceutically acceptable salt thereof for use in treating or preventing diseases induced by production, secretion or deposition of amyloid β proteins.
(27) A method for treating or preventing dementia of the Alzheimer's type comprising administering the compound according to any one of items (1), (1-1) to (1-6) and (2) to (18), or a pharmaceutically acceptable salt thereof.
(27') A method for treating or preventing Alzheimer's disease comprising administering the compound according to any one of items (1), (1-1) to (1-6) and (2) to (18), or a pharmaceutically acceptable salt thereof.
(28) Use of a compound according to any one of items (1), (1-1) to (1-6) and (2) to (18), or a pharmaceutically acceptable salt thereof for manufacturing a medicament for treating or preventing dementia of the Alzheimer's type.
(28') Use of a compound according to any one of items (1), (1-1) to (1-6) and (2) to (18), or a pharmaceutically acceptable salt thereof for manufacturing a medicament for treating or preventing Alzheimer's disease.
(29) A compound according to any one of items (1), (1-1) to (1-6) and (2) to (18), or a pharmaceutically acceptable salt thereof for use in treating or preventing dementia of the Alzheimer's type.
(29') A compound according to any one of items (1), (1-1) to (1-6) and (2) to (18), or a pharmaceutically acceptable salt thereof for use in treating or preventing Alzheimer's disease.
(30) The pharmaceutical composition according to item (19) or (20) for treating or preventing a disease induced by production, secretion or deposition of amyloid β proteins.
(31) A pharmaceutical composition according to item (19) or (20) for treating or preventing dementia of the Alzheimer's type.
(31') A pharmaceutical composition according to item (19) or (20) for treating or preventing Alzheimer's disease.

Effect of the Invention

The compound of the present invention has BACE1 inhibitory activity and is useful as an agent for treating or preventing disease induced by production, secretion or deposition of amyloid β proteins such as dementia of the Alzheimer's type.

MODE FOR CARRYING OUT THE INVENTION

Each meaning of terms used herein is described below. Both when used alone and in combination unless otherwise noted, each term is used in the same meaning.

In the specification, the "halogen" includes fluorine, chlorine, bromine, and iodine. Fluorine and chlorine are preferable.

In the specification, the "alkyl" includes linear or branched alkyl of a carbon number of 1 to 15, for example, a carbon number of 1 to 10, for example, a carbon number of 1 to 6, and for example, a carbon number of 1 to 4. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl. Examples are methyl, ethyl, n-propyl, isopropyl, n-butyl, isobutyl, sec-butyl, tert-butyl and n-pentyl.

In one embodiment, "alkyl" is methyl, ethyl, n-propyl, isopropyl or tert-butyl.

The term "alkenyl" includes linear or branched alkenyl of a carbon number or 2 to 15, for example, a carbon number of 2 to 10, for example, a carbon number of 2 to 6, and for example, a carbon number of 2 to 4, having one or more double bonds at any available positions. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl. Examples are vinyl, allyl, propenyl, isopropenyl and butenyl.

The term "alkynyl" includes a linear or branched alkynyl of a carbon number of 2 to 15, for example, a carbon number of 2 to 10, for example, a carbon number of 2 to 8, for example, a carbon number of 2 to 6, and for example, a carbon number of 2 to 4 having one or more triple bonds at optionally positions. Specific examples are ethynyl, propynyl, butynyl, pentynyl, hexynyl, heptynyl, octynyl, nonynyl and decynyl. These may have further a double bond at any available position. Examples are ethynyl, propynyl, butynyl and pentynyl.

The term "alkylene" include a linear or branched divalent carbon chain of a carbon number of 1 to 15, for example, a carbon number of 1 to 10, for example, a carbon number of 1 to 6, and for example a carbon number of 1 to 4. Examples are methylene, dimethylene, trimethylene, tetramethylene, pentamethylene and hexamethylene.

Alkylene portion in "alkylenedioxy" is the same as the above "alkylene". Examples are methylenedioxy and dimethylenedioxy.

The term "alkenylene" includes a linear or branched divalent carbon chain of a carbon number of 2 to 15, for example, a carbon number of 2 to 10, for example, a carbon number of 2 to 6, and for example, a carbon number of 2 to 4, having one or more double bonds at any available position. Examples are vinylene, propenylene, butenylene, butadienylene, methylpropenylene, pentenylene and hexenylene.

The term "alkynylene", includes a linear or branched divalent carbon chain of a carbon number of 2 to 15, for example, a carbon number of 2 to 10, for example, a carbon number of 2 to 6, and for example, a carbon number of 2 to 4, having one or more triple bonds at any available position. These may have further a double bond at any available position. Examples are ethynylene, propynylene, butynylene, pentynylene and hexynylene.

The term of "aromatic carbocyclyl" includes an aromatic hydrocarbon group which is monocyclic or which consists of two or more rings. Examples are an aromatic hydrocarbon group of a carbon number of 6 to 14, and specific examples are phenyl, naphthyl, anthryl and phenanthryl.

In one embodiment, "aromatic carbocyclyl is phenyl.

The term of "non-aromatic carbocyclyl" includes saturated carbocyclyl or unsaturated non-aromatic carbocyclyl which is monocyclic or which consists of two or more rings. A "non-aromatic carbocyclyl" of two or more rings includes a fused cyclic group wherein a non-aromatic monocyclic carbocycle or a non-aromatic carbocycle of two or more rings is fused with a ring of the above "aromatic carbocyclyl".

In addition, the "non-aromatic carbocyclyl" also includes a cyclic group having a bridge or a cyclic group to form a spiro ring as follows:

[Chemical Formula 23]

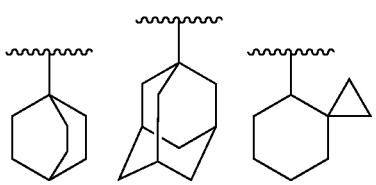

The term "non-aromatic monocyclic carbocyclyl" includes a group having 3 to 16 carbon atoms, for example, 3 to 12 carbon atoms, and for example, 4 to 8 carbon atoms. Examples are cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl and cyclohexadienyl.

Examples of non-aromatic carbocyclyl consisting of two or more rings includes a group having 6 to 14 carbon atoms, and examples are indanyl, indenyl, acenaphthyl, tetrahydronaphthyl and fluorenyl.

The term "cycloalkyl" includes a carbocyclic group of a carbon number of 3 to 10, for example, a carbon number of 3 to 8, and for example, a carbon number 4 to 8. Examples are cyclopropyl, cyclobutyl, cyclopentyl, cyclohexyl, cycloheptyl, cyclooctyl, cyclononyl and cyclodecyl.

The term "cycloalkane" includes a carbocycle of a carbon number of 3 to 10, for example, a carbon number of 3 to 8, and for example, a carbon number 4 to 8. Examples are cyclopropane, cyclobutane, cyclopentane, cyclohexane, cycloheptane, cyclooctane, cyclononane and cyclodecane.

Cycloalkyl portion in "cycloalkylalkyl" and "cycloalkylamino" are the same as the above "cycloalkane".

The term of "aromatic heterocyclyl" includes an aromatic group which is monocyclic, or which consists of two or more rings, containing one or more of heteroatoms selected independently from oxygen, sulfur and nitrogen atoms.

An "aromatic heterocyclyl" of two or more rings includes a fused cyclic group wherein aromatic monocyclic heterocyclyl or non-aromatic heterocyclyl consisting of two or more rings is fused with a ring of the above "aromatic carbocyclyl".

The term "aromatic monocyclic heterocyclyl" includes a 5- to 8-membered group, and for example, 5- to 6-membered group. Examples are pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl and thiadiazolyl.

Examples of aromatic bicyclic heterocyclyl includes a 9- to 10-membered group, and examples are indolinyl, isoindolinyl, indazolinyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl and thiazolopyridyl.

Examples of an aromatic heterocyclyl of three or more rings includes a 13 to 14-membered group, and examples are carbazolyl, acridinyl, xanthenyl, phenothiazinyl, phenoxathiinyl, phenoxazinyl and dibenzofuryl.

The term of "non-aromatic heterocyclyl" includes a non-aromatic group which is monocyclic, or which consists of two or more rings, containing one or more of heteroatoms selected independently from oxygen, sulfur and nitrogen atoms.

A "non-aromatic heterocyclyl" of two or more rings includes a fused cyclic group wherein a non-aromatic monocyclic heterocyclyl or a non-aromatic heterocyclyl of two or more rings is fused with a ring of the above "aromatic carbocyclyl", "non-aromatic carbocyclyl" and/or "aromatic heterocyclyl".

In addition, the "non-aromatic heterocyclyl" also includes a cyclic group having a bridge or a cyclic group to form a spiro ring as follows:

[Chemical Formula 24]

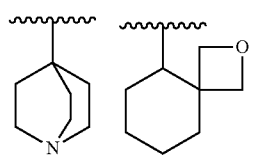

The term "a non-aromatic monocyclic heterocyclyl" includes a 3- to 8-membered ring, and for example, 4-, 5- or 6-membered ring. Examples are dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl and thiazinyl.

Examples of a non-aromatic heterocyclyl of two or more rings includes a 9 to 14-membered group, and examples are indolinyl, isoindolinyl, chromanyl and isochromanyl.

The term of "hydroxyalkyl" includes a group wherein one or more hydrogen atoms attached to one or more carbon atoms of the above "alkyl" are replaced with one or more hydroxy groups. Examples are hydroxymethyl, 1-hydroxyethyl, 2-hydroxyethyl, 1-hydroxypropyl, 2-hydroxypropyl and 1,2-dihydroxyethyl.

In one embodiment, "hydroxyalkyl" is hydroxymethyl.

The term of "alkyloxy" includes a group wherein an oxygen atom is substituted with the above "alkyl". Examples are methyloxy, ethyloxy, n-propyloxy, isopropyloxy, n-butyloxy, tert-butyloxy, isobutyloxy, sec-butyloxy, pentyloxy, isopentyloxy and hexyloxy.

In one embodiment, "alkyloxy" is methyloxy, ethyloxy, n-propyloxy, isopropyloxy or tert-butyloxy.

The term of "alkenyloxy" includes a group wherein an oxygen atom is substituted with the above "alkenyl". Examples are vinyloxy, allyloxy, 1-propenyloxy, 2-butenyloxy, 2-pentenyloxy, 2-hexenyloxy, 2-heptenyloxy and 2-octenyloxy.

The term of "alkynyloxy" includes a group wherein an oxygen atom is substituted with the above "alkynyl". Examples are ethynyloxy, 1-propynyloxy, 2-propynyloxy, 2-butynyloxy, 2-pentynyloxy, 2-hexynyloxy, 2-heptynyloxy and 2-octynyloxy.

The term of "haloalkyl" includes a group wherein one or more hydrogen atoms attached to one or more carbon atoms of the above "alkyl" are replaced with one or more above "halogen". Examples are monofluoromethyl, monofluoroethyl, monofluoropropyl, difluoromethyl, 2,2,3,3,3-pentafluoropropyl, monochloromethyl, trifluoromethyl, trichloromethyl, 2,2,2-trifluoroethyl, 2,2,2-trichloroethyl, 2,2-difluoroethyl, 1,1-difluoroethyl, 2,2,2-trifluoroethyl, 1,2-dibromoethyl, and 1,1,1-trifluoropropan-2-yl. Examples are monofluoromethyl, difluoromethyl, trifluoromethyl and 2,2-difluoroethyl. Examples are monofluoromethyl and difluoromethyl.

The term of "haloalkenyl" includes a group wherein one or more hydrogen atoms attached to one or more carbon atoms of the above "alkenyl" are replaced with one or more above "halogen". Examples are monofluorovinyl, monofluoroallyl, monofluoropropenyl, difluorovinyl, difluoroallyl and difluoropropenyl.

The term of "haloalkynyl" includes a group wherein one or more hydrogen atoms attached to one or more carbon atoms of the above "alkynyl" are replaced with one or more above "halogen". Examples are fluoroethynyl, monofluoropropynyl, difluoropropynyl, monofluorobutynyl, chloroethynyl, monochloropropynyl, monochlorobutynyl and dichloropropynyl.

The term of "haloalkyloxy" includes a group wherein an oxygen atom is substituted with the above "haloalkyl". Examples are monofluoromethyloxy, monofluoroethyloxy, difluoromethyloxy, 1,1-difluoroethyloxy, 2,2-difluoroethyloxy, trifluoromethyloxy, trichloromethyloxy, 2,2,2-trifluoroethyloxy and trichloroethyloxy.

In one embodiment, "haloalkyloxy" is difluoromethyloxy, 2,2,2-difluoroethyloxy, trifluoromethyloxy, 2,2,2-trifluoroethyloxy, or trichloromethyloxy.

The term of "cyanoalkyloxy" includes a group wherein the above "alkyloxy" is substituted with a cyano group. Examples are cyanomethyloxy and cyanoethyloxy.

The term of "alkyloxyalkyl" includes a group wherein the above "alkyl" is substituted with the above "alkyloxy". Examples are methoxymethyl, methoxyethyl and ethoxymethyl.

The term of "alkyloxyalkyloxy" includes a group wherein the above "alkyloxy" is substituted with the above "alkyloxy". Examples are methyloxymethyloxy, methyloxyethyloxy, ethyloxymethyloxy and ethyloxyethyloxy.

The term of "alkylcarbonyl" includes a group wherein a carbonyl group is substituted with the above "alkyl". Examples are methylcarbonyl, ethylcarbonyl, n-propylcarbonyl, isopropylcarbonyl, tert-butylcarbonyl, isobutylcarbonyl, sec-butylcarbonyl, pentylcarbonyl, isopentylcarbonyl and hexylcarbonyl. Examples are methylcarbonyl, ethylcarbonyl and n-propylcarbonyl.

The term of "alkenylcarbonyl" includes a group wherein a carbonyl group is substituted with the above "alkenyl". Examples are ethylenylcarbonyl, propenylcarbonyl and butenylcarbonyl.

The term of "alkynylcarbonyl" includes a group wherein a carbonyl group is substituted with the above "alkynyl". Examples are ethynylcarbonyl, propynylcarbonyl and butynylcarbonyl.

The term of "monoalkylamino" includes a group wherein a hydrogen atom attached to a nitrogen atom of an amino group is replaced with the above "alkyl". Examples are methylamino, ethylamino and isopropylamino.

In one embodiment, "monoalkylamino" is methylamino or ethylamino.

The term of "dialkylamino" includes a group wherein two hydrogen atoms attached to a nitrogen atom of an amino group are replaced with two above "alkyl". These two alkyl groups may be the same or different. Examples are dimethylamino, diethylamino, N,N-diisopropylamino, N-methyl-N-ethylamino and N-isopropyl-N-ethylamino.

In one embodiment, "dialkylamino" is dimethylamino or diethylamino.

The term of "alkylsulfonyl" includes a group wherein a sulfonyl group is substituted with the above "alkyl". Examples are methylsulfonyl, ethylsulfonyl, propylsulfonyl, isopropylsulfonyl, tert-butylsulfonyl, isobutylsulfonyl and sec-butylsulfonyl.

In one embodiment, "alkylsulfonyl" is methylsulfonyl or ethylsulfonyl.

The term of "alkenylsulfonyl" includes a group wherein a sulfonyl group is substituted with the above "alkenyl". Examples are ethylenylsulfonyl, propenylsulfonyl and butenylsulfonyl.

The term of "alkynylsulfonyl" includes a group wherein a sulfonyl group is substituted with the above "alkynyl". Examples are ethynylsulfonyl, propynylsulfonyl and butynylsulfonyl.

The term of "monoalkylcarbonylamino" includes a group wherein a hydrogen atom attached to a nitrogen atom of an amino group is replaced with the above "alkylcarbonyl". Examples are methylcarbonylamino, ethylcarbonylamino, propylcarbonylamino, isopropylcarbonylamino, tert-butylcarbonylamino, isobutylcarbonylamino and sec-butylcarbonylamino.

In one embodiment, "monoalkylcarbonylamino" is methylcarbonylamino or ethylcarbonylamino.

The term of "dialkylcarbonylamino" includes a group wherein two hydrogen atoms attached to a nitrogen atom of an amino group are replaced with two above "alkylcarbonyl". These two alkylcarbonyl groups may be the same or different. Examples are dimethylcarbonylamino, diethylcarbonylamino and N,N-diisopropylcarbonylamino.

In one embodiment, "dialkylcarbonylamino" is dimethylcarbonylamino or diethylcarbonylamino.

The term of "monoalkylsulfonylamino" includes a group wherein a hydrogen atom attached to a nitrogen atom of an amino group is replaced with the above "alkylsulfonyl". Examples are methylsulfonylamino, ethylsulfonylamino, propylsulfonylamino, isopropylsulfonylamino, tert-butylsulfonylamino, isobutylsulfonylamino and sec-butylsulfonylamino. In one embodiment, monoalkylsulfonylamino" is methylsulfonylamino or ethylsulfonylamino.

The term of "dialkylsulfonylamino" includes a group wherein two hydrogen atoms attached to a nitrogen atom of an amino group are replaced with two above "alkylsulfonyl". These two alkylsulfonyl groups may be the same or different. Examples are dimethylsulfonylamino, diethylsulfonylamino and N,N-diisopropylsulfonylamino. In one embodiment, "dialkylsulfonylamino" is dimethylsulfonylamino or diethylsulfonylamino.

The term of "alkylimino" includes a group wherein a hydrogen atom attached to a nitrogen atom of an imino group is replaced with the above "alkyl". Examples are methylimino, ethylimino, n-propylimino and isopropylimino.

The term of "alkenylimino" includes a group wherein a hydrogen atom attached to a nitrogen atom of an imino group is replaced with the above "alkenyl". Examples are ethylenylimino and propenylimino.

The term of "alkynylimino" includes a group wherein a hydrogen atom attached to a nitrogen atom of an imino group is replaced with the above "alkynyl". Examples are ethynylimino and propynylimino.

The term of "alkylcarbonylimino" includes a group wherein a hydrogen atom attached to a nitrogen atom of an imino group is replaced with the above "alkylcarbonyl". Examples are methylcarbonylimino, ethylcarbonylimino, n-propylcarbonylimino and isopropylcarbonylimino.

The term of "alkenylcarbonylimino" includes a group wherein a hydrogen atom attached to a nitrogen atom of an imino group is replaced with the above "alkenylcarbonyl". Examples are ethylenylcarbonylimino and propenylcarbonylimino.

The term of "alkynylcarbonylimino" includes a group wherein a hydrogen atom attached to a nitrogen atom of an imino group is replaced with the above "alkynylcarbonyl". Examples are ethynylcarbonylimino and propynylcarbonylimino.

The term of "alkyloxyimino" includes a group wherein a hydrogen atom attached to a nitrogen atom of an imino group is replaced with the above "alkyloxy". Examples are methyloxyimino, ethyloxyimino, n-propyloxyimino and isopropyloxyimino.

The term of "alkenyloxyimino" includes a group wherein a hydrogen atom attached to a nitrogen atom of an imino group is replaced with the above "alkenyloxy". Examples are ethylenyloxyimino and propenyloxyimino.

The term of "alkynyloxyimino" includes a group wherein a hydrogen atom attached to a nitrogen atom of an imino group is replaced with the above "alkynyloxy". Examples are ethynyloxyimino and propynyloxyimino.

The term of "alkylcarbonyloxy" includes a group wherein an oxygen atom is substituted with the above "alkylcarbonyl". Examples are methylcarbonyloxy, ethylcarbonyloxy, propylcarbonyloxy, isopropylcarbonyloxy, tert-butylcarbonyloxy, isobutylcarbonyloxy and sec-butylcarbonyloxy. In one embodiment, "alkylcarbonyloxy" is methylcarbonyloxy or ethylcarbonyloxy.

The term of "alkenylcarbonyloxy" includes a group wherein an oxygen atom is substituted with the above "alkenylcarbonyl". Examples are ethylenylcarbonyloxy and propenylcarbonyloxy The term of "alkynylcarbonyloxy" includes a group wherein an oxygen atom is substituted with the above "alkynylcarbonyl". Examples are ethynylcarbonyloxy and propynylcarbonyloxy.

The term of "alkyloxycarbonyl" includes a group wherein a carbonyl group is substituted with the above "alkyloxy". Examples are methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl and hexyloxycarbonyl. In one embodiment, "alkyloxycarbonyl" is methyloxycarbonyl, ethyloxycarbonyl or propyloxycarbonyl.

The term of "alkenyloxycarbonyl" includes a group wherein a carbonyl group is substituted with the above "alkenyloxy". Examples are ethylenyloxycarbonyl, propenyloxycarbonyl and butenyloxycarbonyl.

The term of "alkynyloxycarbonyl" includes a group wherein a carbonyl group is substituted with the above "alkynyloxy". Examples are ethynyloxycarbonyl, propynyloxycarbonyl and butynyloxyarbonyl.

The term of "alkylsulfanyl" includes a group wherein a hydrogen atom attached to a sulfur atom of a sulfanyl group is replaced with the above "alkyl". Examples are methylsulfanyl, ethylsulfanyl, n-propylsulfanyl, isopropylsulfanyl, tert-butylsulfanyl and isobutylsulfanyl.

The term "cyanoalkylsulfanyl" includes a group wherein the above "alkylsulfanyl" is substituted with a cyano group. Examples are cyanomethylsulfanyl, cyanoethylsulfanyl and cyanopropylsulfanyl.

The term of "alkenylsulfanyl" includes a group wherein a hydrogen atom attached to a sulfur atom of a sulfanyl group is replaced with the above "alkenyl". Examples are ethylenylsulfanyl, propenylsulfanyl and butenylsulfanyl.

The term of "alkynylsulfanyl" includes a group wherein a hydrogen atom attached to a sulfur atom of a sulfanyl group is replaced with the above "alkynyl". Examples are ethynylsulfanyl, propynylsulfanyl and butynylsulfanyl.

The term of "alkylsulfinyl" includes a group wherein a sulfinyl group is substituted with the above "alkyl". Examples are methylsulfinyl, ethylsulfinyl, n-propylsulfinyl and isopropylsulfinyl.

The term of "alkenylsulfinyl" includes a group wherein a sulfinyl group is substituted with the above "alkenyl". Examples are ethylenylsulfinyl, propenylsulfinyl and butenylsulfinyl.

The term of "alkynylsulfinyl" includes a group wherein a sulfinyl group is substituted with the above "alkynyl". Examples are ethynylsulfinyl, propynylsulfinyl and butynylsulfinyl.

The term of "monoalkylcarbamoyl" includes a group wherein a hydrogen atom attached to a nitrogen atom of a carbamoyl group is replaced with the above "alkyl". Examples are methylcarbamoyl, ethylcarbamoyl, n-propylcarbamoyl and isopropylcarbamoyl.

The term of "dialkylcarbamoyl" includes a group wherein two hydrogen atom attached to a nitrogen atom of a carbamoyl group are replaced with two above "alkyl". These two alkyl groups may be the same or different. Examples are dimethylcarbamoyl, diethylcarbamoyl and N-methyl-N-ethylcarbamoyl.

The term of "monoalkylsulfamoyl" includes a group wherein a hydrogen atom attached to a nitrogen atom of a sulfamoyl group is replaced with the above "alkyl". Examples are methylsulfamoyl, ethylsulfamoyl, n-propylsulfamoyl and isopropylsulfamoyl.

The term of "dialkylsulfamoyl" includes a group wherein two hydrogen atoms attached to a nitrogen atom of a sulfamoyl group are replaced with two above "alkyl". These two alkyl groups may be the same or different. Examples are dimethylsulfamoyl, diethylsulfamoyl and N-methyl-N-ethylsulfamoyl.

The term of "trialkylsilyl" includes a group wherein a silicon atom is substituted with three above "alkyl". These three alkyl groups may be the same or different. Examples are trimethylsilyl, triethylsilyl and tert-butyldimethylsilyl.

The term of "alkylidene" includes a divalent group derived from alkane by removing two hydrogen atoms from the same carbon atom. Examples are methylidene, ethylidene, propylidene, isopropylidene, butylidene, pentylidene and hexylidene.

The alkenyl portion of "alkenylcarbonylamino", "alkyloxyalkenyloxy", "alkenylsulfanyl" and "alkenylamino" means the above "alkenyl".

The alkynyl portion of "alkynylcarbonylamino", "alkyloxyalkynyloxy", "alkynylsulfanyl" and "alkynylamino" means the above "alkynyl".

The alkyl portion of "hydroxyalkyloxy", "monoalkylcarbonylamino", "dialkylcarbonylamino", "monoalkylamino", "dialkylamino", "aminoalkyl", "alkyloxyalkenyloxy", "alkyloxyalkynyloxy", "alkylcarbonyl", "monoalkylcarbamoyl", "dialkylcarbamoyl", "hydroxyalkylcarbamoyl", "alkyloxyamino", "alkylsulfanyl", "monoalkylsulfonylamino", "dialkylsulfonylamino", "alkylsulfonylalkylamino", "alkylsulfonylimino", "alkylsulfinylamino", "alkylsulfinylalkylamino", "alkylsulfinylimino", "monoalkylsulfamoyl", "dialkylsulfamoyl", "aromatic carbocyclylalkyl", "non-aromatic carbocyclylalkyl", "aromatic heterocyclylalkyl" and "non-aromatic heterocyclylalkyl", "aromatic carbocyclylalkyloxy", "non-aromatic carbocyclylalkyloxy", "aromatic heterocyclylalkyloxy" and "non-aromatic heterocyclylalkyloxy", "aromatic carbocyclylalkyloxycarbonyl", "non-aromatic carbocyclylalkyloxycarbonyl", "aromatic heterocyclylalkyloxycarbonyl" and "non-aromatic heterocyclylalkyloxycarbonyl", "aromatic carbocyclylalkyloxyalkyl", "non-aromatic carbocyclylalkyloxyalkyl", "aromatic heterocyclylalkyloxyalkyl" and "non-aromatic heterocyclylalkyloxyalkyl", and "aromatic carbocyclylalkylamino", "non-aromatic carbocyclylalkylamino", "aromatic heterocyclylalkylamino" and "non-aromatic heterocyclylalkylamino", "aromatic carbocyclylalkylcarbamoyl", "non-aromatic carbocyclylalkylcarbamoyl", "aromatic heterocyclylalkylcarbamoyl" and "non-aromatic heterocyclylalkylcarbamoyl", and "cycloalkylalkyl" means the above "alkyl".

The term of "aromatic carbocyclylalkyl" includes alkyl substituted with one or more above "aromatic carbocyclyl". Examples are benzyl, phenethyl, phenylpropyl, benzhydryl, trityl, naphthylmethyl and a group of the formula of

[Chemical Formula 25]

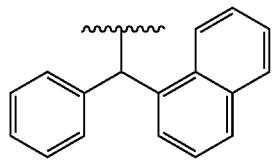

In one embodiment, "aromatic carbocyclylalkyl" is benzyl, phenethyl or benzhydryl.

The term of "non-aromatic carbocyclylalkyl" includes alkyl substituted with one or more above "non-aromatic carbocyclyl". Also, "non-aromatic carbocyclylalkyl" includes a "non-aromatic carbocyclyl alkyl" wherein the alkyl portion thereof is substituted with one or more above "aromatic carbocyclyl". Examples are cyclopropylmethyl, cyclobutylmethyl, cyclopentylmethyl, cyclohexylmethyl and a group of the formula of

[Chemical Formula 26]

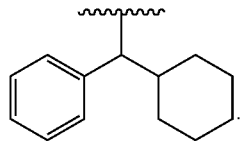

The term of "aromatic heterocyclyl alkyl" includes alkyl substituted with one or more above "aromatic heterocyclyl". Also, "aromatic heterocyclyl alkyl" includes "aromatic heterocyclyl alkyl" wherein the alkyl portion thereof is substituted with one or more above "aromatic carbocyclyl", and/or "non-aromatic carbocyclyl". Examples are pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl and groups of the formula of

[Chemical Formula 27]

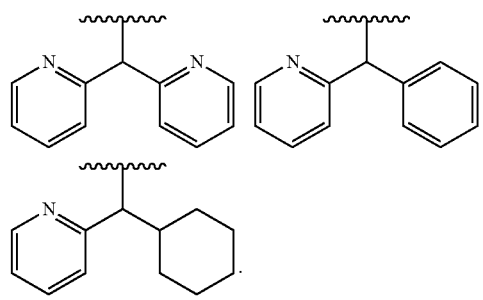

The term of "non-aromatic heterocyclyl alkyl" includes alkyl substituted with one or more above "non-aromatic heterocyclyl". Also, "non-aromatic heterocyclyl alkyl" includes a "non-aromatic heterocyclylalkyl" wherein the alkyl portion thereof is substituted with one or more above "aromatic carbocyclyl", "non-aromatic carbocyclyl" and/or "aromatic heterocyclyl". Examples are tetrahydropyranylmethyl, morpholinylmethyl, morpholinylethyl, piperidinylmethyl, piperazinylmethyl and groups of the formula of

[Chemical Formula 28]

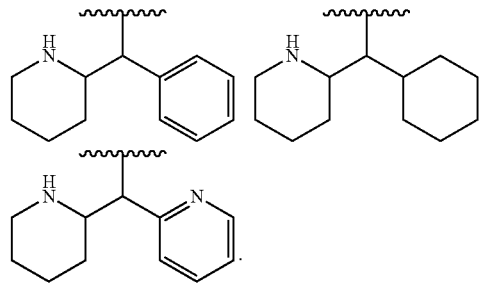

The term of "aromatic carbocyclylalkyloxy" includes alkyloxy substituted with one or more above "aromatic carbocyclyl". Examples are benzyloxy, phenethyloxy, phenylpropyloxy, benzhydryloxy, trityloxy, naphthylmethyloxy and a group of the formula of

[Chemical Formula 29]

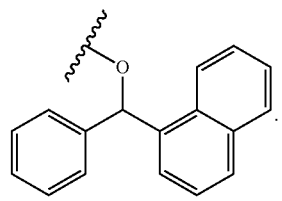

The term of "non-aromatic carbocyclylalkyloxy" includes alkyloxy substituted with one or more above "non-aromatic carbocyclyl". Also, "non-aromatic carbocyclylalkyloxy" includes a "non-aromatic carbocyclylalkyloxy" wherein the alkyl portion thereof is substituted with one or more above "aromatic carbocyclyl". Examples are cyclopropylmethyloxy, cyclobutylmethyloxy, cyclopentylmethyloxy, cyclohexylmethyloxy and a group of the formula of

[Chemical Formula 30]

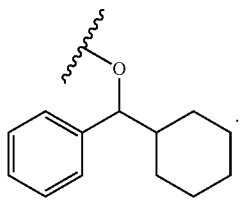

The term of "aromatic heterocyclyl alkyloxy" includes alkyloxy substituted with one or more above "aromatic heterocyclyl". Also, "aromatic heterocyclylalkyloxy" includes "aromatic heterocyclylalkyloxy" wherein the alkyl portion thereof is substituted with one or more above "aromatic carbocyclyl", and/or "non-aromatic carbocyclyl". Examples are pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy and groups of the formula of

[Chemical Formula 31]

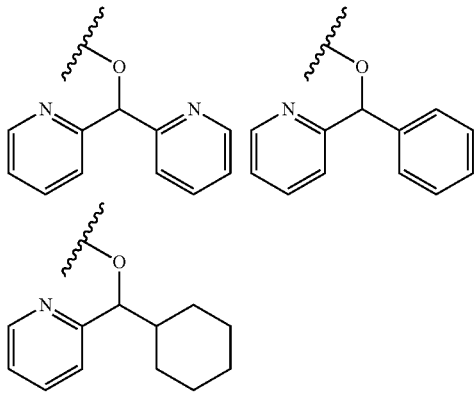

The term of "non-aromatic heterocyclylalkyloxy" includes alkyloxy substituted with one or more above "non-aromatic heterocyclyl". Also, "non-aromatic heterocyclylalkyloxy" includes a "non-aromatic heterocyclylalkyloxy" wherein the alkyl portion thereof is substituted with one or more above "aromatic carbocyclyl", "non-aromatic carbocyclyl" and/or "aromatic heterocyclyl". Examples are tetrahydropyranylmethyloxy, morpholinylmethyloxy, morpholinylethyloxy, piperidinylmethyloxy, piperazinylmethyloxy and groups of the formula of

[Chemical Formula 32]

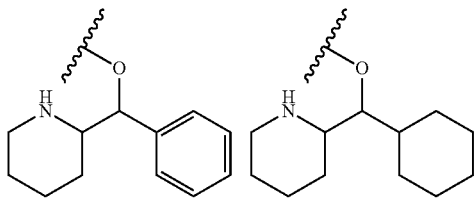

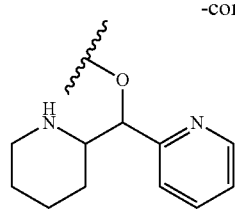

The term of "aromatic carbocyclyl alkyloxycarbonyl" includes alkyloxycarbonyl substituted with one or more above "aromatic carbocyclyl". Examples are benzyloxycarbonyl, phenethyloxycarbonyl, phenylpropyloxycarbonyl, benzhydryloxycarbonyl, trityloxycarbonyl, naphthylmethyloxycarbonyl and a group of the formula of

[Chemical Formula 33]

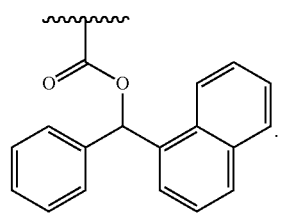

The term of "non-aromatic carbocyclylalkyloxycarbonyl" includes alkyloxycarbonyl substituted with one or more above "non-aromatic carbocyclyl". Also, "non-aromatic carbocyclylalkyloxycarbonyl" includes "non-aromatic carbocyclylalkyloxycarbonyl" wherein the alkyl portion thereof is substituted with one or more above "aromatic carbocyclyl". Examples are cyclopropylmethyloxycarbonyl, cyclobutylmethyloxycarbonyl, cyclopentylmethyloxycarbonyl, cyclohexylmethyloxycarbonyl and a group of the formula of

[Chemical Formula 34]

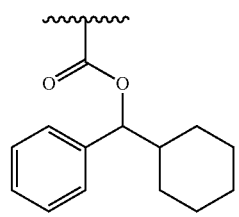

The term of "aromatic heterocyclyl alkyloxycarbonyl" includes alkyloxycarbonyl substituted with one or more above "aromatic heterocyclyl". Also, "aromatic heterocyclyl alkyloxycarbonyl" includes "aromatic heterocyclyl alkyloxycarbonyl" wherein the alkyl portion thereof is substituted with one or more above "aromatic carbocyclyl", and/or "non-aromatic carbocyclyl". Examples are pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl and groups of the formula of

[Chemical Formula 35]

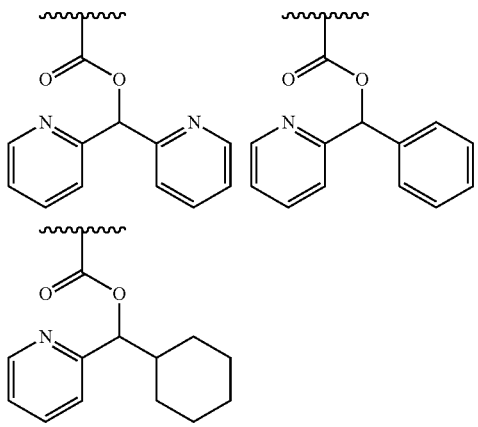

The term of "non-aromatic heterocyclyl alkyloxycarbonyl" includes alkyloxycarbonyl substituted with one or more above "non-aromatic heterocyclyl". Also, "non-aromatic heterocyclyl alkyloxycarbonyl" includes "non-aromatic heterocyclyl alkyloxycarbonyl" wherein the alkyl portion thereof is substituted with one or more above "aromatic carbocyclyl", "non-aromatic carbocyclyl" and/or "aromatic heterocyclyl". Examples are tetrahydropyranylmethyloxycarbonyl, morpholinylmethyloxycarbonyl, morpholinylethyloxycarbonyl, piperidinylmethyloxycarbonyl, piperazinylmethyloxycarbonyl and groups of the formula of

[Chemical Formula 36]

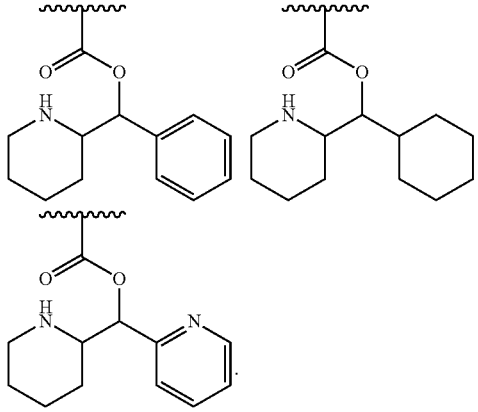

The term of "aromatic carbocyclylalkyloxyalkyl" includes alkyloxyalkyl substituted with one or more above "aromatic carbocyclyl". Examples are benzyloxymethyl, phenethyloxymethyl, phenylpropyloxymethyl, benzhydryloxymethyl, trityloxymethyl, naphthylmethyloxymethyl and a group of the formula of

[Chemical Formula 37]

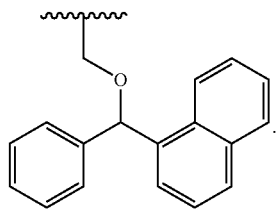

The term of "non-aromatic carbocyclylalkyloxyalkyl" includes alkyloxyalkyl substituted with one or more above "non-aromatic carbocyclyl". Also, "non-aromatic carbocyclylalkyloxyalkyl" includes a "non-aromatic carbocyclylalkyloxyalkyl" wherein the alkyl portion attached to a non-aromatic carbocyclyl is substituted with one or more above "aromatic carbocyclyl". Examples are cyclopropylmethyloxymethyl, cyclobutylmethyloxymethyl, cyclopentylmethyloxymethyl, cyclohexylmethyloxymethyl and a group of the formula of

[Chemical Formula 38]

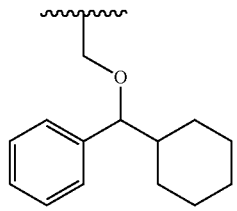

The term of "aromatic heterocyclylalkyloxyalkyl" includes alkyloxyalkyl substituted with one or more above "aromatic heterocyclyl". Also, "aromatic heterocyclylalkyloxyalkyl" includes "aromatic heterocyclylalkyloxyalkyl" wherein the alkyl portion attached to aromatic heterocyclyl is substituted with one or more above "aromatic carbocyclyl" and/or "non-aromatic carbocyclyl". Examples are pyridylmethyloxymethyl, furanylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl and groups of the formula of

[Chemical Formula 39]

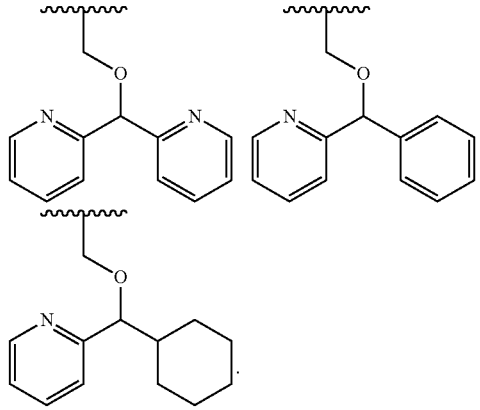

The term of "non-aromatic heterocyclylalkyloxyalkyl" includes alkyloxyalkyl substituted with one or more above "non-aromatic heterocyclyl". Also, "non-aromatic heterocyclylalkyloxyalkyl" includes "non-aromatic heterocyclylalkyloxyalkyl" wherein the alkyl portion attached to non-aromatic heterocyclyl is substituted with one or more above "aromatic carbocyclyl", "non-aromatic carbocyclyl" and/or "aromatic heterocyclyl". Examples are tetrahydropyranylmethyloxymethyl, morpholinylmethyloxymethyl, morpholinylethyloxymethyl, piperidinylmethyloxymethyl, piperazinylmethyloxymethyl and groups of the formula of

[Chemical Formula 40]

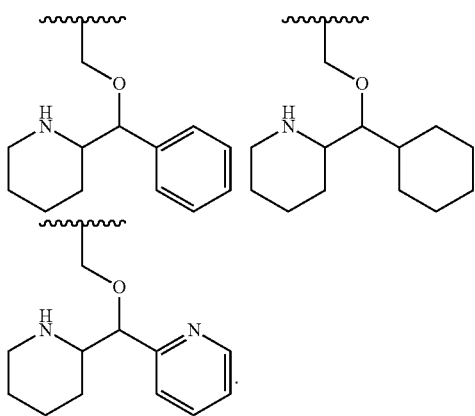

The term of "aromatic carbocyclylalkylamino" includes a group wherein one or two hydrogen atoms attached to a nitrogen atom of an amino group is replaced with the above "aromatic carbocyclylalkyl". Examples are benzylamino, phenethylamino, phenylpropylamino, benzhydrylamino, tritylamino, naphthylmethylamino and dibenzylamino.

The term of "non-aromatic carbocyclylalkylamino" includes a group wherein one or two hydrogen atoms attached to a nitrogen atom of an amino group is replaced with the above "non-aromatic carbocyclylalkyl". Examples are cyclopropylmethylamino, cyclobutylmethylamino, cyclopentylmethylamino and cyclohexylmethylamino.

The term of "aromatic heterocyclylalkylamino" includes a group wherein one or two hydrogen atoms attached to a nitrogen atom of an amino group is replaced with the above "aromatic heterocyclylalkyl". Examples are pyridylmethylamino, furanylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolidinylmethylamino and benzoxazolylmethylamino.

The term of "non-aromatic heterocyclylalkylamino" includes a group wherein one or two hydrogen atoms attached to a nitrogen atom of an amino group is replaced with the above "non-aromatic heterocyclyl alkyl". Examples are tetrahydropyranylmethylamino, morpholinylethylamino, piperidinylmethylamino and piperazinylmethyamino.

The term of "aromatic carbocyclylalkylcarbamoyl" includes a group wherein one or two hydrogen atoms attached to a nitrogen atom of a carbamoyl group is replaced with the above "aromatic carbocyclylalkyl". Examples are benzylcarbamoyl, phenethylcarbamoyl, phenylpropylcarbamoyl, benzhydrylcarbamoyl, tritylcarbamoyl, naphthylmethylcarbamoyl and dibenzylcarbamoyl.

The term of "non-aromatic carbocyclylalkylcarbamoyl" includes a group wherein one or two hydrogen atoms attached to a nitrogen atom of a carbamoyl group is replaced with the above "non-aromatic carbocyclylalkyl". Examples are cyclopropylmethylcarbamoyl, cyclobutylmethylcarbamoyl, cyclopentylmethylcarbamoyl and cyclohexylmethylcarbamoyl.

The term of "aromatic heterocyclylalkylcarbamoyl" includes a group wherein one or two hydrogen atoms attached to a nitrogen atom of a carbamoyl group is replaced with the above "aromatic heterocyclylalkyl". Examples are pyridylmethylcarbamoyl, furanylmethylcarbamoyl, imidazolylmethylcarbamoyl, indolylmethylcarbamoyl, benzothiophenylmethylcarbamoyl, oxazolylmethylcarbamoyl, isoxazolylmethylcarbamoyl, thiazolylmethylcarbamoyl, isothiazolylmethylcarbamoyl, pyrazolylmethylcarbamoyl, isopyrazolylmethylcarbamoyl, pyrrolidinylmethylcarbamoyl and benzoxazolylmethylcarbamoyl.

The term of "non-aromatic heterocyclylalkylcarbamoyl" includes a group wherein one or two hydrogen atoms attached to a nitrogen atom of a carbamoyl group is replaced with the above "non-aromatic heterocyclyl alkyl". Examples are tetrahydropyranylmethylcarbamoyl, morpholinylethylcarbamoyl, piperidinylmethylcarbamoyl and piperazinylmethycarbamoyl.

The "aromatic carbocycle" portion of "aromatic carbocycle", "aromatic carbocyclyloxy", "aromatic carbocyclylcarbonyl", "aromatic carbocyclylcarbonyloxy", "aromatic carbocyclyloxycarbonyl", "aromatic carbocyclylcarbonylamino", "aromatic carbocyclylamino", "aromatic carbocyclylsulfanyl" and "aromatic carbocyclyl sulfonyl", "aromatic carbocyclylsulfamoyl" and "aromatic carbocyclylcarbamoyl" means the above "aromatic carbocyclyl".

The term of "aromatic carbocyclyloxy" includes a group wherein an oxygen atom is substituted with the above "aromatic carbocyclyl". Examples are phenyloxy and naphthyloxy.

The term of "aromatic carbocyclylcarbonyl" includes a group wherein a carbonyl group is substituted with the above "aromatic carbocyclyl". Examples are phenylcarbonyl and naphthylcarbony.

The term of "aromatic carbocyclylcarbonyloxy" includes a group wherein a carbonyloxy group is substituted with the above "aromatic carbocyclyl". Examples are phenylcarbonyloxy and naphthylcarbonyloxy.

The term of "aromatic carbocyclyloxycarbonyl" includes a group wherein a carbonyl group is substituted with the above "aromatic carbocyclyloxy". Examples are phenyloxycarbonyl and naphthyloxycarbonyl.

The term of "aromatic carbocyclylcarbonylamino" includes a group wherein one or two hydrogen atoms attached to a nitrogen atom of an amino group is replaced with the above "aromatic carbocyclylcarbonyl". Examples are benzoylamino and naphthylcarbonylamino.

The term of "aromatic carbocyclylamino" includes a group wherein one or two hydrogen atoms attached to a nitrogen atom of an amino group is replaced with the above "aromatic carbocyclyl". Examples are phenylamino and naphthylamino.

The term of "aromatic carbocyclylsulfanyl" includes a group wherein a hydrogen atom attached to a sulfur atom of sulfanyl is replaced with the above "aromatic carbocyclyl". Examples are phenylsulfanyl and naphthylsulfanyl.

The term of "aromatic carbocyclylsulfonyl" includes a group wherein a sulfonyl group is substituted with the above "aromatic carbocyclyl". Examples are phenylsulfonyl and naphthylsulfonyl.

The term of "aromatic carbocyclylsulfamoyl" includes a group wherein one or two hydrogen atoms attached to a nitrogen atom of a sulfamoyl group is replaced with the above "aromatic carbocyclyl". Examples are phenylsulfamoyl and naphthylsulfamoyl.

The term of "aromatic carbocyclylcarbamoyl" includes a group wherein one or two hydrogen atoms attached to a nitrogen atom of a carbamoyl group is replaced with the above "aromatic carbocyclyl". Examples are phenylcarbamoyl and naphthylcarbamoyl.

The "non-aromatic carbocycle" portion of "non-aromatic carbocycle", "non-aromatic carbocyclyloxy", "non-aromatic carbocyclylcarbonyloxy", "non-aromatic carbocyclylcarbonyl", "non-aromatic carbocyclyloxycarbonyl", "non-aromatic carbocyclylcarbonylamino", "non-aromatic carbocyclylamino", "non-aromatic carbocyclylsulfanyl", "non-aromatic carbocyclylsulfonyl", "non-aromatic carbocyclylsulfamoyl" and "non-aromatic carbocyclylcarbamoyl" means the above "non-aromatic carbocyclyl".

The term of "non-aromatic carbocyclyloxy" includes a group wherein an oxygen atom is substituted with the above "non-aromatic carbocyclyl". Examples are cyclopropyloxy, cyclohexyloxy and cyclohexenyloxy.

The term of "non-aromatic carbocyclylcarbonyl" includes a group wherein a carbonyl group is substituted with the above "non-aromatic carbocyclyl". Examples are cyclopropylcarbonyl, cyclohexylcarbonyl and cyclohexenylcarbonyl.

The term of "non-aromatic carbocyclylcarbonyloxy" includes a group wherein a carbonyloxy group is substituted with the above "non-aromatic carbocyclyl". Examples are cyclopropylcarbonyloxy, cyclohexylcarbonyloxy and cyclohexenylcarbonyloxy.

The term of "non-aromatic carbocyclyloxycarbonyl" includes a group wherein a carbonyl group is substituted with the above "non-aromatic carbocyclyloxy". Examples are cyclopropyloxycarbonyl, cyclohexyloxycarbonyl and cyclohexenyloxycarbonyl.

The term of "non-aromatic carbocyclylcarbonylamino" includes a group wherein one or two hydrogen atoms attached to a nitrogen atom of an amino group is replaced with the above "non-aromatic carbocyclylcarbonyl". Examples are cyclopropylcarbonylamino, cyclohexylcarbonylamino and cyclohexenylcarbonylamino.

The term of "non-aromatic carbocyclylamino" includes a group wherein one or two hydrogen atoms attached to a nitrogen atom of an amino group is replaced with the above "non-aromatic carbocyclyl". Examples are cyclopropylamino, cyclohexylamino and cyclohexenylamino.

The term of "non-aromatic carbocyclylsulfanyl" includes a group wherein a hydrogen atom attached to a sulfur atom of a sulfanyl is replaced with the above "non-aromatic carbocyclyl". Examples are cyclopropylsulfanyl, cyclohexylsulfanyl and cyclohexenylsulfanyl.

The term of "non-aromatic carbocyclylsulfonyl" includes a group wherein a sulfonyl group is substituted with the above "non-aromatic carbocyclyl". Examples are cyclopropylsulfonyl, cyclohexylsulfonyl and cyclohexenylsulfonyl.

The term of "non-aromatic carbocyclylsulfamoyl" includes a group wherein one or two hydrogen atoms attached to a nitrogen atom of a sulfamoyl group is replaced with the above "non-aromatic carbocyclyl". Examples are cyclopropylsulfamoyl, cyclohexylsulfamoyl and cyclohexenylsulfamoyl.

The term of "non-aromatic carbocyclylcarbamoyl" includes a group wherein one or two hydrogen atoms attached to a nitrogen atom of a carbamoyl group is replaced with the above "non-aromatic carbocyclyl". Examples are cyclopropylcarbamoyl, cyclohexylcarbamoyl and cyclohexenylcarbamoyl.

The "aromatic heterocyclyl" portion of "aromatic heterocyclyloxy", "aromatic heterocyclylcarbonyl", "aromatic heterocyclylcarbonyloxy", "aromatic heterocyclyloxycarbonyl", "aromatic heterocyclylcarbonylamino", "aromatic heterocyclylamino", "aromatic heterocyclylsulfanyl", "aromatic heterocyclylsulfonyl", "aromatic heterocyclylsulfamoyl" and "aromatic heterocyclylcarbamoyl" means the above "aromatic heterocyclyl".

The term of "aromatic heterocyclyloxy" includes a group wherein an oxygen atom is substituted with the above "aromatic heterocyclyl". Examples are pyridyloxy and oxazolyloxy.

The term of "aromatic heterocyclylcarbonyl" includes a group wherein a carbonyl group is substituted with the above "aromatic heterocyclyl". Examples are pyridylcarbonyl and oxazolylcarbonyl.

The term of "aromatic heterocyclylcarbonyloxy" includes a group wherein a carbonyloxy group is substituted with the above "aromatic heterocyclyl". Examples are pyridylcarbonyloxy and oxazolylcarbonyloxy.

The term of "aromatic heterocyclyloxycarbonyl" includes a group wherein a carbonyl group is substituted with the above "aromatic heterocyclyloxy". Examples are pyridyloxycarbonyl and oxazolyloxycarbonyl.

The term of "aromatic heterocyclylcarbonylamino" includes a group wherein one or two hydrogen atoms attached to a nitrogen atom of an amino group is replaced with the above "aromatic heterocyclylcarbonyl". Examples are pyridylcarbonylamino and oxazolylcarbonylamino.

The term of "aromatic heterocyclylamino" includes a group wherein one or two hydrogen atoms attached to a nitrogen atom of an amino group is replaced with the above "aromatic heterocyclyl". Examples are pyridylamino and oxazolylamino.

The term of "aromatic heterocyclylsulfanyl" includes a group wherein a hydrogen atom attached to a sulfur atom of sulfanyl is replaced with the above "aromatic heterocyclyl". Examples are pyridylsulfanyl and oxazolylsulfanyl.

The term of "aromatic heterocyclylsulfonyl" includes a group wherein a sulfonyl group is substituted with the above "aromatic heterocyclyl". Examples are pyridylsulfonyl and oxazolylsulfonyl.

The term of "aromatic heterocyclylsulfamoyl" includes a group wherein one or two hydrogen atoms attached to a nitrogen atom of a sulfamoyl group is replaced with the above "aromatic heterocyclyl". Examples are pyridylsulfamoyl and oxazolylsulfamoyl.

The term of "aromatic heterocyclylcarbamoyl" includes a group wherein one or two hydrogen atoms attached to a nitrogen atom of a carbamoyl group is replaced with the above "aromatic heterocyclyl". Examples are pyridylcarbamoyl and oxazolylcarbamoyl.

The "non-aromatic heterocyclyl" portion of "non-aromatic heterocyclyloxy", "non-aromatic heterocyclylcarbonyl", "non-aromatic heterocyclylcarbonyloxy", "non-aromatic heterocyclyloxycarbonyl", "non-aromatic heterocyclylcarbonylamino", "non-aromatic heterocyclylamino", "non-aromatic heterocyclylsulfanyl", "non-aromatic heterocyclylsulfonyl", "non-aromatic heterocyclylsulfamoyl" and "non-aromatic heterocyclylcarbamoyl" means the above "non-aromatic heterocyclyl".

The term of "non-aromatic heterocyclyloxy" includes a group wherein an oxygen atom is substituted with the above "non-aromatic heterocyclyl". Examples are piperidinyloxy and tetrahydrofuryloxy.

The term of "non-aromatic heterocyclylcarbonyl" includes a group wherein a carbonyl group is substituted with the above "non-aromatic heterocyclyl". Examples are piperidinylcarbonyl and tetrahydrofurylcarbonyl.

The term of "non-aromatic heterocyclylcarbonyloxy" includes a group wherein a carbonyloxy group is substituted with the above "non-aromatic heterocyclyl". Examples are piperidinylcarbonyloxy and tetrahydrofurylcarbonyloxy.

The term of "non-aromatic heterocyclyloxycarbonyl" includes a group wherein a carbonyl group is substituted with the above "non-aromatic heterocyclyloxy". Examples are piperidinyloxycarbonyl and tetrahydrofuryloxycarbonyl.

The term of "non-aromatic heterocyclylcarbonylamino" includes a group wherein one or two hydrogen atoms attached to a nitrogen atom of an amino group is replaced with the above "non-aromatic heterocyclylcarbonyl". Examples are pipieidinylcarbonylamino and tetrahydrofurylcarbonylamino.

The term of "non-aromatic heterocyclylamino" includes a group wherein one or two hydrogen atoms attached to a nitrogen atom of an amino group is replaced with the above "non-aromatic heterocyclyl". Examples are piperidinylamino and tetrahydrofurylamino.

The term of "non-aromatic heterocyclylsulfanyl" includes a group wherein a hydrogen atom attached to a sulfur atom of sulfanyl is replaced with the above "non-aromatic heterocyclyl". Examples are piperidinylsulfanyl and tetrahydrofurylsulfanyl.

The term of "non-aromatic heterocyclylsulfonyl" includes a group wherein a sulfonyl group is substituted with the above "non-aromatic heterocyclyl". Examples are piperidinylsulfonyl and tetrahydrofurylsulfonyl.

The term of "non-aromatic heterocyclylsulfamoyl" includes a group wherein one or two hydrogen atoms attached to a nitrogen atom of a sulfamoyl group is replaced with the above "non-aromatic heterocyclyl". Examples are piperidinylsulfamoyl and tetrahydrofurylsulfamoyl.

The term of "non-aromatic heterocyclylcarbamoyl" includes a group wherein one or two hydrogen atoms attached to a nitrogen atom of a carbamoyl group is replaced with the above "non-aromatic heterocyclyl". Examples are piperidinylcarbamoyl and tetrahydrofurylcarbamoyl.

Examples of substituents of "substituted or unsubstituted alkyl", "substituted or unsubstituted alkenyl", "substituted or unsubstituted alkynyl", "substituted or unsubstituted alkylene", "substituted or unsubstituted alkenylene", "substituted or unsubstituted alkynylene" and "substituted or unsubstituted alkyloxy" are the group as follows. A carbon atom at any possible position(s) can be substituted with one or more substituents selected from the following groups. Substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclyl alkyloxy, non-aromatic carbocyclyl alkyloxy, aromatic heterocyclyl alkyloxy, non-aromatic heterocyclyl alkyloxy, aromatic carbocyclyl alkyloxycarbonyl, non-aromatic carbocyclyl alkyloxycarbonyl, aromatic heterocyclyl alkyloxycarbonyl, non-aromatic heterocyclyl alkyloxycarbonyl, aromatic carbocyclyl alkylamino, non-aromatic carbocyclyl alkylamino, aromatic heterocyclyl alkylamino, non-aromatic heterocyclyl alkylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, and non-aromatic heterocyclylsulfonyl.

Examples of substituents of "substituted or unsubstituted alkyl" are one or more groups selected from the following substituent group α.

The substituent group α is a group consisting of halogen, hydroxy, alkyloxy, haloalkyloxy, hydroxyalkyloxy, alkyloxyalkyloxy, formyl, alkylcarbonyl, alkenylcarbonyl, alkynylcarbonyl, aromatic carbocyclylcarbonyl, non-aromatic carbocyclylcarbonyl, aromatic heterocyclylcarbonyl, non-aromatic heterocyclylcarbonyl, alkylcarbonyloxy, alkenylcarbonyloxy, aromatic carbocyclylcarbonyloxy, non-aromatic carbocyclylcarbonyloxy, aromatic heterocyclylcarbonyloxy, non-aromatic heterocyclylcarbonyloxy, carboxy, alkyloxycarbonyl, amino, monoalkylcarbonylamino, dialkylcarbonylamino, alkenylcarbonylamino, alkynylcarbonylamino, aromatic carbocyclylcarbonylamino, non-aromatic carbocyclylcarbonylamino, aromatic heterocyclylcarbonylamino, non-aromatic heterocyclylcarbonylamino, monoalkylamino, dialkylamino, imino, hydroxyimino, alkyloxyamino, alkylsulfanyl, carbamoyl, monoalkylcarbamoyl, dialkylcarbamoyl, hydroxyalkylcarbamoyl, sulfamoyl, monoalkylsulfamoyl, dialkylsulfamoyl, alkylsulfinyl, alkylsulfonyl, monoalkylsulfonylamino, dialkylsulfonylamino, alkylsulfonylalkylamino, alkylsulfonylimino, alkylsulfinylamino, alkylsulfinylalkylamino, alkylsulfinylimino, cyano, nitro, aromatic carbocyclyl, non-aromatic carbocyclyl, aromatic heterocyclyl and non-aromatic heterocyclyl (each of aromatic carbocycle, non-aromatic carbocycle, aromatic heterocycle and non-aromatic heterocycle is optionally substituted with one or more selected from halogen, alkyl, hydroxy and alkyloxy).

The substituents of "substituted or unsubstituted alkyl" are, for example, halogen, hydroxy and the like.

Examples of substituents of "substituted or unsubstituted alkylene", "substituted or unsubstituted alkenylene", "substituted or unsubstituted alkynylene", "substituted or unsubstituted alkyloxy", "substituted or unsubstituted alkenyl" and "substituted or unsubstituted alkynyl" are one or more selected from the above substituent group α. Specific examples are halogen, hydroxy and the like.

Examples of substituents of "substituted or unsubstituted amino" are one or two selected from alkyl, alkylcarbonyl, alkenylcarbonyl, alkynylcarbonyl, aromatic carbocyclylcarbonyl, non-aromatic carbocyclylcarbonyl, aromatic heterocyclylcarbonyl, non-aromatic heterocyclylcarbonyl, hydroxy, alkyloxy, alkyloxycarbonyl, aromatic carbocyclyl, non-aromatic carbocyclyl, aromatic heterocyclyl and non-aromatic heterocyclyl and the like. Specific examples are alkyl, alkylcarbonyl and the like.

Examples of substituents on "aromatic carbocycle", "non-aromatic carbocycle", "cycloalkyl", "aromatic heterocycle" and "non-aromatic heterocycle" of "substituted or unsubstituted aromatic carbocyclyl", "substituted or unsubstituted non-aromatic carbocyclyl", "substituted or unsubstituted cycloalkyl", "substituted or unsubstituted aromatic heterocyclyl", and "substituted or unsubstituted non-aromatic heterocyclyl" include the group as follows. One or more atoms at any possible position(s) on each ring can be substituted with one or more substituents selected from the following group.

Substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxy carbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclylalkylamino, aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

A "substituted or unsubstituted non-aromatic carbocyclyl" and "substituted or unsubstituted non-aromatic heterocyclyl" can be substituted with "oxo". A group wherein two hydrogen atoms attached to the same carbon atom are replaced with oxo as follows is included:

[Chemical Formula 41]

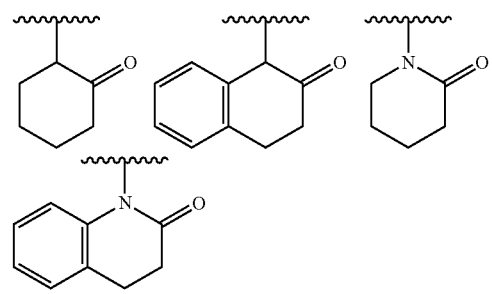

Examples of the substituent of "substituted or unsubstituted aromatic carbocycle", "substituted or unsubstituted non-aromatic carbocycle", "substituted or unsubstituted aromatic heterocycle", "substituted or unsubstituted non-aromatic heterocycle", "substituted or unsubstituted benzene" and "substituted or unsubstituted pyridine" in ring A and ring B include (a) a group selected from the substituent group α, for example, halogen, hydroxy, alkyloxy, formyl, alkylcarbonyl, alkenylcarbonyl, alkynylcarbonyl, aromatic carbocyclylcarbonyl, non-aromatic carbocyclylcarbonyl, aromatic heterocyclylcarbonyl, non-aromatic heterocyclylcarbonyl, formyloxy, alkylcarbonyloxy, alkenylcarbonyloxy, alkynylcarbonyloxy, aromatic carbocyclylcarbonyloxy, non-aromatic carbocyclylcarbonyloxy, aromatic heterocyclic carbonyloxy, non-aromatic heterocyclic carbonyloxy, carboxy, alkyloxycarbonyl, carbamoyl, amino, cyano, monoalkylamino, dialkylamino and/or alkylsulfanyl;

(b) unsubstituted alkyl or alkyl substituted with one or more groups selected from the substituent group α, hydroxyimino and alkyloxyimino;

(c) aminoalkyl substituted with one or more groups selected from the substituent group α;

(d) unsubstituted alkenyl or alkenyl substituted with one or more substituents selected from the substituent group α;

(e) unsubstituted alkynyl or alkynyl substituted with one or more substituents selected from the substituent group α;

(f) alkyloxy substituted with one or more substituents selected from the substituent group α;

(g) alkyloxyalkyloxy substituted with one or more substituents selected from the substituent group α;

(h) unsubstituted alkenyloxy or alkenyloxy substituted with one or more substituents selected from the substituent group α;

(i) alkyloxyalkenyloxy substituted with one or more substituents selected from the substituent group α;

(j) unsubstituted alkynyloxy or alkynyloxy substituted with one or more substituents selected from the substituent group α;

(k) alkyloxyalkynyloxy substituted with one or more groups selected from the substituent group α;

(l) unsubstituted alkylsulfanyl or alkylsulfanyl substituted with one or more substituents selected from the substituent group α;

(m) unsubstituted alkenylsulfanyl or alkenylsulfanyl substituted with one or more substituents selected from the substituent group α;
(n) unsubstituted alkynylsulfanyl or alkynylsulfanyl substituted with one or more substituents selected from the substituent group α; or;
(o) monoalkylamino substituted with one or more substituents selected from the substituent group α;
(p) dialkylamino substituted with one or more substituents selected from the substituent group α;
(q) alkenylamino substituted with one or more substituents selected from the substituent group α;
(r) alkynylamino substituted with one or more substituents selected from the substituent group α;
(s) unsubstituted aminooxy or aminooxy substituted with one or more substituents selected from the substituent group α and alkylidene;
(t) alkylcarbonyl substituted with one or more substituents selected from the substituent group α;
(u) alkenylcarbonyl substituted with one or more substituents selected from the substituent group α;
(v) alkynylcarbonyl substituted with one or more substituents selected from the substituent group α;
(w) aromatic carbocyclylcarbonyl substituted with one or more substituents selected from the substituent group α;
(x) non-aromatic carbocyclylcarbonyl substituted with one or more substituents selected from the substituent group α;
(y) aromatic heterocyclylcarbonyl substituted with one or more substituents selected from the substituent group α;
(z) non-aromatic heterocyclylcarbonyl substituted with one or more substituents selected from the substituent group α;
(aa) monoalkylcarbamoyl substituted with one or more substituents selected from the substituent group α;
(ab) dialkylcarbamoyl substituted with one or more substituents selected from the substituent group α;
(ac) alkyloxycarbonyl substituted with one or more substituents selected from the substituent group α;
(ad) unsubstituted alkylsulfonyl or alkylsulfonyl substituted with one or more substituents selected from the substituent group α;
(ae) unsubstituted alkylsulfinyl or alkylsulfinyl substituted with one or more substituents selected from the substituent group α;
(af) monoalkylsulfamoyl substituted with one or more substituents selected from the substituent group α;
(ag) dialkylsulfamoyl substituted with one or more substituents selected from the substituent group α;
(ah) aromatic carbocyclyl substituted with one or more substituents selected from the substituent group α, azide, alkyl and haloalkyl;
(ai) non-aromatic carbocyclyl substituted with one or more substituents selected from the substituent group α, azide, alkyl and haloalkyl;
(aj) aromatic heterocyclyl substituted with one or more substituents selected from the substituent group α, azide, alkyl and haloalkyl;
(ak) non-aromatic heterocyclyl substituted with one or more substituents selected from the substituent group α, azide, alkyl and haloalkyl;
(al) unsubstituted aromatic carbocyclylalkyl or aromatic carbocyclylalkyl substituted with one or more substituents selected from the substituent group α, azide, alkyl and haloalkyl;
(am) unsubstituted non-aromatic carbocyclylalkyl or non-aromatic carbocyclylalkyl substituted with one or more substituents selected from the substituent group α, azide, alkyl and haloalkyl;
(an) unsubstituted aromatic heterocyclylalkyl or aromatic heterocyclylalkyl substituted with one or more substituents selected from the substituent group α, azide, alkyl and haloalkyl;
(ao) unsubstituted non-aromatic heterocyclylalkyl or non-aromatic heterocyclylalkyl substituted with one or more substituents selected from the substituent group α, azide, alkyl and haloalkyl;
(ap) unsubstituted aromatic carbocyclyloxy or aromatic carbocyclyloxy substituted with one or more substituents selected from the substituent group α, azide, alkyl and haloalkyl;
(aq) unsubstituted non-aromatic carbocyclyloxy or non-aromatic carbocyclyloxy substituted with one or more substituents selected from the substituent group α, azide, alkyl and haloalkyl;
(ar) unsubstituted aromatic heterocyclyloxy or aromatic heterocyclyloxy substituted with one or more substituents selected from the substituent group α, azide, alkyl and haloalkyl;
(as) unsubstituted non-aromatic heterocyclyloxy or non-aromatic heterocyclyloxy substituted with one or more substituents selected from the substituent group α, azide, alkyl and haloalkyl;
(at) unsubstituted aromatic carbocyclylalkyloxy or aromatic carbocyclylalkyloxy substituted with one or more substituents selected from the substituent group α, azide, alkyl and haloalkyl;
(au) unsubstituted non-aromatic carbocyclylalkyloxy or non-aromatic carbocyclylalkyloxy substituted with one or more substituents selected from the substituent group α, azide, alkyl and haloalkyl;
(av) unsubstituted aromatic heterocyclylalkyloxy or aromatic heterocyclylalkyloxy substituted with one or more substituents selected from the substituent group α, azide, alkyl and haloalkyl;
(aw) unsubstituted non-aromatic heterocyclylalkyloxy or non-aromatic heterocyclylalkyloxy substituted with one or more substituents selected from the substituent group α, azide, alkyl and haloalkyl;
(ax) unsubstituted aromatic carbocyclylalkyloxycarbonyl or aromatic carbocyclylalkyloxycarbonyl substituted with one or more substituents selected from the substituent group α, azide, alkyl and haloalkyl;
(ay) unsubstituted non-aromatic carbocyclylalkyloxycarbonyl or non-aromatic carbocyclylalkyloxycarbonyl substituted with one or more substituents selected from the substituent group α, azide, alkyl and haloalkyl;
(az) unsubstituted aromatic heterocyclylalkyloxycarbonyl or aromatic heterocyclylalkyloxycarbonyl substituted with one or more substituents selected from the substituent group α, azide, alkyl and haloalkyl;
(ba) unsubstituted non-aromatic heterocyclylalkyloxycarbonyl or non-aromatic heterocyclylalkyloxycarbonyl substituted with one or more substituents selected from the substituent group α, azide, alkyl and haloalkyl;
(bb) unsubstituted aromatic carbocyclylsulfanyl or aromatic carbocyclylsulfanyl substituted with one or more substituents selected from the substituent group α, azide, alkyl and haloalkyl;
(bc) unsubstituted non-aromatic carbocyclylsulfanyl or non-aromatic carbocyclylsulfanyl substituted with one or more substituents selected from the substituent group α, azide, alkyl and haloalkyl;

(bd) unsubstituted aromatic heterocyclylsulfanyl or aromatic heterocyclylsulfanyl substituted with one or more substituents selected from the substituent group α, azide, alkyl and haloalkyl;

(be) unsubstituted non-aromatic heterocyclylsulfanyl or non-aromatic heterocyclylsulfanyl substituted with one or more substituents selected from the (bf) substituent group α, azide, alkyl and haloalkyl;

(bf) unsubstituted aromatic carbocyclylamino or aromatic carbocyclylamino substituted with one or more substituents selected from the substituent group α, azide, alkyl and haloalkyl;

(bg) unsubstituted non-aromatic carbocyclylamino or non-aromatic carbocyclylamino substituted with one or more substituents selected from the substituent group α, azide, alkyl and haloalkyl;

(bh) unsubstituted aromatic heterocyclylamino or aromatic heterocyclylamino substituted with one or more substituents selected from the substituent group α, azide, alkyl and haloalkyl;

(bi) unsubstituted non-aromatic heterocyclylamino or non-aromatic heterocyclylamino substituted with one or more substituents selected from the substituent group α, azide, alkyl and haloalkyl;

(bj) unsubstituted aromatic carbocyclylalkylamino or aromatic carbocyclylalkylamino substituted with one or more substituents selected from the substituent group α, azide, alkyl and haloalkyl;

(bk) unsubstituted non-aromatic carbocyclylalkylamino or non-aromatic carbocyclylalkylamino substituted with one or more substituents selected from the substituent group α, azide, alkyl and haloalkyl;

(bl) unsubstituted aromatic heterocyclylalkylamino or aromatic heterocyclylalkylamino substituted with one or more substituents selected from the substituent group α, azide, alkyl and haloalkyl;

(bm) unsubstituted non-aromatic heterocyclylalkylamino or non-aromatic heterocyclylalkylamino substituted with one or more substituents selected from the substituent group α, azide, alkyl and haloalkyl;

(bn) unsubstituted aromatic carbocyclylsulfamoyl or aromatic carbocyclylsulfamoyl substituted with one or more substituents selected from the substituent group α, azide, alkyl and haloalkyl;

(bo) unsubstituted non-aromatic carbocyclylsulfamoyl or non-aromatic carbocyclylsulfamoyl substituted with one or more substituents selected from the substituent group α, azide, alkyl and haloalkyl;

(bp) unsubstituted aromatic heterocyclylsulfamoyl or aromatic heterocyclylsulfamoyl substituted with one or more substituents selected from the substituent group α, azide, alkyl and haloalkyl;

(bq) unsubstituted non-aromatic heterocyclylsulfamoyl or non-aromatic heterocyclylsulfamoyl substituted with one or more substituents selected from the substituent group α, azide, alkyl and haloalkyl;

(br) unsubstituted aromatic carbocyclylsulfonyl or aromatic carbocyclylsulfonyl substituted with one or more substituents selected from the substituent group α, azide, alkyl and haloalkyl;

(bs) unsubstituted non-aromatic carbocyclylsulfonyl or non-aromatic carbocyclylsulfonyl substituted with one or more substituents selected from the substituent group α, azide, alkyl and haloalkyl;

(bt) unsubstituted aromatic heterocyclylsulfonyl or aromatic heterocyclylsulfonyl substituted with one or more substituents selected from the substituent group α, azide, alkyl and haloalkyl;

(bu) unsubstituted non-aromatic heterocyclylsulfonyl or non-aromatic heterocyclylsulfonyl substituted with one or more substituents selected from the substituent group α, azide, alkyl and haloalkyl;

(bv) unsubstituted aromatic carbocyclylcarbamoyl or aromatic carbocyclylcarbamoyl substituted with one or more substituents selected from the substituent group α, azide, alkyl and haloalkyl;

(bw) unsubstituted non-aromatic carbocyclylcarbamoyl or non-aromatic carbocyclylcarbamoyl substituted with one or more substituents selected from the substituent group α, azide, alkyl and haloalkyl;

(bx) unsubstituted aromatic heterocyclylcarbamoyl or aromatic heterocyclylcarbamoyl substituted with one or more substituents selected from the substituent group α, azide, alkyl and haloalkyl;

(by) unsubstituted non-aromatic heterocyclylcarbamoyl or non-aromatic heterocyclylcarbamoyl substituted with one or more substituents selected from the substituent group α, azide, alkyl and haloalkyl;

(bz) unsubstituted aromatic carbocyclylalkylcarbamoyl or aromatic carbocyclylalkylcarbamoyl substituted with one or more substituents selected from the substituent group α, azide, alkyl and haloalkyl;

(ca) unsubstituted non-aromatic carbocyclylalkylcarbamoyl or non-aromatic carbocyclylalkylcarbamoyl substituted with one or more substituents selected from the substituent group α, azide, alkyl and haloalkyl;

(cb) unsubstituted aromatic heterocyclylalkylcarbamoyl or aromatic heterocyclylalkylcarbamoyl substituted with one or more substituents selected from the substituent group α, azide, alkyl and haloalkyl;

(cc) unsubstituted non-aromatic heterocyclylalkylcarbamoyl or non-aromatic heterocyclylalkylcarbamoyl substituted with one or more substituents selected from the substituent group α, azide, alkyl and haloalkyl;

(cd) unsubstituted aromatic carbocyclyloxycarbonyl or aromatic carbocyclyloxycarbonyl substituted with one or more substituents selected from the substituent group α, azide, alkyl and haloalkyl;

(ce) unsubstituted non-aromatic carbocyclyloxycarbonyl or non-aromatic carbocyclyloxycarbonyl substituted with one or more substituents selected from the substituent group α, azide, alkyl and haloalkyl;

(cf) unsubstituted aromatic heterocyclyloxycarbonyl or aromatic heterocyclyloxycarbonyl substituted with one or more substituents selected from the substituent group α, azide, alkyl and haloalkyl;

(cg) unsubstituted non-aromatic heterocyclyloxycarbonyl or non-aromatic heterocyclyloxycarbonyl substituted with one or more substituents selected from the substituent group α, azide, alkyl and haloalkyl;

(ch) unsubstituted alkylenedioxy or alkylenedioxy substituted with halogen;

(ci) oxo; and (cj) azide.

Each cyclic group in "substituted or unsubstituted aromatic carbocycle", "substituted or unsubstituted non-aromatic carbocycle", "substituted or unsubstituted benzene", "substituted or unsubstituted aromatic heterocycle", "substituted or unsubstituted non-aromatic heterocycle" and "substituted or unsubstituted pyridine" may be substituted with one or more substituents selected from the above substituents.

Examples of substituents of "substituted or unsubstituted aromatic carbocycle", "substituted or unsubstituted non-aromatic carbocycle", "substituted or unsubstituted benzene", "substituted or unsubstituted aromatic heterocycle", "substituted or unsubstituted non-aromatic heterocycle" and "substituted or unsubstituted pyridine" are one or more selected from
halogen;
cyano;
hydroxy;
nitro;
carboxy;
alkyl substituted with one or more substituents selected from the substituent group α,
unsubstituted alkyl;
alkenyl substituted with one or more substituents selected from the substituent group α,
unsubstituted alkenyl;
alkynyl substituted with one or more substituents selected from the substituent group α,
unsubstituted alkynyl;
alkyloxy substituted with one or more substituents selected from the substituent group α,
unsubstituted alkyloxy;
alkenyloxy substituted with one or more substituents selected from the substituent group α,
unsubstituted alkenyloxy;
alkynyloxy substituted with one or more substituents selected from the substituent group α,
unsubstituted alkynyloxy;
alkylsulfanyl substituted with one or more substituents selected from the substituent group α,
unsubstituted alkylsulfanyl;
alkenylsulfanyl substituted with one or more substituents selected from the substituent group α,
unsubstituted alkenylsulfanyl;
alkynylsulfanyl substituted with one or more substituents selected from the substituent group α,
unsubstituted alkynylsulfanyl;
amino substituted with one or more substituents selected from the substituent group α,
unsubstituted amino;
monoalkylamino substituted with one or more substituents selected from the substituent group α,
unsubstituted monoalkylamino;
dialkylamino substituted with one or more substituents selected from the substituent group α,
unsubstituted dialkylamino;
cycloalkylamino substituted with one or more substituents selected from the substituent group α,
unsubstituted cycloalkylamino;
carbamoyl substituted with one or more substituents selected from the substituent group α,
unsubstituted carbamoyl;
monoalkylcarbamoyl substituted with one or more substituents selected from the substituent group α,
unsubstituted monoalkylcarbamoyl;
dialkylcarbamoyl substituted with one or more substituents selected from the substituent group α,
unsubstituted dialkylcarbamoyl;
alkyloxycarbonyl substituted with one or more substituents selected from the substituent group α,
unsubstituted alkyloxycarbonyl;
an aromatic carbocyclyl substituted with one or more substituents selected from the substituent group α, unsubstituted alkyl, and alkyl substituted with one or more substituents selected from the substituent group α;
an unsubstituted aromatic carbocyclyl;
a non-aromatic carbocyclyl substituted with one or more substituents selected from the substituent group α, unsubstituted alkyl, and alkyl substituted with one or more substituents selected from the substituent group α;
a non-unsubstituted aromatic carbocyclyl;
aromatic heterocyclyl substituted with one or more substituents selected from the substituent group α, unsubstituted alkyl, and alkyl substituted with one or more substituents selected from the substituent group α;
unsubstituted aromatic heterocyclyl;
non-aromatic heterocyclyl substituted with one or more substituents selected from the substituent group α, unsubstituted alkyl, and alkyl substituted with one or more substituents selected from the substituent group α; and
non-unsubstituted aromatic heterocyclyl.

In one embodiment, substituents are one or more selected from halogen, cyano, hydroxy, alkyl, haloalkyl, cycloalkylalkyl, alkyloxy, haloalkyloxy, alkyloxyalkyloxy, cyanoalkyloxy, alkenyl, haloalkenyl, alkynyl, haloalkynyl, alkenyloxy, alkynyloxy, alkylsulfanyl, cyanoalkylsulfanyl, amino, monoalkylamino, dialkylamino, cycloalkylamino and cycloalkyl.

In another embodiment, substituents are one or more selected from halogen, cyano, alkyl, haloalkyl, alkyloxy and haloalkyloxy.

In another embodiment, substituents of ring A is halogen.

In one embodiment, the substituents of "substituted or unsubstituted cycloalkyl" are one or more selected from the substituent group α, unsubstituted alkyl and alkyl substituted with one or more substituents selected from the substituent group α.

In another embodiment, "substituted or unsubstituted cycloalkyl" is unsubstituted cycloalkyl.

When X is —C($R^{3a}$)($R^{3b}$)—C($R^{3c}$)($R^{3d}$)— or —C($R^{3a}$)=C($R^{3c}$)—, then the carbon atom connected to $R^{3a}$ is adjacent to the carbon atom connected to $R^{2a}$.

When L is —C(=O)NH—, then a carbonyl group binds to ring B.

When L is -$L^1$-NH-$L^2$-, then $L^1$ binds to ring B.

The phrase "$R^{2a}$ and $R^{3a}$ attached to adjacent carbon atoms, together with the carbon atoms to which they are attached, may form

[Chemical Formula 42]

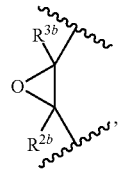
(i)

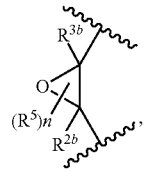
(ii)

-continued
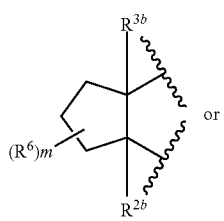 or
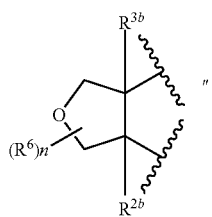 "
includes
[Chemical Formula 43]
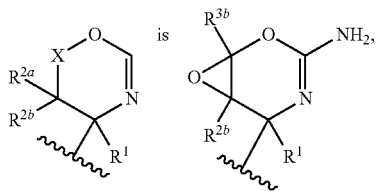
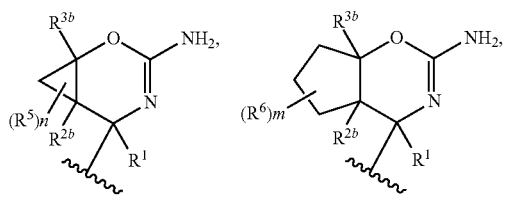
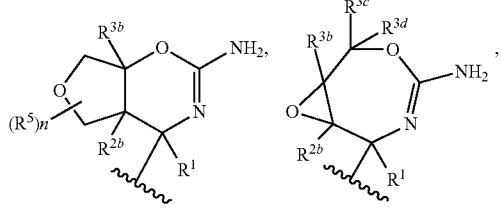
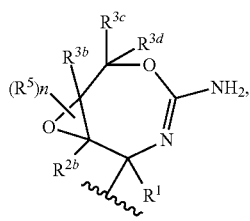
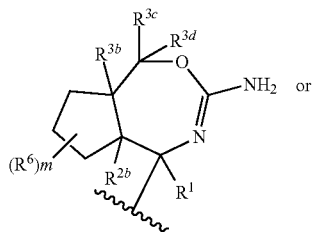
-continued
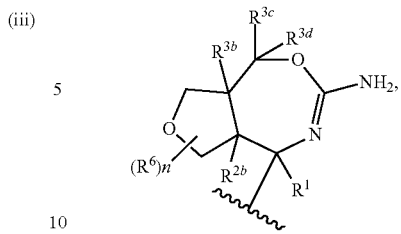
wherein each symbol is the same as defined above.
The phrase "$R^{3a}$ and $R^{3b}$ together with the carbon atom to which they are attached may form
[Chemical Formula 44]
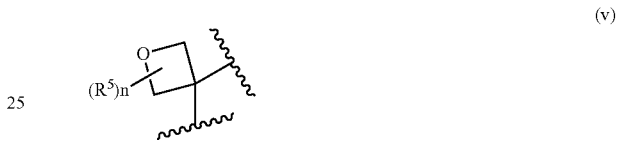
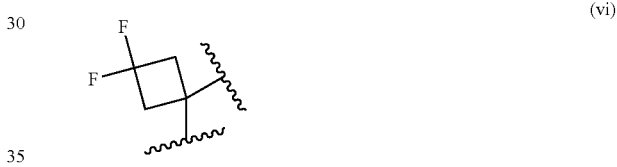
includes
[Chemical Formula 45]
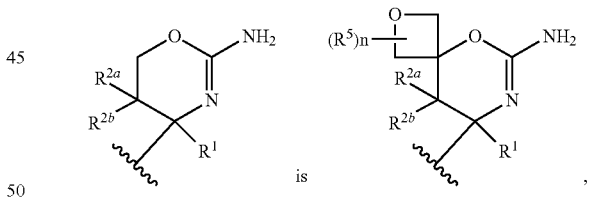
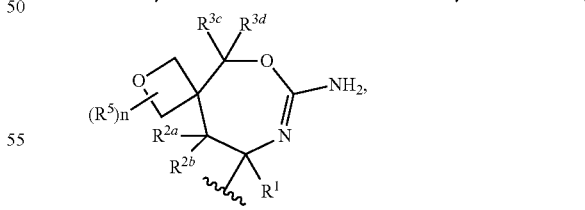
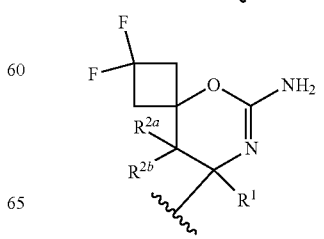
or -continued

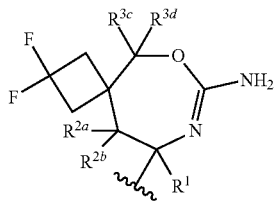

wherein each symbol is the same as defined above.

The phrase "$R^1$ and $R^{2a}$ together with the carbon atoms to which they are attached, may form

[Chemical Formula 46]

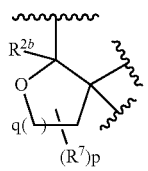

(vii)

includes

[Chemical Formula 47]

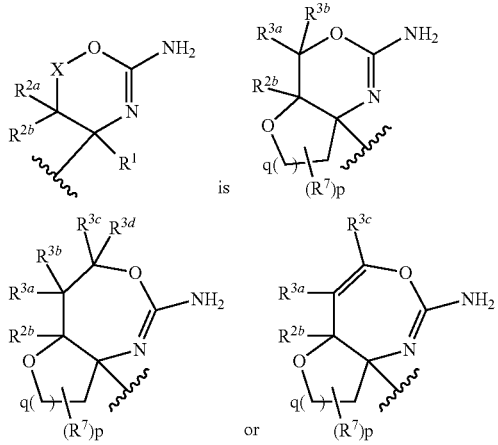

wherein each symbol is the same as defined above.

The phrase "when $R^1$ and $R^{2a}$ together with the carbon atoms to which they are attached form the above (vii), then $R^{3a}$ and $R^{3b}$ together with the carbon atom to which they are attached may form

[Chemical Formula 48]

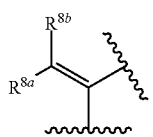

(viii)

includes

[Chemical Formula 49]

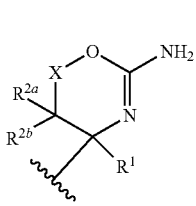 is 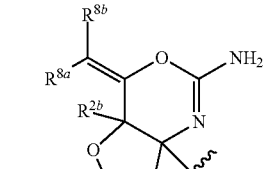 or

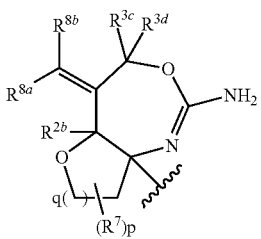

wherein each symbol is the same as defined above.

In case that plural $R^5$, plural $R^6$ or plural $R^7$ are exist, each $R^5$, each $R^6$, each $R^7$ may be the same or different.

Specific embodiments of the present invention are illustrated below. The compound of the following formulas (IA) to (IO):

[Chemical Formula 50]

(IA)

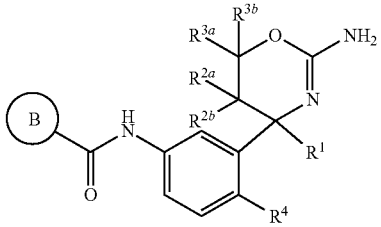

(IB)

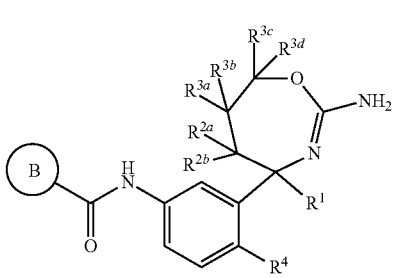

(IC)

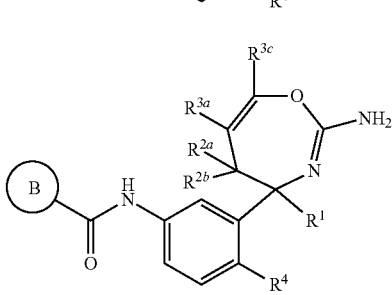

-continued

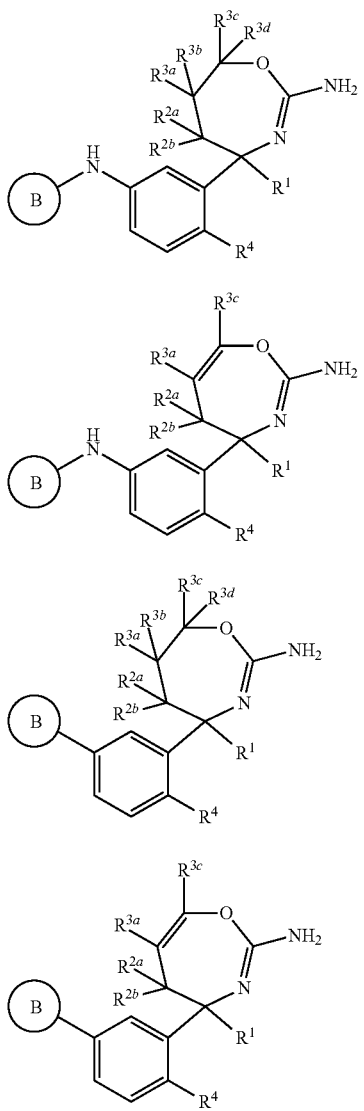

(ID)

(IE)

(IF)

(IG)

[Chemical Formula 51]

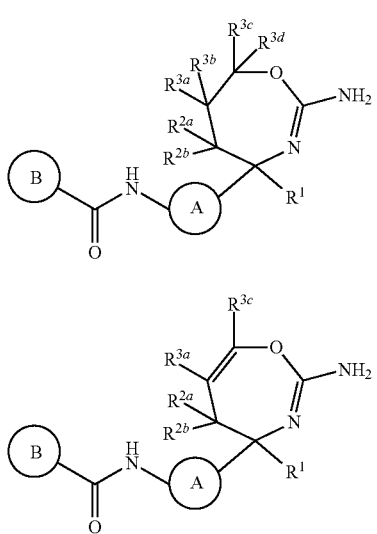

(IH)

(II)

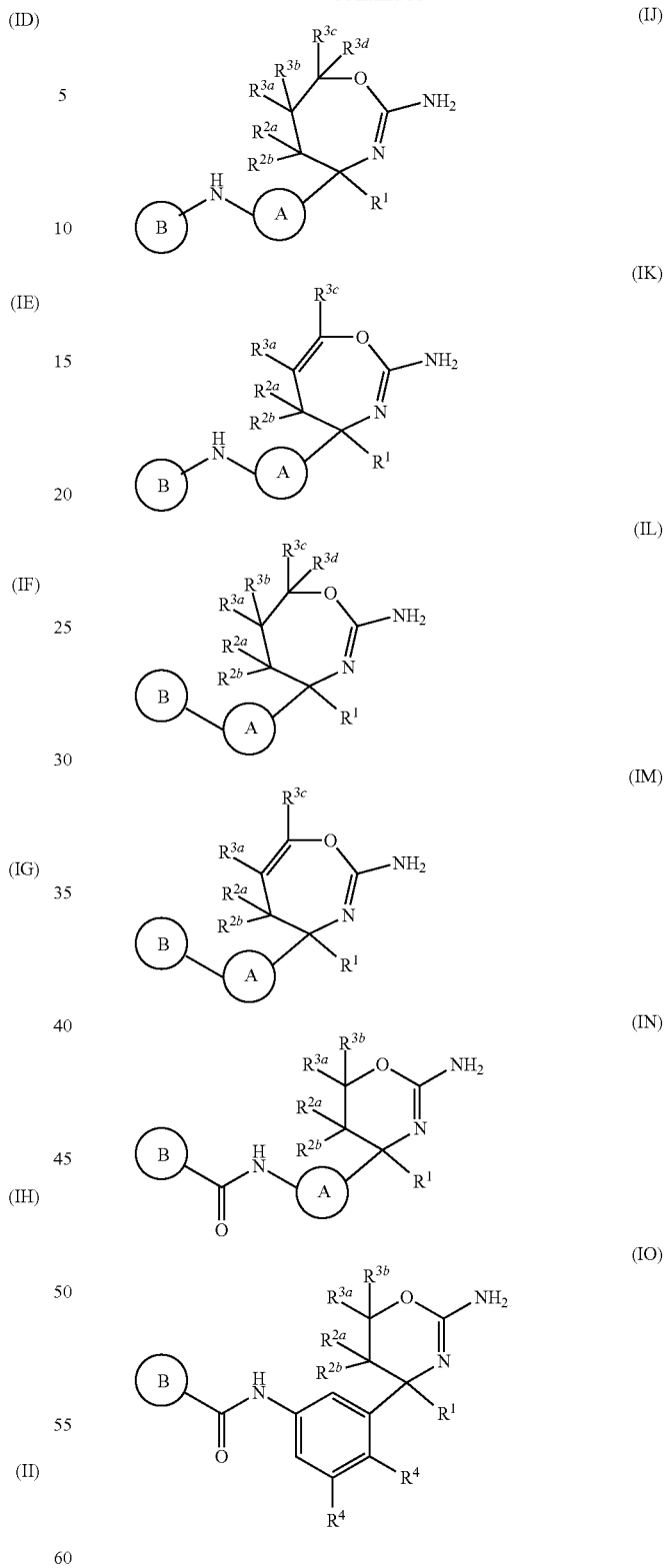

(IJ)

(IK)

(IL)

(IM)

(IN)

(IO)

wherein each symbol is the same as defined above, or a pharmaceutically acceptable salt thereof.

Specific embodiments of each symbol are illustrated below. All combination of these embodiments are examples of the compounds of formulas (I) and (IA) to (IO).

In any of the formula (I), (IA) to (IO), preferably (IA) or (IB), and preferably (IA), $R^1$ is alkyl, haloalkyl, alkenyl, haloalkenyl, alkynyl, haloalkynyl or cycloalkyl (hereinafter referred to as R11).

$R^1$ is alkyl, haloalkyl alkynyl or cycloalkyl (hereinafter referred to as R12).

$R^1$ is haloalkyl (hereinafter referred to as R13).

$R^1$ is alkynyl (hereinafter referred to as R14).

$R^1$ is cycloalkyl (hereinafter referred to as R15).

$R^1$ is alkyl (hereinafter referred to as R16).

$R^1$ is $CH_2F$, $CHF_2$, or $CF_3$ (hereinafter referred to as R17).

$R^1$ is $CH_2F$ or $CHF_2$ (hereinafter referred to as R18).

$R^4$ is hydrogen (hereinafter referred to as R41).

$R^4$ is halogen (hereinafter referred to as R42).

$R^{2a}$, $R^{2b}$, $R^{3a}$, $R^{3b}$, $R^{3c}$ and $R^{3d}$ are hydrogen (provided that $R^{3c}$ and $R^{3d}$ are absence in the compound of the above formulas (IA), (IN) and (IO), and $R^{3b}$ and $R^{3d}$ are absence in the compounds of formulas (IC), (IE), (IG), (II), (IK) and (IM). Hereinafter referred to as R231).

$R^{2a}$, $R^{2b}$, $R^{3a}$, $R^{3c}$ and $R^{3d}$ are hydrogen, and $R^{3b}$ is halogen, substituted or unsubstituted alkyl, substituted or unsubstituted alkenyl, cyano or substituted or unsubstituted cycloalkyl (provided that $R^{3c}$ and $R^{3d}$ are absence in the compound of the above formulas (IA), (IN) and (IO), and $R^{3b}$ and $R^{3d}$ are absence in formulas (IC), (IE), (IG), (II), (IK) and (IM). Hereinafter referred to as R232).

$R^{2a}$, $R^{2b}$, $R^{3c}$ and $R^{3d}$ are hydrogen and, both of $R^{3a}$ and $R^{3b}$ are alkyl (provided that $R^{3c}$ and $R^{3d}$ are absence in the compound of the above formulas (IA), (IN) and (IO), and $R^{3b}$ and $R^{3d}$ are absence in the compounds of formulas of (IC), (IE), (IG), (II), (IK) and (IM) Hereinafter referred to as R233).

At least one of the existing $R^{2a}$, $R^{2b}$, $R^{3a}$, $R^{3b}$, $R^{3c}$ and $R^{3d}$ is halogen, substituted or unsubstituted alkyl, substituted or unsubstituted alkenyl, cyano or substituted or unsubstituted cycloalkyl (provided that $R^{3c}$ and $R^{3d}$ are absence in the compound of formulas (IA), (IN) and (IO), and $R^{3b}$ and $R^{3d}$ are absence in formulas (IC), (IE), (IG), (II), (IK) and (IM). Hereinafter referred to as R234).

At least one of the existing $R^{2a}$, $R^{2b}$, $R^{3a}$, $R^{3b}$, $R^{3c}$ and $R^{3d}$ is halogen or substituted or unsubstituted alkyl (provided that $R^{3c}$ and $R^{3d}$ are absence in the compound of formulas (IA), (IN) and (IO), and $R^{3b}$ and $R^{3d}$ are absence in the compounds of formulas (IC), (IE), (IG), (II), (IK) and (IM). Hereinafter referred to as R235).

At least one of the existing $R^{2a}$, $R^{2b}$, $R^{3a}$, $R^{3b}$, $R^{3c}$ and $R^{3d}$ is substituted or unsubstituted alkyl wherein the substituents are selected from one or more substituents selected from halogen and hydroxy (provided that $R^{3c}$ and $R^{3d}$ are absence in the compound of formulas (IA), (IN) and (IO), and $R^{3b}$ and $R^{3d}$ are absence in the compounds of formulas (IC), (IE), (IG), (II), (IK) and (IM). Hereinafter referred to as R236).

At least one of the existing $R^{2a}$, $R^{2b}$, $R^{3a}$, $R^{3b}$, $R^{3c}$ and $R^{3d}$ is substituted or unsubstituted alkyl wherein the substituents are selected from one or more substituents selected from halogen and the others of the existing $R^{2a}$, $R^{2b}$, $R^{3a}$, $R^{3b}$, $R^{3c}$ and $R^{3d}$ are hydrogen, halogen or alkyloxy (provided that $R^{3c}$ and $R^{3d}$ are absence in the compounds of formulas (IA), (IN) and (IO), and $R^{3b}$ and $R^{3d}$ are absence in the compounds of formulas (IC), (IE), (IG), (II), (IK) and (IM). Hereinafter referred to as R237).

One of $R^{2a}$ and $R^{2b}$ is halogen and the other is hydrogen, one of $R^{3a}$, $R^{3b}$, $R^{3c}$ and $R^{3d}$ is haloalkyl and the others are hydrogen (provided that $R^{3c}$ are $R^{3d}$ are absence in the compound of the formula (IA), (IN) and (IO), and $R^{3b}$ and $R^{3d}$ are absence in the compounds of the formulas (IC), (IE), (IG), (II), (IK) and (IM). Hereinafter referred to as R238).

One of $R^{2a}$ and $R^{2b}$ is halogen or alkyloxy and the other is hydrogen, one of $R^{3a}$, $R^{3b}$, $R^{3c}$ and $R^{3d}$ is haloalkyl and the others are hydrogen (provided that $R^{3c}$ and $R^{3d}$ are absence in the compound of formulas (IA), (IN) and (IO), and $R^{3b}$ and $R^{3d}$ are absence in the compounds of formulas (IC), (IE), (IG), (II), (IK) and (IM).

Hereinafter referred to as R239).

One of $R^{2a}$ and $R^{2b}$ is halogen or alkyloxy and the other is hydrogen, one of $R^{3a}$ and $R^{3b}$ is $CH_2F$ or $CHF_2$ and the other is hydrogen, $R^{3c}$ and $R^{3d}$ are hydrogen (provided that $R^{3c}$ and $R^{3d}$ are absence in the compound of formulas (IA), (IN) and (IO), and $R^{3b}$ and $R^{3d}$ are absence in the compounds of formulas (IC), (IE), (IG), (II), (IK) and (IM). Hereinafter referred to as R2310).

Both of $R^{2a}$ and $R^{2b}$ are hydrogen, one of $R^{3a}$, $R^{3b}$, $R^{3c}$ and $R^{3d}$ is haloalkyl and the others are hydrogen (provided that $R^{3c}$ and $R^{3d}$ are absence in the compound of formulas (IA), (IN) and (IO), and $R^{3b}$ and $R^{3d}$ are absence in the compounds of formulas (IC), (IE), (IG), (II), (IK) and (IM). Hereinafter referred to as R2311).

[Chemical Formula 52]

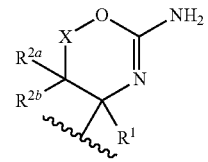 means

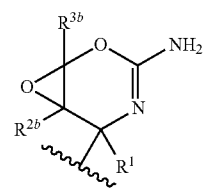 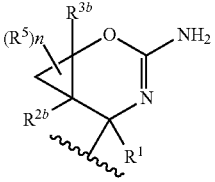

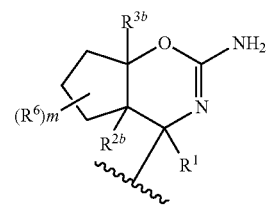 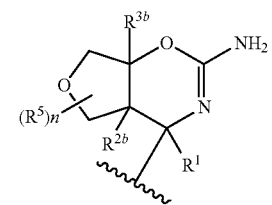

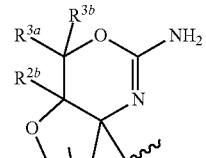 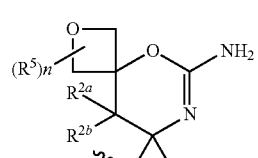

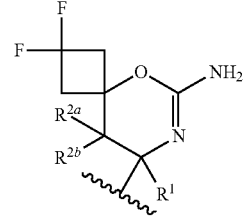 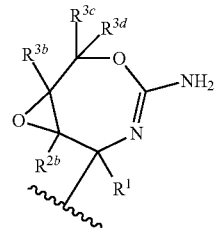

-continued

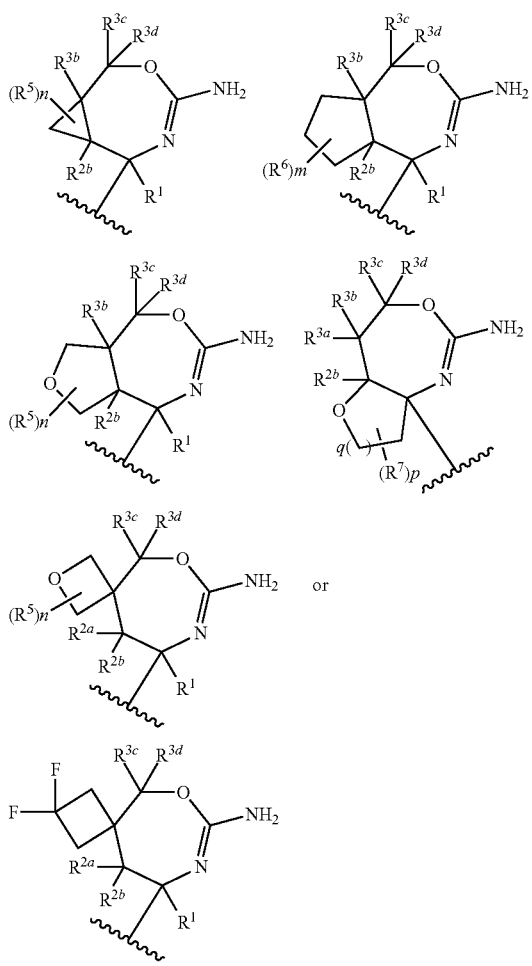

wherein $R^{2a}$, $R^{2b}$, $R^{3b}$, $R^{3c}$, $R^{3d}$, $R^5$, $R^6$, $R^7$, n, m and p are the same as defined above (hereinafter referred to as R2312).

[Chemical Formula 53]

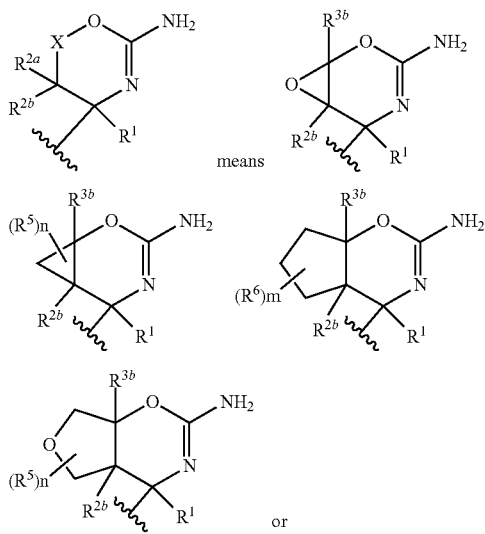

-continued

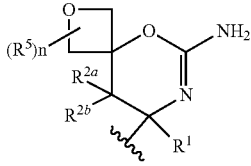

wherein $R^{2a}$, $R^{2b}$, $R^{3b}$, $R^5$, R6, n and m are the same as defined above (hereinafter referred to as R2313).

Ring B is a substituted or unsubstituted aromatic carbocycle, a substituted or unsubstituted non-aromatic carbocycle, a substituted or unsubstituted aromatic heterocycle or a substituted or unsubstituted non-aromatic heterocycle (hereinafter referred to as B1).

Ring B is a substituted or unsubstituted aromatic heterocycle or a substituted or unsubstituted non-aromatic heterocycle (hereinafter referred to as B2).

Ring B is a substituted or unsubstituted aromatic heterocycle (hereinafter referred to as B3).

Ring B is substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzene, substituted or unsubstituted benzoxazole, substituted or unsubstituted benzothiazole (hereinafter referred to as B4).

Ring B is a group of the following formula (hereinafter referred to as B5):

[Chemical Formula 54]

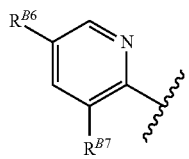

wherein $R^{B6}$ is halogen or cyano, and $R^{B7}$ is hydrogen, substituted or unsubstituted alkyl, halogen, hydroxy, substituted or unsubstituted amino or substituted or unsubstituted cycloalkyl.

Ring B is a group of the following formula (hereinafter referred to as B6).

[Chemical Formula 55]

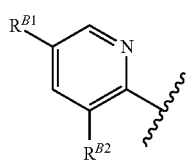

wherein $R^{B1}$ is halogen or cyano, and $R^{B2}$ is substituted or unsubstituted alkyl, halogen, hydroxy, substituted or unsubstituted amino or substituted or unsubstituted cycloalkyl.

Ring B s a group of the following formula (hereinafter referred to as B7).

[Chemical Formula 56]

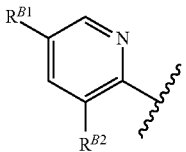

wherein $R^{B1}$ is halogen or cyano, and $R^{B2}$ is substituted or unsubstituted alkyl, Ring B s a group of the following formula (hereinafter referred to as B8).

[Chemical Formula 57]

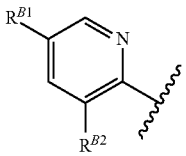

wherein $R^{B1}$ is cyano, and $R^{B2}$ is alkyl, ring B is a group of the following formula (hereinafter referred to as B9).

[Chemical Formula 58]

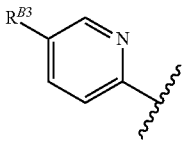

wherein $R^{B3}$ is halogen.

ring B is a group of the following formula (hereinafter referred to as B10).

[Chemical Formula 59]

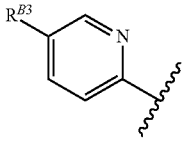

wherein $R^{B3}$ is cyano.

Ring B is a group of the following formula (hereinafter referred to as B11).

[Chemical Formula 60]

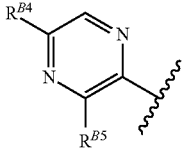

wherein $R^{B4}$ is substituted or unsubstituted alkyl or substituted or unsubstituted alkyloxy, and $R^{B5}$ is hydrogen or substituted or unsubstituted amino.

Ring B is a group of the following formula (hereinafter referred to as B12).

[Chemical Formula 61]

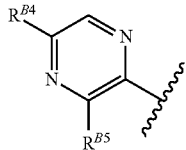

wherein $R^{B4}$ is substituted or unsubstituted alkyloxy and $R^{B5}$ is hydrogen or substituted or unsubstituted amino.

Ring B is a group of the following formula (hereinafter referred to as B13).

[Chemical Formula 62]

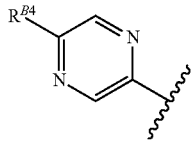

wherein $R^{B4}$ is alkyloxy or haloalkyloxy.

Ring B is pyridine, pyrimidine, pyrazine, oxazole, thiazole, pyrazole, benzene, benzoxazole or benzothiazole wherein each ring is optionally substituted with one or more substituents selected from the following groups (hereinafter referred to as B14):

halogen;
cyano;
hydroxy;
nitro;
alkyl substituted with one or more substituents selected from the substituent group α;
unsubstituted alkyl;
alkenyl substituted with one or more substituents selected from the substituent group α;
unsubstituted alkenyl;
alkynyl substituted with one or more substituents selected from the substituent group α;
unsubstituted alkynyl;
alkyloxy substituted with one or more substituents selected from the substituent group α;
unsubstituted alkyloxy;
alkenyloxy substituted with one or more substituents selected from the substituent group α;
unsubstituted alkenyloxy;
alkynyloxy substituted with one or more substituents selected from the substituent group α;
unsubstituted alkynyloxy;
alkynylsulfanyl substituted with one or more substituents selected from the substituent group α;
unsubstituted alkylsulfanyl;
alkenylsulfanyl substituted with one or more substituents selected from the substituent group α;
unsubstituted alkenylsulfanyl;
alkynylsulfanyl substituted with one or more substituents selected from the substituent group α;
unsubstituted alkynylsulfanyl;
unsubstituted amino;
monoalkylamino substituted with one or more substituents selected from the substituent group α;

unsubstituted monoalkylamino;
dialkylamino substituted with one or more substituents selected from the substituent group α;
unsubstituted dialkylamino;
cycloalkylamino substituted with one or more substituents selected from the substituent group α;
unsubstituted cycloalkylamino;
unsubstituted carbamoyl;
monoalkylcarbamoyl substituted with one or more substituents selected from the substituent group α;
unsubstituted monoalkylcarbamoyl;
dialkylcarbamoyl substituted with one or more substituents selected from the substituent group α;
unsubstituted dialkylcarbamoyl;
alkyloxycarbonyl substituted with one or more substituents selected from the substituent group α;
unsubstituted alkyloxycarbonyl;
carbocyclyl substituted with one or more substituents selected from the substituent group α, alkyl and haloalkyl;
unsubstituted carbocyclyl;
heterocyclyl substituted with one or more substituents selected from the substituent group α, alkyl and haloalkyl; and
unsubstituted heterocyclyl.

Ring B is pyridine, pyrimidine, pyrazine, oxazole, thiazole, pyrazole, benzene, benzoxazole or benzothiazole wherein each ring is optionally substituted with one or more substituents selected from the following groups (hereinafter referred to as B15):
halogen, cyano, hydroxy, alkyl, haloalkyl, cycloalkylalkyl, alkyloxy, haloalkyloxy, alkyloxyalkyloxy, cyanoalkyloxy, alkenyl, haloalkenyl, alkynyl, haloalkynyl, alkenyloxy, alkynyloxy, alkylsulfanyl, cyanoalkylsulfanyl, amino, monoalkylamino, dialkylamino, cycloalkylamino and cycloalkyl.

Ring B is pyridine, pyrazine, oxazole, thiazole, pyrazole, benzoxazole or benzothiazole wherein each ring is optionally substituted with one or more substituents selected from the following groups (hereinafter referred to as B16). halogen, cyano, hydroxy, alkyl, haloalkyl, cycloalkylalkyl, alkyloxy, haloalkyloxy, alkenyl, haloalkenyl, alkynyl, haloalkynyl, amino, monoalkylamino, dialkylamino, cycloalkylamino and cycloalkyl.

Ring B is pyridine or pyrazine wherein each ring is optionally substituted with one or more substituents selected from the following groups (hereinafter referred to as B17). halogen, cyano, hydroxy, alkyl, haloalkyl, cycloalkylalkyl, alkyloxy, haloalkyloxy, alkenyl, haloalkenyl, alkynyl, haloalkynyl, amino, monoalkylamino, dialkylamino, cycloalkylamino and cycloalkyl.

Ring B is a group of the following formula (hereinafter referred to as B18):

[Chemical Formula 63]

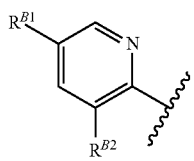

wherein $R^{B1}$ is cyano and $R^{B2}$ is (i) hydroxy, (ii) alkyl optionally substituted with one or more substituents selected from the substituent group α, (iii) alkyloxy, (iv) alkynyl, (v) monoalkylamino, (vi) dialkylamino, (vii) cycloalkylamino or (viii) cycloalkyl.

Ring B is a group of the following formula (hereinafter referred to as B19).

[Chemical Formula 64]

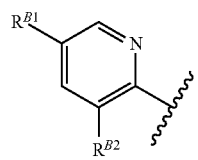

wherein $R^{B1}$ is cyano, $R^{B2}$ is hydroxy, alkyl, haloalkyl, cycloalkylalkyl, alkyloxy, alkynyl, monoalkylamino, dialkylamino or cycloalkyl.

Ring B is a group of the following formula (hereinafter referred to as B20).

[Chemical Formula 65]

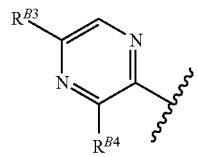

wherein $R^{B3}$ is alkyl, haloalkyl or haloalkyloxy and $R^{B4}$ is hydrogen, hydroxy, amino, monoalkylamino, dialkylamino or cycloalkylamino.

Ring B is a group of the following formula (hereinafter referred to as B21).

[Chemical Formula 66]

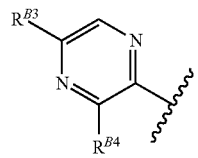

wherein $R^{B3}$ is alkyl, haloalkyl or haloalkyloxy, and $R^{B4}$ is hydroxy, amino, monoalkylamino, dialkylamino or cycloalkylamino.

Ring A is a substituted or unsubstituted aromatic carbocycle or a substituted or unsubstituted aromatic heterocycle (hereinafter referred to as A1).

Ring A is substituted or unsubstituted benzene, substituted or unsubstituted pyridine, substituted or unsubstituted pyrimidine, substituted or unsubstituted pyrazine, substituted or unsubstituted oxazole, substituted or unsubstituted thiazole, substituted or unsubstituted pyrazole, substituted or unsubstituted benzoxazole or substituted or unsubstituted benzothiazole (hereinafter referred to as A2).

Ring A is substituted or unsubstituted benzene or substituted or unsubstituted pyridine (hereinafter referred to as A3).

Ring A is unsubstituted pyridine or benzene optionally substituted with halogen (hereinafter referred to as A4).

Ring A is benzene optionally substituted with halogen (hereinafter referred to as A5).

Examples of combination of $R^1$, $R^4$, $R^{2a}$, $R^{2b}$, $R^{3a}$, $R^{3b}$ ($R^1$, $R^4$, "$R^{2a}$, $R^{2b}$, $R^{3a}$, $R^{3b}$, $R^{3c}$ and $R^{3d}$") of the compounds of formula (IA) are as follows:
(R11, R41, R235), (R11, R42, R235), (R11, R41, R236), (R11, R42, R236), (R11, R41, R237), (R11, R42, R237), (R11, R41, R238), (R11, R42, R238), (R11, R41, R239), (R11, R42, R239), (R11, R41, R2310), (R11, R42, R2310) (R12, R41, R235), (R12, R42, R235), (R12, R41, R236), (R12, R42, R236), (R12, R41, R237), (R12, R42, R237), (R12, R41, R238), (R12, R42, R238), (R12, R41, R239), (R12, R42, R239), (R12, R41, R2310), (R12, R42, R2310) (R13, R41, R235), (R13, R42, R235), (R13, R41, R236), (R13, R42, R236), (R13, R41, R237), (R13, R42, R237), (R13, R41, R238), (R13, R42, R238), (R13, R41, R239), (R13, R42, R239), (R13, R41, R2310), (R13, R42, R2310) (R14, R41, R235), (R14, R42, R235), (R14, R41, R236), (R14, R42, R236), (R14, R41, R237), (R14, R42, R237), (R14, R41, R238), (R14, R42, R238), (R14, R41, R239), (R14, R42, R239), (R14, R41, R2310), (R14, R42, R2310).

Examples of the compound (IA) are as follows:
At least one of the existing $R^{2a}$, $R^{2b}$, $R^{3a}$ and $R^{3b}$ is halogen or substituted or unsubstituted alkyl and
the others are each independently hydrogen, halogen, hydroxy, substituted or unsubstituted alkyl, substituted or unsubstituted alkenyl, cyano or substituted or unsubstituted cycloalkyl, and
when at least one of the existing $R^{2b}$ and $R^{3b}$ is halogen or substituted or unsubstituted alkyl, then $R^{2a}$ and $R^{3a}$ together with the carbon atoms to which they are attached, may form

[Chemical Formula 67]

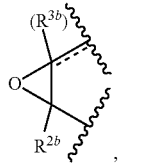
(i)

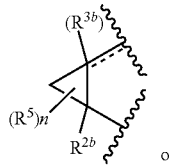
(ii)

or

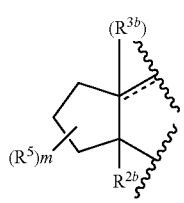
(iii)

wherein $R^5$ is halogen or substituted or unsubstituted alkyl,
n is an integer of 0 to 2,
m is an integer of 1 or 2,
provided that the following compounds are excluded:
(a) a compound wherein $R^1$ is alkyl, X is —C($R^{3a}$)($R^{3b}$)—, and both of $R^{2a}$ and $R^{2b}$ are fluorine.

Examples of the compound (IA) are as follows:
At least one of the existing $R^{2a}$, $R^{2b}$, $R^{3a}$ and $R^{3b}$ is substituted alkyl and the others are each independently hydrogen, halogen, hydroxy, substituted or unsubstituted alkyl, substituted or unsubstituted alkenyl, cyano or substituted or unsubstituted cycloalkyl, and
when at least one of the existing $R^{2b}$ and $R^{3b}$ is substituted alkyl, then $R^{2a}$ and $R^{3a}$ together with the carbon atoms to which they are attached, may form

[Chemical Formula 68]

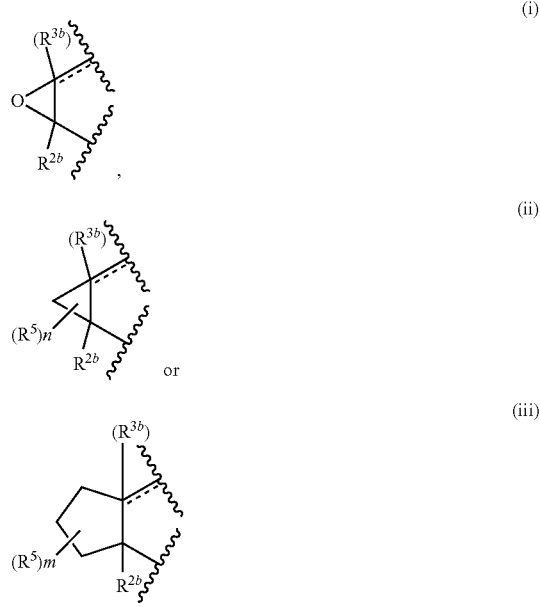

wherein $R^5$ is halogen or substituted or unsubstituted alkyl,
n is an integer of 0 to 2,
m is an integer of 1 or 2,
provided that the following compounds are excluded:
(a) a compound wherein $R^1$ is alkyl, X is —C($R^{3a}$)($R^{3b}$)—, and both of $R^{2a}$ and $R^{2b}$ are fluorine, and
(d) the following compounds:

[Chemical Formula 69]

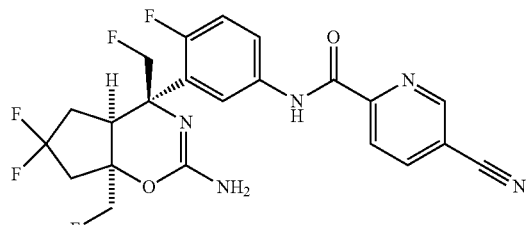

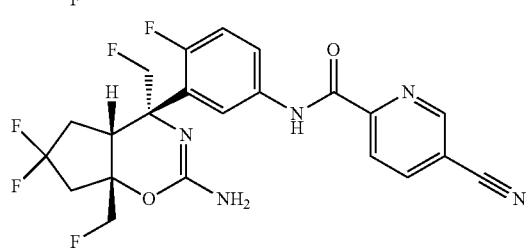

-continued

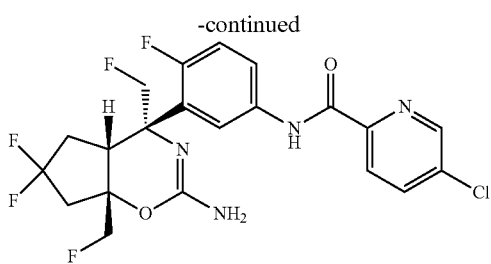

Examples of the compound (IA) are as follows:
At least one of the existing $R^{3a}$ and $R^{3b}$ is halogen, or substituted or unsubstituted alkyl and
the other is hydrogen, halogen, hydroxy, substituted or unsubstituted alkyl, substituted or unsubstituted alkenyl, cyano or substituted or unsubstituted cycloalkyl, and
$R^{2a}$ and $R^{3a}$ attached to adjacent carbon atoms, together with the carbon atoms to which they are attached, may form

[Chemical Formula 70]

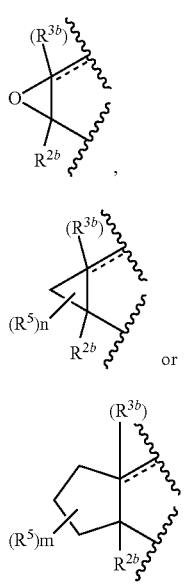

wherein $R^5$ is halogen or substituted or unsubstituted alkyl,
n is an integer of 0 to 2,
m is an integer of 1 or 2,
provided that the following compounds are excluded:
(a) a compound wherein $R^1$ is alkyl, X is —C($R^{3a}$)($R^{3b}$)—, and both of $R^{2a}$ and $R^{2b}$ are fluorine, and
(d) the following compounds:

[Chemical Formula 71]

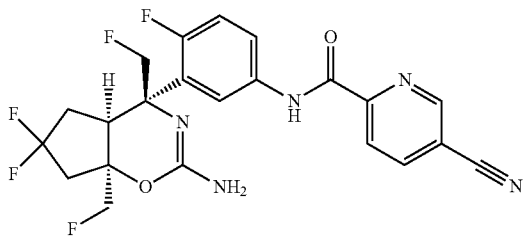

-continued

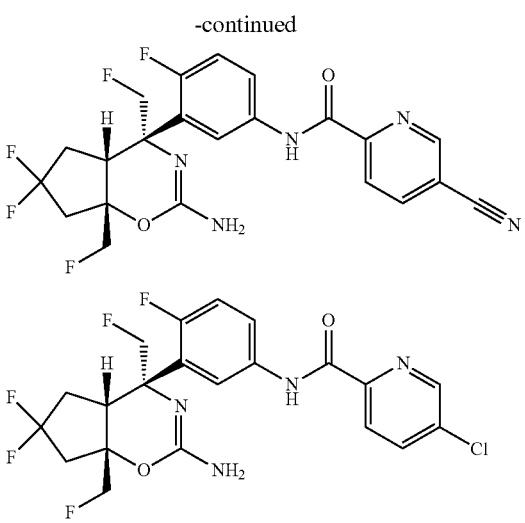

Examples of the compound (IA) are as follows:

[Chemical Formula 72]

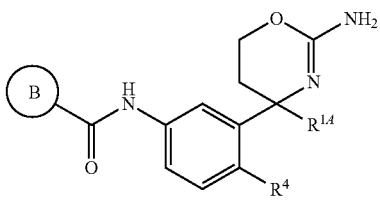

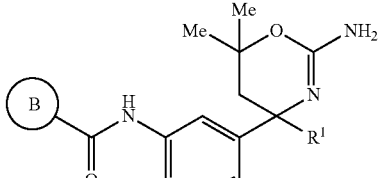

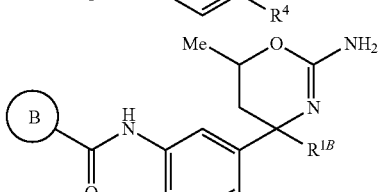

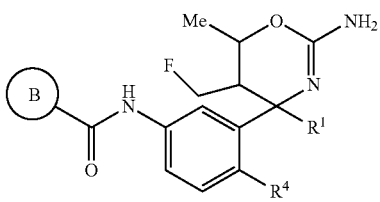

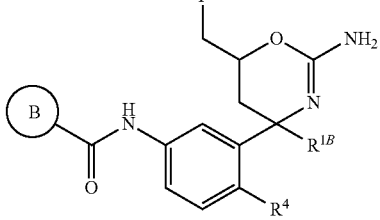

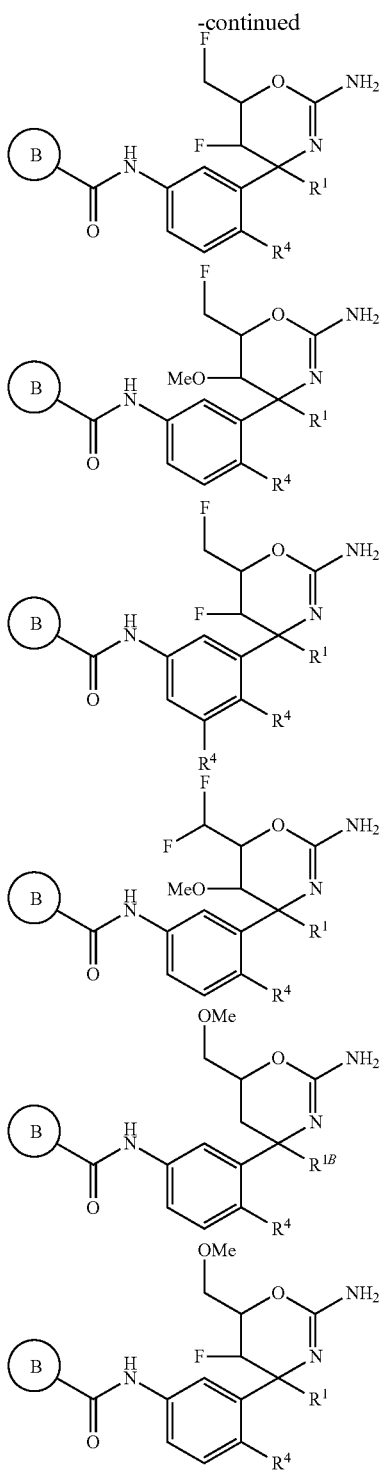

wherein Me is methyl, R¹ is "R13", "R14", "R15", "R16" or "R17", $R^{1A}$ is "R13", "R14" or "R17", $R^{1B}$ is "R132 or "R17" and ring B is any one of "B1" to "B21".

Examples of combination of R¹, R⁴, $R^{2a}$, $R^{2b}$, $R^{3a}$, $R^{3b}$, $R^{3c}$ and $R^{3d}$, ring B and ring A (R¹, R⁴, "$R^{2a}$", $R^{2b}$, $R^{3a}$, $R^{3b}$, $R^{3c}$ and $R^{3d}$", ring B, ring A) of the compounds of any of the formulas (I) and (IA) to (IO), preferably (IA) or (IB), and preferably (IA), are as follows:

(R13,R41,R231,B1, A4), (R13,R41,R231,B2, A4), (R13, R41,R231,B3, A4), (R13,R41,R231, B4, A4), (R13,R41, R231,B5, A4), (R13,R41,R231,B6, A4), (R13,R41,R231, B7, A4), (R13,R41,R231,B8, A4), (R13,R41,R231,B9, A4), (R13,R41,R231,B10, A4), (R13,R41,R231,B11, A4), (R13, R41,R231,B12, A4), (R13,R41,R231,B13, A4), (R13,R41, R231,B14, A4), (R13,R41,R231,B15, A4), (R13,R41,R231, B16, A4), (R13,R41,R231,B17, A4), (R13,R41,R231,B18, A4), (R13,R41,R231,B19, A4), (R13,R41,R231,B20, A4), (R13,R41,R231,B21, A4), (R13,R41,R232,B1, A4), (R13, R41,R232,B2, A4), (R13,R41,R232,B3, A4), (R13,R41, R232,B4, A4), (R13, R41,R232,B5, A4), (R13,R41,R232, B6,A4), (R13,R41,R232,B7, A4), (R13,R41,R232,B8, A4), (R13,R41,R232,B9, A4), (R13,R41,R232,B10, A4), (R13, R41,R232,B11, A4), (R13,R41,R232,B12, A4), (R13,R41, R232,B13, A4), (R13,R41,R232,B14, A4), (R13,R41,R232, B15, A4), (R13,R41,R232,B16, A4), (R13,R41,R232,B17, A4), (R13,R41,R232,B18, A4), (R13,R41,R232,B19, A4), (R13,R41,R232,B20, A4), (R13,R41,R232,B21, A4), (R13, R41,R233,B1, A4), (R13,R41,R233,B2, A4), (R13,R41, R233,B3, A4), (R13,R41,R233,B4, A4), (R13,R41,R233, B5, A4), (R13,R41,R233,B6, A4), (R3,R41,R233,B7, A4), (R13,R41,R233,B8, A4), (R13,R41,R233,B9, A4), (R13, R41,R233,B10, A4), (R13,R41,R233,B11, A4), (R13,R41, R233,B12, A4), (R13,R41,R233,B13, A4), (R13,R41,R233, B14, A4), (R13,R41,R233,B15, A4), (R13,R41,R233,B16, A4), (R13,R41,R233,B17, A4), (R13,R41,R233,B18, A4), (R13,R41,R233,B19, A4), (R13,R41,R233,B20, A4), (R13, R41,R233,B21, A4), (R13,R41,R234,B1, A4), (R13,R41, R234, B2, A4), (R13,R41,R234,B3, A4), (R13,R41,R234, B4,A4), (R13,R41,R234,B5, A4), (R13,R41,R234,B6, A4), (R13,R41,R234,B7, A4), (R13,R41,R234,B8, A4), (R13, R41,R234,B9, A4), (R13,R41,R234,B10, A4), (R13,R41, R234,B11, A4), (R13,R41,R234,B12, A4), (R13,R41,R234, B13, A4), (R13,R41,R234,B14, A4), (R13,R41,R234,B15, A4), (R13,R41,R234,B16, A4), (R13,R41,R234,B17, A4), (R13,R41,R234,B18, A4), (R13,R41,R234,B19, A4), (R13, R41,R234,B20, A4), (R13,R41,R234,B21, A4), (R13,R41, R235,B1, A4), (R13,R41,R235,B2, A4), (R13, R41,R235, B3, A4), (R13,R41,R235,B4, A4), (R13,R41,R235,B5, A4), (R13,R41,R235,B6, A4), (R13,R41,R235,B7, A4), (R13, R41,R235,B8, A4), (R13,R41,R235,B9, A4), (R13,R41, R235,B10, A4), (R13,R41,R235,B11, A4), (R13,R41,R235, B12, A4), (R13,R41,R235,B13, A4), (R13,R41,R235,B14, A4), (R13,R41,R235,B15, A4), (R13,R41,R235,B16, A4), (R13,R41,R235, B17, A4), (R13,R41,R235,B18, A4), (R13, R41,R235,B19, A4), (R13,R41,R235,B20, A4), (R13,R41, R235,B21, A4), (R13,R41,R236,B1, A4), (R13,R41,R236, B2, A4), (R13,R41,R236,B3, A4), (R13,R41,R236,B4, A4), (R13,R41,R236,B5, A4), (R13,R41,R236,B6, A4), (R13, R41,R236,B7, A4), (R13,R41,R236,B8, A4), (R13,R41, R236,B9, A4), (R13,R41,R236,B10, A4), (R13,R41,R236, B11, A4), (R13,R41,R236,B12, A4), (R13,R41,R236,B13, A4), (R13,R41,R236, B14, A4), (R13,R41,R236,B15, A4), (R13,R41,R236,B16, A4), (R13,R41,R236,B17, A4), (R13, R41,R236,B18, A4), (R13,R41,R236,B19, A4), (R13,R41, R236,B20, A4), (R13,R41,R236, B21, A4), (R13,R41,R237, B1, A4), (R13,R41,R237,B2, A4), (R13,R41,R237,B3, A4), (R13,R41,R237,B4, A4), (R13,R41,R237,B5, A4), (R13, R41,R237,B6, A4), (R13,R41,R237,B7, A4), (R13,R41, R237,B8, A4), (R13,R41,R237,B9, A4), (R13,R41,R237, B10, A4), (R13,R41,R237,B11, A4), (R13,R41,R237,B12, A4), (R13,R41,R237,B13, A4), (R13,R41,R237,B14, A4), (R13,R41,R237,B15, A4), (R13,R41,R237,B16, A4), (R13, R41,R237,B17, A4), (R13,R41,R237, B18, A4), (R13,R41, R237,B19, A4), (R13,R41,R237,B20, A4), (R13,R41,R237, B21, A4), (R13,R41,R238,B1, A4), (R13,R41,R238,B2, A4), (R13,R41,R238,B3, A4), (R13,R41,R238,B4, A4), (R13,R41,R238,B5, A4), (R13,R41,R238,B6, A4), (R13,

R41,R238,B7, A4), (R13,R41,R238, B8, A4), (R13,R41, R238, B9,A4), (R13, R41,R238, B10, A4), (R13,R41,R238, B11, A4), (R13,R41,R238,B12, A4), (R13,R41,R238,B13, A4), (R13,R41,R238,B14, A4), (R13,R41,R238,B15, A4), (R13,R41,R238,B16, A4), (R13,R41,R238,B17, A4), (R13, R41,R238,B18, A4), (R13,R41,R238,B19, A4), (R13,R41, R238,B20, A4), (R13,R41,R238,B21, A4), (R13,R41,R239, B1, A4), (R13,R41,R239, B2, A4), (R13,R41,R239, B3, A4), (R13,R41,R239, B4, A4), (R13, R41,R239,B5, A4), (R13,R41,R239,B6, A4), (R13,R41,R239,B7, A4), (R13, R41,R239,B8, A4), (R13,R41,R239,B9, A4), (R13,R41, R239,B10, A4), (R13,R41,R239,B11, A4), (R13,R41,R239, B12, A4), (R13,R41,R239,B13, A4), (R13,R41,R239,B14, A4), (R13,R41,R239,B15, A4), (R13,R41,R239,B16, A4), (R13,R41,R239,B17, A4), (R13,R41,R239,B18, A4), (R13, R41,R239, B19, A4), (R13,R41,R239,B20, A4), (R13,R41, R239,B21, A4), (R13,R41,R2310,B1, A4), (R13,R41, R2310,B2, A4), (R13,R41,R2310,B3, A4), (R13,R41, R2310, B4, A4), (R13,R41,R2310,B5, A4), (R13,R41, R2310,B6, A4), (R13,R41,R2310,B7, A4), (R13,R41, R2310,B8, A4), (R13,R41,R2310,B9, A4), (R13,R41, R2310,B10, A4), (R13,R41,R2310,B11, A4), (R13,R41, R2310,B12, A4), (R13,R41,R2310,B13, A4), (R13,R41, R2310,B14, A4), (R13,R41,R2310,B15, A4), (R13,R41, R2310,B16, A4), (R13,R41,R2310,B17, A4), (R13,R41, R2310,B18, A4), (R13,R41,R2310,B19, A4), (R13,R41, R2310,B20, A4), (R13,R41,R2310,B21, A4), (R13,R41, R2311, B1, A4), (R13,R41,R2311,B2, A4), (R13,R41, R2311,B3, A4), (R13,R41,R2311,B4, A4), (R13, R41, R2311,B5, A4), (R13,R41,R2311,B6, A4), (R13,R41, R2311,B7, A4), (R13,R41,R2311,B 8, A4), (R13,R41, R2311,B9, A4), (R13,R41,R2311,B10, A4), (R13,R41, R2311,B11, A4), (R13,R41,R2311,B12, A4), (R13,R41, R2311,B13, A4), (R13,R41,R2311,B14, A4), (R13,R41, R2311,B15, A4), (R13,R41,R2311,B16, A4), (R13,R41, R2311,B17, A4), (R13,R41,R2311,B18, A 4), (R13,R41, R2311,B19, A4), (R13,R41,R2311,B20, A4), (R13,R41, R2311,B21, A4), (R13,R41,R2312,B1, A4), (R13,R41, R2312,B2, A4), (R13,R41,R2312,B3, A4), (R13,R41, R2312,B4, A4), (R13,R41,R2312,B5, A4), (R13,R41, R2312,B6, A4), (R13,R41,R2312,B7, A4), (R13,R41, R2312,B8, A4), (R13,R41,R2312,B9, A4), (R13,R41, R2312,B10, A4), (R13,R41,R2312,B11, A4), (R13,R41, R2312,B12, A4), (R13,R41,R2312,B13, A4), (R13,R41, R2312,B14, A4), (R13,R41,R2312,B15, A4), (R13,R41, R2312,B16, A4), (R13,R41,R2312,B17, A4), (R13,R41, R2312,B18, A4), (R13,R41,R2312,B19, A4), (R13,R41, R2312,B20, A4), (R13,R41,R2312,B21, A4), (R13,R41, R2313,B1, A4), (R13,R41,R2313,B2, A4), (R13,R41, R2313,B3, A4), (R13,R41,R2313,B4, A4), (R13,R41, R2313,B5, A4), (R13,R41,R2313,B6, A4), (R13,R41, R2313,B7, A4), (R13,R41,R2313,B8, A4), (R13,R41, R2313,B9, A4), (R13,R41,R2313,B10, A4), (R13,R41, R2313,B11, A4), (R13,R41,R2313,B12, A4), (R13,R41, R2313,B13, A4), (R13,R41,R2313,B14, A4), (R13,R41, R2313,B15, A4), (R13,R41,R2313,B16, A4), (R13,R41, R2313,B17, A4), (R13,R41,R2313,B18, A4), (R13,R41, R2313,B19, A4), (R13,R41,R2313,B20, A4), (R13,R41, R2313,B21, A4), (R13,R42,R231,B1, A4), (R13,R42,R231, B2, A4), (R13,R42,R231,B3, A4), (R13,R42,R231,B4, A4), (R13,R42,R231,B5, A4), (R13,R42,R231,B6, A4), (R13, R42,R231, B7, A4), (R13,R42,R231,B8, A4), (R13,R42, R231,B9, A4), (R13,R42,R231,B10, A4), (R13,R42,R231, B11, A4), (R13,R42,R231,B12, A4), (R13,R42,R231,B13, A4), (R13,R42,R231,B14, A4), (R13,R42,R231,B15, A4), (R13,R42,R231,B16, A4), (R13,R42,R231,B17, A4), (R13, R42,R231,B18, A4), (R13,R42,R231,B19, A4), (R13,R42, R231,B20, A4), (R13,R42,R231,B21, A4), (R13,R42,R232, B1, A4), (R13,R42,R232,B2, A4), (R13,R42,R232,B3, A4), (R13,R42,R232,B4, A4), (R13,R42,R232,B5, A4), (R13, R42,R232,B6, A4), (R13,R42,R232,B7, A4), (R13,R42, R232,B8, A4), (R13,R42,R232,B9, A4), (R13,R42,R232, B10, A4), (R13,R42,R232,B11, A4), (R13,R42,R232,B12, A4), (R13,R42,R232,B13, A4), (R13,R42,R232,B14, A4), (R13,R42,R232, B15, A4), (R13,R42,R232, B16, A4), (R13, R42, R232, B17, A4), (R13,R42,R232, B18, A4), (R13,R42, R232,B19, A4), (R13,R42,R232,B20, A4), (R13,R42,R232, B21, A4), (R13,R42,R233,B1, A4), (R13,R42,R233,B2, A4), (R13,R42,R233,B3, A4), (R13,R42,R233,B4, A4), (R13,R42,R233,B5, A4), (R13,R42,R233,B6, A4), (R13, R42,R233,B7, A4), (R13,R42,R233,B 8, A4), (R13,R42, R233,B9, A4), (R13,R42,R233,B10, A4), (R13,R42,R233, B11, A4), (R13,R42,R233,B12, A4), (R13,R42,R233,B13, A4), (R13,R42,R233,B14, A4), (R13,R42,R233,B15, A4), (R13,R42,R233,B16, A4), (R13,R42,R233,B17, A4), (R13, R42,R233,B18, A4), (R13,R42,R233,B19, A4), (R13,R42, R233,B20, A4), (R13,R42,R233,B21, A4), (R13,R42,R234, B1, A 4), (R13,R42,R234,B2, A4), (R13,R42,R234,B3, A4), (R13,R42,R234,B4, A4), (R13,R42,R234,B5, A4), (R13, R42,R234,B6, A4), (R13,R42,R234,B7, A4), (R13,R42, R234,B8, A4), (R13,R42,R234,B9, A4), (R13,R42,R234, B10, A4), (R13,R42,R234,B11, A4), (R13,R42,R234,B12, A4), (R13,R42,R234,B13, A4), (R13,R42,R234,B14, A4), (R13,R42,R234,B15, A4), (R13,R42,R234,B16, A4), (R13, R42,R234,B17, A4), (R13,R42,R234,B18, A4), (R13,R42, R234,B19, A4), (R13,R42,R234,B20, A4), (R13,R42,R234, B21, A4), (R13,R42,R235,B1, A4), (R13,R42, R235, B2, A4), (R13,R42,R235, B3, A4), (R13, R42, R235, B4, A4), (R13,R42,R235, B5, A4), (R13,R42,R235,B6, A4), (R13, R42,R235,B7, A4), (R13,R42,R235,B8, A4), (R13,R42, R235,B9, A4), (R13,R42,R235,B10, A4), (R13,R42,R235, B11, A4), (R13,R42,R235,B12, A4), (R13,R42,R235,B13, A4), (R13,R42,R235,B14, A4), (R13,R42,R235,B15, A4), (R13,R42,R235,B16, A4), (R13,R42,R235,B17, A4), (R13, R42,R235,B18, A4), (R13,R42,R235,B19, A4), (R13,R42, R235,B20, A4), (R13,R42,R235,B21, A4), (R13,R42,R236, B1, A4), (R13,R42,R236,B2, A4), (R13,R42,R236,B3, A4), (R13,R42,R236,B4, A4), (R13,R42,R236,B5, A4), (R13, R42,R236,B6, A4), (R13,R42,R236,B7, A4), (R13,R42, R236,B8, A4), (R13,R42,R236,B9, A4), (R13,R42,R236, B10, A4), (R13,R42,R236,B11, A4), (R13,R42,R236,B12, A4), (R13,R42,R236,B13, A4), (R13,R42,R236,B14, A4), (R13,R42,R236,B15, A4), (R13,R42,R236,B16, A4), (R13, R42,R236,B17, A4), (R13,R42,R236,B18, A4), (R13,R42, R236,B19, A4), (R13,R42,R236,B20, A4), (R13,R42,R236, B21, A4), (R13,R42,R237,B1, A4), (R13,R42,R237,B2, A4), (R13,R42, R237,B3, A4), (R13, R42,R237,B4, A4), (R3, R42, R237,B5, A4), (R13,R42,R237,B6, A4), (R13, R42,R237,B7, A4), (R13,R42,R237,B8, A4), (R13,R42, R237,B9, A4), (R13,R42,R237,B10, A4), (R13,R42,R237, B11, A4), (R13,R42,R237,B12, A4), (R13,R42,R237,B13, A4), (R13,R42,R237,B14, A4), (R13,R42,R237,B15, A4), (R13,R42,R237, B16, A4), (R13,R42,R237,B17, A4), (R13, R42,R237,B18, A4), (R13,R42,R237,B19, A4), (R13,R42, R237,B20, A4), (R13,R42,R237,B21, A4), (R13,R42,R238, B1, A4), (R13,R42,R238,B2, A4), (R13,R42,R238,B3, A4), (R13,R42,R238,B4, A4), (R13,R42,R238,B5, A4), (R13, R42,R238,B6, A4), (R13,R42,R238, B7, A4), (R13,R42, R238,B8, A4), (R13,R42,R238,B9, A4), (R13,R42,R238, B10, A4), (R13,R42,R238,B11, A4), (R13,R42,R238,B12, A4), (R13,R42,R238,B13, A4), (R13,R42,R238,B14, A4), (R13,R42,R238,B15, A4), (R13,R42,R238,B16, A4), (R13, R42,R238,B17, A4), (R13,R42,R238,B18, A4), (R13,R42, R238,B19, A4), (R13,R42,R238,B20, A4), (R13,R42,R238,

B21, A4), (R13,R42,R239,B1, A4), (R13,R42,R239,B2, A4), (R13,R42,R239,B3, A4), (R13,R42,R239,B4, A4), (R13,R42,R239,B5, A4), (R13,R42,R239,B6, A4), (R13,R42,R239,B7, A4), (R13,R42,R239,B8, A4), (R13,R42,R239,B9, A4), (R13,R42,R239,B10, A4), (R13,R42,R239,B11, A4), (R13,R42,R239,B12, A4), (R13,R42,R239,B13, A4), (R13,R42,R239,B14, A4), (R13,R42,R239,B15, A4), (R13,R42,R239,B16, A4), (R13,R42,R239,B17, A4), (R13,R42,R239,B18, A4), (R13,R42,R239,B19, A4), (R13,R42,R239,B20, A4), (R13,R42,R239,B21, A4), (R13,R42,R2310,B1, A4), (R13,R42,R2310,B2, A4), (R13,R42,R2310,B3, A4), (R13,R42,R2310,B4, A4), (R13,R42,R2310,B5, A4), (R13,R42,R2310,B6, A4), (R13,R42,R2310,B7, A4), (R13,R42,R2310,B8, A4), (R13,R42,R2310,B9, A4), (R13,R42,R2310,B10, A4), (R13,R42,R2310,B11, A4), (R13,R42,R2310,B12, A4), (R13,R42,R2310,B13, A4), (R13,R42,R2310,B14, A4), (R13,R42,R2310,B15, A4), (R13,R42,R2310,B16, A4), (R13,R42,R2310,B17, A4), (R13,R42,R2310,B18, A4), (R13,R42,R2310,B19, A4), (R13,R42,R2310,B20, A4), (R13,R42,R2310,B21, A4), (R13,R42,R2311,B1, A4), (R13,R42,R2311,B2, A4), (R13,R42,R2311,B3, A4), (R13,R42,R2311,B4, A4), (R13,R42,R2311,B5, A4), (R13,R42,R2311,B6, A4), (R13,R42,R2311,B7, A 4), (R13,R42,R2311,B8, A4), (R13,R42,R2311,B9, A4), (R13,R42,R2311,B10, A4), (R13,R42,R2311,B11, A4), (R13,R42,R2311,B12, A4), (R13,R42,R2311,B13, A4), (R13,R42,R2311,B 14, A4), (R13,R42,R2311,B15, A4), (R13,R42,R2311, B16, A4), (R13,R42,R2311,B17, A4), (R13,R42,R2311,B18, A4), (R13,R42,R2311,B19, A4), (R13,R42,R2311,B20, A4), (R13,R42,R2311,B21, A4), (R13,R42,R2312,B1, A4), (R13,R42,R2312,B2, A4), (R13,R42,R2312,B3, A4), (R13,R42,R2312,B4, A4), (R13,R42,R2312,B5, A4), (R13,R42,R2312,B6, A4), (R13,R42,R2312,B7, A4), (R13,R42,R2312,B8, A4), (R13,R42,R2312,B9, A4), (R13,R42,R2312,B10, A4), (R13,R42,R2312,B11, A4), (R13,R42,R2312,B12, A4), (R13,R42,R2312,B13, A4), (R13,R42,R2312,B14, A4), (R13,R42,R2312,B15, A4), (R13,R42,R2312,B16, A4), (R13,R42,R2312, B17, A4), (R13,R42,R2312,B18, A4), (R13,R42,R2312,B19, A4), (R13,R42,R2312,B20, A4), (R13,R42,R2312,B21, A4), (R13,R42,R2313,B1, A4), (R13,R42,R2313,B2, A4), (R13,R42,R2313,B3, A4), (R13,R42,R2313,B4, A4), (R13,R42,R2313,B5, A4), (R13,R42,R2313,B6, A4), (R13,R42,R2313, B7, A4), (R13,R42,R2313,B8, A4), (R13,R42,R2313, B9, A4), (R13,R42,R2313,B10, A4), (R13,R42,R2313,B11, A4), (R13,R42,R2313,B12, A4), (R13,R42,R2313,B13, A 4), (R13,R42,R2313,B14, A4), (R13,R42,R2313,B15, A4), (R13,R42,R2313,B16, A4), (R13,R42,R2313,B17, A4), (R13,R42,R2313,B18, A4), (R13,R42,R2313,B19, A4), (R13,R42,R2313,B20, A4), (R13,R42,R2313,B21, A4), (R14,R41,R231,B1, A4), (R14,R41,R231,B2, A4), (R14, R41,R231,B3, A4), (R14,R41,R231,B4, A4), (R14,R41,R231,B5, A4), (R14,R41,R231,B6, A 4), (R14,R41,R231,B7, A4), (R14, R41,R231,B8, A4), (R14,R41,R231,B9, A4), (R14,R41,R231,B10, A4), (R14,R41,R231,B11, A4), (R14,R41,R231,B12, A4), (R14,R41,R231,B13, A4), (R14,R41,R231,B14, A4), (R14,R41,R231,B15, A4), (R14,R41,R231,B16, A4), (R14,R41,R231,B17, A4), (R14,R41,R231,B18, A4), (R14, R41,R231,B19, A4), (R14,R41,R231,B20, A4), (R14,R41, R231,B21, A4), (R14,R41,R232,B1, A4), (R14,R41,R232, B2, A4), (R14,R41,R232,B3, A4), (R14,R41,R232,B4, A4), (R14,R41,R232,B5, A4), (R14,R41,R232,B6, A4), (R14, R41,R232, B7, A4), (R14,R41,R232, B8, A4), (R14, R41, R232, B9, A4), (R14,R41,R232,B10, A4), (R14,R41,R232, B11, A4), (R14,R41,R232,B12, A4), (R14,R41,R232,B13, A4), (R14,R41,R232, B14, A4), (R14,R41,R232,B15, A4), (R14,R41,R232,B16, A4), (R14,R41,R232,B17, A4), (R14, R41,R232,B18, A4), (R14,R41,R232,B19, A4), (R14,R41, R232,B20, A4), (R14,R41,R232, B21, A4), (R14,R41,R233, B1, A4), (R14,R41,R233,B2, A4), (R14,R41,R233,B3, A4), (R14,R41,R233,B4, A4), (R14,R41,R233,B5, A4), (R14, R41,R233,B6, A4), (R14,R41,R233,B7, A4), (R14,R41, R233,B8, A4), (R14,R41,R233,B9, A4), (R14,R41,R233, B10, A4), (R14,R41,R233,B11, A4), (R14,R41,R233,B12, A4), (R14,R41,R233,B13, A4), (R14,R41,R233,B14, A4), (R14,R41,R233,B15, A4), (R14,R41,R233,B16, A4), (R14, R41,R233,B17, A4), (R14,R41,R233, B18, A4), (R14,R41, R233,B19, A4), (R14,R41,R233,B20, A4), (R14,R41,R233, B21, A4), (R14,R41,R234,B1, A4), (R14,R41,R234,B2, A4), (R14,R41,R234,B3, A4), (R14,R41,R234,B4, A4), (R14,R41,R234,B5, A4), (R14,R41,R234,B6, A4), (R14, R41,R234,B7, A4), (R14,R41,R234,B8, A4), (R14,R41, R234,B9, A4), (R14,R41,R234,B10, A4), (R14,R41,R234, B11, A4), (R14,R41,R234,B12, A4), (R14,R41,R234,B13, A4), (R14,R41,R234,B14, A4), (R14,R41,R234, B15, A4), (R14,R41,R234,B16, A4), (R14,R41,R234,B17, A4), (R14, R41,R234,B18, A4), (R14,R41,R234,B19, A4), (R14,R41, R234,B20, A4), (R14,R41,R234,B21, A4), (R14,R41,R235, B1, A4), (R14,R41,R235,B2, A4), (R14,R41,R235,B3, A4), (R14,R41,R235,B4, A4), (R14,R41,R235,B5, A4), (R14, R41,R235,B6, A4), (R14,R41,R235,B7, A4), (R14,R41, R235,B8, A4), (R14,R41,R235,B9, A4), (R14,R41,R235, B10, A4), (R14,R41,R235,B11, A4), (R14,R41,R235,B12, A4), (R14,R41,R235,B13, A4), (R14,R41,R235,B14, A4), (R14,R41,R235,B15, A4), (R14,R41,R235,B16, A4), (R14, R41,R235,B17, A4), (R14,R41,R235,B18, A4), (R14,R41, R235, B19, A4), (R14,R41,R235,B20, A4), (R14,R41,R235, B21, A4), (R14,R41,R236,B1, A4), (R14, R41,R236,B2, A4), (R14,R41,R236,B3, A4), (R14,R41,R236,B4, A4), (R14,R41,R236,B5, A4), (R14,R41,R236,B6, A4), (R14, R41,R236,B7, A4), (R14,R41,R236,B8, A4), (R14,R41, R236, B9, A4), (R14,R41,R236,B10, A4), (R14,R41,R236, B11, A4), (R14,R41,R236,B12, A4), (R14, R41,R236,B13, A4), (R14,R41,R236,B14, A4), (R14,R41,R236,B15, A4), (R14,R41,R236,B 16, A4), (R14,R41,R236,B17, A4), (R14, R41,R236,B18, A4), (R14,R41,R236,B19, A4), (R14, R41, R236,B20, A4), (R14,R41,R236,B21, A4), (R14,R41,R237, B1, A4), (R14,R41,R237,B2, A4), (R14,R41,R237,B3, A4), (R14,R41,R237,B4, A4), (R14,R41,R237,B5, A4), (R14, R41,R237,B6, A4), (R14,R41,R237,B7, A4), (R14,R41, R237,B8, A4), (R14,R41,R237,B9, A4), (R14, R41,R237, B10, A4), (R14,R41,R237,B11, A4), (R14,R41,R237,B12, A4), (R14,R41,R237,B 13, A4), (R14,R41,R237,B14, A4), (R14,R41,R237,B15, A4), (R14,R41,R237,B16, A4), (R14, R41,R237,B17, A4), (R14,R41,R237,B18, A4), (R14,R41, R237,B19, A4), (R14,R41,R237,B20, A4), (R14,R41,R237, B21, A4), (R14,R41,R238,B1, A4), (R14,R41,R238,B2, A4), (R14,R41, R238,B3, A4), (R14,R41,R238,B4, A4), (R14,R41,R238,B5, A4), (R14,R41,R238,B6, A4), (R14, R41,R238,B7, A4), (R14,R41,R238,B8, A4), (R14,R41, R238,B9, A4), (R14,R41,R238,B10, A4), (R14,R41,R238, B11, A4), (R14,R41,R238,B12, A4), (R14,R41,R238,B13, A4), (R14,R41,R238,B14, A4), (R14,R41,R238,B15, A4), (R14,R41,R238,B16, A4), (R14,R41,R238,B17, A4), (R14, R41,R238,B18, A4), (R14,R41,R238,B19, A4), (R14,R41, R238,B20, A4), (R14,R41,R238,B21, A4), (R14,R41,R239, B1, A4), (R14,R41,R239,B2, A4), (R14,R41,R239,B3, A4), (R14,R41,R239,B4, A4), (R14,R41,R239,B5, A4), (R14, R41,R239,B6, A4), (R14,R41,R239, B7, A4), (R14,R41, R239,B8, A4), (R14,R41,R239,B9, A4), (R14,R41,R239, B10, A4), (R14,R41,R239,B11, A4), (R14,R41,R239,B12, A4), (R14,R41,R239,B13, A4), (R14,R41,R239,B14, A4), (R14,R41,R239,B15, A4), (R14,R41,R239,B16, A4), (R14, R41,R239,B17, A4), (R14,R41,R239,B18, A4), (R14,R41, R239,B19, A4), (R14,R41,R239,B20, A4), (R14,R41,R239, B21, A4), (R14,R41,R2310,B1, A4), (R14,R41,R2310,B2, A4), (R14,R41,R2310,B3, A4), (R14,R41,R2310,B4, A4), (R14,R41,R2310,B5, A4), (R14,R41,R2310,B6, A4), (R14, R41,R2310,B7, A4), (R14,R41,R2310,B8, A4), (R14,R41, R2310,B9, A4), (R14,R41,R2310,B10, A4), (R14,R41, R2310,B11, A4), (R14,R41,R2310,B12, A4), (R14,R41, R2310,B13, A4), (R14,R41,R2310, B14, A4), (R14,R41, R2310,B15, A4), (R14,R41,R2310,B16, A4), (R14,R41, R2310,B17, A4), (R14,R41,R2310,B18, A4), (R14,R41, R2310,B19, A4), (R14,R41,R2310,B20, A4), (R14,R41, R2310,B21, A4), (R14,R41,R2311,B1, A4), (R14,R41, R2311,B2, A4), (R14,R41,R2311,B3, A4), (R14,R41, R2311,B4, A4), (R14,R41,R2311,B5, A4), (R14,R41, R2311,B6, A4), (R14,R41,R2311,B7, A4), (R14,R41, R2311,B8, A4), (R14,R41,R2311,B9, A4), (R14,R41, R2311,B10, A4), (R14,R41,R2311,B11, A4), (R14,R41, R2311,B12, A4), (R14,R41,R2311,B13, A4), (R14, R41, R2311,B14, A4), (R14,R41,R2311,B15, A4), (R14,R41, R2311,B16, A4), (R14,R41,R2311,B17, A4), (R14,R41, R2311,B18, A4), (R14,R41,R2311,B19, A4), (R14,R41, R2311,B20, A4), (R14,R41,R2311,B21, A4), (R14,R41, R2312,B1, A4), (R14,R41,R2312,B2, A4), (R14,R41, R2312,B3, A4), (R14,R41,R2312,B4, A4), (R14,R41, R2312,B5, A4), (R14,R41,R2312,B6, A4), (R14,R41, R2312,B7, A4), (R14,R41,R2312,B8, A4), (R14,R41, R2312,B9, A4), (R14,R41,R2312,B10, A4), (R14,R41, R2312,B11, A4), (R14,R41,R2312,B12, A4), (R14,R41, R2312,B13, A4), (R14,R41,R2312,B14, A4), (R14,R41, R2312,B15, A4), (R14,R41,R2312,B16, A4), (R14, R41, R2312,B17, A4), (R14,R41,R2312,B18, A4), (R14,R41, R2312,B19, A4), (R14,R41,R2312,B20, A4), (R14,R41, R2312,B21, A4), (R14,R41,R2313,B1, A4), (R14,R41, R2313,B2, A4), (R14,R41,R2313,B3, A4), (R14,R41, R2313,B4, A4), (R14,R41,R2313,B5, A4), (R14,R41, R2313,B6, A4), (R14,R41,R2313,B7, A4), (R14,R41, R2313,B8, A4), (R14,R41,R2313,B9, A4), (R14,R41, R2313,B10, A4), (R14,R41,R2313,B11, A4), (R14,R41, R2313,B12, A4), (R14,R41, R2313,B13, A4), (R14,R41, R2313,B14, A4), (R14,R41,R2313,B15, A4), (R14,R41, R2313,B 16, A4), (R14,R41,R2313,B17, A4), (R14,R41, R2313,B18, A4), (R14,R41,R2313,B19, A4), (R14,R41, R2313,B20, A4), (R14,R41,R2313,B21, A4), (R14,R42, R231,B1, A4), (R14,R42,R231,B2, A4), (R14,R42,R231, B3, A4), (R14,R42,R231,B4, A4), (R14,R42,R231,B5, A4), (R14,R42,R231,B6, A4), (R14,R42,R231,B7, A4), (R14, R42,R231,B8, A4), (R14,R42,R231,B9, A4), (R14,R42, R231,B10, A4), (R14,R42,R231,B11, A4), (R14,R42,R231, B12, A4), (R14,R42,R231,B13, A4), (R14,R42,R231,B14, A4), (R14,R42,R231,B15, A4), (R14,R42,R231,B16, A4), (R14,R42,R231,B17, A4), (R14,R42,R231,B18, A4), (R14, R42,R231,B19, A4), (R14,R42,R231,B20, A4), (R14,R42, R231,B21, A4), (R14,R42,R232,B1, A4), (R14,R42,R232, B2, A4), (R14, R42,R232,B3, A4), (R14,R42,R232,B4, A4), (R14,R42,R232,B5, A4), (R14,R42,R232,B6, A 4), (R14, R42,R232,B7, A4), (R14,R42,R232,B8, A4), (R14,R42, R232,B9, A4), (R14,R42,R232,B10, A4), (R14,R42,R232, B11, A4), (R14,R42,R232,B12, A4), (R14,R42,R232,B13, A4), (R14,R42,R232,B14, A4), (R14,R42,R232,B15, A4), (R14,R42,R232,B16, A4), (R14,R42,R232, B17, A4), (R14, R42,R232,B18, A4), (R14,R42,R232,B19, A4), (R14,R42, R232,B20, A4), (R14,R42,R232,B21, A4), (R14,R42,R233, B1, A4), (R14,R42,R233,B2, A4), (R14,R42,R233,B3, A4), (R14,R42,R233,B4, A4), (R14,R42,R233,B5, A4), (R14, R42,R233,B6, A4), (R14,R42,R233,B7, A4), (R14,R42, R233,B8, A4), (R14,R42,R233,B9, A4), (R14,R42,R233, B10, A4), (R14,R42,R233,B11, A4), (R14,R42,R233,B12, A4), (R14,R42,R233,B13, A4), (R14,R42,R233, B14, A4), (R14,R42,R233,B15, A4), (R14,R42,R233,B16, A4), (R14, R42,R233,B17, A4), (R14,R42,R233,B18, A4), (R14,R42, R233,B19, A4), (R14,R42,R233,B20, A4), (R14,R42,R233, B21, A4), (R14,R42,R234,B1, A4), (R14,R42,R234,B2, A4), (R14,R42,R234,B3, A4), (R14,R42,R234,B4, A4), (R14,R42,R234,B5, A4), (R14,R42,R234,B6, A4), (R14, R42,R234,B7, A4), (R14,R42,R234,B8, A4), (R14,R42, R234,B9, A4), (R14,R42,R234,B10, A4), (R14,R42,R234, B11, A4), (R14,R42,R234,B12, A4), (R14,R42,R234,B13, A4), (R14,R42,R234,B14, A4), (R14,R42,R234,B15, A4), (R14,R42,R234,B16, A4), (R14,R42,R234,B17, A4), (R14, R42,R234, B18, A4), (R14,R42,R234,B19, A4), (R14,R42, R234,B20, A4), (R14,R42,R234,B21, A4), (R14,R42,R235, B1, A4), (R14,R42,R235,B2, A4), (R14,R42,R235,B3, A4), (R14,R42,R235,B4, A4), (R14,R42,R235,B5, A4), (R14, R42,R235,B6, A4), (R14,R42,R235,B7, A4), (R14,R42, R235,B8, A4), (R14,R42,R235,B9, A4), (R14,R42,R235, B10, A4), (R14,R42,R235,B11, A4), (R14,R42,R235,B12, A4), (R14,R42,R235,B13, A4), (R14,R42,R235,B14, A4), (R14,R42,R235, B15, A4), (R14,R42,R235,B16, A4), (R14, R42,R235,B17, A4), (R14,R42,R235,B18, A4), (R14,R42, R235,B19, A4), (R14,R42,R235,B20, A4), (R14,R42,R235, B21, A4), (R14,R42,R236, B1, A4), (R14,R42,R236,B2, A4), (R14,R42,R236,B3, A4), (R14,R42,R236,B4, A4), (R14,R42,R236,B5, A4), (R14,R42,R236,B6, A4), (R14, R42,R236,B7, A4), (R14,R42,R236,B8, A4), (R14,R42, R236,B9, A4), (R14,R42,R236,B10, A4), (R14,R42,R236, B11, A4), (R14,R42,R236, B12, A4), (R14,R42,R236,B13, A4), (R14,R42,R236,B14, A4), (R14,R42,R236,B15, A4), (R14,R42,R236,B16, A4), (R14,R42,R236,B17, A4), (R14, R42,R236,B18, A4), (R14,R42,R236, B19, A4), (R14,R42, R236,B20, A4), (R14,R42,R236,B21, A4), (R14,R42,R237, B1, A4), (R14, R42,R237,B2, A4), (R14,R42,R237,B3, A4), (R14,R42,R237,B4, A4), (R14,R42,R237,B5, A4), (R14, R42,R237,B6, A4), (R14,R42,R237,B7, A4), (R14,R42, R237,B8, A4), (R14,R42,R237, B9, A4), (R14,R42,R237, B10, A4), (R14,R42,R237,B11, A4), (R14,R42,R237,B12, A4), (R14, R42,R237,B13, A4), (R14,R42,R237,B14, A4), (R14,R42,R237,B15, A4), (R14,R42,R237,B 16, A4), (R14, R42,R237,B17, A4), (R14,R42,R237,B18, A4), (R14,R42, R237,B19, A4), (R14, R42,R237,B20, A4), (R14,R42,R237, B21, A4), (R14,R42,R238,B1, A4), (R14,R42,R238,B2, A4), (R14,R42,R238,B3, A4), (R14,R42,R238,B4, A4), (R14,R42,R238,B5, A4), (R14,R42,R238,B6, A4), (R14, R42,R238,B7, A4), (R14,R42,R238,B8, A4), (R14,R42, R238,B9, A4), (R14, R42,R238,B10, A4), (R14,R42,R238, B11, A4), (R14,R42,R238,B12, A4), (R14,R42,R238,B 13, A4), (R14,R42,R238,B14, A4), (R14,R42,R238,B15, A4), (R14,R42,R238,B16, A4), (R14, R42,R238,B17, A4), (R14, R42,R238,B18, A4), (R14,R42,R238,B19, A4), (R14,R42, R238,B20, A4), (R14,R42,R238,B21, A4), (R14,R42,R239, B1,A4), (R14,R42,R239,B2, A4), (R14, R42, R239,B3, A4), (R14,R42,R239,B4, A4), (R14,R42,R239,B5, A4), (R14, R42,R239,B6, A4), (R14,R42,R239,B7, A4), (R14,R42, R239,B8, A4), (R14,R42,R239,B9, A4), (R14,R42,R239, B10, A4), (R14,R42,R239,B11, A4), (R14,R42,R239,B12, A4), (R14,R42,R239,B13, A4), (R14,R42,R239,B14, A4), (R14,R42,R239,B15, A4), (R14,R42,R239,B16, A4), (R14, R42,R239,B17,A4), (R14,R42,R239,B18, A4), (R14,R42, R239,B19, A4), (R14,R42,R239,B20, A4), (R14,R42,R239, B21, A4), (R14,R42,R2310,B1, A4), (R14,R42,R2310,B2, A4), (R14,R42,R2310,B3, A4), (R14,R42,R2310,B4, A4), (R14,R42,R2310,B5, A4), (R14,R42,R2310,B6, A4), (R14, R42,R2310,B7, A4), (R14,R42,R2310,B8, A4), (R14,R42,

R2310,B9, A4), (R14,R42,R2310,B10, A4), (R14,R42, R2310,B11, A4), (R14,R42,R2310,B12, A4), (R14,R42, R2310,B13, A4), (R14, R42,R2310,B14, A4), (R14,R42, R2310,B15, A4), (R14,R42,R2310,B16, A4), (R14,R42, R2310,B17, A4), (R14,R42,R2310,B18, A4), (R14,R42, R2310,B19, A4), (R14,R42,R2310,B20, A 4), (R14,R42, R2310,B21, A4), (R14,R42,R2311,B1, A4), (R14,R42, R2311,B2, A4), (R14,R42, R2311,B3, A4), (R14,R42, R2311,B4, A4), (R14,R42,R2311,B5, A4), (R14,R42, R2311,B6, A 4), (R14,R42,R2311,B7, A4), (R14,R42, R2311,B8, A4), (R14,R42,R2311,B9, A4), (R14,R42, R2311,B10, A4), (R14,R42,R2311,B11, A4), (R14,R42, R2311,B12, A4), (R14,R42,R2311,B13, A4), (R14,R42, R2311,B14, A4), (R14,R42,R2311,B15, A4), (R14,R42, R2311,B16, A4), (R14,R42,R2311,B17, A4), (R14,R42, R2311,B18, A4), (R14,R42,R2311,B19, A4), (R14,R42, R2311,B20, A4), (R14,R42,R2311,B21, A4), (R14,R42, R2312,B1, A4), (R14,R42,R2312,B2, A4), (R14,R42, R2312,B3, A4), (R14,R42,R2312,B4, A4), (R14,R42, R2312,B5, A4), (R14,R42,R2312,B6, A4), (R14,R42, R2312,B7, A4), (R14,R42,R2312,B8, A4), (R14,R42, R2312,B9, A4), (R14,R42,R2312,B10, A4), (R14,R42, R2312,B11, A4), (R14,R42,R2312,B12, A4), (R14,R42, R2312,B13, A4), (R14,R42,R2312,B14, A4), (R14,R42, R2312,B15, A4), (R14,R42,R2312,B 16, A4), (R14,R42, R2312,B17, A4), (R14,R42,R2312,B18, A4), (R14,R42, R2312,B19, A4), (R14,R42,R2312,B20, A4), (R14,R42, R2312,B21, A4), (R14,R42,R2313,B1, A4), (R14,R42, R2313,B2, A4), (R14,R42,R2313,B3, A4), (R14,R42, R2313,B4, A4), (R14,R42,R2313,B5, A4), (R14,R42, R2313,B6, A4), (R14,R42,R2313,B7, A4), (R14,R42, R2313,B8, A4), (R14,R42,R2313,B9, A4), (R14,R42, R2313,B10, A4), (R14,R42,R2313,B11, A4), (R14,R42, R2313,B12, A4), (R14,R42,R2313,B13, A4), (R14,R42, R2313,B14, A4), (R14,R42,R2313,B15, A4), (R14,R42, R2313,B16, A4), (R14,R42,R2313,B17, A4), (R14,R42, R2313,B18, A4), (R14,R42,R2313, B19, A4), (R14,R42, R2313,B20, A4), (R14,R42,R2313,B21, A4), (R15,R41, R231,B1, A4), (R15,R41,R231,B2, A4), (R15,R41,R231, B3, A4), (R15,R41,R231,B4, A4), (R15,R41,R231,B5, A4), (R15,R41,R231,B6, A4), (R15,R41,R231,B7, A4), (R15, R41,R231,B8, A4), (R15,R41,R231,B9, A4), (R15,R41, R231,B10, A4), (R15,R41,R231,B11, A4), (R15,R41,R231, B12, A4), (R15,R41,R231,B13, A4), (R15,R41,R231,B14, A4), (R15,R41,R231,B15, A4), (R15,R41,R231,B16, A4), (R15,R41,R231,B17, A4), (R15,R41,R231,B18, A4), (R15, R41,R231,B19, A4), (R15,R41,R231,B20, A4), (R15,R41, R231,B21, A4), (R15,R41,R232,B1, A4), (R15,R41,R232, B2, A4), (R15,R41,R232, B3, A4), (R15,R41,R232, B4, A4), (R15,R41,R232, B5, A4), (R15, R41,R232,B6, A4), (R15,R41,R232,B7, A4), (R15,R41,R232,B8, A4), (R15, R41,R232,B9, A4),(R15,R41,R232,B10, A4), (R15,R41, R232,B11, A4), (R15,R41,R232,B12, A4), (R15,R41,R232, B13, A4), (R15,R41,R232,B14, A4), (R15,R41,R232,B15, A4), (R15,R41,R232,B16, A4), (R15,R41,R232,B17, A4), (R15,R41,R232,B18, A4), (R15,R41,R232,B19, A4), (R15, R41,R232, B20, A4), (R15,R41,R232,B21, A4), (R15,R41, R233,B1, A4), (R15,R41,R233,B2, A4), (R15, R41,R233, B3, A4), (R15,R41,R233,B4, A4), (R15,R41,R233,B5, A4), (R15,R41,R233,B6, A4), (R15,R41,R233,B7, A4), (R15, R41,R233,B8, A4), (R15,R41,R233,B9, A4), (R15,R41, R233, B10, A4), (R15,R41,R233,B11, A4), (R15,R41,R233, B12, A4), (R15,R41,R233,B13, A4), (R15,R41,R233,B14, A4), (R15,R41,R233,B15, A4), (R15,R41,R233,B16, A4), (R15,R41,R233, B17, A4), (R15,R41,R233,B18, A4), (R15, R41,R233,B19, A4), (R15,R41,R233,B20, A4), (R15,R41, R233,B21, A4), (R15,R41,R234,B1, A4), (R15,R41,R234, B2, A4), (R15,R41,R234,B3, A4), (R15,R41,R234,B4, A4), (R15,R41,R234,B5, A4), (R15,R41,R234,B6, A4), (R15, R41,R234, B7, A4), (R15,R41,R234, B8, A4), (R15, R41, R234, B9, A4), (R15,R41,R234,B10, A4), (R15,R41,R234, B11, A4), (R15,R41,R234,B12, A4), (R15,R41,R234,B13, A4), (R15,R41,R234, B14, A4), (R15,R41,R234,B15, A4), (R15,R41,R234,B16, A4), (R15,R41,R234,B17, A4), (R15, R41,R234,B18, A4), (R15,R41,R234,B19, A4), (R15,R41, R234,B20, A4), (R15,R41,R234, B21, A4), (R15,R41,R235, B1, A4), (R15,R41,R235,B2, A4), (R15,R41,R235,B3, A4), (R15,R41,R235,B4, A4), (R15,R41,R235,B5, A4), (R15, R41,R235,B6, A4), (R15,R41,R235,B7, A4), (R15,R41, R235,B8, A4), (R15,R41,R235,B9, A4), (R15,R41,R235, B10, A4), (R15,R41,R235, B11, A4), (R15,R41,R235,B12, A4), (R15,R41,R235,B13, A4), (R15,R41,R235,B14, A4), (R15,R41,R235,B15, A4), (R15,R41,R235,B16, A4), (R15, R41,R235,B17, A4), (R15,R41,R235, B18, A4), (R15,R41, R235,B19, A4), (R15,R41,R235,B20, A4), (R15,R41,R235, B21, A4), (R15,R41,R236,B1, A4), (R15,R41,R236,B2, A4), (R15,R41,R236,B3, A4), (R15,R41,R236,B4, A4), (R15,R41,R236,B5, A4), (R15,R41,R236,B6, A4), (R15, R41,R236,B7, A4), (R15,R41,R236,B8, A4), (R15,R41, R236,B9, A4), (R15,R41,R236,B10, A4), (R15,R41,R236, B11, A4), (R15,R41,R236,B12, A4), (R15,R41,R236,B13, A4), (R15,R41,R236,B14, A4), (R15,R41,R236, B15, A4), (R15,R41,R236,B16, A4), (R15,R41,R236,B17, A4), (R15, R41,R236,B18, A4), (R15,R41,R236,B19, A4), (R15,R41, R236,B20, A4), (R15,R41,R236,B21, A4), (R15,R41,R237, B1, A4), (R15,R41,R237, B2, A4), (R15,R41,R237, B3, A4), (R15, R41,R237, B4, A4), (R15, R41,R237,B5, A4), (R15,R41,R237,B6, A4), (R15,R41,R237,B7, A4), (R15, R41,R237,B8, A4), (R15,R41,R237,B9, A4), (R15,R41, R237,B10, A4), (R15,R41,R237,B11, A4), (R15,R41,R237, B12, A4), (R15,R41,R237,B13, A4), (R15,R41,R237,B14, A4), (R15,R41,R237,B15, A4), (R15,R41,R237,B16, A4), (R15,R41,R237,B17, A4), (R15,R41,R237,B18, A4), (R15, R41,R237, B19, A4), (R15,R41,R237,B20, A4), (R15,R41, R237,B21, A4), (R15,R41,R238,B1, A4), (R15, R41,R238, B2, A4), (R15,R41,R238,B3, A4), (R15,R41,R238,B4, A4), (R15,R41,R238,B5, A4),(R15, R41, R238, B6, A4), (R15, R41,R238, B7, A4), (R15,R41,R238, B8, A4), (R15, R41, R238, B9, A4), (R15,R41,R238,B10, A4), (R15,R41,R238, B11, A4), (R15,R41,R238,B12, A4), (R15, R41,R238,B13, A4), (R15,R41,R238,B14, A4), (R15,R41,R238,B15, A4), (R15,R41,R238,B 16, A4), (R15,R41,R238,B17, A4), (R15, R41,R238,B18, A4), (R15,R41,R238,B19, A4), (R15, R41, R238,B20, A4), (R15,R41,R238,B21, A4), (R15,R41,R239, B1, A4), (R15,R41,R239,B2, A4), (R15,R41,R239,B3, A4), (R15,R41,R239,B4, A4), (R15,R41,R239,B5, A4), (R15, R41,R239, B6, A4), (R15,R41,R239, B7, A4), (R15, R41, R239, B8, A4), (R15,R41,R239, B9, A4), (R15, R41,R239, B10, A4), (R15,R41,R239,B11, A4), (R15,R41,R239,B12, A4), (R15,R41,R239,B 13, A4), (R15,R41,R239,B14, A4), (R15,R41,R239,B15, A4), (R15,R41,R239,B16, A4), (R15, R41,R239,B17, A4), (R15,R41,R239,B18, A4), (R15,R41, R239,B19, A4), (R15,R41,R239,B20, A4), (R15,R41,R239, B21, A4), (R15,R41,R2310,B1, A4), (R15,R41,R2310,B2, A4), (R15,R41,R2310,B3, A4), (R15,R41,R2310,B4, A4), (R15,R41,R2310,B5, A4), (R15,R41,R2310,B6, A4), (R15, R41,R2310,B7, A4), (R15,R41,R2310,B8, A4), (R15,R41, R2310,B9, A4), (R15,R41,R2310,B10, A4), (R15,R41, R2310,B11, A4), (R15,R41,R2310,B12, A4), (R15,R41, R2310, B13, A4), (R15,R41,R2310,B14, A4), (R15,R41, R2310,B15, A4), (R15,R41,R2310,B16, A4), (R15,R41, R2310,B17, A4), (R15,R41,R2310,B18, A4), (R15,R41, R2310,B19, A4), (R15,R41, R2310, B20, A4), (R15,R41, R2310,B21, A4), (R15,R41,R2311,B1, A4), (R15,R41,

R2311,B2, A4), (R15,R41,R2311,B3, A4), (R15,R41, R2311,B4, A4), (R15,R41,R2311,B5, A4), (R15,R41, R2311,B6, A4), (R15,R41,R2311,B7, A4), (R15,R41, R2311,B8, A4), (R15,R41,R2311,B9, A 4), (R15,R41, R2311,B10, A4), (R15,R41,R2311,B11, A4), (R15,R41, R2311,B2, A4), (R15,R41,R2311,B13, A4), (R15,R41, R2311,B14, A4), (R15,R41,R2311,B15, A4), (R15,R41, R2311, B16, A4), (R15,R41,R2311,B17, A4), (R15,R41, R2311,B18, A4), (R15,R41,R2311,B19, A4), (R15,R41, R2311,B20, A4), (R15,R41,R2311,B21, A4), (R15,R41, R2312,B1, A4), (R15,R41, R2312,B2, A4), (R15,R41, R2312,B3, A4), (R15,R41,R2312,B4, A4), (R15,R41, R2312,B5, A4), (R15,R41,R2312,B6, A4), (R15,R41, R2312,B7, A4), (R15,R41,R2312,B8, A4), (R15,R41, R2312,B9, A4), (R15,R41,R2312,B10, A4), (R15,R41, R2312,B11, A4), (R15,R41,R2312,B12, A4), (R15,R41, R2312,B13, A4), (R15,R41,R2312,B14, A4), (R15,R41, R2312,B15, A4), (R15, R41,R2312,B16, A4), (R15,R41, R2312,B17, A4), (R15,R41,R2312,B18, A4), (R15,R41, R2312,B19, A4), (R15,R41,R2312,B20, A4), (R15,R41, R2312,B21, A4), (R15,R41,R2313,B1, A4), (R15,R41, R2313,B2, A4), (R15,R41,R2313,B3, A4), (R15,R41, R2313,B4, A4), (R15,R41,R2313,B5, A4), (R15,R41, R2313,B6, A4), (R15,R41,R2313,B7, A4), (R15,R41, R2313,B8, A4), (R15,R41,R2313,B9, A4), (R15,R41, R2313,B10, A4), (R15,R41,R2313,B11, A4), (R15,R41, R2313,B12, A4), (R15,R41,R2313,B13, A4), (R15,R41, R2313,B14, A4), (R15,R41,R2313,B 15, A4), (R15,R41, R2313,B16, A4), (R15,R41,R2313,B17, A4), (R15,R41, R2313,B18, A4), (R 15,R41,R2313,B19, A4), (R15,R41, R2313,B20, A4), (R15,R41,R2313,B21, A4), (R15,R42, R231,B1, A4), (R15,R42,R231,B2, A4), (R15,R42,R231, B3, A4), (R15,R42,R231,B4, A4), (R15, R42,R231,B5, A4), (R15,R42,R231,B6, A4), (R15,R42,R231,B7, A4), (R15, R42,R231,B8, A 4), (R15,R42,R231,B9, A4), (R15,R42, R231,B10, A4), (R15,R42,R231,B11, A4), (R15,R42,R231, B12, A4), (R15,R42,R231,B13, A4), (R15,R42,R231,B14, A4), (R15,R42,R231,B15, A4), (R15,R42,R231,B16, A4), (R15,R42,R231,B17, A4), (R15,R42,R231,B18, A4), (R15, R42,R231,B19, A4), (R15,R42,R231,B20, A4), (R15,R42, R231,B21, A4), (R15,R42,R232,B1, A4), (R15,R42,R232, B2, A4), (R15,R42,R232,B3, A4), (R15,R42,R232,B4, A4), (R15,R42,R232,B5, A4), (R15,R42,R232,B6, A4), (R15, R42,R232,B7, A4), (R15,R42,R232,B8, A4), (R15,R42, R232,B9, A4), (R15,R42,R232,B10, A4), (R15,R42,R232, B11, A4), (R15,R42,R232,B12, A4), (R15,R42,R232,B13, A4), (R15,R42,R232,B14, A4), (R15,R42,R232,B15, A4), (R15,R42,R232,B16, A4), (R15,R42,R232,B17, A4), (R15, R42,R232,B18, A4), (R15,R42,R232,B19, A4), (R15,R42, R232,B20, A4), (R15,R42,R232,B21, A4), (R15,R42,R233, B1, A4), (R15,R42,R233, B2, A4), (R15,R42,R233, B3, A4), (R15,R42,R233, B4, A4), (R15,R42,R233, B5, A4), (R15, R42,R233,B6, A4), (R15,R42,R233,B7, A4), (R15, R42,R233,B8, A4), (R15,R42,R233,B9, A4), (R15,R42, R233,B10, A4), (R15,R42,R233,B11, A4), (R15,R42,R233, B12, A4), (R15,R42,R233,B13, A4), (R15,R42,R233,B14, A4), (R15,R42,R233,B15, A4), (R15,R42,R233,B16, A4), (R15,R42,R233,B17, A4), (R15,R42,R233,B18, A4), (R15, R42,R233,B19, A4), (R15,R42,R233, B20, A4), (R15,R42, R233,B21, A4), (R15,R42,R234,B1, A4), (R15,R42,R234, B2, A4), (R15, R42,R234,B3, A4), (R15,R42,R234,B4, A4), (R15,R42,R234,B5, A4), (R15,R42,R234,B6, A4), (R15, R42,R234,B7, A4), (R15,R42,R234,B8, A4), (R15,R42, R234,B9, A4), (R15,R42,R234, B 10, A4), (R15,R42,R234, B11, A4), (R15,R42,R234,B12, A4), (R15,R42,R234,B13, A4), (R15,R42,R234,B14, A4), (R15,R42,R234,B15, A4), (R15,R42,R234,B16, A4), (R15,R42,R234, B 17, A4), (R15, R42,R234,B18, A4), (R15,R42,R234,B19, A4), (R15,R42, R234,B20, A4), (R15,R42,R234,B21, A4), (R15,R42,R235, B1, A4), (R15,R42,R235,B2, A4), (R15,R42,R235,B3, A4), (R15,R42,R235,B4, A4), (R15,R42,R235,B5, A4), (R15, R42,R235,B6, A4), (R15,R42,R235,B7, A4), (R15,R42, R235,B8, A4), (R15,R42,R235,B9, A4), (R15,R42,R235, B10, A4), (R15,R42,R235,B11, A4), (R15,R42,R235,B12, A4), (R15,R42,R235,B13, A4), (R15,R42,R235, B14, A4), (R15,R42,R235,B15, A4), (R15,R42,R235,B16, A4), (R15, R42,R235,B17, A4), (R15,R42,R235,B18, A4), (R15,R42, R235,B19, A4), (R15,R42,R235,B20, A4), (R15,R42,R235, B21, A4), (R15,R42,R236,B1, A4), (R15,R42,R236,B2, A4), (R15,R42,R236,B3, A4), (R15,R42,R236,B4, A4), (R15,R42,R236,B5, A4), (R15,R42,R236,B6, A4), (R15, R42,R236,B7, A4), (R15,R42,R236,B8, A4), (R15,R42, R236,B9, A4), (R15,R42,R236,B10, A4), (R15,R42,R236, B11, A4), (R15,R42,R236,B12, A4), (R15,R42,R236,B13, A4), (R15,R42,R236,B14, A4), (R15,R42,R236, B15, A4), (R5,R42,R236, B16, A4), (R5,R42,R236, B17, A4), (R5, R42,R236, B18, A4), (R15,R42,R236,B19, A4), (R15,R42, R236,B20, A4), (R15,R42,R236,B21, A4), (R15,R42,R237, B1, A4), (R5,R42,R237, B2, A4), (R15, R42,R237, B3, A4), (R5,R42,R237, B4, A4), (R15, R42,R237, B5, A4), (R15, R42,R237, B6, A4), (R15, R42,R237, B7, A4), (R15,R42, R237,B8, A4), (R15,R42,R237,B9, A4), (R15,R42,R237, B10, A4), (R15,R42,R237,B11, A4), (R15,R42,R237, B12, A4), (R15,R42,R237, B13, A4), (R15,R42,R237, B14, A4), (R15,R42,R237, B15, A4), (R15,R42,R237, B16, A4), (R15, R42,R237, B17, A4), (R15,R42,R237, B18, A4), (R15,R42, R237,B19, A4), (R15,R42,R237,B20, A4), (R15,R42,R237, B21, A4), (R15,R42,R238, B1, A4), (R15,R42,R238,B2, A4), (R15,R42,R238,B3, A4), (R15,R42,R238,B4, A4), (R15,R42,R238,B5, A4), (R15,R42,R238,B6, A4), (R15, R42,R238,B7, A4), (R15,R42,R238,B8, A4), (R15,R42, R238, B9, A4), (R15,R42,R238,B10, A4), (R15,R42,R238, B11, A4), (R1,R42,R238, B12, A4), (R15,R42,R238, B13, A4), (R15,R42,R238, B14, A4), (R15,R42,R238, B15, A4), (R15,R42,R238,B16, A4), (R15,R42,R238,B17, A4), (R15, R42,R238,B18, A4), (R15,R42,R238, B19, A4), (R15,R42, R238,B20, A4), (R15,R42,R238,B21, A4), (R15,R42,R239, B1, A4), (R15, R42,R239,B2, A4), (R15,R42,R239,B3, A4), (R15,R42,R239,B4, A4), (R15,R42,R239,B5, A4), (R15, R42,R239,B6, A4), (R15,R42,R239,B7, A4), (R15,R42, R239,B8, A4), (R15,R42,R239, B9, A4), (R15,R42,R239, B10, A4), (R15,R42,R239, B11, A4), (R15,R42,R239, B12, A4), (R15, R42,R239, B13, A4), (R15,R42,R239, B14, A4), (R15,R42,R239, B15, A4), (R15,R42,R239, B 16, A4), (R15,R42,R239, B17, A4), (R15,R42,R239, B18, A4), (R15, R42,R239, B19, A4), (R15, R42,R239,B20, A4), (R15,R42, R239,B21, A4), (R15,R42,R2310,B1, A4), (R15,R42, R2310,B 2, A4), (R15,R42,R2310,B3, A4), (R15,R42, R2310,B4, A4), (R15,R42,R2310,B5, A4), (R15,R42, R2310,B6, A4), (R15,R42,R2310,B7, A4), (R15,R42, R2310,B8, A4), (R15,R42,R2310,B9, A4), (R15,R42, R2310,B10, A4), (R15,R42,R2310,B11, A4), (R15,R42, R2310,B12, A4), (R15, R42,R2310,B13, A4), (R15,R42, R2310, B14, A4), (R15,R42,R2310, B15, A4), (R15,R42, R2310,B16, A4), (R15,R42,R2310, B17, A4), (R15,R42, R2310,B18, A4), (R15,R42,R2310, B19, A 4), (R15,R42, R2310,B20, A4), (R15,R42,R2310,B21, A4), (R15,R42, R2311,B1, A4), (R5,R42,R2311,B2, A4), (R15,R42,R2311, B3, A4), (R15,R42,R2311,B4, A4), (R15,R42,R2311,B5, A4), (R15,R42,R2311,B6, A4), (R15,R42,R2311,B7, A4), (R15,R42,R2311,B8, A4), (R15, R42, R2311, B9, A4), (R15, R42,R2311,B10, A4), (R15,R42,R2311,B11, A4), (R15, R42,R2311, B12, A4), (R15, R42,R2311,B13, A4), (R15, R42,R2311,B14, A4), (R15, R42,R2311,B15, A4), (R15,

R42,R2311, B16, A4), (R15,R42,R2311,B17, A4), (R15, R42,R2311, B18, A4), (R15,R42,R2311,B19, A4), (R15, R42,R2311,B20, A4), (R15,R42,R2311,B21, A4), (R15, R42,R2312,B1, A 4), (R15,R42,R2312,B2, A4), (R15,R42, R2312,B3, A4), (R15,R42,R2312,B4, A4), (R15,R42, R2312,B5, A4), (R15,R42,R2312,B6, A4), (R15,R42, R2312,B7, A4), (R15,R42,R2312,B8, A4),(R15,R42, R2312,B9, A4), (R15,R42,R2312,B10, A4), (R15,R42, R2312,B11, A4), (R15,R42, R2312,B12, A4), (R15,R42, R2312,B13, A4), (R15,R42,R2312,B14, A4), (R15,R42, R2312,B 15, A4), (R15,R42,R2312,B16, A4), (R15,R42, R2312,B17, A4), (R15,R42,R2312,B18, A4), (R15,R42, R2312,B19, A4), (R15,R42,R2312,B20, A4), (R15,R42, R2312,B21, A4), (R15,R42,R2313,B1, A4), (R15,R42, R2313,B2, A4), (R15,R42,R2313,B3, A4), (R15,R42, R2313,B4, A4), (R15,R42,R2313,B5, A4), (R15,R42, R2313,B6, A4), (R15,R42,R2313,B7, A4), (R15,R42, R2313,B8, A4), (R15,R42,R2313,B9, A4), (R15,R42, R2313,B10, A4), (R15,R42,R2313,B11, A4), (R15,R42, R2313,B12, A4), (R15,R42,R2313,B13, A4), (R15,R42, R2313,B14, A4), (R15,R42,R2313,B15, A4), (R15,R42, R2313,B16, A4), (R15,R42,R2313,B17, A4), (R15,R42, R2313, B18, A4), (R15,R42,R2313,B19, A4), (R15,R42, R2313,B20, A4), (R15,R42,R2313,B21, A4), (R16,R41, R231,B1, A4), (R16,R41,R231,B2, A4), (R16,R41,R231, B3, A4), (R16,R41,R231,B 4, A4), (R16,R41,R231,B5, A4), (R16,R41,R231,B6, A4), (R16,R41,R231,B7, A4), (R16, R41, R231,B8, A4), (R16,R41,R231,B9, A4), (R16,R41, R231,B10, A4), (R16,R41,R231,B11, A4), (R16,R41,R231, B12, A4), (R16,R41,R231,B13, A4), (R16,R41,R231,B14, A4), (R16, R41, R231,B15, A4), (R16,R41,R231,B16, A4), (R16,R41,R231,B17, A4), (R16,R41,R231,B18, A4), (R16, R41,R231,B19, A4), (R16,R41,R231,B20, A4), (R16,R41, R231,B21, A4), (R16,R41,R232, B1, A4), (R16,R41,R232, B2, A4), (R16,R41,R232,B3, A4), (R16,R41,R232,B4, A4), (R16,R41,R232,B5, A4), (R16,R41,R232,B6, A4), (R16, R41,R232,B7, A4), (R16,R41,R232,B8, A4), (R16,R41, R232,B9, A4), (R16,R41,R232,B10, A4), (R16,R41,R232, B11, A4), (R16,R41,R232, B12, A4), (R16,R41,R232,B13, A4), (R16,R41,R232,B14, A4), (R16,R41,R232,B15, A4), (R16,R41,R232,B16, A4), (R16,R41,R232,B17, A4), (R16, R41,R232,B18, A4), (R16,R41,R232, B19, A4), (R16,R41, R232,B20, A4), (R16,R41,R232,B21, A4), (R16,R41,R233, B1, A4), (R16,R41,R233,B2, A4), (R16, R41,R233,B3, A4), (R16,R41,R233,B4, A4), (R16,R41,R233,B5, A4), (R16, R41,R233,B6, A4), (R16,R41,R233,B7, A4), (R16,R41, R233,B8, A4), (R16,R41,R233, B9, A4), (R16,R41,R233, B10, A4), (R16,R41,R233,B11, A4), (R16,R41,R233,B12, A4), (R16, R41,R233,B13, A4), (R16,R41,R233,B14, A4), (R16,R41,R233,B15, A4), (R16,R41,R233,B 16, A4), (R16, R41,R233,B17, A4), (R16,R41,R233,B18, A4), (R16,R41, R233,B19, A4), (R16, R41,R233,B20, A4), (R16,R41,R233, B21, A4), (R16,R41,R234,B1, A4), (R16,R41,R234,B2, A4), (R16,R41,R234,B3, A4), (R16,R41,R234,B4, A4), (R16,R41,R234,B5, A4), (R16,R41,R234,B6, A4), (R16, R41,R234,B7, A4), (R16,R41,R234,B8, A4), (R16,R41, R234,B9, A4), (R16, R41,R234,B10, A4), (R16,R41,R234, B11, A4), (R16,R41,R234,B12, A4), (R16,R41,R234,B 13, A4), (R16,R41,R234,B14, A4), (R16,R41,R234,B15, A4), (R16,R41,R234,B16, A4), (R16, R41,R234,B17, A4), (R16, R41,R234,B18, A4), (R16,R41,R234,B19, A4), (R16,R41, R234,B20, A4), (R16,R41,R234,B21, A4), (R16,R41,R235, B1, A4), (R16,R41,R235,B2, A4), (R16,R41,R235,B3, A4), (R16,R41,R235,B4, A4), (R16,R41,R235,B5, A4), (R16, R41,R235,B6, A4), (R16,R41,R235,B7, A4), (R16,R41, R235,B8, A4), (R16,R41,R235,B9, A4), (R16,R41,R235, B10, A4), (R16,R41,R235,B11, A4), (R16,R41,R235,B12, A4), (R16,R41,R235,B13, A4), (R16,R41,R235,B14, A4), (R16,R41,R235,B15, A4), (R16,R41,R235,B16, A4), (R16, R41,R235,B17, A4), (R16,R41,R235,B18, A4), (R16,R41, R235,B19, A4), (R16,R41,R235,B20, A4), (R16,R41,R235, B21, A4), (R16,R41,R236,B1, A4), (R16,R41,R236,B2, A4), (R16,R41,R236,B3, A4), (R16,R41,R236,B4, A4), (R16,R41,R236,B5, A4), (R16,R41,R236,B6, A4), (R16, R41,R236, B7, A4), (R16,R41,R236,B8, A4), (R16,R41, R236,B9, A4), (R16,R41,R236,B10, A4), (R16,R41,R236, B11, A4), (R16,R41,R236,B12, A4), (R16,R41,R236,B13, A4), (R16,R41,R236,B14, A4), (R16,R41,R236,B15, A4), (R16,R41,R236,B16, A4), (R16,R41,R236,B17, A4), (R16, R41,R236,B18, A4), (R16,R41,R236,B19, A4), (R16,R41, R236,B20, A4), (R16,R41,R236,B21, A4), (R16,R41,R237, B1, A4), (R16,R41,R237,B2, A4), (R16,R41,R237,B3, A4), (R16,R41,R237,B4, A4), (R16,R41,R237,B5, A4), (R16, R41,R237,B6, A4), (R16,R41,R237,B7, A4), (R16, R41, R237,B8, A4), (R16,R41,R237,B9, A4), (R16,R41,R237, B10, A4), (R16,R41,R237,B11, A4), (R16,R41,R237,B12, A4), (R16,R41,R237,B13, A4), (R16,R41,R237,B14, A4), (R16,R41,R237,B15, A4), (R16,R41,R237,B16, A4), (R16, R41,R237,B17, A4), (R16,R41,R237,B18, A4), (R16,R41, R237,B19, A4), (R16,R41,R237,B20, A4), (R16,R41,R237, B21, A4), (R16,R41,R238,B1, A4), (R16,R41,R238,B2, A4), (R16,R41,R238,B3, A4), (R16,R41,R238,B4, A4), (R16,R41,R238,B5, A4), (R16,R41,R238,B6, A4), (R16, R41,R238,B7, A4), (R16,R41,R238,B 8, A4), (R16,R41, R238,B9, A4), (R16,R41,R238,B10, A4), (R16,R41,R238, B11, A4), (R16,R41,R238,B12, A4), (R16,R41,R238,B13, A4), (R16,R41,R238,B14, A4), (R16,R41,R238,B15, A4), (R16,R41,R238,B16, A4), (R16,R41,R238,B17, A4), (R16, R41,R238,B18, A4), (R16,R41,R238,B19, A4), (R16,R41, R238,B20, A4), (R16,R41,R238,B21, A4), (R16,R41,R239, B1, A 4), (R16,R41,R239,B2, A4), (R16,R41,R239,B3, A4), (R16,R41,R239,B4, A4), (R16,R41,R239,B5, A4), (R16, R41,R239,B6, A4), (R16,R41,R239,B7, A4), (R16,R41, R239,B8, A4), (R16,R41,R239,B9, A4), (R16,R41,R239, B10, A4), (R16,R41,R239,B11, A4), (R16,R41,R239,B12, A4), (R16,R41,R239,B13, A4), (R16,R41,R239,B14, A4), (R16,R41,R239,B15, A4), (R16,R41,R239,B16, A4), (R16, R41,R239,B17, A4), (R16,R41,R239,B18, A4), (R16,R41, R239,B19, A4), (R16,R41,R239,B20, A4), (R16,R41,R239, B21, A4), (R16,R41,R2310,B1, A4), (R16,R41,R2310,B2, A4), (R16,R41,R2310,B3, A4), (R16,R41,R2310,B4, A4), (R16,R41,R2310,B5, A4), (R16,R41,R2310,B6, A4), (R16, R41,R2310,B7, A4), (R16,R41,R2310,B8, A4), (R16,R41, R2310,B9, A4), (R16,R41,R2310,B10, A4), (R16,R41, R2310,B11, A4), (R16,R41,R2310,B 12, A4), (R16,R41, R2310,B13, A4), (R16,R41,R2310,B14, A4), (R16,R41, R2310,B15, A4), (R16,R41,R2310,B16, A4), (R16,R41, R2310,B17, A4), (R16,R41,R2310,B18, A4), (R16,R41,R 2310,B19, A4), (R16,R41,R2310,B20, A4), (R16,R41, R2310,B21, A4), (R16,R41,R2311,B1, A4), (R16,R41, R2311,B2, A4), (R16,R41,R2311,B3, A4), (R16,R41, R2311,B4, A4), (R16,R41, R2311,B5, A4), (R16,R41, R2311,B6, A4), (R16,R41,R2311,B7, A4), (R16,R41, R2311,B8, A 4), (R16,R41,R2311,B9, A4), (R16,R41, R2311,B10, A4), (R16,R41,R2311,B11, A4), (R16,R41, R2311,B12, A4), (R16,R41,R2311,B13, A4), (R16,R41, R2311,B14, A4), (R16,R41,R2311, B15, A4), (R16,R41, R2311,B16, A4), (R16,R41,R2311,B17, A4), (R16,R41, R2311,B18, A4), (R16,R41,R2311,B19, A4), (R16,R41, R2311,B20, A4), (R16,R41,R2311,B21, A4), (R16,R41, R2312,B1, A4), (R16,R41,R2312,B2, A4), (R16,R41, R2312,B3, A4), (R16,R41,R2312,B4, A4), (R16,R41, R2312,B5, A4), (R16,R41,R2312,B6, A4), (R16,R41, R2312,B7, A4), (R16,R41,R2312,B8, A4), (R16,R41,

R2312,B9, A4), (R16,R41,R2312,B10, A4), (R16,R41, R2312,B11, A4), (R16,R41,R2312,B12, A4), (R16,R41, R2312,B13, A4), (R16,R41,R2312,B14, A4), (R16,R41, R2312,B15, A4), (R16,R41,R2312,B16, A4), (R16,R41, R2312,B17, A4), (R16,R41,R2312, B18, A4), (R16,R41, R2312,B19, A4), (R16,R41,R2312,B20, A4), (R16,R41, R2312,B21, A4), (R16,R41,R2313,B1, A4), (R16,R41, R2313,B2, A4), (R16,R41,R2313,B3, A4), (R16,R41, R2313,B4, A4), (R16,R41,R2313,B5, A4), (R16,R41, R2313,B6, A4), (R16,R41,R2313,B7, A4), (R16,R41, R2313,B8, A4), (R16,R41,R2313,B9, A4), (R16,R41, R2313,B10, A4), (R16,R41,R2313,B11, A4), (R16,R41, R2313,B12, A4), (R16,R41,R2313,B13, A4), (R16,R41, R2313,B14, A4), (R16,R41,R2313,B15, A4), (R16,R41, R2313,B16, A4), (R16,R41,R2313,B17, A4), (R16, R41, R2313,B18, A4), (R16,R41,R2313,B19, A4), (R16,R41, R2313,B20, A4), (R16,R41,R2313,B21, A4), (R16,R42, R231,B1, A4), (R16,R42,R231,B2, A4), (R16,R42,R231, B3, A4), (R16, R42,R231,B4, A4), (R16,R42,R231,B5, A4), (R16,R42,R231,B6, A4), (R16,R42,R231,B7, A 4), (R16, R42,R231,B8, A4), (R16,R42,R231,B9, A4), (R16,R42, R231,B10, A4), (R16,R42,R231,B11, A4), (R16,R42,R231, B12, A4), (R16,R42,R231,B13, A4), (R16,R42,R231,B14, A4), (R16,R42,R231,B15, A4), (R16,R42,R231,B16, A4), (R16,R42,R231,B17, A4), (R16,R42,R231,B18, A4), (R16, R42,R231,B19, A4), (R16,R42,R231,B20, A4), (R16,R42, R231,B21, A4), (R16,R42,R232,B1, A4), (R16,R42,R232, B2, A4), (R16,R42,R232,B3, A4), (R16,R42,R232,B4, A4), (R16,R42,R232,B5, A4), (R16,R42,R232,B6, A4), (R16, R42,R232,B7, A4), (R16,R42,R232,B8, A4), (R16,R42, R232,B9, A4), (R16,R42,R232,B10, A4), (R16,R42,R232, B11, A4), (R16,R42,R232,B12, A4), (R16,R42,R232,B13, A4), (R16,R42,R232,B14, A4), (R16,R42,R232, B15, A4), (R16,R42,R232,B16, A4), (R16,R42,R232,B17, A4), (R16, R42,R232,B18, A4), (R16,R42,R232,B19, A4), (R16,R42, R232,B20, A4), (R16,R42,R232,B21, A4), (R16,R42,R233, B1, A4), (R16,R42,R233,B2, A4), (R16,R42,R233,B3, A4), (R16,R42,R233,B4, A4), (R16,R42,R233,B5, A4), (R16, R42,R233,B6, A4), (R16,R42,R233,B7, A4), (R16,R42, R233,B8, A4), (R16,R42,R233,B9, A4), (R16,R42,R233, B10, A4), (R16,R42,R233,B11, A4), (R16,R42,R233,B12, A4), (R16,R42,R233,B13, A4), (R16,R42,R233,B14, A4), (R16,R42,R233,B15, A4), (R16,R42,R233,B16, A4), (R16, R42,R233,B17, A4), (R16,R42,R233,B18, A4), (R16,R42, R233, B19, A4), (R16,R42,R233,B20, A4), (R16,R42,R233, B21, A4), (R16,R42,R234,B1, A4), (R16, R42,R234,B2, A4), (R16,R42,R234,B3, A4), (R16,R42,R234,B4, A4), (R16,R42,R234,B5, A4), (R16,R42,R234,B6, A4), (R16, R42,R234,B7, A4), (R16,R42,R234,B8, A4), (R16,R42, R234, B9, A4), (R16,R42,R234,B10, A4), (R16,R42,R234, B11, A4), (R16,R42,R234,B12, A4), (R16, R42,R234,B13, A4), (R16,R42,R234,B14, A4), (R16,R42,R234,B15, A4), (R16,R42,R234,B 16, A4), (R16,R42,R234,B17, A4), (R16, R42,R234,B18, A4), (R16,R42,R234,B19, A4), (R16, R42, R234,B20, A4), (R16,R42,R234,B21, A4), (R16,R42,R235, B1, A4), (R16,R42,R235,B2, A4), (R16,R42,R235,B3, A4), (R16,R42,R235,B4, A4), (R16,R42,R235,B5, A4), (R16, R42,R235, B6, A4), (R16,R42,R235, B7, A4), (R16, R42, R235, B8, A4), (R16,R42,R235, B9, A4), (R16, R42,R235, B10, A4), (R16,R42,R235,B11, A4), (R16,R42,R235,B12, A4), (R16,R42,R235,B 13, A4), (R16,R42,R235,B14, A4), (R16,R42,R235,B15, A4), (R16,R42,R235,B16, A4), (R16, R42,R235,B17, A4), (R16,R42,R235,B18, A4), (R16,R42, R235,B19, A4), (R16,R42,R235,B20, A4), (R16,R42,R235, B21, A4), (R16,R42,R236,B1, A4), (R16,R42,R236,B2, A4), (R16,R42, R236,B3, A4), (R16,R42, R236,B4, A4), (R16,R42,R236,B5, A4), (R16,R42,R236,B6, A4), (R16, R42,R236,B7, A4), (R16,R42,R236,B8, A4), (R16,R42, R236,B9, A4), (R16,R42,R236,B10, A4), (R16,R42,R236, B11, A4), (R16,R42,R236,B12, A4), (R16,R42,R236,B13, A4), (R16,R42,R236,B14, A4), (R16,R42,R236,B15, A4), (R16,R42,R236,B16, A4), (R16,R42,R236,B17, A4), (R16, R42,R236,B18, A4), (R16,R42,R236,B19, A4), (R16,R42, R236,B20, A4), (R16,R42,R236,B21, A4), (R16,R42,R237, B1, A4), (R16,R42,R237,B2, A4), (R16,R42,R237,B3, A4), (R16,R42,R237,B4, A4), (R16,R42,R237,B5, A4), (R16, R42,R237,B6, A4), (R16,R42,R237, B7, A4), (R16,R42, R237,B8, A4), (R16,R42,R237,B9, A4), (R16,R42,R237, B10, A4), (R16,R42,R237,B11, A4), (R16,R42,R237,B12, A4), (R16,R42,R237,B13, A4), (R16,R42,R237,B14, A4), (R16,R42,R237,B15, A4), (R16,R42,R237,B16, A4), (R16, R42,R237,B17, A4), (R16,R42,R237,B18, A4), (R16,R42, R237,B19, A4), (R16,R42,R237,B20, A4), (R16,R42,R237, B21, A4), (R16,R42,R238,B1, A4), (R16,R42,R238,B2, A4), (R16,R42,R238,B3, A4), (R16,R42,R238,B4, A4), (R16,R42,R238,B5, A4), (R16,R42,R238,B6, A4), (R16, R42,R238,B7, A4), (R16, R42,R238,B8, A4), (R16,R42, R238,B9, A4), (R16,R42,R238,B10, A4), (R16,R42,R238, B11, A4), (R16,R42,R238,B12, A4), (R16,R42,R238,B13, A4), (R16,R42,R238,B14, A4), (R16,R42,R238,B15, A4), (R16,R42,R238,B16, A4), (R16,R42,R238,B17, A4), (R16, R42,R238,B18, A4), (R16,R42,R238,B19, A4), (R16,R42, R238,B20, A4), (R16,R42,R238,B21, A4), (R16,R42,R239, B1, A4), (R16,R42,R239,B2, A4), (R16,R42,R239,B3, A4), (R16,R42,R239,B4, A4), (R16,R42,R239,B5, A4), (R16, R42,R239,B6, A4), (R16,R42,R239,B7, A4), (R16,R42, R239,B 8, A4), (R16,R42,R239,B9, A4), (R16,R42,R239, B10, A4), (R16,R42,R239,B11, A4), (R16,R42,R239,B12, A4), (R16,R42,R239,B13, A4), (R16,R42,R239,B14, A4), (R16,R42,R239,B15, A4), (R16,R42,R239,B16, A4), (R16, R42,R239,B17, A4), (R16,R42,R239,B18, A4), (R16,R42, R239,B19, A4), (R16,R42,R239,B20, A4), (R16,R42,R239, B21, A4), (R16,R42,R2310,B1, A4), (R16,R42,R2310,B2, A4), (R16,R42,R2310,B3, A4), (R16,R42,R2310,B4, A4), (R16,R42,R2310,B5, A4), (R16,R42,R2310,B6, A4), (R16, R42,R2310,B7, A4), (R16,R42,R2310,B8, A4), (R16,R42, R2310,B9, A4), (R16,R42,R2310, B10, A4), (R16,R42, R2310,B11, A4), (R16, R42,R2310,B12, A4), (R16,R42, R2310,B13, A4), (R16,R42,R2310,B14, A4), (R16,R42, R2310,B15, A4), (R16,R42,R2310,B16, A4), (R16,R42, R2310,B17, A4), (R16,R42,R2310,B18, A 4), (R16,R42, R2310,B19, A4), (R16,R42,R2310,B20, A4), (R16,R42, R2310,B21, A4), (R16,R42,R2311,B1, A4), (R16,R42, R2311,B2, A4), (R16,R42,R2311,B3, A4), (R16,R42, R2311,B4, A4), (R16,R42,R2311,B5, A4), (R16,R42, R2311,B6, A4), (R16,R42,R2311,B7, A4), (R16,R42, R2311,B8, A4), (R16,R42,R2311,B9, A4), (R16,R42, R2311,B10, A4), (R16,R42,R2311,B11, A4), (R16,R42, R2311,B12, A4), (R16,R42,R2311,B13, A4), (R16,R42, R2311,B14, A4), (R16, R42,R2311,B15, A4), (R16,R42, R2311,B16, A4), (R16,R42,R2311,B17, A4), (R16,R42, R2311,B18, A4), (R16,R42,R2311,B19, A4), (R16,R42, R2311,B20, A4), (R16,R42,R2311,B21, A4), (R16,R42, R2312,B1, A4), (R16,R42,R2312,B2, A4), (R16,R42, R2312,B3, A4), (R16,R42,R2312,B4, A4), (R16,R42, R2312,B5, A4), (R16,R42,R2312,B6, A4), (R16,R42, R2312,B7, A4), (R16,R42,R2312,B8, A4), (R16,R42, R2312,B9, A4), (R16,R42,R2312,B10, A4), (R16,R42, R2312,B11, A4), (R16,R42,R2312,B12, A4), (R16,R42, R2312,B13, A4), (R16,R42,R2312,B14, A4), (R16,R42, R2312,B15, A4), (R16,R42,R2312,B16, A4), (R16,R42, R2312,B17, A4), (R16, R42,R2312,B18, A4), (R16,R42, R2312,B19, A4), (R16,R42,R2312,B20, A4), (R16,R42, R2312,B21, A4), (R16,R42,R2313,B1, A4), (R16,R42,

R2313,B2, A4), (R16,R42,R2313,B3, A4), (R16,R42, R2313, B4, A4), (R16,R42,R2313,B5, A4), (R16,R42, R2313, B6, A4), (R16,R42,R2313,B7, A4), (R16,R42, R2313,B8, A4), (R16,R42,R2313,B9, A4), (R16,R42, R2313,B10, A4), (R16,R42,R2313,B11, A4), (R16,R42, R2313,B12, A4), (R16,R42,R2313,B13, A4), (R16,R42, R2313,B14, A4), (R16,R42,R2313,B15, A4), (R16,R42, R2313,B16, A4), (R16,R42,R2313,B 17, A4), (R16,R42, R2313,B18, A4), (R16,R42,R2313,B19, A4), (R16,R42, R2313,B20, A4), (R16,R42,R2313,B21, A4), (R17,R41, R231,B1, A4), (R17,R41,R231,B2, A4), (R17,R41,R231, B3, A4), (R17,R41,R231,B4, A4), (R17,R41,R231,B5, A4), (R17,R41,R231,B6, A4), (R17,R41,R231,B7, A4), (R17, R41,R231,B8, A4), (R17,R41,R231,B9, A4), (R17,R41, R231,B10, A4), (R17,R41,R231,B11, A4), (R17,R41,R231, B12, A4), (R17,R41,R231,B13, A4), (R17,R41,R231,B14, A4), (R17,R41,R231,B15, A4), (R17,R41,R231,B16, A4), (R17,R41,R231,B17, A4), (R17,R41,R231,B18, A4), (R17, R41,R231,B19, A4), (R17,R41,R231,B20, A4), (R17,R41, R231,B21, A4), (R17,R41,R232,B1, A4), (R17,R41,R232, B2, A4), (R17,R41,R232,B3, A4), (R17,R41,R232,B4, A4), (R17,R41,R232,B5, A4), (R17,R41,R232,B6, A4), (R17, R41,R232,B7, A4), (R17,R41,R232,B8, A4), (R17,R41, R232,B9, A4), (R17,R41,R232,B10, A4), (R17,R41,R232, B11, A4), (R17,R41,R232,B12, A4), (R17,R41,R232,B13, A4), (R17,R41,R232,B14, A4), (R17,R41,R232,B15, A4), (R17,R41,R232,B16, A4), (R17,R41,R232,B17, A4), (R17, R41,R232, B18, A4), (R17,R41,R232,B19, A4), (R17,R41, R232,B20, A4), (R17,R41,R232,B21, A4), (R17,R41,R233, B1, A4), (R17,R41,R233,B2, A4), (R17,R41,R233,B3, A4), (R17,R41,R233,B4, A4), (R17,R41,R233,B5, A4), (R17, R41,R233,B6, A4), (R17,R41,R233,B7, A4), (R17,R41, R233,B8, A4), (R17,R41,R233,B9, A4), (R17,R41,R233, B10, A4), (R17,R41,R233,B11, A4), (R17,R41,R233,B12, A4), (R17,R41,R233,B13, A4), (R17,R41,R233,B14, A4), (R17,R41,R233, B15, A4), (R17,R41,R233,B16, A4), (R17, R41,R233,B17, A4), (R17,R41,R233,B18, A4), (R17,R41, R233,B19, A4), (R17,R41,R233,B20, A4), (R17,R41,R233, B21, A4), (R17,R41,R234, B1, A4), (R17,R41,R234,B2, A4), (R17,R41,R234,B3, A4), (R17,R41,R234,B4, A4), (R17,R41,R234,B5, A4), (R17,R41,R234,B6, A4), (R17, R41,R234,B7, A4), (R17,R41,R234,B8, A4), (R17,R41, R234,B9, A4), (R17,R41,R234,B10, A4), (R17,R41,R234, B11, A4), (R17,R41,R234, B12, A4), (R17,R41,R234,B13, A4), (R17,R41,R234,B14, A4), (R17,R41,R234,B15, A4), (R17,R41,R234,B16, A4), (R17,R41,R234,B17, A4), (R17, R41,R234,B18, A4), (R17,R41,R234, B19, A4), (R17,R41, R234,B20, A4), (R17,R41,R234,B21, A4), (R17,R41,R235, B1, A4), (R17, R41,R235,B2, A4), (R17,R41,R235,B3, A4), (R17,R41,R235,B4, A4), (R17,R41,R235,B5, A4), (R17, R41,R235,B6, A4), (R17,R41,R235,B7, A4), (R17,R41, R235,B8, A4), (R17,R41,R235, B9, A4), (R17,R41,R235, B10, A4), (R17,R41,R235,B11, A4), (R17,R41,R235,B12, A4), (R17, R41,R235,B13, A4), (R17,R41,R235,B14, A4), (R17,R41,R235,B15, A4), (R17,R41,R235,B 16, A4), (R17, R41,R235,B17, A4), (R17,R41,R235,B18, A4), (R17,R41, R235,B19, A4), (R17, R41,R235,B20, A4), (R17,R41,R235, B21, A4), (R17,R41,R236,B1, A4), (R17,R41,R236,B2, A4), (R17,R41,R236,B3, A4), (R17,R41,R236,B4, A4), (R17,R41,R236,B5, A4), (R17,R41,R236, B6, A4), (R17, R41,R236, B7, A4), (R17, R41,R236, B8, A4), (R17,R41, R236, B9, A4), (R17, R41,R236,B10, A4), (R17,R41,R236, B11, A4), (R17,R41,R236,B12, A4), (R17,R41,R236,B 13, A4), (R17,R41,R236,B14, A4), (R17,R41,R236,B15, A4), (R17,R41,R236,B16, A4), (R17, R41,R236,B17, A4), (R17, R41,R236,B18, A4), (R17,R41,R236,B19, A4), (R17,R41, R236,B20, A4), (R17,R41,R236,B21, A4), (R17,R41,R237, B1, A4), (R17,R41,R237,B2, A4), (R17,R41, R237,B3, A4), (R17,R41,R237,B4, A4), (R17,R41,R237,B5, A4), (R17, R41,R237,B6, A4), (R17,R41,R237,B7, A4), (R17,R41, R237,B8, A4), (R17,R41,R237,B9, A4), (R17,R41,R237, B10, A4), (R17,R41,R237,B11, A4), (R17,R41,R237,B12, A4), (R17,R41,R237,B13, A4), (R17,R41,R237,B14, A4), (R17,R41,R237,B15, A4), (R17,R41,R237,B16, A4), (R17, R41,R237,B17,A4), (R17, R41,R237, B18, A4), (R17,R41, R237, B19, A4), (R17, R41,R237, B20, A4), (R17, R41, R237,B21, A4), (R17,R41,R238,B1, A4), (R17,R41,R238, B2, A4), (R17,R41,R238,B3, A4), (R17,R41,R238,B4, A4), (R17,R41,R238,B6, A4), (R17,R41,R238,B6, A4), (R17, R41,R238, B7, A4), (R17,R41,R238,B8, A4), (R17,R41, R238,B9, A4), (R17,R41,R238,B10, A4), (R17,R41,R238, B11, A4), (R17,R41,R238,B12, A4), (R17,R41,R238,B13, A4), (R17,R41,R238,B14, A4), (R17, R41,R238, B15, A4), (R17,R41,R238, B16, A4), (R17, R41,R238, B17, A4), (R17, R41,R238,B18, A4), (R17,R41,R238,B19, A4), (R17, R41,R238,B20, A4), (R17,R41,R238,B21, A4), (R17, R41, R239, B1, A4), (R17, R41,R239, B2, A4), (R17, R41,R239, B3, A4), (R17,R41, R239, B4, A4), (R17,R41,R239, B5, A4), (R17, R41,R239, B6, A4), (R17,R41,R239, B7, A4), (R17, R41,R239,B8, A4), (R17,R41,R239,B9, A4), (R17, R41,R239,B10, A4), (R17,R41,R239,B11, A4), (R17, R41, R239, B12, A4), (R17, R41,R239, B13, A4), (R17,R41, R239, B14, A4), (R17,R41,R239, B15, A4), (R17,R41, R239, B16, A4), (R17, R41, 239, B17, A4), (R17,R41, R239, B18, A4), (R17,R41,R239,B19, A4), (R17,R41,R239, B20, A4), (R17,R41,R239,B21, A4), (R17,R41,R2310,B1, A4), (R17,R41,R2310,B2, A4), (R17,R41,R2310,B3, A4), (R17,R41,R2310,B4, A4), (R17,R41,R2310,B5, A4), (R17, R41,R2310,B6, A4), (R17,R41,R2310,B7, A4), (R17,R41, R2310,B8, A4), (R17,R41,R2310,B9, A4), (R17,R41, R2310,B10, A4), (R17,R41,R2310,B11, A4), (R17,R41, R2310,B12, A4), (R17,R41,R2310,B13, A4), (R17,R41, R2310,B14, A4), (R17,R41,R2310,B15, A4), (R17,R41, R2310,B16, A4), (R17,R41,R2310,B17, A4), (R17,R41, R2310,B18, A4), (R17,R41,R2310,B19, A4), (R17,R41, R2310,B20, A4), (R17,R41,R2310,B21, A4), (R17,R41, R2311,B1, A4), (R17,R41,R2311,B2, A4), (R17,R41, R2311,B3, A4), (R17,R41, R2311,B4, A4), (R17,R41, R2311,B5, A4), (R17,R41,R2311,B6, A4), (R17,R41, R2311,B7, A 4), (R17,R41,R2311,B8, A4), (R17,R41, R2311,B9, A4), (R17,R41,R2311,B10, A4), (R17,R41, R2311,B11, A4), (R17,R41,R2311,B12, A4), (R17,R41, R2311,B13, A4), (R17,R41,R2311,B 14, A4), (R17,R41, R2311,B15, A4), (R17,R41,R2311,B16, A4), (R17,R41, R2311,B17, A4), (R17,R41,R2311,B18, A4), (R17,R41, R2311,B19, A4), (R17,R41,R2311,B20, A4), (R17,R41, R2311,B21, A4), (R17,R41,R2312,B1, A4), (R17,R41, R2312,B2, A4), (R17,R41,R2312,B3, A4), (R17,R41, R2312,B4, A4), (R17,R41,R2312,B5, A4), (R17,R41, R2312,B6, A4), (R17,R41,R2312,B7, A4), (R17,R41, R2312, B8, A4), (R17,R41,R2312,B9, A4), (R17,R41, R2312,B10, A4), (R17,R41,R2312,B11, A4), (R17,R41, R2312,B2, A4), (R17,R41,R232,B3, A4), (R17,R41,R2312, B14, A4), (R17,R41,R2312, B15, A4), (R17,R41,R2312, B16, A4), (R17,R41,R2312, B17, A4), (R17,R41,R2312, B18, A4), (R17,R41,R2312,B19, A4), (R17,R41,R2312, B20, A4), (R17,R41,R2312,B21, A4), (R17,R41,R2313,B1, A4), (R17,R41,R2313,B2, A4), (R17,R41,R2313,B3, A4), (R17,R41,R2313,B4, A4), (R17,R41,R2313,B5, A4), (R17, R41,R2313,B6, A4), (R17,R41,R2313,B7, A4), (R17,R41, R2313,B8, A4), (R17,R41,R2313,B9, A4), (R17,R41, R2313,B10, A4), (R17,R41,R2313,B11, A4), (R17,R41, R2313,B12, A4), (R17,R41,R2313,B13, A 4), (R17,R41, R2313,B14, A4), (R17,R41,R2313,B15, A4), (R17,R41,

R2313,B16, A4), (R17,R41,R2313,B17, A4), (R17,R41, R2313,B18, A4), (R17,R41,R2313,B19, A4), (R17,R41, R2313, B20, A4), (R17,R41,R2313,B21, A4), (R17,R42, R231,B1, A4), (R17,R42,R231,B2, A4), (R17, R42,R231, B3, A4), (R17,R42,R231,B4, A4), (R17,R42,R231,B5, A4), (R17,R42,R231,B6, A 4), (R17,R42,R231,B7, A4), (R17, R42,R231,B8, A4), (R17,R42,R231,B9, A4), (R17,R42, R231,B10, A4), (R17,R42,R231,B11, A4), (R17,R42,R231, B12, A4), (R17,R42,R231,B13, A4), (R17,R42,R231,B14, A4), (R17,R42,R231,B15, A4), (R17,R42,R231,B16, A4), (R17,R42,R231, B17, A4), (R17,R42,R231,B18, A4), (R17, R42,R231,B19, A4), (R17,R42,R231,B20, A4), (R17,R42, R231,B21, A4), (R17,R42,R232,B1, A4), (R17,R42,R232, B2, A4), (R17,R42,R232,B3, A4), (R17,R42,R232,B4, A4), (R17,R42,R232,B5, A4), (R17,R42,R232,B6, A4), (R17, R42,R232,B7, A4), (R17,R42,R232,B8, A4), (R17,R42, R232,B9, A4), (R17,R42,R232,B10, A4), (R17,R42,R232, B11, A4), (R17,R42,R232,B12, A4), (R17,R42,R232,B13, A4), (R17,R42,R232, B14, A4), (R17,R42,R232,B15, A4), (R17,R42,R232,B16, A4), (R17,R42,R232,B17, A4), (R17, R42,R232,B18, A4), (R17,R42,R232,B19, A4), (R17,R42, R232,B20, A4), (R17,R42,R232, B21, A4), (R17,R42,R233, B1, A4), (R17,R42,R233,B2, A4), (R17,R42,R233,B3, A4), (R17,R42,R233,B4, A4), (R17,R42,R233,B5, A4), (R17, R42,R233,B6, A4), (R17,R42,R233,B7, A4), (R17,R42, R233,B8, A4), (R17,R42,R233,B9, A4), (R17,R42,R233, B10, A4), (R17,R42,R233, B11, A4), (R17,R42,R233,B12, A4), (R17,R42,R233,B13, A4), (R17,R42,R233,B14, A4), (R17,R42,R233,B15, A4), (R17,R42,R233,B16, A4), (R17, R42,R233,B17, A4), (R17,R42,R233, B18, A4), (R17,R42, R233,B19, A4), (R17,R42,R233,B20, A4), (R17,R42,R233, B21, A4), (R17,R42,R234,B1, A4), (R17,R42,R234,B2, A4), (R17,R42,R234,B3, A4), (R17,R42,R234,B4, A4), (R17,R42,R234,B5, A4), (R17,R42,R234,B6, A4), (R17, R42,R234,B7, A4), (R17,R42,R234,B8, A4), (R17,R42, R234,B9, A4), (R17,R42,R234,B10, A4), (R17,R42,R234, B11, A4), (R17,R42,R234,B12, A4), (R17,R42,R234,B13, A4), (R17,R42,R234,B14, A4), (R17,R42,R234, B15, A4), (R17, R42,R234, B16, A4), (R17,R42, R234, B17, A4), (R17,R42,R234, B18, A4), (R17,R42,R234,B19, A4), (R17, R42,R234,B20, A4), (R17,R42,R234,B21, A4), (R17,R42, R235, B1, A4), (R17,R42,R235, B2, A4), (R17,R42,R235, B3, A4), (R17,R42,R235, B4, A4), (R17, R42,R235,B5, A4), (R17,R42,R235,B6, A4), (R17,R42,R235,B7, A4), (R17,R42,R235,B8, A4), (R17,R42,R235,B9, A4), (R17, R42,R235,B10, A4), (R17,R42,R235,B11, A4), (R17,R42, R235, B12, A4), (R17,R42,R235,B13, A4), (R17,R42,R235, B14, A4), (R17,R42,R235,B15, A4), (R17,R42,R235,B16, A4), (R17,R42,R235,B17, A4), (R17,R42,R235,B18, A4), (R17,R42,R235, B19, A4), (R17,R42,R235,B20, A4), (R17, R42,R235,B21, A4), (R17,R42,R236,B1, A4), (R17, R42, R236,B2, A4), (R17,R42,R236,B3, A4), (R17,R42,R236, B4, A4), (R17,R42,R236,B5, A4),(R17,R42,R236,B6, A4), (R17,R42,R236,B7, A4), (R17,R42,R236,B8, A4), (R17, R42,R236, B9, A4), (R17,R42,R236,B10, A4), (R17,R42, R236,B11, A4), (R17,R42,R236,B12, A4), (R17, R42,R236, B13, A4), (R17,R42,R236,B14, A4), (R17,R42,R236,B15, A4), (R17,R42,R236,B 16, A4), (R17,R42,R236,B17, A4), (R17,R42,R236,B18, A4), (R17,R42,R236,B19, A4), (R17, R42,R236,B20, A4), (R17,R42,R236,B21, A4), (R17,R42, R237,B1, A4), (R17,R42,R237,B2, A4), (R17, R42, R237, B3, A4), (R17,R42, R237, B4, A4), (R17, R42,R237, B5, A4), (R17, R42, R237, B6, A4), (R17,R42,R237, B7, A4), (R17, R42, R237, B8, A4), (R17,R42,R237, B9, A4), (R17, R42,R237,B10, A4), (R17,R42,R237,B11, A4), (R17,R42, R237,B12, A4), (R17,R42, R237,B 13 A4), (R17,R42,R237, B14, A4), (R17,R42,R237,B15, A4), (R17,R42,R237,B16, A4), (R17, R42,R237,B17, A4), (R17,R42,R237,B18, A4), (R17,R42,R237,B19, A4), (R17,R42,R237,B20, A4), (R17, R42,R237,B21, A4), (R17,R42,R238,B1, A4), (R17,R42, R238,B2, A4), (R17,R42, R238,B3, A4), (R17,R42,R238, B4, A4), (R17,R42,R238,B5, A4), (R17,R42,R238,B6, A4), (R17,R42,R238,B7, A4), (R17,R42,R238,B8, A4), (R17, R42,R238,B9, A4), (R17,R42,R238,B10, A4), (R17,R42, R238,B11, A4), (R17,R42,R238,B12, A4), (R17,R42,R238, B13, A4), (R17,R42,R238,B14, A4), (R17,R42,R238,B15, A4), (R17,R42,R238,B16, A4), (R17,R42,R238,B17, A4), (R17,R42,R238,B18, A4), (R17,R42,R238,B19, A4), (R17, R42,R238,B20, A4), (R17,R42,R238,B21, A4), (R17,R42, R239,B1, A4), (R17,R42,R239,B2, A4), (R17,R42,R239, B3, A4), (R17,R42,R239,B4, A4), (R17,R42,R239,B5, A4), (R17,R42,R239,B6, A4), (R17,R42,R239, B7, A4), (R17, R42,R239, B8, A4), (R17,R42,R239, B9, A4), (R17,R42, R239,B10, A4), (R17,R42,R239,B11, A4), (R17,R42,R239, B12, A4), (R17,R42,R239,B13, A4), (R17,R42,R239,B14, A4), (R17,R42,R239,B15, A4), (R17,R42,R239,B16, A4), (R17,R42,R239,B17, A4), (R17,R42,R239,B18, A4), (R17, R42,R239,B19, A4), (R17,R42,R239,B20, A4), (R17,R42, R239,B21, A4), (R17,R42,R2310,B1, A4), (R17,R42, R2310,B2, A4), (R17,R42,R2310,B3, A4), (R17,R42, R2310,B4, A4), (R17,R42,R2310,B5, A4), (R17,R42, R2310,B6, A4), (R17,R42,R2310,B7, A4), (R17,R42, R2310,B8, A4), (R17,R42,R2310,B9, A4), (R17,R42, R2310,B10, A4), (R17,R42,R2310,B11, A4), (R17,R42, R2310,B12, A4), (R17,R42,R2310,B13, A4), (R17,R42, R2310, B14, A4), (R17,R42,R2310,B15, A4), (R17,R42, R2310,B16, A4), (R17,R42,R2310,B17, A4), (R17,R42, R2310,B18, A4), (R17,R42,R2310, B19, A4), (R17,R42, R2310,B20, A4), (R17,R42, R2310,B21, A4), (R17,R42, R2311,B1, A4), (R17,R42,R2311,B2, A4), (R17,R42, R2311,B3, A4), (R17,R42,R2311,B4, A4), (R17,R42, R2311,B5, A4), (R17,R42,R2311,B6, A4), (R17,R42, R2311,B7, A4), (R17,R42,R2311,B8, A4), (R17,R42, R2311,B9, A4), (R17,R42,R2311,B10, A4), (R17,R42, R2311,B11, A4), (R17,R42,R2311,B12, A4), (R17,R42, R2311,B13, A4), (R17, R42,R2311,B14, A4), (R17,R42, R2311,B15, A4), (R17,R42,R2311,B16, A4), (R17,R42, R2311,B17, A4), (R17,R42,R2311,B18, A4), (R17,R42, R2311,B19, A4), (R17,R42,R2311,B20, A4),(R17,R42, R2311,B21, A4), (R17,R42,R2312,B1, A4), (R17,R42, R2312,B2, A4), (R17,R42, R2312,B3, A4), (R17,R42, R2312,B4, A4), (R17,R42,R2312,B5, A4), (R17,R42, R2312,B6, A4), (R17,R42,R2312,B7, A4), (R17,R42, R2312,B8, A4), (R17,R42,R2312,B9, A4), (R17,R42, R2312,B10, A4), (R17,R42,R2312,B11, A4), (R17,R42, R2312,B12, A4), (R17,R42,R2312,B13, A4), (R17,R42, R2312,B14, A4), (R17,R42,R2312,B15, A4), (R17,R42, R2312,B16, A4), (R17, R42,R2312,B17, A4), (R17,R42, R2312,B18, A4), (R17,R42,R2312,B19, A4), (R17,R42, R2312,B20, A4), (R17,R42,R2312,B21, A4), (R17,R42, R2313,B1, A4), (R17,R42,R2313,B2, A4), (R17,R42, R2313,B3, A4), (R17,R42,R2313,B4, A4), (R17,R42, R2313,B5, A4), (R17,R42,R2313,B6, A4), (R17,R42, R2313,B7, A4), (R17,R42,R2313,B8, A4), (R17,R42, R2313,B9, A4), (R17,R42,R2313,B10, A4), (R17,R42, R2313,B11, A4), (R17,R42,R2313,B12, A4), (R17,R42, R2313,B13, A4), (R17,R42,R2313,B14, A4), (R17,R42, R2313,B15, A4), (R17,R42,R2313,B 16, A4), (R17,R42, R2313,B17, A4), (R17,R42,R2313,B18, A4), (R17,R42, R2313,B19, A4), (R17,R42,R2313,B20, A4), (R17,R42, R2313,B21, A4), (R18,R41,R231,B1, A4), (R18,R41,R231, B2, A4), (R18,R41,R231,B3, A4), (R18,R41,R231,B4, A4), (R18,R41,R231,B5, A4), (R18,R41,R231,B6, A4), (R18, R41,R231,B7, A4), (R18,R41,R231,B8, A4), (R18,R41,

R231,B9, A4), (R18,R41,R231,B10, A4), (R18,R41,R231, B11, A4), (R18,R41,R231,B12, A4), (R18,R41,R231,B13, A4), (R18,R41,R231,B14, A4), (R18,R41,R231,B15, A4), (R18,R41,R231,B16, A4), (R18,R41,R231,B17, A4), (R18, R41,R231,B18, A4), (R18,R41,R231,B19, A4), (R18,R41, R231,B20, A4), (R18,R41,R231,B21, A4), (R18,R41,R232, B1,A4), (R18,R41,R232,B2, A4), (R18, R41,R232,B3, A4), (R18,R41,R232,B4, A4), (R18,R41,R232,B5, A4), (R18, R41,R232,B6, A 4), (R18,R41,R232,B7, A4), (R18,R41, R232,B8, A4), (R18,R41,R232,B9, A4), (R18,R41,R232, B10, A4), (R18,R41,R232,B11, A4), (R18,R41,R232,B12, A4), (R18,R41,R232,B13, A4), (R18,R41,R232,B14, A4), (R18,R41,R232,B15, A4), (R18,R41,R232,B16, A4), (R18, R41,R232, B7, A4), (R18,R41,R232,B18, A4), (R18,R41, R232,B19, A4), (R18,R41,R232,B20, A4), (R18,R41,R232, B21, A4), (R18,R41,R233,B1, A4), (R18,R41,R233,B2, A4), (R18,R41,R233,B3, A4), (R18,R41,R233,B4, A4), (R18,R41,R233,B5, A4), (R18,R41,R233,B6, A4), (R18, R41,R233,B7, A4), (R18,R41,R233,B8, A4), (R18,R41, R233,B9, A4), (R18,R41,R233,B10, A4), (R18,R41,R233, B11, A4), (R18,R41,R233,B12, A4), (R18,R41,R233,B13, A4), (R18,R41,R233, B14, A4), (R18,R41,R233,B15, A4), (R18,R41,R233,B16, A4), (R18,R41,R233,B17, A4), (R18, R41,R233,B18, A4), (R18,R41,R233,B19, A4), (R18,R41, R233,B20, A4), (R18,R41,R233, B21, A4), (R18,R41,R234, B1, A4), (R18,R41,R234,B2, A4), (R18,R41,R234,B3, A4), (R18,R41,R234,B4, A4), (R18,R41,R234,B5, A4), (R18, R41,R234,B6, A4), (R18,R41,R234,B7, A4), (R18,R41, R234,B8, A4), (R18,R41,R234,B9, A4), (R18,R41,R234, B10, A4), (R18,R41,R234, B11, A4), (R18,R41,R234,B12, A4), (R18,R41,R234,B13, A4), (R18,R41,R234,B14, A4), (R18,R41,R234,B15, A4), (R18,R41,R234,B16, A4), (R18, R41,R234,B17, A4), (R18,R41,R234, B18, A4), (R18,R41, R234,B19, A4), (R18,R41,R234,B20, A4), (R18,R41,R234, B21, A4), (R18,R41,R235,B1, A4), (R18,R41,R235,B2, A4), (R8,R41,R235,B3, A4), (R18,R41,R235,B4, A4), (R18,R41,R235,B5, A4), (R8,R41,R235,B6, A4), (R18,R41, R235,B7, A4), (R8,R41,R235,B8, A4), (R18,R41,R235,B9, A4), (R18,R41,R235,B10, A4), (R18,R41,R235,B11, A4), (R18,R41,R235,B12, A4), (R18,R41,R235,B13, A4), (R18, R41,R235,B14, A4), (R18,R41,R235, B15, A4), (R18,R41, R235,B16, A4), (R18,R41,R235,B17, A4), (R18,R41,R235, B18, A4), (R18,R41,R235,B19, A4), (R18,R41,R235,B20, A4), (R18,R41,R235,B21, A4), (R18,R41,R236, B1, A4), (R18,R41,R236,B2, A4), (R18,R41,R236,B3, A4), (R18, R41,R236,B4, A4), (R18,R41,R236,B5, A4), (R18,R41, R236,B6, A4), (R18,R41,R236,B7, A4), (R18,R41,R236, B8, A4), (R18,R41,R236,B9, A4), (R18,R41,R236,B10, A4), (R18,R41,R236,B11, A4), (R18,R41,R236, B12, A4), (R18,R41,R236,B13, A4), (R18,R41,R236,B14, A4), (R18, R41,R236,B15, A4), (R18,R41,R236,B16, A4), (R18,R41, R236,B17, A4), (R18,R41,R236,B18, A4), (R18,R41,R236, B19, A4), (R18,R41,R236,B20, A4), (R18,R41,R236,B21, A4), (R18,R41,R237,B1, A4), (R18, R41,R237,B2, A4), (R18,R41,R237,B3, A4), (R18,R41,R237,B4, A4), (R18, R41,R237,B5, A4), (R18,R41,R237,B6, A4), (R18,R41, R237,B7, A4), (R18,R41,R237,B8, A4), (R18,R41,R237, B9, A4), (R18,R41,R237,B10, A4), (R18,R41,R237,B11, A4), (R18,R41,R237,B12, A4), (R18, R41,R237,B13, A4), (R18,R41,R237,B14, A4), (R18,R41,R237,B15, A4), (R18, R41,R237,B 16, A4), (R18,R41,R237,B17, A4), (R18,R41, R237,B18, A4), (R18,R41,R237,B19, A4), (R18, R41,R237, B20, A4), (R18,R41,R237,B21, A4), (R18,R41,R238,B1, A4), (R18,R41,R238,B2, A4), (R18,R41,R238,B3, A4), (R18,R41,R238,B4, A4), (R18,R41,R238,B5, A4), (R18, R41,R238,B6, A4), (R18,R41,R238,B7, A4), (R18,R41, R238,B8, A4), (R18,R41,R238,B9, A4), (R18, R41,R238, B10, A4), (R18,R41,R238,B11, A4), (R18,R41,R238,B12, A4), (R18,R41,R238,B 13, A4), (R18,R41,R238,B14, A4), (R18,R41,R238,B15, A4), (R18,R41,R238,B16, A4), (R18, R41,R238,B17, A4), (R18,R41,R238,B18, A4), (R18,R41, R238,B19, A4), (R18,R41,R238,B20, A4), (R18,R41,R238, B21, A4), (R18,R41,R239,B1, A4), (R18,R41,R239,B2, A4), (R18,R41, R239,B3, A4), (R18,R41,R239,B4, A4), (R18,R41,R239,B5, A4), (R18,R41,R239,B6, A4), (R18, R41,R239,B7, A4), (R18,R41,R239,B8, A4), (R18,R41, R239,B9, A4), (R18,R41,R239,B10, A4), (R18,R41,R239, B11, A4), (R18,R41,R239,B12, A4), (R18,R41,R239,B13, A4), (R18,R41,R239,B14, A4), (R18,R41,R239,B15, A4), (R18,R41,R239,B16, A4), (R18,R41,R239,B17, A4), (R18, R41,R239,B18, A4), (R18,R41,R239,B19, A4), (R18,R41, R239,B20, A4), (R18,R41,R239,B21, A4), (R18,R41, R2310,B1, A4), (R18,R41,R2310,B2, A4), (R18,R41, R2310,B3, A4), (R18,R41,R2310,B4, A4), (R18,R41, R2310,B5, A4), (R18,R41,R2310,B6, A4), (R18,R41, R2310,B7, A4), (R18,R41,R2310,B8, A4), (R18,R41, R2310,B9, A4), (R18,R41,R2310,B10,A4), (R18,R41, R2310,B11, A4), (R18,R41,R2310,B12, A4), (R18,R41, R2310,B13, A4), (R18, R41,R2310,B14, A4), (R18,R41, R2310,B15, A4), (R18,R41,R2310,B16, A4), (R18,R41, R2310,B17, A4), (R18,R41,R2310, B18, A4), (R18,R41, R2310,B19, A4), (R18,R41,R2310,B20, A 4), (R18,R41, R2310,B21, A4), (R18,R41,R2311,B1, A4), (R18,R41, R2311,B2, A4), (R18,R41, R2311,B3, A4), (R18,R41, R2311,B4, A4), (R18,R41,R2311,B5, A4), (R18,R41, R2311,B6, A 4), (R18,R41,R2311,B7, A4), (R18,R41, R2311,B8, A4), (R18,R41,R2311,B9, A4), (R18,R41, R2311,B10, A4), (R18,R41,R2311,B11, A4), (R18,R41, R2311,B12, A4), (R18,R41,R2311,B13, A4), (R18,R41, R2311,B14, A4), (R18,R41,R2311,B15, A4), (R18,R41, R2311,B16, A4), (R18,R41,R2311,B17, A4), (R18,R41, R2311,B18, A4), (R18,R41,R2311,B19, A4), (R18,R41, R2311,B20, A4), (R18,R41,R2311,B21, A4), (R18,R41, R2312,B1, A4), (R18,R41,R2312,B2, A4), (R18,R41, R2312,B3, A4), (R18,R41,R2312,B4, A4), (R18,R41, R2312,B5, A4), (R18,R41,R2312,B6, A4), (R18,R41, R2312,B7, A4), (R18,R41,R2312,B8, A4), (R18,R41, R2312,B9, A4), (R18,R41,R2312,B10, A4), (R18,R41, R2312, B11, A4), (R18,R41,R2312,B12, A4), (R18,R41, R2312,B13, A4), (R18,R41,R2312,B14, A4), (R18,R41, R2312,B15, A4), (R18,R41,R2312,B 16, A4), (R18,R41, R2312,B17, A4), (R18,R41,R2312,B18, A4), (R18,R41, R2312,B19, A4), (R18,R41,R2312,B20, A4), (R18,R41, R2312,B21, A4), (R18,R41,R2313,B1, A4), (R18,R41, R2313,B2, A4), (R18,R41,R2313,B3, A4), (R18,R41, R2313,B4, A4), (R18,R41,R2313,B5, A4), (R18,R41, R2313,B6, A4), (R18,R41,R2313,B7, A4), (R18,R41, R2313,B8, A4), (R18,R41,R2313,B9, A4), (R18,R41, R2313,B10, A4), (R18,R41,R2313, B11, A4), (R18,R41, R2313,B12, A4), (R18,R41,R2313,B13, A4), (R18,R41, R2313,B14, A4), (R18,R41,R2313,B15, A4), (R18,R41, R2313,B16, A4), (R18,R41,R2313,B17, A4), (R18,R41, R2313,B18, A4), (R18,R41,R2313, B19, A4), (R18,R41, R2313,B20, A4), (R18,R41,R2313,B21, A4), (R18,R42, R231,B1, A4), (R18,R42,R231,B2, A4), (R18,R42,R231, B3, A4), (R18,R42,R231,B4, A4), (R18,R42,R231,B5, A4), (R18,R42,R231,B6, A4), (R18,R42,R231,B7, A4), (R18, R42,R231,B8, A4), (R18,R42,R231,B9, A4), (R18,R42, R231,B10, A4), (R18,R42,R231,B11, A4), (R18,R42,R231, B12, A4), (R18,R42,R231,B13, A4), (R18,R42,R231,B14, A4), (R18,R42,R231,B15, A4), (R18,R42,R231,B16, A4), (R18,R42,R231,B17, A4), (R18,R42,R231,B18, A4), (R18, R42,R231,B19, A4), (R18,R42,R231,B20, A4), (R18,R42, R231,B21, A4), (R18,R42,R232,B1, A4), (R18,R42,R232,

B2, A4), (R18,R42,R232,B3, A4), (R18,R42,R232,B4, A4), (R18,R42,R232,B5, A4), (R18,R42,R232,B6, A4), (R18, R42,R232,B7, A4), (R18,R42,R232,B8, A4), (R18,R42, R232,B9, A4), (R18,R42,R232,B10, A4), (R18,R42,R232, B11, A4), (R18,R42,R232,B12, A4), (R18,R42,R232, B13, A4), (R8,R42,R232, B14, A4), (R18, R42,R232, B15, A4), (R18,R42,R232, B16, A4), (R18,R42,R232, B17, A4), (R18, R42,R232, B18, A4), (R8,R42,R232, B19, A4), (R18, R42, R232, B20, A4), (R18,R42,R232,B21, A4), (R18,R42,R233, B1, A4), (R18,R42,R233,B2, A4), (R18, R42,R233,B3, A4), (R18,R42,R233,B4, A4), (R18,R42,R233,B5, A4), (R18, R42,R233,B6, A4), (R18,R42,R233,B7, A4), (R18,R42, R233,B8, A4), (R18,R42,R233,B9, A4), (R18,R42,R233, B10, A4), (R18, R42,R233, B11, A4), (R18, R42,R233, B12, A4), (R8,R42,R233, B13, A4), (R18,R42,R233, B14, A4), (R18,R42,R233, B15, A4), (R8,R42,R233, B16, A4), (R18, R42,R233, B17, A4), (R18,R42,R233,B18, A4), (R18,R42, R233,B19, A4), (R18,R42,R233,B20, A4), (R18,R42,R233, B21, A4), (R18,R42,R234,B1, A4), (R18,R42,R234,B2, A4), (R18,R42,R234,B3, A4), (R18,R42,R234,B4, A4), (R18,R42,R234,B5, A4), (R18,R42,R234,B6, A4), (R18, R42,R234,B7, A4), (R18,R42,R234,B8, A4), (R18,R42, R234,B9, A4), (R18,R42,R234,B1, A4), (R18,R42,R234, B11, A4), (R18,R42,R234,B12, A4), (R18,R42,R234,B13, A4), (R18,R42,R234, B14, A4), (R18,R42,R234,B15, A4), (R18,R42,R234,B16, A4), (R18,R42,R234,B17, A4), (R18, R42,R234,B18, A4), (R18,R42,R234,B19, A4), (R18,R42, R234,B20, A4), (R18,R42,R234, B21, A4), (R18,R42,R235, B1, A4), (R18,R42,R235,B2, A4), (R18,R42,R235,B3, A4), (R18,R42,R235,B4, A4), (R18,R42,R235,B5, A4), (R18, R42,R235,B6, A4), (R18,R42,R235,B7, A4), (R18,R42, R235,B8, A4), (R18,R42,R235,B9, A4), (R18,R42,R235, B10, A4), (R18,R42,R23515,B11, A4), (R18,R42,R235, B12, A4), (R18,R42,R235,B13, A4), (R18,R42,R235,B14, A4), (R18,R42,R235, B15, A4), (R8,R42,R235, B16, A4), (R18,R42,R235, B17, A4), (R18, R42,R235, B18, A4), (R18,R42,R235,B19, A4), (R18,R42,R235,B20, A4), (R18, R42,R235,B21, A4), (R18,R42,R236,B1, A4), (R18,R42, R236,B2, A4), (R18,R42,R236,B3, A4), (R18,R42,R236, B4, A4), (R18,R42,R236,B5, A4), (R18,R42,R236,B6, A4), (R18,R42,R236,B7, A4), (R18,R42,R236,B8, A4), (R18, R42,R236,B9, A4), (R18,R42,R236,B10, A4), (R18,R42, R236,B11, A4), (R18,R42,R236, B12, A4), (R18, R42, R236, B13, A4), (R18,R42,R236, B14, A4), (R18, R42, R236, B15, A4), (R18, R42,R236, B16, A4), (R18,R42, R236, B17, A4), (R18,R42,R236, B18, A4), (R18,R42, R236,B19, A4), (R18,R42,R236,B20, A4), (R18,R42,R236, B21, A4), (R18,R42,R237, B1, A4), (R18,R42,R237,B2, A4), (R18,R42,R237,B3, A4), (R18,R42,R237,B4, A4), (R18,R42,R237,B5, A4), (R18,R42,R237,B6, A4), (R18, R42,R237,B7, A4), (R18,R42,R237,B8, A4), (R18,R42, R237, B9, A4), (R118, R42,R237, B10, A4), (R18,R42, R237, B11, A4), (R18,R42,R237, B12, A4), (R18,R42, R237, B13, A4), (R18,R42,R237, B14, A4), (R18,R42, R237, B15, A4), (R18,R42,R237, B16, A4), (R18,R42, R237, B17, A4), (R18,R42,R237, B18, A4), (R18,R42, R237, B19, A4), (R18,R42,R237,B20, A4), (R18,R42,R237, B21, A4), (R18,R42,R238,B1, A4), (R18, R42,R238,B2, A4), (R18,R42,R238,B3, A4), (R18,R42,R238,B4, A4), (R18,R42,R238,B5, A4), (R18,R42,R238,B6, A4), (R18, R42,R238,B7, A4), (R18,R42,R238,B8, A4), (R18,R42, R238, B9, A4), (R18,R42,R238,B10, A4), (R18,R42,R238, B11, A4), (R18,R42,R238,B12, A4), (R18, R42,R238,B13, A4), (R18,R42,R238,B14, A4), (R18,R42,R238,B15, A4), (R18,R42,R238,B 16, A4), (R18,R42,R238,B17, A4), (R18, R42,R238,B18, A4), (R18,R42,R238,B19, A4), (R18, R42, R238,B20, A4), (R18,R42,R238,B21, A4), (R18,R42,R239, B1, A4), (R18,R42,R239,B2, A4), (R18,R42,R239,B3, A4), (R18,R42,R239,B4, A4), (R18,R42,R239,B5, A4), (R18, R42,R239,B6, A4), (R18,R42,R239,B7, A4), (R18,R42, R239,B8, A4), (R18,R42,R239,B9, A4), (R18, R42,R239, B10, A4), (R18,R42,R239,B11, A4), (R18,R42,R239,B12, A4), (R18,R42,R239,B 13, A4), (R18,R42,R239,B14, A4), (R18,R42,R239,B15, A4), (R18,R42,R239,B16, A4), (R18, R42,R239,B17, A4), (R18,R42,R239,B18, A4), (R18,R42, R239,B19, A4), (R18,R42,R239,B20, A4), (R18,R42,R239, B21, A4), (R18,R42,R2310,B1, A4), (R18,R42,R2310,B2, A4), (R18,R42,R2310,B3, A4), (R18,R42,R2310,B4, A4), (R18,R42,R2310,B5, A4), (R18,R42,R2310,B6, A4), (R18, R42,R2310,B7, A4), (R18,R42,R2310,B8, A4), (R18,R42, R2310,B9, A4), (R18,R42,R2310,B10, A4), (R18,R42, R2310,B11, A4), (R18,R42,R2310,B12, A4), (R18,R42, R2310, B13, A4), (R18,R42,R2310,B14, A4), (R18,R42, R2310,B15, A4), (R18,R42,R2310,B16, A4), (R18,R42, R2310,B17, A4), (R18,R42,R2310,B18, A4), (R18,R42, R2310,B19, A4), (R18,R42, R2310,B20, A4), (R18,R42, R2310,B21, A4), (R18,R42,R2311,B1, A4), (R18,R42, R2311,B2, A4), (R18,R42,R2311,B3, A4), (R18,R42, R2311,B4, A4), (R18,R42,R2311,B5, A4), (R18,R42, R2311,B6, A4), (R18,R42,R2311,B7, A4), (R18,R42, R2311,B8, A4), (R18,R42,R2311,B9, A 4), (R18,R42, R2311,B10, A4), (R18,R42,R2311,B11, A4), (R18,R42, R2311,B12, A4), (R18,R42,R2311,B13, A4), (R18,R42, R2311,B14, A4), (R18,R42,R2311,B15, A4), (R18,R42, R2311, B16, A4), (R18,R42,R2311,B17, A4), (R18,R42, R2311,B18, A4), (R18,R42,R2311,B19, A4), (R18,R42, R2311,B20, A4), (R18,R42,R2311,B21, A4), (R18,R42, R2312,B1, A4), (R18,R42, R2312,B2, A4), (R18,R42, R2312,B3, A4), (R18,R42,R2312,B4, A4), (R18,R42, R2312,B5, A4), (R18,R42,R2312,B6, A4), (R18,R42, R2312,B7, A4), (R18,R42,R2312,B8, A4), (R18,R42, R2312,B9, A4), (R18,R42,R2312,B10, A4), (R18,R42, R2312,B11, A4), (R18,R42,R2312,B12, A4), (R18,R42, R2312,B13, A4), (R18,R42,R2312,B14, A4), (R18,R42, R2312,B15, A4), (R18, R42,R2312,B16, A4), (R18,R42, R2312,B17, A4), (R18,R42,R2312,B18, A4), (R18,R42, R2312,B19, A4), (R18,R42,R2312,B20, A4), (R18,R42, R2312,B21, A4), (R18,R42,R2313,B1, A4), (R18,R42, R2313,B2, A4), (R18,R42,R2313,B3, A4), (R18,R42, R2313,B4, A4), (R18,R42,R2313,B5, A4), (R18,R42, R2313,B6, A4), (R18,R42,R2313,B7, A4), (R18,R42, R2313,B8, A4), (R18,R42,R2313,B9, A4), (R18,R42, R2313,B10, A4), (R18,R42,R2313,B11, A4), (R18,R42, R2313,B12, A4), (R18,R42,R2313,B13, A4), (R18,R42, R2313,B14, A4), (R18,R42,R2313,B 15, A4), (R18,R42, R2313,B16, A4), (R18,R42,R2313,B17, A4), (R18,R42, R2313,B18, A4), (R18,R42,R2313,B19, A4), (R18,R42, R2313,B20, A4), (R18,R42,R2313,B21, A4),

In one embodiment, the compounds of the present invention are as follows:

A compound of formula (I) wherein

X is —C($R^{3a}$)($R^{3b}$)— or —C($R^{3a}$)($R^{3b}$)—C($R^{3c}$)($R^{3d}$)—,

L is —C(=O)NH—,

Ring A is substituted or unsubstituted benzene,

Ring B is substituted or unsubstituted pyridine, substituted or unsubstituted pyrazine or substituted or unsubstituted oxazole, $R^1$ is alkyl, haloalkyl or alkynyl, $R^{2a}$ and $R^{2b}$ are each independently hydrogen, halogen, alkyloxy or haloalkyl, $R^{3a}$ and $R^{3b}$ are each independently hydrogen, hydroxy, alkyl, alkyloxyalkyl or haloalkyl, $R^{3c}$ and $R^{3d}$ are hydrogen, $R^{2a}$ and $R^{3a}$ attached to adjacent carbon atoms, together with the carbon atoms to which they are attached, may form

[Chemical Formula 73]

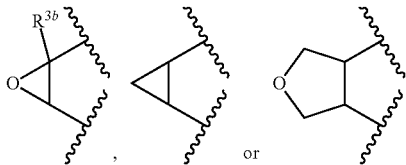

and $R^{3a}$ and $R^{3b}$ together with the carbon atom to which they are attached may form

[Chemical Formula 74]

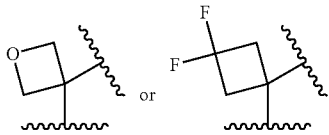

provided that the following compounds are excluded:
(1) a compound wherein X is —CH$_2$—, and at least one of $R^{2a}$ and $R^{2b}$ is halogen, or alkyloxy,
(2) a compound wherein X is —C($R^{3a}$)($R^{3b}$)—, $R^1$ is alkyl, and both of $R^{2a}$ and $R^{2b}$ are fluorine,
(3) a compound wherein X is —CH$_2$—, $R^1$ is alkyl, and both of $R^{2a}$ and $R^{2b}$ are hydrogen,
(4) a compound wherein X is —C($R^{3a}$)($R^{3b}$)—, $R^1$ is alkyl or haloalkyl, and $R^{2a}$ and $R^{3a}$ attached to adjacent carbon atoms, together with the carbon atoms to which they are attached, may form

[Chemical Formula 75]

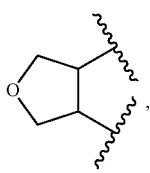

and
(5) the following compounds:

[Chemical Formula 76]

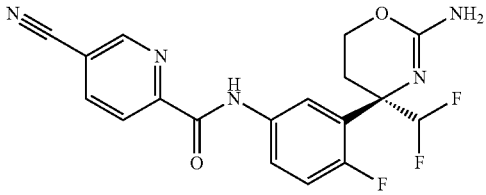

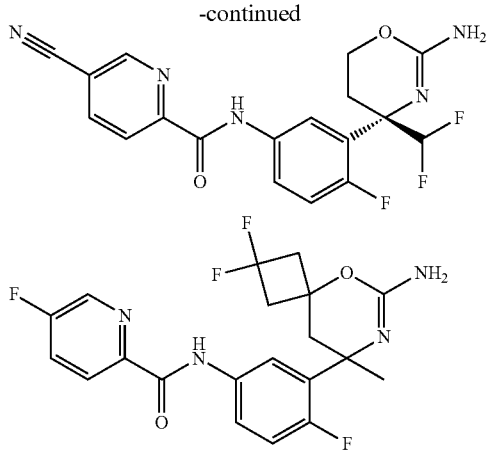

or a pharmaceutically acceptable salt thereof.

The compound of formula (I) is not limited to a specific isomer, and includes all possible isomers such as keto-enol isomers, imine-enamine isomers, diastereoisomers, optical isomers and rotation isomers, racemate and the mixture thereof. For example, the compound of formula (I) includes the following tautomers.

[Chemical Formula 77]

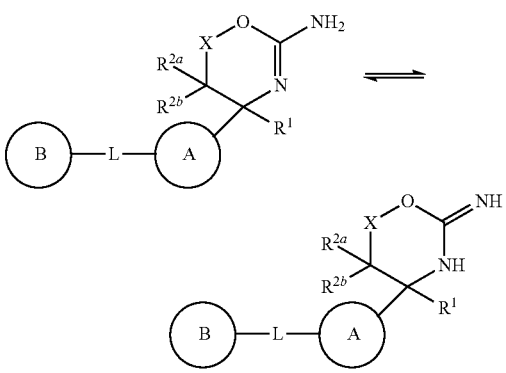

The compound of formula (I) has an asymmetric carbon atom and the compound includes the following optical isomers.

[Chemical Formula 78]

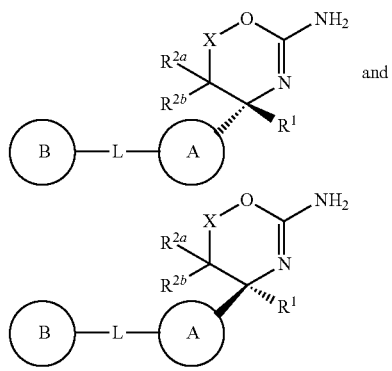

In one embodiment, the compound of the present invention is as follows:

[Chemical Formula 79]

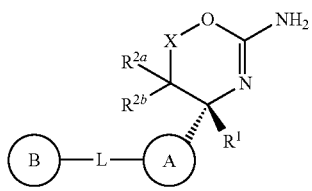

Optically active compounds of formula (I) can be produced by employing an optically active starting material, by obtaining an optically active intermediate by asymmetry synthesis at a suitable stage, or by performing optical resolution of an intermediate or an objective compound, each of which is a racemate, at a suitable stage. Examples of a method for optical resolution is separation of an optical isomer using an optically active column; kinetic optical resolution utilizing an enzymatic reaction; crystallization resolution of a diastereomer by salt formation using a chiral acid or a chiral base; and preferential crystallization method.

One or more hydrogen, carbon and/or other atoms of a compound of formula (I) can be replaced with an isotope of hydrogen, carbon and/or other atoms, respectively. Examples of isotopes include isotopes of hydrogen, carbon, nitrogen, oxygen, phosphorous, sulfur, fluorine, iodine and chlorine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I and $^{36}$Cl, respectively. The compound of formula (I) also includes the compound replaced with such isotopes. The compound replaced with such isotopes is useful also as a medicament, and includes all the radiolabeled compounds of the compound of formula (I). The invention includes "radiolabelling method" for manufacturing the "radiolabeled compound" and the method is useful as a tool of metabolic pharmacokinetic research, the research in binding assay and/or diagnosis.

A radiolabeled compound of the compound of formula (I) can be prepared by methods known in the art. For example, tritiated compounds of formula (I) can be prepared by introducing tritium into the particular compound of formula (I) such as by catalytic dehalogenation with tritium. This method may include reacting a suitably halogenated precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). A $^{14}$C-labeled compound can be prepared by employing starting materials having $^{14}$C carbon.

As pharmaceutically acceptable salt of the compound of formula (I), examples include salts with alkaline metals (e.g. lithium, sodium and potassium), alkaline earth metals (e.g. calcium and barium), magnesium, transition metal (e.g. zinc and iron), ammonia, organic bases (e.g. trimethylamine, triethylamine, dicyclohexylamine, ethanolamine, diethanolamine, triethanolamine, meglumine, diethanolamine, ethylenediamine, pyridine, picoline, quinoline), and amino acids, and salts with inorganic acids (e.g. hydrochloric acid, sulfuric acid, nitric acid, carbonic acid, hydrobromic acid, phosphoric acid and hydroiodic acid) and organic acids (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid and ethanesulfonic acid). Specific Examples are salts with hydrochloric acid, sulfuric acid, phosphoric acid, tartaric acid, or methanesulfonic acid. These salts can be formed by the usual method.

The compounds of the present invention represented by formula (I) or pharmaceutically acceptable salts thereof may form solvates (e.g., hydrates etc.) and/or crystal polymorphs. The present invention encompasses those various solvates and crystal polymorphs. "Solvates" may be those wherein any number of solvent molecules (e.g., water molecules etc.) are coordinated with the compounds represented by formula (I). When the compounds represented by formula (I) or pharmaceutically acceptable salts thereof are allowed to stand in the atmosphere, the compounds may absorb water, resulting in attachment of adsorbed water or formation of hydrates. Recrystallization of the compounds represented by formula (I) or pharmaceutically acceptable salts thereof may produce crystal polymorphs.

The compounds of the present invention represented by formula (I) or pharmaceutically acceptable salts thereof may form prodrugs. The present invention also encompasses such various prodrugs. Prodrugs are derivatives of the compounds of the present invention that have chemically or metabolically degradable groups and are compounds that are converted to the pharmaceutically active compounds of the present invention through solvolysis or under physiological conditions in vivo. Prodrugs include compounds that are converted to the compounds represented by formula (I) through enzymatic oxidation, reduction, hydrolysis and the like under physiological conditions in vivo and compounds that are converted to the compounds represented by formula (I) through hydrolysis by gastric acid and the like. Methods for selecting and preparing suitable prodrug derivatives are described, for example, in the Design of Prodrugs, Elsevier, Amsterdam 1985. Prodrugs themselves may be active compounds.

When the compounds of formula (I) or pharmaceutically acceptable salts thereof have a hydroxy group, prodrugs include acyloxy derivatives and sulfonyloxy derivatives which can be prepared by reacting a compound having a hydroxy group with a suitable acid halide, suitable acid anhydride, suitable sulfonyl chloride, suitable sulfonylanhydride and mixed anhydride or with a condensing agent. Examples are $CH_3COO-$, $C_2H_5COO-$, t-BuCOO-, $C_{15}H_{31}COO-$, PhCOO-, (m-NaOOCPh)COO-, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3$-O-$PhSO_3-$, $PhSO_3-$ and p-$CH_3PhSO_3-$.

The compound of formula (I) can be prepared, for example, by the general synthetic procedure shown below. The methods for extraction, purification, and the like may be carried out by using the usual method for the experiments of organic chemistry.

The compounds of the present invention can be synthesized in consideration of the condition of the known methods in the art.

In the case that a substituent which inhibits a reaction (e.g. hydroxy, mercapto, amino, formyl, carbonyl and carboxy) exists in any of the above steps, the substituent may be preliminarily protected by, for example, the method described in "Protective Groups in Organic Synthesis, Theodora W Green (John Wiley & Sons)", and the protecting group may be removed at an appropriate step.

During all the following steps, the order of the steps to be performed may be appropriately changed. In each step, an intermediate may be isolated and then used in the next step. All of reaction time, reaction temperature, solvents, reagents, protecting groups, etc. are mere exemplification and not limited as long as they do not cause an adverse effect on a reaction.

esters. This type of reactions can be conducted using the conditions described in Chem. Rev. 2010, 110, 3600-3740. Preferably, enolates can be prepared from corresponding esters, lithium diisopropylamide (LDA), and TiCl(Oi-Pr)$_3$, which can be then reacted with A1 to give compounds of formula A2. The solvent used in this step is not particularly limited in so far as these do not interfere with the reaction.

(General Procedure 1)

[Chemical Formula 80]

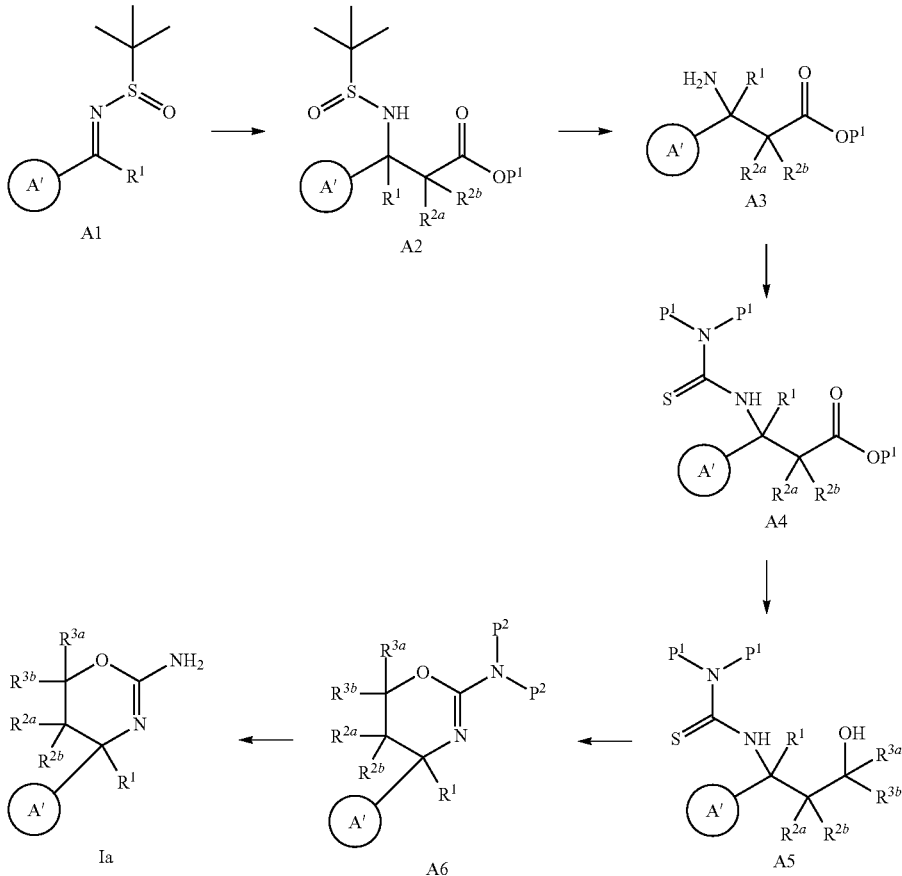

wherein ring A' is a substituted or unsubstituted aromatic carbocyclyl, a substituted or unsubstituted non-aromatic carbocyclyl, a substituted or unsubstituted aromatic heterocyclyl or a substituted or unsubstituted non-aromatic heterocyclyl, each of which is substituted with -L-ring B or can be substituted with -L-ring B by any of the General Procedures 6 to 8 mentioned below, and $P^1$ is hydrogen, substituted or unsubstituted alkyl or substituted or unsubstituted alkylcarbonyl or the like. One of two $P^1$ is other than hydrogen and the other symbols are the same as defined above.

General Procedure 1 is a method for preparing compounds of formula Ia according to the present invention from compound of formula A1 through multiple steps of Step 1 to Step 6. Compounds of formula A1 can be prepared in a manner similar to the conditions described in Chem. Rev. 2010, 110, 3600-3740.

Step 1:
Compounds of formula A2 can be prepared by Mannich reaction of sulfinyl imine A1 with enolates derived from esters. Examples of the solvent include tetrahydrofuran, 1,4-dioxanne, 1,2-dimethoxyethane, diethyl ether, toluene, and benzene. The reaction temperature is preferably −78~−30° C. The reaction time is not particularly limited and is usually 5 minutes to 24 hours, preferably 30 minutes to 6 hours.

Step 2:
Compounds of formula A3 can be prepared by deprotection of A2. This deprotection reaction is known to a person skilled in the art and can be performed under the conditions described in Chem. Rev. 2010, 110, 3600-3740. The reaction can be conducted under acidic conditions using e.g. hydrochloric acid at room temperature to 60° C. Examples of the solvent include methanol, 1,4-dioxane, and ethyl acetate. The reaction time is not particularly limited and is usually 1 hour to 24 hours, preferably 1 hour to 6 hours.

Step 3:
Compounds of formula A4 can be prepared by reaction of A3 with reagents such as benzoyl isothiocyanate and benzyl isothiocyanate. Those skilled in the art will appreciate that the isothiocyanate generated from A3 and reagents such as thiophosgene and thiocarbonyl diimidazole can be reacted with primary or secondary amines to afford compounds of formula A4. The solvent used in this step is not particularly limited in so far as it does not interfere with the reaction. Examples of the solvent include dichloromethane, tetrahydrofuran, 1,4-dioxane, 1,2-dimethoxyethane, and toluene. The reaction time is not particularly limited and is usually 1 hour to 24 hours, preferably 3 to 6 hours. The reaction temperature is usually 0 to 60° C., preferably 0° C. to room temperature. Reagents for the thiourea formation in this step is not particularly limited if these can be deprotected in Step 6 and preferably include benzoyl isothiocyanate.

Step 4:

Compounds of formula A5 can be prepared by the reaction of A4 with Grignard reagents such as methyl magnesium bromide and ethyl magnesium bromide and alkyl lithium reagents such as methyllithium, butyllithium, and phenyllithium. Stepwise addition of these nucleophiles can allow for compounds of formula A5 with various substituents of $R^{3a}$ and $R^{3b}$. The solvent used is not particularly limited in so far as it does not interfere with the reaction. Preferable examples of the solvent include tetrahydrofuran, 1,4-dioxane, 1,2-dimethoxyethane, diethyl ether, toluene, and benzene. The reaction temperature is not particularly limited and is usually 5 minutes to 24 hours, preferably 5 minutes to 6 hours. The reaction temperature is usually −100° C. to room temperature, preferably −78 to 0° C.

Step 5:

Compounds of formula A6 can be prepared by the cyclization reaction of A5 using reagents such as m-CPBA, hydrogen peroxide, and carbodiimide reagents (e.g. 1-ethyl-3-(3-dimethylaminopropyl)carbodiimide). Alternatively, A6 can be obtained by reacting A5 with alkylating reagents followed by the cyclization reaction under basic conditions. In the former case, suitable reagents include m-CPBA, and the reaction temperature is usually 0° C. to room temperature, and preferably room temperature. Appropriate solvents include dichloromethane and chloroform. In the latter case, suitable alkylating reagents include methyl iodide, and suitable bases include sodium hydride, sodium bicarbonate, and potassium carbonate.

Step 6:

Compounds of formula Ia wherein $P^1$ is as defined above can be prepared by the deprotection reactions known to a person skilled in the art. The reaction conditions are described in Greene's Protective Groups in Organic Synthesis, 4th ed. When the protecting group is benzoyl, the deprotecting reaction can be conducted in an acidic solution containing acids such as hydrazine, sulfuric acid, and hydrochloric acid or in an alkaline solution containing bases such as sodium hydroxide. Examples of the solvent include water, methanol, ethanol, and a mixed solvent thereof, and preferably a mixed solvent of water and tetrahydrofuran. The reaction temperature is usually room temperature to 100° C. and preferably room temperature to 80° C. Alternatively, the deprotection of benzoyl group can be performed using bases such as potassium carbonate in methanol following Boc protection of the remaining hydrogen of the benzoyl amide, which is then treated with trifluoroacetic acid to afford Ia.

(General Procedure 2)

[Chemical Formula 81]

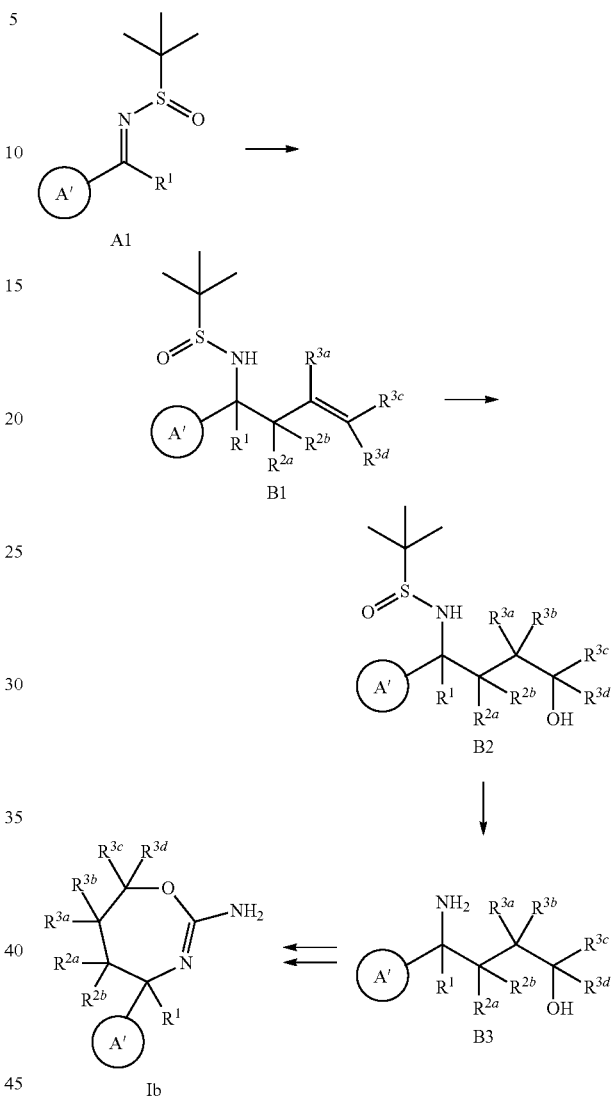

wherein each symbol is the same as defined above.

General Procedure 2 is a method for preparing compounds of formula Ib according to the present invention from compound of formula A1 through multiple steps.

Compounds of formula B3 can be prepared in 3 steps, which can be then converted to compounds of formula Ib in a manner similar to Steps 3, 5 and 6 of General Procedure 1.

Step 1:

Compounds of formula B1 can be prepared by the reaction of A1 with Grignard reagents, which is known to those skilled in the art. Examples of Grignard reagent include methyl magnesium bromide and ethyl magnesium bromide, but are not particularly limited to these reagents. The solvent used is not particularly limited in so far as it does not interfere with the reaction. Preferable examples of the solvent include tetrahydrofuran, 1,4-dioxane, 1,2-dimethoxyethane, diethyl ether, toluene, and benzene. The reaction temperature is not particularly limited and is usually 5 minutes to 24 hours, preferably 5 minutes to 6 hours. The reaction temperature is usually −78° C. to room temperature, preferably −45 to 0° C.

Step 2:

Compounds of formula B2 can be prepared by hydroboration reaction of B1 with appropriate boron reagents followed by oxidation. This reaction is known to those skilled in the art. Examples of boron reagents include borane-tetrahydrofuran complex, disiamylborane, thexylborane, and 9-borabicyclo[3.3.1]nonane (9-BBN). The following oxidation can be conducted, for example using alkaline hydrogen peroxide. The reaction temperature is usually −45° C. to room temperature and preferably 0° C. to room temperature. The reaction time is not particularly limited and is usually 1 hour to 24 hours, and preferably 1 hour to 6 hours.

(General Procedure 3)

[Chemical Formula 82]

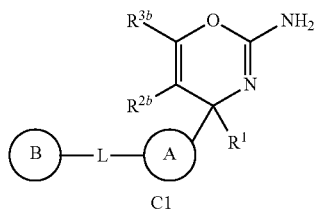

C1

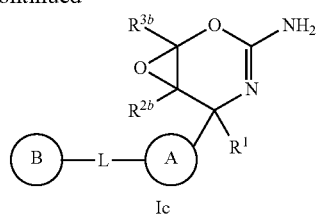

Ic wherein each symbol is the same as defined above.

General Procedure 3 is a method for preparing compounds of formula Ic according to the present invention from compounds of formula C1.

Step 1:

Compounds of formula Ic can be prepared by oxidation reaction of compounds of formula C1 with appropriate oxidation reagents, examples of which include m-CPBA and hydrogen peroxide. Alternatively, this reaction can be conducted using enzymes such as cytochrome P450. The reaction temperature is usually room temperature to 40° C. and preferably room temperature. The reaction time is not particularly limited and is usually 1 hour to 24 hours, preferably 1 hour to 6 hours.

(General Procedure 4)

[Chemical Formula 83]

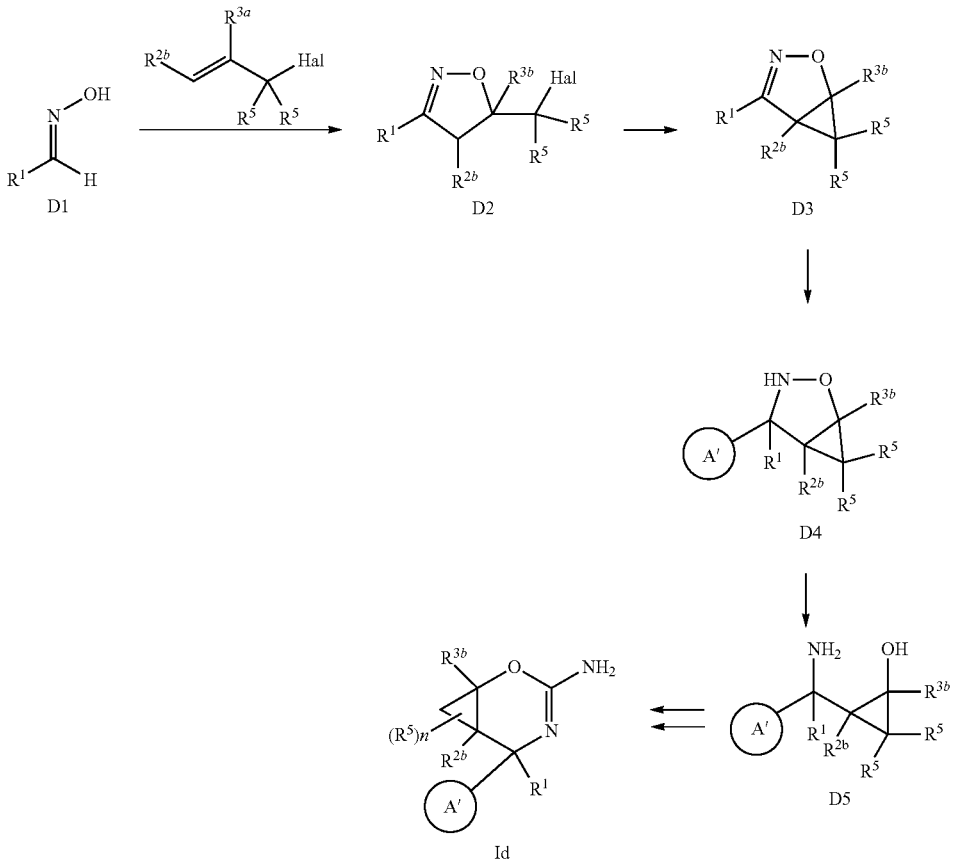

wherein Hal is halogen and other each symbol is the same as defined above. General Procedure 4 is a method for preparing compounds of formula Id according to the present invention from compounds of formula D1 through multiple steps. Compounds of formula D5 can be prepared in 4 steps, which can be then converted to compounds of formula Ib in a manner similar to Steps 3, 5, and 6 of General Procedure 1. Compounds of formula D1 can be synthesized by a method known to a person skilled in the art using commercially available aldehyde.

Step 1:

Compounds of formula D2 can be prepared by converting compounds of formula D1 to the corresponding nitrile oxides using sodium hypochlorite, chlorine, and N-chlorosuccinimide in the presence or absence of bases such as triethylamine followed by 1,3-dipolar cycloaddition with substituted olefins. The reaction temperature is usually 0° C. to 80° C. and is preferably 0° C. to room temperature. The reaction time is not particularly limited and is usually 1 hour to 24 hours, preferably 1 hour to 6 hours.

Step 2:

Compounds of formula D3 can be prepared by cyclization reaction of compounds of formula D2 in the presence of bases such as lithium diisopropylamide (LDA), lithium bis(trimethylsilyl)amide (LHMDS), and sodium hydride. The reaction temperature is usually −78° C. to 0° C. and is preferably −78° C. to −45° C. The reaction time is not particularly limited and is usually 1 hour to 12 hours, preferably 1 hour to 6 hours.

Step 3:

Compound of formula D4 can be prepared by nucleophilic addition of compounds of formula D3 with appropriate nucleophiles. When A' is a substituted or unsubstituted aromatic carbocycle, a substituted or unsubstituted aromatic heterocycle, compounds of formula D4 can be prepared by the reaction of the corresponding aryllithium or Grignard reagents with compounds of formula D3 in the presence of Lewis acids such as boron trifluoride ethyl ether complex. When A' is a substituted or unsubstituted non-aromatic carbocycle, a substituted or unsubstituted non-aromatic heterocycle, compounds of formula D4 can be prepared by the reaction of the corresponding alkyllithium or Grignard reagents in the presence of Lewis acids such as boron trifluoride ethyl ether complex. The aryllithium or Grignard reagent can be prepared by a method known to a person skilled in the art. The reaction temperature is −100° C. to 0° C., preferably −78° C. to −30° C. The reaction time is not particularly limited and is usually 5 minutes to 12 hours and is preferably 1 hour to 6 hours.

Step 4:

Compounds of formula D5 can be prepared by reduction of compounds of formula D4 with reducing reagents such as lithium aluminum hydride (LAH), Raney nickel, and palladium on carbon/H2. The reaction temperature is usually 0° C. to 50° C. and is preferably 0° C. to room temperature. The reaction time is not particularly limited and is usually 30 minutes to 12 hours, preferably 30 minutes to 6 hours.

(General Procedure 5)

[Chemical Formula 84]

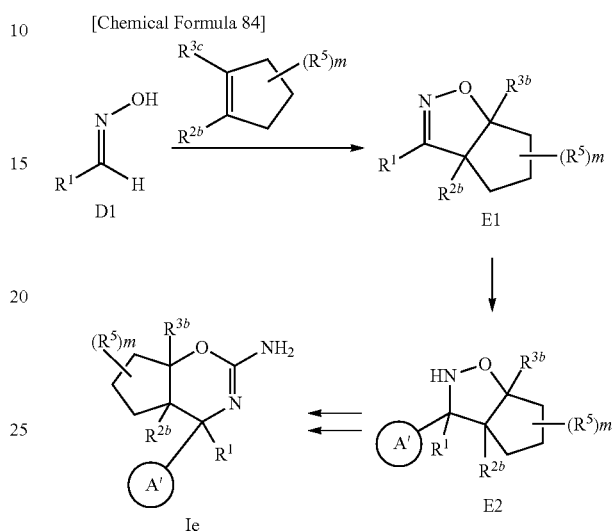

wherein each symbol is the same as defined above.

General Procedure 5 is a method for preparing compounds of formula Ie according to the present invention from compounds of formula D1 though 2 steps of Step 1 to Step 2 followed by Step 4 (reduction) described in General Procedure 4, Step 3 (thiourea formation), Step 5 (cyclization), and Step 6 (deprotection) described in General Procedure 1.

Step 1:

Compounds of formula E1 can be prepared by converting compounds of formula D1 to the corresponding nitrile oxides followed by 1,3-dipolar cycloaddition with substituted olefins. The reaction in this step can be performed in a manner similar to Step 1 described in General Procedure 4.

Step 2:

Compound of formula E2 can be prepared by nucleophilic addition of compounds of formula E1 with appropriate nucleophiles. The reaction in this step can be performed in a manner similar to Step 3 in General Procedure 4.

(General Procedure 6)

[Chemical Formula 85]

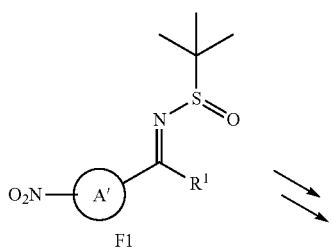

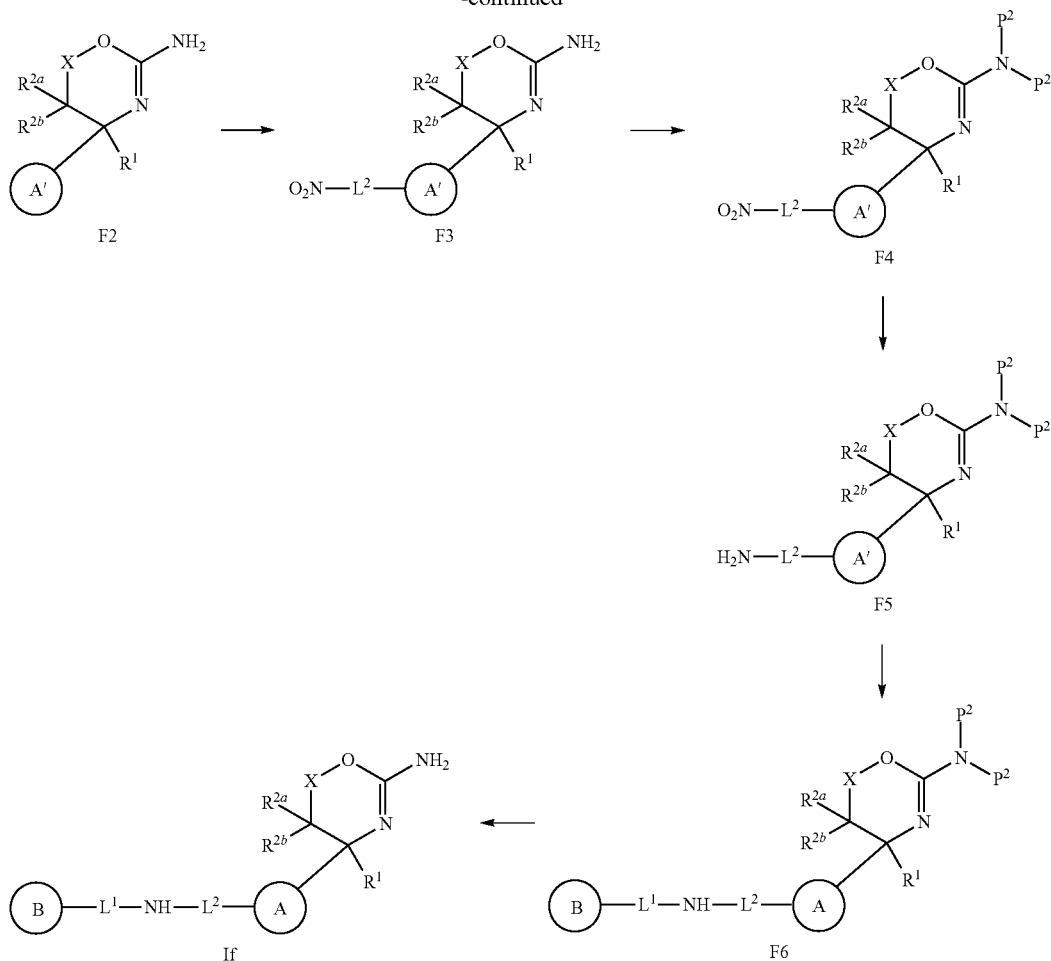

In the formula, $P^2$ is a protective group for the amino group in formula F2, one of which is at least hydrogen, substituted or unsubstituted alkyl, substituted or unsubstituted alkyloxycarbonyl, substituted or unsubstituted alkylcarbonyl. Other symbols are the same as defined above.

General Procedure 6 is a method for preparing compounds of formula If according to the present invention using compounds of formula Ia, Ib, Id, and Ie described in General Procedure 1, 2, 4, and 5, respectively. Compounds of formula If can be prepared from compounds of formula F2 in 5 steps. Alternatively, compounds of formula If can be prepared from compounds of formula F1 according to General Procedure 1 and 2.

Step 1:
Compounds of formula F3 can be prepared by nitration of compounds of formula F2. This reaction is known to a person skilled in the art. For example, compounds of formula F2 can be obtained by use of nitric acid or nitrate in a solvent such as sulfuric acid or a mixed solvent of sulfuric and trifluoroacetic acid. The reaction temperature is usually −30° C. to 0° C. and is preferably −20° C. to 0° C. The reaction time is usually 1 minute to 3 hours and is preferably 1 minute to 1 hour.

Step 2:
Compounds of formula F4 can be prepared by protection of compounds of formula F3 under the conditions described in Greene's Protective Groups in Organic Synthesis, 4th ed. For example, when both P2 are tert-butoxycarbonyl (Boc), Boc protection can be conducted using di-tert-butyl dicarbonate in the presence of catalytic amount of N,N-dimethyl-4-aminopyridine. The reaction temperature is usually 0° C. to 60° C. and is preferably 0° C. to room temperature. The reaction time is not particularly limited and is usually 30 minutes to 24 hours, preferably 1 hour to 12 hours.

Step 3:
Compounds of formula F5 can be prepared by reduction of compounds of formula F5. This reaction is known to a person skilled in the art and the following condition can be used: 1) a method using iron powder in the presence of hydrochloric acid or ammonium chloride; 2) a method using palladium on carbon under hydrogen atmosphere. Examples of the solvent include water, methanol, ethanol, ethyl acetate, tetrahydrofuran, and mixtures of those solvents. The reaction temperature is usually room temperature to 100° C., preferably 50° C. to 80° C. The reaction time is usually 1 hour to 24 hours and is preferably 3 to 8 hours.

Step 4:
Compounds of formula F6 can be prepared using compounds of formula F5. This type of reaction is known to a person skilled in the art. Substituent B can be introduced by: (1) alkylation reaction with alkyl halides; (2) arylation reaction with aryl halides; (3) reductive alkylation with aldehydes. Reaction (1) can be conducted by use of commercially available alkyl halides or alkyl halides synthesized by known methods in the presence of bases such as triethylamine, diisopropylethylamine, sodium hydride, and sodium hydroxide. The solvent used in this reaction is not particularly limited in so far as it does not interfere the reaction. Examples of the solvent include tetrahydrofuran, 1,4-dioxane, N,N-dimethylformamide, ethyl acetate, and acetone. The reaction temperature is usually 0° C. to 100° C. is preferably room temperature to 60° C. The reaction time is usually 1 hour to 24 hours and is preferably 1 hour to 6 hours.

Reaction (2) can be conducted by use of aryl halides with electron withdrawing groups such as nitro or cyano groups in solvents such as tetrahydrofuran, N,N-dimethylformamide, ethyl acetate, and acetone at temperatures ranging from room temperature to 100° C. When using aryl halide other than the above, this reaction can be conducted according to the methods described in Metal-Catalyzed Cross-Coupling Reactions, 2nd ed. For example, this reaction can be performed by use of transition metal catalysts such as tris(dibenzylideneacetone) dipalladium and palladium acetate and ligands such as 2,2'-bis(diphenylphosphino)-1,1'-binaphthyl (BINAP), 4,5-Bis(diphenylphosphino)-9,9-dimethylxanthene (Xantphos), and 2-Dicyclohexylphosphino-2',4',6'-triisopropylbiphenyl (X-Phos) in the presence of bases such as sodium tert-butoxide, cesium carbonate, and potassium phosphate. The reaction temperature is usually 40° C. to 150° C. and is preferably 60° C. to 100° C. This reaction may be accelerated by microwave irradiation. Examples of the solvent include toluene, benzene, xylene, tetrahydrofuran, 1,4-dioxane, and 1,2-dimethoxyethane.

Reaction (3) can be conducted by use of commercially available aldehydes or aldehydes synthesized by known methods. Examples of reducing reagents include sodium cyanoborohydride, sodium triacetoxyborohydride, and sodium borohydride. The solvent used in the reaction is not particularly limited in so far as it does not interfere with the reaction. Examples of the solvent include dichloromethane, tetrahydrofuran, and toluene. The reaction temperature is usually 30 minutes to 24 hours and is preferably 30 minutes to 6 hours.

Step 5:

Compounds of formula If can be prepared by deprotection of compounds of formula F6. This reaction is known to a person skilled in the art and is conducted under the conditions described in Greene's Protective Groups in Organic Synthesis, 4th ed. For example, when both $P^2$ are tert-butoxycarbonyl (Boc), Boc deprotection can be conducted using trifluoroacetic acid or hydrochloric acid. Examples of the solvent include dichloromethane. The reaction temperature is usually 0° C. to 50° C. and is preferably room temperature. The reaction time is not particularly limited and is usually 30 minutes to 24 hours, preferably 1 hour to 12 hours.

(General Procedure 7)

[Chemical Formula 86]

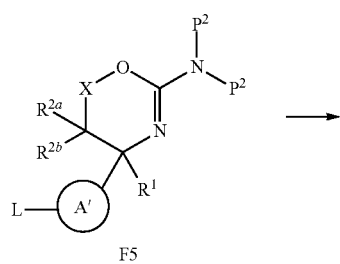

F5

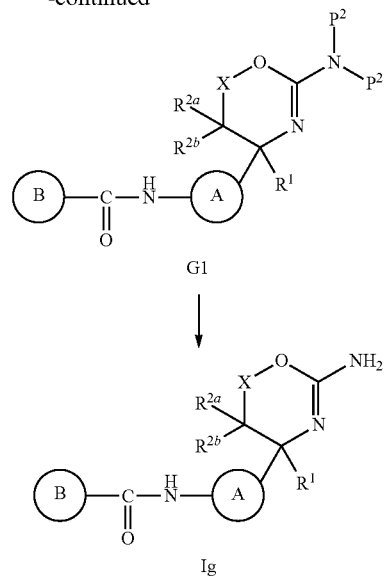

wherein each symbol is the same as defined above.

General Procedure 7 is a method for preparing compounds of formula Ig from compounds of formula F5 in 2 steps of Step 1 and Step 2.

Step 1:

Compounds of formula G1 can be prepared by amidation reaction with compounds of formula F5. This reaction is known to a person skilled in the art and can be conducted under the conditions described in Chem. Rev. 2011, 111, 6557-6602, which include: (1) reactions using condensation reagents; (2) reactions using acid chlorides or fluorides.

Reaction (1) can be conducted by use of condensation reagents such as dicyclohexylcarbodiimide (DCC), diisopropylcarbodiimide (DIC), 1-ethyl-3-(3-dimethylaminopropyl) carbodiimide hydrochloride (EDC hydrochloride), O-(7-aza-1H-benzotriazol-1-yl)-N,N,N',N-tetramethyluronium hexafluorophosphate (HATU), and 1H-Benzotriazol-1-yloxy-tri(pyrrolidino)phosphonium hexafluorophosphate (PyBOP). When using uronium or phosphonium salts such as HATU and PyBOP, the reaction can be performed in the presence of bases such as triethylamine and diisopropylethylamine. The reaction may be accelerated by use of catalysts such as 1-hydroxy-benzotriazole (HOBt) and 1-hydroxy-7-aza-benzotriazole (HOAt). The solvent used in the reaction is not particularly limited in so far as it does not interfere with the reaction. Examples of the solvent include dichloromethane, N,N-dimethylformamide, N-methylpyrrolidone, and tetrahydrofuran. The reaction temperature is usually 0° C. to 50° C. and is preferably room temperature.

Reaction (2) can be performed by use of commercially available acid chlorides or those synthesized by known methods to a person skilled in the art in solvents such as dichloromethane, tetrahydrofuran, and ethyl acetate in the presence of bases such as triethylamine, diisopropylethylamine, pyridine, and N,N-dimethyl-4-aminopyridine. The reaction temperature is usually 0° C. to 60° C. and is preferably 0° C. to room temperature. The reaction time is not particularly limited and is usually 5 minutes to 24 hours, preferably 30 minutes to 6 hours.

Step 2:

Compounds of formula Ig can be prepared by deprotection of G1 according to Step 5 of General Procedure 6.

(General Procedure 8)

[Chemical Formula 87]

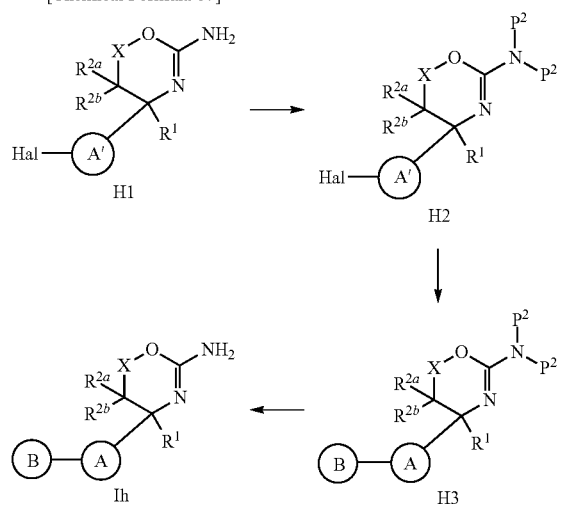

wherein Hal is halogen and other each symbol is the same as defined above. General Procedure 8 is a method for preparing compounds of formula Ih from compounds of formula H1 in 3 steps.

Step 1:
Compounds of formula H2 can be prepared by protection of compounds of formula H1 according to Step 2 of General Procedure 6.

Step 2:
Compounds of formula H3 can be prepared by coupling reaction with compounds of formula H2. This reaction can be conducted according to the methods described in Metal-Catalyzed Cross-Coupling Reactions, 2nd ed. For example, the reaction of H2 with organometallics such as organoborons, organotins, organozincs, or organomagnesiums can be performed by use of transition metal catalysts such as Tetrakis(triphenylphosphine)palladium, bis(triphenylphosphine)palladium(II) dichloride, and 1,1'-bis(diphenylphosphino)ferrocene-palladium(II)dichloride dichloromethane complex. The corresponding organometallic reagents are usually commercially available, but they can be prepared by a method known to a person skilled in the art. Examples of the solvent include water, tetrahydrofuran, 1,4-dioxane, toluene, 1,2-dimethoxyethane, N,N-dimethylformamide, and mixtures of those solvents. When using organoboron reagents, the reaction can be conducted in the presence of bases such as sodium carbonate, potassium carbonate, cesium carbonate, triethylamine, and potassium phosphate. The reaction temperature is usually 40° C. to 150° C. and is preferably 50° C. to 100° C. This reaction may be accelerated by microwave irradiation. The reaction temperature is usually 1 hour to 24 hours and is preferably 1 hour to 6 hours.

Step 3:
Compounds of formula Ih can be prepared by deprotection of compounds of formula H3 according to Step 5 of General Procedure 6.

(General Procedure 9)

[Chemical Formula 88]

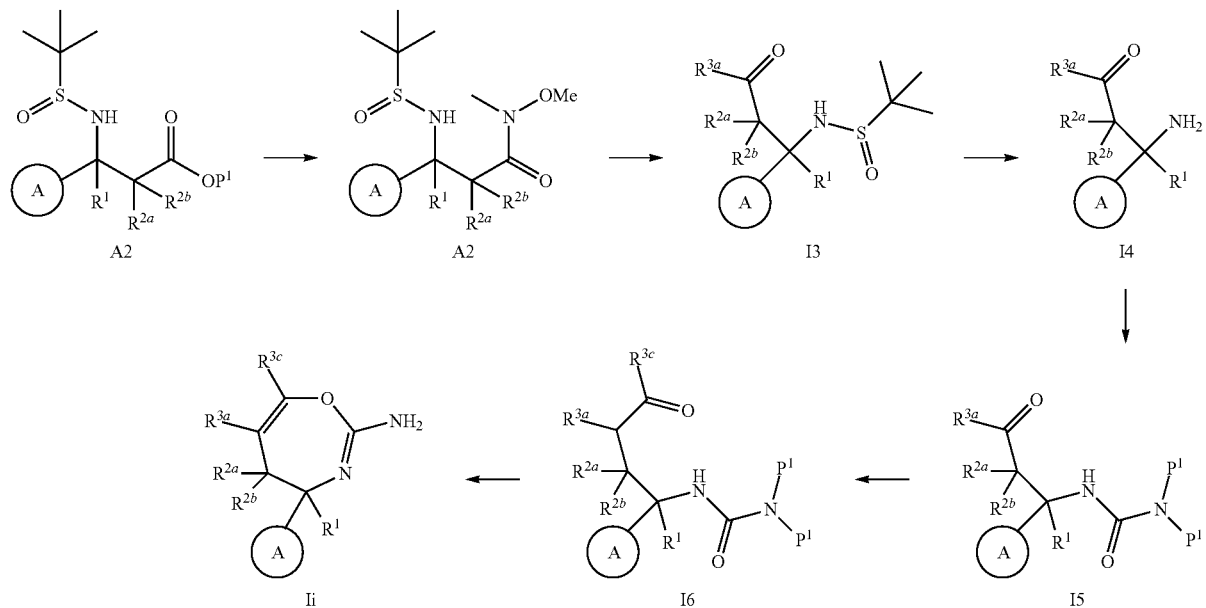

wherein $P^1$ is alkyl and other each symbol is the same as defined above, General Procedure 9 is a method for preparing compounds of formula Ii which correspond to formula I according to the present invention in 6 steps.

Step 1:
Compounds of formula I2 can be prepared by hydrolysis of A2 followed by amidation reaction. Hydrolysis is known to a person skilled in the art and is performed by use of bases such as sodium hydroxide, potassium hydroxide, and lithium hydroxide in solvents such as methanol, tetrahydrofuran, and mixture of those solvents and water. Amidation reaction can be conducted according to Step 1 of General Procedure 7 using N,O-dimethylhydroxylamine.

Step 2:

Compounds of formula I3 can be prepared by nucleophilic addition of Grignard reagents, which are usually commercially available and are also prepared from the corresponding alkyl or aryl halide in the presence of magnesium according to conditions known to those skilled in the art. Examples of the solvent include tetrahydrofuran and ethyl ether. The reaction time is not particularly limited and is usually 0.5 to 6 hours. The reaction temperature is usually −50° C. to 0° C.

Step 3:

Compounds of formula I4 can be prepared by deprotection of compounds of formula I3 according to the method described in Step 2 of General Procedure 1.

Step 4:

Compounds of formula I5 can be prepared by urea formation of compounds of formula I4. This type of reaction is known to those skilled in the art and is usually performed by treatment of compounds of formula I4 with reagents such as triphosgene, 4-nitrophenyl chloroformate, and carbonyl diimidazole followed by addition of amines such as bis(2, 4-dimethoxybenzyl)amine. Preferable combination of these reagents may be 4-nitrophenyl chloroformate and bis(2,4-dimethoxybenzyl)amine. In such case, the reaction can be performed in the presence of bases such as sodium bicarbonate in solvents such as water, tetrahydrofuran, ethyl acetate, and mixture of those solvents. The reaction temperature is usually 0° C. to room temperature. The reaction time is not particularly limited and is usually 1 to 12 hours.

Step 5:

Compounds of formula I6 can be prepared by Wittig reaction of compounds of formula I5 with the corresponding phosphonium ylides. This type of reaction is known to those skilled in the art and is generally conducted by treatment of the corresponding alkyl halide with triphenylphosphine followed by bases such as n-butyl lithium, which can be reacted with compounds of formula I5. Examples of the solvent include tetrahydrofuran. The reaction time is not particularly limited and is usually 1 to 12 hours.

Step 6:

Compounds of formula Ii can be prepared by cyclization of compounds of formula I6. This reaction can be conducted by use of dehydration reagents such as Burgess reagent. Examples of the solvent include tetrahydrofuran and ethyl acetate. The reaction temperature is usually room temperature to 80° C. The reaction time is usually 0.5 to 6 hours.

(General procedure 10)

[Chemical Formula 89]

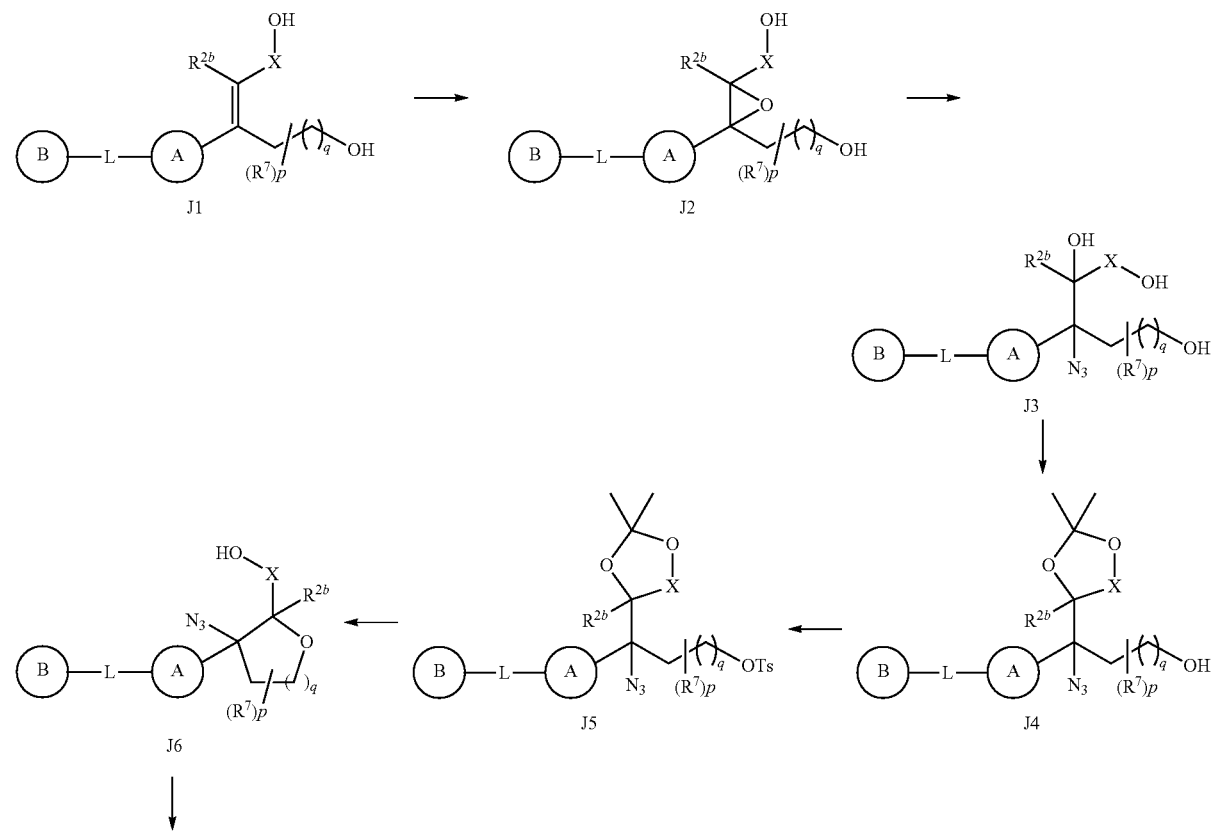

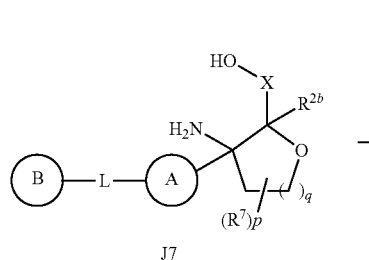 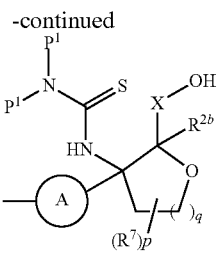 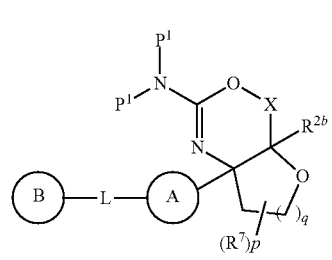

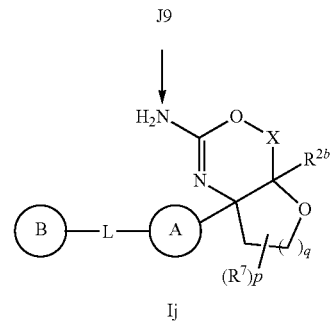

wherein each symbol is the same as defined above.

General procedure 10 is a method for preparing compounds of formula Ij from compound J1 in 9 steps. The starting material of formula J1 can be prepared by a method known to a person skilled in the art. To obtain chiral compounds of formula Ij, the chiral separation can be performed for compounds of formulas J7, J8, J9, and Ij, if these are separable by use of chiral HPLC or SFC.

Step 1:

Compounds of formula J2 can be prepared by epoxidation of compounds of formula J1. Epoxidation is known to a person skilled in the art and is performed by use of oxidants such as m-CPBA and tert-butyl hydroperoxide in solvents such as dichloromethane and chloroform. The reaction time is not particularly limited and is usually 0.5 to 3 hours. The reaction temperature is usually −50° C. to room temperature. Asymmetric epoxidation such as Sharpless asymmetric epoxidation can be also applied to this step using methods known to those skilled in the art, which would be helpful to synthesize chiral compounds without chiral separation.

Step 2:

Compounds of formula J3 can be prepared by ring opening reaction using sodium azide, which can be catalyzed by Lewis acid such as Ti(OEt)$_4$. Examples of the solvent include solvents such as THF, toluene, and ethyl ether. The reaction time is not particularly limited and is usually 1 to 24 hours. The reaction temperature is usually room temperature.

Step 3:

Compounds of formula J4 can be prepared by protection of the diol moiety in compounds of formula J3. The reaction conditions are described in Greene's Protective Groups in Organic Synthesis, 4th ed. Briefly, this reaction can be performed using reagents such as acetone and 1,2-dimethoxypropane in the presence of catalytic amount of acids such as pyridinium p-toluenesulfonate and p-toluenesulfonic acid. Examples of the solvent include dichloromethane, 1,2-dimethoxyethane, and N,N-dimethylformamide. Preferable reaction temperature is room temperature.

Step 4:

Compounds of formula J5 can be prepared using tosyl chloride in the presence of bases such as triethylamine and potassium carbonate in solvents such as THF and dichloromethane. This reaction is also known to those skilled in the art.

Step 5:

Compounds of formula J6 can be prepared by deprotection of compounds of formula J5 under the conditions described in Greene's Protective Groups in Organic Synthesis, 4th ed. Briefly, this reaction can be performed using catalytic amount of acids such as pyridinium p-toluenesulfonate, hydrochloric acid, and p-toluenesulfonic acid in solvents such as methanol and water. The reaction temperature is preferably room temperature.

Step 6:

Compounds of formula J7 can be prepared by reduction of compounds of formula J6. This reaction is known to a person skilled in the art. In general, the following conditions are used: 1) a method using iron powder in the presence of hydrochloric acid or ammonium chloride; 2) a method using palladium on carbon under hydrogen atmosphere. Examples of the solvent include solvents such as water, methanol, ethanol, ethyl acetate, tetrahydrofuran, and mixtures of those solvents. The reaction temperature is usually room temperature to 100° C., preferably 50° C. to 80° C. The reaction time is usually 1 hour to 24 hours and is preferably 3 to 8 hours.

Step 7:

Compounds of formula J8 can be prepared by reaction of J7 with reagents such as benzoyl isothiocyanate and benzyl isothiocyanate. The solvent used in this step is not particularly limited in so far as it does not interfere with the reaction. Examples of the solvent include dichloromethane, tetrahydrofran, 1,4-dioxane, 1,2-dimethoxyethane, and toluene. The reaction time is not particularly limited and is usually 1 hour to 24 hours, preferably 1 to 6 hours. The reaction temperature is usually 0 to 60° C., preferably 0° C. to room temperature.

Step 8:

Compounds of formula J9 can be prepared by the cyclization reaction of J8 using reagents such as m-CPBA, hydrogen peroxide, and carbodiimide reagents (e.g. 1-ethyl-3-(3-dimethylaminopropyl)carbodiimide). Alternatively, J9 can be obtained by reacting J8 with alkylating reagents followed by the cyclization reaction under basic conditions.

In the former case, suitable reagents include m-CPBA and 1-ethyl-3-(3-dimethylaminopropyl)carbodiimide, and the reaction temperature is usually 0° C. to room temperature, and preferably room temperature. Appropriate solvents include dichloromethane, chloroform, and acetonitrile. In the latter case, suitable alkylating reagents include methyl iodide, and bases include sodium hydride, sodium bicarbonate, and potassium carbonate.

Step 9:

Compounds of formula Ij can be prepared by the deprotection reactions known to a person skilled in the art. The reaction conditions are described in Greene's Protective Groups in Organic Synthesis, 4th ed. When the protecting group is benzoyl, the deprotecting reaction can be conducted in an acidic solution containing acids such as hydrazine, sulfuric acid, and hydrochloric acid. Alternatively, this reaction can be conducted in an alkaline solution containing bases such as sodium hydroxide. Examples of the solvent include water, methanol, ethanol, and mixed solvents thereof, and preferably mixed solvents of water and tetrahydrofuran. The reaction temperature is usually room temperature to 100° C. and preferably room temperature to 80° C. Alternatively, the deprotection of benzoyl group can be performed using bases such as potassium carbonate in methanol following Boc protection of the remaining hydrogen of the benzoyl amide, which can be then treated with trifluoroacetic acid to afford compounds of formula Ij.

The compounds of the present invention have BACE1 inhibitory activity and are effective in treatment and/or prevention, and symptom improvement of disease induced by the production, secretion or deposition of-amyloid β protein, Alzheimer's disease (dementia of the Alzheimer's type, senile dementia of Alzheimer type etc.), prodromal Alzheimer's disease, Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia such as coexist Alzheimer's disease with vascular type dementia, dementia with Parkinson's Disease, dementia with progressive supranuclear palsy, dementia with Cortico-basal degeneration, Alzheimer's disease with diffuse Lewy body disease, age-related macular degeneration, Parkinson's Disease, amyloid angiopathy.

In the present invention, "treating dementia of the Alzheimer's type" includes prevention of progression of MCI and prevention of onset of familial Alzheimer's disease. In the present invention, "a pharmaceutical composition for treating dementia of the Alzheimer's type" includes a pharmaceutical composition for preventing progression of MCI and a pharmaceutical composition for preventing onset of familial Alzheimer's disease.

The compound of the present invention has not only BACE1 inhibitory activity but the beneficialness as a medicament. The compound has any or all of the following superior properties.

a) The compound has weak inhibitory activity for CYP enzymes such as CYP1A2, CYP2C9, CYP2C19, CYP2D6, CYP3A4.

b) The compound show excellent pharmacokinetics such as high bioavailability or moderate clearance.

c) The compound has high metabolic stability.

d) The compound does not show irreversible inhibition to CYP enzyme such as CYP3A4 in the range of the concentration of the measurement conditions described in this description.

e) The compound does not show mutagenesis.

f) The compound is associated with a low risk of cardiovascular systems.

g) The compound shows high solubility.

h) The compound shows high brain distribution.

i) The compound has high oral absorption.

j) The compound has long half-life period.

k) The compound has high protein unbinding ratio.

l) The compound is negative in the Ames test.

Since the compound of the present invention has high inhibitory activity on BACE1 and/or high selectivity on other enzymes, it can be a medicament with reduced side effect. Further, since the compound has high effect of reducing amyloid β production in a cell system, particularly, has high effect of reducing amyloid β production in brain, it can be an excellent medicament. In addition, by converting the compound into an optically active compound having suitable stereochemistry, the compound can be a medicament having a wider safety margin on the side effect.

When a pharmaceutical composition of the present invention is administered, it can be administered orally or parenterally. The composition for oral administration can be administered in usual dosage forms such as tablets, granules, powders, capsules which can be prepared according to the conventional manners. The composition for parenteral administration can be administered suitably in usual parenteral dosage forms such as injections. The compounds of the present invention can be preferably administered in an oral dosage form because of their high oral absorbability.

A pharmaceutical composition can be formulated by mixing various additive agents for medicaments, if needed, such as excipients, binders, disintegrating agents, and lubricants which are suitable for the formulations with an effective amount of the compound of the present invention.

The dosage of a pharmaceutical composition of the present invention should be determined in consideration of the patient's age and body weight, the type and degree of diseases, the administration route and the like. The usual oral dosage for adults is in the range of 0.05 to 100 mg/kg/day and preferable is 0.1 to 10 mg/kg/day. For parenteral administration, the dosage highly varies with administration routes and the usual dosage is in the range of 0.005 to 10 mg/kg/day and preferably 0.01 to 1 mg/kg/day. The dosage may be administered once or several times per day.

The compound of the present invention can be used in combination with other drugs for treating Alzheimer's disease, dementia of the Alzheimer's type or the like such as acetylcholinesterase inhibitor (hereinafter referred to as a concomitant medicament) for the purpose of enforcement of the activity of the compound or reduction of the amount of medication of the compound or the like. In this case, timing of administration of the compound of the present invention and the concomitant medicament is not limited and these may be administered to the subject simultaneously or at regular intervals. Furthermore, the compound of the present invention and concomitant medicament may be administered as two different compositions containing each active ingredient or as a single composition containing both active ingredient.

The dose of the concomitant medicament can be suitably selected on the basis of the dose used on clinical. Moreover, the mix ratio of the compound of the present invention and a concomitant medicament can be suitably selected in consideration of the subject of administration, administration route, target diseases, symptoms, combinations, etc. For example, when the subject of administration is human, the concomitant medicament can be used in the range of 0.01 to 100 parts by weight relative to 1 part by weight of the compounds of the present invention.

Examples of a concomitant medicament are Donepezil hydrochloride, Tacrine, Galanthamine, Rivastigmine, Zanapezil, Memantine and Vinpocetine.

EXAMPLE

Following examples and test examples illustrate the present invention in more detail, but the present invention is not limited by these examples.

In examples, the meaning of each abbreviation is as follows:
Me methyl
Boc tert-butoxycarbonyl
Bz benzoyl
t-Bu tert-butyl
TFA trifluoroacetic acid
DMF N,N-dimethylformamide
DMAP 4-dimethylaminopyridine
DMSO dimethylsulfoxide
m-CPBA meta-chloroperbenzoic acid
EDC 1-ethyl-3-(3-dimethylaminopropyl)carbodiimide
HOBt 1-hydroxybenzotriazole
TIPS triisopropylsilyl
TBAF tetrabutylammonium fluoride
LDA lithium diisopropylamide $^1$H NMR spectra were recorded on Bruker Advance 400 MHz spectrometer with chemical shift reported relative to tetramethylsilane or the residual solvent peak (CDCl$_3$=7.26 ppm, DMSO-d$_6$=2.50 ppm).

Analytical LC/MS (ESI positive or negative, retention time (RT)) data were recorded on Shimadzu UFLC or Waters UPLC system under the following conditions:
Column: Shim-pack XR-ODS (2.2 μm, i.d. 50×3.0 mm) (Shimadzu)
Flow rate: 1.6 mL/min
Column oven: 50° C.
UV detection wavelength: 254 nm
Mobile phase: [A] 0.1% formic acid-containing aqueous solution; [B] 0.1% formic acid-containing acetonitrile solution
Gradient: linear gradient from 10% to 100% solvent [B] for 3 minutes and 100% solvent [B] for 1 minute Example 1

Synthesis of Compound (I-10

[Chemical Formula 90]

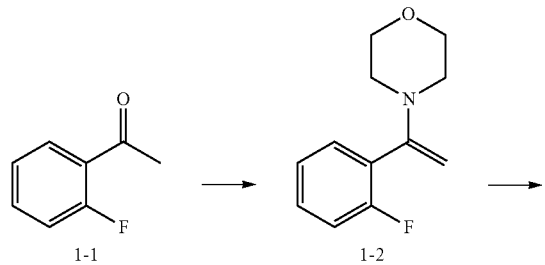

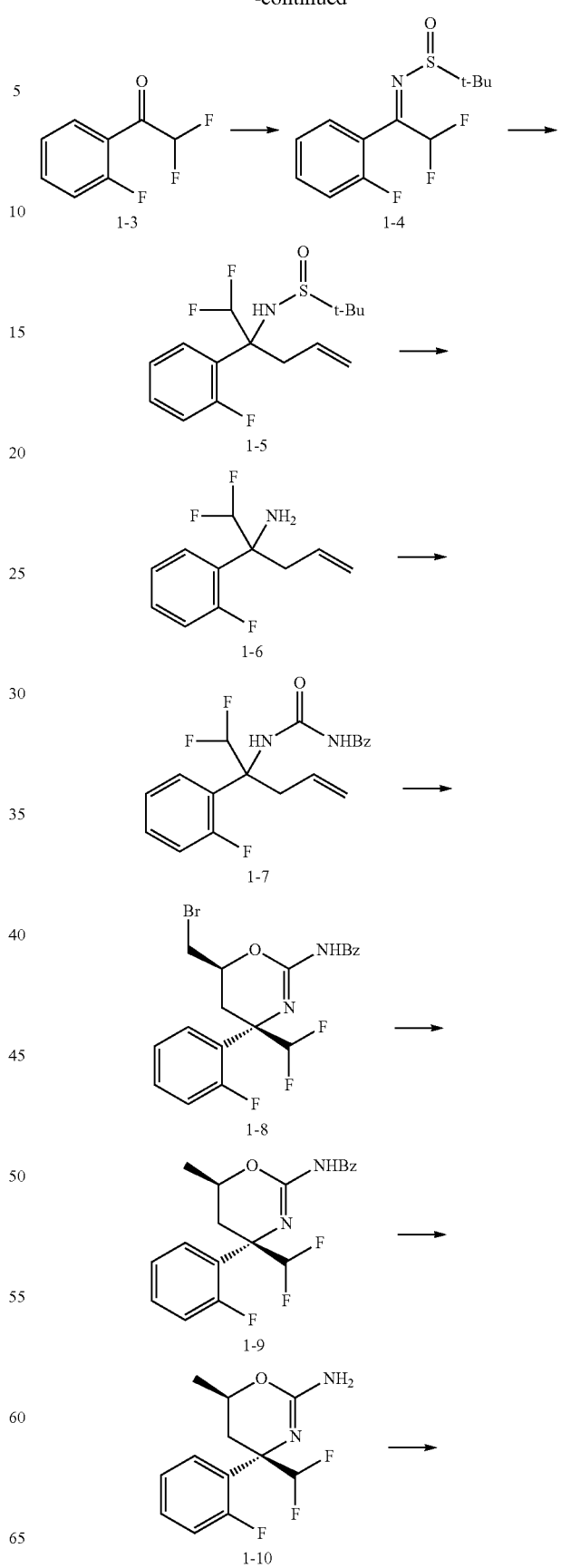

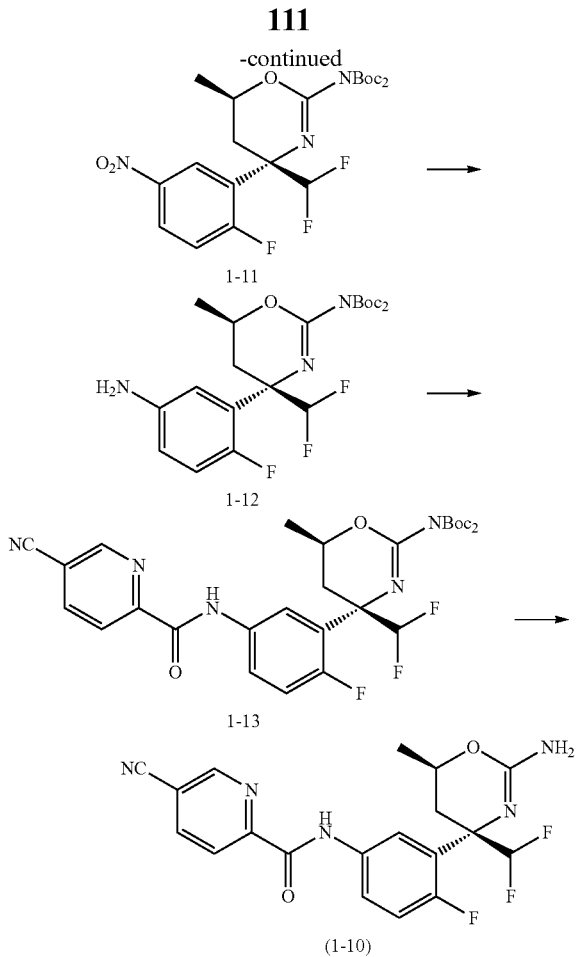

Step 1: Synthesis of Compound 1-2

A solution of compound 1-1 (25 g, 181 mmol) in toluene (500 mL) was cooled to −43° C. with dry ice-acetone bath under nitrogen atmosphere. To the solution was added morpholine (63.1 mL, 724 mmol), and the mixture was warmed to room temperature over 30 minutes. The solution was stirred for 6 hours at room temperature. The reaction solution was filtered with Celite and the filtrate was evaporated under reduced pressure to give compound 1-2 (37.5 g, 100% yield).

$^1$H-NMR (CDCl$_3$) δ: 2.84 (t, J=4.5 Hz, 1H), 3.74 (t, J=4.5 Hz, 1H), 4.24 (s, 1H), 4.32 (s, 1H), 7.05 (t, J=9.3 Hz, 1H), 7.12 (t, J=7.5 Hz, 1H), 7.26-7.31 (m, 1H), 7.38 (t, J=7.5 Hz, 1H).

Step 2: Synthesis of Compound 1-3

To a suspension of molecular sieves 4A (75 g) and Selectfluor (Registered trademark) (13 g, 371 mmol) in acetonitrile (750 mL) was dropwised a solution of compound 1-2 (37.5 g, 181 mmol) in acetonitrile (50 mL) at −40° C. over 25 minutes under nitrogen atmosphere. The mixture was stirred at −32° C. for 18 minutes. The insoluble material was removed by filtration and was washed with acetonitrile. The filtrate was treated with silica gel and was evaporated under reduced pressure. The resulting residue was purified by silica gel chromatography (hexane-ethyl acetate) to give compound 1-3 (1.38 g, 44% yield).

$^1$H-NMR (CDCl$_3$) δ: 6.45 (td, J=53.3, 2.2 Hz, 1H), 7.22 (t, J=9.8 Hz, 1H), 7.33 (t, J=7.6 Hz, 1H), 7.67 (dd, J=13.7, 7.1 Hz, 1H), 7.97 (t, J=7.4 Hz, 1H).

Step 3: Synthesis of Compound 1-4

To a solution of compound 1-3 (10 g, 57.4 mmol) in toluene (50 mL) were added ethyl orthotitanate (20.4 mL, 98 mmol) and t-butylsulfinamide (8.35 g, 68.9 mmol) under nitrogen atmosphere, and the mixture was stirred at 80° C. for 30 minutes. The reaction mixture was treated with acetonitrile (200 mL) and water (7.1 mL) at room temperature, and the mixture was stirred for 5 minutes. The insoluble material was filtered-off and was washed with acetonitrile. The filtrate was evaporated under reduced pressure and the residue was purified by silica gel column chromatography (hexane-ethyl acetate) to give compound 1-4 (6.0 g, 38% yield).

$^1$H-NMR (CDCl$_3$) δ: 6.25 (t, J=55.0, 1H), 7.14 (t, J=9.0 Hz, 1H), 7.21 (t, J=7.5 Hz, 1H), 7.38 (s, 1H), 7.47 (dd, J=13.9, 7.3 Hz, 1H).

Step 4: Synthesis of Compound 1-5

Allyl magnesium bromide (1 mmol/L diethyl ether solution, 29 mL, 29 mmol) was cooled to −40° C. with dry ice-acetone bath under nitrogen atmosphere. To the mixture was added dropwise a solution of compound 1-4 (2.68 g, 9.67 mmol) in diethyl ether (11 mL), and the mixture was stirred at −40° C. for 30 minutes. An aqueous solution of ammonium chloride was added and the mixture was warmed to room temperature. The aqueous layer was and extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 1-5 (2.84 g, 92%, a diastereomer ratio of 3:2).

MS: m/z=320.15 [M+H]+.

Step 5: Synthesis of Compound 1-6

To a solution of compound 1-5 (2.84 g, 8.89 mmol) in methanol (28 mL) was added hydrochloric acid (4 mmol/L 1,4-dioxane solution, 3.33 mL, 13.34 mmol), and the mixture was stirred at room temperature for 1 hour. To the mixture were added ethyl acetate and water, and the organic layer was washed with an aqueous hydrochloric acid solution (2 mmol/L). The aqueous layer was made alkaline with an aqueous sodium hydroxide solution (2 mmol/L), and the aqueous layer was extracted with ethyl acetate. The organic layer was washed with brine and dried over anhydrous sodium sulfate. The solvent was evaporated under reduced pressure to give compound 1-6 (1.76 g, 91% yield).

$^1$H-NMR (CDCl$_3$) δ: 2.46 (dd, J=14.1, 7.5 Hz, 1H), 2.87 (dd, J=14.1, 7.0 Hz), 5.02 (d, J=10.2 Hz, 1H), 5.07 (d, J=17.1 Hz, 1H), 5.47-5.57 (m, 1H), 6.25 (t, J=57.3 Hz, 1H), 7.05 (dd, J=12.5, 8.2 Hz, 1H), 7.18 (t, J=7.5 Hz, 1H), 7.32 (dd, J=13.4, 7.1 Hz, 1H), 7.64 (d, J=8.0 Hz, 1H).

Step 6: Synthesis of Compound 1-7

To a solution of compound 1-6 (765 mg, 3.55 mmol) in tetrahydrofuran (15 ml) was added benzoylisocyanate (0.52 mL, 3.73 mmol) under nitrogen atmosphere, and the mixture was stirred at room temperature for 2.5 hours. The solvent was evaporated under reduced pressure, and the residue was purified by silica gel chromatography (hexane-ethyl acetate) to give compound 1-7 (1.22 g, 95% yield).

$^1$H-NMR (CDCl$_3$) δ: 3.08-3.20 (m, 2H), 5.19 (d, J=10.0 Hz, 1H), 5.27 (d, J=17.1 Hz, 1H), 5.74-5.84 (m, 1H), 6.60 (t, J=56.0 Hz, 1H), 7.09 (dd, J=12.7, 8.2 Hz, 1H), 7.17 (t, J=7.7 Hz, 1H), 7.33 (dd, J=12.8, 7.5 Hz, 1H), 7.45 (t, J=7.4 Hz, 3H), 7.60 (t, J=7.5 Hz, 1H), 7.86 (d, J=8.0 Hz, 2H), 8.73 (s, 1H), 9.58 (s, 1H).

Step 7: Synthesis of Compound 1-8

To a solution of Compound 1-7 (1.67 g, 4.61 mmol) in tetrahydrofuran (33 mL) was added N-bromosuccinimide (0.98 g, 5.53 mmol) under nitrogen atmosphere, and the mixture was stirred at room temperature for 3 hours. To the mixture was added an aqueous saturated sodium thiosulfate solution and the aqueous layer was extracted with ethyl acetate. The organic layer was washed with brine and dried over anhydrous sodium sulfate. The residue was purified by silica gel chromatography (hexane-ethyl acetate) to give compound 1-8 (1.86 g, 92% yield).

$^1$H-NMR (CDCl$_3$) δ: 2.40 (t, J=12.9 Hz, 1H), 2.98 (d, J=14.1 Hz, 1H), 3.56 (dd, J=10.8, 6.5 Hz, 1H), 3.63 (dd, J=10.8 Hz, 3.9 Hz, 1H), 4.22-4.24 (m, 1H), 6.36 (t, J=55.0 Hz, 1H), 7.20 (dd, J=12.2, 8.4 Hz, 1H), 7.29 (d, J=7.5 Hz, 1H), 7.42-7.54 (m, 5H), 8.27 (d, J=7.8 Hz, 2H).

Step 8: Synthesis of Compound 1-9

To a solution of compound 1-8 (0.75 g, 1.70 mmol) in toluene (10 mL) were added azobisisobutyronitrile (0.14 g, 0.850 mmol) and tributyltin hydride (1.37 mL, 5.10 mmol) under nitrogen atmosphere, and the mixture was stirred at 80° C. for 4.5 hours. After the mixture was cooled to room temperature, tributyltin hydride (1.37 mL, 5.10 mmol) was added to the reaction mixture, which was then stirred at 80° C. for 1 hour. After cooling to room temperature, the reaction mixture was evaporated under reduced pressure, and the residue was purified by silica gel chromatography (hexane-ethyl acetate) to give compound 1-9 (0.43 g, 70% yield).

$^1$H-NMR (CDCl$_3$) δ: 1.48 (d, J=6.0 Hz, 3H), 2.26 (t, J=12.9 Hz, 1H), 2.68 (d, J=13.8 Hz, 1H), 4.15-4.22 (m, 1H), 6.35 (t, J=55.2 Hz, 1H), 7.17 (dd, J=12.3, 8.3 Hz, 1H), 7.25-7.29 (m, 1H), 7.41-7.55 (m, 5H), 8.28 (d, J=8.0 Hz, 2H), 12.3 (s, 1H).

Step 9: Synthesis of Compound 1-10

To a solution of compound 1-9 (0.56 g, 1.55 mmol) in tetrahydrofuran (20 mL) were added di-t-butyl dicarbonate (0.54 mL, 2.32 mmol) and 4-dimethylaminopyridine (18.9 mg, 0.155 mmol) under nitrogen atmosphere, and the mixture was stirred at room temperature for 1.5 hours. To the mixture was added water, and the aqueous layer was extracted with ethyl acetate. The organic layer was washed with brine and dried over anhydrous sodium sulfate. The solvent was evaporated under reduced pressure, and the residue was dissolved in tetrahydrofuran (5 mL), methanol (5 mL), and water (5 mL) and was then added potassium carbonate (0.64 g, 4.64 mmol). The mixture was stirred at room temperature for 21.5 hours and then at 50° C. for 5 hours. The mixture was cooled to room temperature and the aqueous layer was extracted with ethyl acetate. The organic layer was washed with brine and dried over anhydrous sodium sulfate. The extract was evaporated under reduced pressure and was dissolved in dichloromethane (15 mL). To the mixture was added trifluoroacetic acid (1.79 mL, 23.2 mmol) and the mixture was stirred at room temperature for 4.5 hours. The mixture was treated with an aqueous saturated potassium carbonate solution. The aqueous layer was extracted with dichloromethane, and the organic layer was dried over anhydrous sodium sulfate. The solvent was evaporated under reduced pressure, and the residue was purified by silica gel chromatography (hexane-ethyl acetate) to give compound 1-10 (328 mg, 82% yield).

$^1$H-NMR (CDCl$_3$) δ: 1.26 (d, J=6.0 Hz, 3H), 1.83 (t, J=12.8 Hz, 1H), 2.53 (d, J=13.6 Hz, 1H), 3.81-3.88 (m, 1H), 4.41 (s, 2H), 6.09 (t, J=56.3 Hz, 1H), 7.04 (dd, J=12.4, 8.2 Hz, 1H), 7.17 (t, J=7.5 Hz, 1H), 7.31 (dd, J=13.2, 7.2 Hz, 1H), 7.59 (t, J=8.0 Hz, 1H).

Step 10: Synthesis of Compound 1-11

To a solution of compound 1-10 (328 mg, 1.27 mmol) in trifluoroacetic acid (2 mL) was added concentrated sulfuric acid (0.5 mL) and cooled to −25° C. with dry ice-acetone bath. To the mixture was added concentrated nitric acid (0.12 mL, 1.91 mmol), and the mixture was stirred at −20° C. for 30 minutes. The reaction mixture was poured into a mixture of crushed ice and an aqueous sodium hydroxide solution (2 mmol/L), and the aqueous layer was extracted with ethyl acetate. The organic layer was washed with brine and dried over anhydrous sodium sulfate. The extract was evaporated under reduced pressure, and the residue was dissolved in dichloromethane (12 mL). To the mixture were added di-tert-butyl dicarbonate (0.886 mL, 3.82 mmol) and 4-dimethylaminopyridine (31.1 mg, 0.155 mmol), and the mixture was stirred at room temperature for 2.5 hours. To the mixture was added water, and the aqueous layer was extracted with ethyl acetate. The organic layer was washed with brine and dried over anhydrous sodium sulfate. The extract was evaporated under reduced pressure, and the residue was purified by silica gel chromatography (hexane-ethyl acetate) to give 1-10 (604 mg, 94% yield).

$^1$H-NMR (CDCl$_3$) δ: 1.39 (d, J=6.1 Hz, 3H), 1.51 (s, 18H), 2.01 (t, J=13.2 Hz, 1H), 2.73 (d, J=14.2 Hz, 1H), 4.03-4.06 (m, 1H), 6.02 (t, J=55.6 Hz, 1H), 7.24-7.29 (m, 1H), 8.26-8.28 (m, 1H), 8.65-8.66 (m, 1H).

Step 11: Synthesis of Compound 1-12

To a solution of compound 1-11 (604 mg, 1.20 mmol) in ethanol (6 mL) and tetrahydrofuran (3 mL) were added an aqueous sodium chloride solution (770 mg, 14.4 mmol) in water (3 mL) and iron powder (536 mg, 9.60 mmol), and the mixture was stirred at 60° C. for 2 hours. After the mixture was cooled to room temperature, celite and ethyl acetate were added, and the mixture was stirred for 5 minutes. The insoluble material was removed by filtration and was washed with ethyl acetate. The filtrate was extracted with ethyl acetate, and the organic layer was washed with brine and dried over anhydrous sodium sulfate. The solvent was evaporated under reduced pressure, and the residue was purified by silica gel chromatography (hexane-ethyl acetate) to give compound 1-12 (414 mg, 73% yield).

$^1$H-NMR (CDCl$_3$) δ: 1.35 (d, J=6.3 Hz, 3H), 1.51 (s, 18H), 1.88 (t, J=12.9 Hz, 1H), 2.62 (d, J=13.6 Hz, 1H), 3.57 (s, 1H), 4.06-4.12 (m, 1H), 6.12 (t, J=55.7 Hz, 1H), 6.57-6.60 (m, 1H), 6.86 (dd, J=11.8, 8.8 Hz, 1H), 6.94 (dd, J=6.4, 2.4 Hz, 1H).

Step 12: Synthesis of Compound 1-13

To a solution of compound 1-12 (34.0 mg, 0.072 mmol) in dimethylformamide (1 mL) were added ethyldiisopropylamine (0.025 mL, 0.144 mmol), HATU (32.8 mg, 0.086 mmol), and 5-cyanopicolinic acid (14.3 mg, 0.086 mmol), and the mixture was stirred at room temperature for 2 hours. To the mixture was added water, and the aqueous layer was extracted with ethyl acetate. The organic layer was washed with brine and dried over anhydrous sodium sulfate. The solvent was evaporated under reduced pressure, and the residue was purified by silica gel chromatography (hexane-ethyl acetate) to give compound 1-13 (36.8 mg, 85% yield).

$^1$H-NMR (CDCl$_3$) δ: 1.37 (d, J=6.3 Hz, 3H), 1.55 (s, 18H), 1.94 (t, 12.9 Hz, 1H), 2.64 (d, 13.8 Hz, 1H), 4.05-4.15 (m, 1H), 6.17 (t, J=55.6 Hz, 1H), 7.15 (t, J=10.2 Hz, 1H), 7.62 (d, J=6.3 Hz, 1H), 8.21 (d, J=8.0 Hz, 1H), 8.40-8.44 (m, 2H), 8.80 (s, 1H), 9.99 (s, 1H).

Step 13: Synthesis of Compound (I-10)

To compound 1-13 (36.8 mg, 0.061 mmol) was added formic acid (0.23 mL, 6.10 mmol), and the mixture was stirred at room temperature for 2 hours. The reaction mixture was made alkaline with an aqueous sodium carbonate solution, and the aqueous layer was extracted with ethyl acetate. The organic layer was washed with brine and dried over anhydrous sodium sulfate. The solvent was evaporated under reduced pressure, and the residue was washed with diethyl ether and dichloromethane to give compound (I-10) (13.7 mg, 56%)

¹H-NMR (CDCl₃) δ: 1.29 (d, J=4.9 Hz, 3H), 1.87 (t, J=12.8 Hz, 1H), 2.58 (d, J=13.6 Hz, 1H), 3.89-3.94 (m, 1H), 4.36 (s, 1H), 6.06 (t, J=56.0 Hz, 1H), 7.12 (dd, J=10.9, 9.2 Hz, 1H), 7.61 (d, J=6.3 Hz, 1H), 8.10-8.13 (m, 1H), 8.20 (d, J=8.0 Hz, 1H), 8.42 (d, J=8.0 Hz, 1H), 8.90 (s, 1H), 9.89 (s, 1H).

Example 2

Synthesis of Compound I-13

[Chemical Formula 91]

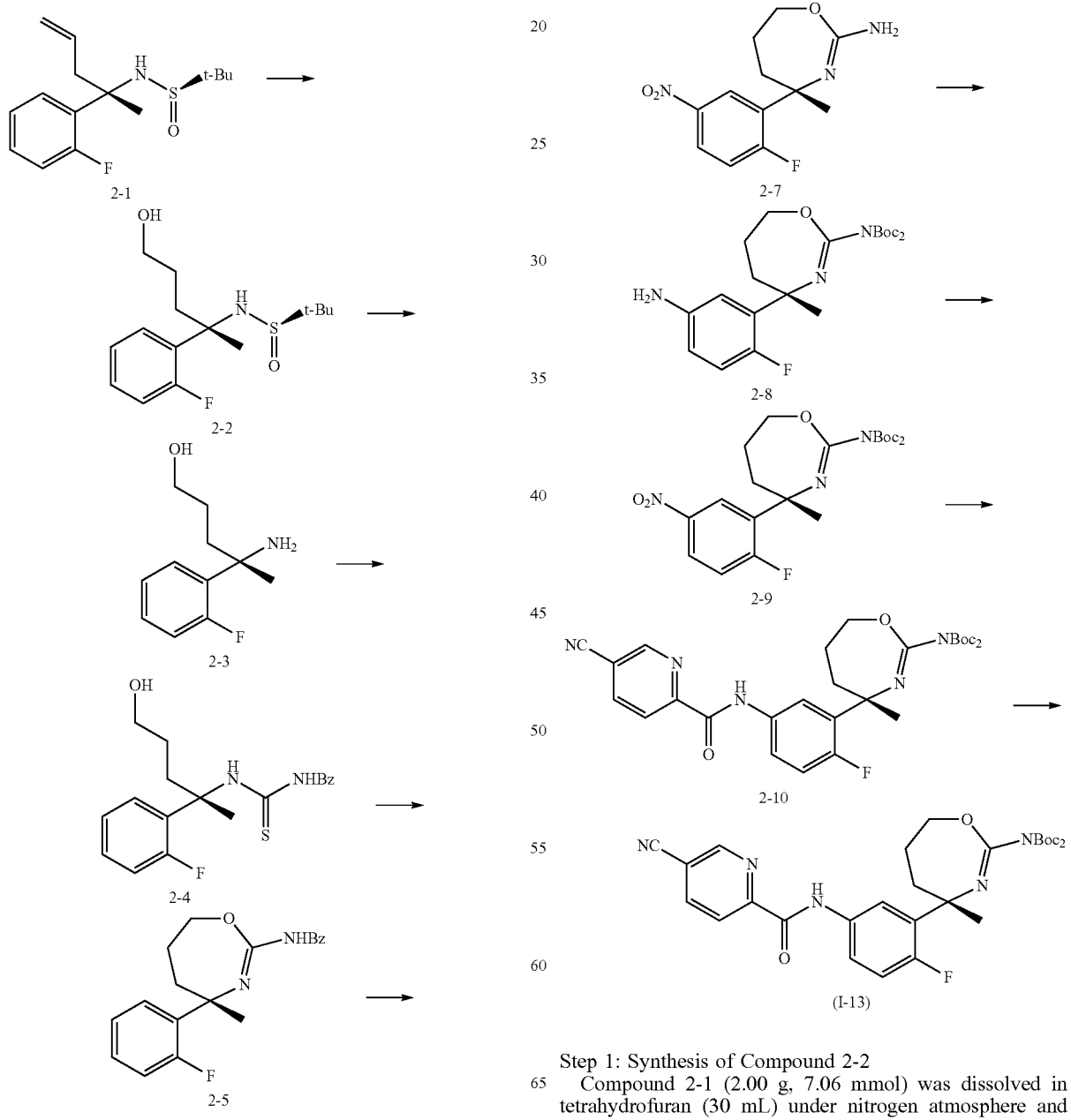

Step 1: Synthesis of Compound 2-2

Compound 2-1 (2.00 g, 7.06 mmol) was dissolved in tetrahydrofuran (30 mL) under nitrogen atmosphere and cooled at 0° C. To the mixture was added borane-tetrahydrofuran complex (1 mol/L tetrahydrofuran solution, 17.6 mL, 17.6 mmol), and the mixture was stirred at room temperature for 1 hour. After the solution was cooled to 0° C., sodium hydroxide (2 mol/L, 17.6 mL, 35.5 mmol) and aqueous hydrogen peroxide (30%, 10.81 mL, 106 mmol) were added. The mixture was stirred at room temperature for 1 hour and was then added an aqueous ammonium chloride solution (20 mL). The aqueous layer was extracted with ethyl acetate. The organic layer was washed with brine and dried over anhydrous sodium sulfate. The solvent was evaporated under reduced pressure, and the residue was purified by silica gel chromatography (hexane-ethyl acetate) to give compound 2-2 (1.6 g, 75% yield).

$^1$H-NMR (CDCl$_3$) δ: 1.23 (s, 9H), 1.37 (m, 1H), 1.55 (m, 1H), 1.65 (m, 2H), 1.79 (s, 3H), 2.25 (m, 2H), 3.61 (t, J=8 Hz, 2H), 4.13 (m, 1H), 7.04 (dd, J=12, 8 Hz, 1H), 7.13 (d, J=8 Hz, 1H), 7.22 (m, 1H), 7.39 (d, J=8 Hz, 1H).

Step 2: Synthesis of Compound 2-3

Compound 2-2 (6.16 g, 20.4 mmol) was dissolved in dioxane (50 mL) and cooled to 0° C. To the mixture was added hydrochloric acid (4 mol/L dioxane solution, 7.66 mL, 30.7 mmol), and the mixture was stirred at room temperature for 3 hours. The reaction solution was neutralized with a saturated aqueous sodium bicarbonate solution, and the aqueous layer was extracted with ethyl acetate. The organic layer was washed with brine and dried over anhydrous sodium sulfate. The solvent was evaporated under reduced pressure to give compound 2-3 (4.03 g, 100% yield).

$^1$H-NMR (CDCl$_3$) δ: 1.47 (m, 1H), 1.58 (m, 1H), 1.59 (s, 3H), 1.85 (m, 2H), 2.12 (m, 2H), 3.62 (m, 2H), 7.04 (dd, J=12, 8 Hz, 1H), 7.12 (t, J=8 Hz, 1H), 7.23 (m, 1H), 7.39 (t, J=8 Hz, 1H).

Step 3: Synthesis of Compound 2-4

To a solution of compound 2-3 (4.03 g, 20.4 mmol) in dichloromethane (60 mL) was added benzoyl isocyanate (2.76 mL, 20.43 mmol), and the mixture was stirred at room temperature for 1 hour. To the reaction solution was added a saturated aqueous sodium bicarbonate solution (40 mL), and the aqueous layer was extracted with ethyl acetate. The organic layer was washed with brine and dried over anhydrous sodium sulfate. The solvent was evaporated under reduced pressure, and the residue was purified by silica gel chromatography (hexane-ethyl acetate) to give compound 2-4 (4.84 g, 66% yield).

$^1$H-NMR (CDCl$_3$) δ: 1.38 (m, 1H), 1.64 (m, 1H), 2.03 (s, 3H), 2.19 (m, 1H), 2.51 (m, 1H), 3.69 (m, 2H), 7.02 (dd, J=12, 8 Hz, 1H), 7.14 (t, J=8 Hz, 1H), 7.26 (m, 1H), 7.38 (t, J=8 Hz), 7.52 (t, J=8 Hz, 2H), 7.62 (t, J=8 Hz, 1H), 7.85 (d, J=8 Hz, 2H), 8.80 (s, 1H), 11.39 (2, 1H).

Step 4: Synthesis of Compound 2-5

To a solution of compound 2-4 (4.84 g, 13.43 mmol) in acetonitrile (50 mL) and DMF (5 mL) was added EDC (3.09 g, 16.11 mmol), and the mixture was stirred at room temperature for 20 hours. To the reaction solution was added a saturated aqueous sodium bicarbonate solution (40 mL), and the aqueous layer was extracted with ethyl acetate. The organic layer was washed with brine and dried over anhydrous sodium sulfate. The solvent was evaporated under reduced pressure, and the residue was purified by silica gel chromatography (hexane-ethyl acetate) to give compound 2-5 (3.98 g, 91% yield).

$^1$H-NMR (CDCl$_3$) δ: 1.71 (m, 1H), 1.76 (s, 3H), 2.09 (m, 1H), 2.18 (m, 1H), 2.84 (m, 1H), 4.13 (m, 1H), 4.28 (m, 1H), 7.09 (dd, J=12, 8 Hz, 1H), 7.18 (t, J=8 Hz, 1H), 7.30 (m, 1H), 7.42-7.53 (m, 4H), 8.26 (d, J=8 Hz, 2H), 11.64 (m, 1H).

Step 5: Synthesis of Compound 2-6

To a solution of compound 2-5 (1.963 g, 6.01 mmol) in tetrahydrofuran (40 mL) were added Boc$_2$O (2.095 mL, 9.02 mmol) and DMAP (0.147 g, 1.203 mmol), and the mixture was stirred at room temperature for 20 hours. To the reaction solution was added a saturated aqueous sodium bicarbonate solution (20 mL), and the aqueous layer was extracted with ethyl acetate. The organic layer was washed with brine and dried over anhydrous sodium sulfate. The solvent was evaporated under reduced pressure. The resulting residue was dissolved in tetrahydrofuran/methanol/water (28 mL, 3:3:1) and was added potassium carbonate (2.50 g, 18.0 mmol). The mixture was stirred at room temperature for 24 hours. To the reaction mixture was added water (20 mL), and the aqueous layer was extracted with ethyl acetate. The organic layer was washed with brine and dried over anhydrous sodium sulfate. The solvent was evaporated under reduced pressure, and the residue was purified by silica gel chromatography (hexane-ethyl acetate) to give compound 2-6 (1.81 g, 93% yield).

$^1$H-NMR (CDCl$_3$) δ: 1.52 (s, 9H), 1.65 (m, 1H), 1.69 (m, 1H), 1.88 (m, 1H), 2.01 (m, 1H), 2.80 (m, 1H), 3.96 (m, 1H), 4.18 (m, 1H), 7.06 (dd, J=12, 8 Hz, 1H), 7.15 (t, J=8 Hz, 1H), 7.30 (m, 1H), 7.35 (d, J=8 Hz, 1H), 9.83 (m, 1H).

Step 6: Synthesis of Compound 2-7

To a solution of compound 2-6 (1.812 g, 5.62 mmol) in dichloromethane (9 mL) was added trifluoroacetic acid (2.2 mL, 28.6 mmol), and the mixture was stirred at room temperature for 1 hour. To the reaction mixture was added a saturated aqueous sodium bicarbonate solution, and the aqueous layer was extracted with ethyl acetate. The organic layer was washed with brine, dried over anhydrous sodium sulfate, and evaporated under reduced pressure. The residue was dissolved in trifluoroacetic acid and cooled to −20° C. To the solution were added concentrated sulfuric acid (1.529 mL, 28.7 mmol) and nitric acid (0.308 mL, 6.88 mmol), and the mixture was stirred at 0° C. for 2 hours. To the reaction solution was added ice-water, and this was neutralized with sodium hydroxide (1 mol/L). The aqueous layer was extracted with ethyl acetate, and the organic layer was washed with brine and dried over anhydrous sodium sulfate. The solvent was evaporated under reduced pressure, and the residue was purified by silica gel chromatography (hexane-ethyl acetate) to give compound 2-7 (1.23 g, 87% yield).

$^1$H-NMR (CDCl$_3$) δ: 1.74 (m, 1H), 1.81 (s, 3H), 2.09-2.21 (m, 2H), 2.85 (m, 2H), 4.23-4.35 (m, 2H), 7.30 (d, J=8 Hz, 1H), 8.25 (m, 1H), 8.37 (m, 1H).

Step 7: Synthesis of Compound 2-8

To a solution of compound 2-7 (1.23 g, 4.59 mmol) in tetrahydrofuran (20 mL) were added Boc$_2$O (3.2 mL, 13.77 mmol) and 4-dimethylaminopyridine (56 mg, 0.459 mmol), and the mixture was stirred at room temperature for 20 hours. The reaction solution was concentrated, and the resulting residue was purified by silica gel chromatography (hexane-ethyl acetate) to give compound 2-8 (884 mg, 41% yield).

$^1$H-NMR (CDCl$_3$) δ: 1.54 (s, 18H), 1.62 (s, 3H), 1.66 (m, 1H), 2.21 (m, 2H), 2.42 (m, 1H), 3.99 (m, 1H), 4.15 (m, 1H), 7.18 (t, J=8 Hz, 1H), 8.16 (m, 1H), 8.71 (m, 1H).

Step 8: Synthesis of Compound 2-9

A suspension of compound 2-8 (837 mg, 1.79 mmol) palladium-carbon (80 mg) in methanol (15 mL) was stirred at room temperature for 2 hours under hydrogen atmosphere. The mixture was filtered through Celite, and the filtrate was evaporated under reduced pressure to give compound 2-9 (680 mg, 87% yield).

$^1$H-NMR (CDCl$_3$) δ: 1.54 (s, 18H), 1.60 (s, 3H), 1.61 (m, 1H), 2.10 (m, 1H), 2.33 (m, 1H), 2.42 (m, 1H), 4.00 (m, 1H), 4.17 (m, 1H), 6.50 (m, 1H), 6.82 (t, J=8 Hz, 1H), 6.95 (m, 1H).

Step 9: Synthesis of Compound 2-10

To a solution of compound 2-9 (330 mg, 0.75 mmol) in dimethylformamide (3 mL) were added 5-cyanopicolinic acid monohydrate (125 mg, 0.75 mmol), HATU (287 mg, 0.75 mmol), and triethylamine (0.136 mL, 0.98 mmol), and the mixture was stirred at room temperature for 20 hours. To the reaction mixture was added water, and the aqueous layer was extracted with ethyl acetate. The organic layer was washed with brine and dried over anhydrous sodium sulfate. The solvent was evaporated under reduced pressure, and the residue was purified by silica gel chromatography (hexane-ethyl acetate) to give compound 2-10 (400 mg, 93% yield).

$^1$H-NMR (CDCl$_3$) δ: 1.55 (s, 18H), 1.59 (s, 3H), 1.67 (m, 1H), 2.18 (m, 1H), 2.41 (m, 2H), 4.10 (m, 2H), 7.10 (m, 1H), 7.61 (m, 1H), 8.22 (m, 1H), 8.24 (m, 1H), 8.43 (d, J=8 Hz), 8.84 (s, 1H). 9.90 (s, 1H).

Step 10: Synthesis of Compound I-13

To a solution of compound 10 (400 mg, 0.71 mmol) in formic acid (2 mL) was added trifluoroacetic acid (0.5 mL), and the mixture was stirred at room temperature for 3 hours. The reaction solution was neutralized with an aqueous sodium bicarbonate solution, and the aqueous layer was extracted with ethyl acetate. The organic layer was washed with brine and dried over anhydrous sodium sulfate. The solvent was evaporated under reduced pressure and the residue was purified by silica gel chromatography (hexane-ethyl acetate) to give compound I-13 (230 mg, 89% yield).

$^1$H-NMR (CDCl$_3$) δ: 1.70 (m, 1H), 1.79 (s, 3H), 2.09 (m, 2H), 2.90 (m, 1H), 4.23 (m, 1H), 4.40 (m, 1H), 6.01 (m, 1H), 7.13 (t, J=4 Hz, 1H), 7.71 (d, J=4 Hz, 1H), 7.87 (m, 1H), 8.19 (d, J=4 Hz, 1H), 8.38 (d, J=4 Hz, 1H), 9.98 (s, 1H), 11.46 (m, 2H).

Example 3

Synthesis of Compound I-16

[Chemical Formula 92]

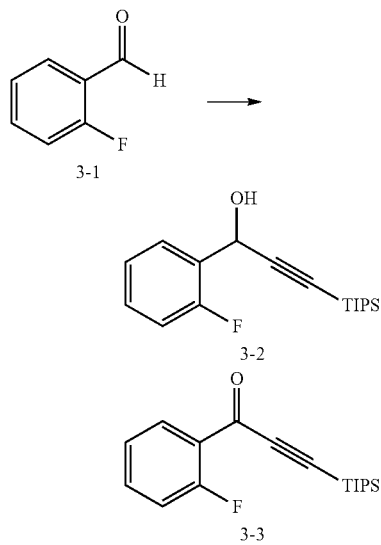

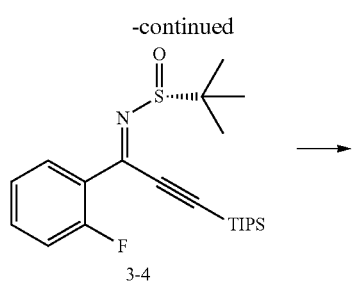

3-4

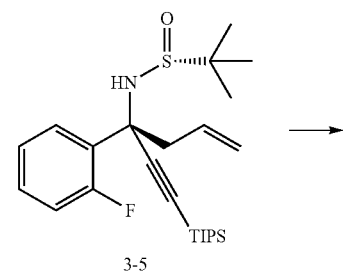

3-5

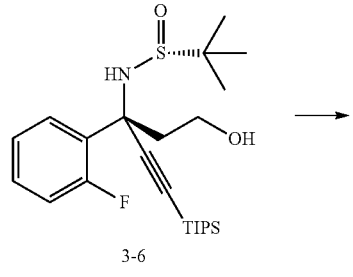

3-6

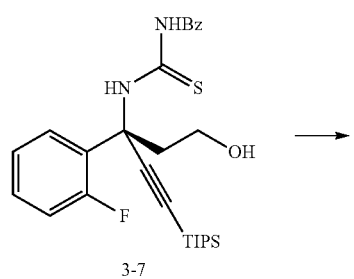

3-7

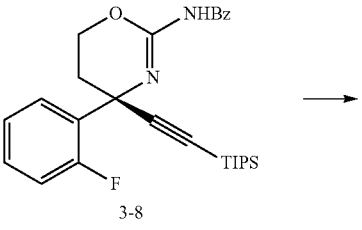

3-8

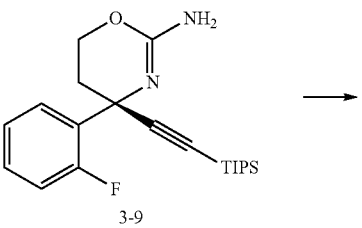

3-9

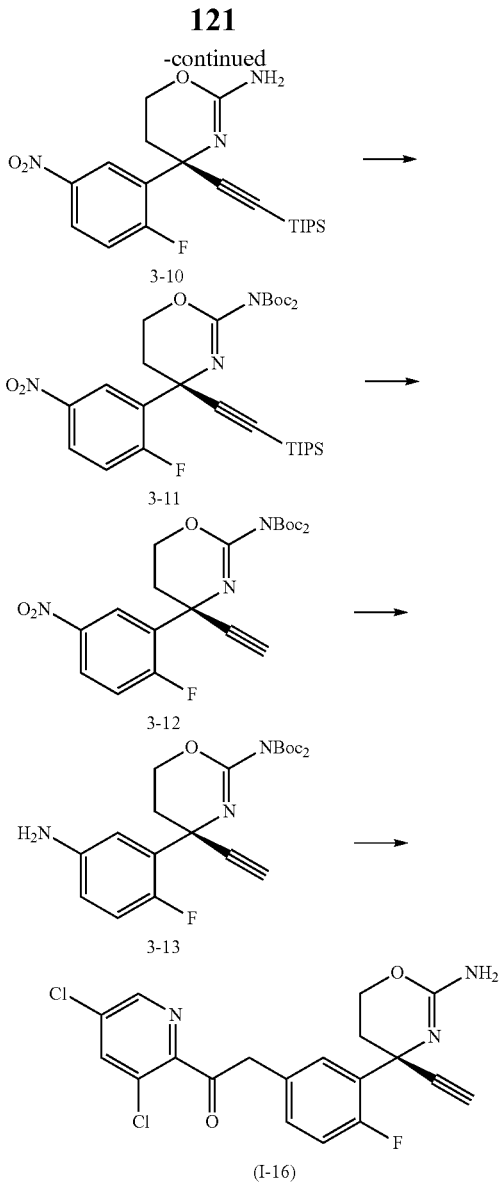

Step 1: Synthesis of Compound 3-2

A solution of ethynyltriisopropyl silane (1176 mg, 6.45 mmol) in tetrahydrofuran (4.7 mL) was cooled to −78° C. with dry ice-acetone bath under nitrogen atmosphere. To the solution was added dropwise 3 mol/L of isopropylmagnesium chloride-lithium chloride-tetrahydrofuran solution (4.46 mL, 5.80 mmol), and the mixture was stirred at 0° C. for 1 hour. The solution was cooled to −78° C. and then added compound 3-1 (400 mg, 3.22 mmol) in tetrahydrofuran (2.8 mL). The solution was stirred at room temperature for 1 hour, and saturated aqueous ammonium chloride (2 mL) was added at 0° C. The mixture was diluted with water, and the aqueous layer was extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 3-2 (931 mg, 94% yield).

$^1$H-NMR (400 MHz, CDCl$_3$) δ: 7.70 (td, J=7.7, 1.9 Hz, 1H), 7.32 (tdd, J=7.7, 5.5, 1.9 Hz, 1H), 7.18 (t, J=7.7 Hz, 1H), 7.07 (t, J=9.3 Hz, 1H), 5.77 (d, J=6.3 Hz, 1H), 2.27 (d, J=6.3 Hz, 1H), 1.08 (s, 21H).

Step 2: Synthesis of Compound 3-3

To a solution of compound 3-2 (930 mg, 3.03 mmol) in ethyl acetate (10 mL) was added 2-iodoxy benzoic acid (1699 mg, 6.07 mmol). The mixture was refluxed for 14 hours and was then stirred at room temperature for 30 minutes. The insoluble material was removed by filtration and washed with ethyl acetate. The filtrate was evaporated under reduced pressure to give compound 3-3 (924 mg, 100% yield).

$^1$H-NMR (400 MHz, CDCl$_3$) δ: 8.07 (t, J=7.7 Hz, 1H), 7.57 (dd, J=13.3, 7.0 Hz, 1H), 7.25-7.23 (m, 1H), 7.15 (t, J=9.6 Hz, 1H), 1.24-0.99 (m, 21H).

Step 3: Synthesis of Compound 3-4

A solution of compound 3-3 (922 mg, 3.03 mmol) in toluene (4.6 ml) was added to titanium ethoxide (1.267 mL, 6.05 mmol) under nitrogen atmosphere. To the mixture was added (R)-(+)-t-butyl sulfinamide (477 mg, 3.93 mmol), and the mixture was stirred at 80° C. for 16 hours. To the mixture were added acetonitrile (18.5 mL) and water (0.382 mL) at room temperature, and the mixture was stirred for 5 minutes. The insoluble material was removed by filtration and was washed with acetonitrile. The filtrate was evaporated under reduced pressure, and the residue was purified by silica gel chromatography (hexane-ethyl acetate) to give compound 3-4 (751 mg, 61% yield).

$^1$H-NMR (400 MHz, CDCl$_3$) δ: 7.96 (td, J=7.7, 1.3 Hz, 1H), 7.51-7.46 (m, 1H), 7.21 (t, J=7.7 Hz, 1H), 7.14 (dd, J=11.0, 8.3 Hz, 1H), 1.31 (s, 9H), 1.24-0.94 (m, 21H).

Step 4: Synthesis of Compound 3-5

To diethyl ether (2 mL) was added a 1 mol/L solution of allyl magnesium bromide-diethyl ether (5.49 mL, 5.49 mmol) under nitrogen atmosphere and cooled to −35° C. with dry ice-acetone. A solution of compound 3-4 (749 mg, 1.83 mmol) in diethyl ether (4.2 mL) was added dropwise at the same temperature, and the mixture was stirred for 14 minutes. An aqueous ammonium chloride solution was added, and the mixture was extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 3-5 (772 mg, 92% yield).

$^1$H-NMR (400 MHz, CDCl$_3$) δ: 7.87 (td, J=8.0, 1.7 Hz, 1H), 7.33-7.28 (m, 4H), 7.14 (td, J=7.6, 1.1 Hz, 1H), 7.04 (dd, J=12.7, 8.0 Hz, 1H), 5.74-5.64 (m, 1H), 5.09 (dd, J=17.1, 1.5 Hz, 1H), 5.03 (d, J=10.3 Hz, 1H), 4.05 (d, J=4.5 Hz, 1H), 3.08 (ddd, J=35.6, 13.4, 7.1 Hz, 2H), 1.32-0.94 (m, 30H).

Step 5: Synthesis of Compound 3-6

A solution of Compound 3-5 (767 mg, 1.67 mmol) in dichloromethane (11.5 mL) was cooled to −78° C. with dry ice-acetone bath under nitrogen atmosphere. A solution was stirred for 35 minutes under ozone atmosphere and then stirred for 40 minutes under nitrogen atmosphere. Triethylamine (1.3 mL, 9.38 mmol) was added dropwise at the same temperature and the mixture was stirred at room temperature for 1 hour. To the mixture was added water, and the aqueous layer was extracted with dichloromethane. The organic layer was dried over anhydrous magnesium sulfate. The solvent was evaporated under reduced pressure, and the residue (728 mg) was dissolved in tetrahydrofuran (10 mL). Sodium borohydride (73.2 mg, 1.94 mmol) was added to the mixture under nitrogen atmosphere. After the addition of methanol (2 mL), the mixture was stirred at room temperature for 1 hour. An aqueous ammonium chloride solution was added, and the aqueous layer was extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 3-6 (475 mg, 65% yield).

$^1$H-NMR (400 MHz, CDCl$_3$) δ: 7.83 (td, J=8.2, 1.7 Hz, 1H), 7.33-7.28 (m, 1H), 7.14 (td, J=7.6, 1.1 Hz, 1H), 7.06 (ddd, J=12.4, 8.2, 1.1 Hz, 1H), 4.73 (d, J=2.5 Hz, 1H), 4.27 (t, J=10.0 Hz, 1H), 3.80-3.72 (m, 2H), 2.65-2.59 (m, 1H), 2.19 (dq, J=14.7, 2.6 Hz, 1H), 1.20-1.00 (m, 30H).

Step 6: Synthesis of Compound 3-7

To a solution of compound 3-6 (6.30 g, 13.88 mmol) in methanol (40 mL) was added a solution of hydrochloric acid in dioxane (5.21 mL, 20.83 mmol), and the mixture was stirred at room temperature for 110 minutes. After the solution was diluted with ethyl acetate (15 mL), the organic layer was washed with brine and dried over anhydrous magnesium sulfate. The solvent was evaporated under reduced pressure, and the residue (5 g) was dissolved in methanol (50 mL). To the solution was added dropwise a solution of benzoyl isothiocyanate (2.22 g, 13.60 mmol) in dichloromethane (6 mL) at 0° C. The mixture was stirred at room temperature for 50 minutes, and the solvent was evaporated under reduced pressure. The residue was purified by silica gel chromatography (hexane-ethyl acetate) to give compound 3-7 (6.87 g, 94% yield).

$^1$H-NMR (400 MHz, CDCl$_3$) δ: 11.60 (s, 1H), 8.81 (s, 1H), 7.96 (td, J=8.0, 1.8 Hz, 1H), 7.85 (t, J=4.3 Hz, 2H), 7.61 (tt, J=7.4, 1.4 Hz, 1H), 7.50 (t, J=7.7 Hz, 2H), 7.32-7.28 (m, 1H), 7.17 (td, J=7.6, 1.2 Hz, 1H), 7.00 (ddd, J=12.3, 8.1, 1.0 Hz, 1H), 4.15-4.08 (m, 1H), 3.92 (dt, J=16.7, 5.5 Hz, 1H), 2.79 (ddd, J=13.8, 7.8, 5.5 Hz, 1H), 2.42 (dt, J=14.0, 5.5 Hz, 1H), 1.93 (t, J=5.7 Hz, 1H), 1.15-1.09 (m, 21H).

Step 7: Synthesis of Compound 3-8

To a solution of compound 3-7 (330 mg, 0.624 mmol) in acetonitrile (6 mL) was added EDC hydrochloride (180 mg, 0.936 mmol) under nitrogen atmosphere. The mixture was stirred at room temperature for 2 days. To the mixture was added an aqueous sodium bicarbonate solution, and the aqueous layer was extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 3-8 (6302 mg, 96% yield).

$^1$H-NMR (400 MHz, CDCl$_3$) δ: 11.83 (s, 1H), 8.24-8.21 (m, 2H), 7.74 (td, J=8.0, 1.7 Hz, 1H), 7.51-7.47 (m, 1H), 7.43-7.36 (m, 3H), 7.21 (td, J=7.6, 1.2 Hz, 1H), 7.13 (ddd, J=11.8, 8.2, 1.1 Hz, 1H), 4.77 (td, J=10.9, 2.4 Hz, 1H), 4.47 (dt, J=11.5, 4.2 Hz, 1H), 2.72 (ddd, J=14.0, 10.3, 3.7 Hz, 1H), 2.54 (ddd, J=14.0, 4.2, 2.9 Hz, 1H), 1.15-1.02 (m, 21H).

Step 8: Synthesis of Compound 3-9

To a solution of compound 3-8 (292 mg, 0.578 mmol) in tetrahydrofuran (2 mL) were added Boc$_2$O (0.201 mL, 0.867 mmol) and DMAP (7.06 mg, 0.058 mmol). The mixture was stirred at room temperature for 30 minutes and then added methanol (2 mL). An aqueous solution of potassium carbonate (1198 mg, 8.67 mmol) in water (2 mL) was added, and the mixture was stirred at room temperature for 4 days. After the extraction with ethyl acetate, the organic layer was washed with brine and dried over anhydrous magnesium sulfate. The solvent was evaporated under reduced pressure, and the residue was dissolved in dichloromethane (4.5 mL). To the solution was added TFA (0.668 mL, 8.67 mmol), and the mixture was stirred at room temperature for 6 hours. To the mixture was added a 1 mol/L aqueous potassium carbonate solution (6 mL, 6 mmol), and the aqueous layer was extracted with dichloromethane. The organic layer was dried over anhydrous magnesium sulfate, and the solvent was evaporated under reduced pressure. The residue was purified by silica gel chromatography (chloroform-methanol) to give compound 3-9 (220 mg, 100% yield).

$^1$H-NMR (400 MHz, CDCl$_3$) δ: 7.79 (td, J=8.0, 1.6 Hz, 1H), 7.28-7.24 (m, 1H), 7.13 (t, J=7.5 Hz, 1H), 7.03 (dd, J=11.8, 8.0 Hz, 1H), 4.61 (td, J=10.9, 2.9 Hz, 1H), 4.23 (dt, J=10.6, 3.9 Hz, 1H), 2.47 (dt, J=13.9, 3.0 Hz, 1H), 2.23-2.16 (m, 1H), 1.27-0.85 (m, 21H).

Step 9: Synthesis of Compound 3-10

A solution of compound 3-9 (219 mg, 0.584 mmol) in TFA (1.3 mL, 17.5 mmol) was cooled to −20° C. with dry ice-acetone bath. To the solution were added dropwise concentrated sulfuric acid (0.327 mL, 6.13 mmol) and nitric acid (0.039 mL, 0.875 mmol) at the same temperature. The mixture was stirred for 2 minutes and poured into a mixture of crushed ice and a saturated aqueous sodium bicarbonate solution, and the aqueous layer was extracted with ethyl acetate. The organic layer was washed with brine and dried over anhydrous magnesium sulfate. The solvent was evaporated under reduced pressure, and the residue was purified silica gel chromatography (chloroform-methanol) to give compound 3-10 (243 mg, 93% yield).

$^1$H-NMR (400 MHz, CDCl$_3$) δ: 8.83 (dd, J=6.8, 3.0 Hz, 1H), 8.18 (ddd, J=8.9, 4.0, 3.0 Hz, 1H), 7.18 (dd, J=10.3, 8.9 Hz, 1H), 4.65 (ddd, J=12.7, 10.2, 1.9 Hz, 1H), 4.30 (ddd, J=10.8, 4.4, 2.6 Hz, 1H), 4.18 (br s, 2H), 2.52 (ddd, J=13.5, 4.4, 2.6 Hz, 1H), 2.03 (dt, J=18.5, 6.4 Hz, 1H), 1.07-1.05 (m, 21H).

Step 10: Synthesis of Compound 3-11

To a solution of compound 3-10 (4.78 g, 11.39 mmol) in dichloromethane (24 mL) were added Boc$_2$O (7.94 mL, 34.2 mmol) and DMAP (278 mg, 2.28 mmol). The mixture was stirred at room temperature for 40 minutes, and the solvent was evaporated under reduced pressure. The residue was purified by silica gel chromatography (hexane-ethyl acetate) to give compound 3-11 (6.27 g, 88% yield).

$^1$H-NMR (400 MHz, CDCl$_3$) δ: 8.71 (dd, J=6.8, 3.0 Hz, 1H), 8.22 (dt, J=8.9, 3.5 Hz, 1H), 7.22 (t, J=9.5 Hz, 1H), 4.68 (td, J=11.4, 2.4 Hz, 1H), 4.42 (td, J=7.3, 3.7 Hz, 1H), 2.73 (dd, J=13.8, 1.3 Hz, 1H), 2.04 (ddd, J=14.7, 10.7, 3.0 Hz, 1H), 1.52 (s, 18H), 1.46-0.84 (m, 21H).

Step 11: Synthesis of Compound 3-12

To a solution of compound 3-11 (295 mg, 0.469 mmol) in tetrahydrofuran (6 mL) was added 1 mol/L of TBAF-tetrahydrofuran solution (0.938 mL, 0.938 mmol) at 0° C. After stirring at the same temperature for 15 minutes, the mixture was extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 3-12 (218 mg, 94% yield).

$^1$H-NMR (400 MHz, CDCl$_3$) δ: 8.68 (dd, J=6.7, 3.0 Hz, 1H), 8.24 (ddd, J=8.9, 3.9, 3.0 Hz, 1H), 7.25 (t, J=9.5 Hz, 1H), 4.71 (td, J=11.6, 2.6 Hz, 1H), 4.45 (ddd, J=11.3, 4.2, 2.9 Hz, 1H), 2.71 (dd, J=13.9, 1.4 Hz, 1H), 2.61 (s, 1H), 1.99 (ddd, J=15.1, 10.8, 2.9 Hz, 1H), 1.53 (s, 18H).

Step 12: Synthesis of Compound 3-13

To a mixture of compound 3-12 (218 mg, 0.442 mmol) in ethanol (2.2 mL) and tetrahydrofuran (1.1 mL) were added a solution of aqueous ammonium chloride (283 mg, 5.30 mmol) in water (1.1 mL) and iron powder (197 mg, 3.53 mmol). After stirring at 60° C. for 220 minutes, celite (500 mg) and ethyl acetate (2 mL) were added, and the mixture was stirred at room temperature for 5 minutes. The insoluble material was removed by filtration and was washed with ethyl acetate. The filtrate was extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 3-13 (171 mg, 89% yield).

$^1$H-NMR (400 MHz, CDCl$_3$) δ: 7.02 (dd, J=6.5, 3.0 Hz, 1H), 6.87 (dd, J=11.2, 8.5 Hz, 1H), 6.56 (dt, J=8.5, 3.4 Hz, 1H), 4.62 (td, J=11.0, 2.9 Hz, 1H), 4.33 (dt, J=11.0, 4.0 Hz, 1H), 3.54 (br s, 2H), 2.63 (dt, J=14.1, 2.9 Hz, 1H), 2.53 (s, 1H), 2.08 (ddd, J=14.2, 10.6, 3.7 Hz, 1H), 1.52 (s, 18H).

Step 13: Synthesis of Compound I-16 To a mixture of compound 3-13 (28.2 mg, 0.065 mmol), 3,5-dichloropicolinic acid (13.74 mg, 0.072 mmol), HOBt monohydrate (11.96 mg, 0.078 mmol) and DMAP (0.8 mg, 0.007 mmol) in DMF (0.5 mL) was added EDC hydrochloride (14.97 mg, 0.078 mmol), and the mixture was stirred at room temperature for 1 hour. The mixture was treated with an aqueous sodium bicarbonate solution, and the aqueous layer was extracted with ethyl acetate. The organic layer was washed with brine and dried over anhydrous magnesium sulfate. The solvent was evaporated under reduced pressure, and the residue was purified by silica gel chromatography (hexane-ethyl acetate). The resulting compound was dissolved in formic acid (0.225 mL, 5.86 mmol), and the solution was stirred at room temperature for 5.5 hours. To the solution was added a saturated aqueous sodium bicarbonate solution, and the aqueous layer was extracted with ethyl acetate. The organic layer was washed with brine, and dried over anhydrous magnesium sulfate. The solvent was evaporated under reduced pressure, and the residue was purified by silica gel chromatography (chloroform-methanol) to give compound (I-16) (21.9 mg, 83% yield).

$^1$H-NMR (400 MHz, CDCl$_3$) δ: 9.77 (s, 1H), 8.48 (s, 1H), 8.08 (dt, J=8.2, 3.6 Hz, 1H), 7.91 (s, 1H), 7.72 (dd, J=6.8, 2.5 Hz, 1H), 7.09 (dd, J=10.2, 9.7 Hz, 1H), 4.55 (td, J=10.8, 2.5 Hz, 1H), 4.20 (dt, J=10.7, 4.1 Hz, 1H), 2.59 (d, J=14.2 Hz, 1H), 2.54 (s, 1H), 2.13 (ddd, J=14.0, 10.5, 3.6 Hz, 1H).

Example 4

Synthesis of Compound I-21

[Chemical Formula 93]

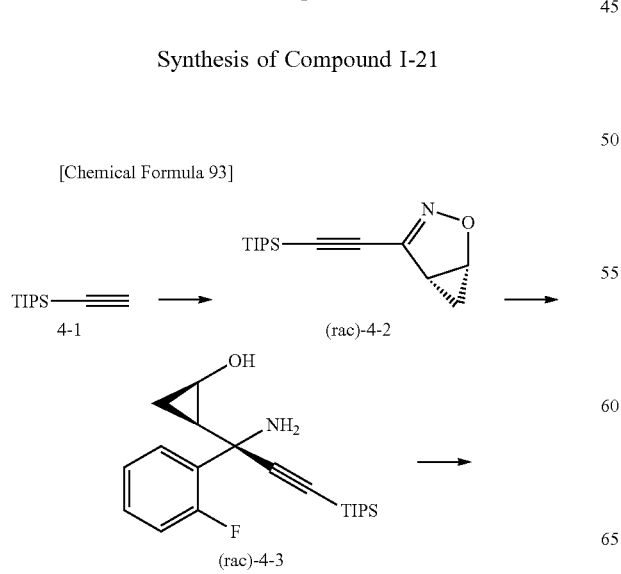

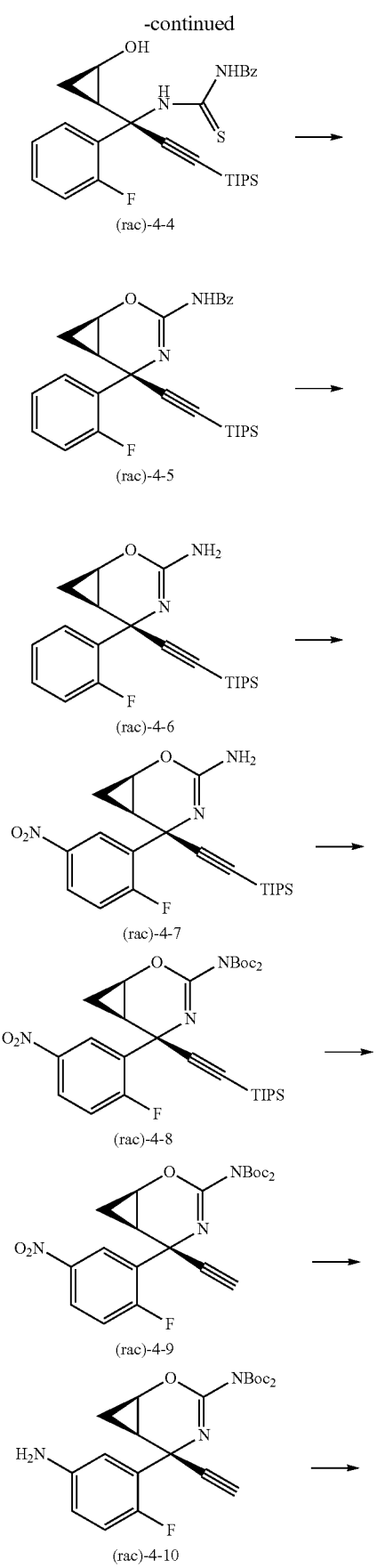

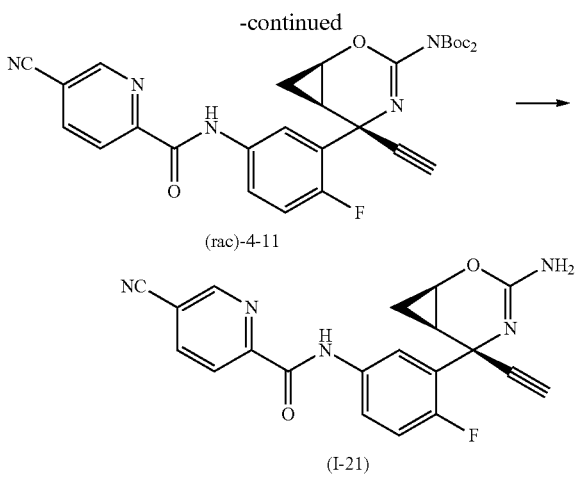

wherein Compounds 4-2 to 4-11 are racemates and the final compound is a chiral compound.

Step 1: Synthesis of Compound 4-2

To a solution of ethynyl triisopropylsilane 4-1 (20 g, 110 mmol) in diethyl ether (180 mL) was added dropwise 2.69 mol/L of n-butyl lithium-hexane solution (44.8 mL, 121 mmol) at 0° C. under nitrogen atmosphere. After dropwise addition of diethyl ether (20 mL), the mixture was stirred at the same temperature for 15 minutes. The mixture was cooled to −78° C. with dry ice-acetone bath and was added dropwise a solution of DMF (25.6 mL, 329 mmol) in diethyl ether (160 mL). After stirring at the same temperature for 20 minutes, the mixture was stirred under ice-cooling for 1 hour. To the reaction mixture was added a 5% aqueous sulfuric acid solution (240 mL), and the mixture was stirred under ice-cooling for 10 minutes. The organic layer was washed with water and brine and dried over anhydrous magnesium sulfate. The solvent was evaporated under reduced pressure, and the residue (22.6 g) was dissolved in methanol (300 mL). To the mixture were added hydroxylamine hydrochloride (11.2 g, 161 mmol) and sodium bicarbonate (13.54 mL, 161 mmol), and the mixture was stirred at room temperature for 20 minutes. This was diluted with ethyl acetate was added and evaporated under reduced pressure. After addition of water and ethyl acetate, the aqueous layer was extracted. The organic layer was washed with brine and dried over anhydrous magnesium sulfate. The solvent was evaporated under reduced pressure to give the residue (24.36 g) and 1 g of this was dissolved in tetrahydrofuran (20 mL). To the solution was added allyl bromide (0.576 mL, 6.65 mmol) and the mixture was cooled with ice bath. To the mixture was added an aqueous sodium hypochlorite solution (6.6 mL), and the mixture was stirred at the same temperature for 10 minutes. After stirring at room temperature for 20 minutes, water and ethyl acetate were added. The organic layer was washed with brine and dried over anhydrous magnesium sulfate. The solvent was evaporated under reduced pressure, and the residue (1.18 g) was dissolved in tetrahydrofuran (21 mL). The solution was cooled to −78° C. with dry ice-acetone bath and was added dropwise 1.8 mol/L of LDA-tetrahydrofuran solution (3.8 mL, 6.84 mmol). After stirring at the same temperature for 15 minutes, an aqueous ammonium chloride was added, and the mixture was extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 4-2 (444 mg, 37% yield).

$^1$H-NMR (400 MHz, CDCl$_3$) δ: 5.02-4.99 (m, 1H), 2.69-2.65 (m, 1H), 1.16-1.09 (m, 21H), 1.01-0.95 (m, 1H), 0.43-0.40 (m, 1H).

Step 2: Synthesis of Compound 4-3

To a mixture of 1-bromo-2-fluorobenzene (590 mg, 3.37 mmol) in tetrahydrofuran (3.7 mL) and toluene (14.5 mL) was added dropwise 2.69 mol/L of n-butyllithium-hexane solution (1.25 mL, 3.37 mmol) −78° C. under nitrogen atmosphere, followed by boron trifluoride-diethyl ether complex (0.213 mL, 1.69 mmol), and the mixture was stirred at the same temperature for 15 minutes. To the reaction mixture was added dropwise a solution of compound 4-2 (444 mg, 1.69 mmol) in toluene (22.5 mL), and the mixture was stirred at the same temperature for 90 minutes. An aqueous ammonium chloride solution was added, and the aqueous layer was extracted with ethyl acetate. The organic layer was washed with brine and dried over anhydrous magnesium sulfate. The solvent was evaporated under reduced pressure, and the residue (634 mg) was dissolved in diethyl ether (6 mL). After the solution was cooled with ice bath, a suspension of lithium aluminium hydride (64 mg, 1.69 mmol) in diethyl ether (4 mL) was added, and the mixture was then stirred at room temperature for 1 hour. The mixture was cooled with ice bath and then treated with an aqueous sodium hydroxide solution. The mixture was stirred at room temperature for 1 hour. The organic layer was dried over anhydrous magnesium sulfate, and the insoluble material was removed by filtration. The filtrate was evaporated under reduced pressure, and the residue was purified by silica gel chromatography (hexane-ethyl acetate) to give compound 4-3 (327 mg, 53% yield).

$^1$H-NMR (400 MHz, CDCl$_3$) δ: 7.80 (t, J=7.9 Hz, 1H), 7.30 (dd, J=13.3, 6.7 Hz, 1H), 7.16 (t, J=7.9 Hz, 1H), 7.09 (dd, J=11.9, 8.2 Hz, 1H), 3.65 (dd, J=10.4, 6.7 Hz, 1H), 1.39 (dd, J=16.4, 6.7 Hz, 1H), 1.15-0.87 (m, 23H).

Step 3: Synthesis of Compound 4-4

To a solution of compound 4-3 (327 mg, 0.888 mmol) in methanol (4 mL) was added dropwise a solution of benzoyl isothiocyanate (145 mg, 0.888 mmol) in dichloromethane (0.8 mL) under ice-cooling. After the solution was stirred at the same temperature for 90 minutes, the solvent was evaporated under reduced pressure. The residue was purified by silica gel chromatography (hexane-ethyl acetate) to give compound 4-4 (395 mg, 79% yield).

$^1$H-NMR (400 MHz, CDCl$_3$) δ: 11.70 (s, 1H), 8.84 (s, 1H), 7.87 (q, J=8.4 Hz, 3H), 7.62 (t, J=7.3 Hz, 1H), 7.51 (t, J=7.3 Hz, 2H), 7.31 (dd, J=13.1, 7.2 Hz, 1H), 7.18 (t, J=7.6 Hz, 1H), 7.03 (dd, J=12.0, 8.3 Hz, 1H), 3.81-3.74 (m, 1H), 2.90 (d, J=7.9 Hz, 1H), 1.83 (dd, J=16.1, 7.3 Hz, 1H), 1.36 (dd, J=11.0, 5.9 Hz, 1H), 1.18-1.08 (m, 21H), 0.96 (dd, J=16.2, 7.9 Hz, 1H).

Step 4: Synthesis of Compound 4-5

To a solution of compound 4-4 (395 mg, 0.701 mmol) in acetonitrile (8 mL) was added EDC hydrochloride (269 mg, 1.40 mmol). After the solution was stirred at room temperature for 20 hours, water was added and the aqueous layer was extracted with ethyl acetate. The organic layer was washed with brine and dried over anhydrous magnesium sulfate. The solvent was evaporated under reduced pressure, and the residue was purified by silica gel chromatography (hexane-ethyl acetate) to give compound 4-5 (352 mg, 98% yield).

$^1$H-NMR (400 MHz, CDCl$_3$) δ: 11.65 (s, 1H), 8.20 (d, J=7.8 Hz, 2H), 7.77 (t, J=8.0 Hz, 1H), 7.47 (t, J=7.3 Hz, 1H), 7.41-7.34 (m, 3H), 7.17 (t, J=7.7 Hz, 1H), 7.12 (dd, J=11.5, 8.3 Hz, 1H), 4.38-4.34 (m, 1H), 1.97 (dd, J=16.7, 7.2 Hz, 1H), 1.52-1.47 (m, 1H), 1.28-1.22 (m, 1H), 1.12 (s, 21H).

Step 5: Synthesis of Compound 4-6

To a solution of compound 4-5 (357 mg, 0.697 mmol) in tetrahydrofuran (2.1 mL) were added $Boc_2O$ (0.486 mL, 2.09 mmol) and DMAP (8.52 mg, 0.07 mmol). After the mixture was stirred at room temperature for 30 minutes, methanol (2.1 mL) and water (2.1 mL) were added. To the mixture was added potassium carbonate (1446 mg, 10.46 mmol) under ice-cooling, and the mixture was stirred at room temperature for 100 minutes. The mixture was treated with tetrahydrofuran (1.5 mL), methanol (1.5 mL), and water (1.5 mL) and was then stirred at room temperature for 15 hours. After stirring at 50° C. for 8.5 hours, the solution was stirred at room temperature for 18 hours. The aqueous layer was extracted with ethyl acetate. The organic layer was washed with brine and dried over anhydrous magnesium sulfate. The solvent was evaporated under reduced pressure, and the residue was dissolved in dichloromethane (5 mL). To the solution was added TFA (0.806 mL, 10.46 mmol), and the mixture was stirred at room temperature for 4 hours, which was then treated with 1 mol/L of aqueous potassium carbonate solution, and the aqueous layer was extracted with dichloromethane. The organic layer was dried over anhydrous magnesium sulfate, and the solvent was evaporated under reduced pressure. The residue was purified by silica gel chromatography (chloroform-methanol) to give compound 4-6 (258 mg, 90% yield).

$^1$H-NMR (400 MHz, $CDCl_3$) δ: 7.90 (t, J=7.7 Hz, 1H), 7.28-7.23 (m, 1H), 7.11 (t, J=7.3 Hz, 1H), 7.03 (dd, J=11.0, 8.8 Hz, 1H), 4.07-4.03 (m, 1H), 3.96 (br s, 2H), 1.66-1.62 (m, 1H), 1.19-0.95 (m, 23H).

Step 6: Synthesis of Compound 4-7

A solution of compound 4-6 (50 mg, 0.122 mmol) in TFA (0.3 mL, 3.89 mmol) was cooled to −20° C. with dry ice-acetone bath. To the mixture were added dropwise concentrated sulfuric acid (0.075 mL, 1.41 mmol) and nitric acid (0.008 mL, 0.182 mmol) at the same temperature, and the mixture was stirred for 20 minutes. After addition of ethyl acetate, 1 mol/L of aqueous potassium carbonate solution was added under ice-cooling. The aqueous layer was extracted with ethyl acetate. The organic layer was washed with brine and dried over anhydrous magnesium sulfate. The solvent was evaporated under reduced pressure, and the resulting residue was purified by silica gel chromatography (hexane-ethyl acetate) to give Compound 4-7 (38.7 mg, 71% yield).

$^1$H-NMR (400 MHz, $CDCl_3$) δ: 8.92 (d, J=6.7 Hz, 1H), 8.21-8.19 (m, 1H), 7.19 (t, J=9.5 Hz, 1H), 4.13-4.08 (m, 3H), 1.59-1.55 (m, 1H), 1.23-1.19 (m, 1H), 1.12-1.05 (m, 23H).

Step 7: Synthesis of Compound 4-8

To a solution of compound 4-7 (37.5 mg, 0.087 mmol) in dichloromethane (1 mL) were added $Boc_2O$ (0.061 mL, 0.261 mmol) and DMAP (2.12 mg, 0.017 mmol). After stirring at room temperature for 100 minutes, the solvent was evaporated under reduced pressure. The residue was purified by silica gel chromatography (hexane-ethyl acetate) to give compound 4-8 (51.4 mg, 94% yield).

$^1$H-NMR (400 MHz, $CDCl_3$) δ: 8.94 (d, J=6.3 Hz, 1H), 8.25-8.23 (m, 1H), 7.22 (t, J=9.4 Hz, 1H), 4.30-4.26 (m, 1H), 1.73 (dd, J=16.8, 7.2 Hz, 1H), 1.49 (s, 18H), 1.34-1.30 (m, 1H), 1.22 (dd, J=16.8, 7.2 Hz, 1H), 1.11 (s, 21H).

Step 8: Synthesis of Compound 4-9

To a solution of compound 4-8 (49.8 mg, 0.079 mmol) in tetrahydrofuran (1 mL) was added 1 mol/L of TBAF-tetrahydrofuran solution (0.1 mL, 0.100 mmol) under ice-cooling. The mixture was stirred at the same temperature for 20 minutes and extracted with ethyl acetate. The organic layer was washed with brine and dried over anhydrous magnesium sulfate. The solvent was evaporated under reduced pressure, and the residue was purified by silica gel chromatography (hexane-ethyl acetate) to give Compound 4-9 (37.6 mg, 97% yield).

$^1$H-NMR (400 MHz, $CDCl_3$) δ: 8.81 (dd, J=6.8, 3.0 Hz, 1H), 8.26 (ddd, J=8.9, 4.0, 3.0 Hz, 1H), 7.25 (dd, J=10.0, 8.9 Hz, 2H), 4.24 (dt, J=10.1, 3.2 Hz, 1H), 2.67 (s, 1H), 1.75-1.66 (m, 1H), 1.51 (s, 18H), 1.32 (dt, J=10.8, 3.7 Hz, 1H), 1.24 (t, J=6.9 Hz, 1H).

Step 9: Synthesis of Compound 4-10

To a solution of compound 4-9 (35 mg, 0.074 mmol) in ethanol (0.4 mL) and tetrahydrofuran (0.2 mL) were added an aqueous ammonium chloride solution (47.3 mg, 0.883 mmol) in water (0.2 mL) and reduced iron (32.9 mg, 0.586 mmol). After stirring at 60° C. for 2.5 hours, celite (50 mg) and ethyl acetate (2 mL) were added and the mixture was then stirred at room temperature for 5 minutes. The insoluble material was removed by filtration and washed with ethyl acetate. The filtrate was extracted with ethyl acetate, and the organic layer was washed with brine and dried over anhydrous magnesium sulfate. The solvent was evaporated under reduced pressure and the residue was purified by silica gel chromatography (hexane-ethyl acetate) to give compound 4-10 (23.9 mg, 70% yield).

$^1$H-NMR (400 MHz, $CDCl_3$) δ: 7.18 (d, J=6.7 Hz, 1H), 6.86 (t, J=9.9 Hz, 1H), 6.59-6.57 (m, 1H), 4.22-4.19 (m, 1H), 3.58 (br s, 1H), 2.59 (s, 1H), 1.77 (dd, J=16.7, 7.5 Hz, 1H), 1.49 (s, 18H), 1.28-1.26 (m, 2H), 1.16 (dd, J=16.5, 7.3 Hz, 1H).

Step 10: Synthesis of Compound 4-11

To a solution of Compound 4-10 (23.5 mg, 0.051 mmol), 5-cyanopicolinic acid monohydrate (9.29 mg, 0.056 mmol), HOBt monohydrate (9.34 mg, 0.061 mmol) and DMAP (0.6 mg, 0.005 mmol) in DMF (0.5 mL) was added EDC hydrochloride (13.7 mg, 0.071 mmol). The mixture was stirred at room temperature for 40 minutes. This was treated with an aqueous sodium bicarbonate solution, and the aqueous layer was extracted with ethyl acetate. The organic layer was washed with brine and dried over anhydrous magnesium sulfate. The solvent was evaporated under reduced pressure and the residue was purified by silica gel chromatography (hexane-ethyl acetate) to give compound 4-11 (26.8 mg, 90% yield).

$^1$H-NMR (400 MHz, $CDCl_3$) δ: 9.92 (s, 1H), 8.83 (s, 1H), 8.44 (d, J=8.3 Hz, 1H), 8.22 (t, J=7.0 Hz, 2H), 7.91 (d, J=6.5 Hz, 1H), 7.15 (t, J=9.8 Hz, 1H), 4.23-4.19 (m, 1H), 2.62 (s, 1H), 1.85 (dd, J=16.7, 7.2 Hz, 1H), 1.53 (s, 18H), 1.35 (t, J=7.2 Hz, 1H), 1.19 (dd, J=16.7, 7.2 Hz, 1H).

Step 11: Synthesis of Compound I-21

A solution of compound 4-11 (192 mg, 0.329 mmol) in formic acid (1.26 mL, 32.9 mmol) was stirred at room temperature for 4.3 h. To the solution was added an aqueous sodium bicarbonate solution, and the aqueous layer was extracted with ethyl acetate. The organic layer was washed with brine and dried over anhydrous magnesium sulfate. The solvent was evaporated under reduced pressure and the residue was purified by supercritical fluid chromatography (SFC) (Chiralpak (Registered trademark) IA; 45% isopropylalcohol with 0.1% diethylamine) to give compound I-21 (30 mg, 24% yield).

1H-NMR (400 MHz, CDCl₃) δ: 9.85 (s, 1H), 8.91 (s, 1H), 8.44 (d, J=8.3 Hz, 1H), 8.21 (d, J=8.0 Hz, 1H), 7.96-7.92 (m, 2H), 7.13 (t, J=9.8 Hz, 1H), 4.08-4.04 (m, 1H), 2.63 (s, 1H), 1.72 (dd, J=16.6, 7.5 Hz, 1H), 1.27-1.23 (m, 1H), 1.08 (dd, J=16.6, 6.8 Hz, 1H).
Example 5
Synthesis of Compound I-26
[Chemical Formula 94]
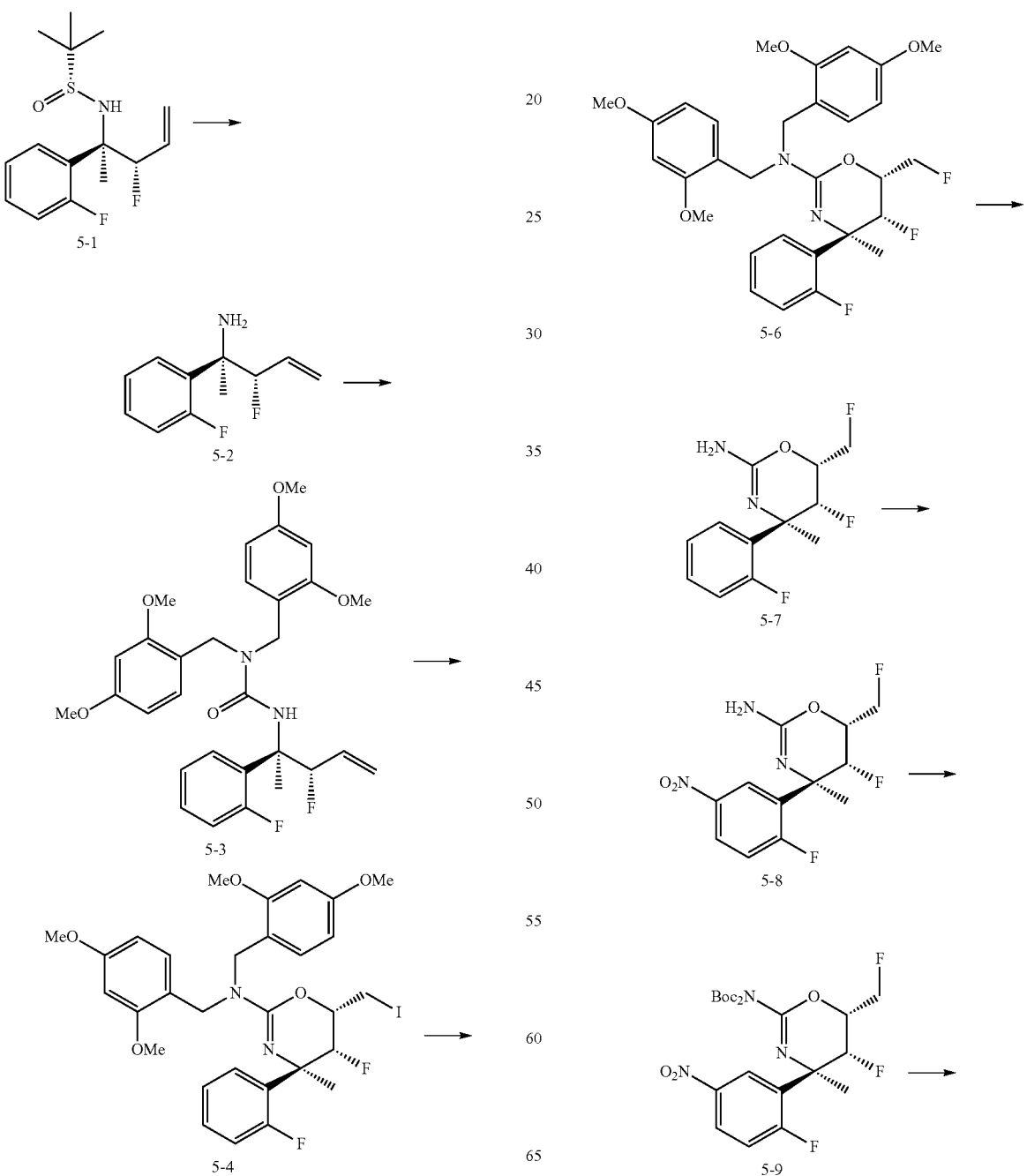

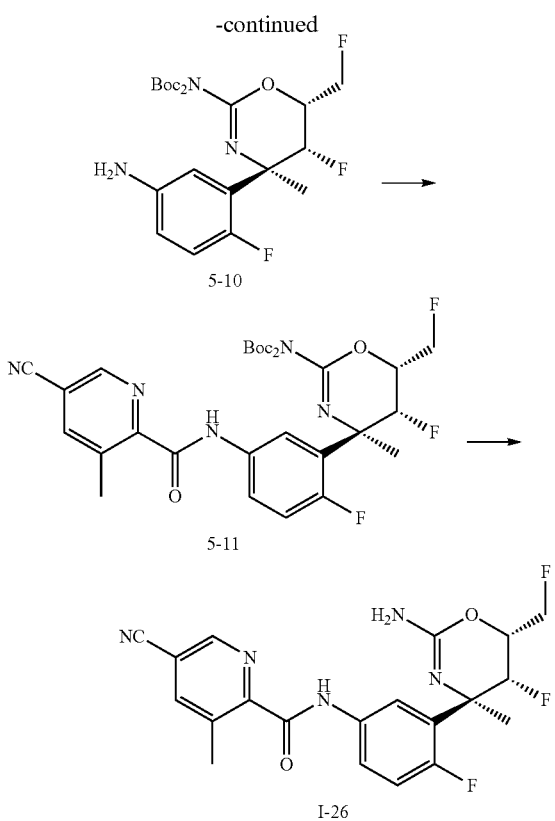

Step 1: Synthesis of Compound 5-3

To a solution of 5-1 (600 mg, 1.99 mmol) in MeOH (6 ml) was added 4 mol/L HCl in dioxane (0.747 ml, 2.99 mmol) at room temperature. After stirring for 30 min at the same temperature, the reaction mixture was treated with aqueous NaHCO$_3$ and the aqueous layer was extracted with AcOEt. The combined organic layer was washed with H$_2$O and brine, dried over Na$_2$SO$_4$ and filtered. The filtrate was concentrated under vacuum to give 5-2 as a brown oil that was used for the next step without purification.

To a solution of 5-2 in EtOAc (4 ml) and H$_2$O (2 ml) were added NaHCO$_3$ (586 mg, 6.97 mmol) and 4-nitrophenyl carbonochloridate (442 mg, 2.19 mmol) at 0° C. After stirring for 1 h at the same temperature, to the reaction mixture was added bis(2,4-dimethoxybenzyl)amine (696 mg, 2.19 mmol). After stirring for 2 h at the same temperature, the reaction mixture was treated with H$_2$O, and the aqueous layer was extracted with AcOEt. The organic layer was dried over Na$_2$SO$_4$, filtered and concentrated. The crude product was added to a silica gel column and eluted with hexane/EtOAc 0% to 30%. Collected fractions were evaporated to afford 5-3 (1.06 g, 1.96 mmol, 98%) as a yellow oil.

$^1$H-NMR (400 MHz, CDCl$_3$) δ: 1.84 (s, 3H), 3.78 (s, 6H), 3.81 (s, 6H), 4.39 (s, 4H), 5.14 (d, J=10.5 Hz, 1H), 5.27 (d, J=17.3 Hz, 1H), 5.58-5.69 (m, 2H), 6.44 (s, 4H), 6.94-7.02 (m, 1H), 7.06-7.14 (m, 3H), 7.18-7.24 (m, 1H), 7.35-7.42 (m, 1H).

Step 2: Synthesis of Compound 5-4

To a solution of iodine (995 mg, 3.92 mmol) in MeCN (70 ml) was added 5-3 (1.06 g, 1.96 mmol) in MeCN (30 ml) at 0° C. After stirring for 3.5 h at the same temperature, the reaction mixture was treated with aqueous NaHCO$_3$ and Na$_2$S$_2$O$_3$. The aqueous layer was extracted with AcOEt, and the organic layer was dried over Na$_2$SO$_4$, filtered and concentrated. The crude product was added to a silica gel column and eluted with hexane/EtOAc 0% to 20%. Collected fractions were evaporated to afford 5-4 (1.07 g, 1.61 mmol, 82%) as a white amorphous.

$^1$H-NMR (400 MHz, CDCl$_3$) δ: 1.64 (s, 3H), 3.16-3.21 (m, 2H), 3.75 (s, 6H), 3.82 (s, 6H), 4.48 (d, J=15.6 Hz, 2H), 4.61 (d, J=15.6 Hz, 2H), 5.31 (d, J=48.7 Hz, 1H), 6.42-6.49 (m, 4H), 6.97-7.07 (m, 2H), 7.25-7.17 (m, 3H), 7.38 (t, J=7.8 Hz, 1H).

Step 3: Synthesis of Compound 5-5

To a solution of 5-4 (1.07 g, 1.61 mmol) in MeNO$_2$ (11 ml) and H$_2$O (4.4 ml) was added (2,2,2-trifluoroacetoxy)silver (1.42 g, 6.42 mmol) at room temperature. After stirring for 7 h at 80° C., to the reaction mixture was further added (2,2,2-trifluoroacetoxy)silver (0.71 g, 3.21 mmol). After stirring for additional 17 h, the reaction mixture was treated with aqueous NaHCO$_3$, and the mixture was filtrated through a pad of Celite. The aqueous layer was extracted with AcOEt, and the organic layer was dried over Na$_2$SO$_4$, filtered and concentrated. The crude product was added to a silica gel column and eluted with hexane/EtOAc 0% to 50%. Collected fractions were evaporated to afford 5-5 (506 mg, 0.909 mmol, 57%) as a white amorphous.

$^1$H-NMR (400 MHz, CDCl$_3$) δ: 1.63 (s, 3H), 3.59-3.67 (m, 1H), 3.71-3.75 (m, 2H), 3.76 (s, 6H), 3.81 (s, 6H), 4.48 (d, J=15.8 Hz, 2H), 4.63 (d, J=15.8 Hz, 2H), 5.13 (d, J=48.9 Hz, 1H), 6.43-6.50 (m, 4H), 6.94-7.06 (m, 2H), 7.25-7.17 (m, 3H), 7.39 (t, J=8.1 Hz, 1H).

Step 4: Synthesis of Compound 5-6

To a solution of 5-5 (506 mg, 0.909 mmol) in CH$_2$Cl$_2$ (5 ml) was added DAST (0.400 ml, 2.73 mmol) at −78° C. After stirring for 2.5 h at room temperature, the reaction mixture was treated with aqueous NaHCO$_3$. The aqueous layer was extracted with AcOEt, and the organic layer was dried over Na$_2$SO$_4$, filtered and concentrated. The crude product was added to a silica gel column and eluted with hexane/EtOAc 0% to 30%. Collected fractions were evaporated to afford 5-6 (386 mg, 0.691 mmol, 76%) as a white amorphous.

$^1$H-NMR (400 MHz, CDCl$_3$) δ: 1.64 (s, 3H), 3.76 (s, 6H), 3.82 (s, 6H), 3.90-4.07 (m, 1H), 4.36-4.68 (m, 6H), 5.18 (d, J=48.7 Hz, 1H), 6.42-6.49 (m, 4H), 6.95-7.06 (m, 2H), 7.25-7.16 (m, 3H), 7.38 (t, J=7.7 Hz, 1H).

Step 5: Synthesis of Compound 5-7

To a solution of 5-6 (3.60 g, 6.44 mmol) in TFA (15 ml) was added anisole (2.96 ml, 27.1 mmol) at room temperature. After stirring for 24 h at 80° C., the reaction mixture was treated with aqueous K$_2$CO$_3$. The aqueous layer was extracted with AcOEt, and the organic layer was dried over Na$_2$SO$_4$, filtered and concentrated. The crude product was added to a silica gel column and eluted with hexane/EtOAc 30% to 100%. Collected fractions were evaporated to afford 5-7 (1.62 g, 6.27 mmol, 97%) as a white amorphous.

$^1$H-NMR (400 MHz, CDCl$_3$) δ: 1.78 (s, 3H), 4.20-4.29 (m, 1H), 4.64 (dd, J=46.6, 5.0 Hz, 2H), 5.27 (d, J=47.8 Hz, 1H), 7.10 (t, J=10.2 Hz, 1H), 7.20-7.25 (m, 1H), 7.44-7.32 (m, 2H).

Step 6: Synthesis of Compound 5-8

To a solution of 5-7 (1.62 g, 6.27 mmol) in TFA (12 ml) was added sulfuric acid (3.14 ml, 59.0 mmol) at −20° C. After stirring for 5 min at 0° C., HNO$_3$ (0.421 ml, 9.41 mmol) was added to the reaction mixture at −20° C. After stirring for 15 min at 0° C., the reaction mixture was treated with aqueous K$_2$CO$_3$. The aqueous layer was extracted with AcOEt, and the organic layer was dried over Na$_2$SO$_4$, filtered and concentrated to afford 5-8 (1.90 g, 6.27 mmol, 100%) as a tan amorphous.

¹H-NMR (400 MHz, CDCl₃) δ: 1.83 (s, 3H), 4.20-4.31 (m, 1H), 4.66 (dd, J=46.2, 5.3 Hz, 2H), 5.27 (d, J=46.8 Hz, 1H), 7.28-7.34 (m, 1H), 8.29 (d, J=6.3 Hz, 1H), 8.37 (d, J=6.3 Hz, 1H).

Step 7: Synthesis of Compound 5-9

To a solution of 5-8 (1.90 g, 6.27 mmol) in THF (20 ml) were added Boc₂O (4.36 ml, 18.8 mmol) and DMAP (306 mg, 2.51 mmol) at room temperature. After stirring for 30 min at the same temperature, the mixture was concentrated under vacuum. The crude product was added to a silica gel column and eluted with hexane/EtOAc 0% to 30%. Collected fractions were evaporated to afford 5-8 (3.15 g, 6.26 mmol, 100%) as a tan amorphous.

¹H-NMR (400 MHz, CDCl₃) δ: 1.56 (s, 18H), 1.74 (dd, J=3.3, 1.8 Hz, 3H), 4.04-4.14 (m, 1H), 4.65 (dd, J=46.2, 6.1 Hz, 2H), 5.22 (d, J=47.3 Hz, 1H), 7.24-7.30 (m, 1H), 8.28-8.23 (m, 1H), 8.57 (dd, J=6.7, 2.8 Hz, 1H).

Step 8: Synthesis of Compound 5-10

To a solution of 5-9 (1.50 g, 2.98 mmol) in MeOH (30 ml) was added 10% Pd/C (154 mg) and hydrogenated at room temperature. After stirring for 1.5 h at the same temperature, the mixture was filtrated through a pad of Celite. The filtrate was concentrated under vacuum to give 5-10 (1.41 g, 2.98 mmol, 100%) as a white amorphous that was used for the next step without purification.

¹H-NMR (400 MHz, CDCl₃) δ: 1.53 (s, 18H), 1.70 (dd, J=1.5, 2.8 Hz, 3H), 3.57 (s, 2H), 4.15-4.30 (m, 1H), 4.63 (dd, J=46.3, 5.6 Hz, 2H), 5.19 (d, J=47.7 Hz, 1H), 6.56 (dt, J=8.5, 3.4 Hz, 1H), 6.90-6.85 (m, 2H).

Step 9: Synthesis of Compound 5-11

To a solution of 5-10 (47 mg, 0.0990 mmol) in DMF (1 ml) were added 5-cyano-3-methylpicolinic acid (16.9 mg, 0.104 mmol), HATU (45.3 mg, 0.119 mmol) and DIPEA (0.0350 ml, 0.199 mmol) at room temperature. After stirring for 20 min at the same temperature, the reaction mixture was treated with H₂O. The aqueous layer was extracted with AcOEt, and the organic layer was dried over Na₂SO₄, filtered and concentrated. The crude product was added to a silica gel column and eluted with hexane/EtOAc 0% to 40%. Collected fractions were evaporated to afford 5-11 (61.3 mg, 0.0990 mmol, 100%) as a colorless oil.

¹H-NMR (400 MHz, CDCl₃) δ: 1.56 (s, 18H), 1.76 (s, 3H), 2.87 (s, 3H), 4.15-4.30 (m, 1H), 4.64 (dd, J=46.3, 5.9 Hz, 2H), 5.23 (d, J=47.9 Hz, 1H), 7.13 (dd, J=11.5, 9.0 Hz, 1H), 7.52 (dd, J=6.7, 2.9 Hz, 1H), 7.95 (d, J=1.3 Hz, 1H), 8.31-8.36 (m, 1H), 8.62 (d, J=1.3 Hz, 1H), 10.16 (s, 1H).

Step 10: Synthesis of I-26

To a solution of 5-11 (61.3 mg, 0.0990 mmol) was added formic acid (1 ml) at room temperature. After stirring for 12 h at the same temperature, the reaction mixture was treated with aqueous K₂CO₃. The aqueous layer was extracted with AcOEt, and the organic layer was dried over Na₂SO₄, filtered and concentrated to afford I-26 (20.0 mg, 0.0480 mmol, 48%) as a white powder.

¹H-NMR (400 MHz, DMSO-D6) δ: 1.49 (s, 3H), 2.53 (s, 3H), 3.85-4.01 (m, 1H), 4.53 (dt, J=47.8, 8.9 Hz, 1H), 4.73 (ddd, J=3.8, 10.2, 45.7 Hz, 1H), 5.14 (d, J=48.7 Hz, 1H), 5.83 (s, 2H), 7.21 (dd, J=11.7, 8.8 Hz, 1H), 7.71-7.75 (m, 1H), 7.82-7.87 (m, 1H), 8.38 (d, J=1.5 Hz, 1H), 8.97 (d, J=1.5 Hz, 1H), 10.79 (s, 1H).

Example 6

Synthesis of I-29

[Chemical Formula 95]

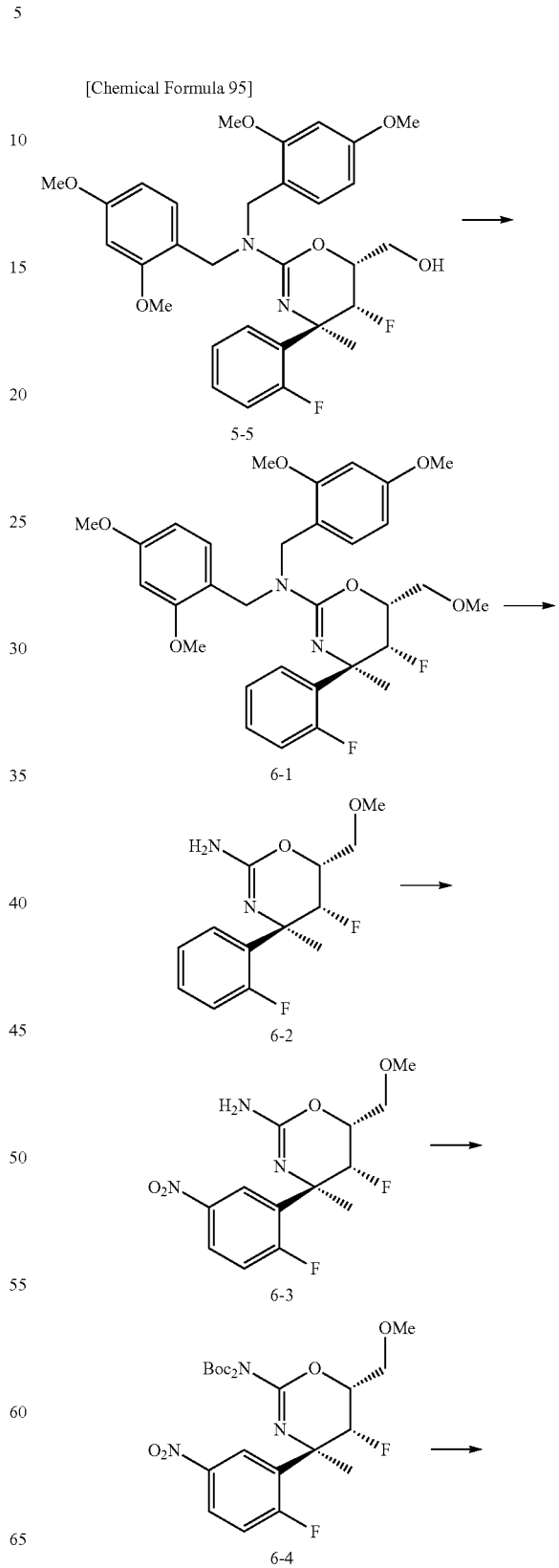

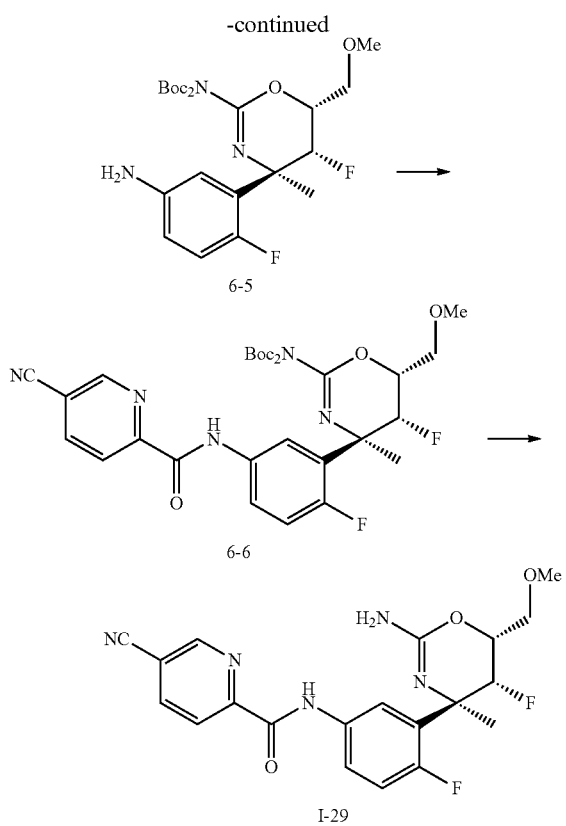

Step 1: Synthesis of Compound 12

To a solution of 5-5 (265 mg, 0.476 mmol) in THF (5 ml) were added 60% NaH (57.1 mg, 1.43 mmol) and MeI (0.0450 ml, 0.714 ml) at room temperature. After stirring for 30 min at the same temperature, the reaction mixture was treated with H$_2$O. The aqueous layer was extracted with AcOEt, and the organic layer was dried over Na$_2$SO$_4$, filtered and concentrated. The crude product was added to a silica gel column and eluted with hexane/EtOAc 10% to 40%. Collected fractions were evaporated to afford 6-1 (234 mg, 0.410 mmol, 86%) as a white amorphous.

$^1$H-NMR (400 MHz, CDCl$_3$) δ: 1.63 (s, 3H), 3.25 (s, 3H), 3.41-3.47 (m, 1H), 3.53-3.58 (m, 1H), 3.75 (s, 6H), 3.81 (s, 6H), 4.52 (dd, J=78.7, 15.8 Hz, 4H), 5.15 (d, J=48.5 Hz, 1H), 6.42-6.49 (m, 4H), 7.04-6.93 (m, 2H), 7.23-7.15 (m, 3H), 7.38 (t, J=8.0 Hz, 1H).

Step 2: Synthesis of Compound 6-2

To a solution of 6-1 (234 mg, 0.410 mmol) in TFA (1.6 ml) was added anisole (0.314 ml, 2.87 mmol) at room temperature. After stirring for 19 h at 80° C., the reaction mixture was treated with aqueous K$_2$CO$_3$. The aqueous layer was extracted with AcOEt and the organic layer was dried over Na$_2$SO$_4$, filtered and concentrated. The crude product was added to a silica gel column and eluted with hexane/EtOAc 60% to 100%. Collected fractions were evaporated to afford 6-2 (103 mg, 0.381 mmol, 93%) as a white amorphous.

$^1$H-NMR (400 MHz, CDCl$_3$) δ: 1.65 (s, 3H), 3.35 (s, 3H), 3.53-3.65 (m, 2H), 3.90 (dt, J=30.2, 6.3 Hz, 1H), 4.22 (br s, 2H), 5.13 (d, J=48.0 Hz, 1H), 7.02 (dd, J=12.0, 8.0 Hz, 1H), 7.13 (t, J=7.5 Hz, 1H), 7.28-7.24 (m, 5H), 7.45 (t, J=7.5 Hz, 1H).

Step 3: Synthesis of Compound 6-4

To a solution of 6-2 (103 mg, 0.381 mmol) in TFA (1 ml) was added sulfuric acid (0.254 ml, 4.76 mmol) at −20° C. After stirring for 5 min at 0° C., the reaction mixture was added to HNO$_3$ (0.0260 ml, 0.572 mmol) at −20° C. After stirring for 15 min at 0° C., the reaction mixture was treated with aqueous K$_2$CO$_3$. The aqueous layer was extracted with AcOEt and the organic layer was dried over Na$_2$SO$_4$. The filtrate was concentrated under vacuum to give 6-3 as a white amorphous that was used for the next step without purification.

To a solution of 6-3 in THF (2 ml) was added Boc$_2$O (0.265 ml, 1.14 mmol) and DMAP (18.6 mg, 0.152 mmol) at room temperature. After stirring for 1 h at the same temperature, the mixture was concentrated under vacuum. The crude product was added to a silica gel column and eluted with hexane/EtOAc 0% to 30%.

Collected fractions were evaporated to afford 6-4 (171 mg, 0.332 mmol, 87%) as a white amorphous.

$^1$H-NMR (400 MHz, CDCl$_3$) δ: 1.54 (s, 18H), 1.73 (s, 3H), 3.36 (s, 3H), 3.58-3.70 (m, 2H), 3.96 (dt, J=28.5, 6.6 Hz, 1H), 5.19 (d, J=47.0 Hz, 1H), 7.21-7.27 (m, 1H), 8.25-8.20 (m, 1H), 8.56 (dd, J=6.4, 2.7 Hz, 1H).

Step 4: Synthesis of Compound 6-5

To a solution of 6-4 (171 mg, 0.332 mmol) in EtOH (2 ml), THF (1 ml) and H$_2$O (1 ml) were added NH$_4$Cl (213 mg, 3.98 mmol) and Fe (148 mg, 2.65 mmol) at room temperature. After stirring for 2 h at 60° C., the mixture was treated with H$_2$O and filtrated through a pad of Celite. The aqueous layer was extracted with AcOEt, and the organic layer was dried over Na$_2$SO$_4$, filtered and concentrated. The crude product was added to a silica gel column and eluted with hexane/EtOAc 0% to 40%. Collected fractions were evaporated to afford 6-5 (108 mg, 0.222 mmol, 67%) as a yellow amorphous.

$^1$H-NMR (400 MHz, CDCl$_3$) δ: 1.54 (s, 18H), 1.69 (s, 3H), 3.35 (s, 3H), 3.54 (s, 2H), 3.63 (d, J=5.3 Hz, 2H), 4.03-4.07 (m, 1H), 5.16 (d, J=47.5 Hz, 1H), 6.56-6.51 (m, 1H), 6.90-6.80 (m, 2H).

Step 5: Synthesis of Compound 6-6

To a solution of 6-5 (60 mg, 0.124 mmol) in DMF (1 ml) were added 5-cyanopicolinic acid hydrate (21.6 mg, 0.130 mmol), HATU (56.4 mg, 0.148 mmol) and DIPEA (0.0430 ml, 0.247 mmol) at room temperature. After stirring for 10 min at the same temperature, the reaction mixture was treated with H$_2$O. The aqueous layer was extracted with AcOEt, and the organic layer was dried over Na$_2$SO$_4$, filtered and concentrated. The crude product was added to a silica gel column and eluted with hexane/EtOAc 0% to 40%. Collected fractions were evaporated to afford 6-6 (76.0 mg, 0.123 mmol, 100%) as a yellow solid.

$^1$H-NMR (400 MHz, CDCl$_3$) δ: 1.56 (s, 18H), 1.76 (s, 3H), 3.35 (s, 3H), 3.59-3.69 (m, 2H), 4.04 (t, J=6.1 Hz, 1H), 5.19 (d, J=47.6 Hz, 1H), 7.10-7.16 (m, 1H), 7.57-7.61 (m, 1H), 8.21 (d, J=8.2 Hz, 1H), 8.40-8.35 (m, 1H), 8.43 (d, J=8.2 Hz, 1H), 8.79 (s, 1H), 9.97 (s, 1H).

Step 6: Synthesis of I-29

To a solution of 6-6 (76.0 mg, 0.123 mmol) was added formic acid (1 ml) at room temperature. After stirring for 12 h at the same temperature, the reaction mixture was treated with aqueous K$_2$CO$_3$. The aqueous layer was extracted with AcOEt and the organic layer was dried over Na$_2$SO$_4$, filtered and concentrated to afford I-29 (38.0 mg, 0.0910 mmol, 74%) as a yellow powder.

$^1$H-NMR (400 MHz, CDCl$_3$) δ: 1.67 (s, 3H), 3.36 (s, 3H), 3.55-3.66 (m, 2H), 3.96 (dt, J=29.8, 5.8 Hz, 1H), 5.16 (d, J=48.0 Hz, 1H), 7.09 (dd, J=8.8, 11.1 Hz, 1H), 7.50 (dd, J=2.8, 6.8 Hz, 1H), 8.01-8.06 (m, 1H), 8.20 (dd, J=1.8, 8.1 Hz, 1H), 8.42 (d, J=8.1 Hz, 1H), 8.90 (s, 1H), 9.85 (s, 1H).
Example 7
Synthesis of I-28
[Chemical Formula 96]
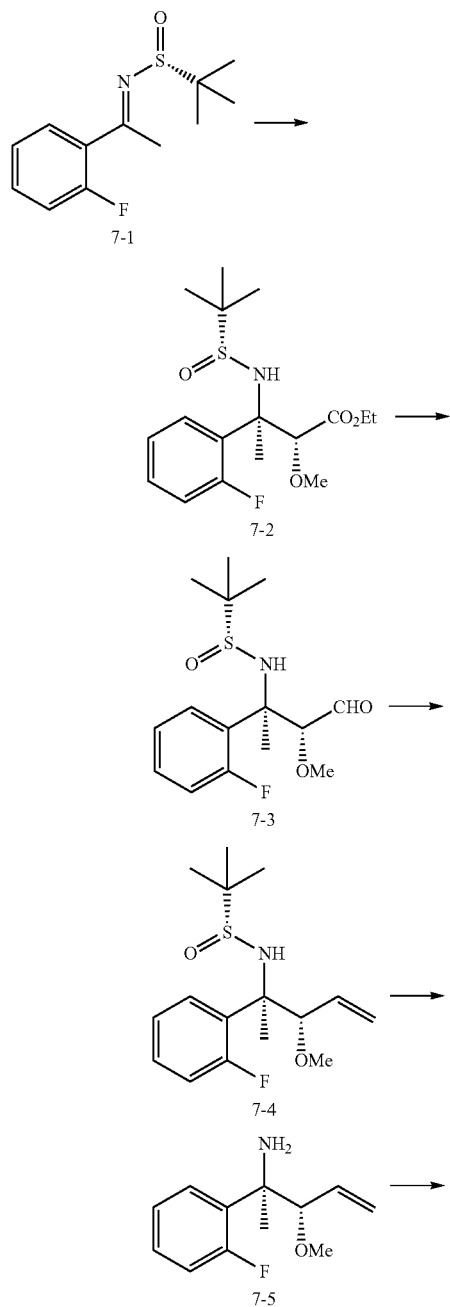
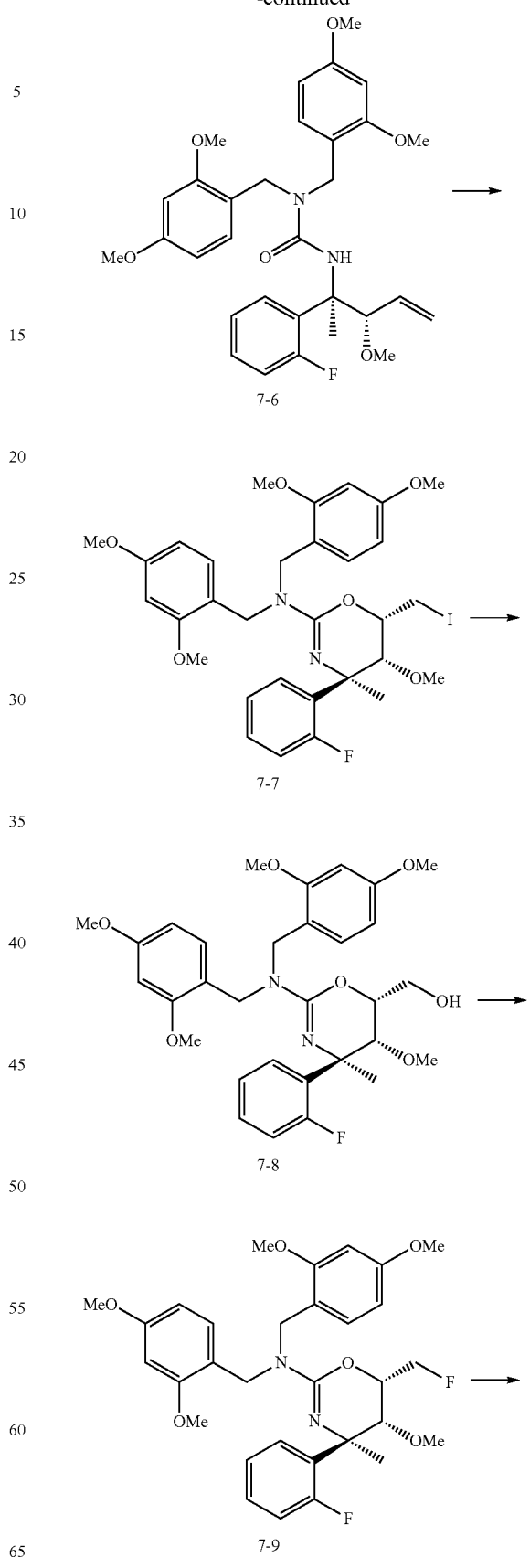

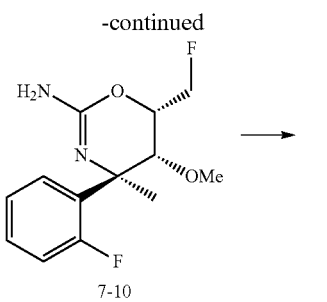

7-10

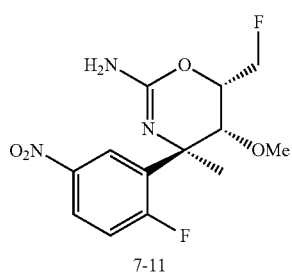

7-11

[Chemical Formula 97]

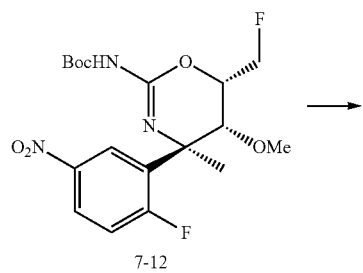

7-12

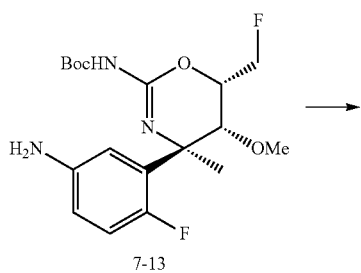

7-13

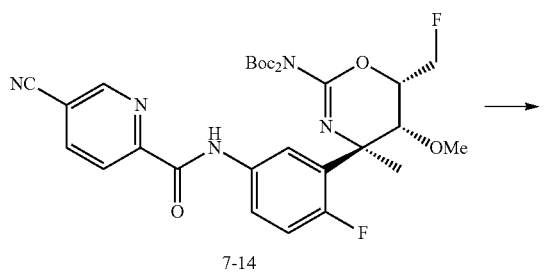

7-14

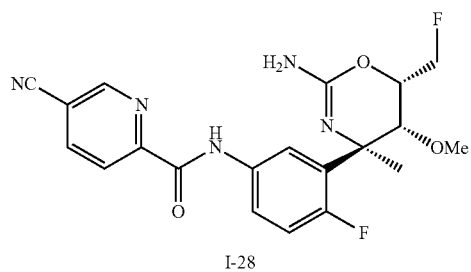

I-28

Step 1: Synthesis of Compound 7-2

To a solution of diisopropylamine (1.38 ml, 13.7 mmol) in THF (14 ml) was added 1.64 mol/L of n-BuLi (8.09 ml, 13.3 mmol) at −78° C. After stirring for 30 min at the same temperature, to the mixture was added ethyl 2-methoxyacetate (1.46 ml, 12.4 mmol), and this was stirred for 30 min followed by addition of a solution of 7-1 (1.00 g, 4.14 mmol) in THF (6 ml) at −78° C. The mixture was stirred for 1 h at the same temperature and was treated with saturated aqueous NH$_4$Cl. The aqueous layer was extracted with AcOEt, and the combined organic layer was washed with brine, dried over Na$_2$SO$_4$ and filtered. The filtrate was concentrated in vacuo. The crude product was added to a silica gel column and eluted with hexane/EtOAc 50%. Collected fractions were evaporated to afford 7-2 (1.32 g, 3.67 mmol, 89%, including diastereomer) as a yellow oil.

$^1$H-NMR (400 MHz, CDCl$_3$) δ: 1.19-1.28 (m, 12H), 1.90 (s, 3H), 3.31 (s, 3H), 4.14-4.21 (m, 2H), 4.35 (s, 1H), 4.92 (s, 1H), 6.99-7.07 (m, 1H), 7.12 (t, J=7.3 Hz, 1H), 7.33-7.27 (m, 1H), 7.45 (t, J=8.3 Hz, 1H).

Step 2: Synthesis of Compound 7-3

To a solution of 7-2 (1.32 g, 3.67 mmol) in CH$_2$Cl$_2$ (13 ml) was added 1.02 mol/L of DIBAL (11.9 ml, 12.1 mmol) in toluene at −78° C. After stirring for 15 min at the same temperature, the mixture was treated with saturated aqueous Rochelle's salt and stirred for 1.5 h. The aqueous layer was extracted with AcOEt, and the combined organic layer was washed with brine, dried over Na$_2$SO$_4$ and filtered. The filtrate was concentrated in vacuo. The crude product was added to a silica gel column and eluted with hexane/EtOAc 50% to 100%. Collected fractions were evaporated to afford 7-3 (832 mg, 2.64 mmol, 72%, including diastereomer) as a colorless oil.

$^1$H-NMR (400 MHz, CDCl$_3$) δ: 1.24 (s, 9H), 1.92 (s, 3H), 3.41 (s, 3H), 4.06 (s, 1H), 4.68 (s, 1H), 7.01-7.10 (m, 1H), 7.11-7.17 (m, 1H), 7.31 (br s, 1H), 7.40 (t, J=8.5 Hz, 1H), 9.70 (s, 1H).

Step 3: Synthesis of Compound 7-4

To a solution of methyltriphenylphosphonium bromide (2.36 g, 6.59 mmol) in toluene (20 ml) was added 1.00 mol/L of t-BuOK solution in THF (6.07 ml, 6.07 mmol) at room temperature. After stirring for 30 min at the same temperature, to the mixture was added a solution of 7-3 (832 mg, 2.64 mmol) in toluene (13 ml) at 0° C., and the mixture was stirred for 20 min at room temperature. The reaction mixture was treated with saturated aqueous NH$_4$Cl, and the aqueous layer was extracted with AcOEt. The combined organic layer was washed with brine, dried over Na$_2$SO$_4$ and filtered. The filtrate was concentrated in vacuo. The crude product was added to a silica gel column and eluted with Hexane/EtOAc 0% to 70%. Collected fractions were evaporated to afford 7-4 (390 mg, 1.24 mmol, 47%, including diastereomer) as a colorless oil.

$^1$H-NMR (400 MHz, CDCl$_3$) δ: 1.21 (s, 9H), 1.83 (s, 3H), 3.22 (s, 3H), 4.01 (d, J=7.5 Hz, 1H), 4.30 (s, 1H), 5.04-5.16 (m, 1H), 5.32-5.37 (m, 1H), 5.59-5.71 (m, 1H), 6.96-7.05 (m, 1H), 7.07-7.14 (m, 1H), 7.24-7.32 (m, 1H), 7.46-7.38 (m, 1H).

Step 4: Synthesis of Compound 7-6

To a solution of 7-4 (390 mg, 1.24 mmol) in MeOH (4 ml) was added 4 mol/L of HCl in dioxane (0.467 ml, 1.87 mmol) at room temperature. After stirring for 30 min at the same temperature, the reaction mixture was treated with aqueous NaHCO$_3$, and the aqueous layer was extracted with AcOEt. The combined organic layer was washed with H$_2$O and brine, dried over Na$_2$SO$_4$ and filtered. The filtrate was concentrated under vacuum to give 7-5 as a brown oil, which was used for the next step without purification.

To a solution of 7-5 in EtOAc (3 ml) and H$_2$O (1.5 ml) were added NaHCO$_3$ (365 mg, 4.35 mmol) and 4-nitrophenyl carbonochloridate (275 mg, 1.37 mmol) at 0° C. After stirring for 40 min at the same temperature, bis(2,4-dimethoxybenzyl)amine (434 mg, 1.37 mmol) was added to the reaction mixture. After stirring for 2 h at the same temperature, the mixture was treated with H$_2$O, and the aqueous layer was extracted with AcOEt. The organic layer was dried over Na$_2$SO$_4$, filtered and concentrated. The crude product was added to a silica gel column and eluted with hexane/EtOAc 0% to 30%. Collected fractions were evaporated to afford 7-6 (605 mg, 1.10 mmol, 88%, including diastereomer) as a white amorphous.

$^1$H-NMR (400 MHz, CDCl$_3$) δ: 1.86 (s, 3H), 3.16 (s, 3H), 3.77 (s, 6H), 3.81 (s, 6H), 3.93 (d, J=7.3 Hz, 1H), 4.33-4.47 (m, 4H), 5.01-5.13 (m, 2H), 5.30-5.41 (m, 1H), 5.64 (s, 1H), 6.42-6.48 (m, 4H), 6.90-7.00 (m, 1H), 7.01-7.07 (m, 1H), 7.15-7.19 (m, 3H), 7.30-7.23 (m, 1H).

Step 5: Synthesis of Compound 7-7

To a solution of Iodine (556 mg, 2.19 mmol) in MeCN (40 ml) was added 7-6 (605 mg, 1.10 mmol) in MeCN (20 ml) at 0° C. After stirring for 1 h at the same temperature, the reaction mixture was treated with aqueous NaHCO$_3$ and Na$_2$S$_2$O$_3$. The aqueous layer was extracted with AcOEt and the organic layer was dried over Na$_2$SO$_4$, filtered and concentrated. The crude product was added to a silica gel column and eluted with hexane/EtOAc 0% to 30%. Collected fractions were evaporated to afford 7-7 (442 mg, 0.651 mmol, 60%) as a white amorphous.

$^1$H-NMR (400 MHz, CDCl$_3$) δ: 1.63 (s, 3H), 3.15-3.26 (m, 2H), 3.71 (s, 3H), 3.73 (s, 6H), 3.81 (s, 6H), 4.06 (s, 1H), 4.52 (s, 4H), 6.40-6.48 (m, 4H), 6.96-7.07 (m, 2H), 7.27-7.17 (m, 1H), 7.39 (t, J=7.7 Hz, 1H).

Step 6: Synthesis of Compound 7-8

To a solution of 7-7 (442 mg, 0.651 mmol) in MeNO$_2$ (5 ml) and H$_2$O (2 ml) was added (2,2,2-trifluoroacetoxy)silver (576 mg, 2.61 mmol) at room temperature. After stirring for 7 h at 80° C., additional (2,2,2-trifluoroacetoxy)silver (288 mg, 1.30 mmol) was added. After stirring for 17 h, additional (2,2,2-trifluoroacetoxy)silver (288 mg, 1.30 mmol) was added. After stirring for 7 h at 80° C., the reaction mixture was treated with aqueous NaHCO$_3$, and the mixture was filtrated through a pad of Celite. The aqueous layer was extracted with AcOEt, and the organic layer was dried over Na$_2$SO$_4$, filtered and concentrated. The crude product was added to a silica gel column and eluted with hexane/EtOAc 0% to 50%. Collected fractions were evaporated to afford 7-8 (241 mg, 0.424 mmol, 65%) as a yellow oil.

$^1$H-NMR (400 MHz, CDCl$_3$) δ: 1.61 (s, 3H), 3.60-3.62 (m, 4H), 3.68-3.84 (m, 14H), 4.54 (s, 4H), 6.41-6.48 (m, 4H), 6.93-7.05 (m, 2H), 7.13-7.32 (m, 3H), 7.39 (t, J=7.8 Hz, 1H).

Step 7: Synthesis of Compound 7-9

To a solution of 7-8 (241 mg, 0.424 mmol) in CH$_2$Cl$_2$ (3 ml) was added DAST (0.187 ml, 1.27 mmol) at −78° C. After stirring for 2 h at room temperature, the reaction mixture was treated with aqueous NaHCO$_3$. The aqueous layer was extracted with AcOEt and the organic layer was dried over Na$_2$SO$_4$, filtered and concentrated. The crude product was added to a silica gel column and eluted with hexane/EtOAc 0% to 50%. Collected fractions were evaporated to afford 7-9 (117 mg, 0.205 mmol, 48%) as a white amorphous.

$^1$H-NMR (400 MHz, CDCl$_3$) δ: 1.62 (s, 3H), 3.62 (s, 3H), 3.74 (s, 6H), 3.81 (s, 6H), 3.86 (s, 1H), 3.89-4.01 (m, 1H), 4.37-4.60 (m, 6H), 6.40-6.48 (m, 4H), 6.94-7.05 (m, 2H), 7.28-7.16 (m, 3H), 7.37 (t, J=7.8 Hz, 1H).

Step 8: Synthesis of Compound 7-10

To a solution of 7-9 (117 mg, 0.205 mmol) in TFA (0.8 ml) was added anisole (0.157 ml, 1.44 mmol) at room temperature. After stirring for 14 h at 80° C., the reaction mixture was treated with aqueous K$_2$CO$_3$. The aqueous layer was extracted with AcOEt and the organic layer was dried over Na$_2$SO$_4$, filtered and concentrated. The crude product was added to a silica gel column and eluted with hexane/EtOAc 50% to 100%. Collected fractions were evaporated to afford 7-10 (21.0 mg, 0.0780 mmol, 38%) as a yellow solid.

$^1$H-NMR (400 MHz, CDCl$_3$) δ: 1.66 (s, 3H), 3.65 (s, 3H), 3.90 (s, 1H), 3.95-4.03 (m, 1H), 4.46-4.50 (m, 1H), 4.58-4.62 (m, 1H), 6.99-7.07 (m, 1H), 7.14 (t, J=7.9 Hz, 1H), 7.22-7.30 (m, 1H), 7.42 (t, J=7.9 Hz, 1H).

Step 9: Synthesis of Compound 7-12

To a solution of 7-10 (18.0 mg, 0.0670 mmol) in TFA (1 ml) was added sulfuric acid (0.248 ml, 4.66 mmol) at −20° C. After stirring for 5 min at 0° C., to the reaction mixture was added HNO$_3$ (0.00446 ml, 0.100 mmol) at −20° C. After stirring for 20 min at 0° C., the reaction mixture was treated with aqueous K$_2$CO$_3$. The aqueous layer was extracted with AcOEt and the organic layer was dried over Na$_2$SO$_4$, filtered and concentrated to afford 28 as a yellow oil that was used for the next step without purification.

To a solution of 7-11 in THF (1 ml) was added Boc$_2$O (0.0920 ml, 0.400 mmol) at room temperature. After stirring for 21 h at the same temperature, the mixture was concentrated under vacuum. The crude product was added to a silica gel column and eluted with Hexane/EtOAc 0% to 100%. Collected fractions were evaporated to afford 7-12 (14.0 mg, 0.0340 mmol, 51%) as a colorless oil.

$^1$H-NMR (400 MHz, CDCl$_3$) δ: 1.52 (s, 9H), 1.83 (s, 3H), 3.71 (s, 3H), 4.02 (s, 1H), 4.07-4.15 (m, 2H), 4.45-4.54 (m, 1H), 4.56-4.66 (m, 1H), 7.26-7.34 (m, 1H), 8.25-8.34 (m, 2H), 9.97 (br s, 1H).

Step 10: Synthesis of Compound 7-14

To a solution of 7-12 (14.0 mg, 0.0340 mmol) in EtOH (1 ml), THF (0.5 ml) and H$_2$O (0.5 ml) were added NH$_4$Cl (21.6 mg, 0.404 mmol) and Fe (15.1 mg, 0.270 mmol) at room temperature. After stirring for 1 h at 60° C., the mixture was treated with H$_2$O and filtrated through a pad of Celite. The aqueous layer was extracted with AcOEt and the organic layer was dried over Na$_2$SO$_4$, filtered and concentrated to afford 7-13 as a yellow oil, which was used for the next step without purification.

To a solution of 7-13 in DMF (1 ml) were added 5-cyanopicolinic acid hydrate (5.88 mg, 0.0350 mmol), HATU (15.4 mg, 0.0400 mmol) and DIPEA (0.0120 ml, 0.0670 mmol) at room temperature. After stirring for 40 min at the same temperature, the reaction mixture was treated with H$_2$O. The aqueous layer was extracted with AcOEt, and the organic layer was dried over Na$_2$SO$_4$, filtered and concentrated. The crude product was added to a silica gel column and eluted with hexane/EtOAc 50%. Collected fractions were evaporated to afford 7-14 (8.60 mg, 0.0170 mmol, 50%) as a yellow oil.

$^1$H-NMR (400 MHz, CDCl$_3$) δ: 1.54 (s, 9H), 1.84 (s, 3H), 3.70 (s, 3H), 4.03 (s, 1H), 4.16-4.23 (m, 1H), 4.45-4.53 (m, 1H), 4.56-4.65 (m, 1H), 7.18 (dd, J=11.4, 9.1 Hz, 1H), 7.25-7.30 (m, 1H), 8.21 (dd, J=8.2, 1.9 Hz, 1H), 8.23-8.28 (m, 1H), 8.41 (d, J=8.2 Hz, 1H), 8.92 (s, 1H), 9.80 (br s, 1H), 9.93 (s, 1H).

Step 11: Synthesis of I-28

To a solution of 7-14 (8.60 mg, 0.0170 mmol) was added formic acid (0.640 ml) at room temperature. After stirring for 20 h at the same temperature, the reaction mixture was treated with aqueous $K_2CO_3$. The aqueous layer was extracted with AcOEt, and the organic layer was dried over $Na_2SO_4$, filtered, and concentrated to afford I-28 (6.50 mg, 0.0160 mmol, 94%) as a yellow powder.

$^1$H-NMR (400 MHz, $CDCl_3$) δ: 1.69 (s, 3H), 3.66 (s, 3H), 3.95 (s, 1H), 4.04-4.12 (m, 1H), 4.48-4.53 (m, 1H), 4.60-4.64 (m, 1H), 7.11 (dd, J=9.1, 11.4 Hz, 1H), 7.45 (dd, J=2.8, 7.1 Hz, 1H), 8.04-8.09 (m, 1H), 8.20 (dd, J=1.8, 8.1 Hz, 1H), 8.42 (d, J=8.1 Hz, 1H), 8.90 (d, J=1.0 Hz, 1H), 9.87 (s, 1H).

Example 8

Synthesis of I-32

[Chemical Formula 98]

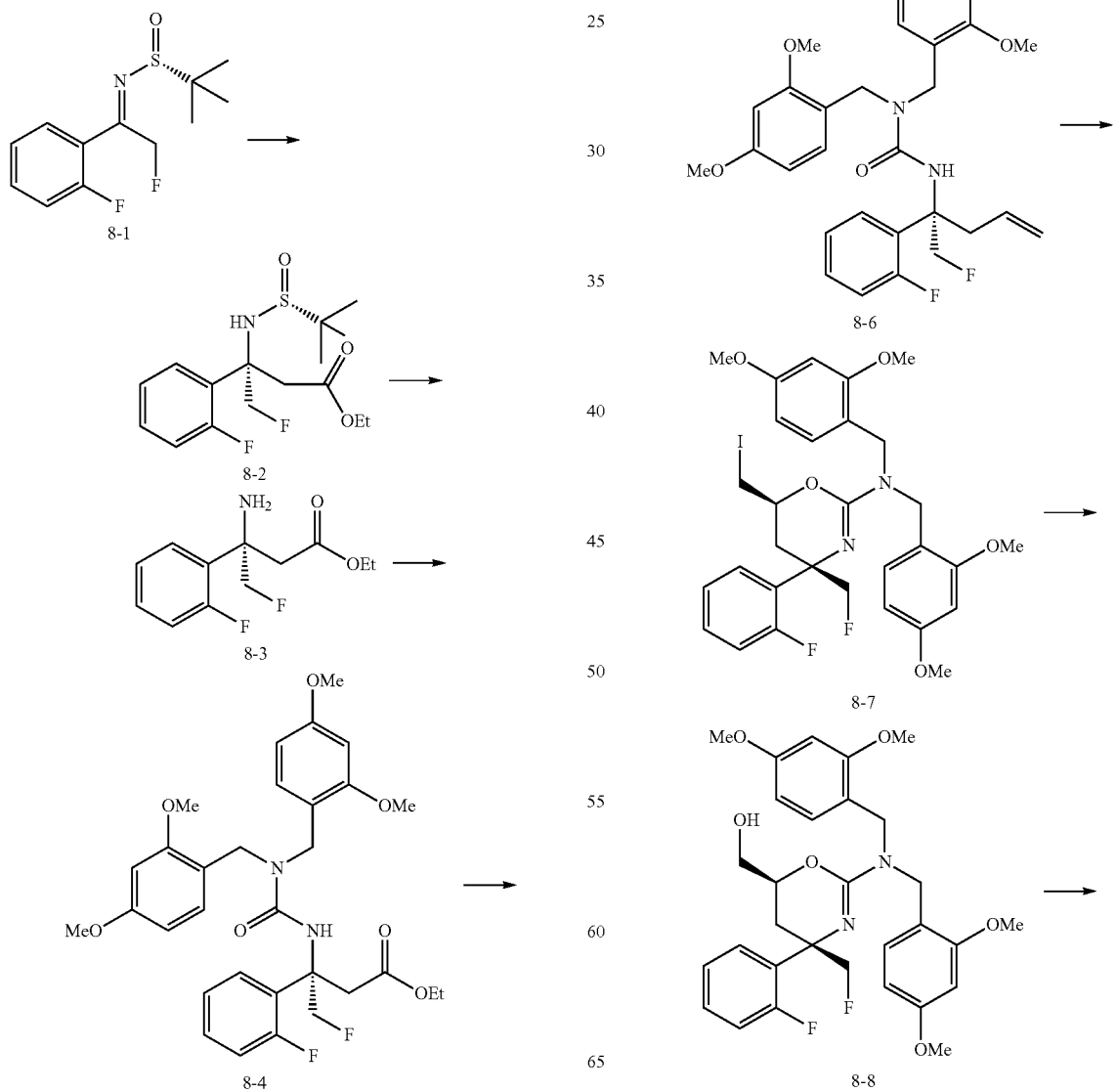

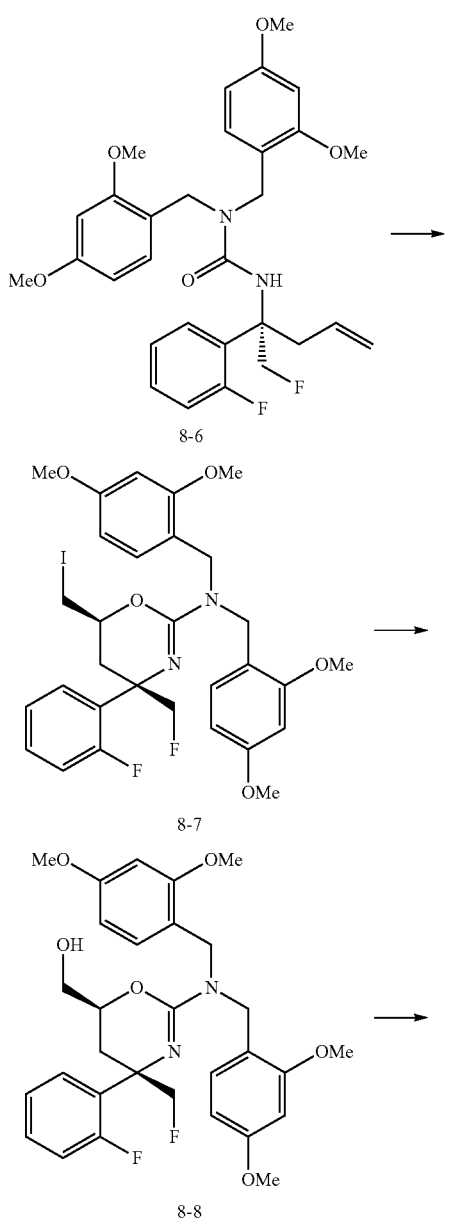

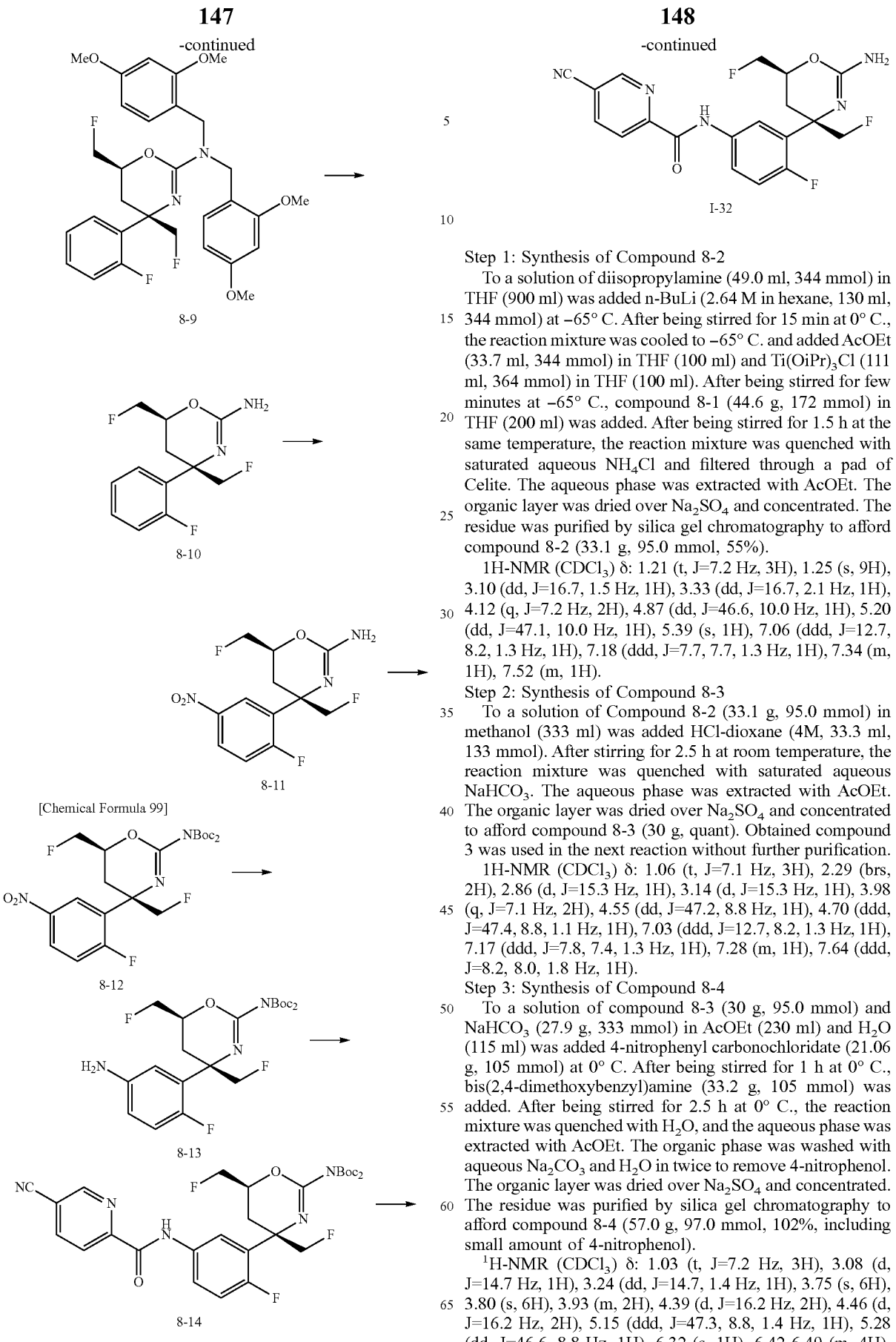

Step 1: Synthesis of Compound 8-2

To a solution of diisopropylamine (49.0 ml, 344 mmol) in THF (900 ml) was added n-BuLi (2.64 M in hexane, 130 ml, 344 mmol) at −65° C. After being stirred for 15 min at 0° C., the reaction mixture was cooled to −65° C. and added AcOEt (33.7 ml, 344 mmol) in THF (100 ml) and Ti(OiPr)$_3$Cl (111 ml, 364 mmol) in THF (100 ml). After being stirred for few minutes at −65° C., compound 8-1 (44.6 g, 172 mmol) in THF (200 ml) was added. After being stirred for 1.5 h at the same temperature, the reaction mixture was quenched with saturated aqueous NH$_4$Cl and filtered through a pad of Celite. The aqueous phase was extracted with AcOEt. The organic layer was dried over Na$_2$SO$_4$ and concentrated. The residue was purified by silica gel chromatography to afford compound 8-2 (33.1 g, 95.0 mmol, 55%).

1H-NMR (CDCl$_3$) δ: 1.21 (t, J=7.2 Hz, 3H), 1.25 (s, 9H), 3.10 (dd, J=16.7, 1.5 Hz, 1H), 3.33 (dd, J=16.7, 2.1 Hz, 1H), 4.12 (q, J=7.2 Hz, 2H), 4.87 (dd, J=46.6, 10.0 Hz, 1H), 5.20 (dd, J=47.1, 10.0 Hz, 1H), 5.39 (s, 1H), 7.06 (ddd, J=12.7, 8.2, 1.3 Hz, 1H), 7.18 (ddd, J=7.7, 7.7, 1.3 Hz, 1H), 7.34 (m, 1H), 7.52 (m, 1H).

Step 2: Synthesis of Compound 8-3

To a solution of Compound 8-2 (33.1 g, 95.0 mmol) in methanol (333 ml) was added HCl-dioxane (4M, 33.3 ml, 133 mmol). After stirring for 2.5 h at room temperature, the reaction mixture was quenched with saturated aqueous NaHCO$_3$. The aqueous phase was extracted with AcOEt. The organic layer was dried over Na$_2$SO$_4$ and concentrated to afford compound 8-3 (30 g, quant). Obtained compound 3 was used in the next reaction without further purification.

1H-NMR (CDCl$_3$) δ: 1.06 (t, J=7.1 Hz, 3H), 2.29 (brs, 2H), 2.86 (d, J=15.3 Hz, 1H), 3.14 (d, J=15.3 Hz, 1H), 3.98 (q, J=7.1 Hz, 2H), 4.55 (dd, J=47.2, 8.8 Hz, 1H), 4.70 (ddd, J=47.4, 8.8, 1.1 Hz, 1H), 7.03 (ddd, J=12.7, 8.2, 1.3 Hz, 1H), 7.17 (ddd, J=7.8, 7.4, 1.3 Hz, 1H), 7.28 (m, 1H), 7.64 (ddd, J=8.2, 8.0, 1.8 Hz, 1H).

Step 3: Synthesis of Compound 8-4

To a solution of compound 8-3 (30 g, 95.0 mmol) and NaHCO$_3$ (27.9 g, 333 mmol) in AcOEt (230 ml) and H$_2$O (115 ml) was added 4-nitrophenyl carbonochloridate (21.06 g, 105 mmol) at 0° C. After being stirred for 1 h at 0° C., bis(2,4-dimethoxybenzyl)amine (33.2 g, 105 mmol) was added. After being stirred for 2.5 h at 0° C., the reaction mixture was quenched with H$_2$O, and the aqueous phase was extracted with AcOEt. The organic phase was washed with aqueous Na$_2$CO$_3$ and H$_2$O in twice to remove 4-nitrophenol. The organic layer was dried over Na$_2$SO$_4$ and concentrated. The residue was purified by silica gel chromatography to afford compound 8-4 (57.0 g, 97.0 mmol, 102%, including small amount of 4-nitrophenol).

$^1$H-NMR (CDCl$_3$) δ: 1.03 (t, J=7.2 Hz, 3H), 3.08 (d, J=14.7 Hz, 1H), 3.24 (dd, J=14.7, 1.4 Hz, 1H), 3.75 (s, 6H), 3.80 (s, 6H), 3.93 (m, 2H), 4.39 (d, J=16.2 Hz, 2H), 4.46 (d, J=16.2 Hz, 2H), 5.15 (ddd, J=47.3, 8.8, 1.4 Hz, 1H), 5.28 (dd, J=46.6, 8.8 Hz, 1H), 6.32 (s, 1H), 6.42-6.49 (m, 4H), 7.01 (ddd, J=12.6, 8.2, 1.3 Hz, 1H), 7.10 (ddd, J=7.8, 7.4, 1.3 Hz, 1H), 7.18 (d, J=8.2 Hz, 2H), 7.25 (m, 1H), 7.36 (ddd, J=8.2, 8.0, 1.6 Hz, 1H).

Step 4: Synthesis of Compound 8-5

To a solution of compound 8-4 (27.0 g, 46.0 mmol, including small amount of 4-nitrophenol) in $CH_2Cl_2$ (270 ml) was added DIBAL (1.02 M in toluene, 149 ml, 152 mmol) at −65° C. After being stirred for 45 min at −65° C. to −60° C., the reaction mixture was quenched with AcOEt and Rochelle's salt (86 g, 304 mmol) in $H_2O$ (300 ml). After being stirred for 1 h at room temperature, the aqueous phase was extracted with AcOEt. The organic layer was dried over $Na_2SO_4$ and concentrated. The residue was purified by silica gel chromatography to afford compound 8-5 (17.5 g, 32.3 mmol, 72%, 3 steps).

$^1$H-NMR (CDCl$_3$) δ: 3.03 (ddd, J=16.4, 2.6, 2.6 Hz, 1H), 3.47 (brd, J=16.4 Hz, 1H), 3.77 (s, 6H), 3.81 (s, 6H), 4.37 (d, J=15.8 Hz, 2H), 4.47 (d, J=15.8 Hz, 2H), 4.75 (dd, J=14.1, 9.1 Hz, 1H), 4.87 (dd, J=13.8, 9.1 Hz, 1H), 6.28 (s, 1H), 6.45-6.51 (m, 4H), 7.05 (ddd, J=12.5, 8.2, 1.0 Hz, 1H), 7.11 (m, 1H), 7.18 (d, J=8.0 Hz, 2H), 7.23-7.32 (m, 2H), 9.60 (brs, 1H).

Step 5: Synthesis of Compound 8-6

To a solution of methyltriphenylphosphonium bromide (26.4 g, 74.0 mmol) in THF (240 ml) was added KHMDS (0.5 M in toluene, 139 ml, 69.3 mmol) at 0° C. After being stirred for 35 min at 0° C., compound 8-5 (12.5 g, 23.1 mmol) in THF (120 ml) was added. After being stirred for 35 min at 0° C., the reaction mixture was quenched with $H_2O$, and the aqueous phase was extracted with AcOEt. The organic layer was dried over $Na_2SO_4$ and concentrated. The residue was purified by silica gel chromatography to afford compound 8-6 (7.62 g, 14.1 mmol, 61%).

$^1$H-NMR (CDCl$_3$) δ: 2.70 (dd, J=13.8, 8.3 Hz, 1H), 2.87 (dd, J=13.8, 6.6 Hz, 1H), 3.76 (s, 6H), 3.81 (s, 6H), 4.40 (d, J=16.3 Hz, 2H), 4.44 (d, J=16.3 Hz, 2H), 4.91 (m, 1H), 5.04 (dd, J=47.3, 8.8 Hz, 1H), 5.20 (dd, J=46.7, 8.8 Hz, 1H), 5.45 (m, 2H), 6.40-6.50 (m, 4H), 7.00 (m, 1H), 7.10 (brt, J=7.4 Hz, 1H), 7.17 (d, J=8.2 Hz, 2H), 7.23 (m, 1H), 7.32 (brt, J=7.9 Hz, 1H).

Step 6: Synthesis of Compound 8-7

To a solution of iodine (1.88 g, 7.40 mmol) in acetonitrile (100 ml) was added compound 8-6 (2.0 g, 3.70 mmol) in acetonitrile (100 ml) at 0° C. After being stirred for 50 min at 0° C., the reaction mixture was quenched with saturated aqueous $NaHCO_3$ and aqueous $Na_2S_2O_3$. The aqueous phase was extracted with AcOEt. The organic layer was dried over $Na_2SO_4$ and concentrated. The residue was purified by silica gel chromatography to afford compound 8-7 (2.17 g, 3.26 mmol, 88%)

$^1$H-NMR (CDCl$_3$) δ: 1.90 (dd, J=13.3, 12.0 Hz, 1H), 2.63 (dd, J=13.3, 2.8 Hz, 1H), 3.11 (dd, J=10.5, 6.8 Hz, 1H), 3.16 (dd, J=10.5, 4.8 Hz, 1H), 3.66 (m, 1H), 3.75 (s, 6H), 3.81 (s, 6H), 4.36 (dd, J=47.4, 8.3 Hz, 1H), 4.53 (d, J=16.1 Hz, 2H), 4.58 (d, J=16.1 Hz, 2H), 4.65 (dd, J=43.7, 8.3 Hz, 1H), 6.41-6.49 (m, 4H), 6.99 (dd, J=12.2, 8.4 Hz, 1H), 7.05 (brt, J=7.5 Hz, 1H), 7.20-7.27 (m, 3H), 7.48 (brt, J=8.0 Hz, 1H).

Step 7: Synthesis of Compound 8-8

To a solution of compound 8-7 (2.34 g, 3.51 mmol) in nitromethane (24 ml) and $H_2O$ (9.6 ml) was added silver trifluoroacetate (2.94 g, 13.3 mmol) at room temperature. After being stirred for 10 h at 80° C., the reaction mixture was cooled to room temperature and quenched with saturated aqueous $NaHCO_3$. The reaction mixture was diluted with AcOEt and filtered through a pad of Celite. The aqueous phase was extracted with AcOEt. The organic layer was dried over $Na_2SO_4$ and concentrated. The residue was purified by silica gel chromatography to afford compound 8-8 (1.77 g, 3.18 mmol, 90%).

$^1$H-NMR (CDCl$_3$) δ: 2.02 (dd, J=13.6, 12.5 Hz, 1H), 2.33 (dd, J=13.6, 2.4 Hz, 1H), 3.43 (dd, J=12.3, 5.0 Hz, 1H), 3.60 (dd, J=12.3, 2.5 Hz, 1H), 3.77 (s, 6H), 3.78 (m, 1H), 3.81 (s, 6H), 4.41 (d, J=15.7 Hz, 2H), 4.42 (dd, J=47.4, 8.3 Hz, 1H), 4.66 (dd, J=47.7, 8.3 Hz, 1H), 4.71 (d, J=15.7 Hz, 2H), 6.43-6.50 (m, 4H), 6.98 (dd, J=12.3, 8.3 Hz, 1H), 7.03 (brt, J=7.5 Hz, 1H), 7.19-7.28 (m, 3H), 7.45 (brt, J=7.9 Hz, 1H).

Step 8: Synthesis of Compound 8-9

To a solution of compound 8-8 (1.69 g, 3.04 mmol) in $CH_2Cl_2$ (17 ml) was added DAST (1.203 ml, 9.11 mmol) at −78° C. After being stirred for 4.5 h at room temperature, the reaction mixture was quenched with saturated aqueous $NaHCO_3$ at 0° C. The aqueous phase was extracted with AcOEt. The organic layer was dried over $Na_2SO_4$ and concentrated. The residue was purified by silica gel chromatography to afford compound 8-9 (1.34 g, 2.40 mmol, 79%).

$^1$H-NMR (CDCl$_3$) δ: 2.01 (dd, J=13.4, 12.7 Hz, 1H), 2.41 (d, J=13.4 Hz, 1H), 3.75 (s, 6H), 3.82 (s, 6H), 3.93 (m, 1H), 4.23-4.75 (m, 8H), 6.41-6.49 (m, 4H), 7.00 (dd, J=12.3, 8.3 Hz, 1H), 7.05 (brt, J=7.5 Hz, 1H), 7.18-7.29 (m, 3H), 7.48 (brt, J=7.9 Hz, 1H).

Step 9: Synthesis of Compound 8-10

To a mixture of compound 8-9 (1.34 g, 2.40 mmol) and anisole (1.83 ml, 16.8 mmol) was added TFA (9.24 ml, 120 mmol) at room temperature. After being stirred for 15.5 h at 80° C., the reaction mixture was cooled to 0° C. and poured into 2M aqueous NaOH. The aqueous phase was extracted with AcOEt. The organic layer was dried over $Na_2SO_4$ and concentrated. The residue was purified by silica gel chromatography to afford compound 8-10 (663 mg, quant.).

$^1$H-NMR (CDCl$_3$) δ: 2.24 (dd, J=13.9, 12.2 Hz, 1H), 2.49 (d, J=13.9 Hz, 1H), 4.09 (m, 1H), 4.35-4.85 (m, 4H), 7.08 (dd, J=12.2, 8.4 Hz, 1H), 7.22 (brt, J=7.6 Hz, 1H), 7.35 (m, 1H), 7.50 (brt, J=8.1 Hz, 1H).

Step 10: Synthesis of Compound 8-11

To a solution of compound 8-10 (663 mg, 2.40 mmol) in TFA (5 ml) was added $H_2SO_4$ (1.25 ml) at −20° C. After being stirred for 5 min at 0° C., the reaction mixture was cooled to −20° C. and HNO$_3$ (161 μl, 3.60 mmol) was added. After being stirred for 30 min at 0° C., the reaction mixture was quenched with saturated aqueous $NaHCO_3$. The aqueous phase was extracted with AcOEt. The organic layer was dried over $Na_2SO_4$ and concentrated. The residue was purified by silica gel chromatography to afford compound 8-11 (766 mg, quant.).

$^1$H-NMR (CDCl$_3$) δ: 2.10 (dd, J=13.9, 12.4 Hz, 1H), 2.45 (d, J=13.9 Hz, 1H), 3.97 (m, 1H), 4.22-4.88 (m, 6H), 7.23 (dd, J=10.5, 8.9 Hz, 1H), 8.23 (m, 1H), 8.52 (brd, J=6.4 Hz, 1H).

Step 11: Synthesis of Compound 8-12

To a solution of compound 8-11 (796 mg, 2.53 mmol) and DMAP (183 mg, 1.50 mmol) in $CH_2Cl_2$ (8 ml) was added Boc$_2$O (2.15 ml, 9.25 mmol) at room temperature. After being stirred for 3 h at room temperature, the reaction mixture was concentrated. The residue was purified by silica gel chromatography to afford compound 8-12 which was then triturated from AcOEt/hexane to give compound 8-12 (972 mg, 1.93 mmol, 76%, 3 steps).

$^1$H-NMR (CDCl$_3$) δ: 1.53 (s, 18H), 2.26 (dd, J=14.1, 12.5 Hz, 1H), 2.53 (d, J=14.1 Hz, 1H), 4.08 (m, 1H), 4.39-4.78 (m, 4H), 7.26 (m, 1H), 8.26 (m, 1H), 8.63 (m, 1H).

Step 12: Synthesis of Compound 8-13

To a solution of compound 8-12 (972 mg, 1.93 mmol) and NH$_4$Cl (1.24 g, 23.2 mmol) in EtOH (10 ml), THF (5 ml)

and H₂O (5 ml) was added Fe (862 mg, 15.4 mmol) at room temperature. After being stirred for 2 h at 60° C., the reaction mixture was cooled to 0° C. and quenched with H₂O. The reaction mixture was diluted with AcOEt and filtered through a pad of Celite. The aqueous phase was extracted with AcOEt. The organic layer was dried over Na₂SO₄ and concentrated. The residue was purified by silica gel chromatography to afford compound 8-13 (880 mg, 1.86 mmol, 96%).

¹H-NMR (CDCl₃) δ: 1.53 (s, 18H), 2.20 (dd, J=13.7, 12.7 Hz, 1H), 2.45 (d, J=13.7 Hz, 1H), 3.58 (s, 2H), 4.16 (m, 1H), 4.36-4.86 (m, 4H), 6.57 (m, 1H), 6.85 (m, 1H), 6.93 (m, 1H).

Step 13: Synthesis of Compound 8-14

To a solution of compound 8-13 (43 mg, 91 μmol), 5-cyanopicolinic acid hydrate (18.1 mg, 109 μmol) and diisopropylethylamine (32 μl, 182 μmol) in DMF (1 ml) was added HATU (41.4 mg, 109 μmol) at room temperature. After being stirred for 1 h at room temperature, the reaction mixture was quenched with H₂O. The aqueous phase was extracted with AcOEt, and the organic phase was washed with H₂O. The organic layer was dried over Na₂SO₄ and concentrated. The residue was purified by silica gel chromatography to afford compound 8-14 (58.3 mg, quant.).

¹H-NMR (CDCl₃) δ: 1.57 (s, 18H), 2.27 (dd, J=13.7, 12.7 Hz, 1H), 2.47 (d, J=13.7 Hz, 1H), 4.15 (m, 1H), 4.36-4.92 (m, 4H), 7.14 (brt, J=10.2 Hz, 1H), 7.62 (brd, J=6.3 Hz, 1H), 8.22 (d, J=8.0 Hz, 1H), 8.41 (m, 1H), 8.43 (d, J=8.0 Hz, 1H), 8.79 (s, 1H), 10.00 (s, 1H).

Step 14: Synthesis of Compound I-32

Compound 8-14 (58.3 mg, 91 mol) was dissolved in formic acid (1 ml) and stirred for 16 h at room temperature. The reaction mixture was quenched with saturated aqueous NaHCO₃, and the aqueous phase was extracted with AcOEt. The organic layer was dried over Na₂SO₄ and concentrated. The residue was triturated from AcOEt/hexane to give compound I-32 (26.8 mg, 66 mol, 73%, 2 steps).

¹H-NMR (CDCl₃) δ: 2.08 (dd, J=13.7, 12.7 Hz, 1H), 2.44 (d, J=13.7 Hz, 1H), 4.03 (m, 1H), 4.20-4.80 (m, 6H), 7.11 (dd, J=11.6, 8.7 Hz, 1H), 7.57 (brd, J=6.6 Hz, 1H), 8.09 (m, 1H), 8.21 (d, J=8.1 Hz, 1H), 8.43 (d, J=8.1 Hz, 1H), 8.91 (s, 1H), 9.89 (s, 1H).

Example 9

Synthesis of I-56

[Chemical Formula 100]

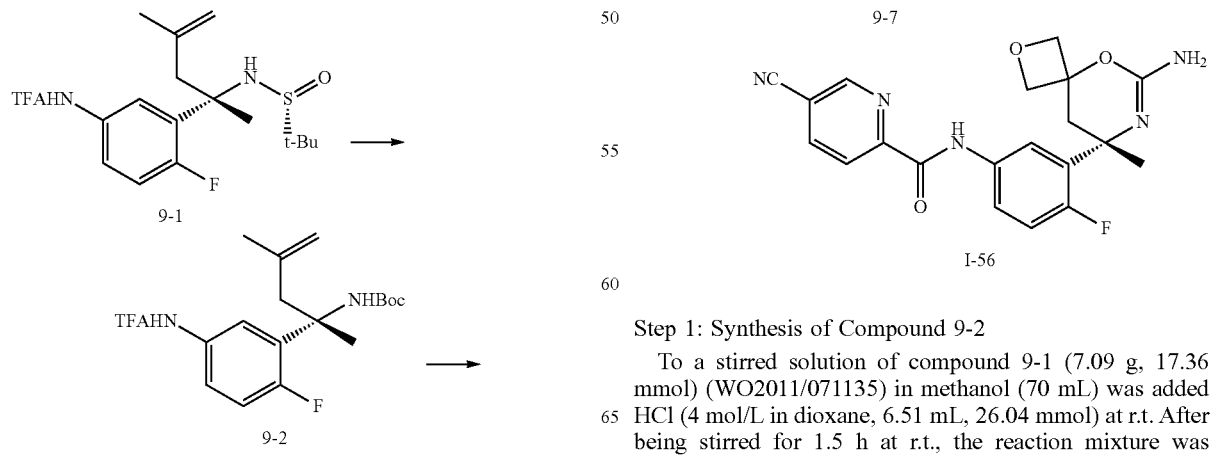

Step 1: Synthesis of Compound 9-2

To a stirred solution of compound 9-1 (7.09 g, 17.36 mmol) (WO2011/071135) in methanol (70 mL) was added HCl (4 mol/L in dioxane, 6.51 mL, 26.04 mmol) at r.t. After being stirred for 1.5 h at r.t., the reaction mixture was quenched with NaOH aq. (2 mol/L) and extracted with dichloromethane. The organic layer was dried over $Na_2SO_4$, filtered and concentrated. The crude product was used for the next reaction without further purification.

To a stirred solution of the crude product in tetrahydrofuran (50 ml) was added $Boc_2O$ (5.34 mL, 24.74 mmol) at r.t. under nitrogen. After being stirred for 6 h at reflux, the reaction mixture was cooled to r.t. and concentrated.

The crude product was added to a silica gel column and eluted with hexane/ethyl acetate=5/1. Collected fractions were triturated with hexane. The resulting solid was filtered through a coarse fritted glass funnel, rinsed with hexane, and collected to afford compound 9-2 (4.56 g, 11.28 mmol, 68% over 2 steps) as a white solid.

$^1$H NMR (400 MHz, $CDCl_3$) δ: 1.40 (s, 9H), 1.47 (s, 3H), 1.80 (s, 3H), 2.56 (d, J=13.4 Hz, 1H), 2.84 (d, J=13.4 Hz, 1H), 4.77 (s, 1H), 4.94 (s, 1H), 5.18 (brs, 1H), 7.03 (t, J=10.2 Hz, 1H), 7.43 (d, J=6.3 Hz, 1H), 7.49 (s, 1H), 7.90 (s, 1H).

Step 2: Synthesis of Compound 9-3

To a stirred solution of compound 9-2 (4.56 g, 11.28 mmol) in dichloromethane (230 mL) were added $MgSO_4$ (2.04 g, 16.92 mmol), $SeO_2$ (0.626 g, 5.64 mmol) and TBHP (5.5 mol/L in decane, 4.10 mL, 22.56 mmol) at r.t. under $N_2$. After being stirred for 7 h at r.t., the reaction mixture was quenched with sat. $NaHCO_3$ and extracted with dichloromethane. The organic layer was dried over $Na_2SO_4$, filtered and concentrated. The crude product was added to a silica gel column and eluted with hexane/ethyl acetate=2/1. Collected fractions were evaporated to afford compound 9-3 (1.42 g, 3.38 mmol, 30%) as a white amorphous.

$^1$H NMR (400 MHz, $CDCl_3$) δ: 1.40 (s, 9H), 1.80 (s, 3H), 2.60 (d, J=14.1 Hz, 1H), 2.95 (d, J=14.1 Hz, 1H), 3.87-3.94 (m, 2H), 4.84 (s, 1H), 5.18 (s, 1H), 5.82 (s, 1H), 7.05 (t, J=10.0 Hz, 1H), 7.43 (d, J=7.3 Hz, 1H), 7.49-7.52 (m, 1H), 7.85 (s, 1H).

Step 3: Synthesis of Compound 9-4

To a stirred solution of compound 9-3 in dichloromethane (28 mL) were added $Ac_2O$ (0.383 mL, 4.05 mmol), triethylamine (0.562 ml, 4.05 mmol) and DMAP (83.0 mg, 0.676 mmol) at r.t. under $N_2$. After being stirred for 2.5 h at r.t., the reaction mixture was quenched with $H_2O$ and extracted with dichloromethane. The organic layer was dried over $Na_2SO_4$, filtered and concentrated. The crude product was used for the next reaction without further purification.

To a stirred solution of the crude product in dichloromethane (22 mL) was added TFA (3.75 mL, 48.7 mmol) at r.t. under $N_2$. After being stirred for 2 h at r.t., the reaction mixture was quenched with sat. $NaHCO_3$ and extracted with dichloromethane. The organic layer was dried over $Na_2SO_4$, filtered and concentrated. The crude product was used for the next reaction without further purification.

To a stirred solution of the crude product in tetrahydrofuran (24 mL) was added benzoyl isocyanate (0.475 mL, 3.40 mmol) in tetrahydrofuran (5 mL) at r.t. under $N_2$. After being stirred for 20 min at r.t., the reaction mixture was concentrated. The crude product was added to a silica gel column and eluted with hexane/ethyl acetate=2/1. Collected fractions were evaporated to afford compound 9-4 (1.35 g, 2.65 mmol, 78% over 3 steps) as a white amorphous.

$^1$H NMR (400 MHz, $CDCl_3$) δ: 1.99 (s, 3H), 2.04 (s, 3H), 2.77 (d, J=13.7 Hz, 1H), 3.07 (d, J=13.7 Hz, 1H), 4.12 (dd, J=19.4, 13.1 Hz, 2H), 5.21 (s, 1H), 5.28 (s, 1H), 6.95 (t, J=10.0 Hz, 1H), 7.35 (t, J=7.4 Hz, 2H), 7.41-7.52 (m, 3H), 7.83 (d, J=7.7 Hz, 2H), 8.15 (s, 1H), 9.08 (brs, 1H), 9.45 (s, 1H).

Step 4: Synthesis of Compound 9-5

To a stirred solution of the compound 9-4 (1.35 g, 2.65 mmol) in methanol (27 mL) was added sodium methoxide (28% in methanol, 0.562 g, 2.65 mmol) at r.t. After being stirred for 2.5 h at r.t., the reaction mixture was quenched with $H_2O$ and extracted with ethyl acetate. The organic layers were combined and washed with brine. The organic layer was dried over $Na_2SO_4$, filtered and concentrated. The crude product was used for the next reaction without further purification.

To a stirred solution of the crude product in dichloromethane (25 mL) were added NBS (1.42 g, 7.96 mmol) at 0° C. under $N_2$. After being stirred for 1 h at r.t., the reaction mixture was quenched with sat. $Na_2S_2O_3$ and extracted with dichloromethane. The organic layer was dried over $Na_2SO_4$, filtered and concentrated. The crude product was added to a silica gel column and eluted with hexane/ethyl acetate=2/1 to 1/1. Collected fractions were evaporated to afford compound 9-5 (1.38 g, 2.53 mmol, 95% over 2 steps, dr=2:1) as a white amorphous.

$^1$H NMR (400 MHz, $CDCl_3$) δ: 1.76 (s, 2H), 1.81 (s, 1H), 2.27 (d, J=15.4 Hz, 1/3H), 2.44 (d, J=14.3 Hz, 2/3H), 2.78 (d, J=10.5 Hz, 1/3H), 3.08 (d, J=14.3 Hz, 2/3H), 3.30-3.44 (m, 8/3H), 3.70 (d, J=10.4 Hz, 2/3H), 3.82 (d, J=10.4 Hz, 2/3H), 6.98-7.04 (m, 1H), 7.39-7.54 (m, 3H), 8.13 (d, J=7.5 Hz, 4/3H), 8.19 (d, J=7.9 Hz, 2/3H), 8.31 (s, 1/3H), 8.43 (s, 2/3H).

Step 5: Synthesis of Compound 9-6

To a stirred solution of compound 9-5 (1.38 g, 2.53 mmol) in DMF (40 mL) was added t-BuOK (1.13 g, 10.1 mmol) at r.t. under $N_2$. After being stirred for 30 min at r.t., the reaction mixture was quenched with sat. $NH_4Cl$, and extracted with ethyl acetate. The organic layers were combined and washed with brine. The organic layer was dried over $Na_2SO_4$, filtered and concentrated. The crude product was added to a silica gel column and eluted with hexane/ethyl acetate=2/1. Collected fractions were evaporated to afford compound 9-6 (1.13 g, 1.97 mmol, 78%) as a white amorphous.

$^1$H NMR (400 MHz, $CDCl_3$) δ: 1.82 (s, 3H), 2.31 (d, J=14.1 Hz, 1H), 3.37 (d, J=14.1 Hz, 1H), 3.66 (d, J=7.3 Hz, 1H), 4.24 (d, J=7.3 Hz, 1H), 4.62 (d, J=7.3 Hz, 1H), 4.95 (d, J=7.3 Hz, 1H), 7.17-7.22 (m, 2H), 7.43-7.47 (m, 2H), 7.53 (d, J=7.0 Hz, 1H), 8.11-8.13 (m, 1H), 8.22 (d, J=7.5 Hz, 2H), 8.95 (s, 1H), 11.8 (s, 1H).

Step 6: Synthesis of Compound 9-7

To a stirred solution of compound 9-6 (429 mg, 0.922 mmol) in methanol (12 mL) was added $K_2CO_3$ (382 mg, 2.77 mmol) at r.t. After being stirred for 17 h at r.t., $H_2O$ (6 ml) was added and stirred for 24 h at r.t. The reaction mixture was diluted with ethyl acetate and extracted with ethyl acetate. The organic layers were combined and washed with brine. The organic layer was dried over $MgSO_4$, filtered and concentrated. The crude product was added to a silica gel column and eluted with chloroform/methanol=100/0 to 96/4. Collected fractions were evaporated to afford compound 9-7 (174 mg, 0.656 mmol, 71%) as a white solid.

$^1$H NMR (400 MHz, $CDCl_3$) δ: 1.54 (s, 3H), 2.00 (d, J=14.6 Hz, 1H), 2.97 (d, J=14.6 Hz, 1H), 3.51 (s, 2H), 3.82 (d, J=7.5 Hz, 1H), 4.11 (brs, 1H), 4.17 (d, J=7.5 Hz, 1H), 4.59 (d, J=7.3 Hz, 1H), 4.67 (d, J=7.3 Hz, 1H), 6.48-6.50 (m, 1H), 6.66-6.68 (m, 1H), 6.80 (t, J=10.2 Hz, 1H).

Step 7: Synthesis of Compound I-56

To a stirred solution of compound 9-7 (17.0 mg, 0.064 mmol) in methanol (0.5 mL) were added HCl aq. (2 mol/L, 0.032 ml, 0.064 mmol), 5-cyanopicolinic acid hydrate (11.2 mg, 0.067 mmol) and water-soluble carbodiimide hydrochloride (14.7 mg, 0.077 mmol) at r.t. After being stirred for 20 min at r.t., the reaction mixture was quenched with NaOH aq. (2 mol/L) and extracted with dichloromethane. The organic layer was dried over Na₂SO₄, filtered and concentrated. The crude product was added to an amino silica gel column and eluted with ethyl acetate. Collected fractions were evaporated to afford I-56 (17.7 mg, 0.045 mmol, 70%) as a white solid.

$^1$H NMR (400 MHz, CDCl₃) δ: 1.59 (s, 3H), 2.17 (d, J=13.6 Hz, 1H), 2.93 (d, J=13.6 Hz, 1H), 3.86 (d, J=7.4 Hz, 1H), 4.23 (d, J=7.4 Hz, 1H), 4.64 (d, J=7.4 Hz, 1H), 4.70 (d, J=7.4 Hz, 1H), 7.09 (t, J=10.0 Hz, 1H), 7.49 (d, J=6.7 Hz, 1H), 7.97-8.00 (m, 1H), 8.21 (d, J=7.9 Hz, 1H), 8.43 (d, J=7.9 Hz, 1H), 8.90 (s, 1H), 9.83 (s, 1H).

Example 10

Synthesis of I-65

[Chemical Formula 101]

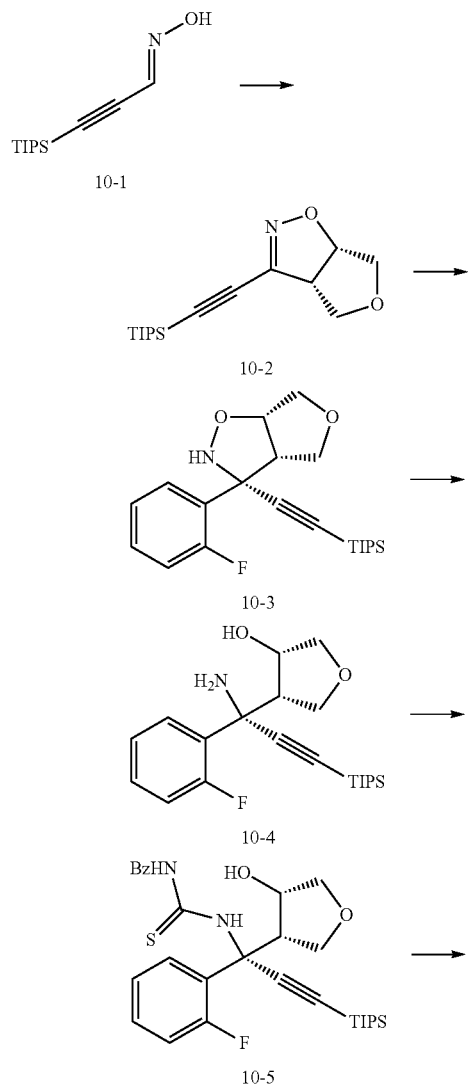

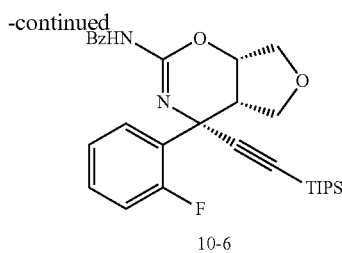

Step 1: Synthesis of Compound 10-2

To a stirred suspension of NCS (592 mg, 4.44 mmol) and pyridine (35.1 mg, 0.444 mmol) in chloroform (5 mL) was added compound 10-1 (1.00 g, 4.44 mmol) in chloroform (2 mL) at room temperature under nitrogen. The reaction mixture was stirred at the same temperature for 20 min, and then 2,5-dihydrofuran (389 mg, 5.55 mmol) was added followed by dropwise addition of triethylamine (471 mg, 4.66 mmol) in chloroform (23 mL). After being stirred for 3 h at the same temperature, the reaction mixture was diluted with H₂O and extracted with chloroform. The organic layers were combined, dried over MgSO₄, filtered and concentrated. The residue was added to a silica gel column and eluted with hexane/ethyl acetate 5% to 15%. Collected fractions were evaporated to afford racemate 10-2 (627 mg, 2.14 mmol, 48%) as an orange oil.

$^1$H-NMR (400 MHz, CDCl₃) δ: 1.07-1.16 (m, 21H), 3.65-3.72 (m, 2H), 3.90 (dd, J=9.3, 6.0 Hz, 1H), 4.26 (dd, J=10.0, 4.5 Hz, 2H), 5.30 (dd, J=9.3, 4.0 Hz, 1H).

Step 2: Synthesis of Compound 10-3

To a stirred solution of 1-bromo-2-fluorobenzene (824 mg, 4.71 mmol) in tetrahydrofuran (4.4 mL) and toluene (17 mL) were added dropwise n-BuLi (1.75 mL, 4.71 mmol, 2.69 mol/L solution in hexane) and boron trifluoride etherate (334 mg, 2.35 mmol) at −78° C. Racemate 10-2 (691 mg, 2.35 mmol) in toluene (14 mL) was added dropwise to the reaction mixture at the same temperature over 30 min. After being stirred for 80 min at same temperature, the reaction mixture was quenched with sat. NH₄Cl and extracted with ethyl acetate. The organic layers were washed with brine and combined. The organic layer was dried over MgSO₄, filtered and concentrated. The residue was added to a silica gel column and eluted with hexane/ethyl acetate 0% to 10%. Collected fractions were evaporated to afford racemate 10-3 (409 mg, 1.05 mmol, 45%) as an orange oil.

$^1$H-NMR (400 MHz, CDCl₃) δ: 1.02-1.12 (m, 21H), 3.46 (tt, J=6.7, 2.0 Hz, 1H), 3.63 (dd, J=10.8, 3.8 Hz, 1H), 3.77 (dd, J=10.0, 6.7 Hz, 1H), 4.19 (d, J=10.8 Hz, 1H), 4.70 (dd, J=6.7, 3.8 Hz, 1H), 4.80 (d, J=10.0 Hz, 1H), 5.86 (s, 1H), 7.06 (ddd, J=11.3, 8.2, 1.1 Hz, 1H), 7.14 (td, J=7.7, 1.3 Hz, 1H), 7.25-7.30 (m, 1H), 7.71 (td, J=8.0, 1.8 Hz, 1H).

Step 3: Synthesis of Compound 10-4

To a stirred solution of racemate 10-3 (502 mg, 1.27 mmol) in tetrahydrofuran (5 mL) was added lithium aluminum hydride (97 mg, 2.55 mmol) at 0° C. After being stirred for 80 min at r.t., the reaction mixture was quenched with aq. NaOH and filtered. The filtrate was extracted with ethyl acetate. The organic layers were combined, dried over MgSO₄, filtered and concentrated. The residue was added to a silica gel column and eluted with hexane/ethyl acetate 20% to 33%. Collected fractions were evaporated to afford racemate 10-4 (476 mg, 1.20 mmol, 94%) as a white solid.

$^1$H-NMR (400 MHz, CDCl₃) δ: 0.98-1.14 (m, 21H), 2.45 (br s, 1H), 2.96 (dd, J=13.8, 9.0 Hz, 1H), 3.81-3.87 (m, 2H), 4.01 (t, J=8.4 Hz, 1H), 4.12 (t, J=9.4 Hz, 1H), 4.19 (s, 1H), 7.10 (t, J=10.3 Hz, 1H), 7.18 (t, J=7.8 Hz, 1H), 7.33 (dd, J=12.5, 7.0 Hz, 1H), 7.73 (t, J=7.8 Hz, 1H).

Step 4: Synthesis of Compound 10-5

To a stirred solution of racemate 10-4 (362 mg, 0.923 mmol) in MeOH (4 mL) was added benzoyl isothiocyanate (161 mg, 0.969 mmol) at 0° C. After being stirred for 90 min at r.t., the reaction mixture was concentrated. The residue was added to a silica gel column and eluted with hexane/ ethyl acetate 10% to 25%. Collected fractions were evaporated to afford racemate 10-5 (392 mg, 0.700 mmol, 76%) as a white solid.

$^1$H-NMR (400 MHz, CDCl$_3$) δ: 1.13-1.20 (m, 21H), 3.27-3.35 (m, 2H), 3.65 (t, J=8.7 Hz, 1H), 3.95 (d, J=2.5 Hz, 2H), 4.16 (t, J=9.0 Hz, 1H), 4.67-4.71 (m, 1H), 7.01 (ddd, J=12.4, 8.2, 1.2 Hz, 1H), 7.17 (td, J=7.7, 1.2 Hz, 1H), 7.31 (tt, J=9.4, 3.1 Hz, 1H), 7.51 (t, J=7.7 Hz, 2H), 7.62 (tt, J=7.4, 1.2 Hz, 1H), 7.82-7.88 (m, 3H), 8.86 (s, 1H), 11.96 (s, 1H).

Step 5: Synthesis of Compound 10-6

To a stirred suspension of racemate 10-5 (390 mg, 0.697 mmol) in acetonitrile (8 mL) was added EDC hydrochloride (267 mg, 1.39 mmol) at r.t. After being stirred for 15 h at same temperature, the reaction mixture was diluted with H$_2$O and extracted with ethyl acetate. The organic layers were washed with brine and combined. The organic layer was dried over MgSO$_4$, filtered and concentrated. The residue was added to a silica gel column and eluted with hexane/ethyl acetate 10% to 25%. Collected fractions were evaporated to afford racemate 10-6 (345 mg, 0.658 mmol, 94%) as a colorless amorphous.

$^1$H-NMR (400 MHz, CDCl$_3$) δ: 1.06 (s, 21H), 3.44 (dd, J=13.2, 8.8 Hz, 1H), 4.00 (d, J=10.8 Hz, 1H), 4.21 (t, J=9.4 Hz, 1H), 4.31 (d, J=10.8 Hz, 1H), 4.38 (t, J=8.8 Hz, 1H), 4.62 (s, 1H), 7.14-7.20 (m, 2H), 7.37-7.53 (m, 5H), 8.26 (d, J=7.5 Hz, 2H), 11.84 (s, 1H).

[Chemical Formula 102]

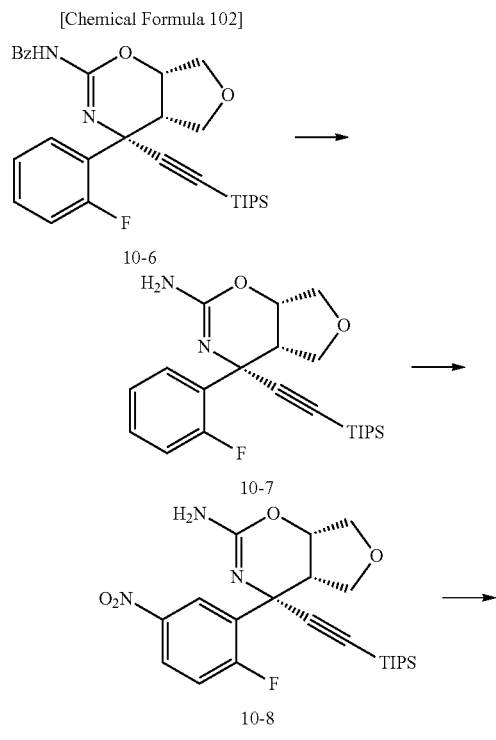

Step 6: Synthesis of Compound 10-7

To a stirred suspension of racemate 10-6 (21.5 g, 40.5 mmol) in MeOH (470 mL) was added K$_2$CO$_3$ (16.79 g, 122 mmol) at r.t. After being stirred for 5 h at 50° C., the reaction mixture was stirred for 14.5 h at r.t. After being stirred for 4 h at 50° C., the reaction mixture was concentrated and diluted with H$_2$O. The mixture was extracted with chloroform. The organic layers were combined, dried over MgSO$_4$, filtered and concentrated. The residue was triturated with hexane until a white solid was appeared. The slurry was filtered to afford racemate 10-7 (15.3 g, 36.7 mmol, 91%) as a white solid.

$^1$H-NMR (400 MHz, CDCl$_3$) δ: 1.04 (s, 21H), 3.24 (dt, J=14.0, 4.9 Hz, 1H), 3.86 (d, J=10.0 Hz, 1H), 4.01 (d, J=10.0 Hz, 1H), 4.09 (t, J=9.4 Hz, 1H), 4.23-4.33 (m, 4H), 7.07 (dd, J=11.5, 8.0 Hz, 1H), 7.13 (t, J=7.3 Hz, 1H), 7.29 (t, J=8.9 Hz, 16H), 7.46 (t, J=8.0 Hz, 1H).

Step 7: Synthesis of Compound 10-8

To a stirred solution of racemate 10-7 (253 mg, 0.608 mmol) in TFA (1.5 mL)/H$_2$SO$_4$ (0.38 mL) was added dropwise HNO$_3$ (0.040 mg, 0.911 mmol) at −20° C.

After being stirred for 5 min at same temperature, the reaction mixture was quenched with aq. K$_2$CO$_3$ and then extracted with ethyl acetate. The organic layer was washed with brine and combined. The organic layer was dried over MgSO$_4$, filtered and concentrated. The crude compound 10-8 (280 mg, 0.599 mmol, 99%) was used for the next reaction without further purification.

$^1$H-NMR (400 MHz, CDCl$_3$) δ: 1.05 (s, 21H), 3.18 (td, J=9.3, 4.4 Hz, 1H), 3.91 (dd, J=10.5, 2.7 Hz, 1H), 4.06 (d, J=10.4 Hz, 1H), 4.11 (t, J=9.3 Hz, 1H), 4.26 (t, J=3.1 Hz, 1H), 4.32 (t, J=8.7 Hz, 1H), 4.37 (br s, 2H), 7.24 (t, J=9.5 Hz, 1H), 8.22 (dt, J=8.7, 3.4 Hz, 1H), 8.47 (dd, J=6.8, 2.7 Hz, 1H).

Step 8: Synthesis of Compound 10-9

To a stirred solution of racemate 10-8 (279 mg, 0.597 mmol) in dichloromethane (3 mL) were added Boc$_2$O (325 mg, 1.49 mmol) and DMAP (14.6 mg, 0.119 mmol) at r.t. After being stirred for 1 h at same temperature, the reaction mixture was concentrated. The residue was added to a silica gel column and eluted with hexane/ethyl acetate 5% to 25%. Collected fractions were evaporated to afford racemate 10-9 (361 mg, 0.544 mmol, 91%) as a colorless amorphous.

$^1$H-NMR (400 MHz, CDCl$_3$) δ: 1.03 (s, 21H), 1.55 (s, 18H), 3.23 (t, J=8.5 Hz, 1H), 4.01-4.17 (m, 3H), 4.37-4.42 (m, 2H), 7.26-7.30 (m, 1H), 8.26 (t, J=4.5 Hz, 1H), 8.65 (d, J=6.7 Hz, 1H).

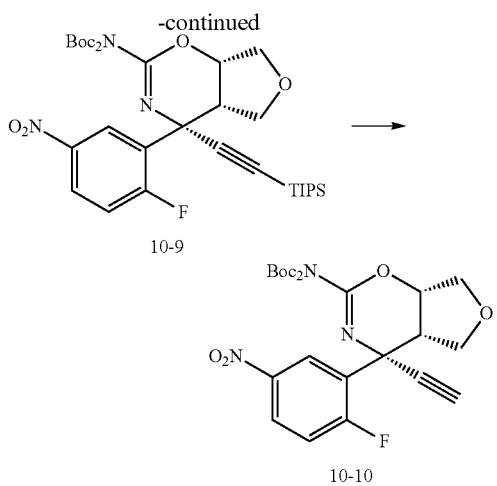

Step 9: Synthesis of Compound 10-10

To a stirred solution of racemate 10-9 (357 mg, 0.537 mmol) in tetrahydrofuran (7 mL) was added dropwise TBAF (0.107 mL, 0.107 mmol, 1 mol/L solution in tetrahydrofuran) at 0° C. After being stirred for 15 min at same temperature, the reaction mixture was diluted with H$_2$O and extracted with ethyl acetate. The organic layers were washed with brine and combined. The organic layer was dried over MgSO$_4$, filtered and concentrated. The residue was added to a silica gel column and eluted with hexane/ethyl acetate 20% to 40%. Collected fractions were evaporated to afford racemate 10-10 (279 mg, 0.527 mmol, 98%) as a colorless amorphous.

$^1$H-NMR (400 MHz, CDCl$_3$) δ: 1.56 (s, 18H), 2.47 (s, 1H), 3.15-3.21 (m, 1H), 4.02-4.16 (m, 3H), 4.36-4.40 (m, 2H), 7.29 (t, J=10.0 Hz, 2H), 8.27 (dt, J=8.3, 3.9 Hz, 1H), 8.66 (dd, J=6.8, 2.5 Hz, 1H).

[Chemical Formula 103]

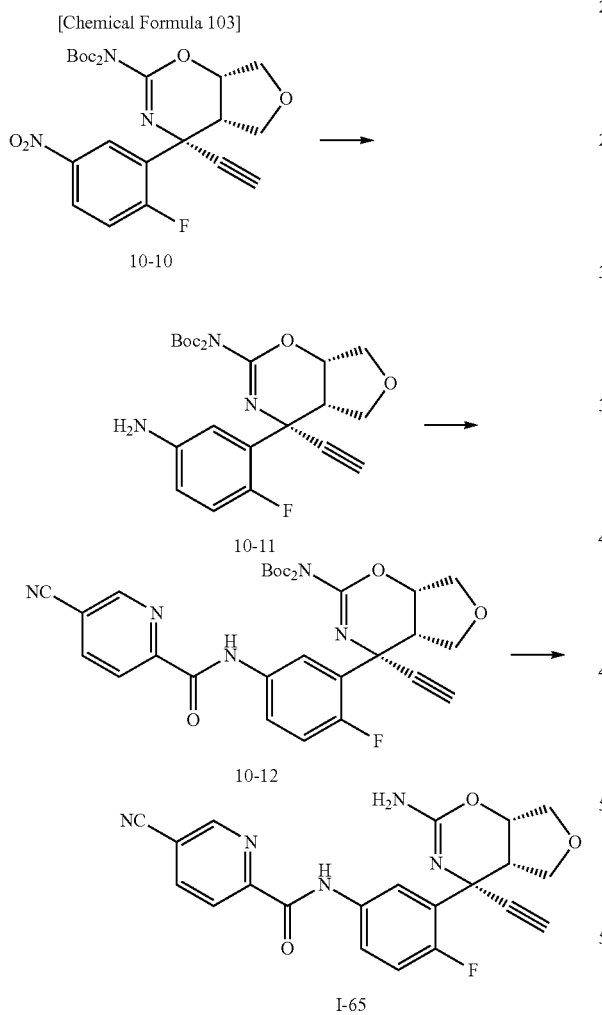

Step 10: Synthesis of Compound 10-11

To a stirred solution of racemate 10-10 (273 mg, 0.540 mmol) in ethanol/tetrahydrofuran/H$_2$O (4.11 mL, 1:1:1) were added NH$_4$Cl (347 mg, 6.48 mmol) and iron (241 mg, 4.32 mmol). After being stirred for 3 h at 60° C., the reaction mixture was diluted with ethyl acetate and filtered with Celite. The organic layer was washed with brine and dried over MgSO$_4$, filtered and concentrated. The residue was added to a silica gel column and eluted with hexane/ethyl acetate 20% to 40%. Collected fractions were evaporated to afford racemate 10-11 (167 mg, 0.330 mmol, 61%) as a beige solid.

MS: m/z=476.20 [M+H]$^+$.

Step 11: Synthesis of Compound 10-12

To a stirred solution of racemate 10-11 (165 mg, 0.326 mmol), 5-cyanopicolinic acid hydrate (65.0 mg, 0.391 mmol), HOBt hydrate (59.9 mg, 0.391 mmol) and DMAP (3.98 mg, 0.033 mmol) in DMF (2 mL) was added EDC hydrochloride (81.0 mg, 0.424 mmol) at r.t. After being stirred for 15 min at same temperature, the reaction mixture was diluted with H$_2$O and extracted with ethyl acetate. The organic layers were washed with brine and combined. The organic layer was dried over MgSO$_4$, filtered and concentrated. The residue was added to a silica gel column and eluted with hexane/ethyl acetate 25% to 45%. Collected fractions were evaporated to afford racemate 10-12 (131 mg, 0.206 mmol, 63%) as a pale orange amorphous.

$^1$H-NMR (400 MHz, CDCl$_3$) δ: 1.60 (s, 18H), 2.45 (s, 1H), 3.26-3.32 (m, 1H), 4.00-4.15 (m, 3H), 4.36 (t, J=8.5 Hz, 1H), 4.44 (t, J=3.0 Hz, 1H), 7.18 (t, J=9.9 Hz, 1H), 7.76 (dd, J=6.8, 2.3 Hz, 1H), 8.21 (d, J=8.0 Hz, 1H), 8.43 (t, J=8.0 Hz, 2H), 8.79 (s, 1H), 10.00 (s, 1H).

Step 12: Synthesis of Compound I-65

Racemate 10-12 (130 mg, 0.204 mmol) was dissolved in formic acid (0.784 mL) and stirred at r.t. for 3.5 h. The reaction mixture was quenched with aq. K$_2$CO$_3$, and the slurry was filtered. The solid was rinsed with H$_2$O and ethyl acetate. The organic layer of the filtrate was separated and washed with brine. The aqueous layer of the filtrate was extracted with chloroform. The organic layers were combined and dried over MgSO$_4$, filtered and concentrated. The residue and solid were combined, dissolved in chloroform/methanol (9:1) and concentrated. The residue was triturated with ethyl acetate/hexane (4.5 mL, 2:1). The slurry was filtered to afford racemate I-65 (65 mg, 0.160 mmol, 79%) as a white solid.

$^1$H-NMR (400 MHz, DMSO-D$_6$) δ: 3.08-3.13 (m, 1H), 3.19 (s, 1H), 3.78-3.81 (m, 3H), 4.10 (t, J=8.4 Hz, 1H), 4.24 (s, 1H), 6.00 (br s, 2H), 7.24 (t, J=9.9 Hz, 1H), 7.85 (d, J=8.5 Hz, 1H), 7.92 (d, J=7.0 Hz, 1H), 8.28 (d, J=8.0 Hz, 1H), 8.58 (d, J=8.0 Hz, 1H), 9.21 (s, 1H), 10.96 (s, 1H).

Example 11

Synthesis of I-74

[Chemical Formula 104]

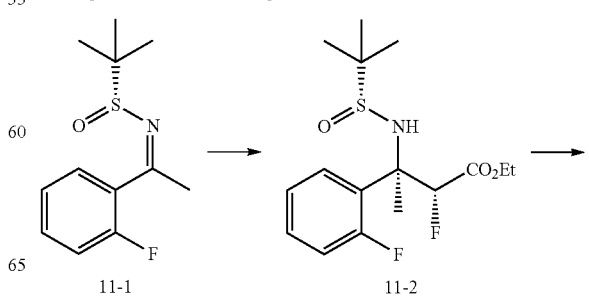

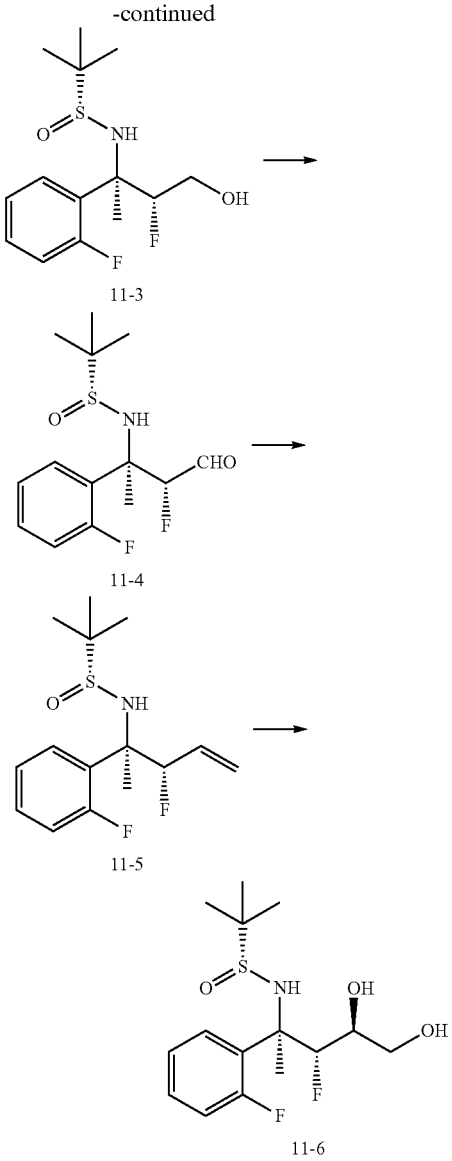

Step 1: Synthesis of Compound 11-2

A stirred suspension of Zn (1.79 g, 27.3 mmol) in THF (55 mL) was heated to reflux. To the solution was added a solution of (R,E)-N-(1-(2-fluorophenyl)ethylidene)-2-methylpropane-2-sulfinamide 11-1 (6 g, 24.9 mmol) in THF (10 mL) under nitrogen at reflux. After being stirred for 4.5 h at the same temperature, the reaction mixture was cooled to r.t. The reaction mixture was quenched with sat. aq. NH₄Cl and extracted with ethyl acetate. The organic layers were combined and washed with brine. The organic layer was dried over Na₂SO₄, filtered and concentrated.

The crude product was added to a silica gel column and eluted with hexane/ethyl acetate 30% to 50%. Collected fractions were evaporated to afford (2R,3R)-ethyl 3-((R)-1,1-dimethylethylsulfinamido)-2-fluoro-3-(2-fluorophenyl)butanoate 11-2 (4.93 g, 14.2 mmol, 57%) as a brown oil.

¹H NMR (400 MHz, CDCl₃) δ: 1.22 (s, 9H), 1.29 (t, J=7.4 Hz, 3H), 1.91 (s, 3H), 4.22-4.30 (m, 2H), 4.82 (brs, 1H), 5.45 (d, J=46.6 Hz, 1H), 7.07 (dd, J=8.3 Hz, 12.6 Hz, 1H), 7.18 (t, J=7.6 Hz, 1H), 7.37 (dd, J=7.6, 12.6 Hz, 1H), 7.46 (ddd J=7.6, 8.3, 12.6 Hz, 1H).

Step 2: Synthesis of Compound 11-3

To a stirred solution of (2R,3R)-ethyl 3-((R)-1,1-dimethylethylsulfinamido)-2-fluoro-3-(2-fluorophenyl)butanoate 11-2 (4.93 g, 14.2 mmol) in THF (50 mL) was added LiBH₄ (618 mg, 28.4 mmol) at 0° C. After being stirred for 2.5 h at the same temperature, the reaction mixture was quenched with aq. AcOH (AcOH: H₂O, 25:1) and then extracted with ethyl acetate. The organic layers were combined and washed with brine. The organic layer was dried over Na₂SO₄, filtered and concentrated.

The crude product was added to a silica gel column and eluted with chloroform/methanol 0% to 5%. Collected fractions were evaporated to afford ((R)—N-((2R,3R)-3-fluoro-2-(2-fluorophenyl)-4-hydroxybutan-2-yl)-2-methylpropane-2-sulfinamide 11-3 (3.77 g, 12.4 mmol, 87%) as a brown solid.

¹H NMR (400 MHz, CDCl₃) δ: 1.22 (s, 9H), 1.87 (s, 3H), 3.62-3.71 (m, 2H), 4.05 (t, J=8.2 Hz, 1H), 4.85 (brs, 1H), 5.04 (d, J=44.4 Hz, 1H), 7.08 (dd, J=8.3 Hz, 12.6 Hz, 1H), 7.18 (t, J=7.6 Hz, 1H), 7.32 (t, J=6.3 Hz, 1H), 7.51 (t J=7.6 Hz, 1H).

Step 3: Synthesis of Compound 11-4

To a stirred solution of ((R)—N-((2R,3R)-3-fluoro-2-(2-fluorophenyl)-4-hydroxybutan-2-yl)-2-methylpropane-2-sulfinamide 11-3 (3.77 g, 12.4 mmol) in dichloromethane (70 mL) was added Dess-Martin Periodinane (9.42 g, 22.2 mmol) at 0° C. under nitrogen. After being stirred for 1.5 h at r.t., the reaction mixture was quenched with 10% aq. Na₂S₂O₃/sat. NaHCO₃ (1:1) and then extracted with ethyl acetate. The organic layers were combined and washed with 10% aq. Na₂S₂O₃/sat. NaHCO₃ (1:1) and brine. The organic layer was dried over Na₂SO₄, filtered and concentrated.

The crude product was added to a silica gel column and eluted with chloroform/methanol 0% to 5%. Collected fractions were evaporated to afford (R)—N-((2R,3R)-3-fluoro-2-(2-fluorophenyl)-4-oxobutan-2-yl)-2-methylpropane-2-sulfinamide 11-4 (3.40 g, 11.2 mmol, 91%) as a yellow amorphous.

Step 4: Synthesis of Compound 11-5

To a stirred suspension of methyltriphenylphosphonium bromide (10.1 g, 28.0 mmol) in toluene (90 mL) was added t-BuOK (25.8 mL, 1.0 mol/L in THF, 25.8 mmol) at r.t. under nitrogen. The reaction mixture was stirred at r.t. for 1 h, and then a solution of (R)—N-((2R,3R)-3-fluoro-2-(2-fluorophenyl)-4-oxobutan-2-yl)-2-methylpropane-2-sulfinamide 11-4 (3.40 g, 11.2 mmol) in toluene (60 mL) was added dropwise to the reaction mixture at 0° C. over 10 min. After being stirred for 30 min at r.t., the reaction mixture was quenched with sat. NH₄Cl and extracted with ethyl acetate. The organic layers were combined and washed with brine. The organic layer was dried over Na₂SO₄, filtered and concentrated.

The crude product was added to a silica gel column and eluted with hexane/ethyl acetate 40% to 70%. Collected fractions were evaporated to afford (R)—N-((2R,3S)-3-fluoro-2-(2-fluorophenyl)pent-4-en-2-yl)-2-methylpropane-2-sulfinamide 11-5 (1.52 g, 5.04 mmol, 45%) as a yellow oil.
¹H NMR (400 MHz, CDCl₃) δ: 1.25 (s, 9H), 1.88 (s, 3H), 3.98 (brs, 1H), 5.30-5.59 (m, 3H), 5.78-5.91 (m, 1H), 7.07 (dd, J=8.3, 12.8 Hz, 1H), 7.16 (t, J=7.6 Hz, 1H), 7.31-7.39 (m, 1H), 7.45 (t, J=7.6 Hz, 1H).

Step 5: Synthesis of Compound 11-6

To a stirred solution of (R)—N-((2R,3S)-3-fluoro-2-(2-fluorophenyl)pent-4-en-2-yl)-2-methylpropane-2-sulfinamide 11-5 (1.08 g, 3.58 mmol) in acetone/H₂O (10 mL, 3:1) were added N-methylmorpholine N-oxide (1.05 g, 8.96 mmol) and potassium osmate dehydrate (264 mg, 0.717 mmol) at r.t. After being stirred for 16 h at the same temperature, the reaction mixture was quenched with aq. Na$_2$S$_2$O$_3$ and extracted with ethyl acetate. The organic layers were combined and washed with brine. The organic layer was dried over Na$_2$SO$_4$, filtered and concentrated.

The crude product was added to a silica gel column and eluted with hexane/ethyl acetate 50% to 70%. Collected fractions were evaporated to afford (R)—N-((2R,3R,4S)-3-fluoro-2-(2-fluorophenyl)-4,5-dihydroxypentan-2-yl)-2-methylpropane-2-sulfinamide 11-6 (853.3 mg, 2.49 mmol, 70%) as a black amorphous.

$^1$H NMR (400 MHz, CDCl$_3$) δ: 1.18 (s, 9H), 2.00 (s, 3H), 2.72 (brs, 1H), 3.57 (m, 1H), 3.81 (m, 1H), 4.10-4.14 (m, 1H), 4.84 (dd, J=8.7, 44.2 Hz, 1H), 5.55 (d, J=14.8 Hz, 1H), 7.06 (dd, J=8.2, 12.6 Hz, 1H), 7.17 (dd, J=9.2, 16.9 Hz, 1H), 7.32 (m, 1H), 7.41 (t, J=8.2 Hz, 1H).

[Chemical Formula 105]

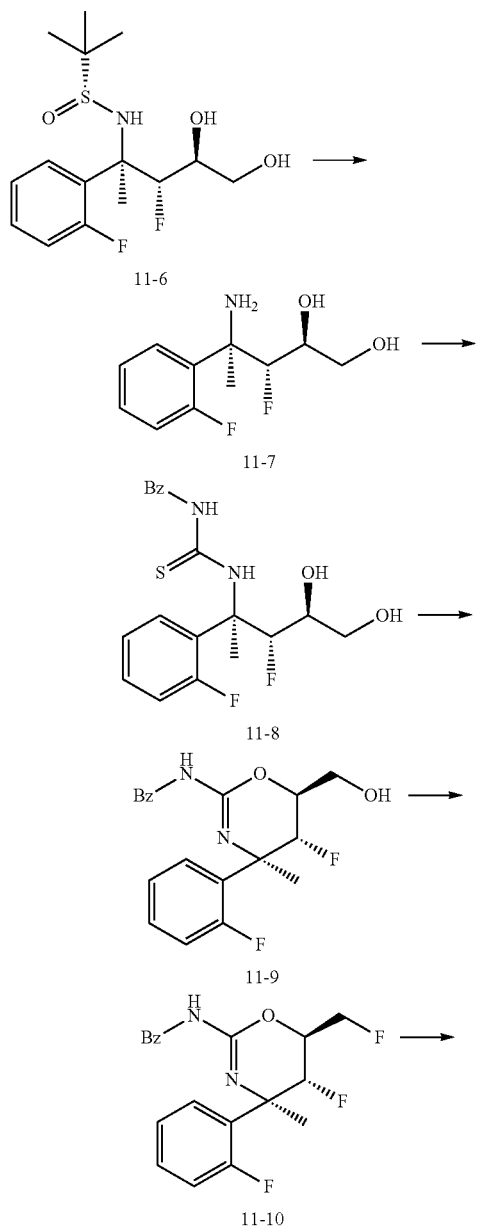

-continued

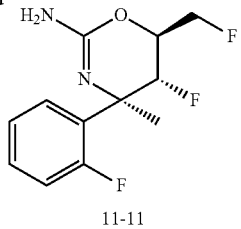

11-11

Step 6: Synthesis of Compound 11-7

To a stirred solution of (R)—N-((2R,3R,4S)-3-fluoro-2-(2-fluorophenyl)-4,5-dihydroxypentan-2-yl)-2-methylpropane-2-sulfinamide 11-6 (835.5 mg, 2.49 mmol) in methanol (8 mL) was added 4 mol/L of HCl in 1,4-dioxane (1.25 mL, 4.98 mmol) at 0° C. After being stirred for 1 h at r.t., the reaction mixture was quenched with 20% aq. Na$_2$CO$_3$ and extracted with ethyl acetate. The organic layers were combined and washed with brine. The organic layer was dried over Na$_2$SO$_4$, filtered and concentrated. The crude compound 11-7 (576 mg, 2.49 mmol, 100%) was used for the next reaction without further purification.

Step 7: Synthesis of Compound 11-8

To a stirred solution of (2S,3R,4R)-4-amino-3-fluoro-4-(2-fluorophenyl)pentane-1,2-diol 11-7 (576 mg, 2.49 mmol) in dichloromethane (6 mL) was added benzoyl isothiocyanate (0.34 mL, 2.54 mmol) at 0° C. After being stirred for 3 h at r.t., the reaction mixture was concentrated, and the resulting residue was added to a silica gel column and eluted with hexane/ethyl acetate 40% to 70%. Collected fractions were evaporated to afford N-((2R,3R,4S)-3-fluoro-2-(2-fluorophenyl)-4,5-dihydroxypentan-2-ylcarbamothioyl)benzamide 11-8 (867.4 mg, 2.20 mmol, 88%) as a yellow amorphous.

$^1$H NMR (400 MHz, CDCl$_3$) δ: 2.20 (s, 3H), 2.95 (d, J=5.9 Hz, 1H), 3.84 (m, 1H), 4.08-4.14 (m, 1H), 4.10-4.14 (m, 1H), 5.08 (dd, J=8.3, 44.1 Hz, 1H), 7.04 (dd, J=8.0, 12.4 Hz, 1H), 7.17 (t, J=7.5 Hz, 1H), 7.30 (t, J=6.3 Hz, 1H), 7.45 (t, J=8.0 Hz, 1H), 7.51 (t, J=7.5 Hz, 1H), 7.62 (t, J=7.3 Hz, 1H), 7.86 (t, J=9.3 Hz, 2H), 8.82 (s, 1H), 11.8 (s, 1H).

Step 8: Synthesis of Compound 11-9

To a stirred solution of N-((2R,3R,4S)-3-fluoro-2-(2-fluorophenyl)-4,5-dihydroxypentan-2-ylcarbamothioyl)benzamide 11-8 (867.4 mg, 2.20 mmol) in acetonitrile (9 mL) was added EDC (843 mg, 4.40 mmol) at r.t. After being stirred for 14 at the same temperature, the reaction mixture was diluted with H$_2$O and extracted with ethyl acetate. The organic layers were combined and washed with brine. The organic layer was dried over Na$_2$SO$_4$, filtered and concentrated.

The crude product was added to a silica gel column and eluted with hexane/ethyl acetate 50% to 70%. Collected fractions were evaporated to afford N-((4R,5R,6S)-5-fluoro-4-(2-fluorophenyl)-6-(hydroxymethyl)-4-methyl-5,6-dihydro-4H-1,3-oxazin-2-yl)benzamide 11-9 (791 mg, 2.20 mmol, 100%) as a pale yellow amorphous.

$^1$H NMR (400 MHz, CDCl$_3$) δ: 1.88 (s, 3H), 3.67 (d, J=2.8 Hz, 1H), 4.69 (dt, J=5.1, 17.5 Hz, 1H), 5.46 (dd, J=6.0, 47.5 Hz, 1H), 7.14-7.24 (m, 2H), 7.36-7.46 (m, 3H), 7.49 (dd, J=9.0, 16.2 Hz, 2H), 8.22 (dd, J=7.8, 16.2 Hz, 2H), 11.8 (brs, 1H).

Step 9: Synthesis of Compound 11-10

To a stirred solution of N-((4R,5R,6S)-5-fluoro-4-(2-fluorophenyl)-6-(hydroxymethyl)-4-methyl-5,6-dihydro-4H-1,3-oxazin-2-yl)benzamide 11-9 (791.3 mg, 2.20 mmol) in dichloromethane (25 mL) was added DAST (1.16 mL, 8.78 mmol) at −78° C. under nitrogen. The reaction mixture was warmed gradually to 0° C. over 30 min and stirred for 3 h. The reaction mixture was quenched with sat. NaHCO₃ and then extracted with ethyl acetate. The organic layers were combined and washed with brine. The organic layer was dried over Na₂SO₄, filtered and concentrated. The crude product was added to a silica gel column and eluted with hexane/ethyl acetate 20% to 40%. Collected fractions were evaporated to afford N-((4R,5R,6S)-5-fluoro-6-(fluoromethyl)-4-(2-fluorophenyl)-4-methyl-5,6-dihydro-4H-1,3-oxazin-2-yl)benzamide 11-10 (112.6 mg, 0.311 mmol, 14%) as a white amorphous.

¹H NMR (400 MHz, CDCl₃) δ: 1.88 (s, 3H), 4.10-4.19 (m, 1H), 4.29 (dd, J=4.3, 10.4 Hz, 1H), 4.33-4.47 (m, 1H), 4.80-4.90 (m, 1H), 5.47 (dd, J=5.1, 46.8 Hz, 1H), 7.00-7.24 (m, 2H), 7.41-7.53 (m, 5H), 8.24 (d, J=7.5 Hz, 2H), 11.8 (brs, 1H).

Step 10: Synthesis of Compound 11-11

To a stirred solution of N-((4R,5R,6S)-5-fluoro-6-(fluoromethyl)-4-(2-fluorophenyl)-4-methyl-5,6-dihydro-4H-1,3-oxazin-2-yl)benzamide 11-10 (332.4 mg, 0.917 mmol) in THF (6 mL) were added Boc₂O (0.32 mL, 1.38 mmol) and DMAP (11.2 mg, 0.092 mmol) at r.t. under nitrogen. After being stirred for 45 min, the reaction mixture was diluted with H₂O and extracted with ethyl acetate. The organic layers were combined and washed with brine. The organic layer was dried over Na₂SO₄, filtered and concentrated. The crude compound was dissolved in methanol (6 mL), and K₂CO₃ was added at 0° C. After being stirred for 30 min at r.t., the reaction mixture was diluted with H₂O and extracted with ethyl acetate. The organic layer was dried over Na₂SO₄, filtered and concentrated. The crude product was added to a silica gel column and eluted with hexane/ethyl acetate 30% to 60%. Collected fractions were evaporated to afford Boc-protected compound. The compound was dissolved in dichloromethane (4 mL) and TFA was added at 0° C. After being stirred for 1.5 h at r.t., the reaction mixture was quenched with 20% aq. Na₂CO₃ and extracted with ethyl acetate. The organic layer was dried over Na₂SO₄, filtered and concentrated. The crude product was added to a silica gel column and eluted with hexane/ethyl acetate 80% to 100%. Collected fractions were evaporated to afford (4R,5R,6S)-5-fluoro-6-(fluoromethyl)-4-(2-fluorophenyl)-4-methyl-5,6-dihydro-4H-1,3-oxazin-2-amine 11-11 (237 mg, 0.918 mmol, 100%) as a colorless amorphous.

¹H NMR (400 MHz, CDCl₃) δ: 1.70 (s, 3H), 4.08-4.15 (m, 2H), 4.21-4.26 (m, 1H), 4.63 (ddt, J=3.7, 13.1, 21.5 Hz, 1H), 5.11 (dd, J=5.4, 47.6 Hz, 1H), 7.06 (ddd, J=1.2, 8.1, 12.4 Hz, 1H), 7.17 (td, J=1.2, 7.7 Hz, 1H), 7.26-7.33 (m, 1H), 7.50 (td, J=1.8, 8.1 Hz, 1H).

[Chemical Formula 106]

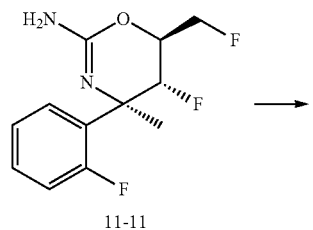

11-11

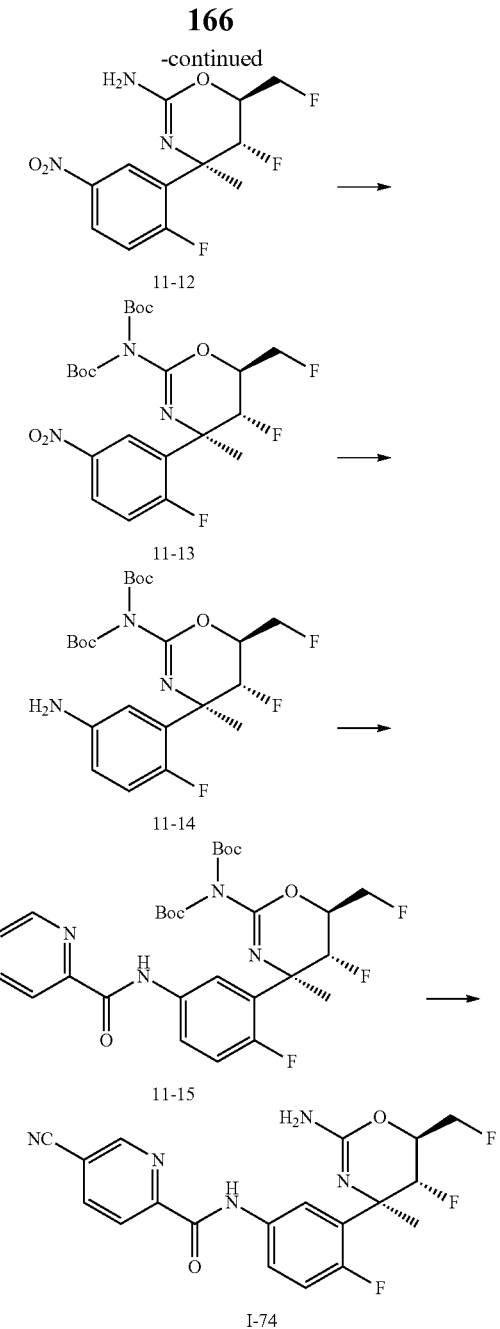

Step 11: Synthesis of Compound 11-12

To a stirred solution of (4R,5R,6S)-5-fluoro-6-(fluoromethyl)-4-(2-fluorophenyl)-4-methyl-5,6-dihydro-4H-1,3-oxazin-2-amine 11-11 (40 mg, 0.155 mmol) in TFA (0.08 mL)/H₂SO₄ (0.32 mL) was added HNO₃ (10 μL, 0.232 mmol) at −20° C. After being stirred for 45 min, the reaction mixture was quenched with 20% aq. Na₂CO₃ and then extracted with ethyl acetate. The organic layer was dried over Na₂SO₄, filtered and concentrated. The crude compound (47 mg, 0.155 mmol, 100%) was used for the next reaction without further purification.

Step 12: Synthesis of Compound 11-13

To a stirred solution of (4R,5R,6S)-5-fluoro-4-(2-fluoro-5-nitrophenyl)-6-(fluoromethyl)-4-methyl-5,6-dihydro-4H-1,3-oxazin-2-amine 11-12 (47 mg, 0.155 mmol) in tetrahydrofuran (1 mL) were added Boc₂O (0.079 mL, 0.341 mmol) and DMAP (1.9 mg, 0.015 mmol) at 0° C. After being stirred for 2 h at the same temperature, the reaction mixture was concentrated. The residue was partitioned between ethyl acetate and H₂O and then extracted with ethyl acetate. The organic layer was dried over Na₂SO₄, filtered and concentrated. The crude product was added to a silica gel column and eluted with hexane/ethyl acetate 20% to 40%. Collected fractions were evaporated to afford compound 11-13 (53.7 mg, 0.107 mmol, 69%) as a white amorphous.

¹H NMR (400 MHz, CDCl₃) δ: 1.54 (s, 9H), 1.56 (s, 9H), 1.81 (s, 3H), 4.54-4.66 (m, 3H), 4.87 (dd, J=8.5, 48.3 Hz, 1H), 7.22-7.26 (m, 1H), 8.24 (d, J=8.7 Hz, 1H), 8.51 (d, J=6.5 Hz, 1H).

Step 13: Synthesis of Compound 11-14

To a stirred solution of compound 11-13 (53.7 mg, 0.107 mmol) in ethanol/tetrahydrofuran/H₂O (1 mL, 2:1:1) were added Fe (47.7 mg, 0.853 mmol) and NH₄Cl (68.5 mg, 1.28 mmol) at r.t. The reaction mixture was heated to 60° C. and stirred for 1 h. The reaction mixture was cooled to r.t. and partitioned between ethyl acetate and H₂O and then extracted with ethyl acetate. The organic layers were combined and washed with brine. The organic layer was dried over Na₂SO₄, filtered and concentrated. The crude product was added to a silica gel column and eluted with hexane/ethyl acetate 20% to 40%. Collected fractions were evaporated to afford compound 11-14 (42.1 mg, 0.089 mmol, 83%) as a yellow solid.

MS: m/z=474.20 [M+H]⁺.

Step 14: Synthesis of Compound 11-15

To a stirred solution of compound 11-14 (42.1 mg, 0.089 mmol) in dichloromethane (1 mL) were added 5-cyanopicolinic acid (15.8 mg, 0.107 mmol), HATU (40.6 mg, 0.107 mmol), and DIEA (0.031 mL, 0.178 mmol) at r.t. After being stirred for 1.5 h, the reaction mixture was concentrated. The crude product was added to a silica gel column and eluted with hexane/ethyl acetate 20% to 40%. Collected fractions were evaporated to afford compound 11-15 (51.9 mg, 0.086 mmol, 97%) as a colorless amorphous.

¹H NMR (400 MHz, CDCl₃) δ: 1.55 (s, 18H), 1.76 (s, 3H), 4.19 (dd, J=3.0, 10.5 Hz, 1H), 4.26-4.33 (m, 1H), 4.39 (dd, J=4.5, 9.8 Hz, 1H), 4.74 (dt, J=7.9, 24.3 Hz, 1H), 5.12 (dd, J=5.6, 46.8 Hz, 1H), 7.15 (dd, J=8.8, 11.3 Hz, 1H), 7.64 (dd, J=2.8, 6.8 Hz, 1H), 8.21 (td, J=2.8, 5.5 Hz, 2H), 8.43 (dd, J=0.8, 8.0 Hz, 1H), 8.82 (dd, J=0.8, 1.9 Hz, 1H), 9.92 (s, 1H).

Step 15: Synthesis of Compound I-74

Compound 11-15 (51.9 mg, 0.086 mmol) was dissolved in formic acid (0.5 mL) and stirred at r.t. for 3 h. The reaction mixture was quenched with 20% aq. Na₂CO₃ and then extracted with ethyl acetate. The organic layers were combined and washed with brine. The organic layer was dried over Na₂SO₄, filtered and concentrated. The crude product was added to a silica gel column and eluted with hexane/ethyl acetate 60% to 90%. Collected fractions were evaporated to afford I-74 (26.0 mg, 0.064 mmol, 75%) as a white solid.

¹H NMR (400 MHz, DMSO-d6) δ: 1.53 (s, 3H), 4.37 (d, J=47.4 Hz, 2H), 4.65 (m, 1H), 4.94 (dd, J=6.6, 48.5 Hz, 1H), 5.78 (brs, 2H), 7.17 (t, J=10.2 Hz, 1H), 7.89 (s, 1H), 8.01 (d, J=6.8 Hz, 1H), 8.29 (d, J=8.0 Hz, 1H), 8.59 (d, J=8.0 Hz, 1H), 9.21 (s, 1H), 10.9 (s, 1H).

Example 12

Synthesis of I-116

[Chemical Formula 107]

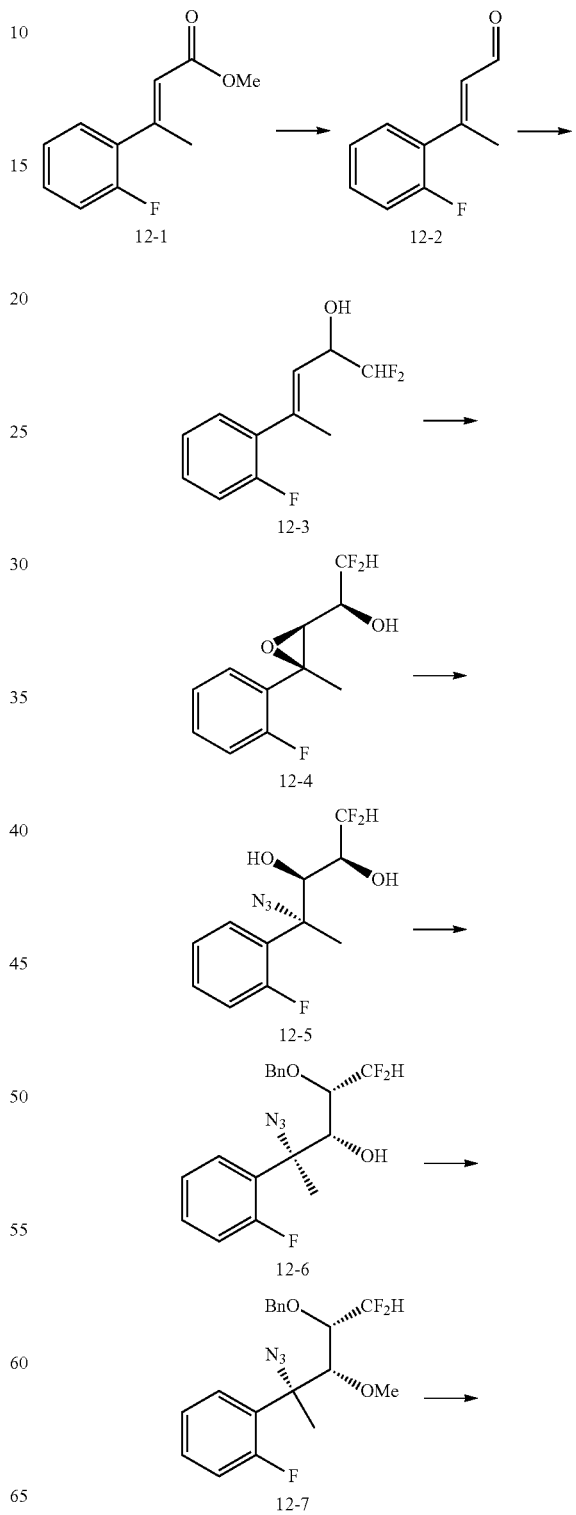

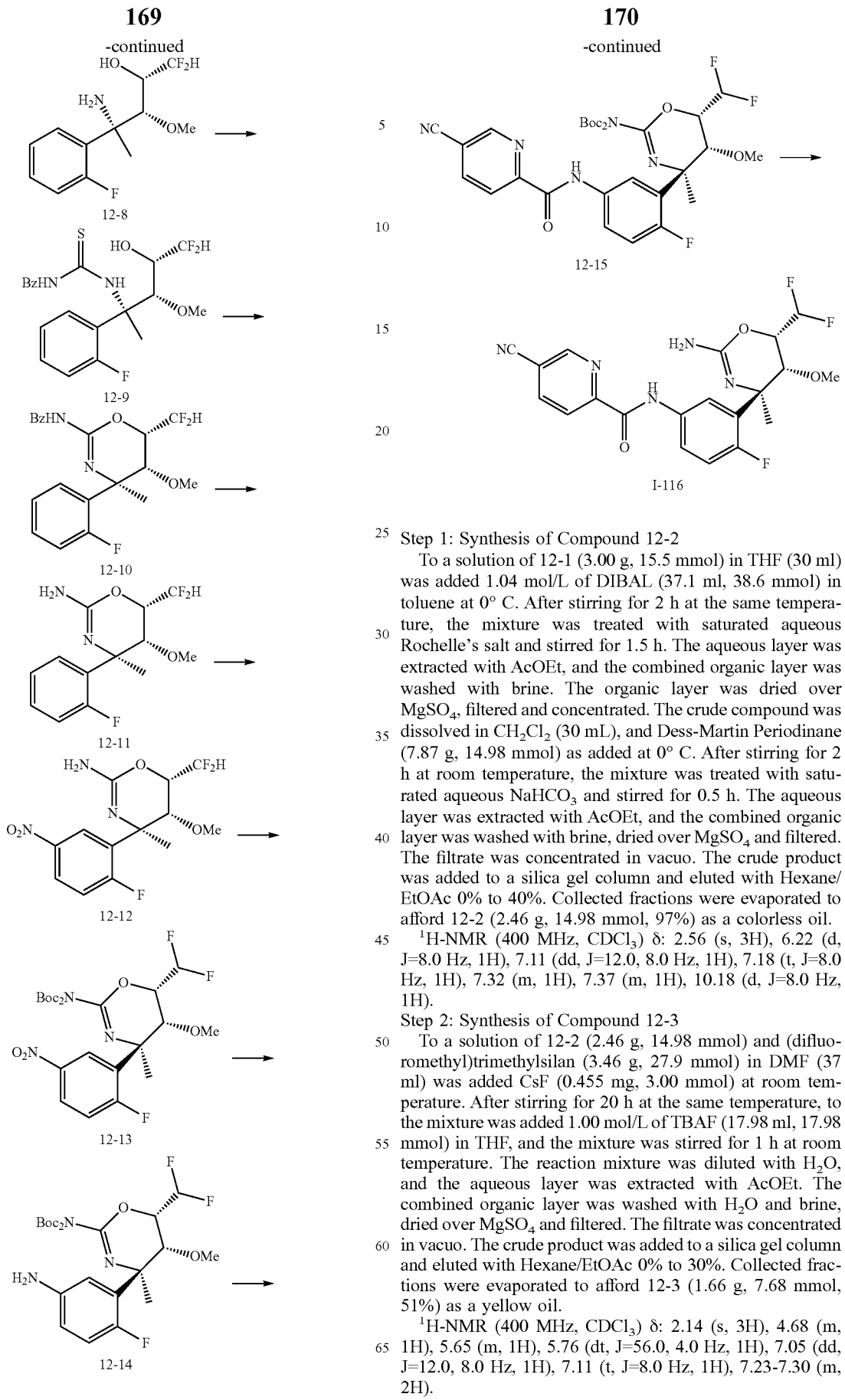

Step 1: Synthesis of Compound 12-2

To a solution of 12-1 (3.00 g, 15.5 mmol) in THF (30 ml) was added 1.04 mol/L of DIBAL (37.1 ml, 38.6 mmol) in toluene at 0° C. After stirring for 2 h at the same temperature, the mixture was treated with saturated aqueous Rochelle's salt and stirred for 1.5 h. The aqueous layer was extracted with AcOEt, and the combined organic layer was washed with brine. The organic layer was dried over $MgSO_4$, filtered and concentrated. The crude compound was dissolved in $CH_2Cl_2$ (30 mL), and Dess-Martin Periodinane (7.87 g, 14.98 mmol) as added at 0° C. After stirring for 2 h at room temperature, the mixture was treated with saturated aqueous $NaHCO_3$ and stirred for 0.5 h. The aqueous layer was extracted with AcOEt, and the combined organic layer was washed with brine, dried over $MgSO_4$ and filtered. The filtrate was concentrated in vacuo. The crude product was added to a silica gel column and eluted with Hexane/EtOAc 0% to 40%. Collected fractions were evaporated to afford 12-2 (2.46 g, 14.98 mmol, 97%) as a colorless oil.

$^1$H-NMR (400 MHz, $CDCl_3$) δ: 2.56 (s, 3H), 6.22 (d, J=8.0 Hz, 1H), 7.11 (dd, J=12.0, 8.0 Hz, 1H), 7.18 (t, J=8.0 Hz, 1H), 7.32 (m, 1H), 7.37 (m, 1H), 10.18 (d, J=8.0 Hz, 1H).

Step 2: Synthesis of Compound 12-3

To a solution of 12-2 (2.46 g, 14.98 mmol) and (difluoromethyl)trimethylsilan (3.46 g, 27.9 mmol) in DMF (37 ml) was added CsF (0.455 mg, 3.00 mmol) at room temperature. After stirring for 20 h at the same temperature, to the mixture was added 1.00 mol/L of TBAF (17.98 ml, 17.98 mmol) in THF, and the mixture was stirred for 1 h at room temperature. The reaction mixture was diluted with $H_2O$, and the aqueous layer was extracted with AcOEt. The combined organic layer was washed with $H_2O$ and brine, dried over $MgSO_4$ and filtered. The filtrate was concentrated in vacuo. The crude product was added to a silica gel column and eluted with Hexane/EtOAc 0% to 30%. Collected fractions were evaporated to afford 12-3 (1.66 g, 7.68 mmol, 51%) as a yellow oil.

$^1$H-NMR (400 MHz, $CDCl_3$) δ: 2.14 (s, 3H), 4.68 (m, 1H), 5.65 (m, 1H), 5.76 (dt, J=56.0, 4.0 Hz, 1H), 7.05 (dd, J=12.0, 8.0 Hz, 1H), 7.11 (t, J=8.0 Hz, 1H), 7.23-7.30 (m, 2H).

Step 3: Synthesis of Compound 12-4

To a solution of 12-3 (1.005 g, 4.65 mmol) in CH$_2$Cl$_2$ (16 ml) was added mCPBA (2.30 g, 9.30 mmol) at 0° C. After stirring for 2 h at room temperature, the mixture was treated with 2N NaOH (2.71 ml) and stirred for 0.5 h. The aqueous layer was extracted with AcOEt, and the combined organic layer was washed with brine, dried over MgSO$_4$ and filtered. The filtrate was concentrated in vacuo. The crude product was added to a silica gel column and eluted with Hexane/EtOAc 0% to 50%. Collected fractions were evaporated to afford 12-4 (788 mg, 3.39 mmol, 73%) as a colorless oil.

$^1$H-NMR (400 MHz, CDCl$_3$) δ: 1.71 (s, 3H), 2.49 (d, J=8.0 Hz, 1H), 3.15 (d, J=8.0 Hz, 1H), 3.97 (m, 1H), 5.91 (dt, J=56.0, 4.0 Hz, 1H), 7.04 (t, J=8.0 Hz, 1H), 7.13 (t, J=8.0 Hz, 1H), 7.30 (m, 1H), 7.38 (m, 1H).

Step 4: Synthesis of Compound 12-5

To a solution of 12-4 (788 mg, 3.39 mmol) and Ti(OEt)$_4$ (4.65 g, 20.4 mmol) in DMF (5 ml) was added NaN$_3$ (882 mg, 13.57 mmol) at room temperature. After stirring for 20 h at the same temperature, the mixture was treated with saturated aqueous citric acid and stirred for 1 h. The aqueous layer was extracted with AcOEt, and the combined organic layer was washed with brine, dried over MgSO$_4$ and filtered. The filtrate was concentrated in vacuo. The crude product was added to a silica gel column and eluted with Hexane/EtOAc 0% to 40%. Collected fractions were evaporated to afford 12-5 (771 mg, 2.80 mmol, 83%) as a yellow solid.

$^1$H-NMR (400 MHz, CDCl$_3$) δ: 1.94 (s, 3H), 2.84-2.87 (m, 2H), 3.52 (m, 1H), 4.31 (d, J=8.0 Hz, 1H), 5.63 (dt, J=56.0, 8.0 Hz, 1H), 7.11 (dd, J=12.0, 8.0 Hz, 1H), 7.22 (t, J=8.0 Hz, 1H), 7.36 (m, 1H), 7.57 (t, J=8.0 Hz, 1H).

Step 5: Synthesis of Compound 12-6

To a solution of 12-5 (956 mg, 3.47 mmol) in Toluene (8 ml) and MeOH (8 ml) was added dibutyltin oxide (1038 mg, 4.17 mmol) at room temperature. After stirring for 3 h at 110° C., the reaction mixture was concentrated. Dry toluene (8 ml) was added to the residue, and a second evaporation to dryness was effected, which was completed under vacuum. The crude compound was dissolved in toluene (8 mL), and tetrabutylammonium bromide (224 mg, 0.695 mmol) and benzyl bromide (1031 ml. 8.68 mmol) were added at room temperature. After being stirred for 20 h at 110° C., the reaction mixture was diluted with H$_2$O and extracted with AcOEt. The organic layer was dried over MgSO$_4$, filtered and concentrated. The crude product was added to a silica gel column and eluted with hexane/ethyl acetate 0% to 30%. Collected fractions were evaporated to afford 12-6 (1100 mg, 3.01 mmol, 87%) as a colorless oil.

$^1$H-NMR (400 MHz, CDCl$_3$) δ: 1.93 (s, 3H), 3.20 (d, J=12.0 Hz, 1H), 3.27 (m, 1H), 4.30 (d, J=12.0 Hz, 1H), 4.66 (s, 2H), 5.61 (dt, J=56.0, 4.0 Hz, 1H), 7.09 (dd, J=12.0, 8.0 Hz, 1H), 7.20 (t, J=8.0 Hz, 1H), 7.31-7.38 (m, 6H), 7.58 (t, J=8.0 Hz, 1H).

Step 6: Synthesis of Compound 12-7

To a solution of NaH (361 mg, 9.03 mmol) in THF (8 ml) was added 12-6 (1100 mg, 3.01 mmol) at 0° C. After stirring for 30 min at room temperature, to the mixture was added MeI (0.941 ml, 15.05 mmol), and the mixture was stirred for 30 min at room temperature. The reaction mixture was treated with saturated aqueous NH$_4$Cl, and the aqueous layer was extracted with AcOEt. The combined organic layer was washed with brine, dried over MgSO$_4$ and filtered. The filtrate was concentrated in vacuo. The crude product was added to a silica gel column and eluted with Hexane/EtOAc 0% to 30%. Collected fractions were evaporated to afford 12-7 (1062 mg, 2.80 mmol, 93%) as a colorless oil.

$^1$H-NMR (400 MHz, CDCl$_3$) δ: 1.92 (s, 3H), 3.47 (m, 1H), 3.51 (s, 3H), 4.05 (s, 1H), 4.60 (m, 2H), 5.65 (dt, J=56.0, 4.0 Hz, 1H), 7.07 (dd, J=12.0, 8.0 Hz, 1H), 7.15 (t, J=8.0 Hz, 1H), 7.28-7.38 (m, 6H), 7.57 (t, J=8.0 Hz, 1H).

Step 7: Synthesis of Compound 12-8

To a solution of 12-7 (1062 mg, 2.80 mmol) in MeOH (10 ml) was added 10% Pd/C (400 mg) and hydrogenated at room temperature. After stirring for 24 h at the same temperature, the mixture was filtrated through a pad of Celite. The filtrate was concentrated under vacuum to give 12-8 (720 mg, 2.73 mmol, 98%) as a white solid that was used for the next step without purification.

$^1$H-NMR (400 MHz, CDCl$_3$) δ: 1.68 (s, 3H), 3.39 (m, 1H), 3.65 (s, 3H), 3.91 (m, 1H), 5.70 (dt, J=56.0, 4.0 Hz, 1H), 7.07 (dd, J=12.0, 8.0 Hz, 1H), 7.19 (t, J=8.0 Hz, 1H), 7.30 (m, 1H), 7.55 (t, J=8.0 Hz, 1H).

Step 8: Synthesis of Compound 12-9

To a stirred solution of 12-8 (720 mg, 2.73 mmol) in CH$_2$Cl$_2$ (10 mL) was added benzoyl isothiocyanate (0.44 mL, 3.28 mmol) at 0° C. After being stirred for 2 h at room temperature, the reaction mixture was concentrated, and the resulting residue was added to a silica gel column and eluted with hexane/ethyl acetate 0% to 50%. Collected fractions were evaporated to afford 12-9 (828 mg, 1.94 mmol, 71%) as a yellow amorphous.

$^1$H-NMR (400 MHz, CDCl$_3$) δ: 2.34 (s, 3H), 3.09 (m, 1H), 3.53 (s, 3H), 3.75 (m, 1H), 3.92 (s, 1H), 5.73 (dt, J=56.0, 4.0 Hz, 1H), 7.07 (dd, J=12.0, 8.0 Hz, 1H), 7.16 (t, J=8.0 Hz, 1H), 7.31 (m, 1H), 7.42 (t, J=8.0 Hz, 1H), 7.51 (t, J=8.0 Hz, 2H), 7.62 (t, J=8.0 Hz, 1H), 7.87 (d, J=8.0 Hz, 2H), 8.88 (s, 1H), 11.66 (s, 1H).

Step 9: Synthesis of Compound 12-10

To a stirred solution of 12-9 (788 mg, 2.85 mmol) in acetonitrile (15 mL) was added EDC (708 mg, 3.70 mmol) at room temperature. After being stirred for 20 h at the same temperature, the reaction mixture was diluted with H$_2$O and extracted with ethyl acetate. The organic layers were combined and washed with brine. The organic layer was dried over MgSO$_4$, filtered and concentrated. The crude product was added to a silica gel column and eluted with hexane/ethyl acetate 0% to 50%. Collected fractions were evaporated to afford 12-10 (677 mg, 1.73 mmol, 93%) as a pale yellow amorphous.

$^1$H-NMR (400 MHz, CDCl$_3$) δ: 1.87 (s, 3H), 3.71 (s, 3H), 4.04 (m, 1H), 4.22 (s, 1H), 6.01 (dt, J=56.0, 8.0 Hz, 1H), 7.16 (dd, J=12.0, 8.0 Hz, 1H), 7.21 (t, J=8.0 Hz, 1H), 7.35-7.45 (m, 4H), 7.51 (m, 1H), 8.26 (d, J=8.0 Hz, 2H), 11.64 (s, 1H).

Step 10: Synthesis of Compound 12-11

To a stirred solution of 12-10 (670 mg, 1.71 mmol) in THF (10 mL) were added Boc$_2$O (0.555 mL, 2.39 mmol) and DMAP (209 mg, 1.71 mmol) at r.t. under nitrogen. After being stirred for 1 h, the reaction mixture was diluted with H$_2$O and extracted with ethyl acetate. The organic layers were combined and washed with brine. The organic layer was dried over MgSO$_4$, filtered and concentrated. The crude compound was dissolved in methanol (10 mL), and K$_2$CO$_3$ (448 mg, 3.24 mmol) was added at 0° C. After being stirred for 2 h at r.t., the reaction mixture was diluted with H$_2$O and extracted with ethyl acetate. The organic layer was dried over MgSO$_4$, filtered and concentrated. The crude product was added to a silica gel column and eluted with hexane/ethyl acetate 0% to 50%. Collected fractions were evaporated to afford Boc-protected compound. The compound was dissolved in CH$_2$Cl$_2$ (4 mL) and TFA (1 ml) was added at 0° C. After being stirred for 2 h at r.t., the reaction mixture was quenched with 20% aq. Na$_2$CO$_3$ and extracted with ethyl acetate. The organic layer was dried over MgSO$_4$ and filtered. The filtrate was concentrated under vacuum to give 12-11 (440 mg, 1.53 mmol, 89%) as a white amorphous that was used for the next step without purification.

$^1$H-NMR (400 MHz, CDCl$_3$) δ: 1.69 (s, 3H), 3.67 (s, 3H), 3.80 (m, 1H), 4.07 (m, 1H), 5.87 (dt, J=52.0, 4.0 Hz, 1H), 7.07 (dd, J=12.0, 8.0 Hz, 1H), 7.16 (t, J=8.0 Hz, 1H), 7.29 (m, 1H), 7.37 (t, J=8.0 Hz, 1H).

Step 11: Synthesis of Compound 12-12

To a solution of 12-11 (440 mg, 1.53 mmol) in TFA (2 ml) was added sulfuric acid (0.508 ml, 26.0 mmol) at −10° C. After stirring for 5 min at −10° C., to the reaction mixture was added HNO$_3$ (0.146 ml, 2.29 mmol) at −10° C. After stirring for 30 min at −10° C., the reaction mixture was treated with aqueous K$_2$CO$_3$. The aqueous layer was extracted with AcOEt and the organic layer was dried over MgSO$_4$, filtered and concentrated. The crude product was purified by supercritical fluid chromatography (SFC) (Chiralpak (Registered trademark) IB; 10-40% isopropylalcohol with 0.1% diethylamine) to give 12-12 (176 mg, 0.165 mmol, 35%) as a yellow solid.

$^1$H-NMR (400 MHz, CDCl$_3$) δ: 1.67 (s, 3H), 3.68 (s, 3H), 3.73 (m, 1H), 4.04 (m, 1H), 5.89 (dt, J=52.0, 8.0 Hz, 1H), 7.42 (dd, J=12.0, 8.0 Hz, 1H), 8.21 (m, 1H), 8.36 (m, 1H).

Step 12: Synthesis of Compound 12-13

To a solution of 12-12 (172 mg, 0.52 mmol), and DMAP (18.9 mg, 0.155 mmol) in (3 ml) was added Boc$_2$O (0.359 ml, 1.55 mmol) at room temperature. After stirring for 2 h at the same temperature, the mixture was concentrated under vacuum. The crude product was added to a silica gel column and eluted with Hexane/EtOAc 0% to 30%. Collected fractions were evaporated to afford 12-13 (239 mg, 0.45 mmol, 87%) as a white amorphous.

$^1$H-NMR (400 MHz, CDCl$_3$) δ: 1.52 (s, 18H), 1.72 (s, 3H), 3.66 (s, 3H), 3.80 (m, 1H), 4.04 (m, 1H), 5.95 (dt, J=56.0, 8.0 Hz, 1H), 7.27 (m, 1H), 8.24 (m, 1H), 8.46 (m, 1H).

Step 13: Synthesis of Compound 12-14

To a solution of 12-13 (250 mg, 0.47 mmol) in MeOH (3 ml) and THF (3 ml) was added 10% Pd/C (50 mg) and hydrogenated at room temperature. After stirring for 2 h at the same temperature, the mixture was filtrated through a pad of Celite. The filtrate was concentrated under vacuum to give 12-14 (232 mg, 0.46 mmol, 98%) as a white amorphous that was used for the next step without purification.

$^1$H-NMR (400 MHz, CDCl$_3$) δ: 1.52 (s, 18H), 1.68 (s, 3H), 3.61 (s, 3H), 3.94 (m, 1H), 4.04 (m, 1H), 5.92 (dt, J=56.0, 4.0 Hz, 1H), 6.58 (m, 1H), 6.81 (m, 1H), 6.87 (m, 1H).

Step 14: Synthesis of Compound 12-15

To a solution of 12-14 (37 mg, 0.073 mmol) in DMF (2 ml) were added 5-cyanopicolinic acid hydrate (13 mg, 0.081 mmol), HATU (31 mg, 0.081 mmol) and DIPEA (0.02 ml, 0.11 mmol) at room temperature. After stirring for 18 h at the same temperature, the reaction mixture was treated with H$_2$O. The aqueous layer was extracted with AcOEt, and the organic layer was dried over MgSO$_4$, filtered and concentrated. The crude product was added to a silica gel column and eluted with hexane/EtOAc 50%. Collected fractions were evaporated to afford 12-15 (44 mg, 0.069 mmol, 95%) as a white amorphous.

$^1$H-NMR (400 MHz, CDCl$_3$) δ: 1.55 (s, 18H), 1.75 (s, 3H), 3.65 (s, 3H), 3.94 (m, 1H), 4.07 (m, 1H), 5.93 (dt, J=52.0, 4.0 Hz, 1H), 7.16 (dd, J=12.0, 8.0 Hz, 1H), 7.49 (dd, J=8.0, 4.0 Hz, 1H), 8.22 (dd, J=8.0, 4.0 Hz, 1H), 8.37 (m, 1H), 8.44 (d, J=8.0 Hz, 1H), 8.80 (m, 1H), 8.96 (s, 1H).

Step 15: Synthesis of I-116

To a solution of 12-15 (44 mg, 0.073 mmol) in CH$_2$Cl$_2$ (1.5 ml) was added TFA (0.5 ml) at 0° C. After being stirred for 2 h at r.t., the reaction mixture was quenched with 20% aq. K$_2$CO$_3$. The aqueous layer was extracted with AcOEt and the organic layers were combined and washed with brine. The organic layer was dried over MgSO$_4$, filtered and concentrated to afford compound I-116 (23 mg, 0.053 mmol, 76%) as a white solid.

$^1$H-NMR (400 MHz, CDCl$_3$) δ: 1.69 (s, 3H), 3.68 (s, 3H), 3.85 (m, 1H), 4.10 (m, 1H), 5.89 (dt, J=52.0, 4.0 Hz, 1H), 7.13 (dd, J=12.0, 8.0 Hz, 1H), 7.46 (dd, J=8.0, 4.0 Hz, 1H), 8.03 (m, 1H), 8.21 (dd, J=8.0, 4.0 Hz, 1H), 8.42 (d, J=8.0 Hz, 1H), 8.90 (d, J=4.0 Hz, 1H), 9.86 (s, 1H).

Example 13

Synthesis of I-108

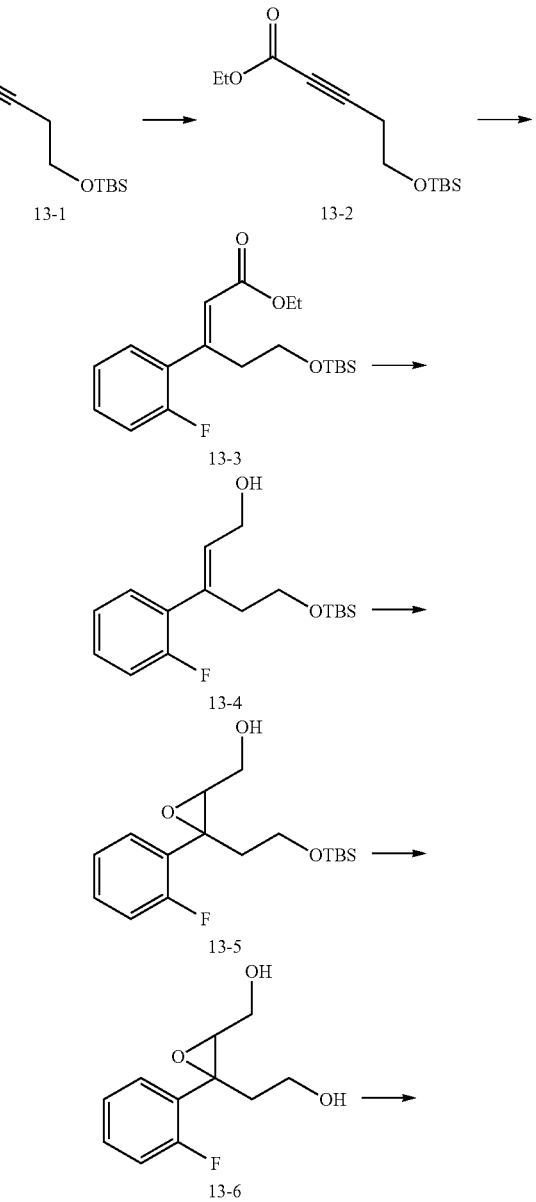

[Chemical Formula 108]

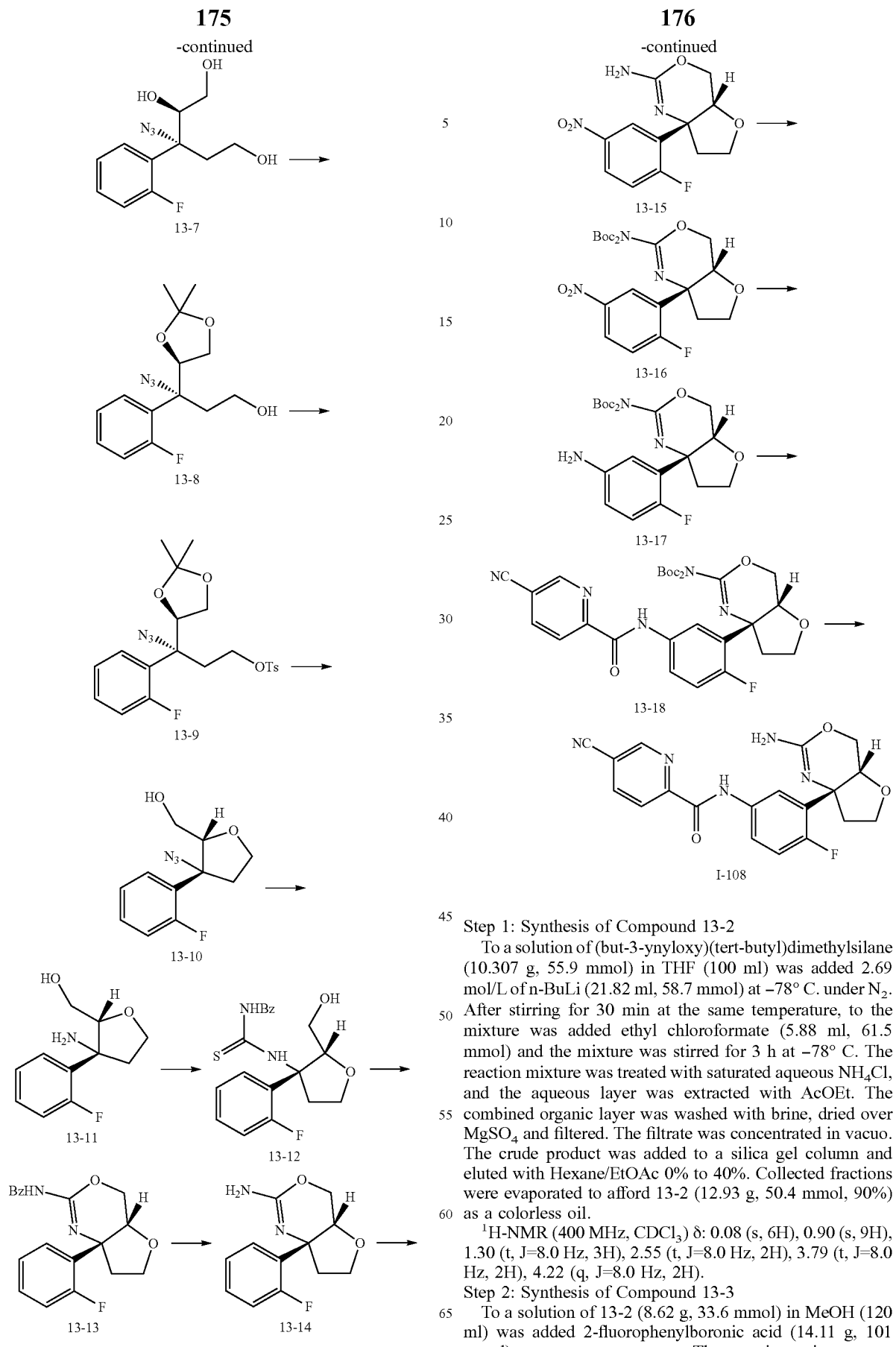

Step 1: Synthesis of Compound 13-2

To a solution of (but-3-ynyloxy)(tert-butyl)dimethylsilane (10.307 g, 55.9 mmol) in THF (100 ml) was added 2.69 mol/L of n-BuLi (21.82 ml, 58.7 mmol) at −78° C. under $N_2$. After stirring for 30 min at the same temperature, to the mixture was added ethyl chloroformate (5.88 ml, 61.5 mmol) and the mixture was stirred for 3 h at −78° C. The reaction mixture was treated with saturated aqueous $NH_4Cl$, and the aqueous layer was extracted with AcOEt. The combined organic layer was washed with brine, dried over $MgSO_4$ and filtered. The filtrate was concentrated in vacuo. The crude product was added to a silica gel column and eluted with Hexane/EtOAc 0% to 40%. Collected fractions were evaporated to afford 13-2 (12.93 g, 50.4 mmol, 90%) as a colorless oil.

$^1$H-NMR (400 MHz, $CDCl_3$) δ: 0.08 (s, 6H), 0.90 (s, 9H), 1.30 (t, J=8.0 Hz, 3H), 2.55 (t, J=8.0 Hz, 2H), 3.79 (t, J=8.0 Hz, 2H), 4.22 (q, J=8.0 Hz, 2H).

Step 2: Synthesis of Compound 13-3

To a solution of 13-2 (8.62 g, 33.6 mmol) in MeOH (120 ml) was added 2-fluorophenylboronic acid (14.11 g, 101 mmol) at room temperature. The reaction mixture was degassed once at −78° C. and acetyl(oxo)copper (0.412 g, 3.36 mmol) was added. The reaction mixture was degassed three times at −78° C. After stirring for 20 h at 28° C., the mixture was filtered through Celite. The filtrate was concentrated in vacuo. The crude product was added to a silica gel column and eluted with Hexane/EtOAc 0% to 20%. Collected fractions were evaporated to afford 13-3 (8.66 g, 24.57 mmol, 73%) as a yellow oil.

$^1$H-NMR (400 MHz, CDCl$_3$) δ: −0.06 (s, 6H), 0.79 (s, 9H), 1.30 (t, J=8.0 Hz, 3H), 3.29 (t, J=8.0 Hz, 2H), 3.69 (t, J=8.0 Hz, 2H), 4.20 (q, J=8.0 Hz, 2H), 5.99 (s, 1H), 7.05 (t, J=8.0 Hz, 1H), 7.12 (t, J=8.0 Hz, 1H), 7.24-7.28 (m, 2H).

Step 3: Synthesis of Compound 13-4

To a solution of 13-3 (2.359 g, 6.69 mmol) in THF (24 ml) was added 1.04 mol/L of DIBAL (16.4 ml, 16.7 mmol) in toluene at 0° C. After stirring for 2 h at the same temperature, the mixture was treated with saturated aqueous Rochelle's salt and stirred for 1.5 h. The aqueous layer was extracted with AcOEt, and the combined organic layer was washed with brine, dried over MgSO$_4$ and filtered. The filtrate was concentrated under vacuum to give 13-4 as a yellow oil, which was used for the next step without purification.

$^1$H-NMR (400 MHz, CDCl$_3$) δ: 0.01 (s, 6H), 0.86 (s, 9H), 2.71 (br, 1H), 2.79 (t, J=8.0 Hz, 2H), 3.55 (t, J=8.0 Hz, 2H), 4.22 (m, 2H), 6.03 (t, J=8.0 Hz, 1H), 7.02 (t, J=8.0 Hz, 1H), 7.09 (t, J=8.0 Hz, 1H), 7.19-7.26 (m, 2H).

Step 4: Synthesis of Compound 13-5

To a solution of 13-4 (840 mg, 2.71 mmol) in CH$_2$Cl$_2$ (10 ml) was added mCPBA (1000 mg, 4.06 mmol) at 0° C. After stirring for 2 h at room temperature, the mixture was treated with 2 mol/L NaOH (2.71 ml) and stirred for 0.5 h. The aqueous layer was extracted with AcOEt, and the combined organic layer was washed with brine, dried over MgSO$_4$ and filtered. The filtrate was concentrated under vacuum to give 13-5 as a yellow oil, which was used for the next step without purification.

$^1$H-NMR (400 MHz, CDCl$_3$) δ: 0.03 (s, 3H), 0.05 (s, 3H), 0.89 (s, 9H), 2.12 (m, 1H), 2.29 (m, 1H), 3.34-3.43 (m, 3H), 3.70-3.76 (m, 2H), 4.04 (m, 1H), 7.06 (t, J=8.0 Hz, 1H), 7.13 (t, J=8.0 Hz, 1H), 7.31 (m, 1H), 7.37 (m, 1H).

Step 5: Synthesis of Compound 13-6

To a solution of 13-5 (883 mg, 2.70 mmol) in THF (8 ml) was added 1.00 mol/L of TBAF (4.06 ml, 4.06 mmol) at 0° C. After stirring for 1 h at the same temperature, the reaction mixture was treated with aqueous NaHCO$_3$, and the aqueous layer was extracted with AcOEt. The combined organic layer was washed with H$_2$O and brine, dried over MgSO$_4$ and filtered. The filtrate was concentrated under vacuum to give 13-6 as a yellow oil, which was used for the next step without purification.

$^1$H-NMR (400 MHz, CDCl$_3$) δ: 2.18 (m, 1H), 2.25 (m, 1H), 3.32 (m, 1H), 3.33 (m, 1H), 3.57 (m, 1H), 3.75-3.83 (m, 2H), 4.05 (m, 1H), 7.07 (t, J=8.0 Hz, 1H), 7.15 (t, J=8.0 Hz, 1H), 7.31 (m, 1H), 7.43 (m, 1H).

Step 6: Synthesis of Compound 13-7

To a solution of 13-6 (574 mg, 2.70 mmol) and Ti(OEt)$_4$ (3.7 g, 16.23 mmol) in DMF (6 ml) was added NaN$_3$ (703 mg, 10.82 mmol) at room temperature. After stirring for 20 h at the same temperature, the mixture was treated with saturated aqueous citric acid and stirred for 1 h. The aqueous layer was extracted with AcOEt, and the combined organic layer was washed with brine, dried over MgSO$_4$ and filtered. The filtrate was concentrated in vacuo. The crude product was added to a silica gel column and eluted with Hexane/EtOAc 30% to 90%. Collected fractions were evaporated to afford 13-7 (682 mg, 2.67 mmol, 98%) as a white solid.

$^1$H-NMR (400 MHz, DMSO-d6) δ: 2.32 (m, 1H), 2.58 (m, 1H), 2.89 (m, 1H), 3.00 (m, 1H), 3.25 (m, 2H), 4.11 (m, 1H), 4.52 (m, 1H), 4.57 (m, 1H), 5.81 (m, 1H), 7.16-7.22 (m, 2H), 7.35 (m, 1H), 7.45 (m, 1H).

Step 7: Synthesis of Compound 13-8

To a solution of 13-7 (689 mg, 2.70 mmol) and 2,2-Dimethoxypropane (1.339 ml, 10.80 mmol) in CH$_2$Cl$_2$ (8 ml) was added CSA (62.7 mg, 0.27 mmol) at room temperature. After stirring for 2 h at the same temperature, the reaction mixture was treated with aqueous NaHCO$_3$, and the aqueous layer was extracted with AcOEt. The combined organic layer was washed with H$_2$O and brine, dried over MgSO$_4$ and filtered. The filtrate was concentrated in vacuo. The crude product was added to a silica gel column and eluted with Hexane/EtOAc 0% to 40%. Collected fractions were evaporated to afford 13-8 (480 mg, 1.63 mmol, 60%) as a colorless oil.

$^1$H-NMR (400 MHz, CDCl$_3$) δ: 1.39 (s, 3H), 1.57, (s, 3H), 2.65 (m, 1H), 2.72 (m, 1H), 3.49-3.70 (m, 4H), 4.79 (t, J=8.0 Hz, 1H), 7.04 (dd, J=12.0, 8.0 Hz, 1H), 7.15 (t, J=8.0 Hz, 1H), 7.31 (m, 1H), 7.62 (t, J=8.0 Hz, 1H).

Step 8: Synthesis of Compound 13-9

To a solution of 13-8 (462 mg, 1.567 mmol) and DMAP (573 mg, 4.69 mmol) in CH$_2$Cl$_2$ (6 ml) was added TsCl (597 mg, 3.13 mmol) at 0° C. After stirring for 2.5 h at room temperature, the reaction mixture was treated with aqueous NaHCO$_3$, and the aqueous layer was extracted with AcOEt. The combined organic layer was washed with H$_2$O and brine, dried over MgSO$_4$ and filtered. The filtrate was concentrated in vacuo. The crude product was added to a silica gel column and eluted with Hexane/EtOAc 0% to 30%. Collected fractions were evaporated to afford 13-9 (597 mg, 1.328 mmol, 85%) as a colorless oil.

$^1$H-NMR (400 MHz, CDCl$_3$) δ: 1.35 (s, 3H), 1.54, (s, 3H), 2.78 (m, 2H), 3.54 (m, 1H), 3.62 (m, 1H), 3.91 (m, 2H), 4.70 (t, J=8.0 Hz, 1H), 6.98 (dd, J=12.0, 8.0 Hz, 1H), 7.09 (t, J=8.0 Hz, 1H), 7.29 (m, 1H), 7.30 (d, J=8.0 Hz, 2H), 7.47 (t, J=8.0 Hz, 1H), 7.66 (d, J=8.0 Hz, 2H).

Step 9: Synthesis of Compound 13-10

To a solution of 13-9 (593 mg, 1.319 mmol) in MeOH (8 ml) was added p-toluenesulfonic acid monohydrate (125 mg, 0.66 mmol) at room temperature. After stirring for 20 h at the same temperature, to the mixture was added K$_2$CO$_3$ (547 mg, 3.96 mmol), and the mixture was stirred for 30 min at room temperature. The reaction mixture was treated with saturated aqueous NaHCO$_3$, and the aqueous layer was extracted with AcOEt. The combined organic layer was washed with brine, dried over MgSO$_4$ and filtered. The filtrate was concentrated in vacuo. The crude product was added to a silica gel column and eluted with Hexane/EtOAc 0% to 50%. Collected fractions were evaporated to afford 13-10 (304 mg, 1.28 mmol, 97%) as a colorless oil.

$^1$H-NMR (400 MHz, CDCl$_3$) δ: 1.86 (m, 1H), 2.63 (m, 1H), 2.84 (m, 1H), 3.76 (m, 1H), 3.89 (m, 1H), 4.11 (m, 1H), 4.22 (m, 1H), 4.25 (m, 1H), 7.13 (dd, J=12.0, 8.0 Hz, 1H), 7.19 (t, J=8.0 Hz, 1H), 7.35 (m, 1H), 7.51 (t, J=8.0 Hz, 1H).

Step 10: Synthesis of Compound 13-11

To a solution of 13-10 (615 mg, 2.59 mmol) in MeOH (10 ml) was added 10% Pd/C (120 mg) and hydrogenated at room temperature. After stirring for 4 h at the same temperature, the mixture was filtrated through a pad of Celite. The filtrate was concentrated under vacuum to give 13-11 (544 mg, 2.58 mmol, 99%) as a white amorphous that was used for the next step without purification.

¹H-NMR (400 MHz, CDCl₃) δ: 2.23 (m, 1H), 2.67 (m, 1H), 3.80-3.99 (m, 3H), 4.19 (m, 2H), 7.09 (dd, J=12.0, 8.0 Hz, 1H), 7.15 (t, J=8.0 Hz, 1H), 7.29 (m, 1H), 7.48 (t, J=8.0 Hz, 1H).

Step 11: Synthesis of Compound 13-12

To a stirred solution of 13-11 (544 mg, 2.58 mmol) in CH₂Cl₂ (10 mL) and acetone (4 ml) was added benzoyl isothiocyanate (0.38 mL, 2.58 mmol) at 0° C. After being stirred for 2 h at r.t., the reaction mixture was concentrated, and the resulting residue was added to a silica gel column and eluted with hexane/ethyl acetate 0% to 50%. Collected fractions were evaporated to afford 13-12 (952 mg, 2.54 mmol, 99%) as a yellow amorphous.

¹H-NMR (400 MHz, CDCl₃) δ: 2.32 (m, 1H), 2.96 (m, 1H), 3.06 (m, 1H), 3.85-4.02 (m, 3H), 4.20 (m, 1H), 4.56 (m, 1H), 7.06 (dd, J=12.0, 8.0 Hz, 1H), 7.17 (t, J=8.0 Hz, 1H), 7.29 (m, 1H), 7.47-7.55 (m, 3H), 7.63 (m, 1H), 7.86 (d, J=8.0 Hz, 2H), 8.89 (s, 1H), 11.75 (s, 1H).

Step 12: Synthesis of Compound 13-13

To a stirred solution of 13-12 (983 mg, 2.63 mmol) in acetonitrile (15 mL) was added EDC (604 mg, 3.15 mmol) at room temperature. After being stirred for 20 h at the same temperature, the reaction mixture was diluted with H₂O and extracted with ethyl acetate. The organic layers were combined and washed with brine. The organic layer was dried over MgSO₄, filtered and concentrated. The crude product was added to a silica gel column and eluted with hexane/ethyl acetate 0% to 50%. Collected fractions were evaporated to afford 13-13 (775 mg, 2.28 mmol, 87%) as a pale yellow amorphous.

¹H-NMR (400 MHz, CDCl₃) δ: 2.42 (m, 1H), 3.02 (m, 1H), 4.10-4.26 (m, 3H), 4.54-4.59 (m, 2H), 7.16 (dd, J=12.0, 8.0 Hz, 1H), 7.24 (m, 1H), 7.36-7.46 (m, 3H), 7.47-7.58 (m, 2H), 8.25 (d, J=8.0 Hz, 2H), 11.88 (br, 1H).

Step 13: Synthesis of Compound 13-14

To a stirred solution of 13-13 (760 mg, 2.23 mmol) in THF (10 mL) were added Boc₂O (0.726 mL, 3.13 mmol) and DMAP (273 mg, 2.23 mmol) at r.t. under nitrogen. After being stirred for 1 h, the reaction mixture was diluted with H₂O and extracted with ethyl acetate. The organic layers were combined and washed with brine. The organic layer was dried over MgSO₄, filtered and concentrated. The crude compound was dissolved in methanol (10 mL), and K₂CO₃ (617 mg, 4.47 mmol) as added at 0° C. After being stirred for 1 h at r.t., the reaction mixture was diluted with H₂O and extracted with ethyl acetate. The organic layer was dried over MgSO₄, filtered and concentrated. The crude product was added to a silica gel column and eluted with hexane/ethyl acetate 0% to 50%. Collected fractions were evaporated to afford Boc-protected compound. The compound was dissolved in CH₂Cl₂ (6 mL) and TFA (2 ml) was added at 0° C. After being stirred for 2 h at r.t., the reaction mixture was quenched with 20% aq. Na₂CO₃ and extracted with ethyl acetate. The organic layer was dried over MgSO₄ and filtered. The filtrate was concentrated under vacuum to give 13-14 (435 mg, 1.84 mmol, 99%) as a white amorphous that was used for the next step without purification.

¹H-NMR (400 MHz, CDCl₃) δ: 2.59 (m, 1H), 2.98 (m, 1H), 4.12 (m, 1H), 4.20 (m, 1H), 4.26 (m, 1H), 4.54 (m, 2H), 7.12 (dd, J=12.0, 8.0 Hz, 1H), 7.27 (t, J=8.0 Hz, 2H), 7.39 (dd, J=12.0, 8.0 Hz, 1H), 7.49 (t, J=8.0 Hz, 2H).

Step 14: Synthesis of Compound 13-15

To a solution of 13-14 (435 mg, 1.84 mmol) in TFA (3 ml) was added sulfuric acid (0.613 ml, 11.5 mmol) at −10° C. After stirring for 5 min at −10° C., to the reaction mixture was added HNO₃ (0.176 ml, 2.76 mmol) at −20° C. After stirring for 30 min at −10° C., the reaction mixture was treated with aqueous K₂CO₃. The aqueous layer was extracted with AcOEt and the organic layer was dried over MgSO₄, filtered and concentrated to afford 13-15 (490 mg, 1.74 mmol, 95%) as a yellow solid that was used for the next step without purification.

¹H-NMR (400 MHz, CDCl₃) δ: 2.13 (m, 1H), 2.85 (m, 1H), 3.80 (m 1H), 4.08 (m, 1H), 4.17 (m, 1H), 4.28 (m, 1H), 4.38 (m, 1H), 7.21 (t, J=8.0 Hz, 1H), 8.20 (m, 1H), 8.62 (m, 1H).

Step 15: Synthesis of Compound 13-16

To a solution of 13-15 (490 mg, 1.74 mmol), and DMAP (21.3 mg, 0.174 mmol) in THF (8 ml) was added Boc₂O (1.01 ml, 4.36 mmol) at room temperature. After stirring for 2 h at the same temperature, the mixture was concentrated under vacuum. The crude product was added to a silica gel column and eluted with Hexane/EtOAc 0% to 30%. Collected fractions were evaporated to afford 13-16 (768 mg, 1.60 mmol, 92%) as a white amorphous.

¹H-NMR (400 MHz, CDCl₃) δ: 1.54 (s, 18H), 2.26 (m, 1H), 2.87 (m, 1H), 3.86 (m 1H), 4.14 (m, 1H), 4.25 (m, 1H), 4.37 (m, 1H), 4.45 (m, 1H), 7.27 (t, J=8.0 Hz, 1H), 8.24 (m, 1H), 8.60 (m, 1H).

Step 16: Synthesis of Compound 13-17

To a solution of 13-16 (758 mg, 1.57 mmol) in EtOH (10 ml), THF (5 ml) and H₂O (5 ml) were added NH₄Cl (1011 mg, 18.89 mmol) and Fe (703 mg, 12.59 mmol) at room temperature. After stirring for 2 h at 60° C., the mixture was treated with H₂O and filtrated through a pad of Celite. The aqueous layer was extracted with AcOEt and the organic layers were combined and washed with brine. The organic layer was dried over MgSO₄, filtered and concentrated. The crude product was added to a silica gel column and eluted with hexane/ethyl acetate 0% to 50%. Collected fractions were evaporated to afford 13-17 (530 mg, 1.17 mmol, 75%) as a white amorphous.

¹H-NMR (400 MHz, CDCl₃) δ: 1.53 (s, 18H), 2.18 (m, 1H), 2.90 (m, 1H), 3.57 (br, 2H), 3.92 (m, 1H), 4.07-4.18 (m, 2H), 4.35 (s, 1H), 4.39 (m, 1H), 6.55 (m, 1H), 6.86 (dd, J=12.0, 8.0 Hz, 1H), 6.92 (dd, J=8.0, 4.0 Hz, 1H).

Step 17: Synthesis of Compound 13-18

To a solution of 13-17 (230 mg, 0.509 mmol) in DMF (2 ml) were added 5-cyanopicolinic acid hydrate (85 mg, 0.509 mmol), HATU (213 mg, 0.560 mmol) and DIPEA (0.107 ml, 0.611 mmol) at room temperature. After stirring for 18 h at the same temperature, the reaction mixture was treated with H₂O. The aqueous layer was extracted with AcOEt, and the organic layer was dried over MgSO₄, filtered and concentrated. The crude product was added to a silica gel column and eluted with hexane/EtOAc 50%. Collected fractions were evaporated to afford 13-18 (296 mg, 0.509 mmol, 100%) as a white amorphous.

¹H-NMR (400 MHz, CDCl₃) δ: 1.56 (s, 18H), 2.24 (m, 1H), 2.96 (m, 1H), 3.93 (m, 1H), 4.10-4.19 (m, 2H), 4.39 (s, 1H), 4.43 (m, 1H), 7.14 (t, J=8.0 Hz, 1H), 7.57 (d, J=8.0 Hz, 1H), 8.22 (d, J=8.0 Hz, 1H), 8.29 (d, J=8.0 Hz, 1H), 8.43 (d, J=8.0 Hz, 1H), 8.81 (s, 1H), 9.94 (s, 1H).

Step 18: Synthesis of Compound I-108

To a solution of 13-18 (296 mg, 0.509 mmol) in CH₂Cl₂ (2 ml) was added TFA (0.5 ml) at 0° C. After being stirred for 2 h at r.t., the reaction mixture was quenched with 20% aq. K₂CO₃. The aqueous layer was extracted with AcOEt and the organic layers were combined and washed with brine. The organic layer was dried over MgSO₄, filtered and concentrated. The crude product was purified by supercritical fluid chromatography (SFC) (Chiralpak (Registered trademark) IB; 10-50% ethanol with 0.1% diethylamine) to give compound I-108 (63 mg, 0.165 mmol, 33%) as a white solid.

¹H-NMR (400 MHz, DMSO-d6) δ: 1.99 (m, 1H), 2.66 (m, 1H), 3.72 (m, 1H), 3.84 (m, 1H), 3.98 (m, 1H), 4.10 (m, 1H), 4.21 (m, 1H), 5.66 (br, 2H), 7.19 (t, J=8.0 Hz, 1H), 7.84 (m, 1H), 8.08 (d, J=4.0 Hz, 1H), 8.28 (d, J=8.0 Hz, 1H), 8.59 (t, J=8.0 Hz, 1H), 9.20 (s, 1H), 10.89 (s, 1H).

Example 14

Synthesis of I-111

[Chemical Formula 109]

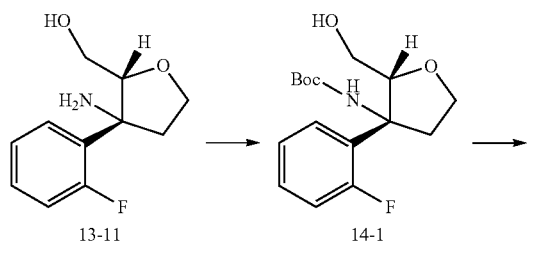
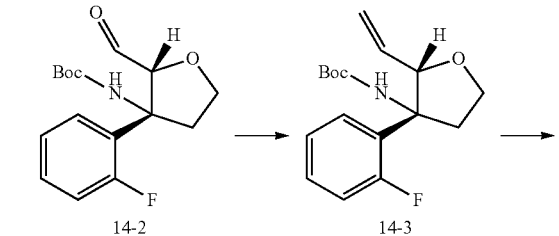
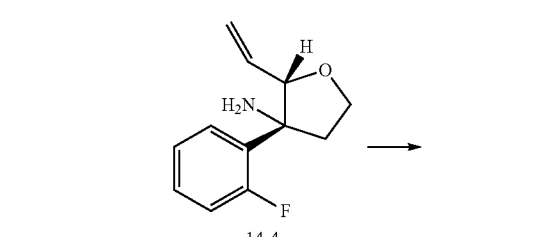
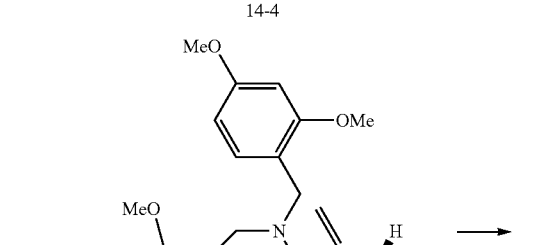
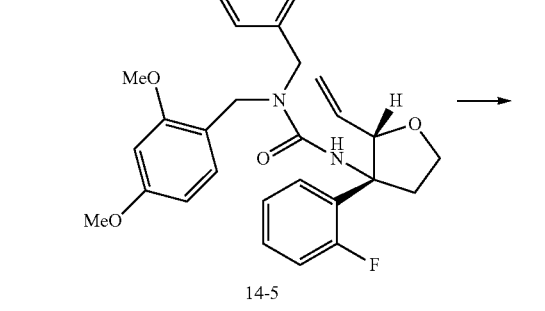

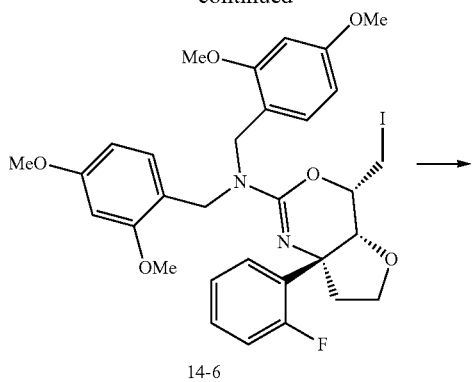
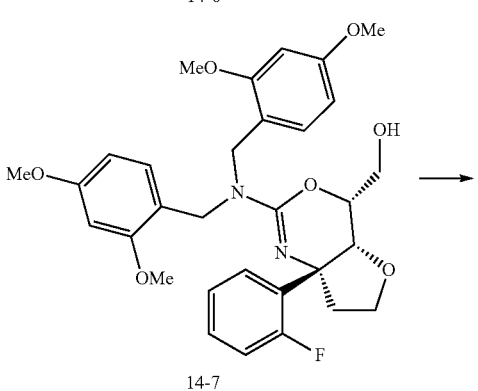
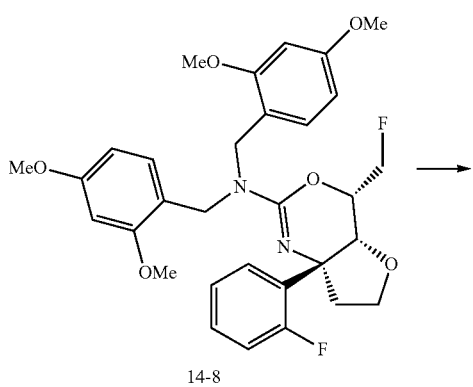
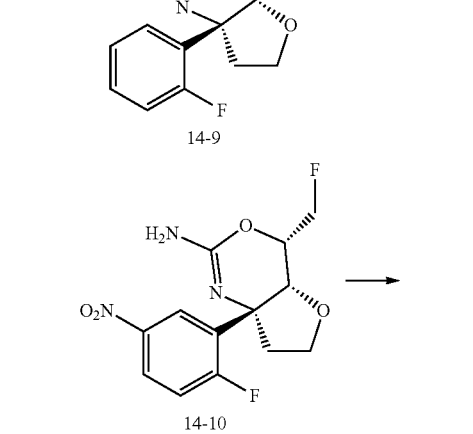

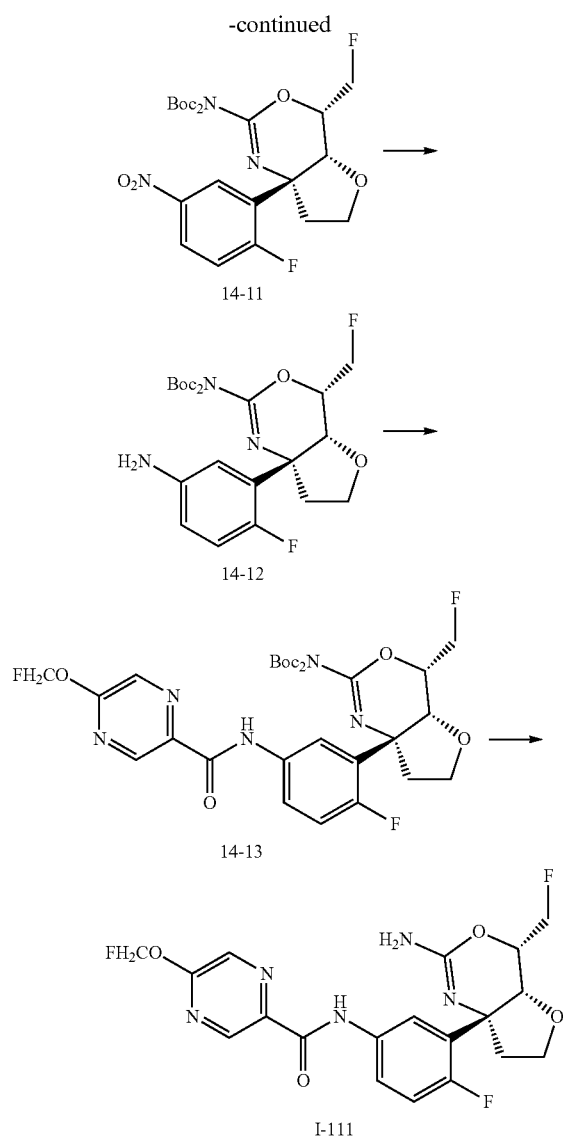

Step 1: Synthesis of Compound 14-1

To a solution of 13-11 (1.683 g, 7.97 mmol) in THF (16 ml) was added Boc₂O (3.70 ml, 15.94 mmol) at room temperature. After stirring for 20 h at 50° C., the mixture was concentrated under vacuum. The crude product was added to a silica gel column and eluted with Hexane/EtOAc 20% to 50%. Collected fractions were evaporated to afford 14-1 (2.398 g, 7.70 mmol, 97%) as a white solid.

$^1$H-NMR (400 MHz, CDCl$_3$) δ: 1.41 (br, 9H), 2.57 (m, 1H), 2.81 (m, 2H), 3.72 (m, 1H), 3.90 (m, 1H), 4.02-4.20 (m, 3H), 6.66 (m, 1H), 7.02 (dd, J=12.0, 8.0 Hz, 1H), 7.14 (t, J=8.0 Hz, 1H), 7.26 (m, 1H), 7.49 (t, J=8.0 Hz, 1H).

Step 2: Synthesis of Compound 14-2

To a solution of 14-1 (504 mg, 1.62 mmol) in DMSO (10 ml) was added IBX (680 mg, 2.43 mmol) at room temperature. After stirring for 1 h at 50° C., the mixture was filtrated through a pad of Celite. The filtrate was diluted with H₂O, and the aqueous layer was extracted with AcOEt. The combined organic layer was washed with brine, dried over MgSO₄ and filtered. The filtrate was concentrated in vacuo. The crude product was added to a silica gel column and eluted with Hexane/EtOAc 0% to 50%. Collected fractions were evaporated to afford 14-2 (456 mg, 1.47 mmol, 91%) as a white amorphous.

$^1$H-NMR (400 MHz, CDCl$_3$) δ: 1.32 (br, 9H), 2.51 (m, 2H), 3.81 (m, 1H), 4.28 (m, 1H), 5.24 (m, 1H), 5.49 (m, 1H), 7.08 (dd, J=12.0, 8.0 Hz, 1H), 7.16 (t, J=8.0 Hz, 1H), 7.33 (m, 1H), 7.46 (t, J=8.0 Hz, 1H), 9.79 (s, 1H).

Step 3: Synthesis of Compound 14-3

To a solution of methyltriphenylphosphonium bromide (1.46 g, 4.09 mmol) in toluene (10 ml) was added 1.00 mol/L of t-BuOK solution in THF (3.43 ml, 3.44 mmol) at room temperature. After stirring for 30 min at the same temperature, to the mixture was added a solution of 14-2 (506 mg, 1.63 mmol) in toluene (5 ml) at 0° C., and the mixture was stirred for 24 h at room temperature. The reaction mixture was treated with saturated aqueous NH₄Cl, and the aqueous layer was extracted with AcOEt. The combined organic layer was washed with brine, dried over MgSO₄ and filtered. The filtrate was concentrated in vacuo. The crude product was added to a silica gel column and eluted with Hexane/EtOAc 0% to 20%. Collected fractions were evaporated to afford 14-3 (319 mg, 1.04 mmol, 63%) as a colorless oil.

$^1$H-NMR (400 MHz, CDCl$_3$) δ: 1.52 (br, 9H), 2.82 (m, 2H), 4.01 (m, 1H), 4.10 (m, 1H), 4.58 (m, 1H), 5.11 (m, 1H), 5.30 (dt, J=12.0, 4.0 Hz, 1H), 5.43 (dt, J=16.0, 4.0 Hz, 1H), 5.61 (m, 1H), 6.98 (dd, J=12.0, 8.0 Hz, 1H), 7.05 (t, J=8.0 Hz, 1H), 7.16 (m, 1H), 7.26 (m, 1H).

Step 4: Synthesis of Compound 14-4

To a solution of 14-3 (594 mg, 1.93 mmol) in dioxane (10 ml) was added 4 mol/L HCl in dioxane (9.66 ml, 38.7 mmol) at room temperature. After stirring for 2 h at the same temperature, the reaction mixture was treated with aqueous K₂CO₃ and the aqueous layer was extracted with AcOEt. The combined organic layer was washed with H₂O and brine, dried over MgSO₄ and filtered. The filtrate was concentrated under vacuum to give 14-4 (333 mg, 1.61 mmol, 83%), as a brown oil that was used for the next step without purification.

$^1$H-NMR (400 MHz, CDCl$_3$) δ: 2.17 (m, 1H), 2.70 (m, 1H), 4.07 (m, 1H), 4.22 (m, 1H), 4.65 (m, 1H), 5.28 (m, 1H), 5.31 (m, 1H), 5.80 (m, 1H), 7.07 (dd, J=12.0, 8.0 Hz, 1H), 7.14 (t, J=8.0 Hz, 1H), 7.26 (m, 1H), 7.53 (t, J=8.0 Hz, 1H).

Step 5: Synthesis of Compound 14-5

To a solution of 14-4 (400 mg, 1.93 mmol) in AcOEt (6 ml) and H₂O (4 ml) were added NaHCO₃ (486 mg, 5.79 mmol) and 4-nitrophenyl carbonochloridate (389 mg, 1.93 mmol) at 0° C. After stirring for 30 min at the same temperature, to the reaction mixture was added bis(2,4-dimethoxybenzyl)amine (613 mg, 1.93 mmol). After stirring for 2 h at the same temperature, the reaction mixture was treated with H₂O, and the aqueous layer was extracted with AcOEt. The organic layer was dried over MgSO₄, filtered and concentrated. The crude product was added to a silica gel column and eluted with hexane/EtOAc 0% to 50%. Collected fractions were evaporated to afford 14-5 (810 mg, 1.47 mmol, 76%) as a white amorphous.

$^1$H-NMR (400 MHz, CDCl$_3$) δ: 2.91 (m, 2H), 3.77 (s, 6H), 3.81 (s, 6H), 4.02 (m, 2H), 4.37 (d, J=16.0 Hz, 2H), 4.46 (d, J=16.0 Hz, 2H), 4.65 (m, 1H), 5.01 (m, 1H), 5.18 (m, 1H), 5.40 (s, 1H), 5.52 (m, 1H), 6.44-6.46 (m, 4H), 7.01 (dd, J=12.0, 8.0 Hz, 1H), 7.09 (t, J=8.0 Hz, 1H), 7.15 (m, 2H), 7.21 (m, 1H), 7.33 (m, 1H).

Step 6: Synthesis of Compound 14-6

To a solution of iodine (747 mg, 2.94 mmol) in MeCN (25 ml) was added 14-5 (0.81 g, 1.47 mmol) in MeCN (7 ml) at 0° C. After stirring for 30 min at the same temperature, the reaction mixture was treated with aqueous $NaHCO_3$ and $Na_2S_2O_3$. The aqueous layer was extracted with AcOEt, and the organic layer was dried over $MgSO_4$, filtered and concentrated. The crude product was added to a silica gel column and eluted with hexane/EtOAc 0% to 30%. Collected fractions were evaporated to afford 14-6 (0.81 g, 1.20 mmol, 81%) as a white amorphous.

$^1$H-NMR (400 MHz, $CDCl_3$) δ: 1.97 (m, 1H), 2.84 (m, 1H), 3.28 (m, 1H), 3.37 (m, 1H), 3.74 (s, 6H), 3.81 (s, 6H), 3.75-3.85 (m, 2H), 4.07 (m, 1H), 4.43 (s, 1H), 4.44 (d, J=16.0 Hz, 2H), 4.66 (d, J=16.0 Hz, 2H), 6.43-6.47 (m, 4H), 7.01 (dd, J=12.0, 8.0 Hz, 1H), 7.08 (t, J=8.0 Hz, 1H), 7.18 (d, J=8.0 Hz, 2H), 7.23 (m, 1H), 7.66 (t, J=8.0 Hz, 1H).

Step 7: Synthesis of Compound 14-7

To a solution of 14-6 (801 mg, 1.18 mmol) in $MeNO_2$ (5.2 ml) and $H_2O$ (2.1 ml) was added (2,2,2-trifluoroacetoxy) silver (1.05 g, 4.74 mmol) at room temperature. After stirring for 20 h at 80° C., the reaction mixture was treated with aqueous $NaHCO_3$, and the mixture was filtrated through a pad of Celite. The aqueous layer was extracted with AcOEt, and the organic layer was dried over $MgSO_4$, filtered and concentrated. The crude product was added to a silica gel column and eluted with hexane/EtOAc 0% to 50%. Collected fractions were evaporated to afford 14-7 (432 mg, 0.762 mmol, 64%) as a white amorphous.

$^1$H-NMR (400 MHz, $CDCl_3$) δ: 1.96 (m, 1H), 2.47 (m, 1H), 2.81 (m, 1H), 3.70-3.78 (m, 2H), 3.75 (s, 6H), 3.81 (s, 6H), 3.88 (m, 2H), 4.08 (m, 1H), 4.37 (s, 1H), 4.44 (d, J=16.0 Hz, 2H), 4.66 (d, J=16.0 Hz, 2H), 6.43-6.48 (m, 4H), 7.00 (dd, J=12.0, 8.0 Hz, 1H), 7.07 (t, J=8.0 Hz, 1H), 7.19 (d, J=8.0 Hz, 2H), 7.23 (m, 1H), 7.66 (t, J=8.0 Hz, 1H).

Step 8: Synthesis of Compound 14-8

To a solution of 14-7 (432 mg, 0.762 mmol) in $CH_2Cl_2$ (6.5 ml) was added DAST (0.302 ml, 2.27 mmol) at −78° C. After stirring for 3 h at room temperature, the reaction mixture was treated with aqueous $NaHCO_3$. The aqueous layer was extracted with AcOEt, and the organic layer was dried over $MgSO_4$, filtered and concentrated. The crude product was added to a silica gel column and eluted with hexane/EtOAc 0% to 30%. Collected fractions were evaporated to afford 14-8 (258 mg, 0.454 mmol, 60%) as a white amorphous.

$^1$H-NMR (400 MHz, $CDCl_3$) δ: 1.96 (m, 1H), 2.82 (m, 1H), 3.75 (s, 6H), 3.81 (s, 6H), 3.88 (m, 1H), 3.96 (m, 1H), 4.07 (m, 1H), 4.31 (s, 1H), 4.47 (d, J=16.0 Hz, 2H), 4.60 (d, J=16.0 Hz, 2H), 4.45-4.72 (m, 2H), 6.42-6.48 (m, 4H), 7.00 (dd, J=12.0, 8.0 Hz, 1H), 7.06 (t, J=8.0 Hz, 1H), 7.17 (d, J=8.0 Hz, 2H), 7.23 (m, 1H), 7.63 (t, J=8.0 Hz, 1H).

Step 9: Synthesis of Compound 14-9

To a solution of 14-8 (247 mg, 0.434 mmol) in TFA (2.5 ml) was added anisole (0.33 ml, 3.04 mmol) at room temperature. After stirring for 24 h at 80° C., the reaction mixture was treated with aqueous $K_2CO_3$. The aqueous layer was extracted with AcOEt, and the organic layer was dried over $Na_2SO_4$, filtered and concentrated. The crude product was added to a silica gel column and eluted with $CHCl_3$/MeOH 0% to 15%. Collected fractions were evaporated to afford 14-9 (118 mg, 0.44 mmol, 100%) as a white solid.

$^1$H-NMR (400 MHz, $CDCl_3$) δ: 2.33 (m, 1H), 2.92 (m, 1H), 4.09-4.27 (m, 3H), 4.39 (s, 1H), 4.65 (m, 2H), 7.09 (dd, J=12.0, 8.0 Hz, 1H), 7.23 (t, J=8.0 Hz, 1H), 7.35 (m, 1H), 7.55 (d, J=8.0 Hz, 1H).

Step 10: Synthesis of Compound 14-10

To a solution of 14-9 (168 mg, 0.63 mmol) in TFA (0.8 ml) was added sulfuric acid (0.22 ml, 4.07 mmol) at −10° C. After stirring for 5 min at −10° C., $HNO_3$ (0.06 ml, 0.94 mmol) was added to the reaction mixture at −10° C. After stirring for 30 min at 0° C., the reaction mixture was treated with aqueous $K_2CO_3$. The aqueous layer was extracted with AcOEt, and the organic layer was dried over $Na_2SO_4$, filtered and concentrated to afford 14-10 (141 mg, 0.45 mmol, 72%) as a white solid.

$^1$H-NMR (400 MHz, $CDCl_3$) δ: 2.08 (m, 1H), 2.81 (m, 1H), 4.01 (m, 2H), 4.13 (m, 1H), 4.31 (m, 2H), 4.32 (m, 1H), 4.62 (m, 2H), 7.22 (dd, J=12.0, 8.0 Hz, 1H), 8.20 (m, 1H), 8.62 (dd, J=8.0, 4.0 Hz, 1H).

Step 11: Synthesis of Compound 14-11

To a solution of 14-10 (141 mg, 0.45 mmol) in THF (4 ml) were added $Boc_2O$ (0.261 ml, 1.13 mmol) and DMAP (5.5 mg, 0.045 mmol) at room temperature. After stirring for 2 h at the same temperature, the mixture was concentrated under vacuum. The crude product was added to a silica gel column and eluted with Hexane/EtOAc 0% to 30%. Collected fractions were evaporated to afford 14-11 (165 mg, 0.321 mmol, 71%) as a white solid.

$^1$H-NMR (400 MHz, $CDCl_3$) δ: 1.53 (s, 18H), 2.23 (m, 1H), 2.87 (m, 1H), 4.06-4.20 (m, 3H), 4.31 (s, 1H), 4.67 (m, 2H), 7.26 (t, J=8.0 Hz, 1H), 8.24 (m, 1H), 8.58 (dd, J=8.0, 4.0 Hz, 1H).

Step 12: Synthesis of Compound 14-12

To a solution of 14-11 (160 mg, 0.312 mmol) in MeOH (2 ml) was added 10% Pd/C (70 mg) and hydrogenated at room temperature. After stirring for 1 h at the same temperature, the mixture was filtrated through a pad of Celite. The filtrate was concentrated under vacuum to give 14-12 (145 mg, 0.3 mmol, 96%) as a white amorphous that was used for the next step without purification.

$^1$H-NMR (400 MHz, $CDCl_3$) δ: 1.53 (s, 18H), 2.16 (m, 1H), 2.88 (m, 1H), 4.04-4.19 (m, 3H), 4.29 (s, 1H), 4.66 (m, 2H), 6.60 (m, 1H), 6.88 (m, 1H), 6.94 (m, 1H).

Step 13: Synthesis of Compound 14-13

To a solution of 14-12 (95 mg, 0.196 mmol) in DMF (1 ml) were added 5-(fluoromethoxy)pyrazine-2-carboxylic acid (37.2 mg, 0.216 mmol), HATU (82 mg, 0.216 mmol) and DIPEA (0.041 ml, 0.236 mmol) at room temperature. After stirring for 20 h at the same temperature, the reaction mixture was treated with $H_2O$. The aqueous layer was extracted with AcOEt, and the organic layer was dried over $Na_2SO_4$, filtered and concentrated. The crude product was added to a silica gel column and eluted with hexane/EtOAc 0% to 40%. Collected fractions were evaporated to afford 14-13 (115 mg, 0.180 mmol, 92%) as a colorless oil.

$^1$H-NMR (400 MHz, $CDCl_3$) δ: 1.54 (s, 18H), 2.22 (m, 1H), 2.95 (m, 1H), 4.07-4.21 (m, 3H), 4.32 (s, 1H), 4.66 (m, 2H), 6.17 (dd, J=48.0, 8.0 Hz, 2H), 7.14 (dd, J=12.0, 8.0 Hz, 1H), 7.54 (dd, J=8.0, 4.0 Hz, 1H), 8.22 (m, 1H), 8.28 (s, 1H), 9.08 (s, 1H), 9.59 (br, 1H).

Step 15: Synthesis of I-111

To a solution of 14-13 (115 mg, 0.180 mmol) in $CH_2Cl_2$ (1.5 ml) was added TFA (0.5 ml) at 0° C. After being stirred for 2 h at room temperature, the reaction mixture was quenched with 20% aq. $K_2CO_3$. The aqueous layer was extracted with AcOEt and the organic layers were combined and washed with brine. The organic layer was dried over $MgSO_4$, filtered and concentrated. The crude product was purified by supercritical fluid chromatography (SFC) (Chiralpak (Registered trademark) IB; 10-50% ethanol with 0.1% diethylamine) to give compound I-ill (34 mg, 0.079 mmol, 44%) as a white solid.

$^1$H-NMR (400 MHz, $CDCl_3$) δ: 2.17 (m, 1H), 2.89 (m, 1H), 4.04 (m, 1H), 4.14 (m, 2H), 4.36 (m, 2H), 4.63 (m, 2H), 6.16 (d, J=48.0 Hz, 2H), 7.12 (dd, J=12.0, 8.0 Hz, 1H), 7.69 (dd, J=8.0, 4.0 Hz, 1H), 8.02 (m, 1H), 8.30 (s, 1H), 9.08 (s, 1H), 9.57 (br, 1H).

Example 15
Synthesis of Compound I-104
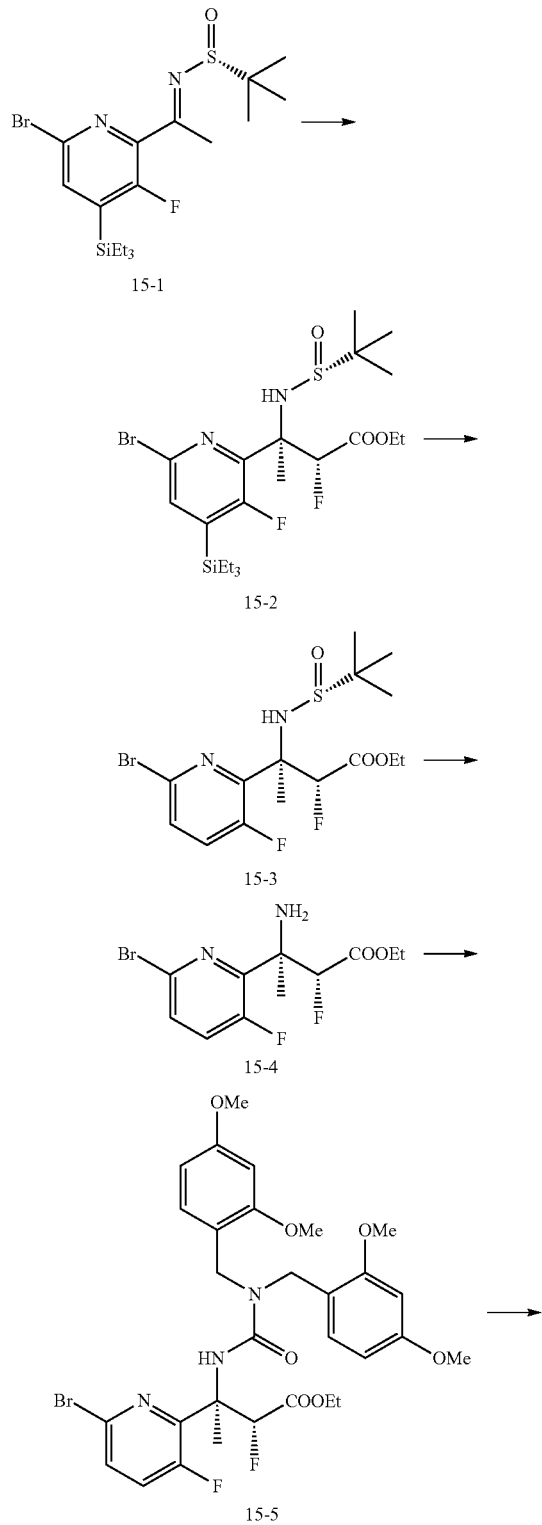
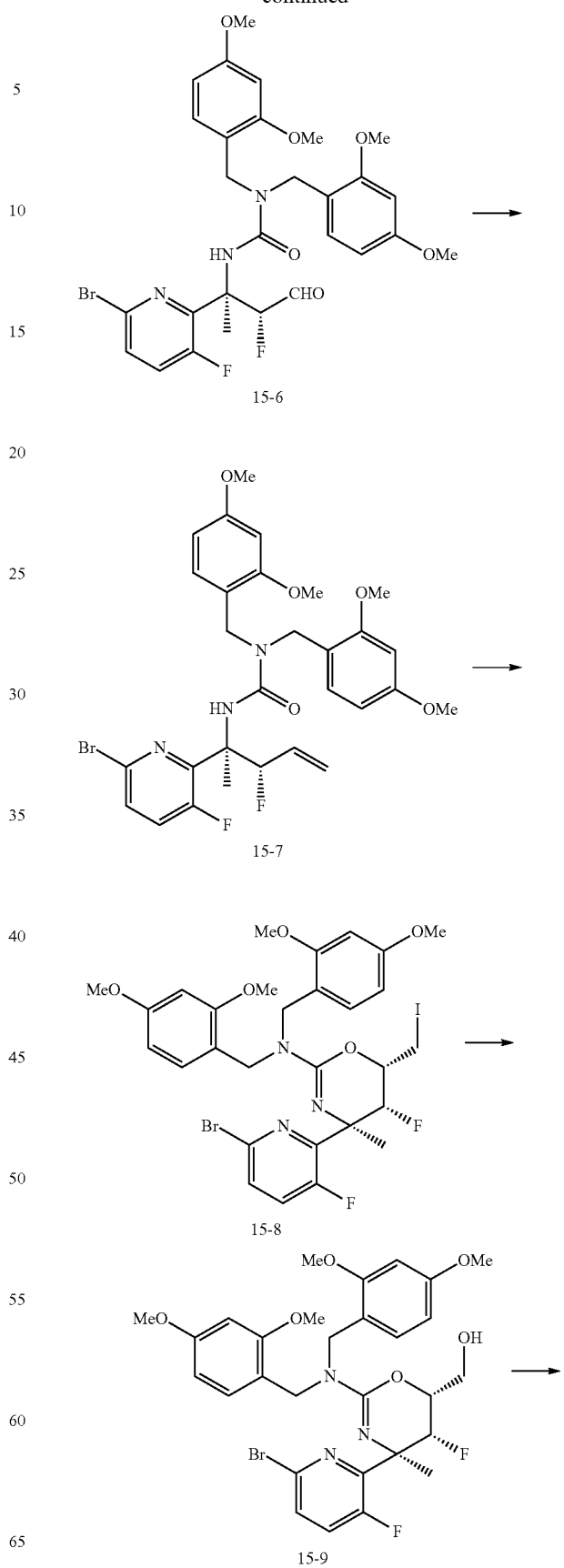

-continued

[Chemical Formula 111]

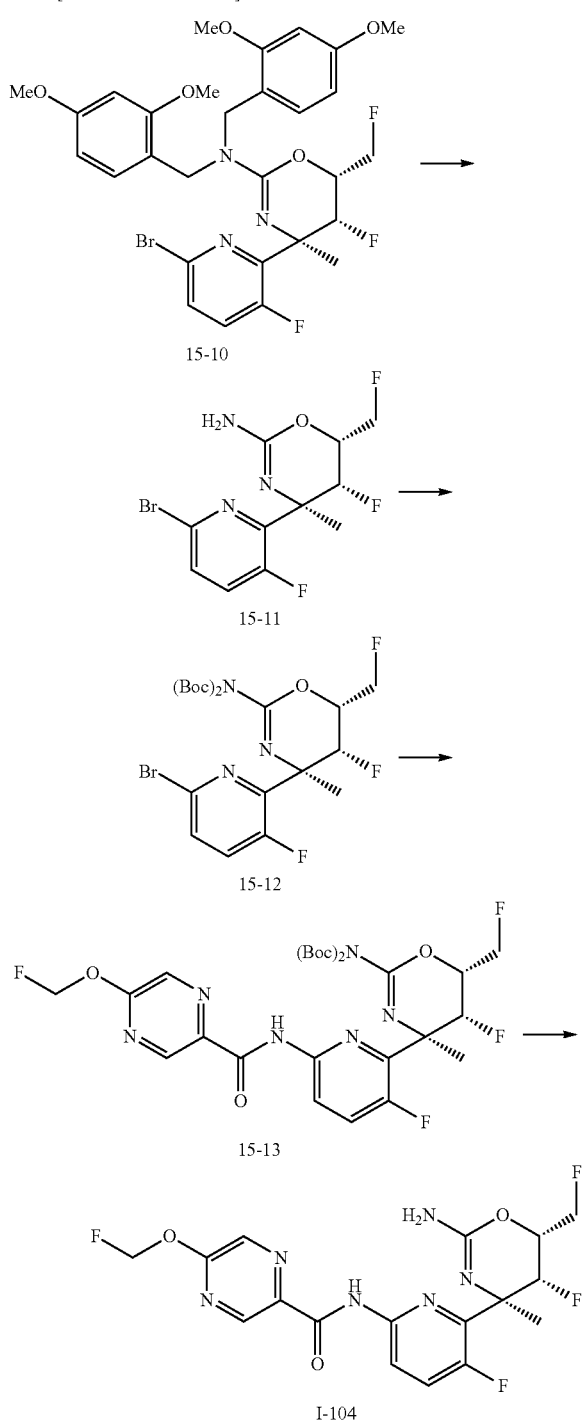

Step 1: Synthesis of Compound 15-2

A stirred suspension of zinc (1.40 g, 21.4 mmol) in THF (80 ml) was heated to reflux. To the suspension were added a solution of compound 15-1 (8.46 g, 19.4 mmol) in THF (20 ml) and a solution of ethyl 2-bromo-2-fluoroacetate (3.95 g, 21.4 mmol) in THF (10 ml). After stirring for 3 h at the same temperature, the reaction mixture was treated with saturated aqueous NH$_4$Cl and the aqueous layer was extracted with AcOEt. The combined organic layer was washed with brine, dried over Na$_2$SO$_4$, filtered and concentrated. The crude product was added to a silica gel column and eluted with Hexane/EtOAc 25%. Collected fractions were evaporated to afford compound 2 (5.76 g, 10.6 mmol, 55%) as a brown oil.

$^1$H-NMR (400 MHz, CDCl$_3$) δ: 0.84-0.89 (m, 6H), 0.94-0.98 (m, 9H), 1.24 (s, 9H), 1.29 (t, J=7.2 Hz, 3H), 1.96 (s, 3H), 4.26 (m, 2H), 5.16 (s, 1H), 5.34 (d, J=46.4 Hz, 1H), 7.37 (d, J=2.6 Hz, 1H).

Step 2: Synthesis of Compound 15-3

KF (1.24 g, 21.3 mmol) was added to a solution of compound 15-2 (5.76 g, 10.6 mmol) and AcOH (1.22 ml, 21.3 mmol) in THF (30 ml). DMF (30 ml) was added and the mixture was stirred at room temperature. After stirring for 2.5 h at the same temperature, the reaction mixture was treated with saturated aqueous NaHCO$_3$ and the aqueous layer was extracted with AcOEt. The combined organic layer was washed with brine, dried over Na$_2$SO$_4$, filtered and concentrated. The crude product was added to a silica gel column and eluted with Hexane/EtOAc 30% to 50%. Collected fractions were evaporated to afford compound 15-3 (4.01 g, 9.38 mmol, 88%) as a brown oil.

$^1$H-NMR (400 MHz, CDCl$_3$) δ: 1.25 (s, 9H), 1.30 (t, J=7.2 Hz, 3H), 1.97 (s, 3H), 4.27 (m, 2H), 5.14 (s, 1H), 5.35 (d, J=46.4 Hz, 1H), 7.29 (dd, J=10.8, 8.4 Hz, 1H), 7.45 (dd, J=8.4, 2.9 Hz, 1H).

Step 3: Synthesis of Compound 15-5

To a solution of compound 15-3 (3.46 g, 8.10 mmol) in MeOH (35 ml) was added 4 mol/L HCl in Dioxane (2.8 ml, 11.3 mmol) at room temperature. After stirring for 1 h at the same temperature, the reaction mixture was treated with aqueous NaHCO$_3$ and the aqueous layer was extracted with AcOEt. The combined organic layer was washed with H$_2$O and brine, dried over Na$_2$SO$_4$, filtered and concentrated to give compound 15-4 as a brown oil that was used for the next step without purification.

To a solution of compound 15-4 in EtOAc (20 ml) and H$_2$O (10 ml) were added NaHCO$_3$ (2.38 g, 28.4 mmol) and 4-nitrophenyl carbonochloridate (1.80 g, 8.91 mmol) at 0° C. After stirring for 1 h at the same temperature, bis(2,4-dimethoxybenzyl)amine (2.83 g, 8.91 mmol) was added to the reaction mixture. After stirring for 3 h at the same temperature, the reaction mixture was treated with H$_2$O and the aqueous layer was extracted with AcOEt. The organic layer was washed with 10% aqueous K$_2$CO$_3$ and brine, dried over Na$_2$SO$_4$, filtered and concentrated. The crude product was added to a silica gel column and eluted with Hexane/EtOAc 10% to 30%. Collected fractions were evaporated to afford compound 15-5 (5.0 g, 7.50 mmol, 93%) as a white amorphous.

$^1$H-NMR (400 MHz, CDCl$_3$) δ: 1.15 (t, J=7.2 Hz, 3H), 1.94 (s, 3H), 3.80 (s, 12H), 3.98-4.20 (m, 2H), 4.30 (d, J=16.3 Hz, 2H), 4.42 (d, J=16.3 Hz, 2H), 5.73 (d, J=47.3 Hz, 1H), 6.43-6.47 (m, 5H), 7.15 (d, J=7.9 Hz, 2H), 7.19 (dd, J=10.7, 8.4 Hz, 1H), 7.35 (dd, J=8.4, 2.9 Hz, 1H).

Step 4: Synthesis of Compound 15-7

To a solution of compound 15-5 (5.0 g, 7.50 mmol) in CH$_2$Cl$_2$ (75 ml) was added 1.04 mol/L DIBAL (15.2 ml, 15.8 mmol) at −78° C. After stirring for 1 h at the same temperature, the mixture was treated with saturated aqueous Rochelle's salt and stirred for 4.5 h. The aqueous layer was extracted with AcOEt and the combined organic layer was washed with brine, dried over Na$_2$SO$_4$ and filtered. The filtrate was concentrated under vacuum to give compound 15-6 as a yellow amorphous that was used for the next step without purification.

To a solution of methyltriphenylphosphonium bromide (6.70 g, 18.8 mmol) in toluene (60 ml) was added 1.00 mol/L t-BuOK solution in THF (17.3 ml, 17.3 mmol) at room temperature. After stirring for 1 h at the same temperature, a solution of compound 15-6 in toluene (50 ml) was added at 0° C. After stirring for 6 h at room temperature, the reaction mixture was treated with saturated aqueous NH₄Cl and the aqueous layer was extracted with AcOEt. The combined organic layer was washed with brine, dried over Na₂SO₄, filtered and concentrated. The crude product was added to a silica gel column and eluted with Hexane/EtOAc 10% to 30%. Collected fractions were evaporated to afford compound 15-7 (3.25 g, 5.24 mmol, 70%) as a white amorphous.

¹H-NMR (400 MHz, CDCl₃) δ: 1.82 (t, J=2.0 Hz, 3H), 3.79 (s, 6H), 3.80 (s, 6H), 4.35 (d, J=16.3 Hz, 2H), 4.40 (d, J=16.3 Hz, 2H), 5.20 (d, J=10.5 Hz, 1H), 5.28 (m, 1H), 5.47 (dd, J=46.7, 6.0 Hz, 1H), 5.81 (m, 1H), 5.91 (s, 1H), 6.44-6.47 (m, 4H), 7.13 (d, J=8.3 Hz, 2H), 7.16 (dd, J=10.8, 8.5 Hz, 1H), 7.31 (dd, J=8.5, 3.0 Hz, 1H).

Step 5: Synthesis of Compound 15-8

To a solution of Iodine (2.66 g, 10.48 mmol) in MeCN (70 ml) was added compound 15-7 (3.25 g, 5.24 mmol) in MeCN (30 ml) at 0° C. After stirring for 1.5 h at the same temperature, the reaction mixture was treated with aqueous NaHCO₃ and Na₂S₂O₃. The aqueous layer was extracted with AcOEt. The combined organic layer was washed with brine, dried over Na₂SO₄, filtered and concentrated. The crude product was added to a silica gel column and eluted with hexane/EtOAc 20% to 30%. Collected fractions were evaporated to afford compound 15-8 (3.25 g, 4.35 mmol, 83%) as a yellow amorphous.

¹H-NMR (400 MHz, CDCl₃) δ: 1.68 (s, 3H), 3.21 (dd, J=9.9, 6.9 Hz, 1H), 3.31 (dd, J=9.9, 8.0 Hz, 1H), 3.70 (s, 6H), 3.79 (s, 6H), 4.24 (dt, J=21.8, 7.2 Hz, 1H), 4.48 (s, 4H), 5.42 (d, J=48.8 Hz, 1H), 6.39 (d, J=2.3 Hz, 2H), 6.44 (dd, J=8.3, 2.3 Hz, 2H), 7.19-7.23 (m, 3H), 7.35 (dd, J=8.4, 3.0 Hz, 1H).

Step 6: Synthesis of Compound 15-9

To a solution of compound 15-8 (3.25 g, 4.35 mmol) in MeNO₂ (33 ml) and H₂O (16 ml) was added (2,2,2-trifluoroacetoxy)silver (3.85 g, 17.4 mmol) at room temperature. After stirring for 18 h at 80° C., the reaction mixture was treated with aqueous NaHCO₃ and brine, and the mixture was filtered through a pad of Celite. The aqueous layer was extracted with AcOEt, and the organic layer was dried over Na₂SO₄, filtered and concentrated. The crude product was added to a silica gel column and eluted with hexane/EtOAc 10% to 60%. Collected fractions were evaporated to afford compound 15-9 (1.18 g, 1.85 mmol, 43%) as a brown amorphous ¹H-NMR (400 MHz, CDCl₃) δ: 1.66 (s, 3H), 3.69-3.81 (m, 14H), 4.16 (m, 1H), 4.46 (d, J=16.2 Hz, 2H), 4.53 (d, J=16.2 Hz, 2H), 5.19 (d, J=49.3 Hz, 1H), 6.40 (d, J=2.3 Hz, 2H), 6.46 (dd, J=8.4, 2.3 Hz, 2H), 7.19-7.26 (m, 3H), 7.34 (dd, J=8.4, 3.0 Hz, 1H).

Step 7: Synthesis of Compound 15-10

To a solution of compound 15-9 (877 mg, 1.38 mmol) in CH₂Cl₂ (9 ml) was added DAST (0.55 ml, 4.13 mmol) at −78° C. After stirring for 6 h at room temperature, the reaction mixture was treated with aqueous NaHCO₃. The aqueous layer was extracted with AcOEt and the organic layer was dried over Na₂SO₄, filtered and concentrated. The crude product was added to a silica gel column and eluted with hexane/EtOAc 10% to 30%. Collected fractions were evaporated to afford compound 15-10 (641 mg, 1.00 mmol, 73%) as a white amorphous.

¹H-NMR (400 MHz, CDCl₃) δ: 1.67 (m, 3H), 3.71 (s, 6H), 3.79 (s, 6H), 4.38-4.69 (m, 8H), 5.24 (dd, J=48.9, 1.0 Hz, 1H), 6.39 (d, J=2.5 Hz, 2H), 6.44 (dd, J=8.3, 2.5 Hz, 2H), 7.20 (d, J=8.3 Hz, 2H), 7.22 (dd, J=10.0, 8.3 Hz, 1H), 7.35 (dd, J=8.3, 3.0 Hz, 1H).

Step 8: Synthesis of Compound 15-11

To a solution of compound 15-10 (750 mg, 1.18 mmol) in TFA (7.5 ml) was added anisole (0.898 ml, 8.22 mmol) at room temperature. After stirring for 18 h at 80° C., the reaction mixture was treated with aqueous K₂CO₃. The aqueous layer was extracted with AcOEt and the organic layer was dried over Na₂SO₄, filtered and concentrated. The crude product was added to an amino silica gel column and eluted with hexane/EtOAc 10% to 40%. Collected fractions were evaporated to afford compound 15-11 (386 mg, 1.14 mmol, 97%) as a yellow amorphous.

¹H-NMR (400 MHz, CDCl₃) δ: 1.66 (m, 3H), 4.50-4.81 (m, 3H), 5.36 (d, J=49.2 Hz, 1H), 7.28 (dd, J=10.3, 8.5 Hz, 1H), 7.38 (dd, J=8.5, 3.1 Hz, 1H).

Step 9: Synthesis of Compound 15-12

To a solution of compound 15-11 (386 mg, 1.14 mmol) in THF (4 ml) were added Boc₂O (0.795 ml, 3.42 mmol) and DMAP (41.8 mg, 0.342 mmol) at room temperature. After stirring for 2 h at the same temperature, the mixture was concentrated under vacuum. The crude product was added to a silica gel column and eluted with Hexane/EtOAc 10% to 30%. Collected fractions were evaporated to afford compound 15-12 (549 mg, 1.02 mmol, 89%) as a white solid.

¹H-NMR (400 MHz, CDCl₃) δ: 1.40 (s, 9H), 1.75 (d, J=3.1 Hz, 3H), 4.63-4.87 (m, 3H), 5.52 (d, J=47.8 Hz, 1H), 7.33 (dd, J=9.9, 8.5 Hz, 1H), 7.43 (dd, J=8.5, 3.1 Hz, 1H).

Step 10: Synthesis of Compound 15-13

A degassed mixture of Pd₂(dba)₃ (26.7 mg, 0.029 mmol) and xantphos (50.6 mg, 0.087 mmol) in dioxane (4.7 ml) was stirred for 1 h at room temperature. To this mixture were added compound 15-12 (157 mg, 0.292 mmol), 5-(fluoromethoxy)pyrazine-2-carboxamide (59.9 mg, 0.350 mmol) and cesium carbonate (114 mg, 0.350 mmol). After stirring for 7 h at 80° C., the reaction mixture was treated with aqueous citric acid and filtered. The aqueous layer was extracted with AcOEt and the organic layer was dried over Na₂SO₄, filtered and concentrated. The crude product was added to a silica gel column and eluted with hexane/EtOAc 10% to 30%. Collected fractions were evaporated to afford compound 15-13 (124 mg, 0.197 mmol, 68%) as a white amorphous.

¹H-NMR (400 MHz, CDCl₃) δ: 1.46 (s, 18H), 1.79 (d, J=2.1 Hz, 3H), 4.46-4.83 (m, 3H), 5.44 (d, J=48.7 Hz, 1H), 6.09 (dd, J=9.2, 2.0 Hz, 1H), 6.22 (dd, J=9.2, 2.0 Hz, 1H), 7.54 (t, J=9.5 Hz, 1H), 8.30 (d, J=1.3 Hz, 1H), 8.39 (dd, J=8.9, 3.0 Hz, 1H), 9.10 (d, J=1.3 Hz, 1H), 9.99 (s, 1H).

Step 11: Synthesis of Compound I-104

A solution of compound 15-13 (124 mg, 0.197 mmol) in formic acid (0.76 ml) was stirred for 4 h at room temperature. The reaction mixture was treated with aqueous K₂CO₃. The aqueous layer was extracted with AcOEt and the organic layer was dried over Na₂SO₄, filtered and concentrated to afford compound I-104 (69.2 mg, 0.162 mmol, 82%) as a white solid.

¹H-NMR (400 MHz, CDCl₃) δ: 1.70 (dd, J=2.8, 1.3 Hz, 3H), 4.40 (m, 1H), 4.57-4.78 (m, 2H), 5.31 (dd, J=48.4, 1.0 Hz, 1H), 6.09 (dd, J=5.5, 2.0 Hz, 1H), 6.22 (dd, J=5.5, 2.0 Hz, 1H), 7.51 (dd, J=10.3, 8.8 Hz, 1H), 8.32-8.35 (m, 2H), 9.09 (d, J=1.3 Hz, 1H), 9.93 (s, 1H).

Example 16

Synthesis of Compound I-25

[Chemical Formula 112]

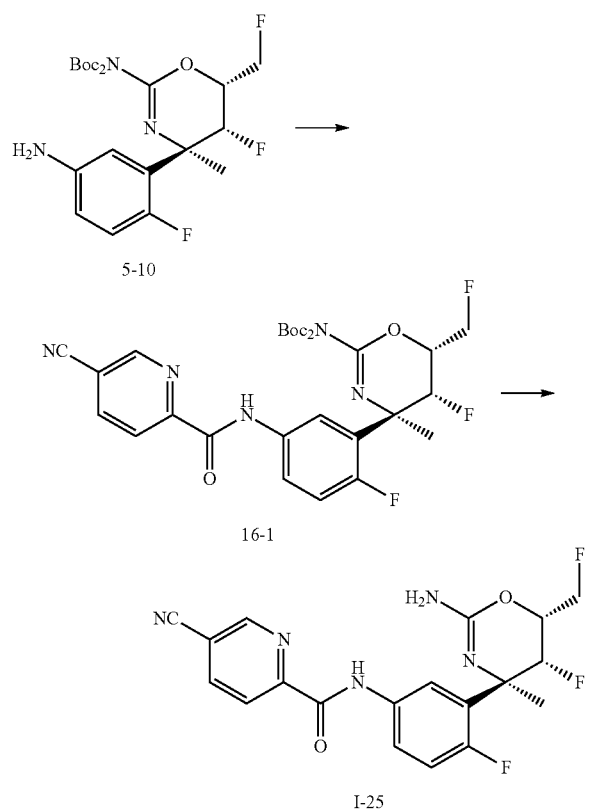

5-10

16-1

I-25

Step 1: Synthesis of Compound 16-1

To a solution of 5-10 (1.46 g, 3.08 mmol) in DMF (15 ml) were added 5-cyano-3-methylpicolinic acid (512 mg, 3.08 mmol), HATU (1.41 g, 3.70 mmol) and DIPEA (1.08 ml, 6.17 mmol) at room temperature. After stirring for 10 min at the same temperature, the reaction mixture was treated with $H_2O$. The aqueous layer was extracted with AcOEt, and the organic layer was dried over $Na_2SO_4$, filtered and concentrated. The crude product was added to a silica gel column and eluted with hexane/EtOAc 0% to 40%. Collected fractions were evaporated to afford 16-1 (1.86 g, 3.08 mmol, 100%) as a white amorphous.

$^1$H-NMR (400 MHz, $CDCl_3$) δ: 1.57 (s, 18H), 1.77 (s, 3H), 4.14-4.30 (m, 1H), 4.64 (dd, J=45.9, 5.5 Hz, 2H), 5.22 (d, J=47.8 Hz, 1H), 7.15 (dd, J=8.9, 11.4 Hz, 1H), 7.60 (dd, J=6.8, 2.7 Hz, 1H), 8.21 (dd, J=8.2, 2.0 Hz, 1H), 8.37-8.42 (m, 1H), 8.43 (d, J=8.2 Hz, 1H), 8.79 (d, J=2.0 Hz, 1H), 9.98 (s, 1H).

Step 2: Synthesis of I-25

To a solution of 16-1 (1.86 g, 3.08 mmol) was added formic acid (10.1 ml) at room temperature. After stirring for 16 h at the same temperature, the reaction mixture was treated with aqueous $K_2CO_3$. The resulting slurry was filtered to afford I-25 (1.14 g, 2.83 mmol, 92%) as a white powder.

$^1$H-NMR (400 MHz, DMSO-D6) δ: 1.50 (s, 3H), 3.84-4.01 (m, 1H), 4.53 (dt, J=48.7, 8.7 Hz, 1H), 4.74 (dd, J=10.0, 45.6 Hz, 1H), 5.13 (d, J=48.3 Hz, 1H), 5.87 (s, 2H), 7.22 (t, J=10.2 Hz, 1H), 7.81-7.88 (m, 1H), 7.89-7.96 (m, 1H), 8.28 (d, J=8.0 Hz, 1H), 9.21 (s, 1H), 10.95 (s, 1H).

The following compounds are prepared in a manner similar to the above. In the tables, RT means LC/MS retention time (minute).

TABLE 1-1

| Compound No. | Structure | NMR (solvent: shift value ascending order) | MS-ESI (m/z) [M + H]+ | LC/MS RT |
|---|---|---|---|---|
| I-1 | 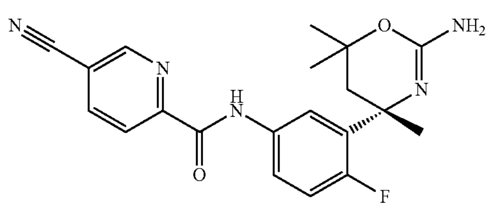 [SMILES: CC1(C)C[C@@](C)(c2cc(NC(=O)c3ccc(C#N)cn3)ccc2F)N=C(N)O1] | 1H-NMR (CDCl3) δ 0.89 (s, 3H), 1.32 (s, 3H), 1.53 (s, 3H), 1.90 (d, J = 14.7 Hz, 1H), 2.66 (d, J = 14.7 Hz, 1H), 7.04 (dd, J = 11.7, 9.1 Hz, 1H), 7.66 (dd, J = 6.8, 2.8 Hz, 1H), 8.02 (td, J = 6.1, 2.9 Hz, 1H), 8.19 (dd, J = 8.1, 2.0 Hz, 1H), 8.42 (d, J = 7.6 Hz, 1H), 8.89 (d, J = 1.0 Hz, 1H), 9.85 (s, 1H). | 382 | 1.24 |
| I-2 | 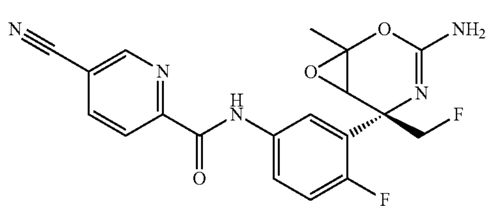 [SMILES: CC12OC(N)=N[C@](CF)(c3cc(NC(=O)c4ccc(C#N)cn4)ccc3F)C1O2] | 1H NMR (400 MHz, CD3CN) δ 1.69 (s, 3H), 3.62 (s, 1H), 4.56-4.90 (m, 2H), 7.19 (dd, J = 11.5, 8.9 Hz, 1H), 7.59 (s, 1H), 7.88 (ddd, J = 8.9, 4.3, 2.8 Hz, 1H), 7.99 (dd, J = 6.9, 1.9 Hz, 1H), 8.32-8.37 (m, 2H), 8.98-9.01 (m, 1H), 10.10 (br. s., 1H) | 400 | |

TABLE 1-1-continued

| Compound No. | Structure | NMR (solvent: shift value ascending order) | MS-ESI (m/z) [M + H]+ | LC/MS RT |
|---|---|---|---|---|
| I-3 | 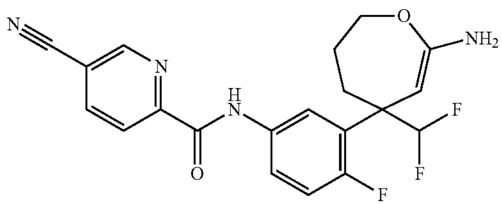 [SMILES: N#Cc1ccc(C(=O)Nc2ccc(F)c(C3(C(F)F)C=C(N)OCCC3)c2)nc1] | 1H-NMR (400 MHz, CDCl3) δ 2.36 (t, J = 6.0 Hz, 1H), 2.78-2.82 (m, 1H), 3.17 (t, J = 6.8 Hz, 1H), 3.23 (t, J = 5.8 Hz, 1H), 3.79-3.84 (m, 1H), 3.99-4.06 (m, 1H), 5.74 (t, J = 56.5 Hz, 1H), 7.06-7.11 (m, 1H), 7.71 (d, J = 6.0 Hz, 1H), 7.70-7.72 (m, 1H), 8.20 (d, J = 8.0 Hz, 1H), 8.41 (d, J = 8.0 Hz, 1H), 8.89 (s, 1H), 9.85 (s, 1H). | 404 | 1 |
| I-4 | 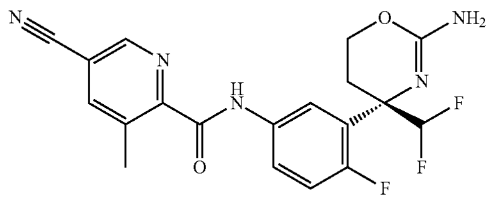 [SMILES: Cc1cc(C#N)cnc1C(=O)Nc1ccc(F)c([C@]2(C(F)F)CCOC(N)=N2)c1] | 1H-NMR (400 MHz, CDCl3) δ 2.33-2.46 (m, 2H), 2.85 (s, 3H), 3.91 (td, 1H, J = 10.3, 3.5 Hz), 4.21-4.26 (m, 1H), 4.34 (s, 2H), 6.06 (t, J = 56.2 Hz, 1H), 7.09 (t, J = 10.0 Hz, 1H), 7.62-7.64 (m, 1H), 7.94 (s, 1H), 8.09-8.11 (m, 1H), 8.70 (s, 1H), 10.1 (s, 1H). | 404 | 1.01 |
| I-5 | 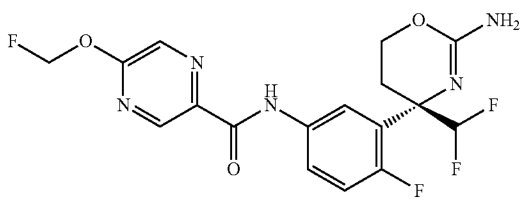 [SMILES: NC1=N[C@@](c2cc(NC(=O)c3cnc(OCF)cn3)ccc2F)(C(F)F)CCO1] | 1H-NMR (400 MHz, CDCl3) δ 2.32-2.45 (m, 2H), 3.91 (td, 1H, J = 10.3, 2.6 Hz), 4.22-4.25 (m, 1H), 4.35 (s, 1H), 5.94-6.22 (m, 3H), 7.10 (t, J = 10.3 Hz, 1H), 7.66 (d, J = 6.7 Hz, 1H), 8.09-8.11 (m, 1H), 8.28 (s, 1H), 9.07 (s, 1H), 9.55 (s, 1H). | 414 | 0.97 |
| I-6 | 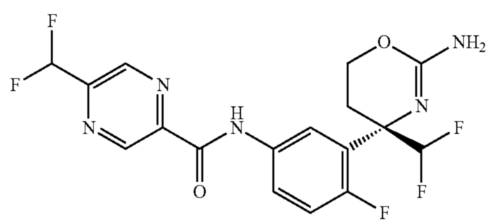 [SMILES: NC1=N[C@@](c2cc(NC(=O)c3cnc(C(F)F)cn3)ccc2F)(C(F)F)CCO1] | 1H-NMR (400 MHz, CDCl3) δ 2.34-2.45 (m, 2H), 3.92 (td, 1H, J = 10.3 Hz, 3.4 Hz), 4.22-4.27 (m, 1H), 4.40 (s, 1H), 6.07 (t, 1H, J = 56.2 Hz), 6.79 (t, 1H, J = 54.3 Hz), 7.12 (dd, J = 10.9, 9.4 Hz, 1H), 7.71-7.73 (m, 1H), 8.09-8.11 (m, 1H), 8.90 (s, 1H), 9.51 (s, 1H), 9.68 (s, 1H). | 416 | 0.96 |

TABLE 1-2

| I-7 | | 1H-NMR (400 MHz, CDCl3) δ 2.33-2.45 (m, 2H), 3.91 (td, J = 10.5, 3.4 Hz, 1H), 4.22-4.25 (m, 1H), 4.34 (s, 1H), 6.07 (t, J = 56.3 Hz, 1H), 7.10 (t, J = 10.3 Hz, 1H), 7.59 (t, J = 8.2 Hz, 1H), 7.67 (d, J = 6.5 Hz, 1H), 8.12-8.14 m, 1H), 8.32 (dd, J = 8.8, 4.5 Hz, 1H), 8.44 (s, 1H), 8.84 (s, 1H). | 383 | 0.97 |
|---|---|---|---|---|
| I-8 | | 1H-NMR (400 MHz, CDCl3) δ 2.32-2.45 (m, 2H), 3.91 (td, J = 10.4, 2.8 Hz, 1H), 4.22-4.24 (m, 1H), 4.34 (s, 1H), 6.08 (t, J = 56.3 Hz, 1H), 7.10 (t, J = 10.4 Hz, 1H), 7.66 (d, J = 5.6 Hz, 1H), 7.88 (d, J = 8.3 Hz, 1H), 8.12-8.14 (m, 1H), 8.23 (d, J = 8.4 Hz, 1H), 8.55 (s, 1H), 9.88 (s, 1H). | 399 | 1.09 |
| I-9 | | 1H-NMR (400 MHz, CDCl3) δ 2.32-2.44 (m, 2H), 3.90 (t, J = 9.0 Hz, 1H), 4.06 (s, 3H), 4.21-4.24 (m, 1H), 4.51 (s, 2H), 6.09 (t, J = 56.3 Hz, 1H), 7.09 (t, J = 10.2 Hz, 1H), 7.67 (d, J = 5.0 Hz, 1H), 8.10 (s, 2H), 8.98 (s, 1H), 9.54 (s, 1H). | 396 | 0.95 |

TABLE 1-2-continued

| | Structure | NMR | MS | RT |
|---|---|---|---|---|
| I-10 (racemate) | 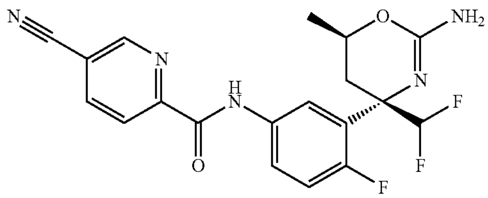 [SMILES: C[C@@H]1C[C@](c2cc(NC(=O)c3ccc(C#N)cn3)ccc2F)(C(F)F)N=C(N)O1] | 1H-NMR (400 MHz, CDCl3) δ 1.29 (d, J = 4.9 Hz, 3H), 1.87 (t, J = 12.8 Hz, 1H), 2.58 (d, J = 13.6 Hz, 1H), 3.89-3.94 (m, 1H), 4.36 (s, 1H), 6.06 (t, J = 56.0 Hz, 1H), 7.12 (dd, J = 10.9, 9.2 Hz, 1H), 7.61 (d, J = 6.3 Hz, 1H), 8.10-8.13 (m, 1H), 8.20 (d, J = 8.0 Hz), 8.42 (d, J = 8.0 Hz, 1H), 8.90 (s, 1H), 9.89 (s, 1H). | 404 | 1.03 |
| I-11 (chiral) | 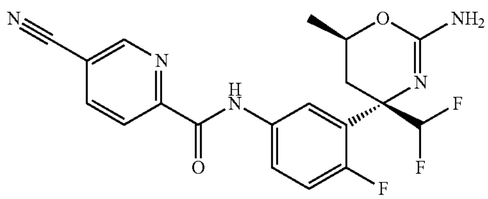 [SMILES: C[C@@H]1C[C@](c2cc(NC(=O)c3ccc(C#N)cn3)ccc2F)(C(F)F)N=C(N)O1] | 1H-NMR (400 MHz, CDCl3) δ 1.29 (d, J = 4.9 Hz, 3H), 1.87 (t, J = 12.8 Hz, 1H), 2.58 (d, J = 13.6 Hz, 1H), 3.89-3.94 (m, 1H), 4.36 (s, 1H), 6.06 (t, J = 56.0 Hz, 1H), 7.12 (dd, J = 10.9, 9.2 Hz, 1H), 7.61 (d, J = 6.3 Hz, 1H), 8.10-8.13 (m, 1H), 8.20 (d, J = 8.0 Hz), 8.42 (d, J = 8.0 Hz, 1H), 8.90 (s, 1H), 9.89 (s, 1H). | 404 | 1.03 |
| I-12 | 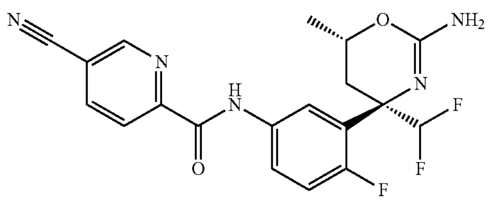 [SMILES: C[C@H]1C[C@@](c2cc(NC(=O)c3ccc(C#N)cn3)ccc2F)(C(F)F)N=C(N)O1] | 1H-NMR (400 MHz, CDCl3) δ 1.29 (d, J = 4.9 Hz, 3H), 1.87 (t, J = 12.8 Hz, 1H), 2.58 (d, J = 13.6 Hz, 1H), 3.89-3.94 (m, 1H), 4.36 (s, 1H), 6.06 (t, J = 56.0 Hz, 1H), 7.12 (dd, J = 10.9, 9.2 Hz, 1H), 7.61 (d, J = 6.3 Hz, 1H), 8.10-8.13 (m, 1H), 8.20 (d, J = 8.0 Hz), 8.42 (d, J = 8.0 Hz, 1H), 8.90 (s, 1H), 9.89 (s, 1H). | 404 | 1.03 |

TABLE 1-3

| | Structure | NMR | MS | RT |
|---|---|---|---|---|
| I-13 | 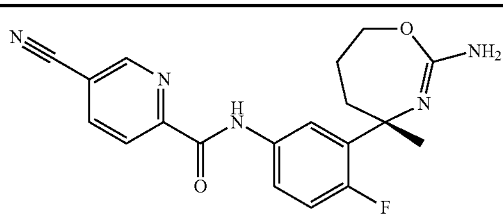 | 1H-NMR (400 MHz, CDCl3) δ: 1.70 (m, 1H), 1.79 (s, 3H), 2.09 (m, 2H), 2.90 (m, 1H), 4.23 (m, 1H), 4.40 (m, 1H), 6.01 (m, 1H), 7.13 (t, J = 4 Hz, 1H), 7.71 (d, J = 4 Hz, 1H), 7.87 (m, 1H), 8.19 (d, J = 4 Hz, 1H), 8.38 (d, J = 4 Hz, 1H), 9.98 (s, 1H), 11.46 (m, 2H). | 368 | 1.08 |
| I-14 | 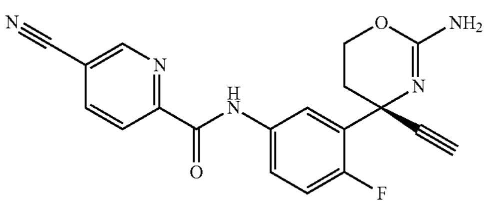 [SMILES: C#C[C@@]1(c2cc(NC(=O)c3ccc(C#N)cn3)ccc2F)CCOC(N)=N1] | 1H-NMR (400 MHz, CDCl3) δ: 9.88 (s, 1H), 8.90 (dd, J = 1.9, 0.7 Hz, 1H), 8.43 (dd, J = 8.2, 0.7 Hz, 1H), 8.21 (dd, J = 8.0, 2.0 Hz, 1H), 8.03 (ddd, J = 8.8, 4.1, 2.9 Hz, 1H), 7.86 (dd, J = 6.9, 2.9 Hz, 1H), 7.12 (dd, J = 11.0, 8.8 Hz, 1H), 4.56 (td, J = 10.9, 2.9 Hz, 1H), 4.23-4.18 (m, 3H), 2.60 (dt, J = 13.7, 2.9 Hz, 1H), 2.54 (s, 1H), 2.12 (ddd, J = 14.2, 10.4, 3.7 Hz, 1H). | 364 | 0.97 |
| I-15 | 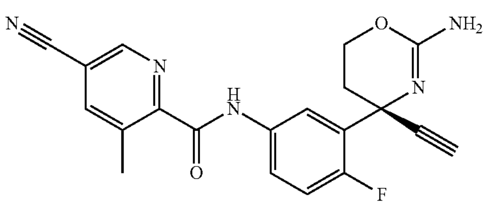 [SMILES: C#C[C@@]1(c2cc(NC(=O)c3ncc(C#N)cc3C)ccc2F)CCOC(N)=N1] | 1H-NMR (400 MHz, CDCl3) δ: 10.06 (s, 1H), 8.72 (s, 1H), 8.02 (dt, J = 8.0, 3.8 Hz, 1H), 7.94 (s, 1H), 7.79 (dd, J = 6.8, 2.3 Hz, 1H), 7.11 (t, J = 9.9 Hz, 1H), 4.58 (td, J = 10.8, 2.3 Hz, 1H), 4.24 (dt, J = 10.8, 4.2 Hz, 1H), 2.86 (s, 3H), 2.62-2.58 (m, 2H), 2.19 (ddd, J = 13.9, 10.5, 3.5 Hz, 1H). | 378 | 1.01 |
| I-16 | 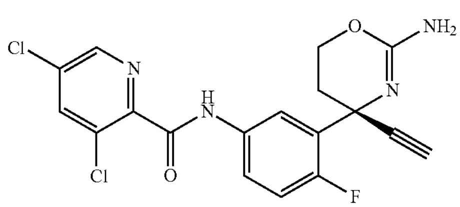 [SMILES: C#C[C@@]1(c2cc(NC(=O)c3ncc(Cl)cc3Cl)ccc2F)CCOC(N)=N1] | 1H-NMR (400 MHz, CDCl3) δ: 9.77 (s, 1H), 8.48 (s, 1H), 8.08 (dt, J = 8.2, 3.6 Hz, 1H), 7.91 (s, 1H), 7.72 (dd, J = 6.8, 2.5 Hz, 1H), 7.09 (dd, J = 10.2, 9.7 Hz, 1H), 4.55 (td, J = 10.8, 2.5 Hz, 1H), 4.20 (dt, J = 10.7, 4.1 Hz, 1H), 2.59 (d, J = 14.2 Hz, 1H), 2.54 (s, 1H), 2.13 (ddd, J = 14.0, 10.5, 3.6 Hz, 1H). | 407 | 1.11 |

TABLE 1-3-continued

| | | | | |
|---|---|---|---|---|
| I-17 | (structure) | 1H-NMR (400 MHz, CDCl3) δ: 9.53 (s, 1H), 9.02 (s, 1H), 8.15 (s, 1H), 8.00 (dt, J = 8.0, 3.7 Hz, 1H), 7.82 (dd, J = 6.8, 2.4 Hz, 1H), 7.10 (dd, J = 10.7, 9.5 Hz, 1H), 4.55 (td, J = 10.7, 2.4 Hz, 1H), 4.25-4.17 (m, 3H), 4.07 (s, 3H), 2.59 (d, J = 13.6 Hz, 1H), 2.54 (s, 1H), 2.14 (ddd, J = 13.7, 10.4, 3.5 Hz, 1H). | 370 | 0.97 |
| I-18 | (structure) | 1H-NMR (400 MHz, CDCl3) δ: 9.82 (s, 1H), 8.45 (s, 1H), 8.33 (dd, J = 8.7, 4.6 Hz, 1H), 8.00-7.98 (m, 1H), 7.85 (d, J = 6.8 Hz, 1H), 7.59 (t, J = 8.3 Hz, 1H), 7.09 (t, J = 9.9 Hz, 1H), 4.55 (t, J = 9.5 Hz, 1H), 4.21-4.18 (m, 3H), 2.59 (d, J = 13.6 Hz, 1H), 2.53 (s, 1H), 2.13 (ddd, J = 13.9, 10.4, 3.6 Hz, 1H). | 357 | 1.01 |

TABLE 1-4

| | | | | |
|---|---|---|---|---|
| I-19 | (structure) | 1H-NMR (CDCl3) δ: 9.66 (s, 1H), 9.53 (s, 1H), 8.92 (s, 1H), 8.00 (dt, J = 8.3, 3.5 Hz, 1H), 7.88 (dd, J = 6.8, 2.3 Hz, 1H), 7.12 (t, J = 9.9 Hz, 1H), 6.79 (t, J = 54.5 Hz, 1H), 4.56 (td, J = 10.9, 2.3 Hz, 1H), 4.23-4.17 (m, 3H), 2.61 (d, J = 14.1 Hz, 1H), 2.54 (s, 1H), 2.12 (ddd, J = 13.9, 10.7, 3.6 Hz, 1H). | 390 | 1 |
| I-20 | (structure) | 1H-NMR (400 MHz, CDCl3) δ: 9.51 (s, 1H), 9.08 (s, 1H), 8.28 (s, 1H), 8.00-7.97 (m, 1H), 7.84 (dd, J = 6.9, 2.6 Hz, 1H), 7.10 (t, J = 9.9 Hz, 1H), 6.15 (dd, J = 51.1, 3.1 Hz, 2H), 4.55 (td, J = 10.7, 2.3 Hz, 1H), 4.22-4.17 (m, 3H), 2.59 (d, J = 14.1 Hz, 1H), 2.53 (s, 1H), 2.13 (ddd, J = 13.9, 10.5, 3.6 Hz, 1H). | 388 | 1.01 |
| I-21 | (structure) | 1H-NMR (400 MHz, CDCl3) δ: 9.85 (s, 1H), 8.91 (s, 1H), 8.44 (d, J = 8.3 Hz, 1H), 8.21 (d, J = 8.0 Hz, 1H), 7.96-7.92 (m, 2H), 7.13 (t, J = 9.8 Hz, 1H), 4.08-4.04 (m, 1H), 2.63 (s, 1H), 1.72 (dd, J = 16.6, 7.5 Hz, 1H), 1.27-1.23 (m, 1H), 1.08 (dd, J = 16.6, 6.8 Hz, 1H). | 376 | 0.99 |
| I-22 | (structure) | 1H NMR (400 MHz, DMSO-d6) δ 2.04-2.14 (m, 1H), 2.54 (br. s., 1H), 4.59 (br. s., 1H), 6.16-6.54 (m, 2H), 6.99 (s, 1H), 7.03 (s, 1H), 7.15-7.32 (m, 1H), 7.99 (d, J = 8.0 Hz, 1H), 8.04 (d, J = 6.8 Hz, 1H), 8.28 (d, J = 8.2 Hz, 1H), 8.59 (d, J = 8.2 Hz, 1H), 9.20 (s, 1H), 10.96 (s, 1H) | 406 | |
| I-23 | (structure) | 1H-NMR (400 MHz, CDCl3) δ: 0.92 (s, 3H), 1.37 (s, 3H), 2.07 (d, J = 14.3 Hz, 1H), 2.71 (d, J = 14.3 Hz, 1H), 4.37 (s, 2H), 5.82 (t, J = 56.7 Hz, 1H), 7.11 (t, J = 10.2 Hz, 1H), 7.82 (d, J = 6.5 Hz, 1H), 8.16-8.21 (m, 2H), 8.41 (d, J = 8.0 Hz, 1H), 8.88 (s, 1H), 9.91 (s, 1H). | 418 | 1.07 |

TABLE 1-4-continued

| I-24 | (structure) | 1H NMR (400 MHz, DMSO-d6) δ 1.41 (br. s., 3H), 2.30 (d, J = 13.1 Hz, 1H), 2.46 (br. s., 2H), 3.46 (br. s., 3H), 4.19 (d, J = 10.3 Hz, 1H), 4.81 (br. s., 1H), 5.30 (br. s., 2H), 7.08 (t, J = 10.0 Hz, 1H), 7.66-7.86 (m, 1H), 8.08 (d, J = 6.5 Hz, 1H), 8.23 (d, J = 8.0 Hz, 1H), 8.53 (d, J = 8.0 Hz, 1H), 9.14 (br. s., 1H), 10.61 (br. s., 1H) | 384 | |

TABLE 1-5

| I-25 | (structure) | 1H-NMR (400 MHz, DMSO-D6) δ: 1.50 (s, 3H), 3.84-4.01 (m, 1H), 4.53 (dt, J = 48.7, 8.7 Hz, 1H), 4.74 (dd, J = 10.0, 45.6 Hz, 1H), 5.13 (d, J = 48.3 Hz, 1H), 5.87 (s, 2H), 7.22 (t, J = 10.2 Hz, 1H), 7.81-7.88 (m, 1H), 7.89-7.96 (m, 1H), 8.28 (d, J = 8.0 Hz, 1H), 8.59 (d, J = 8.0 Hz, 1H), 9.21 (s, 1H), 10.95 (s, 1H). | 404 | 1.21 |
| I-26 | (structure) | 1H-NMR (400 MHz, DMSO-D6) δ: 1.49 (s, 3H), 2.53 (s, 3H), 3.85-4.01 (m, 1H), 4.53 (dt, J = 47.8, 8.9 Hz, 1H), 4.73 (ddd, J = 3.8, 10.2, 45.7 Hz, 1H), 5.14 (d, J = 48.7 Hz, 1H), 5.83 (s, 2H), 7.21 (dd, J = 11.7, 8.8 Hz, 1H), 7.71-7.75 (m, 1H), 7.82-7.87 (m, 1H), 8.38 (d, J = 1.5 Hz, 1H), 8.97 (d, J = 1.5 Hz, 1H), 10.79 (s, 1H). | 418 | 1.31 |
| I-27 | (structure) | 1H-NMR (400 MHz, DMSO-D6) δ: 1.50 (s, 3H), 3.85-4.01 (m, 1H), 4.53 (ddd, J = 7.3, 9.7, 47.7 Hz, 1H), 4.73 (ddd, J = 3.5, 9.7, 45.0 Hz, 1H), 5.13 (d, J = 48.8 Hz, 1H), 5.82 (s, 2H), 6.20 (d, J = 51.6 Hz, 2H), 7.20 (dd, J = 11.7, 8.7 Hz, 1H), 7.79-7.84 (m, 1H), 7.91 (dd, J = 2.6, 7.4 Hz, 1H), 8.58 (d, J = 1.4 Hz, 1H), 8.95 (d, J = 1.3 Hz, 1H), 10.70 (s, 1H). | 428 | 1.17 |
| I-28 | (structure) | 1H-NMR (400 MHz, CDCl3) δ: 1.69 (s, 3H), 3.66 (s, 3H), 3.95 (s, 1H), 4.04-4.12 (m, 1H), 4.48-4.53 (m, 1H), 4.60-4.64 (m, 1H), 7.11 (dd, J = 9.1, 11.4 Hz, 1H), 7.45 (dd, J = 2.8, 7.1 Hz, 1H) 8.04-8.09 (m, 1H) 8.20 (dd, J = 1.8, 8.1 Hz, 1H), 8.42 (d, J = 8.1 Hz, 1H), 8.90 (d, J = 1.0 Hz, 1H), 9.87 (s, 1H). | 416 | 1.21 |
| I-29 | (structure) | 1H-NMR (400 MHz, CDCl3) δ: 1.67 (s, 3H), 3.36 (s, 3H), 3.55-3.66 (m, 2H), 3.96 (dt, J = 29.8, 5.8 Hz, 1H), 5.16 (d, J = 48.0 Hz, 1H), 7.09 (dd, J = 8.8, 11.1 Hz, 1H), 7.50 (dd, J = 2.8, 6.8 Hz, 1H), 8.01-8.06 (m, 1H), 8.20 (dd, J = 1.8, 8.1 Hz, 1H), 8.42 (d, J = 8.1 Hz, 1H), 8.90 (s, 1H), 9.85 (s, 1H). | 416 | 1.19 |

TABLE 1-5-continued

| | | | | |
|---|---|---|---|---|
| I-30 | (structure) | 1H-NMR (CDCl3) δ: 1.88 (dd, J = 14.2, 12.2 Hz, 1H), 2.75 (m, 1H), 4.28-4.63 (m, 5H), 4.70 (m, 1H), 4.84 (ddd, J = 48.6, 8.9, 1.3 Hz, 1H), 7.08 (dd, J = 11.3, 8.8 Hz, 1H), 7.93 (dd, J = 6.8, 2.9 Hz, 1H), 8.05 (ddd, J = 8.8, 4.0, 2.9 Hz, 1H), 8.21 (dd, J = 8.3, 2.0 Hz, 1H), 8.43 (m, 1H), 8.90 (m, 1H), 9.90 (s, 1H). | 404 | 1.06 |

TABLE 1-6

| | | | | |
|---|---|---|---|---|
| I-31 | (structure) | 1H-NMR (CDCl3) δ: 1.88 (dd, J = 14.1, 12.5 Hz, 1H), 2.75 (m, 1H), 2.86 (s, 3H), 4.35 (dd, J = 47.2, 8.8 Hz, 1H), 4.41 (ddd, J = 47.2, 10.3, 5.0 Hz, 1H), 4.54 (ddd, J = 47.2, 10.3, 2.5 Hz, 1H), 4.70 (m, 1H), 4.84 (ddd, J = 48.4, 8.8, 1.5 Hz, 1H), 7.06 (dd, J = 11.4, 8.9 Hz, 1H), 7.87 (dd, J = 6.5, 2.8 Hz, 1H), 7.94 (brs, 1H), 8.01 (ddd, J = 8.9, 4.0, 2.8 Hz, 1H), 8.72 (brs, 1H), 10.06 (s, 1H). | 418 | 1.12 |
| I-32 | (structure) | 1H-NMR (CDCl3) δ: 2.08 (dd, J = 13.7, 12.7 Hz, 1H), 2.44 (d, J = 13.7 Hz, 1H), 4.03 (m, 1H), 4.20-4.80 (m, 6H), 7.11 (dd, J = 11.6, 8.7 Hz, 1H), 7.57 (brd, J = 6.6 Hz, 1H), 8.09 (m, 1H), 8.21 (d, J = 8.1 Hz, 1H), 8.43 (d, J = 8.1 Hz, 1H), 8.91 (s, 1H), 9.89 (s, 1H). | 404 | 1.02 |
| I-33 | (structure) | 1H-NMR (CDCl3) δ: 2.08 (dd, J = 13.7, 12.7 Hz, 1H), 2.44 (d, J = 13.7 Hz, 1H), 2.86 (s, 3H), 4.03 (m, 1H), 4.20-4.80 (m, 6H), 7.10 (dd, J = 11.2, 9.2 Hz, 1H), 7.47 (brd, J = 7.0 Hz, 1H), 7.95 (s, 1H), 8.10 (m, 1H), 8.73 (s, 1H), 10.06 (s, 1H). | 418 | 1.1 |
| I-34 | (structure) | 1H-NMR (CDCl3) δ: 2.51 (m, 1H), 2.82 (brd, J = 14.8 Hz, 1H), 3.96 (m, 1H), 4.29 (m, 1H), 4.46 (brs, 2H), 7.11 (brt, J = 10.3 Hz, 1H), 7.91 (brd, J = 6.4 Hz, 1H), 8.13 (m, 1H), 8.20 (d, J = 8.1 Hz, 1H), 8.40 (d, J = 8.1 Hz, 1H), 8.85 (s, 1H), 9.88 (s, 1H). | 408 | 1.08 |
| I-35 | (structure) | 1H-NMR (CDCl3) δ: 2.50 (m, 1H), 2.82 (m, 1H), 2.86 (s, 3H), 3.95 (brt, J = 10.5 Hz, 1H), 4.29 (m, 1H), 4.33 (brs, 2H), 7.10 (dd, J = 11.8, 8.7 Hz, 1H), 7.82 (brd, J = 6.9 Hz, 1H), 7.95 (s, 1H), 8.14 (m, 1H), 8.72 (s, 1H), 10.08 (s, 1H). | 422 | 1.18 |
| I-36 | (structure) | 1H-NMR (CDCl3) δ: 1.72 (m, 1H), 1.98-2.17 (m, 2H), 2.81 (m, 1H), 3.83 (m, 1H), 4.03 (m, 1H), 5.77 (t, J = 56.6 Hz, 1H), 7.06 (dd, J = 11.6, 8.8 Hz, 1H), 7.59 (m, 1H), 7.68 (d, J = 6.0 Hz, 1H), 8.00 (m, 1H), 8.30 (dd, J = 8.5, 4.5 Hz, 1H), 8.42 (s, 1H), 9.78 (s, 1H). | 397 | 1.08 |

TABLE 1-7

| | | | | | |
|---|---|---|---|---|---|
| I-37 | | | 1H-NMR (CDCl3) δ: 2.03 (brt, J = 13.1 Hz, 1H), 2.41 (dd, J = 13.8, 2.3 Hz, 1H), 3.37 (s, 3H), 3.48 (brs, 1H), 3.49 (d, J = 2.5 Hz, 1H), 3.98 (m, 1H), 4.45-4.74 (m, 2H), 7.10 (dd, J = 11.5, 8.9 Hz, 1H), 7.54 (dd, J = 6.8, 2.9 Hz, 1H), 8.10 (ddd, J = 8.9, 4.3, 2.9 Hz, 1H), 8.20 (dd, J = 8.3, 2.0 Hz, 1H), 8.42 (d, J = 8.3 Hz, 1H), 8.90 (m, 1H), 9.88 (s, 1H). | 416 | 1.04 |
| I-38 | | | 1H-NMR (CDCl3) δ: 2.51 (m, 1H), 2.82 (brd, J = 14.8 Hz, 1H), 3.96 (m, 1H), 4.29 (m, 1H), 4.46 (brs, 2H), 7.11 (brt, J = 10.3 Hz, 1H), 7.91 (brd, J = 6.4 Hz, 1H), 8.13 (m, 1H), 8.20 (d, J = 8.1 Hz, 1H), 8.40 (d, J = 8.1 Hz, 1H), 8.85 (s, 1H), 9.88 (s, 1H). | 408 | 1.09 |
| I-39 | | | 1H-NMR (CDCl3) δ: 2.51 (m, 1H), 2.82 (brd, J = 14.8 Hz, 1H), 3.96 (m, 1H), 4.29 (m, 1H), 4.46 (brs, 2H), 7.11 (brt, J = 10.3 Hz, 1H), 7.91 (brd, J = 6.4 Hz, 1H), 8.13 (m, 1H), 8.20 (d, J = 8.1 Hz, 1H), 8.40 (d, J = 8.1 Hz, 1H), 8.85 (s, 1H), 9.88 (s, 1H). | 408 | 1.1 |
| I-40 | | | 1H-NMR (CDCl3) δ: 2.09 (dd, J = 13.6, 12.9 Hz, 1H), 2.43 (d, J = 13.6 Hz, 1H), 4.04 (m, 1H), 4.33-4.76 (m, 4H), 6.15 (dd, J = 51.2, 6.4 Hz, 2H), 7.10 (dd, J = 11.6, 8.7 Hz, 1H), 7.51 (d, J = 6.7 Hz, 1H), 8.09 (m, 1H), 8.29 (s, 1H), 9.08 (s, 1H), 9.53 (s, 1H). | 428 | 1.03 |
| I-41 | | | 1H-NMR (CDCl3) δ: 2.09 (dd, J = 13.7, 12.6 Hz, 1H), 2.43 (d, J = 13.7 Hz, 1H), 4.04 (m, 1H), 4.32-4.77 (m, 4H), 7.09 (dd, J = 11.8, 8.7 Hz, 1H), 7.53 (brd, J = 6.9 Hz, 1H), 7.60 (brt, J = 8.4 Hz, 1H), 8.09 (m, 1H), 8.32 (dd, J = 8.4, 4.4 Hz, 1H), 8.46 (brs, 1H), 9.84 (s, 1H). | 397 | 1.15 |
| I-42 | | | 1H-NMR (CDCl3) δ: 2.07 (dd, J = 13.8, 12.5 Hz, 1H), 2.40 (d, J = 13.8 Hz, 1H), 2.52 (s, 3H), 4.01 (m, 1H), 4.18-4.76 (m, 6H), 7.06 (dd, J = 11.4, 8.8 Hz, 1H), 7.48 (m, 1H), 7.98 (m, 1H), 8.17 (s, 1H), 8.69 (s, 1H). | 383 | 0.96 |

TABLE 1-8

| | | | | | |
|---|---|---|---|---|---|
| I-43 | | | 1H-NMR (CDCl3) δ: 2.08 (dd, J = 13.6, 12.6 Hz, 1H), 2.42 (d, J = 13.6 Hz, 1H), 3.94 (s, 3H), 4.03 (m, 1H), 4.19-4.78 (m, 6H), 7.08 (brt, J = 10.3 Hz, 1H), 7.34 (d, J = 8.7 Hz, 1H), 7.51 (m, 1H), 8.10 (m, 1H), 8.23 (d, J = 8.7 Hz, 1H), 8.26 (s, 1H), 9.87 (s, 1H). | 409 | 1.23 |

TABLE 1-8-continued

| ID | Structure | NMR | MS | RT |
|---|---|---|---|---|
| I-44 | (structure) | 1H NMR (400Mz, CDCl3): δ 9.72 (br, 1H), 8.77 (s, 1H), 8.33 (d, J = 8.0 Hz, 1H), 8.17 (dd, J = 8.0, 1.6 Hz, 1H), 7.95-7.91 (m, 1H), 7.69 (dd, J = 6.4, 2.4 Hz, 1H), 6.98 (t, J = 2.4 Hz, 1H), 5.86 (J = 56.4 Hz, 1H), 5.30 (br, 2H), 4.10-4.04 (m, 1H), 3.91-3.85 (m, 1H), 2.87 (dd, J = 14.4, 2.4 Hz, 1H), 2.12-2.01 (m, 2H), 1.77-1.70 (m, 1H). | 404 | 2.33 |
| I-45 | (structure) | 1H NMR (400Mz, CDCl3): δ 10.08 (br, 1H), 8.64 (s, 1H), 8.04-8.00 (m, 1H), 7.92 (s, 1H), 7.64 (dd, J = 6.4, 2.0 Hz, 1H), 7.08 (t, J = 11.2 Hz, 1H), 5.91 (t, J = 56.0 Hz, 1H), 4.16-4.02 (m, 2H), 2.91-2.82 (m, 4H), 2.18-2.13 (m, 2H), 1.78 (d, J= 4.0 Hz, 1H). | 418 | 2.44 |
| I-46 | (structure) | 1H NMR (400Mz, CDCl3): δ 9.37 (br, 1H), 8.94 (s, 1H), 8.06 (d, J = 1.2 Hz, 1H), 7.97-7.93 (m, 1H), 7.64 (dd, J = 6.8, 2.8 Hz, 1H), 6.99 (dd, J = 11.6, 8.8 Hz, 1H), 5.80 (t, J = 56.4 Hz, 1H), 4.89 (br, 2H), 4.06-4.00 (m, 4H), 3.84-3.78 (m, 1H), 2.82 (dd, J = 13.6, 3.2 Hz, 1H), 2.11-1.98 (m, 2H), 1.72 (t, J = 7.6 Hz, 1H). | 410 | 2.4 |
| I-47 | (structure) | 1H NMR (400Mz, CDCl3): δ 9.30 (br, 1H), 8.98 (d, J = 1.2 Hz, 1H), 8.16 (d, J = 1.2 Hz, 1H), 7.93-7.89 (m, 1H), 7.63 (dd, J = 6.4, 2.8 Hz, 1H), 6.96 (dd, J = 11.6, 8.8 Hz, 1H), 6.15 (d, J = 51.2 Hz, 2H), 5.82 (t, J = 56.4 Hz, 1H), 4.94 (br, 2H), 4.06-4.01 (m, 1H), 3.84-3.79 (m, 1H), 2.84 (dd, J = 14.0, 3.2 Hz, 1H), 2.05-1.96 (m, 2H), 1.73 (dd, J = 8.0, 5.6 Hz, 1H). | 428 | 2.42 |
| I-48 | (structure) | 1H NMR (400Mz, CDCl3): δ 9.42 (s, 2H), 8.78 (s, 1H), 7.91-7.87 (m, 1H), 7.64 (dd, J = 6.4, 2.4 Hz, 1H), 6.92 (dd, J = 8.8, 4.0 Hz, 1H), 6.72 (d, J = 54.4 Hz, 1H), 5.84 (t, J = 56.4 Hz, 1H), 5.07 (br, 2H), 4.07-4.02 (m, 1H), 3.86-3.80 (m, 1H), 2.87 (dd, J = 14.0, 3.2 Hz, 1H), 2.08-1.97 (m, 2H), 1.75-1.71 (m, 1H). | 430 | 2.44 |

TABLE 1-9

| ID | Structure | NMR | MS | RT |
|---|---|---|---|---|
| I-49 | (structure) | 1H-NMR (400 MHz, DMSO-d6) δ 1.66 (t, J = 12.8 Hz, 1H), 2.70 (d, J = 14.4 Hz, 1H), 4.39-4.65 (m, 3H), 5.94 (s, 2H), 6.19 (t, J = 56.2 Hz, 1H), 7.21 (t, J = 10.2 Hz, 1H), 7.82-7.85 (m, 1H), 8.24-8.29 (m, 2H), 8.59 (d, J = 8.2 Hz, 1H), 9.21 (s, 1H), 10.8 (s, 1H). | 422 | 1.03 |
| I-51 | (structure) | 1H-NMR (400 MHz, CDCl3) δ 2.47 (t, J = 10.7 Hz, 1H), 2.74 (d, J = 13.7 Hz, 1H), 3.85 (t, J = 10.1 Hz, 1H), 4.19-4.21 (m, 1H), 4.41 (brs, 2H), 6.68 (t, J = 56.2 Hz, 1H), 7.42 (s, 1H), 7.84 (s, 1H), 8.16 (d, J = 8.7 Hz, 1H), 8.21 (d, J = 8.2 Hz, 1H), 8.41 (d, J = 7.7 Hz, 1H), 8.88 (s, 1H), 9.94 (s, 1H). | 406 | 1.05 |

TABLE 1-9-continued

| | | | |
|---|---|---|---|
| I-52 | | 1H-NMR (400 MHz, CDCl3) δ 2.11 (t, J = 13.2, 1H), 2.59 (d, J = 13.2 Hz, 1H), 4.00-4.10 (1H, m), 4.36-4.57 (m, 4H), 6.08 (t, J = 56.2 Hz, 1H), 7.14 (t, J = 10.2 Hz, 1H), 7.69 (d, J = 6.5 Hz, 1H), 8.12 (t, J = 4.5 Hz, 1H), 8.21 (d, J = 8.2 Hz, 1H), 8.42 (d, J = 8.2 Hz, 1H), 8.89 (s, 1H), 9.90 (s, 1H). | 422 0.98 |
| I-53 | | 1H-NMR (400 MHz, CDCl3) δ 2.09 (t, J = 13.0 Hz, 1H), 2.58 (d, J = 13.6 Hz, 1H), 4.00-4.09 (m, 1H), 4.35-4.59 (m, 4H), 6.09 (t, J = 56.2 Hz, 1H), 7.12 (t, J = 10.2 Hz, 1H), 7.57-7.62 (m, 2H), 8.11-8.13 (m, 1H), 8.31 (dd, J = 8.5, 4.5 Hz, 1H), 8.43 (s, 1H), 9.85 (s, 1H). | 415 1 |
| I-54 | | 1H-NMR (400 MHz, CDCl3) δ 2.08 (t, J = 13.2 Hz, 1H), 2.57 (d, J = 13.2 Hz, 1H), 4.00-4.07 (m, 4H), 4.35-4.59 (m, 4H), 6.09 (t, J = 56.1 Hz, 1H), 7.12 (t, J = 10.2 Hz, 1H), 7.57 (d, J = 6.4 Hz, 1H), 8.11-8.15 (m, 2H), 9.01 (s, 1H), 9.54 (s, 1H). | 428 1 |

TABLE 1-10

| | | | |
|---|---|---|---|
| I-55 | | 1H-NMR (400 MHz, CDCl3) δ 2.08 (t, J = 13.1 Hz, 1H), 2.52 (s, 3H), 2.56 (d, J = 13.7 Hz, 1H), 3.98-4.07 (m, 1H), 4.35-4.59 (m, 4H), 6.07 (t, J = 56.3 Hz, 1H), 7.09 (t, J = 10.2 Hz, 1H), 7.54 (d, J = 6.5 Hz, 1H), 8.01-8.03 (m, 1H), 8.16 (s, 1H), 8.72 (s, 1H). | 401 0.87 |
| I-56 | | 1H-NMR (400 MHz, CDCl3) δ 1.58 (s, 3H), 2.18 (d, J = 14.1 Hz, 1H), 2.93 (d, J = 14.1 Hz, 1H), 3.87 (d, J = 7.4 Hz), 4.23 (1H, J = 7.4 Hz, 1H), 4.64 (d, J = 7.3 Hz, 1H), 4.70 (d, J = 7.3 Hz, 1H), 7.08 (dd, J = 11.5, 8.8 Hz, 1H), 7.51 (dd, J = 7.0, 2.8 Hz, 1H), 7.94-7.98 (m, 1H), 8.20 (dd, J = 8.0, 2.0 Hz, 1H), 8.42 (d, J = 8.2 Hz, 1H), 8.89 (d, J = 1.3 Hz, 1H), 9.81 (s, 1H). | 396 0.96 |
| I-57 | | 1H-NMR (400 MHz, CDCl3) δ 2.03 (t, J = 12.9 Hz, 1H), 2.55 (d, J = 13.7 Hz, 1H), 3.38 (s, 3H), 3.43 (brd, 2H), 3.97 (brd, 1H), 4.40 (brs, 2H), 6.08 (t, J = 56.5 Hz, 1H), 7.12 (t, J = 9.8 Hz, 1H), 7.58-7.59 (m, 1H), 8.14-8.16 (m, 1H), 8.21 (d, J = 7.8 Hz, 1H), 8.42 (d, J = 7.9 Hz, 1H), 8.89 (s, 1H), 9.89 (s, 1H). | 434 1.18 |
| I-58 | | 1H-NMR (400 MHz, CDCl3) δ 1.58 (s, 3H), 2.16 (d, J = 14.1 Hz, 1H), 2.84 (s, 3H), 2.94 (d, J = 14.1 Hz, 1H), 3.87 (d, J = 7.3 Hz), 4.21 (1H, J = 7.3 Hz, 1H), 4.64 (d, J = 6.9 Hz, 1H), 4.70 (d, J = 6.9 Hz, 1H), 7.06 (t, J = 9.9 Hz, 1H), 7.39 (d, J = 1.0 Hz, 1H), 7.94 (s, 1H), 7.98 (s, 1H), 8.69 (s, 1H), 9.98 (s, 1H). | 410 1.17 |

TABLE 1-10-continued

| | | |
|---|---|---|
| I-59 | [structure] | 1H-NMR (400 MHz, CDCl3) δ 1.58 (s, 3H), 2.15 (d, J = 14.1 Hz, 1H), 2.94 (d, J = 14.1 Hz, 1H), 3.85 (d, J = 7.0 Hz, 1H), 4.21 (d, J = 7.0 Hz, 1H), 4.63 (d, J = 6.8 Hz, 1H), 4.69 (d, J = 6.8 Hz, 1H), 6.14 (dd, J = 51.1, 5.8 Hz, 2H), 7.06 (t, J = 9.9 Hz, 1H), 7.55 (d, J = 5.7 Hz, 1H), 7.91 (s, 1H), 8.22 (s, 1H), 9.02 (s, 1H), 9.49 (s, 1H).    420   1.12 |
| I-60 | [structure] | 1H-NMR (400 MHz, CDCl3) δ 2.02 (t, J = 13.0 Hz, 1H), 2.54 (dd, J = 13.6, 2.0 Hz, 1H), 3.37 (s, 3H), 3.49 (d, J = 4.4 Hz, 2H), 3.97-3.99 (m, 1H), 4.39 (brs, 1H), 5.94-6.22 (m, 3H), 7.11 (dd, J = 11.5, 8.8 Hz, 1H), 7.54 (dd, J = 6.8, 2.7 Hz, 1H), 8.13 (dt, J = 9.0, 3.5 Hz, 1H), 8.29 (s, 1H), 9.07 (s, 1H), 9.53 (s, 1H)    458   1.19 |

TABLE 1-11

| | | |
|---|---|---|
| I-61 | [structure] | 1H-NMR (400 MHz, CDCl3) δ 2.10 (t, J = 12.9 Hz, 1H), 2.55 (dd, J = 13.7, 2.1 Hz, 1H), 2.85 (s, 3H), 3.37 (s, 3H), 3.96-3.99 (m, 1H), 4.42 (brs, 2H), 6.07 (t, J = 56.3 Hz, 1H), 7.10 (dd, J = 11.7, 8.9 Hz, 1H), 7.51 (dd, J = 6.5, 2.8 Hz, 1H), 7.94 (d, J = 1.0 Hz, 1H), 8.12 (ddd, J = 8.8, 4.0, 3.0 Hz, 1H), 8.70 (d, J = 1.5 Hz, 1H), 10.0 (s, 1H).    448   1.65 |
| I-62 | [structure] | 1H-NMR (400 MHz, CDCl3) δ: 1.87 (s, 3H), 2.09 (t, J = 11.8 Hz, 1H), 2.54 (d, J = 13.7 Hz, 1H), 4.15-4.18 (br m, 3H), 4.53 (t, J = 10.5 Hz, 1H), 7.10 (t, J = 9.9 Hz, 1H), 7.81 (d, J = 6.7 Hz, 1H), 8.03-8.05 (br m, 1H), 8.20 (d, J = 8.0 Hz, 1H), 8.43 (d, J = 8.0 Hz, 1H), 8.90 (s, 1H), 9.86 (s, 1H).    378   1.07 |
| I-63 | [structure] | 1H-NMR (400 MHz, CDCl3) δ: 1.04-1.09 (m, 1H), 1.22-1.27 (m, 1H), 1.69-1.75 (m, 1H), 2.62 (s, 1H), 4.05 (dq, J = 7.3, 3.1 Hz, 1H), 4.09 (br s, 2H), 7.08-7.14 (m, 1H), 7.60 (ddd, J = 8.8, 8.1, 2.8 Hz, 1H), 7.90-7.94 (m, 2H), 8.34 (dd, J = 8.8, 4.5 Hz, 1H), 8.46 (d, J = 2.8 Hz, 1H), 9.80 (s, 1H).    369   1.05 |
| I-64 | [structure] | 1H-NMR (400 MHz, CDCl3) δ: 1.04-1.10 (m, 1H), 1.22-1.27 (m, 1H), 1.69-1.75 (m, 1H), 2.63 (s, 1H), 4.06 (dq, J = 7.3, 3.1 Hz, 1H), 4.12 (br s, 2H), 6.15 (d, J = 50.9 Hz, 2H), 7.09-7.14 (m, 1H), 7.89-7.93 (m, 2H), 8.30 (d, J = 1.3 Hz, 1H), 9.09 (d, J = 1.3 Hz, 1H), 9.50 (s, 1H).    400   1.04 |
| I-65 | [structure] | 1H-NMR (400 MHz, DMSO-D6) δ: 3.08-3.13 (m, 1H), 3.19 (s, 1H), 3.78-3.81 (m, 3H), 4.10 (t, J = 8.4 Hz, 1H), 4.24 (s, 1H), 6.00 (br s, 2H), 7.24 (t, J = 9.9 Hz, 1H), 7.85 (d, J = 8.5 Hz, 1H), 7.92 (d, J = 7.0 Hz, 1H), 8.28 (d, J = 8.0 Hz, 1H), 8.58 (d, J = 8.0 Hz, 1H), 9.21 (s, 1H), 10.96 (s, 1H).    406   0.94 |

TABLE 1-11-continued

| | | | |
|---|---|---|---|
| I-66 | (structure) | 1H-NMR (400 MHz, CDCl3) δ: 2.42 (s, 1H), 3.27 (td, J = 9.2, 4.1 Hz, 1H), 3.90 (d, J = 10.5 Hz, 1H), 4.03-4.13 (m, 2H), 4.31-4.36 (m, 2H), 4.38 (br s, 2H), 7.16 (t, J = 10.0 Hz, 1H), 7.62 (d, J = 6.5 Hz, 1H), 7.95-7.97 (br m, 1H), 8.21 (d, J = 8.0 Hz, 1H), 8.44 (d, J = 8.0 Hz, 1H), 8.91 (s, 1H), 9.86 (s, 1H). | 406 | 1.08 |

TABLE 1-12

| | | | |
|---|---|---|---|
| I-67 | (structure) | 1H-NMR (400 MHz, CDCl3) δ: 2.42 (s, 1H), 3.26 (td, J = 9.4, 4.5 Hz, 1H), 3.90 (dd, J = 10.2, 2.6 Hz, 1H), 4.04 (d, J = 10.5 Hz, 1H), 4.07-4.13 (m, 1H), 4.31-4.35 (br m, 4H), 7.16 (t, J = 9.9 Hz, 1H), 7.62 (dd, J = 6.9, 2.4 Hz, 1H), 7.95 (dt, J = 8.4, 3.5 Hz, 1H), 8.21 (dd, J = 8.0, 1.8 Hz, 1H), 8.43 (d, J = 8.0 Hz, 1H), 8.91 (s, 1H), 9.86 (s, 1H). | 406 | 1.07 |
| I-68 | (structure) | 1H-NMR (400 MHz, CDCl3) δ: 2.42 (s, 1H), 2.86 (s, 3H), 3.27 (t, J = 9.3 Hz, 1H), 3.90 (d, J = 10.3 Hz, 1H), 4.02-4.11 (m, 2H), 4.31-4.35 (br m, 2H), 4.41 (br s, 2H), 7.14 (t, J = 10.0 Hz, 1H), 7.45 (d, J = 6.5 Hz, 1H), 7.95 (s, 1H), 8.02 (d, J = 6.5 Hz, 1H), 8.72 (s, 1H), 10.00 (s, 1H). | 420 | 1.16 |
| I-69 | (structure) | 1H-NMR (400 MHz, CDCl3) δ: 2.47 (s, 1H), 3.30 (td, J = 9.4, 4.4 Hz, 1H), 3.90 (dd, J = 10.5, 2.6 Hz, 1H), 4.04-4.14 (m, 2H), 4.33 (t, J = 8.9 Hz, 1H), 4.39 (dd, J = 4.4, 2.6 Hz, 1H), 7.15 (dd, J = 11.0, 8.9 Hz, 1H), 7.58-7.63 (m, 2H), 7.95 (ddd, J = 8.7, 3.9, 2.9 Hz, 1H), 8.33 (dd, J = 8.7, 4.6 Hz, 1H), 8.47 (d, J = 2.6 Hz, 1H), 9.82 (s, 1H). | 399 | 1.11 |
| I-70 | (structure) | 1H-NMR (400 MHz, CDCl3) δ: 2.41 (s, 1H), 3.26 (td, J = 9.4, 4.4 Hz, 1H), 3.89 (dd, J = 10.4, 2.6 Hz, 1H), 4.02-4.11 (m, 2H), 4.07 (s, 3H), 4.30-4.35 (m, 2H), 4.38 (br s, 2H), 7.13 (dd, J = 11.0, 8.9 Hz, 1H), 7.57 (dd, J = 7.0, 2.8 Hz, 1H), 7.94 (ddd, J = 8.9, 3.8, 2.8 Hz, 1H), 8.16 (s, 1H), 9.02 (s, 1H), 9.50 (s, 1H). | 412 | 1.09 |
| I-71 | (structure) | 1H-NMR (400 MHz, CDCl3) δ: 2.43 (s, 1H), 3.28 (td, J = 9.4, 4.4 Hz, 1H), 3.90 (dd, J = 10.5, 2.6 Hz, 1H), 4.03-4.10 (m, 2H), 4.30-4.35 (m, 2H), 4.76 (br s, 2H), 7.14 (dd, J = 11.0, 8.9 Hz, 1H), 7.41 (dd, J = 7.0, 2.7 Hz, 1H), 7.91 (d, J = 2.0 Hz, 1H), 8.07 (ddd, J = 8.9, 3.9, 2.7 Hz, 1H), 8.49 (d, J = 2.0 Hz, 1H), 9.73 (s, 1H). | 449 | 1.26 |

TABLE 1-13

| | | | |
|---|---|---|---|
| I-72 | (structure) | 1H-NMR (400 MHz, CDCl3) δ: 2.41 (d, J = 0.5 Hz, 1H), 3.26 (ddd, J = 10.4, 8.7, 4.3 Hz, 1H), 3.89 (dd, J = 10.4, 2.6 Hz, 1H), 4.02-4.13 (m, 2H), 4.31-4.35 (m, 2H), 4.39 (br s, 2H), 6.15 (ddd, J = 51.2, 5.5, 2.0 Hz, 2H), 7.14 (dd, J = 11.0, 8.8 Hz, 1H), 7.59 (dd, J = 7.0, 2.8 Hz, 1H), 7.93 (ddd, J = 8.8, 4.0, 2.8 Hz, 1H), 8.29 (d, J = 1.3 Hz, 1H), 9.08 (d, J = 1.3 Hz, 1H), 9.49 (s, 1H). | 430 | 1.07 |

TABLE 1-13-continued

| | | | | |
|---|---|---|---|---|
| I-73 | 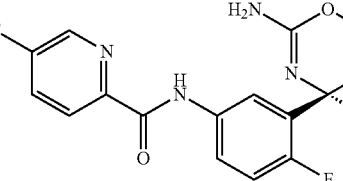 | 1H-NMR (400 MHz, CDCl3) δ: 2.41 (s, 1H), 3.24 (ddd, J = 10.5, 8.7, 4.3 Hz, 1H), 3.89 (dd, J = 10.5, 2.8 Hz, 1H), 4.02-4.11 (m, 2H), 4.29-4.34 (m, 2H), 4.39 (br s, 2H), 6.70 (t, J = 52.5 Hz, 1H), 7.13 (dd, J = 10.9, 8.9 Hz, 1H), 7.57 (dd, J = 7.0, 2.8 Hz, 1H), 7.83 (ddd, J = 8.9, 4.0, 2.8 Hz, 1H), 8.39 (s, 1H), 8.63 (s, 1H). | 421 | 1.01 |
| I-74 | | 1H-NMR (400 MHz, DMSO-d6) δ 1.53 (s, 3H), 4.37 (d, J = 47.4 Hz, 2H), 4.65 (m, 1H), 4.94 (dd, J = 6.6, 48.5 Hz, 1H), 5.78 (brs, 2H), 7.17 (t, J = 10.2 Hz, 1H), 7.89 (s, 1H), 8.01 (d, J = 6.8 Hz, 1H), 8.29 (d, J = 8.0 Hz, 1H), 8.59 (d, J = 8.0 Hz, 1H), 9.21 (s, 1H), 10.9 (s, 1H). | 404 | 1.07 |
| I-75 | | 1H-NMR (400 MHz, CDCl3) δ 1.69 (s, 3H), 4.27 (brs, 2H), 4.33 (d, J = 23.5 Hz, 2H), 4.58 (dt, J = 5.5, 15.7 Hz, 1H), 5.01 (dd, J = 6.3, 48.0 Hz, 1H), 6.15 (d, J = 51.1 Hz, 2H), 7.09 (t, J = 10.2 Hz, 1H), 7.71 (d, J = 6.5 Hz, 1H), 7.91 (t, J = 4.3 Hz, 1H), 8.28 (s, 1H), 9.08 (s, 1H), 9.52 (brs, 1H). | 428 | 1.1 |

TABLE 1-14

| | | | | |
|---|---|---|---|---|
| I-76 | 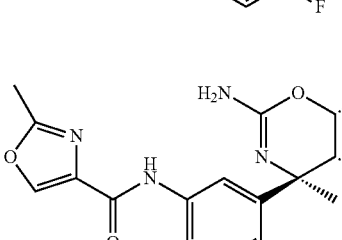 | 1H-NMR (400 MHz, CDCl3) δ: 1.67 (dd, J = 2.5, 1.6 Hz, 3H), 4.02-4.17 (m, 1H), 4.54 (d, J = 5.9 Hz, 1H), 4.65 (d, J = 5.9 Hz, 1H), 5.21 (d, J = 48.1 Hz, 1H), 7.09 (dd, J = 11.4, 8.9 Hz, 1H), 7.53 (dd, J = 6.8, 2.8 Hz, 1H), 7.57-7.63 (m, 1H), 7.98-8.03 (m, 1H), 8.33 (dd, J = 8.9, 4.6 Hz, 1H), 8.46 (d, J = 2.8 Hz, 1H), 9.82 (s, 1H). | 397 | 1.18 |
| I-77 | | 1H-NMR (400 MHz, CDCl3) δ: 1.66 (s, 3H), 2.52 (s, 3H), 4.00-4.15 (m, 1H), 4.53 (d, J = 5.9 Hz, 1H), 4.64 (d, J = 5.9 Hz, 1H), 5.19 (d, J = 48.2 Hz, 1H), 7.06 (dd, J = 8.9, 11.5 Hz, 1H), 7.48 (dd, J = 2.8, 6.8 Hz, 1H), 7.92-7.88 (m, 1H), 8.17 (s, 1H), 8.69 (s, 1H). | 383 | 0.98 |
| I-78 | 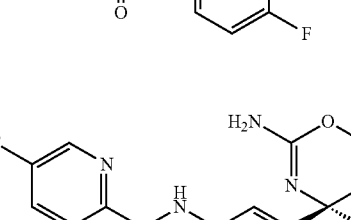 | 1H-NMR (400 MHz, CDCl3) δ: 1.67 (dd, J = 1.7, 2.7 Hz, 3H), 4.09 (m, 1H), 4.53 (d, J = 5.8 Hz, 1H), 4.65 (d, J = 5.8 Hz, 1H), 5.20 (dd, J = 47.9, 0.5 Hz, 1H), 7.09 (dd, J = 11.5, 9.0 Hz, 1H), 7.39 (ddd, J = 10.3, 8.0, 2.3 Hz, 1H), 7.45 (dd, J = 6.8, 2.8 Hz, 1H), 8.04 (ddd, J = 8.8, 4.0, 2.8 Hz, 1H), 8.36 (d, J = 2.3 Hz, 1H), 9.63 (s, 1H). | 415 | 1.07 |

TABLE 1-14-continued

| | | | | | |
|---|---|---|---|---|---|
| I-79 | (structure) | | 1H-NMR (400 MHz, CDCl3) δ: 1.66 (s, 3H), 4.09 (m, 1H), 4.54 (d, J = 5.8 Hz, 1H), 4.65 (d, J = 5.8 Hz, 1H), 5.21 (d, J = 48.4 Hz, 1H), 7.09 (dd, J = 11.3, 8.8 Hz, 1H), 7.39 (dd, J = 6.8, 2.8 Hz, 1H), 7.91 (d, J = 2.0 Hz, 1H), 8.10 (ddd, J = 8.8, 4.0, 2.8 Hz, 1H), 8.49 (d, J = 2.0 Hz, 1H), 9.75 (s, 1H). | 447 | 1.27 |
| I-80 | (structure) | | 1H-NMR (400 MHz, CDCl3) δ: 1.68 (dd, J = 2.5, 1.5 Hz, 3H), 4.09 (m, 1H), 4.54 (d, J = 5.8 Hz, 1H), 4.65 (d, J = 5.8 Hz, 1H), 5.21 (d, J = 48.2 Hz, 1H), 7.09 (dd, J = 11.3, 8.8 Hz, 1H), 7.46 (dd, J = 6.8, 2.8 Hz, 1H), 7.66 (dd, J = 10.0, 2.0 Hz, 1H), 8.05 (ddd, J = 8.8, 4.3, 2.8 Hz, 1H), 8.42 (d, J = 1.5 Hz, 1H), 9.66 (s, 1H). | 431 | 1.05 |
| I-81 | (structure) | | 1H-NMR (400 MHz, CDCl3) δ: 1.67 (dd, J = 2.5, 1.8 Hz, 3H), 4.10 (m, 1H), 4.54 (d, J = 5.8 Hz, 1H), 4.65 (d, J = 5.8 Hz, 1H), 5.21 (d, J = 48.4 Hz, 1H), 7.09 (dd, J = 11.3, 8.8 Hz, 1H), 7.54 (dd, J = 7.0, 3.0 Hz, 1H), 7.89 (dd, J = 8.3, 2.3 Hz, 1H), 8.00 (ddd, J = 8.8, 4.3, 2.8 Hz, 1H), 8.24 (dd, J = 8.3, 0.5 Hz, 1H), 8.57 (dd, J = 2.3, 0.5 Hz, 1H), 9.85 (s, 1H). | 413 | 1.12 |

TABLE 1-15

| | | | | | |
|---|---|---|---|---|---|
| I-82 | (structure) | | 1H-NMR (400 MHz, CDCl3) δ: 1.67 (s, 3H), 4.02-4.17 (m, 1H), 4.07 (s, 3H), 4.53 (d, J = 5.9 Hz, 1H), 4.65 (d, J = 5.9 Hz, 1H), 5.20 (d, J = 48.2 Hz, 1H), 7.09 (dd, J = 11.5, 8.8 Hz, 1H), 7.50 (dd, J = 6.8, 2.8 Hz, 1H), 8.02-7.97 (m, 1H), 8.16 (d, J = 1.3 Hz, 1H), 9.02 (d, J = 1.3 Hz, 1H), 9.52 (s, 1H). | 410 | 1.14 |
| I-83 | (structure) | | 1H-NMR (400 MHz, CDCl3) δ: 1.67 (dd, J = 1.6, 2.6 Hz, 3H), 4.01-4.16 (m, 1H), 4.54 (d, J = 5.9 Hz, 1H), 4.66 (d, J = 5.9 Hz, 1H), 5.21 (d, J = 48.6 Hz, 1H), 6.80 (t, J = 54.5 Hz, 1H), 7.12 (dd, J = 11.4, 8.8 Hz, 1H), 7.57 (dd, J = 6.8, 2.8 Hz, 1H), 8.03-7.98 (m, 1H), 8.93 (s, 1H), 9.53 (s, 1H), 9.66 (s, 1H). | 430 | 1.15 |
| I-84 | (structure) | | 1H-NMR (400 MHz, CDCl3) δ: 1.66 (s, 3H), 4.00-4.16 (m, 1H), 4.54 (d, J = 5.9 Hz, 1H), 4.65 (d, J = 5.9 Hz, 1H), 5.21 (d, J = 48.1 Hz, 1H), 7.11 (dd, J = 11.4, 8.8 Hz, 1H), 7.41 (dd, J = 6.8, 2.8 Hz, 1H), 8.06-8.11 (m, 1H), 8.18 (d, J = 1.8 Hz, 1H), 8.79 (d, J = 1.8 Hz, 1H), 9.72 (s, 1H). | 438 | 1.16 |

TABLE 1-15-continued

| | | | | |
|---|---|---|---|---|
| I-85 | (structure) | 1H-NMR (400 MHz, CDCl3) δ: 1.66 (s, 3H), 4.00-4.15 (m, 1H), 4.53 (d, J = 6.0 Hz, 1H), 4.65 (d, J = 6.0 Hz, 1H), 5.19 (d, J = 48.2 Hz, 1H), 5.44 (d, J = 47.2 Hz, 2H), 7.08 (dd, J = 11.4, 8.9 Hz, 1H), 7.48 (dd, J = 6.8, 2.8 Hz, 1H), 7.94-7.89 (m, 1H), 8.34 (d, J = 1.1 Hz, 1H), 8.67 (s, 1H). | 401 | 1.01 |
| I-86 | (structure) | 1H-NMR (400 MHz, CDCl3) δ: 1.66 (t, J = 2.0 Hz, 3H), 4.00-4.15 (m, 1H), 4.53 (d, J = 5.9 Hz, 1H), 4.65 (d, J = 5.9 Hz, 1H), 5.19 (d, J = 48.1 Hz, 1H), 6.70 (t, J = 52.5 Hz, 1H), 7.08 (dd, J = 11.4, 8.8 Hz, 1H), 7.49 (dd, J = 2.8, 6.8 Hz, 1H), 7.93-7.88 (m, 1H), 8.39 (s, 1H), 8.63 (s, 1H). | 419 | 1.12 |
| I-87 | (structure) | 1H-NMR (400 MHz, CDCl3) δ: 1.66 (s, 3H), 3.36 (s, 3H), 3.56-3.65 (m, 2H), 3.96 (dt, J = 29.9, 6.3 Hz, 1H), 5.16 (d, J = 48.1 Hz, 1H), 6.15 (dq, J = 51.3, 2.0 Hz, 2H), 7.08 (dd, J = 11.4, 8.8 Hz, 1H), 7.44 (dd, J = 6.8, 2.8 Hz, 1H), 8.07-8.02 (m, 1H), 8.29 (d, J = 1.3 Hz, 1H), 9.08 (d, J = 1.3 Hz, 1H), 9.49 (s, 1H). | 440 | 1.21 |

TABLE 1-16

| | | | | |
|---|---|---|---|---|
| I-88 | (structure) | 1H NMR (400 Hz, CDCl3): δ 10.07 (br, 1H), 8.61 (d, J = 1.2 Hz, 1H), 8.11 (dd, J = 8.4, 2.4 Hz, 1H), 7.93 (d, J = 1.2 Hz, 1H), 7.75 (d, J = 2.4 Hz, 1H), 7.33 (d, J = 8.4 Hz, 1H), 6.70 (t, J = 56.0 Hz, 1H), 4.23-4.18 (m, 1H), 3.88-3.82 (m, 1H), 2.84 (s, 3H), 2.79-2.73 (m, 1H), 2.51-2.44 (m, 1H). | 420 | 1.76 |
| I-89 | (structure) | 1H NMR (400 Hz, CDCl3): δ 9.57 (br, 1H), 8.94 (d, J = 1.2 Hz, 1H), 8.13 (dd, J = 8.8, 2.8 Hz, 1H), 8.04 (d, J = 0.8 Hz, 1H), 7.84 (d, J = 2.8 Hz, 1H), 7.37 (d, J = 8.8 Hz, 1H), 6.70 (t, J = 55.6 Hz, 1H), 4.21-4.16 (m, 1H), 4.06 (s, 3H), 3.88-3.82 (m, 1H), 2.78-2.72 (m, 1H), 2.49-2.42 (m, 1H). | 412 | 1.71 |
| I-90 | (structure) | 1H NMR (400 Hz, CDCl3): δ 9.56 (br, 1H), 9.02 (d, J = 1.2 Hz, 1H), 8.19 (d, J = 0.8 Hz, 1H), 8.12 (dd, J = 8.8, 2.8 Hz, 1H), 7.84 (d, J = 2.8 Hz, 1H), 7.38 (d, J = 8.8 Hz, 1H), 6.70 (t, J = 55.6 Hz, 1H), 6.21 (dd, J = 9.2, 1.6 Hz, 1H), 6.08 (dd, J = 8.8, 1.6 Hz, 1H), 4.22-4.18 (m, 1H), 3.88-3.82 (m, 1H), 2.78-2.72 (m, 1H), 2.51-2.43 (m, 1H). | 430 | 1.72 |

TABLE 1-16-continued

| | | | | |
|---|---|---|---|---|
| I-91 | [structure] | 1H NMR (400 Hz, CDCl3): δ 9.61 (br, 1H), 9.43 (s, 1H), 8.76 (s, 1H), 8.04 (dd, J = 8.4, 2.8 Hz, 1H), 7.88 (d, J = 2.8 Hz, 1H), 7.31 (d, J = 8.8 Hz, 1H), 6.92-6.57 (m, 2H), 4.90 (brs, 2H), 4.21-4.19 (m, 1H), 3.86-3.84 (m, 1H), 2.76-2.72 (m, 1H), 2.51-2.48 (m, 1H). | 432 | 1.73 |
| I-92 | [structure] | 1H-NMR (400 MHz, CDCl3) δ 2.42 (d, J = 14.3 Hz, 1H), 2.84 (d, J = 14.3 Hz, 1H), 3.90 (d, J = 7.3 Hz, 1H), 4.27 (d, J = 7.3 Hz, 1H), 4.38 (ddd, J = 47.1, 8.9, 1.6 Hz, 1H), 4.64 (d, J = 7.8 Hz, 1H), 4.70 (ddd, J = 47.1, 8.9, 1.6 Hz, 1H), 4.71 (d, J = 7.8 Hz, 1H), 7.11 (dd, J = 8.2, 0.9 Hz, 1H), 7.63 (dd, J = 6.9, 2.3 Hz, 1H), 8.02 (dt, J = 8.8, 3.5 Hz, 1H), 8.21 (dd, J = 8.0, 2.0 Hz, 1H), 8.42 (dd, J = 8.2, 0.9 Hz, 1H), 8.90 (dd, J = 2.0, 1.0 Hz, 1H), 9.85 (s, 1H). | 414 | 0.99 |

TABLE 1-17

| | | | | |
|---|---|---|---|---|
| I-93 | [structure] | 1H-NMR (400 MHz, CDCl3) δ 1.63 (s, 3H), 2.14 (d, J = 13.1 Hz, 1H), 2.95 (d, J = 13.1 Hz, 1H), 3.85 (d, J = 7.5 Hz, 1H), 4.22 (d, J = 7.5 Hz, 1H), 4.63 (d, J = 7.3 Hz, 1H), 4.69 (d, J = 7.3 Hz, 1H), 6.02 (dd, J = 51.6, 1.1 Hz, 2H), 7.04 (dd, J = 11.5, 8.8 Hz, 1H), 7.39 (dd, J = 7.0, 2.8 Hz, 1H), 7.56 (s, 1H), 7.85 (dt, J = 8.3, 3.5 Hz, 1H), 9.49 (s, 1H). | 435 | 1.16 |
| I-94 | [structure] | 1H-NMR (400 MHz, CDCl3) δ 2.42 (d, J = 14.1 Hz, 1H), 2.84 (d, J = 14.1 Hz, 1H), 3.90 (d, J = 7.5 Hz, 1H), 4.27 (d, J = 7.5 Hz, 1H), 4.38 (dd, J = 47.3, 9.4 Hz, 1H), 4.64 (d, J = 7.3 Hz, 1H), 4.70 (d, J = 7.3 Hz, 1H), 4.70 (ddd, J = 47.3, 9.4, 1.5 Hz, 1H), 6.15 (ddd, J = 51.1, 5.1, 2.0 Hz, 2H), 7.10 (dd, J = 11.4, 8.9 Hz, 1H), 7.58 (dd, J = 6.8, 2.8 Hz, 1H), 8.01 (ddd, J = 8.8, 4.1, 2.9 Hz, 1H), 8.28 (d, J = 1.3 Hz, 1H), 9.07 (d, J = 1.3 Hz, 1H), 9.49 (s, 1H). | 438 | 0.99 |
| I-95 | [structure] | 1H-NMR (400 MHz, CDCl3) δ 1.69 (t, J = 2.0 Hz, 3H), 3.52 (d, J = 7.8 Hz, 1H), 4.07 (dd, J = 7.8, 4.5 Hz, 1H), 4.66 (d, 7.8 Hz, 1H), 4.87 (d, J = 7.8 Hz, 1H), 5.63 (d, J = 46.9 Hz, 1H), 7.11 (dd, J = 11.3, 8.8 Hz, 1H), 7.50 (dd, J = 6.8, 2.8 Hz, 1H), 7.93 (ddd, J = 8.7, 4.1, 2.8 Hz, 1H), 8.21 (dd, J = 8.3, 2.0 Hz, 1H), 8.42 (dd, J = 8.0, 0.8 Hz), 8.89 (dd, J = 2.0, 0.8 Hz, 1H), 9.82 (s, 1H). | 414 | 1.09 |
| I-96 | [structure] | 1H-NMR (400 MHz, CDCl3) δ 1.74 (s, 3H), 4.42 (m, 1H), 4.58-4.80 (m, 2H), 5.33 (d, J = 49.7 Hz, 1H), 7.53 (t, J = 10.0 Hz, 1H), 8.22 (dd, J = 8.0, 1.8 Hz, 1H), 8.36 (dd, J = 9.0, 3.0 Hz, 1H), 8.43 (d, J = 8.0 Hz, 1H), 8.95 (d, J = 1.3 Hz, 1H), 10.25 (brs, 1H). | 405 | 1.04 |

TABLE 1-17-continued

| | | | | |
|---|---|---|---|---|
| I-97 | 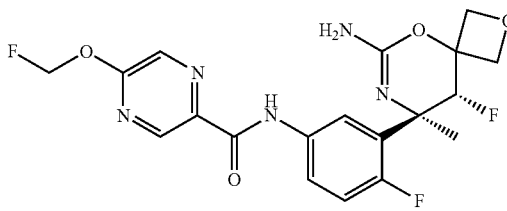 | 1H-NMR (400 MHz, CDCl3) δ 2.04 (s, 3H), 3.52 (d, J = 8.0 Hz, 1H), 4.07 (d, J = 8.0 Hz, 1H), 4.66 (d, J = 7.5 Hz, 1H), 4.87 (d, J = 7.5 Hz, 1H), 5.63 (d, J = 46.7 Hz, 1H), 6.08-6.22 (m, 2H), 7.10 (dd, J = 11.3, 8.8 Hz, 1H), 7.47 (dd, J = 6.8, 2.8 Hz, 1H), 7.91 (ddd, J = 8.8, 4.0, 3.0 Hz, 1H), 8.28 (d, J = 1.3 Hz, 1H), 9.06 (d, J = 1.3 Hz, 1H), 9.47 (s, 1H). | 438 | 0.93 |

TABLE 1-18

| | | | | |
|---|---|---|---|---|
| I-98 | 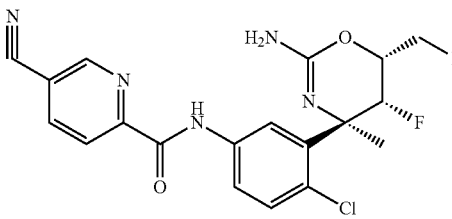 | 1H-NMR (400 MHz, CDCl3) δ 1.81 (d, J = 2.8 Hz, 3H), 3.97-4.11 (m, 1H), 4.60 (dd, J = 46.7, 5.8 Hz, 2H), 5.73 (d, J = 48.2 Hz, 1H), 7.42 (d, J = 8.5 Hz, 1H), 7.72 (d, J = 2.5 Hz, 1H), 8.02 (dd, J = 8.8, 2.8 Hz, 1H), 8.21 (dd, J = 8.3, 2.0 Hz, 1H), 8.43 (dd, J = 8.2, 0.9 Hz, 1H), 8.90 (dd, J = 2.0, 0.8 Hz, 1H), 9.90 (s, 1H). | 420 | 1.17 |
| I-99 | 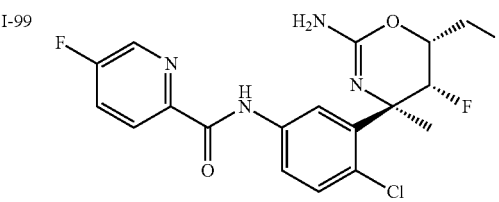 | 1H-NMR (400 MHz, CDCl3) δ 1.80 (d, J = 2.8 Hz, 3H), 3.96-4.10 (m, 1H), 4.60 (dd, J = 46.6, 5.6 Hz, 2H), 5.72 (d, J = 48.2 Hz, 1H), 7.40 (d, J = 8.5 Hz, 1H), 7.60 (dd, J = 8.3, 2.8 Hz, 1H), 7.69 (d, J = 2.8 Hz, 1H), 8.03 (dd, J = 8.8, 2.8 Hz, 1H), 8.33 (dd, J = 8.7, 4.4 Hz, 1H), 8.46 (d, J = 2.8 Hz, 1H), 9.86 (s, 1H). | 413 | 1.22 |
| I-100 | 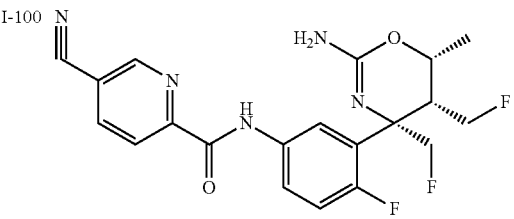 | 1H-NMR (400 MHz, (CD3)2SO) δ 1.20 (d, J = 6.7 Hz, 3H), 2.53 (m, 1H), 3.92 (m, 1H), 4.44-4.86 (m, 4H), 5.73 (s, 2H), 7.19 (dd, J = 11.8, 8.8 Hz, 1H), 7.81 (m, 1H), 7.91 (dd, J = 7.3, 2.8 Hz, 1H), 8.27 (d, J = 8.3 Hz, 1H), 8.56 (dd, J = 8.3, 2.0 Hz, 1H), 9.18 (m, 1H). | 418 | 1.05 |
| I-101 | 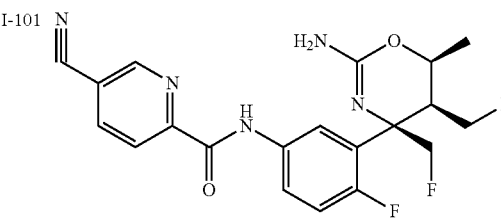 | 1H-NMR (400 MHz, (CD3)2SO) δ 1.20 (d, J = 6.7 Hz, 3H), 2.53 (m, 1H), 3.92 (m, 1H), 4.44-4.86 (m, 4H), 5.73 (s, 2H), 7.19 (dd, J = 11.8, 8.8 Hz, 1H), 7.81 (m, 1H), 7.91 (dd, J = 7.3, 2.8 Hz, 1H), 8.27 (d, J = 8.3 Hz, 1H), 8.56 (dd, J = 8.3, 2.0 Hz, 1H), 9.18 (m, 1H). | 418 | 1.05 |
| I-102 | 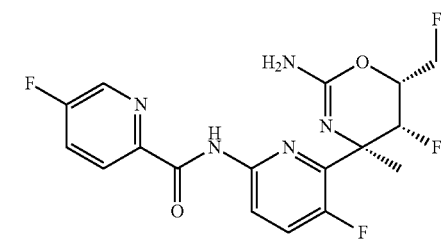 [SMILES: C[C@]1(c2nc(NC(=O)c3ccc(F)cn3)ccc2F)N=C(N)O[C@H](CF)[C@@H]1F] | 1H-NMR (400 MHz, CDCl3) δ 1.74 (d, J = 1.5 Hz, 3H), 4.43 (m, 1H), 4.57-4.79 (m, 2H), 5.33 (d, J = 48.8 Hz, 1H), 7.49 (dd, J = 10.7, 9.2 Hz, 1H), 7.61 (dt, J = 8.2, 2.6 Hz, 1H), 8.32-8.35 (m, 2H), 8.50 (d, J = 2.6 Hz, 1H), 10.21 (s, 1H). | 398 | 1.06 |

TABLE 1-19
| | | | |
|---|---|---|---|
| I-103 | 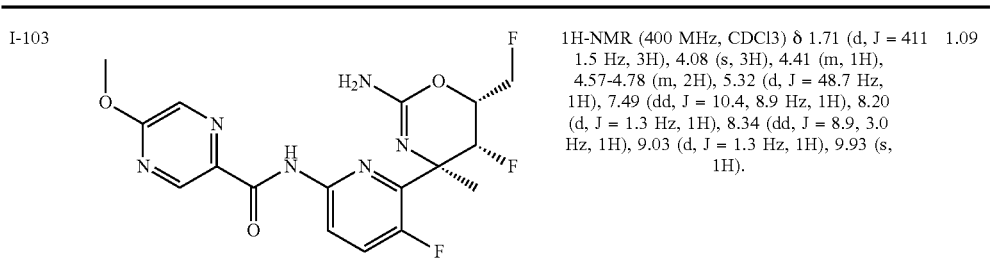 | 1H-NMR (400 MHz, CDCl3) δ 1.71 (d, J = 1.5 Hz, 3H), 4.08 (s, 3H), 4.41 (m, 1H), 4.57-4.78 (m, 2H), 5.32 (d, J = 48.7 Hz, 1H), 7.49 (dd, J = 10.4, 8.9 Hz, 1H), 8.20 (d, J = 1.3 Hz, 1H), 8.34 (dd, J = 8.9, 3.0 Hz, 1H), 9.03 (d, J = 1.3 Hz, 1H), 9.93 (s, 1H). | 411 1.09 |
| I-104 | 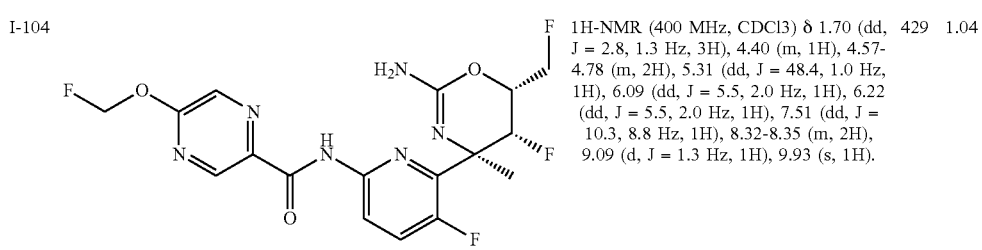 | 1H-NMR (400 MHz, CDCl3) δ 1.70 (dd, J = 2.8, 1.3 Hz, 3H), 4.40 (m, 1H), 4.57-4.78 (m, 2H), 5.31 (dd, J = 48.4, 1.0 Hz, 1H), 6.09 (dd, J = 5.5, 2.0 Hz, 1H), 6.22 (dd, J = 5.5, 2.0 Hz, 1H), 7.51 (dd, J = 10.3, 8.8 Hz, 1H), 8.32-8.35 (m, 2H), 9.09 (d, J = 1.3 Hz, 1H), 9.93 (s, 1H). | 429 1.04 |
TABLE 1-20
| | | | |
|---|---|---|---|
| I-105 (racemate) | 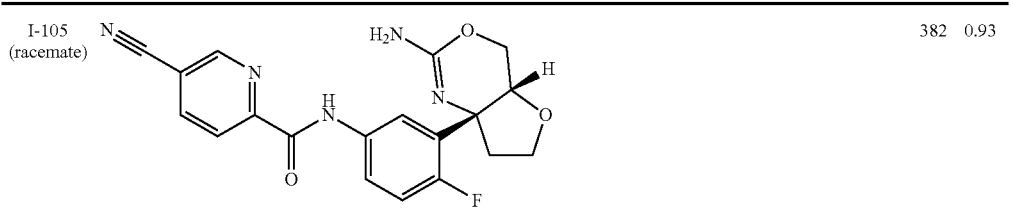 | | 382 0.93 |
| I-106 | 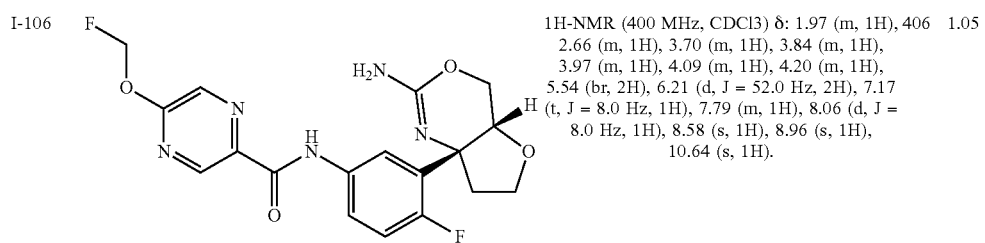 | 1H-NMR (400 MHz, CDCl3) δ: 1.97 (m, 1H), 2.66 (m, 1H), 3.70 (m, 1H), 3.84 (m, 1H), 3.97 (m, 1H), 4.09 (m, 1H), 4.20 (m, 1H), 5.54 (br, 2H), 6.21 (d, J = 52.0 Hz, 2H), 7.17 (t, J = 8.0 Hz, 1H), 7.79 (m, 1H), 8.06 (d, J = 8.0 Hz, 1H), 8.58 (s, 1H), 8.96 (s, 1H), 10.64 (s, 1H). | 406 1.05 |
| I-107 | 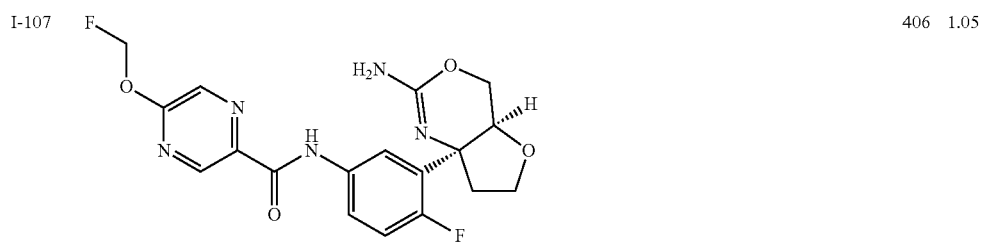 | | 406 1.05 |
| I-108 | 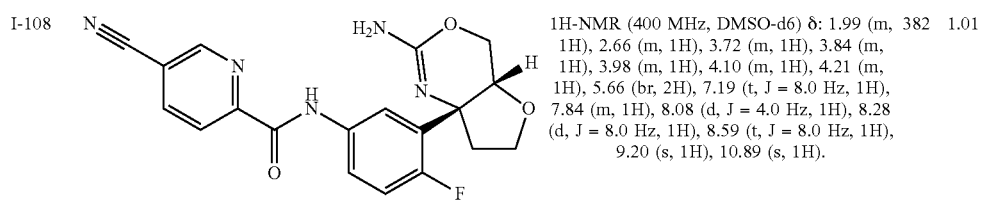 | 1H-NMR (400 MHz, DMSO-d6) δ: 1.99 (m, 1H), 2.66 (m, 1H), 3.72 (m, 1H), 3.84 (m, 1H), 3.98 (m, 1H), 4.10 (m, 1H), 4.21 (m, 1H), 5.66 (br, 2H), 7.19 (t, J = 8.0 Hz, 1H), 7.84 (m, 1H), 8.08 (d, J = 4.0 Hz, 1H), 8.28 (d, J = 8.0 Hz, 1H), 8.59 (t, J = 8.0 Hz, 1H), 9.20 (s, 1H), 10.89 (s, 1H). | 382 1.01 |

TABLE 1-21

| | | | |
|---|---|---|---|
| I-109 | (structure) | 382 | 1.07 |
| I-110 | (structure) | 414 | 1.11 |
| I-111 | (structure) | 1H-NMR (400 MHz, CDCl3) δ: 2.17 (m, 1H), 2.89 (m, 1H), 4.04 (m, 1H), 4.14 (m, 2H), 4.36 (m, 1H), 4.63 (m, 2H), 6.16 (d, J = 48.0 Hz, 1H), 7.12 (dd, J = 12.0, 8.0 Hz, 1H), 7.69 (dd, J = 8.0, 4.0 Hz, 1H), 8.02 (m, 1H), 8.30 (s, 1H), 9.08 (s, 1H), 9.57 (br, 1H). | 438 | 1.07 |
| I-112 | (structure) | 438 | 1.07 |
| I-113 | (structure) | 1H-NMR (400 MHz, CDCl3) δ: 2.04 (m, 1H), 2.91 (m, 1H), 4.10 (m, 1H), 4.19 (m, 1H), 4.24 (m, 1H), 4.40 (m, 1H), 4.72 (m, 2H), 7.15 (dd, J = 12.0, 8.0 Hz, 1H), 7.71 (dd, J = 8.0, 4.0 Hz, 1H), 8.04 (m, 1H), 8.21 (dd, J = 12.0, 4.0 Hz, 1H), 8.43 (d, J = 8.0 Hz, 1H), 8.92 (m, 1H), 9.92 (m, 1H). | 414 | 1.11 |
| I-114 | (structure) | 1H-NMR (400 MHz, CDCl3) δ: 2.24 (m, 1H), 2.87 (m, 1H), 4.12 (m, 2H), 4.31 (br, 2H), 4.49 (d, J = 4.0 Hz, 1H), 4.71 (d, J = 4.0 Hz, 1H), 4.73 (s, 1H), 7.10 (dd, J = 12.0, 8.0 Hz, 1H), 7.62 (dd, J = 8.0, 4.0 Hz, 1H), 7.94 (m, 1H), 8.20 (d, J = 8.0 Hz, 1H), 8.42 (d, J = 8.0 Hz, 1H), 8.89 (m, 1H), 9.84 (s, 1H). | 394 | 1.07 |

TABLE 1-22

| No. | Structure | 1H-NMR | MS | RT |
|---|---|---|---|---|
| I-115 | (structure) | 1H-NMR (400 MHz, CDCl3) δ: 1.02 (s, 3H), 2.67 (m, 1H), 3.33 (m, 1H), 4.13 (m, 1H), 4.22 (m, 1H), 4.34 (m, 1H), 4.41 (m, 1H), 7.17 (dd, J = 12.0, 8.0 Hz, 1H), 7.71 (m, 1H), 8.06 (dd, J = 8.0, 4.0 Hz, 1H), 8.23 (dd, J = 12.0, 4.0 Hz, 1H), 8.41 (d, J = 8.0 Hz, 1H), 8.92 (s, 1H), 9.95 (s, 1H). | 396 | 0.97 |
| I-116 | (structure) | 1H-NMR (400 MHz, CDCl3) δ: 1.69 (s, 3H), 3.68 (s, 3H), 3.85 (m, 1H), 4.10 (m, 1H), 5.89 (dt, J = 52.0, 4.0 Hz, 1H), 7.13 (dd, J = 12.0, 8.0 Hz, 1H), 7.46 (dd, J = 8.0, 4.0 Hz, 1H), 8.03 (m, 1H), 8.21 (dd, J = 8.0, 4.0 Hz, 1H), 8.42 (d, J = 8.0 Hz, 1H), 8.90 (d, J = 4.0 Hz, 1H), 9.86 (s, 1H). | 434 | 1.19 |
| I-117 | (structure) | | 434 | 1.2 |
| I-118 | (structure) | 1H-NMR (400 MHz, CDCl3) δ: 1.69 (s, 3H), 3.68 (s, 3H), 3.86 (m, 1H), 4.10 (m, 1H), 5.89 (dt, J = 56.0, 8.0 Hz, 1H), 6.16 (d, J = 52 Hz, 2H), 7.12 (dd, J = 12.0, 8.0 Hz, 1H), 7.41 (m, 1H), 8.02 (m, 1H), 8.29 (s, 1H), 9.08 (s, 1H), 9.51 (s, 1H). | 458 | 1.22 |
| I-119 | (structure) | 1H-NMR (400 MHz, CDCl3) δ: 1.70 (s, 3H), 3.68 (s, 3H), 3.87 (m, 1H), 4.10 (m, 1H), 5.89 (dt, J = 52.0, 4.0 Hz, 1H), 7.11 (dd, J = 12.0, 8.0 Hz, 1H), 7.43 (dd, J = 8.0, 4.0 Hz, 1H), 7.60 (m, 1H), 8.02 (m, 1H), 8.33 (dd, J = 8.0, 4.0 Hz, 1H), 8.46 (d, J = 4.0 Hz, 1H), 9.82 (s, 1H). | 427 | 1.2 |
| I-120 | (structure) | 1H-NMR (400 MHz, CDCl3) δ: 1.68 (s, 3H), 3.67 (s, 3H), 3.82 (m, 1H), 4.08 (m, 1H), 5.88 (dt, J = 56.0, 8.0 Hz, 1H), 6.70 (t, J = 52.0 Hz, 1H), 7.10 (dd, J = 12.0, 8.0 Hz, 1H), 7.40 (m, 1H), 7.91 (m, 1H), 8.39 (s, 1H), 8.67 (s, 1H). | 449 | 1.16 |

TABLE 1-23

| | | |
|---|---|---|
| I-121 | (structure) | 1H-NMR (400 MHz, CDCl3) δ 1.68 (s, 3H), 4.03-4.15 (m, 1H), 4.61 (dd, J = 46.3, 5.9 Hz, 2H), 5.18 (d, J = 47.9 Hz, 1H), 7.23 (brs, 1H), 8.11-8.16 (m, 1H), 8.22 (d, J = 8.0 Hz, 1H), 8.42 (d, J = 8.0 Hz, 1H), 8.91 (s, 1H), 9.89 (s, 1H). 422 1.17 |
| I-122 | (structure) | 1H-NMR (400 MHz, CDCl3) δ 1.68 (s, 3H), 4.04-4.14 (m, 1H), 4.61 (dd, J = 46.2, 5.5 Hz, 2H), 5.18 (d, J = 47.7 Hz, 1H), 7.18 (brs, 1H), 7.59-7.64 (m, 1H), 8.11-8.16 (m, 1H), 8.33 (dd, J = 9.0, 4.5 Hz, 1H), 8.47 (s, 1H), 9.86 (s, 1H). 415 1.17 |
| I-123 | (structure) | 1H-NMR (400 MHz, CDCl3) δ 1.67 (s, 3H), 4.03-4.14 (m, 1H), 4.61 (dd, J = 46.4, 5.8 Hz, 2H), 5.18 (d, J = 47.9 Hz, 1H), 6.14 (dd, J = 51.2, 4.0 Hz, 2H), 7.18 (brs, 1H), 8.10-8.14 (m, 1H), 8.30 (s, 1H), 9.08 (s, 1H), 9.54 (s, 1H). 446 1.2 |

Test Examples for the compounds of the present invention are mentioned below.

Test Example 1

Assay of BACE1 Inhibiting Activity 48.5 µL of substrate peptide solution (Biotin-XSEVNL-DAEFRHDSGC-Eu: X=ε-amino-n-capronic acid, Eu=Europium cryptate) was added to each well of 96-hole half-area plate (a black plate: Costar), and after addition of 0.5 µl of the compound of the present invention (DMSO solution) and 1 µl of Recombinant human BACE1 (R&D Systems), the reaction mixture was incubated at 30° C. for 3.5 hours. The substrate×peptide was synthesized by reacting Cryptate TBPCOOH mono SMP (CIS bio international) with Biotin-XSEVNLDAEFRHDSGC (Peptide Institute, Inc.). The final concentrations of the substrate peptide and Recombinant human BACE1 were adjusted to 18 nmol/L and 7.4 nmol/L, respectively, and the reaction was performed in sodium acetate buffer (50 mmol/L sodium acetate, pH 5.0, 0.008% Triton X-100).

After the incubation for reaction, 50 µl of 8.0 µg/ml Streptavidin-XL665 (CIS bio international) dissolved in phosphate buffer (150 mmol/L $K_2HPO_4$—$KH_2PO_4$, pH 7.0, 0.008% Triton X-100, 0.8 mol/L KF) was added to each well and left stand at 30° C. for 45 minutes. After then, fluorescence intensity was measured (excitation wavelength: 320 nm, measuring wavelength: 620 nm and 665 nm) using Wallac 1420 multilabel counter (Perkin Elmer life sciences). Enzymatic activity was determined from counting ratio of each wavelength (10,000× Count 665/Count 620) and 50% inhibitory concentration against the enzymatic activity ($IC_{50}$) was calculated.

Compound I-1: $IC_{50}$ value 94.2 nmol/L
Compound I-2: $IC_{50}$ value 77.3 nmol/L
Compound I-4: $IC_{50}$ value 90.2 nmol/L
Compound I-13: $IC_{50}$ value 153 nmol/L
Compound I-14: $IC_{50}$ value 96.8 nmol/L
Compound I-21: $IC_{50}$ value 65.4 nmol/L
Compound I-25: $IC_{50}$ value 22.8 nmol/L
Compound I-27: $IC_{50}$ value 35.5 nmol/L
Compound I-28: $IC_{50}$ value 27.6 nmol/L
Compound I-29: $IC_{50}$ value 25.8 nmol/L
Compound I-56: $IC_{50}$ value 25 nmol/L
Compound I-72: $IC_{50}$ value 13.6 nmol/L
Compound I-86: $IC_{50}$ value 32.9 nmol/L
Compound I-95: $IC_{50}$ value 20.7 nmol/L
Compound I-100: $IC_{50}$ value 113 nmol/L Compounds I-5 to 11, 15 to 20, 22 to 24, 26, 30 to 33, 37, 40 to 43, 47, 50 to 55, 57 to 66, 68 to 71, 73 85, 87 to 94, 96 to 99, 102 to 106, 108, 110, 111, 113 to 115, 116, 118 and 119 also showed the $IC_{50}$ values of 1 µmol/L or less.

Test Example 2

Measurement of β-Amyloid (Aβ) Production Inhibitory Effect in Cell

Neuroblastoma SH-SY5Y cells (SH/APPwt) with human wild-type β-APP excessively expressed therein were prepared at 8×10⁵ cells/mL, and 150 μl portions thereof were inoculated into each well of a 96-well culture plate (Falcon). The cells were cultured for 2 hours at 37° C. in a 5% gaseous carbon dioxide incubator. Then, a solution which have been preliminarily prepared by adding and suspending the compound of the present invention (DMSO (dimethyl sulfoxide) solution) so as to be 2 μl/50 μl medium was added to the cell sap. Namely, the final DMSO concentration was 1%, and the amount of the cell culture was 200 μl. After the incubation was performed for 24 hours from the addition of the test compound, 100 μl of the culture supernatant was collected from each fraction. The amount of the Aβ in each fraction was measured.

The Aβ amount was measured as follows. 10 μl of a homogeneous time resolved fluorescence (HTRF) measurement reagent (Amyloid β1-40 peptide; CIS bio international) and 10 μl of the culture supernatant were put into a 384-well half area microplate (black microplate, Costar) and mixed with each other, and then left standing overnight at 4° C. while the light was shielded. Then, the fluorescence intensity (excitation wavelength: 337 nm, measurement wavelength: 620 nm and 665 nm) was measured with a micro plate reader (Artemis K-101; FURUNO ELECTRIC). The Aβ amount was determined from the count rate at each measurement wavelength (10000× Count 665/Count 620), and the amount needed to inhibit Aβ production by 50% ($IC_{50}$) was calculated from at least six different dosages.

Compound I-38: $IC_{50}$ value 509 nmol/L
The following compounds showed the $IC_{50}$ values of 1 μmol/L or less.
I-1 to 11, 13 to 21, 23 to 33, 35 to 37, 40 to 66, and 68 to 119.

Test Example 3-1

Lowering Effect on Brain β Amyloid in Rats

Compound of the present invention is suspended in 0.5% methylcellulose, the final concentration is adjusted to 2 mg/mL, and this is orally administered to male Crl: SD rat (7 to 9 weeks old) at 10 mg/kg. In a vehicle control group, only 0.5% methylcellulose is administered, and an administration test is performed at 3 to 8 animals per group. A brain is isolated 3 hours after administration, a cerebral hemisphere is isolated, a weight thereof is measured, the hemisphere is rapidly frozen in liquid nitrogen, and stored at −80° C. until extraction date. The frozen cerebral hemisphere is transferred to a homogenizer manufactured by Teflon (Registered trademark) under ice cooling, a 4-fold volume of a weight of an extraction buffer (containing 1% CHAPS ({3-[(3-chloroamidopropyl)dimethylammonio]-1-propanesulfonate}), 20 mmol/L Tris-HCl (pH 8.0), 150 mmol/L NaCl, Complete (Roche) protease inhibitor) is added, up and down movement is repeated, and this is homogenized to solubilize for 2 minutes. The suspension is transferred to a centrifugation tube, allowed to stand on an ice for 3 hours or more and, thereafter centrifuged at 100,000×g, 4° C. for 20 minutes. After centrifugation, the supernatant is transferred to an ELISA plate (product No. 294-62501, Wako Junyaku Kogyo) for measuring β amyloid 40. ELISA measurement is performed according to the attached instruction. The lowering effect is calculated as a ratio compared to the brain β amyloid 40 level of vehicle control group of each test.

Test Example 3-2

Lowering Effect on Brain β Amyloid in Mice

Compound of the present invention is dissolved in 20% hydroxyl-beta-cyclodextrin, the final concentration is adjusted to 2 mg/mL, and this is orally administered to male Crl:CD1 (ICR) mouse (6 to 8 weeks old) at 10 mg/kg. In a vehicle control group, only 20% hydroxyl-beta-cyclodextrin is administered, and an administration test is performed at 3 to 6 animals per group. A brain is isolated 1 to 6 hours after administration, a cerebral hemisphere is isolated, a weight thereof is measured, the hemisphere is rapidly frozen in liquid nitrogen, and stored at −80° C. until extraction date.

The frozen cerebral hemisphere is transferred to a homogenize tube containing ceramic beads in a 8-fold volume of a weight of an extraction buffer (containing 0.4% DEA (diethylamine), 50 mmol/L NaCl, Complete protease inhibitor (Roche)) and incubated on an ice for 20 minutes. Thereafter, the homogenization is done using MP BIO FastPrep(Registered trademark)-24 with Lysing matrix D 1.4 mm ceramic beads (20 seconds at 6 m/s). Then, the tube spins down for 1 minute, the supernatant is transferred to a centrifugation tube, and centrifuged at 221,000×g, 4° C. for 50 minutes. After centrifugation, the supernatant is transferred to Nunc Maxisorp (Registered trademark) plate (Thermo Fisher Scientific) coating with antibody against N-terminal of β amyloid for measuring total β amyloid, and the plate is incubated overnight at 4° C. The plate is washed with TBS-T (Tris buffered saline containing 0.05% Triton X-100), and HRP-conjugated 4G8 dissolved in PBS (pH 7.4) containing 0.1% casein is added in the plate and incubated at 4° C. for 1 hour. After it is washed with TBS-T, SuperSignal ELISA Pico Chemiluminescent Substrate (Thermo Scientific) is added in the plate. Then, the chemi-luminescence counting is measured by ARVO (Registered trademark) MX 1420 Multilabel Counter (Perkin Elmer) as soon as possible. The lowering effect is calculated as a ratio compared to the brain total β amyloid level of vehicle control group of each test.

Test Example 4

CYP3A4 Fluorescent MBI Test

The CYP3A4 fluorescent MBI test is a test of investigating enhancement of CYP3A4 inhibition of a compound by a metabolism reaction. 7-benzyloxytrifluoromethylcoumarin (7-BFC) is debenzylated by the CYP3A4 enzyme (enzyme expressed in *Escherichia coli*) and 7-hydroxytrifluoromethylcoumarin (7-HFC) is produced as a fluorescing metabolite. The test is performed using 7-HFC production reaction as an index.

The reaction conditions are as follows: substrate, 5.6 μmol/L 7-BFC; pre-reaction time, 0 or 30 minutes; substrate reaction time, 15 minutes; reaction temperature, 25° C. (room temperature); CYP3A4 content (expressed in *Escherichia coli*), at pre-reaction time 62.5 pmol/mL, at reaction time 6.25 pmol/mL (at 10-fold dilution); concentrations of the compound of the present invention, 0.625, 1.25, 2.5, 5, 10, 20 μmol/L (six points).

An enzyme in a K-Pi buffer (pH 7.4) and a compound of the present invention solution as a pre-reaction solution are added to a 96-well plate at the composition of the pre-reaction. A part of pre-reaction solution is transferred to another 96-well plate, and 1/10 diluted by a substrate in a K-Pi buffer. NADPH as a co-factor is added to initiate a reaction as an index (without preincubation). After a predetermined time of a reaction, acetonitrile/0.5 mol/L Tris (trishydroxyaminomethane)=4/1 (v/v) solution is added to stop the reaction. On the other hand, NADPH is also added to a remaining pre-reaction solution in order to initiate a preincubation (with preincubation). After a predetermined time of a preincubation, a part is transferred to another 96-well plate, and 1/10 diluted by a substrate in a K-Pi buffer in order to initiate a reaction as an index. After a predetermined time of a reaction, acetonitrile/0.5 mol/L Tris (trishydroxyaminomethane)=4/1 (v/v) solution is added to stop the reaction. Fluorescent values of 7-HFC as a metabolite are measured in each index reaction plate with a fluorescent plate reader (Ex=420 nm, Em=535 nm).

The sample adding DMSO to a reaction system instead of compound of the present invention solution is adopted as a control (100%) because DMSO is used as a solvent to dissolve a compound of the present invention. Remaining activity (%) is calculated at each concentration of the compound of the present invention added as the solution, and $IC_{50}$ value is calculated by reverse-presumption by a logistic model using a concentration and an inhibition rate. When a difference subtracting $IC_{50}$ value with preincubation from that without $IC_{50}$ value is 5 µM or more, this is defined as positive (+). When the difference is 3 µM or less, this is defined as negative (−).

Test Example 5

CYP Inhibition Test

The CYP inhibition test is a test to assess the inhibitory effect of a compound of the present invention towards typical substrate metabolism reactions on CYP enzymes in human liver microsomes. The marker reactions on human main five CYP enzymes (CYP1A2, 2C9, 2C19, 2D6, and 3A4) are used as follows; 7-ethoxyresorufin O-deethylation (CYP1A2), tolbutamide methyl-hydroxylation (CYP2C9), mephenytoin 4'-hydroxylation (CYP2C19), dextromethorphan 0-demethylation (CYP2D6), and terfenedine hydroxylation (CYP3A4). The commercially available pooled human liver microsomes are used as an enzyme resource.

The reaction conditions are as follows: substrate, 0.5 µmol/L ethoxyresorufin (CYP1A2), 100 µmol/L tolbutamide (CYP2C9), 50 µmol/L S-mephenytoin (CYP2C19), 5 µmol/L dextromethorphan (CYP2D6), 1 µmol/L terfenedine (CYP3A4); reaction time, 15 minutes; reaction temperature, 37° C.; enzyme, pooled human liver microsomes 0.2 mg protein/mL; concentrations of the compound of the present invention, 1, 5, 10, 20 µmol/L (four points).

Five kinds of substrates, human liver microsomes, and a compound solution of the present invention in 50 mmol/L Hepes buffer are added to a 96-well plate at the composition as described above as a reaction solution. NADPH as a cofactor is added to this 96-well plate in order to initiate metabolism reactions. After the incubation at 37° C. for 15 minutes, a methanol/acetonitrile=1/1 (v/v) solution is added to stop the reaction. After the centrifugation at 3000 rpm for 15 minutes, resorufin (CYP1A2 metabolite) in the supernatant is quantified by a fluorescent plate reader, and hydroxytolbutamide (CYP2C9 metabolite), 4'-hydroxymephenytoin (CYP2C19 metabolite), dextrorphan (CYP2D6 metabolite), and terfenadine alcohol metabolite (CYP3A4 metabolite) in the supernatant are quantified by LC/MS/MS.

The sample adding DMSO to a reaction system instead of compound of the present invention solution is adopted as a control (100%) because DMSO is used as a solvent to dissolve a compound of the present invention. Remaining activity (%) is calculated at each concentration of a compound of the present invention, and $IC_{50}$ value is calculated by reverse presumption by a logistic model using a concentration and an inhibition rate.

Test Example 6

Fluctuation Ames Test

Each 20 µL of freeze-stored *Salmonella typhimurium* (TA98 and TA100 strain) is inoculated in 10 mL of liquid nutrient medium (2.5% Oxoid nutrient broth No. 2), and the cultures are incubated at 37° C. under shaking for 10 hours. 7.70 mL of TA98 culture is centrifuged (2000×g, 10 minutes) to remove medium, and the bacteria is suspended in 7.70 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4 \cdot 7H_2O$: 0.1 g/L), and the suspension is added to 120 mL of Exposure medium (Micro F buffer containing Biotin: 8 µg/mL, histidine: 0.2 µg/mL, glucose: 8 mg/mL). 3.42 mL of TA100 culture is added to 130 mL of Exposure medium to prepare the test bacterial solution. 588 µL of the test bacterial solution (or mixed solution of 498 µl of the test bacterial solution and 90 µL of the S9 mix in the case with metabolic activation system) are mixed with each 12 µL of the following solution: DMSO solution of the compound of the present invention (several stage dilution from maximum dose 50 mg/mL at 2 to 3-fold ratio); DMSO as negative control; 50 µg/mL of 4-nitroquinoline-1-oxide DMSO solution as positive control for TA98 without metabolic activation system; 0.25 µg/mL of 2-(2-furyl)-3-(5-nitro-2-furyl) acrylamide DMSO solution as positive control for TA100 without metabolic activation system; 40 µg/mL of 2-aminoanthracene DMSO solution as positive control for TA98 with metabolic activation system; or 20 µg/mL of 2-aminoanthracene DMSO solution as positive control for TA100 with metabolic activation system. A mixed solution is incubated at 37° C. under shaking for 90 minutes. 460 µL of the bacterial solution exposed to the compound of the present invention is mixed with 2300 µL of Indicator medium (Micro F buffer containing biotin: 8 µg/mL, histidine: 0.2 µg/mL, glucose: 8 mg/mL, Bromo Cresol Purple: 37.5 µg/mL), each 50 µL is dispensed into 48 wells/dose in the microwell plates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose is counted, and evaluate the mutagenicity by comparing with the negative control group. (−) means that mutagenicity is negative and (+) means positive.

Test Example 7

Solubility Test

The solubility of each compound of the present invention is determined under 1% DMSO addition conditions. A 10 mmol/L solution of the compound is prepared with DMSO, and 2 µL of the compound of the present invention solution is added to 198 µL of an artificial intestinal juice (water and 118 mL of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1 (v/v), and the compound concentration in the filtrate is measured with LC/MS by the absolute calibration method.

Test Example 8

Metabolism Stability Test

Using a commercially available pooled human liver microsomes, a compound of the present invention is reacted for a constant time, a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution is added to 100 µL of a methanol/acetonitrile=1/1 (v/v), mixed and centrifuged at 3000 rpm for 15 minutes. The compound of the present invention in the supernatant is quantified by LC/MS/MS, and a remaining amount of the compound of the present invention after the reaction is calculated, letting a compound amount at 0 minute reaction time to be 100%.

Test Example 9 hERG Test

For the purpose of assessing risk of an electrocardiogram QT interval prolongation, effects on delayed rectifier K+ current ($I_{Kr}$), which plays an important role in the ventricular repolarization process of the compound of the present invention, is studied using HEK293 cells expressing human ether-a-go-go related gene (hERG) channel.

A cell is retained at a membrane potential of −80 mV by whole cell patch clamp method using an automated patch clamp system (QPatch; Sophion Bioscience A/S). After application of leak potential at −50 mV, $I_{Kr}$ induced by depolarization pulse stimulation at +20 mV for 2 seconds and, further, repolarization pulse stimulation at −50 mV for 2 seconds is recorded.

After the generated current is stabilized, extracellular solution (NaCl: 145 mmol/L, KCl: 4 mmol/L, CaCl$_2$:2 mmol/L MgCl$_2$:1 mmol/L, 1 mmol/L, HEPES (4-(2-hydroxyethyl)-1-piperazineethanesulfonic acid: 10 mmol/L, glucose: 10 mmol/L pH=7.4) in which the compound of the present invention have been dissolved at an objective concentration is applied to the cell under the room temperature condition for 10 minutes. From the recording $I_{Kr}$, an absolute value of the tail peak current is measured based on the current value at the resting membrane potential using an analysis software (Falster Patch; Sophion Bioscience A/S). Further, the % inhibition relative to the tail peak current before application of the compound of the present invention is calculated, and compared with the vehicle-applied group (0.1% dimethyl sulfoxide solution) to assess influence of the compound of the present invention on $I_{Kr}$.

Test Example 10

Powder Solubility Test

Appropriate amounts of the compound of the present invention are put into appropriate containers. 200 µL of JP 1st fluid (Dissolve 2.0 g of sodium chloride in 7.0 mL of hydrochloric acid and water to make 1000 mL), 200 µL of JP 2nd fluid (A mixture of phosphate buffer (pH 6.8) and water (1:1)), and 200 µL of JP 2nd fluid containing 20 mmol/L of sodium taurocholate (TCA) (TCA 1.08 g and JP 2nd fluid to make 100 mL) are added to the respective containers When the compound of the present invention is dissolved after the addition of the test fluid, the bulk powder is added as appropriate. The containers are sealed, and shaken for 1 hour at 37° C. The mixtures are filtered, and 100 µL of methanol is added to each of the filtrate (100 µL) so that the filtrates are two-fold diluted. The dilution ratio may be changed if necessary. After confirming that there is no bubbles and precipitates in the diluted solution, the containers are sealed and shaken. Quantification is performed by HPLC with an absolute calibration method.

Test Example 11

BA Test

Materials and methods for studies on oral absorption
(1) Animal: mouse or SD rat
(2) Breeding conditions: mouse or SD rat is allowed free access to the tap water and the solid food.
(3) Dose and grouping: orally or intravenously administered at a predetermined dose; grouping is as follows (Dose depends on the compound)
Oral administration: 1 to 30 mg/kg (n=2 to 3)
Intravenous administration: 0.5 to 10 mg/kg (n=2 to 3)
(4) Dosing formulation: for oral administration, in a solution or a suspension state; for intravenous administration, in a solubilized state
(5) Dosing method: in oral administration, forcedly administer using a syringe attached a flexible feeding tube; in intravenous administration, administer from caudal vein using a syringe attached with a needle.
(6) Evaluation items: blood is collected at the scheduled time, and the plasma concentration of the compound of the present invention is measured by LC/MS/MS
(7) Statistical analysis: regarding the transition of the plasma concentration of the compound of the present invention, the area under the plasma concentration-time curve (AUC) is calculated by non-linear least squares program WinNonlin (Registered trademark), and the bioavailability (BA) of the compound of the present invention is calculated from the AUCs of the oral administration group and intravenous administration group Test Example 12

Brain Distribution Studies

Compound of the present invention is intravenously administered to a rat at 0.5 mg/mL/kg dosage. 30 minutes later, all blood is drawn from the abdominal aorta under isoflurane anesthesia for death from exsanguination.

The brain is enucleated and 20 to 25% of homogenate thereof is prepared with distilled water.

The obtained blood is used as plasma after centrifuging. The control plasma is added to the brain sample at 1:1. The control brain homogenate is added to the plasma sample at 1:1. Each sample is measured using LC/MS/MS. The obtained area ratio (a brain/plasma) is used for the brain Kp value.

Test Example 13

Ames Test

Ames test is performed by using Salmonellas (*Salmonella typhimurium*) TA 98, TA100, TA1535 and TA1537 and *Escherichia coli* WP2uvrA as test strains with or without metabolic activation in the pre-incubation method to check the presence or absence of gene mutagenicity of compounds of the present invention.

Test Example 14

P-gp Substrate Test

Compound of the present invention is added in the culture insert of the Transwell (Registered trademark, CORNING) wherein human MDR1 expressing cells or parent cells are monolayer cultivated, and reacted for a predetermined period of times. The compound of the present invention is investigated whether a P-gp substrate or not by comparing Efflux Ratio (ER) values of MDR1 expressing cells and parent cells. Here, ER is calculated from the membrane permeability coefficients of the direction from Basolateral side to Apical side (B to A) and the direction from Apical side to Basolateral side (A to B)) of MDR1 expressing cells and parent cells.

Test Example 15

Inhibitory Effects on P-gp Transport

Materials
1. Cell line:
   a. MDR1/LLC-PK1 (Becton Dickinson)
   b. LLC-PK1 (Becton Dickinson)
2. Reference substrates:
   a. [$^3$H]Digoxin (1 µM)
   b. [$^{14}$C]Mannitol (5 µM)
3. Reference inhibitor:
   Cyclosporin A (10 µM
Methods and Procedures
1. MDR1 expressing LLC-PK1 cells and its parent cells are routinely cultured in Medium A (Medium 199 (Invitrogen) supplemented with 10% FBS (Invitrogen), gentamycin (0.05 mg/mL, Invitrogen) and hygromycin B (100 µg/mL, Invitrogen)) at 37° C. under 5% $CO_2$/95% $O_2$ gasses. For the transport experiments, these cells are seeded on Transwell insert (24-well, pore size: 0.4 µm, Coaster) at a density of $4×10^4$ cells/insert and added Medium B (Medium 199 supplemented with 10% FBS and gentamycin at 0.05 mg/mL) to the feeder tray. These cells are incubated in a $CO_2$ incubator (5% $CO_2$/95% $O_2$ gasses, 37° C.) and replace apical and basolateral culture medium every 48-72 hr after seeding. These cells are used between 6 and 9 days after seeding.
2. The medium in the culture insert seeded with MDR1 expressing cells or parent cells are removed by aspiration and rinsed by HBSS. The apical side (250 µL) or basolateral side (850 µL) is replaced with transport buffer containing reference substrates with or without the compound of the present invention and then an aliquot (50 µL) of transport buffer in the donor side is collected to estimate initial concentration of reference substrate. After incubation for designed time at 37° C., an aliquot (50 µL) of transport buffer in the donor and receiver side are collected. Assay is performed by triplicate.
3. An aliquot (50 µL) of the transport buffer is mixed with 5 mL of a scintillation cocktail, and the radioactivity is measured using a liquid scintillation counter.
Calculations
Permeated amounts across monolayers of MDR1 expressing and parent cells are determined, and permeation coefficients (Pe) are calculated using Excel 2003 from the following equitation:

$$Pe(\text{cm/sec}) = \text{Permeated amount (pmol)/area of cell membrane (cm}^2\text{)/initial concentration (nM)/incubation time (sec)}$$

Where, permeated amount is calculated from permeation concentration (nM, concentration of the receiver side) of the substance after incubation for the defined time (sec) multiplied by volume. (mL) and area of cell membrane is used 0.33 (cm$^2$). The efflux ratio will be calculated using the following equation:

$$\text{Efflux Ratio} = \text{Basolateral-to-Apical } Pe/\text{Apical-to-Basolateral } Pe$$

The net flux is calculated using the following equation:

$$\text{Net flux} = \text{Efflux Ratio in MDR1 expressing cells/Efflux Ratio in parent cells}$$

The percent of control is calculated as the net efflux ratio of reference compounds in the presence of the compound of the present invention to that in the absence of the compound of the present invention.
$IC_{50}$ values are calculated using WinNonlin (Registered trademark) pharmacokinetic software modeling program.

Test Example 16

P-gp Substrate Test Using mdr1a(−/−) B6 Mice

Materials
Animal: mdr1a(−/−) B6 mice (KO mouse) or C57BL/6J mice (Wild mouse)
Methods and Procedures
1. Animals may be fed prior to dosing of the compounds of the present invention.
2. The compounds of the present invention are dosed to three animals for each time point and blood and brain samples are removed at selected time points (e.g. 15 min, 30 min, 1 hr, 2 hr, 4 hr, 6 hr, 8 hr, or 24 hr) after dosing. Blood (0.3-0.7 mL) is collected via trunk blood collection with syringe containing anticoagulants (EDTA and heparin). Blood and tissue (e.g. brain) samples are immediately placed on melting ice.
3. Blood samples are centrifuged (1780×g for 10 minutes) for cell removal to obtain plasma. Then, plasma samples are transferred to a clean tube and stored in a −70° C. freezer until analysis.
4. Tissue (e.g. brain) samples are homogenized at a 1:3 ratio of tissue weight to ml of stilled water and transferred to a clean tube and stored in a −70° C. freezer until analysis.
5. Plasma and tissue (e.g. brain) samples are prepared using protein precipitation and analyzed by LC/MS/MS. The analytical method is calibrated by including a standard curve constructed with blank plasma or brain samples and known quantities of analyte. Quality control samples are included to monitor the accuracy and precision of the methodology.
6. Plasma and brain concentration values (ng/mL and ng/g) are introduced into an appropriate mathematical tool used for calculating the pharmacokinetic parameters. A common platform is the WinNonlin (Registered trademark) pharmacokinetic software modeling program.

Calculations

Kp; Tissue to Plasma concentration ratio

Kp ratio = Kp in KO mouse/Kp in Wild mouse

KO/Wild ratio of AUC Tissue/AUC Plasma =

{AUC Tissue/AUC Plasma (KO mouse)}/

{AUC Tissue/AUC Plasma (Wild mouse)}

Test Example 17

Anesthetized Guinea Pig Cardiovascular Study

Animal species: Guinea pig (Slc: Hartley, 4-6 weeks old, male), N=4
Study Design:
Dosage: 3, 10, and 30 mg/kg (in principle)
(The compounds of the present invention are administered cumulatively)
Formulation:
Composition of Vehicle; Dimethylacetamide (DMA): Polyethylene glycol 400 (PEG400): Distilled water (D. W.)=1: 7:2 (in principle).
The compounds of the present invention are dissolved with DMA and then added PEG400 and D. W. Finally, 1.5, 5, and 15 mg/mL solutions are prepared.
Dosing Route and Schedule:
Intravenous infusion for 10 min (2 mL/kg).
0 to 10 min: 3 mg/kg, 30 to 40 min: 10 mg/kg, 60 to 70 min: 30 mg/kg
Vehicle is administered by the same schedule as the above.
Group Composition:
Vehicle group and the compound of the present invention group (4 guinea pigs per group). Evaluation method:
Evaluation Items:
Mean blood pressure [mmHg], Heart rate (derived from blood pressure waveform [beats/min]), QTc (ms), and Toxicokinetics.
Experimental Procedure:

Guinea pigs are anesthetized by urethane (1.4 g/kg, i.p.), and inserted polyethylene tubes into carotid artery (for measuring blood pressure and sampling blood) and jugular vein (for infusion test compounds). Electrodes are attached subcutaneously (Lead 2). Blood pressure, heart rate and electrocardiogram (ECG) are measured using PowerLab (Registered trademark) system (ADInstruments).
Toxicokinetics:

Approximately 0.3 mL of blood (approximately 150 μL as plasma) is drawn from carotid artery with a syringe containing heparin sodium and cooled with ice immediately at each evaluation point. Plasma samples are obtained by centrifugation (4° C., 10000 rpm, 9300×g, 2 minutes). The procedure for separation of plasma is conducted on ice or at 4° C. The obtained plasma (TK samples) is stored in a deep freezer (set temperature: −80° C.).
Analysis methods: Mean blood pressure and heart rate are averaged a 30-second period at each evaluation time point. ECG parameters (QT interval [ms] and QTc are derived as the average waveform of a 10-second consecutive beats in the evaluation time points. QTc [Fridericia's formula; QTc=QT/(RR)1/3)] is calculated using the PowerLab (Registered trademark) system. The incidence of arrhythmia is visually evaluated for all ECG recordings (from 0.5 hours before dosing to end of experiment) for all four animals.
Evaluation Time Points:
Before (pre dosing), and 10, 25, 40, 55, 70, and 85 min after the first dosing.
Data Analysis of QTc:
Percentage changes (%) in QTc from the pre-dose value are calculated (the pre-dose value is regarded as 100%). Relative QTc is compared with vehicle value at the same evaluation point.

Formulation Examples

The following Formulation Examples are only exemplified and not intended to limit the scope of the present invention.

Formulation Example 1

Tablet

| Compound of the present invention | 15 mg |
|---|---|
| Lactose | 15 mg |
| Calcium stearate | 3 mg |

All of the above ingredients except for calcium stearate are uniformly mixed. Then the mixture is crushed, granulated and dried to obtain a suitable size of granules. Then, calcium stearate is added to the granules. Finally, tableting is performed under a compression force.

Formulation Example 2

Capsules

| Compound of the present invention | 10 mg |
|---|---|
| Magnesium stearate | 10 mg |
| Lactose | 80 mg |

The above ingredients are mixed uniformly to obtain powders or fine granules, and then the obtained mixture is filled in capsules.

Formulation Example 3

Granules

| Compound of the present invention | 30 g |
|---|---|
| Lactose | 265 g |
| Magnesium stearate | 5 g |

After the above ingredients are mixed uniformly, the mixture is compressed. The compressed matters are crushed, granulated and sieved to obtain suitable size of granules.

INDUSTRIAL APPLICABILITY

The compounds of the present invention can be a medicament useful as an agent for treating or preventing a disease induced by production, secretion and/or deposition of amyloid β proteins.

The invention claimed is:
1. A compound of formula (I):

[Chemical Formula 1]

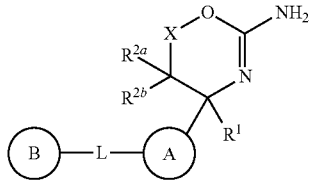

(I)

wherein
X is —C(R$^{3a}$)(R$^{3b}$)—,
L is —C(=O)NH—,
ring A is substituted or unsubstituted aromatic carbocycle,
ring B is represented by following formula (II),

[Chemical Formula 10]

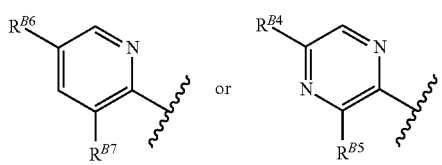

wherein R$^{B6}$ is halogen or cyano,
R$^{B7}$ is substituted or unsubstituted alkyl, halogen, hydroxy, substituted or unsubstituted amino, or substituted or unsubstituted cycloalkyl,
R$^{B4}$ is substituted or unsubstituted alkyl, monofluoromethyloxy, or monofluoroethyloxy, and
R$^{B5}$ is hydrogen or substituted or unsubstituted amino,
R$^1$ is substituted or unsubstituted alkyl, substituted or unsubstituted alkenyl, substituted or unsubstituted alkynyl, or substituted or unsubstituted cycloalkyl,
R$^{2a}$ and R$^{2b}$ are each independently hydrogen, halogen, hydroxy, substituted or unsubstituted alkyl, substituted or unsubstituted alkenyl, cyano, or substituted or unsubstituted cycloalkyl,
R$^{3a}$ is hydrogen, halogen, hydroxy, substituted or unsubstituted alkyl, substituted or unsubstituted alkenyl, cyano, or substituted or unsubstituted cycloalkyl,
R$^{3b}$ is substituted or unsubstituted alkyl,
wherein a substituent of the substituted or unsubstituted aromatic carbocycle, and the substituted or unsubstituted cycloalkyl is one or more groups selected from the group consisting of halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, guanidino, trialkylsilyl, alkyl, alkenyl, alkynyl, haloalkyl, alkyloxy, halkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkyl sulfonyl, alkenyl sulfonyl, alkynylsulfonyl, monoalkylcarbonylamino, dialkylcarbonylamino, mono- alkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, di alkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl,
the substituted or unsubstituted cycloalkyl is optionally substituted with oxo,
a substituent of the substituted or unsubstituted alkyl, the substituted or unsubstituted alkenyl, and the substituted or unsubstituted alkenyl is one or more groups selected from the group consisting of halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkyl sulfonyl, alkenyl sulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, aromatic carbocyclyl sulfonyl, non-aromatic carbocyclylsulfonyl, aromatic heterocyclyl sulfonyl, and non-aromatic heterocyclylsulfonyl, and a substituent of the substituted or unsubstituted amino is one or two groups selected from the group consisting of alkyl, alkylcarbonyl, alkenylcarbonyl, alkynylcarbonyl, aromatic carbocyclylcarbonyl, non-aromatic carbocyclylcarbonyl, aromatic heterocyclylcarbonyl, non-aromatic heterocyclylcarbonyl, hydroxy, alkyloxy, alkyloxycarbonyl, aromatic carbocyclyl, non-aromatic carbocyclyl, aromatic heterocyclyl, and non-aromatic heterocyclyl, provided that a compound wherein $R^1$ is alkyl, and both of $R^{2a}$ and $R^{2b}$ are fluorine is excluded, or a pharmaceutically acceptable salt thereof.

2. The compound according to claim 1 wherein $R^1$ is alkyl, haloalkyl, alkenyl, haloalkenyl, alkynyl, haloalkynyl or cycloalkyl, or a pharmaceutically acceptable salt thereof.

3. The compound according to claim 1 wherein $R^1$ is alkynyl or a pharmaceutically acceptable salt thereof.

4. The compound according to claim 1,
wherein both of $R^{3a}$ and $R^{3b}$ are alkyl,
or a pharmaceutically acceptable salt thereof.

5. The compound according to claim 1,
wherein $R^1$ is haloalkyl,
or a pharmaceutically acceptable salt thereof.

6. The compound according to claim 1,
wherein $R^1$ is haloalkyl and X is —CH($R^{3b}$)—,
or a pharmaceutically acceptable salt thereof.

7. The compound according to claim 1,
wherein X is —CH($R^{3b}$)—, and $R^{2a}$ and $R^{2b}$ are hydrogen,
or a pharmaceutically acceptable salt thereof.

8. The compound according to claim 1,
wherein X is —CH(CH$_2$F)— or —CH(CHF$_2$)—,
or a pharmaceutically acceptable salt thereof.

9. The compound according to claim 8,
wherein one of $R^{2a}$ and $R^{2b}$ is halogen or alkyloxy and the other is hydrogen,
or a pharmaceutically acceptable salt thereof.

10. The compound according to claim 1,
wherein in ring B represented by the formula (II),

[Chemical Formula 10]

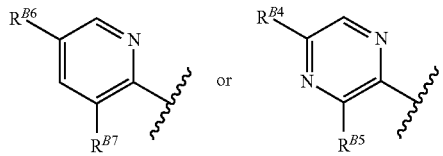

$R^{B7}$ is alkyl, haloalkyl, halogen, hydroxy, amino, or cycloalkyl,
$R^{B4}$ is alkyl, haloalkyl, monofluoromethyloxy, or monofluoroethyloxy, and
$R^{B5}$ is hydrogen or amino,
or a pharmaceutically acceptable salt thereof.

11. The compound according to claim 1,
wherein ring A is represented by following formula (III),

[Chemical Formula 11]

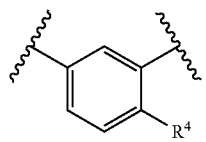

wherein $R^4$ is hydrogen or halogen,
or a pharmaceutically acceptable salt thereof.

12. A compound of formula (IA):

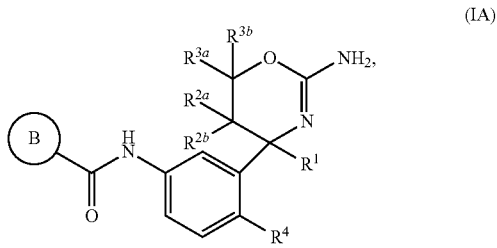

wherein $R^1$ is alkyl, haloalkyl, alkynyl, or cycloalkyl,
$R^{2a}$, $R^{2b}$, and $R^{3a}$ are hydrogen,
$R^{3b}$ is halogen, substituted or unsubstituted alkyl, substituted or unsubstituted alkenyl, cyano, or substituted or unsubstituted cycloalkyl,
$R^4$ is halogen,
ring B is

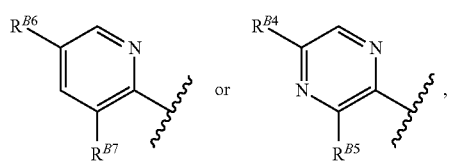

wherein $R^{B6}$ is cyano,
$R^{B7}$ is alkyl, haloalkyl, cycloalkylalkyl, hydroxy, alkyloxy, alkynyl, monoalkylamino, dialkylamino or cycloalkyl, $R^{B4}$ is alkyl, haloalkyl, monofluoromethyloxy or monofluoroethyloxy, and $R^{B5}$ is hydrogen, hydroxy, amino, monoalkylamino, dialkylamino or cycloalkylamino, wherein a substituent of the substituted or unsubstituted alkyl and the substituted or unsubstituted alkenyl is one or more groups selected from the group consisting of halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkyl sulfonyl, alkenyl sulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, di alkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclyl alkyloxycarbonyl, aromatic heterocyclylalkyloxycarbonyl, non-aromatic heterocyclylalkyloxycarbonyl, aromatic carbocyclyl alkylamino, non-aromatic carbocyclylalkylamino, aromatic heterocyclyl alkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, aromatic carbocyclyl sulfonyl, non-aromatic carbocyclyl sulfonyl, aromatic heterocyclylsulfonyl, and non-aromatic heterocyclylsulfonyl, and a substituent of the substituted or unsubstituted cycloalkyl is one or more groups selected from the group consisting of halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkyl sulfonyl, alkenyl sulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclyl sulfonyl, aromatic carbocyclyl sulfonyl, aromatic heterocyclylsulfonyl, non-aromatic heterocyclylsulfonyl, and oxo, or a pharmaceutically acceptable salt thereof.

13. A compound of formula (IA):

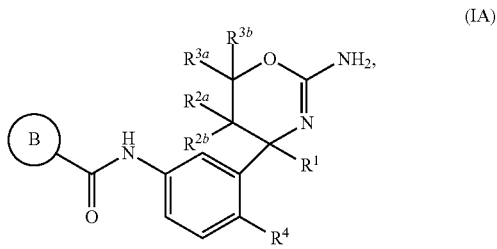

(IA)

wherein $R^1$ is alkyl, haloalkyl, alkynyl, or cycloalkyl, $R^{2a}$, $R^{2b}$, and $R^{3a}$ are hydrogen, $R^{ab}$ is halogen, substituted or unsubstituted alkyl, substituted or unsubstituted alkenyl, cyano, or substituted or unsubstituted cycloalkyl, $R^4$ is halogen, ring B is

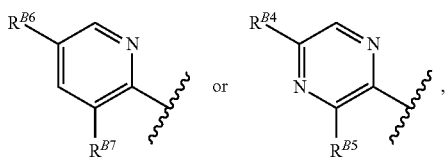

wherein $R^{B6}$ is halogen or cyano,
$R^{B7}$ is substituted or unsubstituted alkyl,
$R^{B4}$ is substituted or unsubstituted alkyl, monofluoromethyloxy or monofluoroethyloxy, and
$R^{B5}$ is hydrogen or substituted or unsubstituted amino,
wherein a substituent of the substituted or unsubstituted alkyl and the substituted or unsubstituted alkenyl is one or more groups selected from the group consisting of halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkyl sulfonyl, alkenyl sulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclyl alkyloxycarbonyl, aromatic carbocyclylalkylamino, non-aromatic carbocyclylalkylamino, aromatic heterocyclyl alkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, aromatic carbocyclyl sulfonyl, non-aromatic carbocyclyl sulfonyl, aromatic heterocyclylsulfonyl, and non-aromatic heterocyclylsulfonyl,
a substituent of the substituted or unsubstituted cycloalkyl is one or more groups selected from the group consisting of halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkyl sulfonyl, alkenyl sulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclyl sulfonyl, aromatic carbocyclyl sulfonyl, aromatic heterocyclylsulfonyl, non-aromatic heterocyclylsulfonyl, and oxo, and
a substituent of the substituted or unsubstituted amino is one or two groups selected from the group consisting of alkyl, alkylcarbonyl, alkenylcarbonyl, alkynylcarbonyl, aromatic carbocyclylcarbonyl, non-aromatic carbocyclylcarbonyl, aromatic heterocyclylcarbonyl, non-aromatic heterocyclylcarbonyl, hydroxy, alkyloxy, alkyloxycarbonyl, aromatic carbocyclyl, non-aromatic carbocyclyl, aromatic heterocyclyl, and non-aromatic heterocyclyl,
or a pharmaceutically acceptable salt thereof.

14. A method for treating at least one disease, comprising administering the compound according to claim 1 or a pharmaceutically acceptable salt thereof, wherein the at least one disease is selected from the group consisting of Alzheimer's disease, dementia of Alzheimer type, senile dementia of Alzheimer type, prodromal Alzheimer's disease, Down's syndrome, memory impairment, prion disease, which has been recognized as Creutzfeldt-Jakob disease, mild cognitive impairment (MCI), Dutch type of hereditary cerebral hemorrhage with amyloidosis, cerebral amyloid angiopathy, coexisting Alzheimer's disease with vascular type dementia, coexisting dementia with Parkinson's disease, coexisting dementia with progressive supranuclear palsy, coexisting dementia with Corticobasal degeneration, coexisting Alzheimer's disease with diffuse Lewy body disease, age-related macular degeneration, Parkinson's disease, and amyloid angiopathy.

15. A method for treating dementia of Alzheimer's type comprising administering the compound according to claim 1, or a pharmaceutically acceptable salt thereof.

16. A method for treating at least one disease, comprising administering the compound according to claim 12 or a pharmaceutically acceptable salt thereof,
wherein the at least one disease is selected from the group consisting of Alzheimer's disease, dementia of Alzheimer type, senile dementia of Alzheimer type, prodromal Alzheimer's disease, Down's syndrome, memory impairment, prion disease, which has been recognized as Creutzfeldt-Jakob disease, mild cognitive impairment (MCI), Dutch type of hereditary cerebral hemorrhage with amyloidosis, cerebral amyloid angiopathy, coexisting Alzheimer's disease with vascular type dementia, coexisting dementia with Parkinson's disease, coexisting dementia with progressive supranuclear palsy, coexisting dementia with Corticobasal degeneration, coexisting Alzheimer's disease with diffuse Lewy body disease, age-related macular degeneration, Parkinson's disease, and amyloid angiopathy.

17. A method for treating dementia of Alzheimer's type comprising administering the compound according to claim 12, or a pharmaceutically acceptable salt thereof.

18. A method for treating at least one disease, comprising administering the compound according to claim 13 or a pharmaceutically acceptable salt thereof,
wherein the at least one disease is selected from the group consisting of Alzheimer's disease, dementia of Alzheimer type, senile dementia of Alzheimer type, prodromal Alzheimer's disease, Down's syndrome, memory impairment, prion disease, which has been recognized as Creutzfeldt-Jakob disease, mild cognitive impairment (MCI), Dutch type of hereditary cerebral hemorrhage with amyloidosis, cerebral amyloid angiopathy, coexisting Alzheimer's disease with vascular type dementia, coexisting dementia with Parkinson's disease, coexisting dementia with progressive supranuclear palsy, coexisting dementia with Corticobasal degeneration, coexisting Alzheimer's disease with diffuse Lewy body disease, age-related macular degeneration, Parkinson's disease, and amyloid angiopathy.

19. A method for treating dementia of Alzheimer's type comprising administering the compound according to claim 13, or a pharmaceutically acceptable salt thereof.

* * * * *